US012110518B2

(12) United States Patent
Li et al.

(10) Patent No.: US 12,110,518 B2
(45) Date of Patent: Oct. 8, 2024

(54) POLYPEPTIDES

(71) Applicant: Novozymes A/S, Bagsvaerd (DK)

(72) Inventors: Ming Li, Beijing (CN); Jesper Salomon, Holte (DK); Dorotea Raventos Segura, Rungsted (DK); Mary Ann Stringer, Soborg (DK); Rebecca Munk Vejborg, Allerod (DK); Dorte Marie Koefoed Klitgaard, Birkerod (DK); Dorota Nissen, Bagsvaerd (DK); Wei Peng, Bagsvaerd (DK); Tianqi Sun, Beijing (CN)

(73) Assignee: Novozymes A/S, Bagsvaerd (DK)

( * ) Notice: Subject to any disclaimer, the term of this patent is extended or adjusted under 35 U.S.C. 154(b) by 904 days.

(21) Appl. No.: 17/051,454

(22) PCT Filed: May 30, 2019

(86) PCT No.: PCT/CN2019/089237
§ 371 (c)(1),
(2) Date: Oct. 29, 2020

(87) PCT Pub. No.: WO2019/228448
PCT Pub. Date: Dec. 5, 2019

(65) Prior Publication Data
US 2021/0163852 A1 Jun. 3, 2021

(30) Foreign Application Priority Data
Jun. 1, 2018 (EP) .................................... 18175572

(51) Int. Cl.
*C12N 9/26* (2006.01)
*C11D 3/00* (2006.01)
(Continued)

(52) U.S. Cl.
CPC .......... *C12N 9/2402* (2013.01); *C11D 3/0036* (2013.01); *C11D 3/38636* (2013.01);
(Continued)

(58) Field of Classification Search
CPC .................................................. C12N 9/2402
See application file for complete search history.

(56) References Cited

U.S. PATENT DOCUMENTS

2009/0176682 A1 7/2009 Boutique
2018/0155802 A1* 6/2018 Lant ...................... C11D 3/386

FOREIGN PATENT DOCUMENTS

EP 3088504 A1 11/2016
WO 2009/087525 7/2009
(Continued)

OTHER PUBLICATIONS

A0A2N3WSQ5_9PSEU. UniProtKB/TrEMBL. Apr. 25, 2018.*
(Continued)

*Primary Examiner* — Yong D Pak
(74) *Attorney, Agent, or Firm* — Elias Lambiris

(57) ABSTRACT

The invention relates to polypeptides having hydrolytic activity and polynucleotides encoding the polypeptides. The invention also relates to nucleic acid constructs, vectors, and host cells comprising the polynucleotides as well as methods of producing and using the polypeptides.

15 Claims, 5 Drawing Sheets

Specification includes a Sequence Listing.

Phylogenetic tree of polypeptides

(51) Int. Cl.
*C11D 3/386* (2006.01)
*C12N 9/24* (2006.01)
(52) U.S. Cl.
CPC ....... *C11D 3/38672* (2013.01); *C11D 2111/12* (2024.01); *C12Y 302/01109* (2013.01)

(56) References Cited

FOREIGN PATENT DOCUMENTS

| | | | |
|---|---|---|---|
| WO | 2011/080267 | A2 | 7/2011 |
| WO | 2012/027374 | A2 | 3/2012 |
| WO | 2014/191322 | A1 | 12/2014 |
| WO | 2017/059802 | A1 | 4/2017 |

OTHER PUBLICATIONS

A0A019ZT99_GIBFU. UniProtKB/TrEMBL Database. Apr. 25, 2018.*
Fransceus. J Ind Microbiol Biotechnol. May 2017;44(4-5):687-695.*
Sanavia. Computational and Structural Biotechnology Journal, vol. 18, 2020, pp. 1968-1979.*
Studer. Residue mutations and their impact on protein structure and function: detecting beneficial and pathogenic changes. Biochem. J. (2013) 449, 581-594.*
C7YJY3_FUSV7. UniProtKB/TrEMBL Database. Aug. 30, 2017.*
CAZy. Glycoside Hydrolase Family 114. Retrieved on Oct. 18, 2023.*
Klenk, EBI Accession No. A0A2N3WSQ5 (2018).
Li, UnipProt Accession No. A0A178K1L7 (2016).
Naumoff et al., Molecular Biology, vol. 45, No. 4, pp. 647-657 (2011).
Naumoff, Molecular Biology, vol. 45, No. 6, pp. 983-992 (2011).
Tamura et al., Journal of Fermentation and Bioengineering, vol. 80, No. 4, pp. 305-310 (1995).

* cited by examiner

Phylogenetic tree of polypeptides

Phylogenetic tree of polypeptides

Multiple alignment of polypeptides
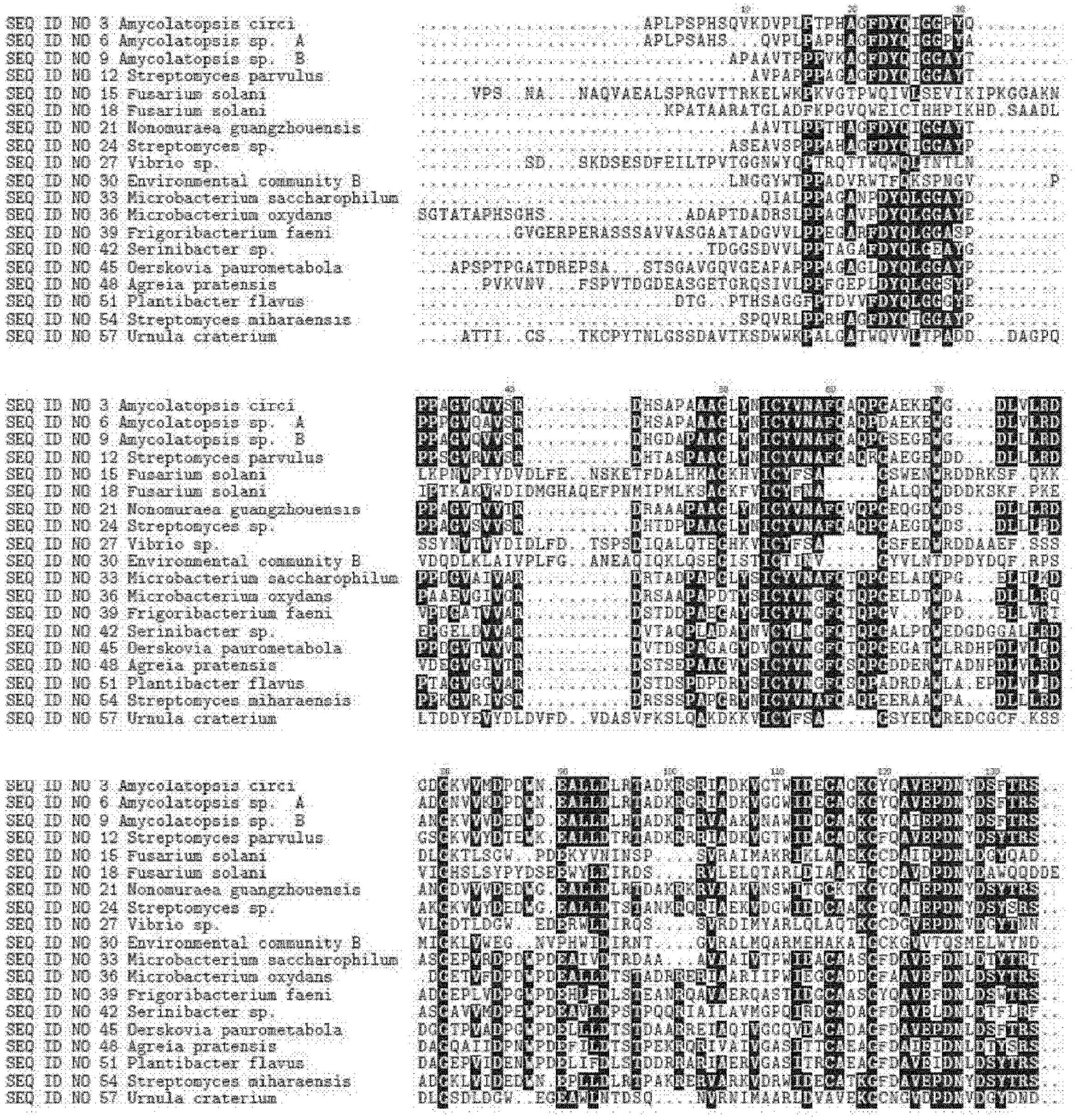
Fig. 3
(continued on next page)

```
                                              140        150              160       170       180
SEQ ID NO 3 Amycolatopsis circi               ...QGLLSARNAQDLVKLLSQRAHGKG......LAIGQKNTSELAS.SRADNGLDFAVAE
SEQ ID NO 6 Amycolatopsis sp. A               ...QDLLTAQDAQDLVKLLSAHAHGKG......LAIAQKNTSELAS.SRTANGLDFAVAE
SEQ ID NO 9 Amycolatopsis sp. B               ...RGLLSDSDAQAYIRLLSAHAHGKG......LAIAQKNTSELAG.QRQANGLDFAIAE
SEQ ID NO 12 Streptomyces parvulus            ...KKLLDAADAQAFVKLLAERAHAGG......LAIGQKNTVELAG.NRVANGLDFAVAE
SEQ ID NO 15 Fusarium solani                  ..NGLGLTEADTISYVKFLSKEAAKYR......NTTGMKNGGSITKQ..VLPYVGFCINE
SEQ ID NO 18 Fusarium solani                  DPTGFKLKSSDYTNYLKNLAKYAHSIKTKDGQPLLVGQKNAPEIAED..LVSTLDFAVLE
SEQ ID NO 21 Nonomuraea guangzhouensis        ...KKLLTASNAQAYIRLLSSHAHTQG......LAIAQKNTVELAG.SRTANGLDFAVAE
SEQ ID NO 24 Streptomyces sp.                 ...GKLLTSAEAEAYITLLSAHAHADG......LAIAQKNTSELAG.DRAKTGLDFAVAE
SEQ ID NO 27 Vibrio sp.                       ..SGFNLGYSTQLMFNRYLANSAHQLG......LSIGLKNDLRQITD..LVEYFDFAVNE
SEQ ID NO 30 Environmental community B        ..TGFYISYGIQLVYNRWLADTAHQLG......LSIGMHNTFFQVND..LVSWFDFGLVE
SEQ ID NO 33 Microbacterium saccharophilum    ...DGTLTRDDNLTVATLLVRAAHDAG......LAAGQKNAAEDARLLHDRAGFDFAVTE
SEQ ID NO 36 Microbacterium oxydans           ...GDALSLDDNLALAALFVDAAHGAG......LAAGQKNAAEDAVVLHEQAGFDFAVTE
SEQ ID NO 39 Frigoribacterium faeni           ...DEAFGEDDAVAFATLLVARAHAAG......LATAQKNTADLGARGRDEVGYDFAVTE
SEQ ID NO 42 Serinibacter sp.                 ...EG.VDRDGALDLATSYVEVAHDAG......LAVGQKNAADVGADAREVAGFDFAVVE
SEQ ID NO 45 Oerskovia paurometabola          ...DGALTRDDNLALAALLIERAHARG......LAIGQKNTVELGG.RGPALGFDFVVTE
SEQ ID NO 48 Agreia pratensis                 ...DGRLDIDDNLALAALFAERAHGLA......LAIGQKNSAELAARGRDEAHFDFAVTE
SEQ ID NO 51 Plantibacter flavus              ...DGRLTVEDAIALATRYAGLAHDAG......LLIGQKNAAELGTRGRDDVGFDFAVAE
SEQ ID NO 54 Streptomyces miharaensis         ...QDLLTADDATAFIALLSRHAHARH......LAIGQKNTPELAS.VRKKAGLDFAVAE
SEQ ID NO 57 Urnula craterium                 ..NGLGLSESTAKSYLQFLSDEAHSRG......LAIGLKNAGSIAAD..VVDSMEWEVNE

                                              190                200       210
SEQ ID NO 3 Amycolatopsis circi               ECGDQD.........NCAEYTQYF..GNRVIVIEYTEDG..........LRNACDK.....
SEQ ID NO 6 Amycolatopsis sp. A               ECGEQD.........NCAEYTQYF..DNHVIVIEYTEAG..........LRNACAK.....
SEQ ID NO 9 Amycolatopsis sp. B               ECGQQK.........NCDEFTPAF..GDHVIVIEYTDGG..........LKTACSR.....
SEQ ID NO 12 Streptomyces parvulus            ECGEWD.........ECGDYTAEF..GDHVIVVEYTAAG..........LRKACSG.....
SEQ ID NO 15 Fusarium solani                  SCIQYS.........ECDLYAPYIKAGKPVFNIEYPAGAPKVKAADK...KRICSV.TGAA
SEQ ID NO 18 Fusarium solani                  SCRGNSDPNEESWPFCEDFQTYIDAGKPVLQIEYPPSVEKTGKVSASDNKYYCTAE....
SEQ ID NO 21 Nonomuraea guangzhouensis        ECGQYK.........ECGDYTAAF..GNNVIVIEYNATG..........LSRACSG.....
SEQ ID NO 24 Streptomyces sp.                 ECGTYD.........ECGDYTAAF..GDHVIVIEYTAKG..........LQKACSG.....
SEQ ID NO 27 Vibrio sp.                       QCFEYN.........ECGYLAPFIDANKAVFNAEYESTYVDNTSARD....ALCNDA....
SEQ ID NO 30 Environmental community B        DCLNSG.........DCETYIPFLSAGKPVLDIEYNSMSSEVD..........ICKAG....
SEQ ID NO 33 Microbacterium saccharophilum    ECAVWD.........ECGAYTAVY..GDAVIAVEYTDDL..PR.....PFAAMCES.....
SEQ ID NO 36 Microbacterium oxydans           ECAVFE.........ECGVYAAVY..GTHVIDIEYSDEL..PR.....SFAEMCAD.....
SEQ ID NO 39 Frigoribacterium faeni           ECDRYD.........ECDAFTDVY..GGLVFDVEYTDDL..RG.....SIAEVCARV...G
SEQ ID NO 42 Serinibacter sp.                 ECAVYD.........ECGTYRAVY..GEHVLQIEYSDTLRDRG....LTVEEVCAL.....
SEQ ID NO 45 Oerskovia paurometabola          DCAVHD.........ECGDYAAAY..GTRVLEIEYDDGPALAE....RLASAC........
SEQ ID NO 48 Agreia pratensis                 ECVRFE.........ECAAFSDVY..GEAVVDIEYTDDL..PG.....SFADVCAT.....
SEQ ID NO 51 Plantibacter flavus              ECHRFD.........ECATYTEVY..GGAVLDIEYTDDL..RG.....TFDEVCAD.....
SEQ ID NO 54 Streptomyces miharaensis         ECGEYD.........ECGTYAEAF..DDRVVVVEYSDKG..........LRKAVAG.....
SEQ ID NO 57 Urnula craterium                 ECIAQE.........NCEDYKTFVDAGKPVFNIEYPPEDHIDDAWTEAEIEERCAQKADAS

                                              220       230          240
SEQ ID NO 3 Amycolatopsis circi               .WGAALSVVRRDRDVTPKGDSAYVRETC...........
SEQ ID NO 6 Amycolatopsis sp. A               .WGATLSVVRRDRDVTPKGDSAYVRETC...........
SEQ ID NO 9 Amycolatopsis sp. B               .WS.SLSIVRRDLDVVPKGASGYVRKTC...........
SEQ ID NO 12 Streptomyces parvulus            .FGDTLSIVRRDLDVSPKGSSSYVRETC...........
SEQ ID NO 15 Fusarium solani                  SGSKGFSKVIKK..MN....LDSWVMYC...........
SEQ ID NO 18 Fusarium solani                  DEDKGFSKIIKWASAQ....LDGWGQYCGEEPFRTPAAKY
SEQ ID NO 21 Nonomuraea guangzhouensis        .WGTKLSIVRRDVDVSPKGSSGYVRKTC...........
SEQ ID NO 24 Streptomyces sp.                 .WGDELSVVRRDLDVSPAGSKGYVRQTC...........
SEQ ID NO 27 Vibrio sp.                       .NQRQFSTLVLP.LYL....DDSFRYSCLSEPF.......
SEQ ID NO 30 Environmental community B        .RELGFNTIIKG..YS....DDTTFVDCRDRR........
SEQ ID NO 33 Microbacterium saccharophilum    ..DLPFSAVLRDRDLTTPGDPAYVFESCR...........
SEQ ID NO 36 Microbacterium oxydans           .TDSPASMVLRDRDLLTPDDPAYVFETCSE..........
SEQ ID NO 39 Frigoribacterium faeni           ELDPAPSTIVRDHDLVPADDPAHAYTAC...........
SEQ ID NO 42 Serinibacter sp.                 .PDRAPLTVVRDRLLVGPDDAAHEREQCPAG.........
SEQ ID NO 45 Oerskovia paurometabola          ..ARGASVVGRDRDLARPREPGYAFASC...........
SEQ ID NO 48 Agreia pratensis                 .KDRPASTTLRDRNLVVKGDADYVFEHC...........
SEQ ID NO 51 Plantibacter flavus              .PQVPFSTILRDRDLRTADDPAHVFDACAR..........
SEQ ID NO 54 Streptomyces miharaensis         .FGDRLSIVRRDRMVSTPGSAGYVRKLRP...........
SEQ ID NO 57 Urnula craterium                 NGATKFSTVLKN.HEN....VDEWIRTCSE..........
```

Fig. 3 continued

Clade hierarchy

POLYPEPTIDES

CROSS-REFERENCE TO RELATED APPLICATIONS

This application is a 35 U.S.C. 371 national application of international application no. PCT/CN2019/089237 filed May 30, 2019, which claims priority or the benefit under 35 U.S.C. 119 of European application no. EP 18175572.9 filed Jun. 1, 2018. The content of each application is fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to polypeptides comprising a GH114 domain having hydrolytic activity and polynucleotides encoding the polypeptides. The invention also relates to nucleic acid constructs, vectors, and host cells comprising the polynucleotides as well as methods of producing and using the polypeptides.

Description of the Related Art

Enzymes have been used in detergents for decades. Usually a cocktail of various enzymes is added to detergent compositions. The enzyme cocktail often comprises various enzymes, wherein each enzyme targets it specific substrate e.g. amylases are active towards starch stains, proteases on protein stains and so forth. Textiles and surfaces such as laundry and dishes become soiled with many different types of soiling. The soiling may compose of proteins, grease, starch etc. Biofilm is an example of soiling and the presence of biofilm provides several disadvantages. Biofilm comprises an extracellular polymeric matrix, composed of e.g. polysaccharides, extracellular DNA (eDNA), and proteins. The extracellular polymeric matrix may be sticky or gluing, which when present on textile, give rise to redeposition or back staining of soil resulting in a greying of the textile. Another drawback is that malodor may be trapped within the organic structure. Biofilm is therefore not desirable in textiles and surfaces associated with cleaning such as washing machines etc. As biofilm is a complex mixture of polysaccharides, proteins, DNA etc. there is a need for enzymes which effectively prevent, remove or reduce components of such soiling e.g. polysaccharides of components hereof on items such of fabrics. There is a need for enzymes which effectively remove or reduce components of organic soiling such as polysaccharides in e.g. the EPS in cleaning processes such as laundry and hard surface cleaning. The object of the present invention is to provide enzymes, which are compatible with cleaning compositions e.g. detergents and which effectively reduce polysaccharides associated e.g. with EPS.

SUMMARY OF THE INVENTION

The present invention provides polypeptides with hydrolase activity, wherein the polypeptides have a GH114 domain (CAZy database, www.cazy.org, Lombard V, et al. 2014, *Nucleic Acids Res* 42:D490-D495). The GH114 domain is a functional domain providing hydrolytic activity to the polypeptide. The invention further provides detergent compositions comprising polypeptides comprising the GH114 domain and the use of such polypeptides for cleaning e.g. deep cleaning in cleaning processes. The polypeptides of the present invention comprising the GH114 domain have beneficial properties such as cleaning e.g. deep cleaning in cleaning processes. Cleaning processes include laundry and dish wash.

In a first aspect the invention relates to a cleaning composition comprising:

(a) at least 0.01 ppm GH114 glycosyl hydrolase enzyme, preferably having alpha-1,4-polygalactosaminidase activity, wherein the GH114 glycosyl comprises one or both motif(s) [VLI]XE[EDSQ]C (SEQ ID NO 60) or CY[FLIV][SDN][ATVG] (SEQ ID NO 61); and (b) one or more cleaning composition components, preferably at least one surfactant, such as an anionic surfactant, wherein the anionic surfactant preferably include sulfates and sulfonates, such as linear alkylbenzenesulfonates (LAS), alpha-olefinsulfonates (AOS) and alkyl alcohol ethersulfates (AES or AEOS or FES).

In a second aspect the invention relates to a method for laundering an item comprising the steps of:

(a) exposing an item to a wash liquor comprising a composition according to the invention;

(b) completing at least one wash cycle; and (c) optionally rinsing the item, wherein the item is a textile.

In a third aspect the invention relates to the use of a GH114 glycosyl hydrolase enzyme, preferably having alpha-1,4-polygalactosaminidase activity, wherein the GH114 glycosyl hydrolase enzyme comprises one or more motif(s), selected from the group consisting of [VLI]XE[EDSQ]C (SEQ ID NO 60), CY[FLIV][SDN][ATVG] (SEQ ID NO 61), DYQ[LI]G (SEQ ID NO 62), FQ[TAV]Q[PSD] (SEQ ID NO 63), AEECG (SEQ ID NO 64), NAFQ[AT]Q (SEQ ID NO 65), WQWQL (SEQ ID NO 66), [VLI][GASD]LKN[DGS][VLIP] (SEQ ID NO 67), GXXVX[NHQTS]IEY[PG] (SEQ ID NO 68), VICYF (SEQ ID NO 69), ICYFSA (SEQ ID NO 70) and DFAVL (SEQ ID NO 71), in a cleaning process, such as laundry and/or dish wash.

In a third aspect the invention relates to use of a GH114 glycosyl hydrolase enzyme, preferably having alpha-1,4-polygalactosaminidase activity, wherein the GH114 glycosyl hydrolase enzyme comprises one or more motif(s), selected from the group consisting of

```
                                    (SEQ ID NO 60)
[VLI]XE[EDSQ]C,
                                    (SEQ ID NO 61)
CY[FLIV][SDN][ATVG],
                                    (SEQ ID NO 62)
DYQ[LI]G,
                                    (SEQ ID NO 63)
FQ[TAV]Q[PSD],
                                    (SEQ ID NO 64)
AEECG,
                                    (SEQ ID NO 65)
NAFQ[AT]Q,
                                    (SEQ ID NO 66)
WQWQL,
```

-continued (SEQ ID NO 67)
[VLI][GASD]LKN[DGS][VLIP], (SEQ ID NO 68)
GXXVX[NHQTS]IEY[PG], (SEQ ID NO 69)
VICYF, (SEQ ID NO 70)
ICYFSA
and (SEQ ID NO 71)
DFAVL, i. for preventing, reducing or removing stickiness of the item;
ii. for preventing, reducing or removing biofilm or biofilm components
iii. for reducing or removing pel stains on the item;
iv. for preventing, reducing or removing redeposition of soil during a wash cycle;
v. for preventing, reducing or removing adherence of soil to the item;
vi. for maintaining or improving whiteness of the item;
vii. for preventing, reducing or removing malodor from the item, wherein the item is a textile.

In one aspect, the present invention relates to a GH114 glycosyl hydrolase comprising the motif [VLI]XE[EDSQ]C (SEQ ID NO 60) and/or CY[FLIV][SDN][ATVG] (SEQ ID NO 61), wherein the GH114 glycosyl hydrolase has hydrolytic activity, and wherein the GH114 glycosyl hydrolase comprises or consist of a polypeptide selected from the group consisting of:

(a) a polypeptide having at least 90%, at least 95%, at least 96%, at least 97%, at least 98%, at least 99% or 100% sequence identity to the polypeptide shown in SEQ ID NO 3;
(b) a polypeptide having at least 90%, at least 95%, at least 96%, at least 97%, at least 98%, at least 99% or 100% sequence identity to the polypeptide shown in SEQ ID NO 6;
(c) a polypeptide having at least 85%, at least 90%, at least 95%, at least 96%, at least 97%, at least 98%, at least 99% or 100% sequence identity to the polypeptide shown in SEQ ID NO 9;
(d) a polypeptide having at least 85%, at least 90%, at least 95%, at least 96%, at least 97%, at least 98%, at least 99% or 100% sequence identity to the polypeptide shown in SEQ ID NO 12;
(e) a polypeptide having at least 75%, at least 80%, at least 85%, at least 90%, at least 95%, at least 96%, at least 97%, at least 98%, at least 99% or 100% sequence identity to the polypeptide shown in SEQ ID NO 21;
(f) a polypeptide having at least 90%, at least 95%, at least 96%, at least 97%, at least 98%, at least 99% or 100% sequence identity to the polypeptide shown in SEQ ID NO 24;
(g) a polypeptide having at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 27;
(h) a polypeptide having, at least 50% at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 30;
(i) a polypeptide having at least 70%, at least 75%, at least 80%, at least 85%, at least 90%, at least 95%, at least 96%, at least 97%, at least 98%, at least 99% or 100% sequence identity to the polypeptide shown in SEQ ID NO 33;
(j) a polypeptide having at least 75%, at least 80%, at least 85%, at least 90%, at least 95%, at least 96%, at least 97%, at least 98%, at least 99% or 100% sequence identity to the polypeptide shown in SEQ ID NO 36;
(k) a polypeptide having at least 99% or 100% sequence identity to the polypeptide shown in SEQ ID NO 39;
(l) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 42;
(m) a polypeptide having at least 85%, at least 90%, at least 95%, at least 96%, at least 97%, at least 98%, at least 99% or 100% sequence identity to the polypeptide shown in SEQ ID NO 45;
(n) a polypeptide having at least 70%, at least 75%, at least 80%, at least 85%, at least 90%, at least 95%, at least 96%, at least 97%, at least 98%, at least 99% or 100% sequence identity to the polypeptide shown in SEQ ID NO 48;
(o) a polypeptide having at least 98%, at least 99% or 100% sequence identity to the polypeptide shown in SEQ ID NO 51;
(p) a polypeptide having at least 80%, at least 85%, at least 90%, at least 95%, at least 96%, at least 97%, at least 98%, at least 99% or 100% sequence identity to the polypeptide shown in SEQ ID NO 54; and
(q) a polypeptide having at least 85%, at least 90%, at least 95%, at least 96%, at least 97%, at least 98%, at least 99% or 100% sequence identity to the polypeptide shown in SEQ ID NO 57.

The present invention also relates to GH114 glycosyl hydrolases. In particular, the invention relates to polypeptides selected from the group consisting of:

(a) a polypeptide having at least 60%, at least 70%, at least 75%, at least 80%, at least 85%, at least 90%, at least 95%, at least 96%, at least 97%, at least 98%, at least 99% or 100% sequence identity to the polypeptide shown in SEQ ID NO 3;
(b) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 6;
(c) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 9;
(d) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 12;
(e) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 15;

(f) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 18;

(g) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 21;

(h) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 24;

(i) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 27;

(j) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 30;

(k) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 33;

(l) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 36;

(m) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 39;

(n) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 42;

(o) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 45;

(p) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 48;

(q) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 51;

(r) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 54;

(s) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 57;

(t) a variant of the polypeptide selected from the group consisting of SEQ ID NO 3, SEQ ID NO 6, SEQ ID NO 9, SEQ ID NO 12, SEQ ID NO 15, SEQ ID NO 18, SEQ ID NO 21, SEQ ID NO 24, SEQ ID NO 27, SEQ ID NO 30 and SEQ ID NO 33, SEQ ID NO 36, SEQ ID NO 39, SEQ ID NO 42, SEQ ID NO 45, SEQ ID NO 48, SEQ ID NO 51, SEQ ID NO 54 and SEQ ID NO 57, wherein the variant has hydrolytic activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19 or 20 positions;

(u) a polypeptide comprising the polypeptide shown in (a) to (t) and a N-terminal and/or C-terminal His-tag and/or HQ-tag;

(v) a polypeptide comprising the polypeptide shown in (a) to (t) and a N-terminal and/or C-terminal extension of between 1 and 10 amino acids; and (w) a fragment of the polypeptide shown in (a) to (t) having hydrolytic activity and having at least 90% of the length of the mature polypeptide.

The invention further relates to a cleaning composition e.g. a detergent composition, a ADW composition, a laundry composition, comprising a polypeptide according to the invention.

One aspect relates to a cleaning composition comprising:

a) at least 0.001 ppm of at least one GH114 glycosyl hydrolase according to the invention; and b) one or more cleaning composition components, preferably selected from surfactants, builders, bleach components, polymers, dispersing agents and additional enzymes.

The invention further relates to a method for laundering an item comprising the steps of:

a. exposing an item to awash liquor comprising a GH114 glycosyl hydrolase according to the invention or a composition according to the invention;

b. completing at least one wash cycle; and c. optionally rinsing the item, wherein the item is a textile.

The invention further relates to use of a polypeptide according to the invention for cleaning e.g. deep cleaning of an item, such as textile e.g. fabric. The invention further relates to the use of a polypeptide according to the invention, (i) for preventing, reducing or removing stickiness of the item;

(ii) for pretreating stains on the item;

(iii) for preventing, reducing or removing redeposition of soil during a wash cycle;

(iv) for preventing, reducing or removing adherence of soil to the item;

(v) for maintaining or improving whiteness of the item;

(vi) for preventing, reducing or removing malodor from the item, wherein the item is a textile.

The invention further relates to the use of a GH114 glycosyl hydrolase in a cleaning process, such as laundry and/or dish wash. The invention also relates to the use of a GH114 glycosyl hydrolase, i. for preventing, reducing or removing stickiness of the item;

ii. for preventing, reducing or removing biofilm or biofilm components iii. for reducing or removing pel stains on the item;
iv. for preventing, reducing or removing redeposition of soil during a wash cycle;
v. for preventing, reducing or removing adherence of soil to the item;
vi. for maintaining or improving whiteness of the item;
vii. for preventing, reducing or removing malodor from the item, wherein the item is a textile.

In one aspect, the invention relates to a granule comprising;

(a) a core comprising a GH114 glycosyl hydrolase according to the invention, and
(b) optionally a coating consisting of one or more layer(s) surrounding the core.

The invention further relates to a polynucleotide encoding the polypeptide of the invention. A nucleic acid construct or expression vector comprising a polynucleotide encoding a polypeptide of the invention, which is operably linked to one or more control sequences that direct the production of the polypeptide in an expression host. The invention further relates to a recombinant host cell comprising a polynucleotide encoding a polypeptide of the invention, which is operably linked to one or more control sequences that direct the production of the polypeptide, wherein the method may further comprise cultivating a cell, which in its wild-type form produces the polypeptide, under conditions conducive for production of the polypeptide and optionally recovering the polypeptide.

OVERVIEW OF FIGURES

FIG. 3 Shows multiple alignment of some of the GH114 glycosyl hydrolase polypeptides.

OVERVIEW OF SEQUENCES

Figure 1:
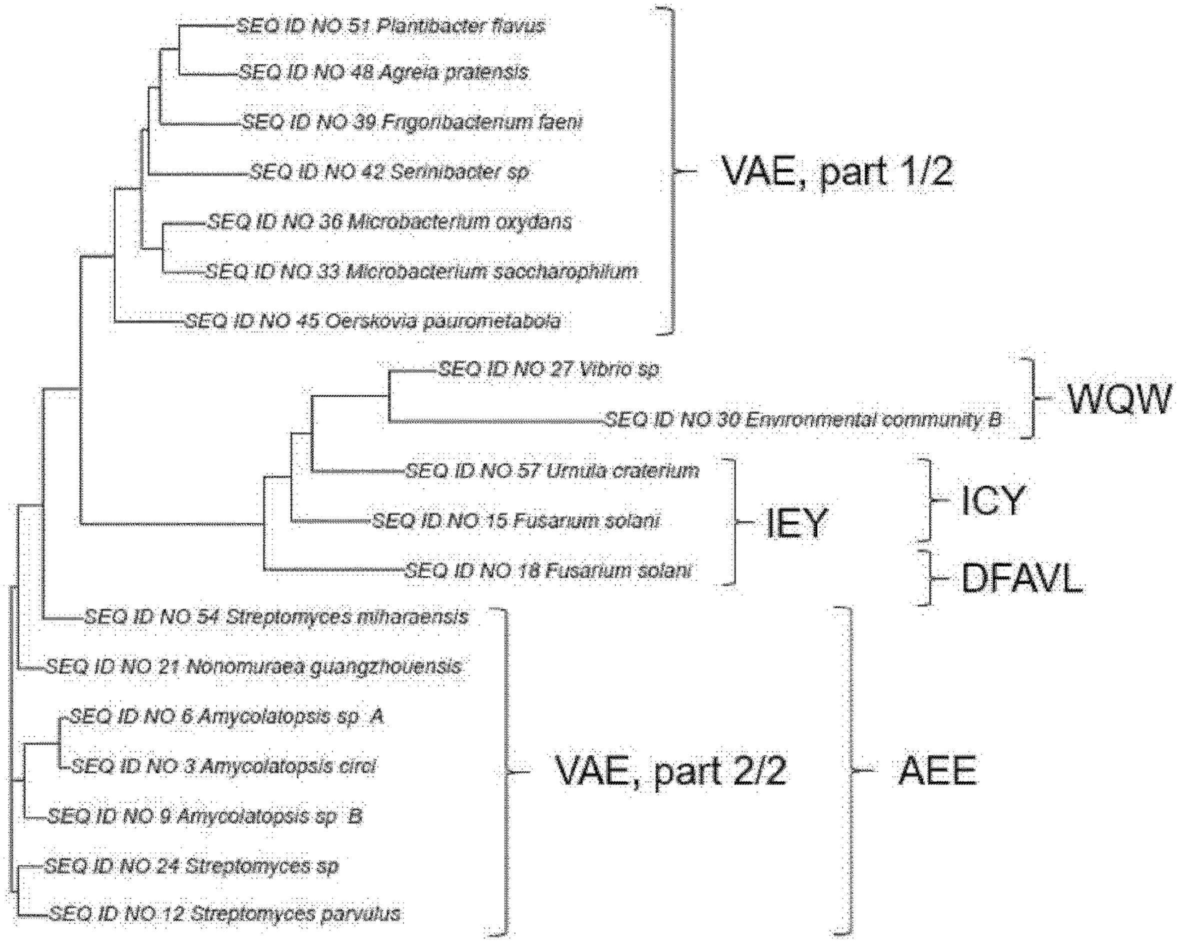
FIG. 1 Shows the phylogenetic tree as well as the clades of some of the GH114 glycosyl hydrolase polypeptides.
Figure 2:
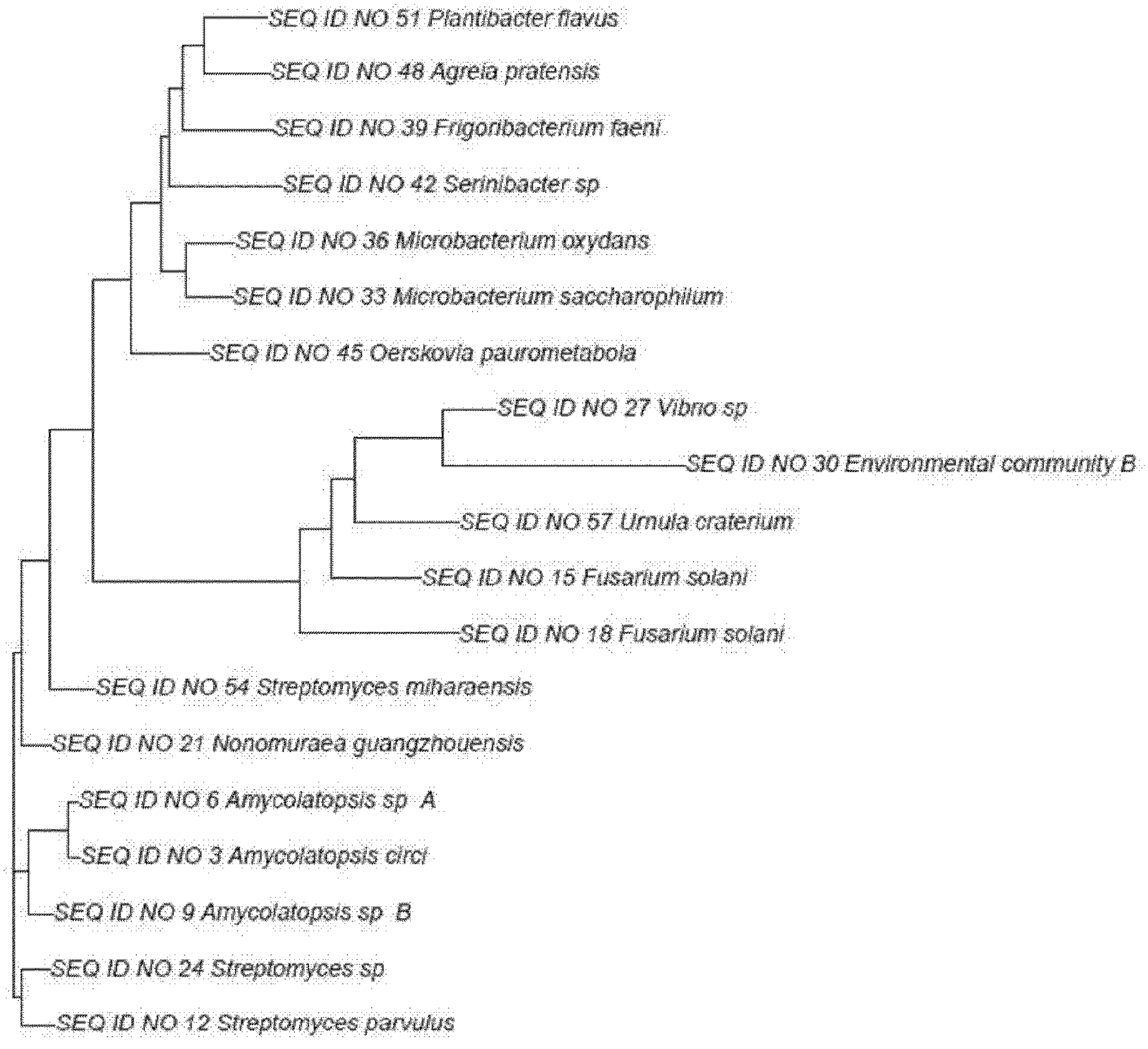
FIG. 2 Shows the phylogenetic of some of the GH114 glycosyl hydrolase polypeptides.

SEQ ID NO 1 DNA encoding full length polypeptide from *Amycolatopsis circi*
SEQ ID NO 2 polypeptide derived from SEQ ID NO 1
SEQ ID NO 3 mature polypeptide obtained from *Amycolatopsis circi*
SEQ ID NO 4 DNA encoding full length polypeptide from *Amycolatopsis* sp.
SEQ ID NO 5 polypeptide derived from SEQ ID NO 4
SEQ ID NO 6 mature polypeptide obtained from *Amycolatopsis* sp.
SEQ ID NO 7 DNA encoding full length polypeptide from *Amycolatopsis* sp.
SEQ ID NO 8 polypeptide derived from SEQ ID NO 7
SEQ ID NO 9 mature polypeptide obtained from *Amycolatopsis* sp.
SEQ ID NO 10 DNA encoding full length polypeptide from *Streptomyces parvulus*
SEQ ID NO 11 polypeptide derived from SEQ ID NO 10
SEQ ID NO 12 mature polypeptide obtained from *Streptomyces parvulus*
SEQ ID NO 13 DNA encoding full length polypeptide from *Fusarium solani*
SEQ ID NO 14 polypeptide derived from SEQ ID NO 13
SEQ ID NO 15 mature polypeptide obtained from *Fusarium solani*
SEQ ID NO 16 DNA encoding full length polypeptide from *Fusarium solani*
SEQ ID NO 17 polypeptide derived from SEQ ID NO 16
SEQ ID NO 18 mature polypeptide obtained from *Fusarium solani*
SEQ ID NO 19 DNA encoding full length polypeptide from *Nonomuraea guangzhouensis*
SEQ ID NO 20 polypeptide derived from SEQ ID NO 19
SEQ ID NO 21 mature polypeptide obtained from *Nonomuraea guangzhouensis*
SEQ ID NO 22 DNA encoding full length polypeptide from *Streptomyces* sp
SEQ ID NO 23 polypeptide derived from SEQ ID NO 22
SEQ ID NO 24 mature polypeptide obtained from *Streptomyces* sp
SEQ ID NO 25 DNA encoding full length polypeptide from *Vibrio* sp
SEQ ID NO 26 polypeptide derived from SEQ ID NO 25
SEQ ID NO 27 mature polypeptide obtained from *Vibrio* sp
SEQ ID NO 28 DNA encoding full length polypeptide from Synthetic gene
SEQ ID NO 29 polypeptide derived from SEQ ID NO 28
SEQ ID NO 30 mature polypeptide obtained from Synthetic gene
SEQ ID NO 31 DNA encoding full length polypeptide from *Microbacterium saccharophilum*
SEQ ID NO 32 polypeptide derived from SEQ ID NO 31
SEQ ID NO 33 mature polypeptide obtained from *Microbacterium saccharophilum*
SEQ ID NO 34 DNA encoding full length polypeptide from *Microbacterium oxydans*
SEQ ID NO 35 polypeptide derived from SEQ ID NO 34
SEQ ID NO 36 mature polypeptide obtained from *Microbacterium oxydans*
SEQ ID NO 37 DNA encoding full length polypeptide from *Frigoribacterium faeni*
SEQ ID NO 38 polypeptide derived from SEQ ID NO 37
SEQ ID NO 39 mature polypeptide obtained from *Frigoribacterium faeni*
SEQ ID NO 40 DNA encoding full length polypeptide from *Serinibactersp.*
SEQ ID NO 41 polypeptide derived from SEQ ID NO 40
SEQ ID NO 42 mature polypeptide obtained from *Serinibactersp.*
SEQ ID NO 43 DNA encoding full length polypeptide from *Oerskovia paurometabola*
SEQ ID NO 44 polypeptide derived from SEQ ID NO 43
SEQ ID NO 45 mature polypeptide obtained from *Oerskovia paurometabola*
SEQ ID NO 46 DNA encoding full length polypeptide from *Agreia pratensis*
SEQ ID NO 47 polypeptide derived from SEQ ID NO 46
SEQ ID NO 48 mature polypeptide obtained from *Agreia pratensis*
SEQ ID NO 49 DNA encoding full length polypeptide from *Plantibacterflavus*
SEQ ID NO 50 polypeptide derived from SEQ ID NO 49
SEQ ID NO 51 mature polypeptide obtained from *Plantibacterflavus*
SEQ ID NO 52 DNA encoding full length polypeptide from *Streptomyces miharaensis*
SEQ ID NO 53 polypeptide derived from SEQ ID NO 52
SEQ ID NO 54 mature polypeptide obtained from *Streptomyces miharaensis*
SEQ ID NO 55 DNA encoding full length polypeptide from *Urnula craterium*

SEQ ID NO 56 polypeptide derived from SEQ ID NO 55
SEQ ID NO 57 mature polypeptide obtained from *Urnula craterium*

```
signal peptide
                                        SEQ ID NO 58
MKKPLGKIVASTALLISVAFSSSIASA

                                        SEQ ID NO 59
HHHHHHPR His-tag

                                        SEQ ID NO 60
[VLI]XE[EDSQ]C

                                        SEQ ID NO 61
CY[FLIV][SDN][ATVG]

                                        SEQ ID NO 62
DYQ[LI]G

                                        SEQ ID NO 63
FQ[TAV]Q[PSD]

                                        SEQ ID NO 64
AEECG

                                        SEQ ID NO 65
NAFQ[AT]Q

                                        SEQ ID NO 66
WQWQL

                                        SEQ ID NO 67
[VLI][GASD]LKN[DGS][VLIP]

                                        SEQ ID NO 68
GXXXVX[NHQTS]IEY[PG]

                                        SEQ ID NO 69
VICYF

                                        SEQ ID NO 70
ICYFSA

                                        SEQ ID NO 71
DFAVL
```

Figure 4:
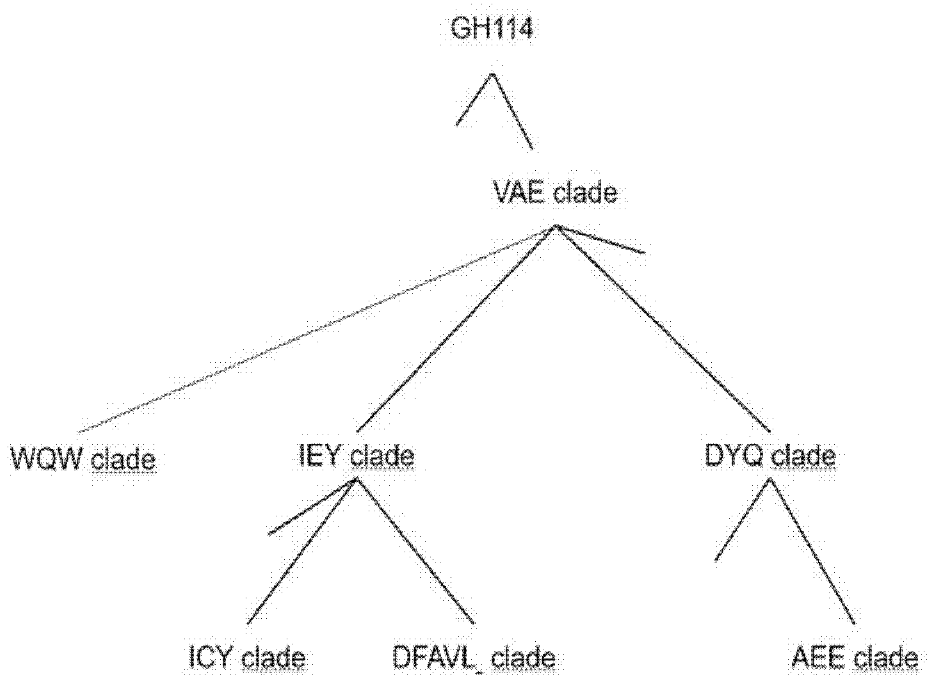
FIG. 4 Shows the clade hierarchy.

Homologue sequences according to clades as shown in FIG. 4.

VAE clade: SEQ ID NO 72-SEQ ID NO 146

DYQ clade: SEQ ID NO 79, SEQ ID NO 82, SEQ ID NO 83, SEQ ID NO 84, SEQ ID NO 85, SEQ ID NO 86, SEQ ID NO 87, SEQ ID NO 88, SEQ ID NO 90, SEQ ID NO 91, SEQ ID NO 92, SEQ ID NO 93, SEQ ID NO 94, SEQ ID NO 96, SEQ ID NO 131, SEQ ID NO 132, SEQ ID NO 134, SEQ ID NO 136, SEQ ID NO 137, SEQ ID NO 138, SEQ ID NO 139, SEQ ID NO 140, SEQ ID NO 141, SEQ ID NO 142, SEQ ID NO 143, SEQ ID NO 144 and SEQ ID NO 145

AEE clade: SEQ ID NO 79, SEQ ID NO 82, SEQ ID NO 83, SEQ ID NO 84, SEQ ID NO 85, SEQ ID NO 132, SEQ ID NO 136, SEQ ID NO 138, and SEQ ID NO 142.

IEY clade: SEQ ID NO 72, SEQ ID NO 73, SEQ ID NO 74, SEQ ID NO 75, SEQ ID NO 76, SEQ ID NO 77, SEQ ID NO 78, SEQ ID NO 97, SEQ ID NO 98, SEQ ID NO 99, SEQ ID NO 100, SEQ ID NO 101, SEQ ID NO 102, SEQ ID NO 103, SEQ ID NO 104, SEQ ID NO 105, SEQ ID NO 106, SEQ ID NO 107, SEQ ID NO 108, SEQ ID NO 109, SEQ ID NO 110, SEQ ID NO 111, SEQ ID NO 112, SEQ ID NO 113, SEQ ID NO 114, SEQ ID NO 115, SEQ ID NO 116, SEQ ID NO 117, SEQ ID NO 118, SEQ ID NO 119, SEQ ID NO 120, SEQ ID NO 121, SEQ ID NO 122, SEQ ID NO 123, SEQ ID NO 124, SEQ ID NO 125, SEQ ID NO 126, SEQ ID NO 127, SEQ ID NO 128, SEQ ID NO 129, SEQ ID NO 130, SEQ ID NO: 133 and SEQ ID NO 135

ICY clade: SEQ ID NO 98, SEQ ID NO 101, SEQ ID NO 104, SEQ ID NO 107, SEQ ID NO 114, SEQ ID NO 115, SEQ ID NO 120, SEQ ID NO 124, SEQ ID NO 125, SEQ ID NO 127, SEQ ID NO 129 and SEQ ID NO: 133

DFAVL clade: SEQ ID NO 72, SEQ ID NO 73, SEQ ID NO 74, SEQ ID NO 75, SEQ ID NO 76, SEQ ID NO 77, SEQ ID NO 78, SEQ ID NO 97, SEQ ID NO 99, SEQ ID NO 100, SEQ ID NO 102, SEQ ID NO 103, SEQ ID NO 105, SEQ ID NO 106, SEQ ID NO 108, SEQ ID NO 110, SEQ ID NO 111, SEQ ID NO 112, SEQ ID NO 113, SEQ ID NO 116, SEQ ID NO 117, SEQ ID NO 118, SEQ ID NO 119, SEQ ID NO 121, SEQ ID NO 123, SEQ ID NO 126, SEQ ID NO 128, SEQ ID NO 130 and SEQ ID NO 135

WQW clade: SEQ ID NO 80, SEQ ID NO 81, SEQ ID NO 89, SEQ ID NO 95 and SEQ ID NO 146

Definitions

Activity: The present inventions relates to glycosyl hydrolases (EC 3.2.1.-), which are a widespread group of enzymes that hydrolyse the glyosidic bond between two or more carbohydrates or between a carbohydrate and a non-carbohydrate moiety. A classification of glycoside hydrolases in families based on amino acid sequence similarities has been proposed. The polypeptides of the invention comprise at least one glycosyl hydrolase domain and are in the present context defined as glycosyl hydrolases. Thus, polypeptides of the invention hydrolyse glyosidic bonds and the polypeptides of the invention have hydrolytic activity. The glycosyl hydrolase domain comprised in the polypeptides of the invention may be classified as a GH114 (GH114, Glycoside Hydrolase Family 114, CAZy database, www.cazy.org, Lombard V, et al. 2014*, Nucleic Acids Res* 42:D490-D495). A single enzyme of GH114 has been characterized; an endo-alpha-1,4-polygalactosaminidase (EC 3.2.1.109) from *Pseudomonas* sp (Tamura, J. et. al. Molecular Cloning and Sequence Analysis of the Gene Encoding an Endo-α-1,4 polygalactosaminidase of *Pseudomonas sp.* 881. J. Fermentation Bioengineer., 1995, 80, 305). This enzyme hydrolyzes alpha-1,4-polygalactosamine to oligosaccharides in an endo-acting manner. Alpha-1,4-Polygalactosamine, also known as galactosaminoglycan, is a polymer consisting of alpha-1,4-linked galactosamine residues, which is only partially N-acetylated, and may also contain N-formyl residues. A GH114 glycosyl hydrolase is in the context of the present invention a glycosyl hydrolase comprising glycosyl hydrolase domain (DUF297), which here is termed GH114 (GH114, Glycoside Hydrolase Family 114, CAZy database, www.cazy.org, Lombard V, et al. 2014, Nucleic Acids Res 42:D490-D495). The GH114 glycosyl hydrolase domain is located at position 13 to 246 in SEQ ID NO 3. The polypeptides of the invention are glycosyl hydrolases, preferably GH114 glycosyl hydrolases. In one embodiment, the polypeptides of the invention are polygalactosaminidases, some GH114 of the invention may comprise α-1,4 polygalactosaminidase activity. The polypeptides of the invention have hydrolytic activity to glyosidic bond. In one or in the context of the present invention the GH114 glycosyl hydrolase is a PelA enzyme, which is active towards the polysaccharide PEL, present in many biofilms. The pellicle (PEL) polysaccharide is synthesized e.g. by *Pseudomonas aerugi-*

*nosa* and is an important biofilm constituent critical for bacterial virulence and persistence. The GH114 of the invention hydrolyse Pel a positively charged exopolysaccharide composed of partially acetylated 1,4 glycosidic linkages of N-acetylgalactosamine and N-acetyl-glucosamine (Jennings et al. PNAS September 2015, vol. 112, no 36, 11353-11358; Marmont et. al. J Biol Chem. 2017 Nov. 24; 292(47):19411-19422. 2017.

Allelic variant: The term "allelic variant" means any of two or more alternative forms of a gene occupying the same chromosomal locus. Allelic variation arises naturally through mutation and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Biofilm: A biofilm is organic matter produced by any group of microorganisms in which cells stick to each other or stick to a surface, such as a textile, dishware or hard surface or another kind of surface. These adherent cells are frequently embedded within a self-produced matrix of extracellular polymeric substance (EPS). Biofilm EPS is a polymeric conglomeration generally composed of extracellular DNA, proteins, and polysaccharides. Biofilms may form on living or non-living surfaces. The microbial cells growing in a biofilm are physiologically distinct from planktonic cells of the same organism, which, by contrast, are single-cells that may float or swim in a liquid medium. Bacteria living in a biofilm usually have significantly different properties from planktonic bacteria of the same species, as the dense and protected environment of the film allows them to cooperate and interact in various ways. One benefit of this environment for the microorganisms is increased resistance to detergents and antibiotics, as the dense extracellular matrix and the outer layer of cells protect the interior of the community. On laundry biofilm or EPS producing bacteria can be found among the following species: *Acinetobacter* sp., *Aeromicrobium* sp., *Brevundimonas* sp., *Microbacterium* sp., *Micrococcus luteus, Pseudomonas* sp., *Staphylococcus epidermidis*, and *Stenotrophomonas sp.* In one aspect, the biofilm producing strain is *Pseudomonas*. In one aspect, the EPS producing strain is *Pseudomonas aeruginosa, Pseudomonas alcaliphila* or *Pseudomonas fluorescens, Pseudomonas composti, Pseudomonas lundensis* and *Pseudomonas* corrugate. In one embodiment, the biofilm is caused by microorganisms or group of microorganisms which produce Pel. In another embodiment, the biofilm produces a polysaccharide that is degradable by the GH114 glycosyl hydrolases of the invention. The biofilm that may be formed on the surface e.g. such as textiles may be caused by any microorganism or group of microorganisms that forms PelA-dependent biofilm including but not limited to; *Acinetobacter* sp., *Aeromicrobium* sp., *Brevundimonas* sp., *Microbacterium* sp., *Micrococcus luteus, Staphylococcus epidermidis, Staphylococcus aureus, Pseudomonas* sp., *Pseudomonas aeruginosa, Pseudomonas alcaliphila, Pseudomonas fluorescens, Stenotrophomonas* sp., *Paraburkholderia, Burkolderia* sp., *Candida* sp., *Bordetella pertussis Yersinia pestis, Escherichia coli* and *Aspergillus* sp.

Catalytic domain: The term "catalytic domain" means the region of an enzyme containing the catalytic machinery of the enzyme.

Clade: A clade is a group of polypeptides clustered together based on homologous features traced to a common ancestor. Polypeptide clades can be visualized as phylogenetic trees and a clade is a group of polypeptides that consists of a common ancestor and all its lineal descendants. Example 10 describes generation of phylogenetic trees.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Deep cleaning: The term "deep cleaning" means disruption, reduction or removal of organic components such as polysaccharides e.g. pel, proteins, DNA, soil or other components present in organic matter such as biofilm. The term includes cleaning i.e. removal of organic stains such as dead cell material, skin debris, sebum, sweat, grease and other stains derived from e.g. humans (body soils) or microbes.

Cleaning component: The cleaning component e.g. a detergent adjunct ingredient is different to the polypeptides of this invention. The precise nature of these additional cleaning or adjunct components, and levels of incorporation thereof, will depend on the physical form of the composition and the nature of the operation for which it is to be used. Suitable cleaning components include, but are not limited to the components described below such as surfactants, builders, flocculating aid, chelating agents, dye transfer inhibitors, enzymes, enzyme stabilizers, enzyme inhibitors, catalytic materials, bleach activators, hydrogen peroxide, sources of hydrogen peroxide, preformed peracids, polymeric agents, clay soil removal/anti-redeposition agents, brighteners, suds suppressors, dyes, perfumes, structure elasticizing agents, fabric softeners, carriers, hydrotropes, builders and co-builders, fabric huing agents, anti-foaming agents, dispersants, processing aids, and/or pigments.

Cleaning Composition: The term cleaning composition includes "detergent composition" and refers to compositions that find use in the removal of undesired compounds from items to be cleaned, such as textiles. The detergent composition may be used to e.g. clean textiles for both household cleaning and industrial cleaning. The terms encompass any materials/compounds selected for the particular type of cleaning composition desired and the form of the product (e.g., liquid, gel, powder, granulate, paste, or spray compositions) and includes, but is not limited to, detergent compositions (e.g., liquid and/or solid laundry detergents and fine fabric detergents; fabric fresheners; fabric softeners; and textile and laundry pre-spotters/pretreatment). In addition to containing the enzyme of the invention, the detergent formulation may contain one or more additional enzymes such as proteases, amylases, lipases, cutinases, cellulases, endoglucanases, xyloglucanases, pectinases, pectin lyases, xanthanases, peroxidases, haloperoxygenases, catalases, mannanases, DNases or any mixture thereof, and/or detergent adjunct ingredients such as surfactants, builders, chelators or chelating agents, bleach system or bleach components, polymers, fabric conditioners, foam boosters, suds suppressors, dyes, perfume, tannish inhibitors, optical brighteners, bactericides, fungicides, soil suspending agents, anti-corrosion agents, enzyme inhibitors or stabilizers, enzyme activators, transferase(s), hydrolytic enzymes, oxido reductases, bluing agents and fluorescent dyes, antioxidants, and solubilizers.

Enzyme Detergency benefit: The term "enzyme detergency benefit" is defined herein as the advantageous effect an enzyme may add to a detergent compared to the same detergent without the enzyme. Important detergency benefits which can be provided by enzymes are stain removal with no or very little visible soils after washing and/or cleaning, prevention or reduction of redeposition of soils released in the washing process (an effect that also is termed anti-redeposition), restoring fully or partly the whiteness of textiles which originally were white but after repeated use and wash have obtained a greyish or yellowish appearance (an effect that also is termed whitening). Textile care benefits, which are not directly related to catalytic stain removal or prevention of redeposition of soils, are also important for enzyme detergency benefits. Examples of enzyme detergency benefit includes deep cleaning. Examples of enzyme detergency benefit includes biofilm reduction activity e.g. as measured in example 8. Examples of such textile care benefits are prevention or reduction of dye transfer from one fabric to another fabric or another part of the same fabric (an effect that is also termed dye transfer inhibition or anti-backstaining), removal of protruding or broken fibers from a fabric surface to decrease pilling tendencies or remove already existing pills or fuzz (an effect that also is termed anti-pilling), improvement of the fabric-softness, color clarification of the fabric and removal of particulate soils which are trapped in the fibers of the fabric or garment. Enzymatic bleaching is a further enzyme detergency benefit where the catalytic activity generally is used to catalyze the formation of bleaching components such as hydrogen peroxide or other peroxides.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Fragment: The term "fragment" means a polypeptide or a catalytic domain having one or more (e.g., several) amino acids absent from the amino and/or carboxyl terminus of a mature polypeptide or domain; wherein the fragment has activity.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance). An isolated substance may be present in a fermentation broth sample; e.g. a host cell may be genetically modified to express the polypeptide of the invention. The fermentation broth from that host cell will comprise the isolated polypeptide.

Improved wash performance: The term "improved wash performance" is defined herein as an enzyme displaying an increased wash performance in a detergent composition relative to the wash performance of same detergent composition without the enzyme e.g. by increased stain removal or less re-deposition. The term "improved wash performance" includes wash performance in laundry. The wash performance may be the same as "enzyme detergency benefit". The term "wash performance" is used as an enzyme's ability to remove stains present on the object to be cleaned during e.g. wash or hard surface cleaning. The improvement in the wash performance may be quantified by calculating the so-called intensity value (Int) defined in Example 18, herein or as ($\Delta L$) as described in example 5 and 7 herein. See also the wash performance test in Example 5, 6, 18 and 19 herein. The term "wash performance" and "dish wash performance" may be used interchangeably.

Laundering: The term "laundering" relates to both household laundering and industrial laundering and means the process of treating textiles with a solution containing a cleaning or detergent composition of the present invention. The laundering process can for example be carried out using e.g. a household or an industrial washing machine or can be carried out by hand.

Malodor: By the term "malodor" is meant an unpleasant odor, which is not desired on clean items. The cleaned item should smell fresh and clean without malodors adhered to the item. One example of malodor is compounds with an unpleasant smell, which may be produced by microorganisms. Another example is unpleasant smells can be sweat or body odor adhered to an item which has been in contact with human or animal. Another example of malodor can be the odor from spices, which sticks to items for example curry or other exotic spices which smells strongly.

Mature polypeptide: The term "mature polypeptide" means a polypeptide in its final form following translation and any post-translational modifications, such as N-terminal processing, C-terminal truncation, glycosylation, phosphorylation, etc. In some aspects, the mature polypeptide is amino acids 1 to 246 of SEQ ID NO 2 and amino acids −34 to −1 of SEQ ID NO 2 is a signal peptide. In one aspect, the mature polypeptide is shown in SEQ ID NO 3. In some aspects, the mature polypeptide is amino acids 1 to 243 of SEQ ID NO 5 and amino acids −34 to −1 of SEQ ID NO 5 is a signal peptide. In one aspect, the mature polypeptide is shown in SEQ ID NO 6. In one aspect, the mature polypeptide is shown in SEQ ID NO 6. In some aspects, the mature polypeptide is amino acids 1 to 237 of SEQ ID NO 8 and amino acids −37 to −1 of SEQ ID NO 8 is a signal peptide. In one aspect, the mature polypeptide is shown in SEQ ID NO 9. In some aspects, the mature polypeptide is amino acids 1 to 237 of SEQ ID NO 11 and amino acids-39 to −1 of SEQ ID NO 11 is a signal peptide. In one aspect, the mature polypeptide is shown in SEQ ID NO 12. In some aspects, the mature polypeptide is amino acids 1 to 274 of SEQ ID NO 14 and amino acids −22 to −1 of SEQ ID NO 14 is a signal peptide. In one aspect, the mature polypeptide is shown in SEQ ID NO 15. In some aspects, the mature polypeptide is amino acids 1 to 296 of SEQ ID NO 17 and amino acids −21 to −1 of SEQ ID NO 17 is a signal peptide. In one aspect, the mature polypeptide is shown in SEQ ID NO 18. In some aspects, the mature polypeptide is amino acids 1 to 237 of SEQ ID NO 20 and amino acids −27 to −1 of SEQ ID NO 20 is a signal peptide. In one aspect, the mature polypeptide is shown in SEQ ID NO 21. In some aspects, the mature polypeptide is amino acids 1 to 239 of SEQ ID NO 23 and amino acids −33 to −1 of SEQ ID NO 23 is a signal peptide. In one aspect, the mature polypeptide is shown in SEQ ID NO 24. In some aspects, the mature polypeptide is amino acids 1 to 264 of SEQ ID NO 26 and amino acids −23 to −1 of SEQ ID NO 26 is a signal peptide. In one aspect, the mature polypeptide is shown in SEQ ID NO 27. In some aspects, the mature polypeptide is amino acids 1 to 242 of SEQ ID NO 29 and amino acids −19 to −1 of SEQ ID NO 29 is a signal peptide. In one aspect, the mature polypeptide is shown in SEQ ID NO 30. In some aspects, the mature polypeptide is amino acids 1 to 238 of SEQ ID NO 32 and amino acids −38 to −1 of SEQ ID NO 32 is a signal peptide. In one aspect, the mature polypeptide is shown in SEQ ID NO 33. In some aspects, the mature polypeptide is amino acids 1 to 261 of SEQ ID NO 35 and amino acids −26 to −1 of SEQ ID NO 35 is a signal peptide. In one aspect, the mature polypeptide is shown in SEQ ID NO 36. In some aspects, the mature polypeptide is amino acids 1 to 265 of SEQ ID NO 38 and amino acids −25 to −1 of SEQ ID NO 38 is a signal peptide. In one aspect, the mature polypeptide is shown in SEQ ID NO 39. In some aspects, the mature polypeptide is amino acids 1 to 254 of SEQ ID NO 41 and amino acids −30 to −1 of SEQ ID NO 41 is a signal peptide. In one aspect, the mature polypeptide is shown in SEQ ID NO 42. In some aspects, the mature polypeptide is amino acids 1 to 268 of SEQ ID NO 44 and amino acids −31 to −1 of SEQ ID NO 44 is a signal peptide. In one aspect, the mature polypeptide is shown in SEQ ID NO 45. In some aspects, the mature polypeptide is amino acids 1 to 267 of SEQ ID NO 47 and amino acids −24 to −1 of SEQ ID NO 47 is a signal peptide. In one aspect, the mature polypeptide is shown in SEQ ID NO 48. In some aspects, the mature polypeptide is amino acids 1 to 251 of SEQ ID NO 50 and amino acids −36 to −1 of SEQ ID NO 50 is a signal peptide. In one aspect, the mature polypeptide is shown in SEQ ID NO 51. In some aspects, the mature polypeptide is amino acids 1 to 239 of SEQ ID NO 53 and amino acids −44 to −1 of SEQ ID NO 53 is a signal peptide. In one aspect, the mature polypeptide is shown in SEQ ID NO 54. In some aspects, the mature polypeptide is amino acids 1 to 279 of SEQ ID NO 56 and amino acids −18 to −1 of SEQ ID NO 56 is a signal peptide. In one aspect, the mature polypeptide is shown in SEQ ID NO 57.

It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide.

Mature polypeptide coding sequence: The term “mature polypeptide coding sequence” means a polynucleotide that encodes a mature polypeptide having activity. In one aspect, the mature polypeptide coding sequence is nucleotides 103 to 840 of SEQ ID NO 1 and nucleotides 1 to 102 of SEQ ID NO 1 encodes a signal peptide. In one aspect, the mature polypeptide coding sequence is nucleotides 103 to 831 of SEQ ID NO 4 and nucleotides 1 to 102 of SEQ ID NO 4 encodes a signal peptide. In one aspect, the mature polypeptide coding sequence is nucleotides 112 to 822 of SEQ ID NO 7 and nucleotides 1 to 111 of SEQ ID NO 7 encodes a signal peptide. In one aspect, the mature polypeptide coding sequence is nucleotides 118 to 828 of SEQ ID NO 10 and nucleotides 1 to 117 of SEQ ID NO 10 encodes a signal peptide. In one aspect, the mature polypeptide coding sequence is nucleotides 67 to 939 of SEQ ID NO 13 and nucleotides 1 to 66 of SEQ ID NO 13 encodes a signal peptide. In one aspect, the mature polypeptide coding sequence is nucleotides 112 to 1061 of SEQ ID NO 16 and nucleotides 1 to 111 of SEQ ID NO 16 encodes a signal peptide. In one aspect, the mature polypeptide coding sequence is nucleotides 82 to 792 of SEQ ID NO 19 and nucleotides 1 to 81 of SEQ ID NO 19 encodes a signal peptide. In one aspect, the mature polypeptide coding sequence is nucleotides 100 to 816 of SEQ ID NO 22 and nucleotides 1 to 99 of SEQ ID NO 22 encodes a signal peptide. In one aspect, the mature polypeptide coding sequence is nucleotides 70 to 861 of SEQ ID NO 25 and nucleotides 1 to 69 of SEQ ID NO 25 encodes a signal peptide. In one aspect, the mature polypeptide coding sequence is nucleotides 58 to 783 of SEQ ID NO 28 and nucleotides 1 to 57 of SEQ ID NO 28 encodes a signal peptide. In one aspect, the mature polypeptide coding sequence is nucleotides 115 to 828 of SEQ ID NO 31 and nucleotides 1 to 114 of SEQ ID NO 31 encodes a signal peptide. In one aspect, the mature polypeptide coding sequence is nucleotides 79 to 861 of SEQ ID NO 34 and nucleotides 1 to 78 of SEQ ID NO 34 encodes a signal peptide. In one aspect, the mature polypeptide coding sequence is nucleotides 76 to 870 of SEQ ID NO 37 and nucleotides 1 to 75 of SEQ ID NO 37 encodes a signal peptide. In one aspect, the mature polypeptide coding sequence is nucleotides 91 to 852 of SEQ ID NO 40 and nucleotides 1 to 90 of SEQ ID NO 40 encodes a signal peptide. In one aspect, the mature polypeptide coding sequence is nucleotides 94 to 897 of SEQ ID NO 43 and nucleotides 1 to 93 of SEQ ID NO 43 encodes a signal peptide. In one aspect, the mature polypeptide coding sequence is nucleotides 73 to 873 of SEQ ID NO 46 and nucleotides 1 to 72 of SEQ ID NO 46 encodes a signal peptide. In one aspect, the mature polypeptide coding sequence is nucleotides 109 to 861 of SEQ ID NO 49 and nucleotides 1 to 108 of SEQ ID NO 49 encodes a signal peptide. In one aspect, the mature polypeptide coding sequence is nucleotides 133 to 849 of SEQ ID NO 52 and nucleotides 1 to 132 of SEQ ID NO 52 encodes a signal peptide. In one aspect, the mature polypeptide coding sequence is nucleotides 55 to 1053 of SEQ ID NO 55 and nucleotides 1 to 54 of SEQ ID NO 55 encodes a signal peptide.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Nomenclature: For purposes of the present invention, the nomenclature [EQ] means that the amino acid at this position may be a glutamic acid (Glu, E) or a glutamine (Gln, Q). Likewise, the nomenclature [VGA] means that the amino acid at this position may be a valine (Val, V), glycine (Gly, G), alanine (Ala, A) or isoleucine (Ile, I), and so forth for other combinations as described herein. Unless otherwise limited further, the amino acid X is defined such that it may be any of the 20 natural amino acids.

Operably linked: The term "operably linked" means a configuration in which a control sequence is placed at an appropriate position relative to the coding sequence of a polynucleotide such that the control sequence directs expression of the coding sequence.

Sequence identity: The relatedness between two amino acid sequences or between two nucleotide sequences is described by the parameter "sequence identity". For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labelled "longest identity" (obtained using the—no brief option) is used as the percent identity and is calculated as follows:

(Identical Residues×100)/(Length of Alignment−Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labelled "longest identity" (obtained using the—no brief option) is used as the percent identity and is calculated as follows:

(Identical Deoxyribonucleotides×100)/(Length of Alignment−Total Number of Gaps in Alignment)

Variant: The term "variant" means a polypeptide having hydrolase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

Conventions for Designation of Homologues i.e. Variants of GH Glycosyl Hydrolases.

For purposes of the present invention, the polypeptide disclosed in SEQ ID NO 18 is used to determine the corresponding amino acid residue in another GH114 glycosyl hydrolase. The amino acid sequence of another GH114 glycosyl hydrolase is aligned with the polypeptide disclosed in SEQ ID NO 18, and based on the alignment, the amino acid position number corresponding to any amino acid residue in the polypeptide disclosed in SEQ ID NO 18 is determined using e.g. the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix.

Identification of the corresponding amino acid residue in another GH114 glycosyl hydrolase can be determined by an alignment of multiple polypeptide sequences using several computer programs including, but not limited to, MUSCLE (multiple sequence comparison by log-expectation; version 3.5 or later; Edgar, 2004, *Nucleic Acids Research* 32: 1792-1797), MAFFT (version 6.857 or later; Katoh and Kuma, 2002, *Nucleic Acids Research* 30: 3059-3066; Katoh et al., 2005, *Nucleic Acids Research* 33: 511-518; Katoh and Toh, 2007, *Bioinformatics* 23: 372-374; Katoh et al., 2009, *Methods in Molecular Biology* 537: 39-64; Katoh and Toh, 2010, *Bioinformatics* 26: 1899-1900), and EMBOSS EMMA employing ClustalW (1.83 or later; Thompson et al., 1994, *Nucleic Acids Research* 22: 4673-4680), using their respective default parameters.

When another enzyme has diverged from the polypeptide of SEQ ID NO: 18 such that traditional sequence-based comparison fails to detect their relationship (Lindahl and Elofsson, 2000, *J. Mol. Biol.* 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the polypeptide has one or more representatives in the protein structure databases. Programs such as GenTHREADER (Jones, 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example, the SCOP super families of proteins have been structurally aligned, and those alignments are accessible and downloadable. Two or more protein structures can be aligned using a variety of algorithms such as the distance alignment matrix (Holm and Sander, 1998, *Proteins* 33: 88-96) or combinatorial extension (Shindyalov and Bourne, 1998, *Protein Engineering* 11: 739-747), and implementation of these algorithms can additionally be utilized to query structure databases with a structure of interest in order to discover possible structural homologs (e.g., Holm and Park, 2000, *Bioinformatics* 16: 566-567).

As different amino acids may be present at a given position depending on the selected parent for the variants the amino acid positions are indicated with #1, #2, etc. in the definitions below. In describing the variants of the present invention, the nomenclature described below is adapted for ease of reference. The accepted IUPAC single letter or three letters amino acid abbreviations are employed.

Substitutions: For an amino acid substitution, the following nomenclature is used: Original amino acid, position, substituted amino acid. Accordingly, the substitution of valine at position #1 with alanine is designated as "Val $\#_1$Ala" or "V $\#_1$A". Multiple mutations are separated by addition marks ("+") or by commas (,), e.g., "Val $\#_1$Ala+ "Pro $\#_2$Gly" or V $\#_1$A, P $\#_2$G, representing substitutions at positions #1 and #2 of valine (V) and proline (P) with alanine (A) and glycine (G), respectively. If more than one amino acid may be substituted in a given position these are listed in brackets, such as [X] or {X}. Thus, if both Trp and Lys may be substituted instead of the amino acid occupying at position #1 this is indicated as X $\#_1$ {W, K}, X $\#_1$ [W, K] or X # [W/K], where the X indicate the amino acid residue present at the position of the parent GH114 glycosyl hydrolase e.g. such as a GH114 glycosyl hydrolase shown in SEQ ID NO: 18. In some cases, the variants may be represented as #1 {W, K} or X $\#_2$P indicating that the amino acids to be substituted vary depending on the parent. For convenience, as SEQ ID NO: 18 is used for numbering the substitutions and the amino acid in the corresponding position in SEQ ID NO: 18 is indicated, e.g. A64S. However, it will be clear to the skilled artisan that a GH114 glycosyl hydrolase variant comprising A64S is not limited to parent GH114 glycosyl hydrolase having alanine at a position corresponding to position 64 of SEQ ID NO: 18. In a parent GH114 glycosyl hydrolase having e.g. asparagine in position 64, the skilled person would translate the mutation specified as A64S to N64S. In the event the parent GH114 glycosyl hydrolase has serine in position 64, the skilled person would recognize that the parent GH114 glycosyl hydrolase is not changed at this position. The same applies for deletions and insertions described below.

Deletions: For an amino acid deletion, the following nomenclature is used: Original amino acid, position, *. Accordingly, the deletion of valine at position #1 is designated as "Val $\#_1$*" or "V $\#_1$*". Multiple deletions are separated by addition marks ("+") or commas, e.g., "Val $\#_1$*+Pro #2*" or "V $\#_1$*, P $\#_2$*".

Insertions: The insertion of an additional amino acid residue such as e.g. a lysine after Val $\#_1$ may be indicated by: Val $\#_1$ValLys or V $\#_1$VK. Alternatively, insertion of an additional amino acid residue such as lysine after V $\#_1$ may be indicated by: *#aK. When more than one amino acid residue is inserted, such as e.g. a Lys, and Gly after #1 this may be indicated as: Val $\#_1$ValLysGly or V $\#_1$VKG. In such cases, the inserted amino acid residue(s) may also be numbered by the addition of lower case letters to the position number of the amino acid residue preceding the inserted amino acid residue(s), in this example: *$\#_1$aK*$\#_1$bG.

Multiple alterations: Variants comprising multiple alterations are separated by addition marks ("+") or by commas (,), e.g., "Val $\#_1$Trp+Pro $\#_2$Gly" or "V $\#_1$W, P $\#_2$G" representing a substitution of valine and proline at positions #1 and #2 with tryptophan and glycine, respectively as described above.

Different alterations: Where different alterations can be introduced at a position, the different alterations may be separated by a comma, e.g., "Val $\#_1$Trp, Lys" or V $\#_1$W, K representing a substitution of valine at position #1 with tryptophan or lysine. Thus, "Val $\#_1$Trp, Lys+Pro $\#_2$Asp" designates the following variants: "Val $\#_1$Trp+Pro $\#_2$Asp", "Val $\#_1$Lys+Pro $\#_2$Asp" or V $\#_1$W, K+P $\#_2$D.

DETAILED DESCRIPTION OF THE INVENTION

Various enzymes are applied in cleaning processes each targeting specific types of soiling such as protein, starch and grease soiling. Enzymes are now standard ingredients in detergents for laundry and dish wash. The effectiveness of these commercial enzymes provides detergents which removes much of the soiling. However, organic matters such as EPS (extracellular polymeric substance) comprised in much biofilm constitute a challenging type of soiling due to the complex nature of such organic matters. None of the commercially available detergents effectively remove or reduce EPS related soiling. Biofilm is produced by a group of microorganisms in which cells stick to each other or stick to a surface, such as a textile, dishware or hard surface or another kind of surface. These adherent cells are frequently embedded within a self-produced matrix of extracellular polymeric substance (EPS), which constitute 50% to 90% of the biofilm's total organic matter. EPS is mostly composed of polysaccharides (exopolysaccharides) and proteins, but include other macro-molecules such as DNA, lipids and human substances. EPS is the construction material of bacterial settlements and either remain attached to the cell's outer surface or is secreted into its growth medium. EPS is required for the development and integrity of biofilms produced by a wide variety of bacteria. The inventors have shown that the GH114 polypeptides comprising the GH114 glycosyl hydrolase domain have hydrolytic activity to EPS components e.g. PEL and thus having the potential to reduce or remove components of EPS and thus reduce or remove EPS and biofilm related soiling e.g. pel of e.g. textiles. It is well known that polypeptides deriving from organisms may share common structural elements, which can be identified by comparing the primary structures e.g. amino acid sequences and grouping the polypeptides according to sequence homology. However, common structural elements may also be identified by comparing the three-dimensional (3D) structure of various polypeptides. Both approaches have been applied in the present invention.

The polypeptides of the invention comprise a domain termed GH114 as defined in CAZY (GH114, Glycoside Hydrolase Family 114, CAZy database, www.cazy.org, Lombard V, et al. 2014, Nucleic Acids Res 42: D490-D495). The polypeptides of the present invention comprise the GH114 domain and several motifs. One example is [VL]XE[EDSQ]C (SEQ ID NO 60) situated in positions 182 to 186 in *Amycolatopsis circi* (SEQ ID NO 3). Another motif which may be comprised by the polypeptides of the invention is CY[FLIV][SDN][ATVG] (SEQ ID NO 61) situated in positions corresponding to positions 55 to 59 in *Amycolatopsis circi* (SEQ ID NO 3). The polypeptides in GH114 can be separated into distinct sub-clusters, where we denoted one sub-cluster comprising the motif [VLI]XE[EDSQ]C (SEQ ID NO 60) as clade or family VAE. Another motif characteristic of this clade is CY[FLIV][SDN][ATVG] (SEQ ID NO 61).

One embodiment of the invention relates a glycosyl hydrolase, preferably a GH114 glycosyl hydrolase polypeptide, preferably comprising the motif [VLI]XE[EDSQ]C (SEQ ID NO 60) and/or the motif CY[FLIV][SDN][ATVG] (SEQ ID NO 61), wherein the polypeptide has hydrolytic activity, and wherein the polypeptide is selected from the group consisting of:

(a) a polypeptide having at least 60%, at least 70%, at least 75%, at least 80%, at least 85%, at least 90%, at least 95%, at least 96%, at least 97%, at least 98%, at least 99% or 100% sequence identity to the polypeptide shown in SEQ ID NO 3;
(b) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 6;
(c) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 9;
(d) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 12;
(e) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 15;
(f) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 18;
(g) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 21;
(h) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 24;
(i) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 27;
(j) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 30;
(k) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 33;
(l) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 36;
(m) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 39;
(n) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 42;
(o) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 45;
(p) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 48;
(q) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 51;
(r) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 54; and
(s) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 57.

One preferred embodiment relates to a GH114 glycosyl hydrolase comprising the motif [VLI]XE[EDSQ]C (SEQ ID NO 60) and/or the motif CY[FLIV][SDN][ATVG] (SEQ ID NO 61), wherein the GH114 glycosyl hydrolase is selected from the group consisting of:

(a) a polypeptide having at least 90%, at least 95%, at least 96%, at least 97%, at least 98%, at least 99% or 100% sequence identity to the polypeptide shown in SEQ ID NO 3;
(b) a polypeptide having at least 90%, at least 95%, at least 96%, at least 97%, at least 98%, at least 99% or 100% sequence identity to the polypeptide shown in SEQ ID NO 6;
(c) a polypeptide having at least 85%, at least 90%, at least 95%, at least 96%, at least 97%, at least 98%, at least 99% or 100% sequence identity to the polypeptide shown in SEQ ID NO 9;
(d) a polypeptide having at least 85%, at least 90%, at least 95%, at least 96%, at least 97%, at least 98%, at least 99% or 100% sequence identity to the polypeptide shown in SEQ ID NO 12;
(e) a polypeptide having at least 75%, at least 80%, at least 85%, at least 90%, at least 95%, at least 96%, at least 97%, at least 98%, at least 99% or 100% sequence identity to the polypeptide shown in SEQ ID NO 21;
(f) a polypeptide having at least 90%, at least 95%, at least 96%, at least 97%, at least 98%, at least 99% or 100% sequence identity to the polypeptide shown in SEQ ID NO 24;

(g) a polypeptide having at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 27;

(h) a polypeptide having, at least 50% at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 30;

(i) a polypeptide having at least 70%, at least 75%, at least 80%, at least 85%, at least 90%, at least 95%, at least 96%, at least 97%, at least 98%, at least 99% or 100% sequence identity to the polypeptide shown in SEQ ID NO 33;

(j) a polypeptide having at least 75%, at least 80%, at least 85%, at least 90%, at least 95%, at least 96%, at least 97%, at least 98%, at least 99% or 100% sequence identity to the polypeptide shown in SEQ ID NO 36;

(k) a polypeptide having at least 99% or 100% sequence identity to the polypeptide shown in SEQ ID NO 39;

(l) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 42;

(m) a polypeptide having at least 85%, at least 90%, at least 95%, at least 96%, at least 97%, at least 98%, at least 99% or 100% sequence identity to the polypeptide shown in SEQ ID NO 45;

(n) a polypeptide having at least 70%, at least 75%, at least 80%, at least 85%, at least 90%, at least 95%, at least 96%, at least 97%, at least 98%, at least 99% or 100% sequence identity to the polypeptide shown in SEQ ID NO 48;

(o) a polypeptide having at least 98%, at least 99% or 100% sequence identity to the polypeptide shown in SEQ ID NO 51;

(p) a polypeptide having at least 80%, at least 85%, at least 90%, at least 95%, at least 96%, at least 97%, at least 98%, at least 99% or 100% sequence identity to the polypeptide shown in SEQ ID NO 54; and (q) a polypeptide having at least 85%, at least 90%, at least 95%, at least 96%, at least 97%, at least 98%, at least 99% or 100% sequence identity to the polypeptide shown in SEQ ID NO 57.

The VAE clade has been identified as a specific group of GH114 glycosyl hydrolases, which has particularly high substrate activity and which are particularly active e.g. in deep cleaning, malodor, biofilm, EPS or pel reduction or removal compared to other GH114 glycosyl hydrolases. Preferably the VAE clade GH114 glycosyl hydrolases have superior wash performance compared to other GH114 glycosyl hydrolases not comprised in the clade i.e. not have the two motifs set forth in SEQ ID NO 60 and SEQ ID NO 61. The clade comprises the motif [VLI]XE[EDSQ]C (SEQ ID NO 60), where the glutamic acid residue (E) at position 184 in SEQ ID NO 3 is fully conserved in the clade, and one of the two catalytic residues. The clade also comprises motif CY[FLIV][SDN][ATVG] (SEQ ID NO 61), where the tyrosine (Y) at position 56 in SEQ ID NO 3 is fully conserved in the clade and involved in substrate binding. The VAE-clade GH114 glycosyl hydrolases have wash performance i.e. capable of removing e.g. pel stains under wash conditions e.g. in a laundry detergent. The VAE-clade GH114 glycosyl hydrolases have wash performance and are stable in cleaning compositions e.g. in a laundry detergent.

One embodiment of the invention relates a glycosyl hydrolase, preferably a GH114 glycosyl hydrolase, preferably comprising the motif [VLI]XE[EDSQ]C (SEQ ID NO 60) and/or the motif CY[FLIV][SDN][ATVG] (SEQ ID NO 61), wherein the GH114 glycosyl hydrolase has hydrolytic activity, and wherein the GH114 glycosyl hydrolase comprises an amino acid sequence selected from the group consisting of amino acid sequences having at least 60%, at least 70%, at least 75%, at least 80%, at least 85%, at least 90%, at least 95%, at least 96%, at least 97%, at least 98%, at least 99% or 100% sequence identity to the polypeptide shown in SEQ ID NO 72, SEQ ID NO 73, SEQ ID NO 74, SEQ ID NO 75, SEQ ID NO 76, SEQ ID NO 77, SEQ ID NO 78, SEQ ID NO 79, SEQ ID NO 80, SEQ ID NO 81, SEQ ID NO 82, SEQ ID NO 83, SEQ ID NO 84, SEQ ID NO 85, SEQ ID NO 86, SEQ ID NO 87, SEQ ID NO 88, SEQ ID NO 89, SEQ ID NO 90, SEQ ID NO 91, SEQ ID NO 92, SEQ ID NO 93, SEQ ID NO 94, SEQ ID NO 95, SEQ ID NO 96, SEQ ID NO 97, SEQ ID NO 98, SEQ ID NO 99, SEQ ID NO 100, SEQ ID NO 101, SEQ ID NO 102, SEQ ID NO 103, SEQ ID NO 104, SEQ ID NO 105, SEQ ID NO 106, SEQ ID NO 107, SEQ ID NO 108, SEQ ID NO 109, SEQ ID NO 110, SEQ ID NO 111, SEQ ID NO 112, SEQ ID NO 113, SEQ ID NO 114, SEQ ID NO 115, SEQ ID NO 116, SEQ ID NO 117, SEQ ID NO 118, SEQ ID NO 119, SEQ ID NO 120, SEQ ID NO 121, SEQ ID NO 122, SEQ ID NO 123, SEQ ID NO 124, SEQ ID NO 125, SEQ ID NO 126, SEQ ID NO 127, SEQ ID NO 128, SEQ ID NO 129, SEQ ID NO 130, SEQ ID NO 131, SEQ ID NO 132, SEQ ED NO: 133, SEQ ID NO 134, SEQ ID NO 135, SEQ ID NO 136, SEQ ID NO 137, SEQ ID NO 138, SEQ ID NO 139, SEQ ID NO 140, SEQ ID NO 141, SEQ ID NO 142, SEQ ID NO 143, SEQ ID NO 144, SEQ ID NO 145 and SEQ ID NO 146.

One embodiment of the invention relates a glycosyl hydrolase, preferably a GH114 glycosyl hydrolase, preferably comprising the motif [VLI]XE[EDSQ]C (SEQ ID NO 60) and/or the motif CY[FLIV][SDN][ATVG] (SEQ ID NO 61), wherein the GH114 glycosyl hydrolase has hydrolytic activity, and wherein the GH114 glycosyl hydrolase comprises an amino acid sequence selected from the group consisting of amino acid sequences having at least 70% sequence identity to the polypeptide shown in SEQ ID NO 72, SEQ ID NO 73, SEQ ID NO 74, SEQ ID NO 75, SEQ ID NO 76, SEQ ID NO 77, SEQ ID NO 78, SEQ ID NO 79, SEQ ID NO 80, SEQ ID NO 81, SEQ ID NO 82, SEQ ID NO 83, SEQ ID NO 84, SEQ ID NO 85, SEQ ID NO 86, SEQ ID NO 87, SEQ ID NO 88, SEQ ID NO 89, SEQ ID NO 90, SEQ ID NO 91, SEQ ID NO 92, SEQ ID NO 93, SEQ ID NO 94, SEQ ID NO 95, SEQ ID NO 96, SEQ ID NO 97, SEQ ID NO 98, SEQ ID NO 99, SEQ ID NO 100, SEQ ID NO 101, SEQ ID NO 102, SEQ ID NO 103, SEQ ID NO 104, SEQ ID NO 105, SEQ ID NO 106, SEQ ID NO 107, SEQ ID NO 108, SEQ ID NO 109, SEQ ID NO 110, SEQ ID NO 111, SEQ ID NO 112, SEQ ID NO 113, SEQ ID NO 114, SEQ ID NO 115, SEQ ID NO 116, SEQ ID NO 117, SEQ ID NO 118, SEQ ID NO 119, SEQ ID NO 120, SEQ ID NO 121, SEQ ID NO 122, SEQ ID NO 123, SEQ ID NO 124, SEQ ID NO 125, SEQ ID NO 126, SEQ ID NO 127, SEQ ID NO 128, SEQ ID NO 129, SEQ ID NO 130, SEQ ID NO 131, SEQ ID NO 132, SEQ ID NO: 133, SEQ ID NO 134, SEQ ID NO 135, SEQ ID NO 136, SEQ ID NO 137, SEQ ID NO 138, SEQ ID NO 139, SEQ ID NO 140, SEQ ID NO 141, SEQ ID NO 142, SEQ ID NO 143, SEQ ID NO 144, SEQ ID NO 145 and SEQ ID NO 146.

One embodiment of the invention relates a glycosyl hydrolase, preferably a GH114 glycosyl hydrolase, preferably comprising the motif [VLI]XE[EDSQ]C (SEQ ID NO 60) and/or the motif CY[FLIV][SDN][ATVG] (SEQ ID NO 61), wherein the GH114 glycosyl hydrolase has hydrolytic activity, and wherein the GH114 glycosyl hydrolase comprises an amino acid sequence selected from the group consisting of amino acid sequences having at least 80% sequence identity to the polypeptide shown in SEQ ID NO 72, SEQ ID NO 73, SEQ ID NO 74, SEQ ID NO 75, SEQ ID NO 76, SEQ ID NO 77, SEQ ID NO 78, SEQ ID NO 79, SEQ ID NO 80, SEQ ID NO 81, SEQ ID NO 82, SEQ ID NO 83, SEQ ID NO 84, SEQ ID NO 85, SEQ ID NO 86, SEQ ID NO 87, SEQ ID NO 88, SEQ ID NO 89, SEQ ID NO 90, SEQ ID NO 91, SEQ ID NO 92, SEQ ID NO 93, SEQ ID NO 94, SEQ ID NO 95, SEQ ID NO 96, SEQ ID NO 97, SEQ ID NO 98, SEQ ID NO 99, SEQ ID NO 100, SEQ ID NO 101, SEQ ID NO 102, SEQ ID NO 103, SEQ ID NO 104, SEQ ID NO 105, SEQ ID NO 106, SEQ ID NO 107, SEQ ID NO 108, SEQ ID NO 109, SEQ ID NO 110, SEQ ID NO 111, SEQ ID NO 112, SEQ ID NO 113, SEQ ID NO 114, SEQ ID NO 115, SEQ ID NO 116, SEQ ID NO 117, SEQ ID NO 118, SEQ ID NO 119, SEQ ID NO 120, SEQ ID NO 121, SEQ ID NO 122, SEQ ID NO 123, SEQ ID NO 124, SEQ ID NO 125, SEQ ID NO 126, SEQ ID NO 127, SEQ ID NO 128, SEQ ID NO 129, SEQ ID NO 130, SEQ ID NO 131, SEQ ID NO 132, SEQ ID NO: 133, SEQ ID NO 134, SEQ ID NO 135, SEQ ID NO 136, SEQ ID NO 137, SEQ ID NO 138, SEQ ID NO 139, SEQ ID NO 140, SEQ ID NO 141, SEQ ID NO 142, SEQ ID NO 143, SEQ ID NO 144, SEQ ID NO 145 and SEQ ID NO 146.

One embodiment of the invention relates a glycosyl hydrolase, preferably a GH114 glycosyl hydrolase, preferably comprising the motif [VLI]XE[EDSQ]C (SEQ ID NO 60) and/or the motif CY[FLIV][SDN][ATVG] (SEQ ID NO 61), wherein the GH114 glycosyl hydrolase has hydrolytic activity, and wherein the GH114 glycosyl hydrolase comprises an amino acid sequence selected from the group consisting of amino acid sequences having at least 90% sequence identity to the polypeptide shown in SEQ ID NO 72, SEQ ID NO 73, SEQ ID NO 74, SEQ ID NO 75, SEQ ID NO 76, SEQ ID NO 77, SEQ ID NO 78, SEQ ID NO 79, SEQ ID NO 80, SEQ ID NO 81, SEQ ID NO 82, SEQ ID NO 83, SEQ ID NO 84, SEQ ID NO 85, SEQ ID NO 86, SEQ ID NO 87, SEQ ID NO 88, SEQ ID NO 89, SEQ ID NO 90, SEQ ID NO 91, SEQ ID NO 92, SEQ ID NO 93, SEQ ID NO 94, SEQ ID NO 95, SEQ ID NO 96, SEQ ID NO 97, SEQ ID NO 98, SEQ ID NO 99, SEQ ID NO 100, SEQ ID NO 101, SEQ ID NO 102, SEQ ID NO 103, SEQ ID NO 104, SEQ ID NO 105, SEQ ID NO 106, SEQ ID NO 107, SEQ ID NO 108, SEQ ID NO 109, SEQ ID NO 110, SEQ ID NO 111, SEQ ID NO 112, SEQ ID NO 113, SEQ ID NO 114, SEQ ID NO 115, SEQ ID NO 116, SEQ ID NO 117, SEQ ID NO 118, SEQ ID NO 119, SEQ ID NO 120, SEQ ID NO 121, SEQ ID NO 122, SEQ ID NO 123, SEQ ID NO 124, SEQ ID NO 125, SEQ ID NO 126, SEQ ID NO 127, SEQ ID NO 128, SEQ ID NO 129, SEQ ID NO 130, SEQ ID NO 131, SEQ ID NO 132, SEQ ID NO: 133, SEQ ID NO 134, SEQ ID NO 135, SEQ ID NO 136, SEQ ID NO 137, SEQ ID NO 138, SEQ ID NO 139, SEQ ID NO 140, SEQ ID NO 141, SEQ ID NO 142, SEQ ID NO 143, SEQ ID NO 144, SEQ ID NO 145 and SEQ ID NO 146.

The polypeptides of the invention preferably belong to the cluster VAE, which comprises the a glycosyl hydrolytic domain GH114 and have hydrolytic activity.

The polypeptides of the VAE clade includes all GH114 glycosyl hydrolases comprising the amino acids sequence shown in SEQ ID NO 3, SEQ ID NO 6, SEQ ID NO 9, SEQ ID NO 12, SEQ ID NO 15, SEQ ID NO 18, SEQ ID NO 21, SEQ ID NO 24, SEQ ID NO 27, SEQ ID NO 30, SEQ ID NO 33, SEQ ID NO 36, SEQ ID NO 39, SEQ ID NO 42, SEQ ID NO 45, SEQ ID NO 48, SEQ ID NO 51, SEQ ID NO 54, SEQ ID NO 57, SEQ ID NO 72, SEQ ID NO 73, SEQ ID NO 74, SEQ ID NO 75, SEQ ID NO 76, SEQ ID NO 77, SEQ ID NO 78, SEQ ID NO 79, SEQ ID NO 80, SEQ ID NO 81, SEQ ID NO 82, SEQ ID NO 83, SEQ ID NO 84, SEQ ID NO 85, SEQ ID NO 86, SEQ ID NO 87, SEQ ID NO 88, SEQ ID NO 89, SEQ ID NO 90, SEQ ID NO 91, SEQ ID NO 92, SEQ ID NO 93, SEQ ID NO 94, SEQ ID NO 95, SEQ ID NO 96, SEQ ID NO 97, SEQ ID NO 98, SEQ ID NO 99, SEQ ID NO 100, SEQ ID NO 101, SEQ ID NO 102, SEQ ID NO 103, SEQ ID NO 104, SEQ ID NO 105, SEQ ID NO 106, SEQ ID NO 107, SEQ ID NO 108, SEQ ID NO 109, SEQ ID NO 110, SEQ ID NO 111, SEQ ID NO 112, SEQ ID NO 113, SEQ ID NO 114, SEQ ID NO 115, SEQ ID NO 116, SEQ ID NO 117, SEQ ID NO 118, SEQ ID NO 119, SEQ ID NO 120, SEQ ID NO 121, SEQ ID NO 122, SEQ ID NO 123, SEQ ID NO 124, SEQ ID NO 125, SEQ ID NO 126, SEQ ID NO 127, SEQ ID NO 128, SEQ ID NO 129, SEQ ID NO 130, SEQ ID NO 131, SEQ ID NO 132, SEQ ID NO: 133, SEQ ID NO 134, SEQ ID NO 135, SEQ ID NO 136, SEQ ID NO 137, SEQ ID NO 138, SEQ ID NO 139, SEQ ID NO 140, SEQ ID NO 141, SEQ ID NO 142, SEQ ID NO 143, SEQ ID NO 144, SEQ ID NO 145 or SEQ ID NO 146. The VAE-clade (or polypeptides of the VAE-clade) may be divided in further clades or sub-clades (see FIG. 1 and FIG. 4), which again may be divided into further sub-clades, see below.

These sub-clades are termed DYQ, AEE, WQW, IEY, ICY and DFAVL clades and comprises polypeptides having hydrolase activity, wherein the polypeptides comprise a GH114 domain and may belong to the VAE clade.

The polypeptides of the DYQ clade comprise the motif DYQ[LI]G (SEQ ID NO 62), corresponding to amino acids DYQIG at positions 23 to 27 in SEQ ID NO 3, where D at position 23 is fully conserved in the polypeptides of this clade. An additional motif of the DYQ clade is FQ[TAV]Q[PSD] (SEQ ID NO 63), corresponding to amino acid 60 to 64 in the reference polypeptide (SEQ ID NO 3). Examples of polypeptides of the DYQ clade includes SEQ ID NO 3, SEQ ID NO 6, SEQ ID NO 9, SEQ ID NO 12, SEQ ID NO 21, SEQ ID NO 24, SEQ ID NO 39, SEQ ID NO 42, SEQ ID NO 45, SEQ ID NO 48, SEQ ID NO 51, and SEQ ID NO 54 as well as the homologue sequences SEQ ID NO 79, SEQ ID NO 82, SEQ ID NO 83, SEQ ID NO 84, SEQ ID NO 85, SEQ ID NO 86, SEQ ID NO 87, SEQ ID NO 88, SEQ ID NO 90, SEQ ID NO 91, SEQ ID NO 92, SEQ ID NO 93, SEQ ID NO 94, SEQ ID NO 96, SEQ ID NO 131, SEQ ID NO 132, SEQ ID NO 134, SEQ ID NO 136, SEQ ID NO 137, SEQ ID NO 138, SEQ ID NO 139, SEQ ID NO 140, SEQ ID NO 141, SEQ ID NO 142, SEQ ID NO 143, SEQ ID NO 144 and SEQ ID NO 145.

One embodiment of the invention relates a glycosyl hydrolase preferably a GH114 glycosyl hydrolase comprising the motif(s) DYQ[LI]G (SEQ ID NO 62) and/or FQ[TAV]Q[PSD](SEQ ID NO 63), wherein the glycosyl hydrolase is selected from the group consisting of:

(a) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 3;

(b) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 6;

(c) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 9;

(d) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 12;

(e) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 21;

(f) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 24;

(g) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 39;

(h) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 42;

(i) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 45;

(j) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 48;

(k) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 51; and (l) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 54.

One preferred embodiment relates to a glycosyl hydrolase, preferably a GH114 glycosyl hydrolase comprising the motif(s) DYQ[LI]G (SEQ ID NO 62) and/or FQ[TAV]Q[PSD] (SEQ ID NO 63), wherein the glycosyl hydrolase is selected from the group consisting:

(a) a polypeptide having at least 90%, at least 95%, at least 96%, at least 97%, at least 98%, at least 99% or 100% sequence identity to the polypeptide shown in SEQ ID NO 3;

(b) a polypeptide having at least 90%, at least 95%, at least 96%, at least 97%, at least 98%, at least 99% or 100% sequence identity to the polypeptide shown in SEQ ID NO 6;

(c) a polypeptide having at least 85%, at least 90%, at least 95%, at least 96%, at least 97%, at least 98%, at least 99% or 100% sequence identity to the polypeptide shown in SEQ ID NO 9;

(d) a polypeptide having at least 85%, at least 90%, at least 95%, at least 96%, at least 97%, at least 98%, at least 99% or 100% sequence identity to the polypeptide shown in SEQ ID NO 12;

(e) a polypeptide having at least 75%, at least 80%, at least 85%, at least 90%, at least 95%, at least 96%, at least 97%, at least 98%, at least 99% or 100% sequence identity to the polypeptide shown in SEQ ID NO 21;

(f) a polypeptide having at least 90%, at least 95%, at least 96%, at least 97%, at least 98%, at least 99% or 100% sequence identity to the polypeptide shown in SEQ ID NO 24;

(g) a polypeptide having at least 99% or 100% sequence identity to the polypeptide shown in SEQ ID NO 39;

(h) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 42;

(i) a polypeptide having at least 85%, at least 90%, at least 95%, at least 96%, at least 97%, at least 98%, at least 99% or 100% sequence identity to the polypeptide shown in SEQ ID NO 45;

(j) a polypeptide having at least 70%, at least 75%, at least 80%, at least 85%, at least 90%, at least 95%, at least 96%, at least 97%, at least 98%, at least 99% or 100% sequence identity to the polypeptide shown in SEQ ID NO 48;

(k) a polypeptide having at least 98%, at least 99% or 100% sequence identity to the polypeptide shown in SEQ ID NO 51; and (l) a polypeptide having at least 80%, at least 85%, at least 90%, at least 95%, at least 96%, at least 97%, at least 98%, at least 99% or 100% sequence identity to the polypeptide shown in SEQ ID NO 54.

One embodiment of the invention relates a glycosyl hydrolase preferably a GH114 glycosyl hydrolase comprising the motif(s) DYQ[LI]G (SEQ ID NO 62) and/or FQ[TAV]Q[PSD](SEQ ID NO 63), wherein the glycosyl hydrolase is selected from the group consisting of: a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 79, SEQ ID NO 82, SEQ ID NO 83, SEQ ID NO 84, SEQ ID NO 85, SEQ ID NO 86, SEQ ID NO 87, SEQ ID NO 88, SEQ ID NO 90, SEQ ID NO 91, SEQ ID NO 92, SEQ ID NO 93, SEQ ID NO 94, SEQ ID NO 96, SEQ ID NO 131, SEQ ID NO 132, SEQ ID NO 134, SEQ ID NO 136, SEQ ID NO 137, SEQ ID NO 138, SEQ ID NO 139, SEQ ID NO 140, SEQ ID NO 141, SEQ ID NO 142, SEQ ID NO 143, SEQ ID NO 144 and SEQ ID NO 145. The glycine G in motif DYQ[LI]G (SEQ ID NO 62) is involved in substrate binding, and fully conserved in the clade.

One embodiment of the invention relates a glycosyl hydrolase preferably a GH114 glycosyl hydrolase comprising the motif(s) DYQ[LI]G (SEQ ID NO 62) and/or FQ[TAV]Q[PSD](SEQ ID NO 63), wherein the glycosyl hydrolase is selected from the group consisting of: a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 3, SEQ ID NO 6, SEQ ID NO 9, SEQ ID NO 12, SEQ ID NO 21, SEQ ID NO 24, SEQ ID NO 39, SEQ ID NO 42, SEQ ID NO 45, SEQ ID NO 48, SEQ ID NO 51, SEQ ID NO 54, SEQ ID NO 79, SEQ ID NO 82, SEQ ID NO 83, SEQ ID NO 84, SEQ ID NO 85, SEQ ID NO 86, SEQ ID NO 87, SEQ ID NO 88, SEQ ID NO 90, SEQ ID NO 91, SEQ ID NO 92, SEQ ID NO 93, SEQ ID NO 94, SEQ ID NO 96, SEQ ID NO 131, SEQ ID NO 132, SEQ ID NO 134, SEQ ID NO 136, SEQ ID NO 137, SEQ ID NO 138, SEQ ID NO 139, SEQ ID NO 140, SEQ ID NO 141, SEQ ID NO 142, SEQ ID NO 143, SEQ ID NO 144 and SEQ ID NO 145.

The DYQ sub-clade may be further be divided into yet another subgroup, which here is termed AEE clade (se FIG. 1 or 4). The AEE clade comprises polypeptides of bacterial origin having hydrolase activity, wherein the polypeptides comprise a GH114 domain and belong to the VAE part 2 clade (and the DYQ-clade). The polypeptides of the clade comprise the motif example AEECG (SEQ ID NO 64), corresponding to amino acids AEECG at positions 183 to 187 of SEQ ID NO 3 where all amino acids are fully conserved in AEE clade. An additional motif of the AEE clade is NAFQ[AT]Q (SEQ ID NO 65), corresponding to amino acid 58 to 63 in the reference polypeptide (SEQ ID NO 3). Examples of polypeptides of the AEE clade includes SEQ ID NO 3, SEQ ID NO 6, SEQ ID NO 9, SEQ ID NO 12, SEQ ID NO 21, SEQ ID NO 24, and SEQ ID NO 54 as well as the homologue sequences SEQ ID NO 79, SEQ ID NO 82, SEQ ID NO 83, SEQ ID NO 84, SEQ ID NO 85, SEQ ID NO 132, SEQ ID NO 136, SEQ ID NO 138 and SEQ ID NO 142.

One embodiment of the invention relates a glycosyl hydrolase, preferably a GH114 glycosyl hydrolase comprising one, two, three or all four motif(s) DYQ[LI]G (SEQ ID NO 62), FQ[TAV]Q[PSD] (SEQ ID NO 63), AEECG (SEQ ID NO 64) and/or NAFQ[AT]Q (SEQ ID NO 65), wherein the glycosyl hydrolase is selected from the group consisting of:

(a) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 3;

(b) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 6;

(c) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 9;

(d) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 12;

(e) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 21;

(f) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 24; and (g) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 54.

One preferred embodiment of the invention relates a GH114 glycosyl hydrolase, comprising one, two, three or all four motif(s) DYQ[LI]G (SEQ ID NO 62), FQ[TAV]Q[PSD] (SEQ ID NO 63), AEECG (SEQ ID NO 64) and/or NAFQ[AT]Q (SEQ ID NO 65), wherein the glycosyl hydrolase is selected from the group consisting of:

(a) a polypeptide having at least 90%, at least 95%, at least 96%, at least 97%, at least 98%, at least 99% or 100% sequence identity to the polypeptide shown in SEQ ID NO 3;

(b) a polypeptide having at least 90%, at least 95%, at least 96%, at least 97%, at least 98%, at least 99% or 100% sequence identity to the polypeptide shown in SEQ ID NO 6;

(c) a polypeptide having at least 85%, at least 90%, at least 95%, at least 96%, at least 97%, at least 98%, at least 99% or 100% sequence identity to the polypeptide shown in SEQ ID NO 9;

(d) a polypeptide having at least 85%, at least 90%, at least 95%, at least 96%, at least 97%, at least 98%, at least 99% or 100% sequence identity to the polypeptide shown in SEQ ID NO 12;

(e) a polypeptide having at least 75%, at least 80%, at least 85%, at least 90%, at least 95%, at least 96%, at least 97%, at least 98%, at least 99% or 100% sequence identity to the polypeptide shown in SEQ ID NO 21;

(f) a polypeptide having at least 90%, at least 95%, at least 96%, at least 97%, at least 98%, at least 99% or 100% sequence identity to the polypeptide shown in SEQ ID NO 24;

(g) a polypeptide having at least 80%, at least 85%, at least 90%, at least 95%, at least 96%, at least 97%, at least 98%, at least 99% or 100% sequence identity to the polypeptide shown in SEQ ID NO 54.

One embodiment of the invention relates a glycosyl hydrolase, preferably a GH114 glycosyl hydrolase comprising one, to, three or all four motif(s) DYQ[LI]G (SEQ ID NO 62), FQ[TAV]Q[PSD] (SEQ ID NO 63), AEECG (SEQ ID NO 64) and/or NAFQ[AT]Q (SEQ ID NO 65), wherein the glycosyl hydrolase is selected from the group consisting of: a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 79, SEQ ID NO 82, SEQ ID NO 83, SEQ ID NO 84, SEQ ID NO 85, SEQ ID NO 132, SEQ ID NO 136, SEQ ID NO 138, and SEQ ID NO 142.

One embodiment of the invention relates a glycosyl hydrolase, preferably a GH114 glycosyl hydrolase comprising one, to, three or all four motif(s) DYQ[LI]G (SEQ ID NO 62), FQ[TAV]Q[PSD] (SEQ ID NO 63), AEECG (SEQ ID NO 64) and/or NAFQ[AT]Q (SEQ ID NO 65), wherein the glycosyl hydrolase is selected from the group consisting of: a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 3, SEQ ID NO 6, SEQ ID NO 9, SEQ ID NO 12, SEQ ID NO 21, SEQ ID NO 24, SEQ ID NO 54, SEQ ID NO 79, SEQ ID NO 82, SEQ ID NO 83, SEQ ID NO 84, SEQ ID NO 85, SEQ ID NO 132, SEQ ID NO 136, SEQ ID NO 138, and SEQ ID NO 142.

Another sub-clade of the VAE clade is the IEY clade. The IEY clade comprises polypeptides of fungal origin, containing a GH114 domain and belong to the VAE clade. The polypeptides of the clade comprise the motif GXXVX[NHQTS]IEY[PG] (SEQ ID NO 68), corresponding to amino acids "GKPVLQIEYP", positions 230 to 239 of SEQ ID NO 18 where E (corresponding to position 237 of SEQ ID NO 3) is fully conserved in IEY clade, part of the substrate binding pocket, and one of the two putative catalytic site residues. An additional motif of the IEY clade is VICYF (SEQ ID NO 69), corresponding to amino acids VICYF positions 68 to 72 of (SEQ ID NO 18), 27 where CYF (corresponding to positions 70 and 72 of SEQ ID NO 18) is fully conserved in IEY clade.

Examples of polypeptides of the IEY clade includes SEQ ID NO 15, SEQ ID NO 18, and, SEQ ID NO 57 as well as the homologue sequences SEQ ID NO 72, SEQ ID NO 73, SEQ ID NO 74, SEQ ID NO 75, SEQ ID NO 76, SEQ ID NO 77, SEQ ID NO 78, SEQ ID NO 97, SEQ ID NO 98, SEQ ID NO 99, SEQ ID NO 100, SEQ ID NO 101, SEQ ID NO 102, SEQ ID NO 103, SEQ ID NO 104, SEQ ID NO 105, SEQ ID NO 106, SEQ ID NO 107, SEQ ID NO 108, SEQ ID NO 109, SEQ ID NO 110, SEQ ID NO 111, SEQ ID NO 112, SEQ ID NO 113, SEQ ID NO 114, SEQ ID NO 115, SEQ ID NO 116, SEQ ID NO 117, SEQ ID NO 118, SEQ ID NO 119, SEQ ID NO 120, SEQ ID NO 121, SEQ ID NO 122, SEQ ID NO 123, SEQ ID NO 124, SEQ ID NO 125, SEQ ID NO 126, SEQ ID NO 127, SEQ ID NO 128, SEQ ID NO 129, SEQ ID NO 130, SEQ ID NO: 133 and SEQ ID NO 135.

One embodiment of the invention relates a glycosyl hydrolase preferably a GH114 glycosyl hydrolase comprising the motif GXXVX[NHQTS]IEY[PG] (SEQ ID NO 68) and/or the motif VICYF (SEQ ID NO 69), wherein the glycosyl hydrolase is selected from the group consisting of:

(a) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 15;

(b) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 18; and (c) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 57.

One preferred embodiment of the invention relates a GH114 glycosyl hydrolase comprising the motif GXXVX[NHQTS]IEY[PG] (SEQ ID NO 68) and/or the motif VICYF (SEQ ID NO 69), wherein the glycosyl hydrolase is a polypeptide having at least 85%, at least 90%, at least 95%, at least 96%, at least 97%, at least 98%, at least 99% or 100% sequence identity to the polypeptide shown in SEQ ID NO 57.

One embodiment of the invention relates a glycosyl hydrolase preferably a GH114 glycosyl hydrolase comprising the motif GXXVX[NHQTS]IEY[PG] (SEQ ID NO 68) and/or the motif VICYF (SEQ ID NO 69), wherein the glycosyl hydrolase is selected from the group consisting of: a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 72, SEQ ID NO 73, SEQ ID NO 74, SEQ ID NO 75, SEQ ID NO 76, SEQ ID NO 77, SEQ ID NO 78, SEQ ID NO 97, SEQ ID NO 98, SEQ ID NO 99, SEQ ID NO 100, SEQ ID NO 101, SEQ ID NO 102, SEQ ID NO 103, SEQ ID NO 104, SEQ ID NO 105, SEQ ID NO 106, SEQ ID NO 107, SEQ ID NO 108, SEQ ID NO 109, SEQ ID NO 110, SEQ ID NO 111, SEQ ID NO 112, SEQ ID NO 113, SEQ ID NO 114, SEQ ID NO 115, SEQ ID NO 116, SEQ ID NO 117, SEQ ID NO 118, SEQ ID NO 119, SEQ ID NO 120, SEQ ID NO 121, SEQ ID NO 122, SEQ ID NO 123, SEQ ID NO 124, SEQ ID NO 125, SEQ ID NO 126, SEQ ID NO 127, SEQ ID NO 128, SEQ ID NO 129, SEQ ID NO 130, SEQ ID NO: 133 and SEQ ID NO 135.

One embodiment of the invention relates a glycosyl hydrolase preferably a GH114 glycosyl hydrolase comprising the motif GXXVX[NHQTS]IEY[PG] (SEQ ID NO 68) and/or the motif VICYF (SEQ ID NO 69), wherein the glycosyl hydrolase is selected from the group consisting of: a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 15, SEQ ID NO 18, SEQ ID NO 57, SEQ ID NO 72, SEQ ID NO 73, SEQ ID NO 74, SEQ ID NO 75, SEQ ID NO 76, SEQ ID NO 77, SEQ ID NO 78, SEQ ID NO 97, SEQ ID NO 98, SEQ ID NO 99, SEQ ID NO 100, SEQ ID NO 101, SEQ ID NO 102, SEQ ID NO 103, SEQ ID NO 104, SEQ ID NO 105, SEQ ID NO 106, SEQ ID NO 107, SEQ ID NO 108, SEQ ID NO 109, SEQ ID NO 110, SEQ ID NO 111, SEQ ID NO 112, SEQ ID NO 113, SEQ ID NO 114, SEQ ID NO 115, SEQ ID NO 116, SEQ ID NO 117, SEQ ID NO 118, SEQ ID NO 119, SEQ ID NO 120, SEQ ID NO 121, SEQ ID NO 122, SEQ ID NO 123, SEQ ID NO 124, SEQ ID NO 125, SEQ ID NO 126, SEQ ID NO 127, SEQ ID NO 128, SEQ ID NO 129, SEQ ID NO 130, SEQ ID NO: 133 and SEQ ID NO 135.

The IEY sub-clade may be further be divided into yet another subgroup, which here is termed ICY clade (se FIG. 1 and FIG. 4). The ICY clade comprises polypeptides of fungal origin having hydrolase activity, wherein the polypeptides comprise a GH114 domain and belong to the IEY clade (and the VAE-clade). The polypeptides of the clade comprise the motif example ICYFSA (SEQ ID NO 70), corresponding to amino acids 81 to 86 in SEQ ID NO 15. Examples of polypeptides of the ICY clade is SEQ ID NO 15, and SEQ ID NO 57 as well as the homologue sequences SEQ ID NO 98, SEQ ID NO 101, SEQ ID NO 104, SEQ ID NO 107, SEQ ID NO 114, SEQ ID NO 115, SEQ ID NO 120, SEQ ID NO 124, SEQ ID NO 125, SEQ ID NO 127, SEQ ID NO 129 and SEQ ID NO: 133.

One embodiment of the invention relates a glycosyl hydrolase preferably a GH114 glycosyl hydrolase comprising one, two or all three motif(s) GXXVX[NHQTS]IEY[PG] (SEQ ID NO 68), VICYF (SEQ ID NO 69) and/or ICYFSA (SEQ ID NO 70), wherein the glycosyl hydrolase is selected from the group consisting of:

(a) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 15; and (b) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 57.

One preferred embodiment of the invention relates a GH114 glycosyl hydrolase comprising one, two or all three motif(s) GXXVX[NHQTS]IEY[PG] (SEQ ID NO 68), VICYF (SEQ ID NO 69) and/or ICYFSA (SEQ ID NO 70), wherein the glycosyl hydrolase is a polypeptide having at least 85%, at least 90%, at least 95%, at least 96%, at least 97%, at least 98%, at least 99% or 100% sequence identity to the polypeptide shown in SEQ ID NO 57.

One embodiment of the invention relates a glycosyl hydrolase preferably a GH114 glycosyl hydrolase comprising one, two or all three motif(s) GXXVX[NHQTS]IEY [PG] (SEQ ID NO 68), VICYF (SEQ ID NO 69) and/or ICYFSA (SEQ ID NO 70), wherein the glycosyl hydrolase is selected from the group consisting of: a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 98, SEQ ID NO 101, SEQ ID NO 104, SEQ ID NO 107, SEQ ID NO 114, SEQ ID NO 115, SEQ ID NO 120, SEQ ID NO 124, SEQ ID NO 125, SEQ ID NO 127, SEQ ID NO 129 and SEQ ID NO: 133.

One embodiment of the invention relates a glycosyl hydrolase preferably a GH114 glycosyl hydrolase comprising one, two or all three motif(s) GXXVX[NHQTS]IEY [PG] (SEQ ID NO 68), VICYF (SEQ ID NO 69) and/or ICYFSA (SEQ ID NO 70), wherein the glycosyl hydrolase is selected from the group consisting of: a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 15, SEQ ID NO 57, SEQ ID NO 98, SEQ ID NO 101, SEQ ID NO 104, SEQ ID NO 107, SEQ ID NO 114, SEQ ID NO 115, SEQ ID NO 120, SEQ ID NO 124, SEQ ID NO 125, SEQ ID NO 127, SEQ ID NO 129 and SEQ ID NO: 133.

The IEY sub-clade may be further be divided into yet another subgroup, which here is termed DFAVL clade (se FIG. 1). The DFAVL clade comprises polypeptides of fungal origin having hydrolase activity, wherein the polypeptides comprise a GH114 domain and belong to the IEY clade (and the VAE-clade). The Leucine L in the motif is fully conserved in the clade, and the adjacent glutamic acid E is one of the two catalytic active site residues. The polypeptides of the clade comprise the motif DFAVL (SEQ ID NO 71), corresponding to amino acids DFAVL at positions 199 to 203 of SEQ ID NO 18.

An example of a polypeptide of the DFAVL clade is SEQ ID NO 18 as well as the homologue sequences SEQ ID NO 72, SEQ ID NO 73, SEQ ID NO 74, SEQ ID NO 75, SEQ ID NO 76, SEQ ID NO 77, SEQ ID NO 78, SEQ ID NO 97, SEQ ID NO 99, SEQ ID NO 100, SEQ ID NO 102, SEQ ID NO 103, SEQ ID NO 105, SEQ ID NO 106, SEQ ID NO 108, SEQ ID NO 110, SEQ ID NO 111, SEQ ID NO 112, SEQ ID NO 113, SEQ ID NO 116, SEQ ID NO 117, SEQ ID NO 118, SEQ ID NO 119, SEQ ID NO 121, SEQ ID NO 123, SEQ ID NO 126, SEQ ID NO 128, SEQ ID NO 130 and SEQ ID NO 135.

One embodiment of the invention relates a glycosyl hydrolase preferably a GH114 glycosyl hydrolase comprising one, two or all three motif(s) GXXVX[NHQTS]IEY [PG] (SEQ ID NO 68), VICYF (SEQ ID NO 69) and/or DFAVL (SEQ ID NO 71), wherein the glycosyl hydrolase is a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 18.

One embodiment of the invention relates a glycosyl hydrolase preferably a GH114 glycosyl hydrolase comprising one, two or all three motif(s) GXXVX[NHQTS]IEY [PG] (SEQ ID NO 68), VICYF (SEQ ID NO 69) and/or DFAVL (SEQ ID NO 71), wherein the glycosyl hydrolase is selected from the group consisting of: a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 72, SEQ ID NO 73, SEQ ID NO 74, SEQ ID NO 75, SEQ ID NO 76, SEQ ID NO 77, SEQ ID NO 78, SEQ ID NO 97, SEQ ID NO 99, SEQ ID NO 100, SEQ ID NO 102, SEQ ID NO 103, SEQ ID NO 105, SEQ ID NO 106, SEQ ID NO 108, SEQ ID NO 110, SEQ ID NO 111, SEQ ID NO 112, SEQ ID NO 113, SEQ ID NO 116, SEQ ID NO 117, SEQ ID NO 118, SEQ ID NO 119, SEQ ID NO 121, SEQ ID NO 123, SEQ ID NO 126, SEQ ID NO 128, SEQ ID NO 130 and SEQ ID NO 135.

One embodiment of the invention relates a glycosyl hydrolase preferably a GH114 glycosyl hydrolase comprising one, two or all three motif(s) GXXVX[NHQTS]IEY [PG] (SEQ ID NO 68), VICYF (SEQ ID NO 69) and/or DFAVL (SEQ ID NO 71), wherein the glycosyl hydrolase is selected from the group consisting of: a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 18, SEQ ID NO 72, SEQ ID NO 73, SEQ ID NO 74, SEQ ID NO 75, SEQ ID NO 76, SEQ ID NO 77, SEQ ID NO 78, SEQ ID NO 97, SEQ ID NO 99, SEQ ID NO 100, SEQ ID NO 102, SEQ ID NO 103, SEQ ID NO 105, SEQ ID NO 106, SEQ ID NO 108, SEQ ID NO 110, SEQ ID NO 111, SEQ ID NO 112, SEQ ID NO 113, SEQ ID NO 116, SEQ ID NO 117, SEQ ID NO 118, SEQ ID NO 119, SEQ ID NO 121, SEQ ID NO 123, SEQ ID NO 126, SEQ ID NO 128, SEQ ID NO 130 and SEQ ID NO 135.

Another sub-clade of the VAE clade is the WQW clade. The WQW clade comprises polypeptides of bacterial and fungal origin, containing a GH114 domain and belonging to the VAE clade, having hydrolase activity. The polypeptides of the clade comprise the motif example WQWQL (SEQ ID NO 66), corresponding to amino acids WQWQL positions 30 to 34 of *Vibrio* sp. SEQ ID NO 27 where WQW (corresponding to positions 30 and 32 of SEQ ID NO 27) is fully conserved in WQW clade. An additional motif of the WQW clade is [VL][GASD]LKN[DGS][VLIP](SEQ ID NO 67), corresponding to amino acids IGLKNDL positions 171 to 177 of *Vibrio sp.* SEQ ID NO 27 where LKN (corresponding to positions 173 and 175 of SEQ ID NO 27) is fully conserved in WQW clade. An example of a polypeptide of the WQW clade includes the polypeptide shown in SEQ ID NO 27. Another example of a polypeptide of the WQW clade is includes the polypeptide shown in SEQ ID NO 33 and SEQ ID NO 36 as well as the homologue sequences SEQ ID NO 80, SEQ ID NO 81, SEQ ID NO 89, SEQ ID NO 95 and SEQ ID NO 146.

One embodiment of the invention relates a glycosyl hydrolase preferably a GH114 glycosyl hydrolase comprising the motif WQWQL (SEQ ID NO 66) and/or the motif [VLI][GASD]LKN[DGS][VLIP] (SEQ ID NO 67), wherein the glycosyl hydrolase is a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 27.

One embodiment of the invention relates a glycosyl hydrolase preferably a GH114 glycosyl hydrolase comprising the motif WQWQL (SEQ ID NO 66) and/or the motif [VLI][GASD]LKN[DGS][VLIP] (SEQ ID NO 67), wherein the glycosyl hydrolase is a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 33.

One embodiment of the invention relates a glycosyl hydrolase preferably a GH114 glycosyl hydrolase comprising the motif WQWQL (SEQ ID NO 66) and/or the motif [VLI][GASD]LKN[DGS][VLIP] (SEQ ID NO 67), wherein the glycosyl hydrolase is a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 36.

One embodiment of the invention relates a glycosyl hydrolase preferably a GH114 glycosyl hydrolase comprising the motif WQWQL (SEQ ID NO 66) and/or the motif [VLI][GASD]LKN[DGS][VLIP] (SEQ ID NO 67), wherein the glycosyl hydrolase is selected from the group consisting of: a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 80, SEQ ID NO 81, SEQ ID NO 89, SEQ ID NO 95 and SEQ ID NO 146.

One embodiment of the invention relates a glycosyl hydrolase preferably a GH114 glycosyl hydrolase comprising the motif WQWQL (SEQ ID NO 66) and/or the motif [VLI][GASD]LKN[DGS][VLIP] (SEQ ID NO 67), wherein the glycosyl hydrolase is selected from the group consisting of: a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 27, SEQ ID NO 33, SEQ ID NO 36, SEQ ID NO 80, SEQ ID NO 81, SEQ ID NO 89, SEQ ID NO 95 and SEQ ID NO 146.

One embodiment of the invention relates to a GH114 glycosyl hydrolase, having alpha-1,4-polygalactosaminidase activity, wherein the polypeptides comprises one or more of the motif(s) selected from the group consisting of: [VLI]XE[EDSQ]C (SEQ ID NO 60), CY[FLIV][SDN][ATVG] (SEQ ID NO 61), DYQ[L]G (SEQ ID NO 62), FQ[TAV]Q[PSD] (SEQ ID NO 63), AEECG (SEQ ID NO 64), NAFQ[AT]Q (SEQ ID NO 65), WQWQL (SEQ ID NO 66), [VLI][GASD]LKN[DGS][VLIP] (SEQ ID NO 67), GXXVX[NHQTS]IEY[PG] (SEQ ID NO 68), VICYF (SEQ ID NO 69), ICYFSA (SEQ ID NO 70) and DFAVL (SEQ ID NO 71).

The polypeptides of the invention have activity to the exopolysaccharide alpha-1,4-polygalactosamine and preferably to pel, which is a polysaccharide component of e.g. some biofilm matrix. One embodiment of the invention relates to the use of a GH114 glycosyl hydrolase according to the invention for reduction or removal of pel or alpha-1,4-polygalactosamine stain, e.g. wherein in the pel or alpha-1,4-polygalactosamine is comprised in a biofilm or biofilm EPS (extracellular polymeric substances). One embodiment of the invention relates to the use of a GH114 glycosyl hydrolase according to the invention for reduction or removal of biofilm. In particular, the GH114 glycosyl hydrolase polypeptides of the invention have activity in cleaning compositions such as laundry or dish wash detergents and is useful in cleaning processes such as laundry and/or dish wash e.g. for cleaning organic stains such as dead cell material, skin debris, sebum, sweat, grease and other stains derived from e.g. humans (body soils) or microbes but also from the environment, from surfaces such as textiles and hard surfaces. In particular, the GH114 glycosyl hydrolase polypeptides of the invention have activity in cleaning compositions such as laundry or dish wash detergents and is useful in cleaning processes such as laundry and/or dish wash e.g. for deep cleaning of surfaces such as textiles and hard surfaces. The present invention also provides a method for preventing, reduction or removal of pel or alpha-1,4-polygalactosamine containing stains from an item comprising applying at least one GH114 glycosyl hydrolase polypeptide of the invention, preferably having alpha-1,4-polygalactosaminidase activity, to an item and optionally rinse the item. The item is preferably a textile or a hard surface e.g. a non-medical hard surface such as dish ware. The present disclosure also provides a method for reduction or removal of dead cell material, skin debris, sebum, sweat and grease stains from an item comprising applying at least one GH114 glycosyl hydrolase polypeptide of the invention to an item and optionally rinse the item. The item is preferably a textile or a hard surface e.g. a non-medical hard surface such as dish ware.

Organic matters such as biofilm EPS, cell debris and body soil or components hereof may have glue-like properties and the presence of biofilm on e.g. textiles and may result in items or areas on items which are “sticky”. Soil will in general adhere to the sticky areas and such soil has shown difficult to remove by commercially available detergent compositions. Further, when dirty laundry items are washed together with less dirty laundry items the dirt present in the wash liquor tend to stick to the organic matter and e.g. EPS. As a result, the laundry item is more “soiled” after wash than before wash. This effect may also be termed re-deposition. One embodiment of the invention relates to the use of a GH114 glycosyl hydrolase polypeptides comprising one or more of the motif(s) [VLI]XE[EDSQ]C (SEQ ID NO 60), CY[FLIV][SDN][ATVG] (SEQ ID NO 61), DYQ[L]G (SEQ ID NO 62), FQ[TAV]Q[PSD] (SEQ ID NO 63), AEECG (SEQ ID NO 64), NAFQ[AT]Q (SEQ ID NO 65), WQWQL (SEQ ID NO 66), [VLI][GASD]LKN[DGS][VLIP] (SEQ ID NO 67), GXXVX[NHQTS]IEY[PG] (SEQ ID NO 68), VICYF (SEQ ID NO 69), ICYFSA (SEQ ID NO 70), DFAVL (SEQ ID NO 71) for reducing or removing re-deposition.

One embodiment of the invention relates to the use of a GH114 glycosyl hydrolase polypeptides comprising one or more of the motif(s) [VL]XE[EDSQ]C (SEQ ID NO 60), CY[FLIV][SDN][ATVG] (SEQ ID NO 61), DYQ[L]G (SEQ ID NO 62), FQ[TAV]Q[PSD] (SEQ ID NO 63), AEECG (SEQ ID NO 64), NAFQ[AT]Q (SEQ ID NO 65), WQWQL (SEQ ID NO 66), [VLI][GASD]LKN[DGS][VLIP] (SEQ ID NO 67), GXXVX[NHQTS]IEY[PG] (SEQ ID NO 68), VICYF (SEQ ID NO 69), ICYFSA (SEQ ID NO 70), DFAVL (SEQ ID NO 71) for reducing or removing malodor of items e.g. being washed. The inventors have surprisingly found that the polypeptides comprising one or more of the motif(s) [VL]XE[EDSQ]C (SEQ ID NO 60), CY[FLIV][SDN][ATVG](SEQ ID NO 61), DYQ[LI]G (SEQ ID NO 62), FQ[TAV]Q[PSD] (SEQ ID NO 63), AEECG (SEQ ID NO 64), NAFQ[AT]Q (SEQ ID NO 65), WQWQL (SEQ ID NO 66), [VLI][GASD]LKN[DGS][VLIP] (SEQ ID NO 67), GXXVX[NHQTS]IEY[PG] (SEQ ID NO 68), VICYF (SEQ ID NO 69), ICYFSA (SEQ ID NO 70), DFAVL (SEQ ID NO 71) as defined above are useful in reducing or removing laundry associated alpha-1,4-polygalactosamine. One embodiment of the invention relates to the use of a GH114 glycosyl hydrolase, having alpha-1,4-polygalactosaminidase activity, wherein the polypeptides comprises one or more of the motif(s) [VLI]XE[EDSQ]C (SEQ ID NO 60), CY[FLIV][SDN][ATVG] (SEQ ID NO 61), DYQ[LI]G (SEQ ID NO 62), FQ[TAV]Q[PSD] (SEQ ID NO 63), AEECG (SEQ ID NO 64), NAFQ[AT]Q (SEQ ID NO 65), WQWQL (SEQ ID NO 66), [VLI][GASD]LKN [DGS][VLIP] (SEQ ID NO 67), GXXVX[NHQTS]IEY [PG] (SEQ ID NO 68), VICYF (SEQ ID NO 69), ICYFSA (SEQ ID NO 70), DFAVL (SEQ ID NO 71) for reducing or removing malodor of an items e.g. a textile.

The polypeptides of the present invention are useful in cleaning compositions and are effective in deep cleaning of surfaces such as fabrics. The polypeptides of the present invention are effective in reducing or removing polysaccharide soiling e.g. polylactosamine from e.g. organic matter. One example of organic matter is biofilm, which is produced by various microorganisms. The extracellular polymeric matrix of biofilm, EPS is composed of polysaccharides, such as polylactosamine e.g. pel, extracellular DNA and proteins. Biofilm EPS may be sticky or gluing, which when present on textile, may give rise to re-deposition or back staining of soil resulting in a greying of the textile. Another drawback of organic matter e.g. biofilm is the malodor as various malodor related molecules are often associated with organic matter e.g. biofilm. One aspect of the invention relates to a method for laundering an item comprising the steps of:

a. exposing an item to a wash liquor comprising a polypeptide or a cleaning composition comprising a polypeptide selected from the group consisting of polypeptides comprising the sequences shown in: SEQ ID NO 3, SEQ ID NO 6, SEQ ID NO 9, SEQ ID NO 12, SEQ ID NO 15, SEQ ID NO 18, SEQ ID NO 21, SEQ ID NO 24, SEQ ID NO 27, SEQ ID NO 30, SEQ ID NO 33, SEQ ID NO 36, SEQ ID NO 39, SEQ ID NO 42, SEQ ID NO 45, SEQ ID NO 48, SEQ ID NO 51, SEQ ID NO 54, SEQ ID NO 57, SEQ ID NO 72, SEQ ID NO 73, SEQ ID NO 74, SEQ ID NO 75, SEQ ID NO 76, SEQ ID NO 77, SEQ ID NO 78, SEQ ID NO 79, SEQ ID NO 80, SEQ ID NO 81, SEQ ID NO 82, SEQ ID NO 83, SEQ ID NO 84, SEQ ID NO 85, SEQ ID NO 86, SEQ ID NO 87, SEQ ID NO 88, SEQ ID NO 89, SEQ ID NO 90, SEQ ID NO 91, SEQ ID NO 92, SEQ ID NO 93, SEQ ID NO 94, SEQ ID NO 95, SEQ ID NO 96, SEQ ID NO 97, SEQ ID NO 98, SEQ ID NO 99, SEQ ID NO 100, SEQ ID NO 101, SEQ ID NO 102, SEQ ID NO 103, SEQ ID NO 104, SEQ ID NO 105, SEQ ID NO 106, SEQ ID NO 107, SEQ ID NO 108, SEQ ID NO 109, SEQ ID NO 110, SEQ ID NO 111, SEQ ID NO 112, SEQ ID NO 113, SEQ ID NO 114, SEQ ID NO 115, SEQ ID NO 116, SEQ ID NO 117, SEQ ID NO 118, SEQ ID NO 119, SEQ ID NO 120, SEQ ID NO 121, SEQ ID NO 122, SEQ ID NO 123, SEQ ID NO 124, SEQ ID NO 125, SEQ ID NO 126, SEQ ID NO 127, SEQ ID NO 128, SEQ ID NO 129, SEQ ID NO 130, SEQ ID NO 131, SEQ ID NO 132, SEQ ED NO: 133, SEQ ID NO 134, SEQ ID NO 135, SEQ ID NO 136, SEQ ID NO 137, SEQ ID NO 138, SEQ ID NO 139, SEQ ID NO 140, SEQ ID NO 141, SEQ ID NO 142, SEQ ID NO 143, SEQ ID NO 144, SEQ ID NO 145 and SEQ ID NO 146 or polypeptides having at least 60%, at least 65%, at least 70%, at least 75%, at least 80%, at least 85%, at least 90%, at least 95%, at least 96%, at least 97%, at least 98%, at least 99% or 100% sequence identity hereto, wherein the polypeptide has hydrolytic activity;
b. completing at least one wash cycle; and
c. optionally rinsing the item, wherein the item is a textile.

The polypeptides of the invention are therefore useful for prevention, reduction or removal of malodor and for prevention, reduction of re-deposition and improving whiteness.

One embodiment of the invention relates to the use of polypeptide selected from the group consisting of polypeptides comprising the sequences shown in: SEQ ID NO 3, SEQ ID NO 6, SEQ ID NO 9, SEQ ID NO 12, SEQ ID NO 15, SEQ ID NO 18, SEQ ID NO 21, SEQ ID NO 24, SEQ ID NO 27, SEQ ID NO 30, SEQ ID NO 33, SEQ ID NO 36, SEQ ID NO 39, SEQ ID NO 42, SEQ ID NO 45, SEQ ID NO 48, SEQ ID NO 51, SEQ ID NO 54, SEQ ID NO 57, SEQ ID NO 72, SEQ ID NO 73, SEQ ID NO 74, SEQ ID NO 75, SEQ ID NO 76, SEQ ID NO 77, SEQ ID NO 78, SEQ ID NO 79, SEQ ID NO 80, SEQ ID NO 81, SEQ ID NO 82, SEQ ID NO 83, SEQ ID NO 84, SEQ ID NO 85, SEQ ID NO 86, SEQ ID NO 87, SEQ ID NO 88, SEQ ID NO 89, SEQ ID NO 90, SEQ ID NO 91, SEQ ID NO 92, SEQ ID NO 93, SEQ ID NO 94, SEQ ID NO 95, SEQ ID NO 96, SEQ ID NO 97, SEQ ID NO 98, SEQ ID NO 99, SEQ ID NO 100, SEQ ID NO 101, SEQ ID NO 102, SEQ ID NO 103, SEQ ID NO 104, SEQ ID NO 105, SEQ ID NO 106, SEQ ID NO 107, SEQ ID NO 108, SEQ ID NO 109, SEQ ID NO 110, SEQ ID NO 111, SEQ ID NO 112, SEQ ID NO 113, SEQ ID NO 114, SEQ ID NO 115, SEQ ID NO 116, SEQ ID NO 117, SEQ ID NO 118, SEQ ID NO 119, SEQ ID NO 120, SEQ ID NO 121, SEQ ID NO 122, SEQ ID NO 123, SEQ ID NO 124, SEQ ID NO 125, SEQ ID NO 126, SEQ ID NO 127, SEQ ID NO 128, SEQ ID NO 129, SEQ ID NO 130, SEQ ID NO 131, SEQ ID NO 132, SEQ ED NO: 133, SEQ ID NO 134, SEQ ID NO 135, SEQ ID NO 136, SEQ ID NO 137, SEQ ID NO 138, SEQ ID NO 139, SEQ ID NO 140, SEQ ID NO 141, SEQ ID NO 142, SEQ ID NO 143, SEQ ID NO 144, SEQ ID NO 145 and SEQ ID NO 146 or polypeptides having at least 60%, at least 65%, at least 70%, at least 75%, at least 80%, at least 85%, at least 90%, at least 95%, at least 96%, at least 97%, at least 98%, at least 99% or 100% sequence identity hereto for deep cleaning of an item, wherein the item is a textile.

One embodiment of the invention relates to the use of polypeptide selected from the group consisting of polypeptides comprising the sequences shown in: SEQ ID NO 3, SEQ ID NO 6, SEQ ID NO 9, SEQ ID NO 12, SEQ ID NO 15, SEQ ID NO 18, SEQ ID NO 21, SEQ ID NO 24, SEQ ID NO 27, SEQ ID NO 30, SEQ ID NO 33, SEQ ID NO 36, SEQ ID NO 39, SEQ ID NO 42, SEQ ID NO 45, SEQ ID NO 48, SEQ ID NO 51, SEQ ID NO 54, SEQ ID NO 57, SEQ ID NO 72, SEQ ID NO 73, SEQ ID NO 74, SEQ ID NO 75, SEQ ID NO 76, SEQ ID NO 77, SEQ ID NO 78, SEQ ID NO 79, SEQ ID NO 80, SEQ ID NO 81, SEQ ID NO 82, SEQ ID NO 83, SEQ ID NO 84, SEQ ID NO 85, SEQ ID NO 86, SEQ ID NO 87, SEQ ID NO 88, SEQ ID NO 89, SEQ ID NO 90, SEQ ID NO 91, SEQ ID NO 92, SEQ ID NO 93, SEQ ID NO 94, SEQ ID NO 95, SEQ ID NO 96, SEQ ID NO 97, SEQ ID NO 98, SEQ ID NO 99, SEQ ID NO 100, SEQ ID NO 101, SEQ ID NO 102, SEQ ID NO 103, SEQ ID NO 104, SEQ ID NO 105, SEQ ID NO 106, SEQ ID NO 107, SEQ ID NO 108, SEQ ID NO 109, SEQ ID NO 110, SEQ ID NO 111, SEQ ID NO 112, SEQ ID NO 113, SEQ ID NO 114, SEQ ID NO 115, SEQ ID NO 116, SEQ ID NO 117, SEQ ID NO 118, SEQ ID NO 119, SEQ ID NO 120, SEQ ID NO 121, SEQ ID NO 122, SEQ ID NO 123, SEQ ID NO 124, SEQ ID NO 125, SEQ ID NO 126, SEQ ID NO 127, SEQ ID NO 128, SEQ ID NO 129, SEQ ID NO 130, SEQ ID NO 131, SEQ ID NO 132, SEQ ED NO: 133, SEQ ID NO 134, SEQ ID NO 135, SEQ ID NO 136, SEQ ID NO 137, SEQ ID NO 138, SEQ ID NO 139, SEQ ID NO 140, SEQ ID NO 141, SEQ ID NO 142, SEQ ID NO 143, SEQ ID NO 144, SEQ ID NO 145 and SEQ ID NO 146 or polypeptides having at least 60%, at least 65%, at least 70%, at least 75%, at least 80%, at least 85%, at least 90%, at least 95%, at least 96%, at least 97%, at least 98%, at least 99% or 100% sequence identity hereto for reduction or removal of dead cell material, skin debris, sebum, sweat or grease stains from an item, wherein the item is a textile.

One embodiment of the invention relates to the use of polypeptide selected from the group consisting of polypeptides comprising the sequences shown in: SEQ ID NO 3, SEQ ID NO 6, SEQ ID NO 9, SEQ ID NO 12, SEQ ID NO 15, SEQ ID NO 18, SEQ ID NO 21, SEQ ID NO 24, SEQ ID NO 27, SEQ ID NO 30, SEQ ID NO 33, SEQ ID NO 36, SEQ ID NO 39, SEQ ID NO 42, SEQ ID NO 45, SEQ ID NO 48, SEQ ID NO 51, SEQ ID NO 54 SEQ ID NO 57, SEQ ID NO 72, SEQ ID NO 73, SEQ ID NO 74, SEQ ID NO 75, SEQ ID NO 76, SEQ ID NO 77, SEQ ID NO 78, SEQ ID NO 79, SEQ ID NO 80, SEQ ID NO 81, SEQ ID NO 82, SEQ ID NO 83, SEQ ID NO 84, SEQ ID NO 85, SEQ ID NO 86, SEQ ID NO 87, SEQ ID NO 88, SEQ ID NO 89, SEQ ID NO 90, SEQ ID NO 91, SEQ ID NO 92, SEQ ID NO 93, SEQ ID NO 94, SEQ ID NO 95, SEQ ID NO 96, SEQ ID NO 97, SEQ ID NO 98, SEQ ID NO 99, SEQ ID NO 100, SEQ ID NO 101, SEQ ID NO 102, SEQ ID NO 103, SEQ ID NO 104, SEQ ID NO 105, SEQ ID NO 106, SEQ ID NO 107, SEQ ID NO 108, SEQ ID NO 109, SEQ ID NO 110, SEQ ID NO 111, SEQ ID NO 112, SEQ ID NO 113, SEQ ID NO 114, SEQ ID NO 115, SEQ ID NO 116, SEQ ID NO 117, SEQ ID NO 118, SEQ ID NO 119, SEQ ID NO 120, SEQ ID NO 121, SEQ ID NO 122, SEQ ID NO 123, SEQ ID NO 124, SEQ ID NO 125, SEQ ID NO 126, SEQ ID NO 127, SEQ ID NO 128, SEQ ID NO 129, SEQ ID NO 130, SEQ ID NO 131, SEQ ID NO 132, SEQ ED NO: 133, SEQ ID NO 134, SEQ ID NO 135, SEQ ID NO 136, SEQ ID NO 137, SEQ ID NO 138, SEQ ID NO 139, SEQ ID NO 140, SEQ ID NO 141, SEQ ID NO 142, SEQ ID NO 143, SEQ ID NO 144, SEQ ID NO 145 and SEQ ID NO 146 or polypeptides having at least 60%, at least 65%, at least 70%, at least 75%, at least 80%, at least 85%, at least 90%, at least 95%, at least 96%, at least 97%, at least 98%, at least 99% or 100% sequence identity hereto;

(i) for preventing, reducing or removing stickiness of the item;
(ii) for pretreating stains on the item;
(iii) for preventing, reducing or removing redeposition of soil during a wash cycle;
(iv) for preventing, reducing or removing adherence of soil to the item;
(v) for maintaining or improving whiteness of the item;
(vi) for preventing, reducing or removal malodor from the item, wherein the item is a textile. The textile may e.g. be cotton or polyester or a mixture hereof.

Further methods and uses are described in the "use" section below.

One embodiment of the invention relates to a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO 3, SEQ ID NO 6, SEQ ID NO 9, SEQ ID NO 12, SEQ ID NO 15, SEQ ID NO 18, SEQ ID NO 21, SEQ ID NO 24, SEQ ID NO 27, SEQ ID NO 30, SEQ ID NO 33, SEQ ID NO 36, SEQ ID NO 39, SEQ ID NO 42, SEQ ID NO 45, SEQ ID NO 48, SEQ ID NO 51, SEQ ID NO 54 SEQ ID NO 57, SEQ ID NO 72, SEQ ID NO 73, SEQ ID NO 74, SEQ ID NO 75, SEQ ID NO 76, SEQ ID NO 77, SEQ ID NO 78, SEQ ID NO 79, SEQ ID NO 80, SEQ ID NO 81, SEQ ID NO 82, SEQ ID NO 83, SEQ ID NO 84, SEQ ID NO 85, SEQ ID NO 86, SEQ ID NO 87, SEQ ID NO 88, SEQ ID NO 89, SEQ ID NO 90, SEQ ID NO 91, SEQ ID NO 92, SEQ ID NO 93, SEQ ID NO 94, SEQ ID NO 95, SEQ ID NO 96, SEQ ID NO 97, SEQ ID NO 98, SEQ ID NO 99, SEQ ID NO 100, SEQ ID NO 101, SEQ ID NO 102, SEQ ID NO 103, SEQ ID NO 104, SEQ ID NO 105, SEQ ID NO 106, SEQ ID NO 107, SEQ ID NO 108, SEQ ID NO 109, SEQ ID NO 110, SEQ ID NO 111, SEQ ID NO 112, SEQ ID NO 113, SEQ ID NO 114, SEQ ID NO 115, SEQ ID NO 116, SEQ ID NO 117, SEQ ID NO 118, SEQ ID NO 119, SEQ ID NO 120, SEQ ID NO 121, SEQ ID NO 122, SEQ ID NO 123, SEQ ID NO 124, SEQ ID NO 125, SEQ ID NO 126, SEQ ID NO 127, SEQ ID NO 128, SEQ ID NO 129, SEQ ID NO 130, SEQ ID NO 131, SEQ ID NO 132, SEQ ED NO: 133, SEQ ID NO 134, SEQ ID NO 135, SEQ ID NO 136, SEQ ID NO 137, SEQ ID NO 138, SEQ ID NO 139, SEQ ID NO 140, SEQ ID NO 141, SEQ ID NO 142, SEQ ID NO 143, SEQ ID NO 144, SEQ ID NO 145 or SEQ ID NO 146.

One embodiment of the invention relates a GH114 glycosyl hydrolase polypeptide, wherein the polypeptide has hydrolytic activity, preferably alpha-1,4-polygalactosaminidase activity and wherein the polypeptide is selected from the group consisting of:

(a) a polypeptide having at least 60%, at least 70%, at least 75%, at least 80%, at least 85%, at least 90%, at least 95%, at least 96%, at least 97%, at least 98%, at least 99% or 100% sequence identity to the polypeptide shown in SEQ ID NO 3;
(b) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 6;
(c) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 9;
(d) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 12;
(e) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 15;
(f) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 18;
(g) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 21;

(h) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 24;

(i) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 27;

(j) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 30;

(k) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 33;

(l) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 36;

(m) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 39;

(n) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 42;

(o) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 45;

(p) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 48;

(q) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 55;

(r) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 51;

(s) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 54;

(t) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 57;

(u) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 72, (v) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 73, (w) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 74, (x) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 75, (y) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 76, (z) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 77, (aa) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 78, (bb) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 79, (cc) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 80, (dd) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 81, (ee) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 82, (ff) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 83, (gg) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 84, (hh) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 85, (ii) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 86, (jj) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 87, (kk) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 88, (ll) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 89, a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 90, (mm) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 91, a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 92, (nn) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 93, (oo) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 94, (pp) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 95, (qq) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 96, (rr) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 97, (ss) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 98, (tt) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 99, (uu) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 100, (vv) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 101, (ww) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 102, (xx) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 103, (yy) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 104, (zz) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 105, (aaa) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 106, (bbb) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 107, (ccc) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 108, (ddd) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 109, (eee) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 110, (fff) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 111, (ggg) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 112, (hhh) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 113, (iii) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 114, (jjj) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 115, (kkk) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 116, (lll) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 117, (mmm) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 118, (nnn) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 119, (ooo) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 120, (ppp) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 121, (qqq) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 122, (rrr) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 123, (sss) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 124, (ttt) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 125, (uuu) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 126, (vvv) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 127, (www) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 128, (xxx) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 129, (yyy) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 130, (zzz) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 131, (aaaa) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 132, (bbbb) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 133, (cccc) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 134, (dddd) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 135, (eeee) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 136, (ffff) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 137, (gggg) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 138, (hhhh) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 139, (iiii) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 140, (jjjj) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 141, (kkkk) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 142, (llll) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 143, (mmmm) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 144, a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 145, and (nnnn) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 146, wherein the polypeptide has glycosyl hydrolase activity, preferably alpha-1,4-polygalactosaminidase activity.

One embodiment of the invention relates a GH114 glycosyl hydrolase polypeptide, wherein the polypeptide has hydrolytic activity, preferably alpha-1,4-polygalactosaminidase activity, and wherein the polypeptide is selected from the group consisting of: a polypeptide shown in SEQ ID NO 72, SEQ ID NO 73, SEQ ID NO 74, SEQ ID NO 75, SEQ ID NO 76, SEQ ID NO 77, SEQ ID NO 78, SEQ ID NO 79, SEQ ID NO 80, SEQ ID NO 81, SEQ ID NO 82, SEQ ID NO 83, SEQ ID NO 84, SEQ ID NO 85, SEQ ID NO 86, SEQ ID NO 87, SEQ ID NO 88, SEQ ID NO 89, SEQ ID NO 90, SEQ ID NO 91, SEQ ID NO 92, SEQ ID NO 93, SEQ ID NO 94, SEQ ID NO 95, SEQ ID NO 96, SEQ ID NO 97, SEQ ID NO 98, SEQ ID NO 99, SEQ ID NO 100, SEQ ID NO 101, SEQ ID NO 102, SEQ ID NO 103, SEQ ID NO 104, SEQ ID NO 105, SEQ ID NO 106, SEQ ID NO 107, SEQ ID NO 108, SEQ ID NO 109, SEQ ID NO 110, SEQ ID NO 111, SEQ ID NO 112, SEQ ID NO 113, SEQ ID NO 114, SEQ ID NO 115, SEQ ID NO 116, SEQ ID NO 117, SEQ ID NO 118, SEQ ID NO 119, SEQ ID NO 120, SEQ ID NO 121, SEQ ID NO 122, SEQ ID NO 123, SEQ ID NO 124, SEQ ID NO 125, SEQ ID NO 126, SEQ ID NO 127, SEQ ID NO 128, SEQ ID NO 129, SEQ ID NO 130, SEQ ID NO 131, SEQ ID NO 132, SEQ ED NO: 133, SEQ ID NO 134, SEQ ID NO 135, SEQ ID NO 136, SEQ ID NO 137, SEQ ID NO 138, SEQ ID NO 139, SEQ ID NO 140, SEQ ID NO 141, SEQ ID NO 142, SEQ ID NO 143, SEQ ID NO 144, SEQ ID NO 145 and SEQ ID NO 146 or a polypeptide having at least 60%, at least 70%, at least 75%, at least 80%, at least 85%, at least 90%, at least 95%, at least 96%, at least 97%, at least 98%, at least 99% or 100% sequence identity hereto.

One preferred embodiment relates to a GH114 glycosyl hydrolase polypeptide, wherein the polypeptide has hydrolytic activity, preferably alpha-1,4-polygalactosaminidase activity, and wherein the polypeptide is selected from the group consisting of:

(a) a polypeptide having at least 90%, at least 95%, at least 96%, at least 97%, at least 98%, at least 99% or 100% sequence identity to the polypeptide shown in SEQ ID NO 3;

(b) a polypeptide having at least 90%, at least 95%, at least 96%, at least 97%, at least 98%, at least 99% or 100% sequence identity to the polypeptide shown in SEQ ID NO 6;

(c) a polypeptide having at least 85%, at least 90%, at least 95%, at least 96%, at least 97%, at least 98%, at least 99% or 100% sequence identity to the polypeptide shown in SEQ ID NO 9;

(d) a polypeptide having at least 85%, at least 90%, at least 95%, at least 96%, at least 97%, at least 98%, at least 99% or 100% sequence identity to the polypeptide shown in SEQ ID NO 12;

(e) a polypeptide having at least 75%, at least 80%, at least 85%, at least 90%, at least 95%, at least 96%, at least 97%, at least 98%, at least 99% or 100% sequence identity to the polypeptide shown in SEQ ID NO 21;

(f) a polypeptide having at least 90%, at least 95%, at least 96%, at least 97%, at least 98%, at least 99% or 100% sequence identity to the polypeptide shown in SEQ ID NO 24;

(g) a polypeptide having at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 27;

(h) a polypeptide having, at least 50% at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 30;

(i) a polypeptide having at least 70%, at least 75%, at least 80%, at least 85%, at least 90%, at least 95%, at least 96%, at least 97%, at least 98%, at least 99% or 100% sequence identity to the polypeptide shown in SEQ ID NO 33;

(j) a polypeptide having at least 75%, at least 80%, at least 85%, at least 90%, at least 95%, at least 96%, at least 97%, at least 98%, at least 99% or 100% sequence identity to the polypeptide shown in SEQ ID NO 36;

(k) a polypeptide having at least 99% or 100% sequence identity to the polypeptide shown in SEQ ID NO 39;

(l) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 42;

(m) a polypeptide having at least 85%, at least 90%, at least 95%, at least 96%, at least 97%, at least 98%, at least 99% or 100% sequence identity to the polypeptide shown in SEQ ID NO 45;

(n) a polypeptide having at least 70%, at least 75%, at least 80%, at least 85%, at least 90%, at least 95%, at least 96%, at least 97%, at least 98%, at least 99% or 100% sequence identity to the polypeptide shown in SEQ ID NO 48;

(o) a polypeptide having at least 98%, at least 99% or 100% sequence identity to the polypeptide shown in SEQ ID NO 51;

(p) a polypeptide having at least 80%, at least 85%, at least 90%, at least 95%, at least 96%, at least 97%, at least 98%, at least 99% or 100% sequence identity to the polypeptide shown in SEQ ID NO 54; and (q) a polypeptide having at least 85%, at least 90%, at least 95%, at least 96%, at least 97%, at least 98%, at least 99% or 100% sequence identity to the polypeptide shown in SEQ ID NO 57.

Another preferred embodiment of the invention relates a GH114 glycosyl hydrolase polypeptide comprising one, two, three, four or five of the motifs [VL]XE[EDSQ]C (SEQ ID NO 60), CY[FLIV][SDN][ATVG] (SEQ ID NO 61), DYQ[LI]G (SEQ ID NO 62), FQ[TAV]Q[PSD] (SEQ ID NO 63), AEECG (SEQ ID NO 64), NAFQ[AT]Q (SEQ ID NO 65), WQWQL (SEQ ID NO 66), [VLI][GASD]LKN [DGS][VLIP] (SEQ ID NO 67), GXXVX[NHQTS]IEY [PG] (SEQ ID NO 68), VICYF (SEQ ID NO 69), ICYFSA (SEQ ID NO 70), DFAVL (SEQ ID NO 71), wherein the polypeptide has hydrolytic activity, (preferably?) alpha-1,4-polygalactosaminidase activity, and wherein the polypeptide is selected from the group consisting of:

(a) a polypeptide having at least 90%, at least 95%, at least 96%, at least 97%, at least 98%, at least 99% or 100% sequence identity to the polypeptide shown in SEQ ID NO 3;

(b) a polypeptide having at least 90%, at least 95%, at least 96%, at least 97%, at least 98%, at least 99% or 100% sequence identity to the polypeptide shown in SEQ ID NO 6;

(c) a polypeptide having at least 85%, at least 90%, at least 95%, at least 96%, at least 97%, at least 98%, at least 99% or 100% sequence identity to the polypeptide shown in SEQ ID NO 9;

(d) a polypeptide having at least 85%, at least 90%, at least 95%, at least 96%, at least 97%, at least 98%, at least 99% or 100% sequence identity to the polypeptide shown in SEQ ID NO 12;

(e) a polypeptide having at least 75%, at least 80%, at least 85%, at least 90%, at least 95%, at least 96%, at least 97%, at least 98%, at least 99% or 100% sequence identity to the polypeptide shown in SEQ ID NO 21;

(f) a polypeptide having at least 90%, at least 95%, at least 96%, at least 97%, at least 98%, at least 99% or 100% sequence identity to the polypeptide shown in SEQ ID NO 24;

(g) a polypeptide having at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 27;

(h) a polypeptide having, at least 50% at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 30;

(i) a polypeptide having at least 70%, at least 75%, at least 80%, at least 85%, at least 90%, at least 95%, at least 96%, at least 97%, at least 98%, at least 99% or 100% sequence identity to the polypeptide shown in SEQ ID NO 33;

(j) a polypeptide having at least 75%, at least 80%, at least 85%, at least 90%, at least 95%, at least 96%, at least 97%, at least 98%, at least 99% or 100% sequence identity to the polypeptide shown in SEQ ID NO 36;

(k) a polypeptide having at least 99% or 100% sequence identity to the polypeptide shown in SEQ ID NO 39;

(l) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 42;

(m) a polypeptide having at least 85%, at least 90%, at least 95%, at least 96%, at least 97%, at least 98%, at least 99% or 100% sequence identity to the polypeptide shown in SEQ ID NO 45;

(n) a polypeptide having at least 70%, at least 75%, at least 80%, at least 85%, at least 90%, at least 95%, at least 96%, at least 97%, at least 98%, at least 99% or 100% sequence identity to the polypeptide shown in SEQ ID NO 48;

(o) a polypeptide having at least 98%, at least 99% or 100% sequence identity to the polypeptide shown in SEQ ID NO 51;

(p) a polypeptide having at least 80%, at least 85%, at least 90%, at least 95%, at least 96%, at least 97%, at least 98%, at least 99% or 100% sequence identity to the polypeptide shown in SEQ ID NO 54; and (q) a polypeptide having at least 85%, at least 90%, at least 95%, at least 96%, at least 97%, at least 98%, at least 99% or 100% sequence identity to the polypeptide shown in SEQ ID NO 57.

Another preferred embodiment of the invention relates a GH114 glycosyl hydrolase polypeptide comprising one, two, three, four or five of the motifs [VL]XE[EDSQ]C (SEQ ID NO 60), CY[FLIV][SDN][ATVG] (SEQ ID NO 61), DYQ[LI]G (SEQ ID NO 62), FQ[TAV]Q[PSD] (SEQ ID NO 63), AEECG (SEQ ID NO 64), NAFQ[AT]Q (SEQ ID NO 65), WQWQL (SEQ ID NO 66), [VLI][GASD]LKN [DGS][VLIP] (SEQ ID NO 67), GXXVX[NHQTS]IEY [PG] (SEQ ID NO 68), VICYF (SEQ ID NO 69), ICYFSA (SEQ ID NO 70), DFAVL (SEQ ID NO 71), wherein the polypeptide has hydrolytic activity, preferably alpha-1,4-polygalactosaminidase activity, and wherein the polypeptide is selected from the group consisting of: a polypeptide shown in SEQ ID NO 72, SEQ ID NO 73, SEQ ID NO 74, SEQ ID NO 75, SEQ ID NO 76, SEQ ID NO 77, SEQ ID NO 78, SEQ ID NO 79, SEQ ID NO 80, SEQ ID NO 81, SEQ ID NO 82, SEQ ID NO 83, SEQ ID NO 84, SEQ ID NO 85, SEQ ID NO 86, SEQ ID NO 87, SEQ ID NO 88, SEQ ID NO 89, SEQ ID NO 90, SEQ ID NO 91, SEQ ID NO 92, SEQ ID NO 93, SEQ ID NO 94, SEQ ID NO 95, SEQ ID NO 96, SEQ ID NO 97, SEQ ID NO 98, SEQ ID NO 99, SEQ ID NO 100, SEQ ID NO 101, SEQ ID NO 102, SEQ ID NO 103, SEQ ID NO 104, SEQ ID NO 105, SEQ ID NO 106, SEQ ID NO 107, SEQ ID NO 108, SEQ ID NO 109, SEQ ID NO 110, SEQ ID NO 111, SEQ ID NO 112, SEQ ID NO 113, SEQ ID NO 114, SEQ ID NO 115, SEQ ID NO 116, SEQ ID NO 117, SEQ ID NO 118, SEQ ID NO 119, SEQ ID NO 120, SEQ ID NO 121, SEQ ID NO 122, SEQ ID NO 123, SEQ ID NO 124, SEQ ID NO 125, SEQ ID NO 126, SEQ ID NO 127, SEQ ID NO 128, SEQ ID NO 129, SEQ ID NO 130, SEQ ID NO 131, SEQ ID NO 132, SEQ ED NO: 133, SEQ ID NO 134, SEQ ID NO 135, SEQ ID NO 136, SEQ ID NO 137, SEQ ID NO 138, SEQ ID NO 139, SEQ ID NO 140, SEQ ID NO 141, SEQ ID NO 142, SEQ ID NO 143, SEQ ID NO 144, SEQ ID NO 145 and SEQ ID NO 146 or a polypeptide having at least 60%, at least 70%, at least 75%, at least 80%, at least 85%, at least 90%, at least 95%, at least 96%, at least 97%, at least 98%, at least 99% or 100% sequence identity hereto.

In one embodiment, the present invention relates to polypeptides having a sequence identity to the mature polypeptide of SEQ ID NO 2 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the hydrolytic activity of the mature polypeptide of SEQ ID NO 2.

In a particular embodiment, the invention relates to polypeptides having a sequence identity to the mature polypeptide of SEQ ID NO 5 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the hydrolytic activity of the mature polypeptide of SEQ ID NO 5.

In a particular embodiment, the invention relates to polypeptides having a sequence identity to the mature polypeptide of SEQ ID NO 8 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the hydrolytic activity of the mature polypeptide of SEQ ID NO 8.

In a particular embodiment, the invention relates to polypeptides having a sequence identity to the mature polypeptide of SEQ ID NO 11 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the hydrolytic activity of the mature polypeptide of SEQ ID NO 11.

In a particular embodiment, the invention relates to polypeptides having a sequence identity to the mature polypeptide of SEQ ID NO 14 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the hydrolytic activity of the mature polypeptide of SEQ ID NO 14.

In some embodiment, the present invention relates to polypeptides having a sequence identity to the mature polypeptide of SEQ ID NO 17 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the hydrolytic activity of the mature polypeptide of SEQ ID NO 7.

In a particular embodiment, the invention relates to polypeptides having a sequence identity to the mature polypeptide of SEQ ID NO 20 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the hydrolytic activity of the mature polypeptide of SEQ ID NO 20.

In a particular embodiment, the invention relates to polypeptides having a sequence identity to the mature polypeptide of SEQ ID NO 23 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the hydrolytic activity of the mature polypeptide of SEQ ID NO 23.

In a particular embodiment, the invention relates to polypeptides having a sequence identity to the mature polypeptide of SEQ ID NO 26 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the hydrolytic activity of the mature polypeptide of SEQ ID NO 26.

In a particular embodiment, the invention relates to polypeptides having a sequence identity to the mature polypeptide of SEQ ID NO 29 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the hydrolytic activity of the mature polypeptide of SEQ ID NO 29.

In a particular embodiment, the invention relates to polypeptides having a sequence identity to the mature polypeptide of SEQ ID NO 32 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the hydrolytic activity of the mature polypeptide of SEQ ID NO 32.

In a particular embodiment, the invention relates to polypeptides having a sequence identity to the mature polypeptide of SEQ ID NO 35 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the hydrolytic activity of the mature polypeptide of SEQ ID NO 35.

In a particular embodiment, the invention relates to polypeptides having a sequence identity to the mature polypeptide of SEQ ID NO 38 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the hydrolytic activity of the mature polypeptide of SEQ ID NO 38.

In a particular embodiment, the invention relates to polypeptides having a sequence identity to the mature polypeptide of SEQ ID NO 41 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the hydrolytic activity of the mature polypeptide of SEQ ID NO 41.

In a particular embodiment, the invention relates to polypeptides having a sequence identity to the mature polypeptide of SEQ ID NO 44 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the hydrolytic activity of the mature polypeptide of SEQ ID NO 44.

v In a particular embodiment, the invention relates to polypeptides having a sequence identity to the mature polypeptide of SEQ ID NO 47 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the hydrolytic activity of the mature polypeptide of SEQ ID NO 47.

In a particular embodiment, the invention relates to polypeptides having a sequence identity to the mature polypeptide of SEQ ID NO 50 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the hydrolytic activity of the mature polypeptide of SEQ ID NO 50.

In a particular embodiment, the invention relates to polypeptides having a sequence identity to the mature polypeptide of SEQ ID NO 53 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the hydrolytic activity of the mature polypeptide of SEQ ID NO 53.

In a particular embodiment, the invention relates to polypeptides having a sequence identity to the mature polypeptide of SEQ ID NO 56 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the hydrolytic activity of the mature polypeptide of SEQ ID NO 56.

In some embodiment, the polypeptide has been isolated. A polypeptide of the present invention preferably comprises or consists of the amino acid sequence shown in SEQ ID NO 3 or an allelic variant thereof; or is a fragment thereof having hydrolytic activity. In another aspect, the polypeptide comprises or consists of the mature polypeptide of SEQ ID NO 2. In another aspect, the polypeptide comprises or consists of amino acids 1 to 246 of SEQ ID NO 2.

In one embodiment, the polypeptide preferably comprises or consists of the amino acid sequence shown in SEQ ID NO 3; comprises the amino acid sequence shown in SEQ ID NO 3 and a N-terminal and/or C-terminal His-tag and/or HQ-tag; comprises the amino acid sequence of SEQ ID NO 3 and a N-terminal and/or C-terminal extension of between 1 and 10 amino acids; or is a fragment thereof having hydrolytic activity and having at least 50% such as at least 60%, at least 70%, at least 75%, at least 80%, at least 85%, at least 90%, at least 95%, at least 96%, at least 97%, at least 98% or at least 99% of the length of SEQ ID NO 3.

In some embodiment, the polypeptide has been isolated. A polypeptide of the present invention preferably comprises or consists of the amino acid sequence shown in SEQ ID NO 6 or an allelic variant thereof; or is a fragment thereof having hydrolytic activity. In another aspect, the polypeptide comprises or consists of the mature polypeptide of SEQ ID NO 5. In another aspect, the polypeptide comprises or consists of amino acids 1 to 243 of SEQ ID NO 5.

In one embodiment, the polypeptide preferably comprises or consists of the amino acid sequence shown in SEQ ID NO 6; comprises the amino acid sequence shown in SEQ ID NO 6 and a N-terminal and/or C-terminal His-tag and/or HQ-tag; comprises the amino acid sequence of SEQ ID NO 6 and a N-terminal and/or C-terminal extension of between 1 and 10 amino acids; or is a fragment thereof having hydrolytic activity and having at least 50% such as at least 60%, at least 70%, at least 75%, at least 80%, at least 85%, at least 90%, at least 95%, at least 96%, at least 97%, at least 98% or at least 99% of the length of SEQ ID NO 6.

In some embodiment, the polypeptide has been isolated. A polypeptide of the present invention preferably comprises or consists of the amino acid sequence shown in SEQ ID NO 9 or an allelic variant thereof; or is a fragment thereof having hydrolytic activity. In another aspect, the polypeptide comprises or consists of the mature polypeptide of SEQ ID NO 8. In another aspect, the polypeptide comprises or consists of amino acids 1 to 237 of SEQ ID NO 8.

In one embodiment, the polypeptide preferably comprises or consists of the amino acid sequence shown in SEQ ID NO 9; comprises the amino acid sequence shown in SEQ ID NO 9 and a N-terminal and/or C-terminal His-tag and/or HQ-tag; comprises the amino acid sequence of SEQ ID NO 9 and a N-terminal and/or C-terminal extension of between 1 and 10 amino acids; or is a fragment thereof having hydrolytic activity and having at least 50% such as at least 60%, at least 70%, at least 75%, at least 80%, at least 85%, at least 90%, at least 95%, at least 96%, at least 97%, at least 98% or at least 99% of the length of SEQ ID NO 9.

In some embodiment, the polypeptide has been isolated. A polypeptide of the present invention preferably comprises or consists of the amino acid sequence shown in SEQ ID NO 12 or an allelic variant thereof; or is a fragment thereof having hydrolytic activity. In another aspect, the polypeptide comprises or consists of the mature polypeptide of SEQ ID NO 11. In another aspect, the polypeptide comprises or consists of amino acids 1 to 237 of SEQ ID NO 11.

In one embodiment, the polypeptide preferably comprises or consists of the amino acid sequence shown in SEQ ID NO 12; comprises the amino acid sequence shown in SEQ ID NO 12 and a N-terminal and/or C-terminal His-tag and/or HQ-tag; comprises the amino acid sequence of SEQ ID NO 12 and a N-terminal and/or C-terminal extension of between 1 and 10 amino acids; or is a fragment thereof having hydrolytic activity and having at least 50% such as at least 60%, at least 70%, at least 75%, at least 80%, at least 85%, at least 90%, at least 95%, at least 96%, at least 97%, at least 98% or at least 99% of the length of SEQ ID NO 12.

In some embodiment, the polypeptide has been isolated. A polypeptide of the present invention preferably comprises or consists of the amino acid sequence shown in SEQ ID NO 15 or an allelic variant thereof; or is a fragment thereof having hydrolytic activity. In another aspect, the polypeptide comprises or consists of the mature polypeptide of SEQ ID NO 14. In another aspect, the polypeptide comprises or consists of amino acids 1 to 274 of SEQ ID NO 14.

In one embodiment, the polypeptide preferably comprises or consists of the amino acid sequence shown in SEQ ID NO 15; comprises the amino acid sequence shown in SEQ ID NO 15 and a N-terminal and/or C-terminal His-tag and/or HQ-tag; comprises the amino acid sequence of SEQ ID NO 15 and a N-terminal and/or C-terminal extension of between 1 and 10 amino acids; or is a fragment thereof having hydrolytic activity and having at least 50% such as at least 60%, at least 70%, at least 75%, at least 80%, at least 85%, at least 90%, at least 95%, at least 96%, at least 97%, at least 98% or at least 99% of the length of SEQ ID NO 15.

In some embodiment, the polypeptide has been isolated. A polypeptide of the present invention preferably comprises or consists of the amino acid sequence shown in SEQ ID NO 18 or an allelic variant thereof; or is a fragment thereof having hydrolytic activity. In another aspect, the polypeptide comprises or consists of the mature polypeptide of SEQ ID NO 17. In another aspect, the polypeptide comprises or consists of amino acids 1 to 296 of SEQ ID NO 17.

In one embodiment, the polypeptide preferably comprises or consists of the amino acid sequence shown in SEQ ID NO 18; comprises the amino acid sequence shown in SEQ ID NO 18 and a N-terminal and/or C-terminal His-tag and/or HQ-tag; comprises the amino acid sequence of SEQ ID NO 18 and a N-terminal and/or C-terminal extension of between 1 and 10 amino acids; or is a fragment thereof having hydrolytic activity and having at least 50% such as at least 60%, at least 70%, at least 75%, at least 80%, at least 85%, at least 90%, at least 95%, at least 96%, at least 97%, at least 98% or at least 99% of the length of SEQ ID NO 18.

In some embodiment, the polypeptide has been isolated. A polypeptide of the present invention preferably comprises or consists of the amino acid sequence shown in SEQ ID NO 21 or an allelic variant thereof; or is a fragment thereof having hydrolytic activity. In another aspect, the polypeptide comprises or consists of the mature polypeptide of SEQ ID NO 20. In another aspect, the polypeptide comprises or consists of amino acids 1 to 237 of SEQ ID NO 20.

In one embodiment, the polypeptide preferably comprises or consists of the amino acid sequence shown in SEQ ID NO 21; comprises the amino acid sequence shown in SEQ ID NO 21 and a N-terminal and/or C-terminal His-tag and/or HQ-tag; comprises the amino acid sequence of SEQ ID NO 21 and a N-terminal and/or C-terminal extension of between 1 and 10 amino acids; or is a fragment thereof having hydrolytic activity and having at least 50% such as at least 60%, at least 70%, at least 75%, at least 80%, at least 85%, at least 90%, at least 95%, at least 96%, at least 97%, at least 98% or at least 99% of the length of SEQ ID NO 21.

In some embodiment, the polypeptide has been isolated. A polypeptide of the present invention preferably comprises or consists of the amino acid sequence shown in SEQ ID NO 24 or an allelic variant thereof; or is a fragment thereof having hydrolytic activity. In another aspect, the polypeptide comprises or consists of the mature polypeptide of SEQ ID NO 23. In another aspect, the polypeptide comprises or consists of amino acids 1 to 239 of SEQ ID NO 23.

In one embodiment, the polypeptide preferably comprises or consists of the amino acid sequence shown in SEQ ID NO 24; comprises the amino acid sequence shown in SEQ ID NO 24 and a N-terminal and/or C-terminal His-tag and/or HQ-tag; comprises the amino acid sequence of SEQ ID NO 24 and a N-terminal and/or C-terminal extension of between 1 and 10 amino acids; or is a fragment thereof having hydrolytic activity and having at least 50% such as at least 60%, at least 70%, at least 75%, at least 80%, at least 85%, at least 90%, at least 95%, at least 96%, at least 97%, at least 98% or at least 99% of the length of SEQ ID NO 24.

In some embodiment, the polypeptide has been isolated. A polypeptide of the present invention preferably comprises or consists of the amino acid sequence shown in SEQ ID NO 27 or an allelic variant thereof; or is a fragment thereof having hydrolytic activity. In another aspect, the polypeptide comprises or consists of the mature polypeptide of SEQ ID NO 26. In another aspect, the polypeptide comprises or consists of amino acids 1 to 234 of SEQ ID NO 26.

In one embodiment, the polypeptide preferably comprises or consists of the amino acid sequence shown in SEQ ID NO 27; comprises the amino acid sequence shown in SEQ ID NO 27 and a N-terminal and/or C-terminal His-tag and/or HQ-tag; comprises the amino acid sequence of SEQ ID NO 27 and a N-terminal and/or C-terminal extension of between 1 and 10 amino acids; or is a fragment thereof having hydrolytic activity and having at least 50% such as at least 60%, at least 70%, at least 75%, at least 80%, at least 85%, at least 90%, at least 95%, at least 96%, at least 97%, at least 98% or at least 99% of the length of SEQ ID NO 27.

In some embodiment, the polypeptide has been isolated. A polypeptide of the present invention preferably comprises or consists of the amino acid sequence shown in SEQ ID NO 30 or an allelic variant thereof; or is a fragment thereof having hydrolytic activity. In another aspect, the polypeptide comprises or consists of the mature polypeptide of SEQ ID NO 29. In another aspect, the polypeptide comprises or consists of amino acids 1 to 242 of SEQ ID NO 29.

In one embodiment, the polypeptide preferably comprises or consists of the amino acid sequence shown in SEQ ID NO 30; comprises the amino acid sequence shown in SEQ ID NO 30 and a N-terminal and/or C-terminal His-tag and/or HQ-tag; comprises the amino acid sequence of SEQ ID NO 30 and a N-terminal and/or C-terminal extension of between 1 and 10 amino acids; or is a fragment thereof having hydrolytic activity and having at least 50% such as at least 60%, at least 70%, at least 75%, at least 80%, at least 85%, at least 90%, at least 95%, at least 96%, at least 97%, at least 98% or at least 99% of the length of SEQ ID NO 30.

In some embodiment, the polypeptide has been isolated. A polypeptide of the present invention preferably comprises or consists of the amino acid sequence shown in SEQ ID NO 33 or an allelic variant thereof; or is a fragment thereof having hydrolytic activity. In another aspect, the polypeptide comprises or consists of the mature polypeptide of SEQ ID NO 32. In another aspect, the polypeptide comprises or consists of amino acids 1 to 238 of SEQ ID NO 32.

In one embodiment, the polypeptide preferably comprises or consists of the amino acid sequence shown in SEQ ID NO 33; comprises the amino acid sequence shown in SEQ ID NO 33 and a N-terminal and/or C-terminal His-tag and/or HQ-tag; comprises the amino acid sequence of SEQ ID NO 33 and a N-terminal and/or C-terminal extension of between 1 and 10 amino acids; or is a fragment thereof having hydrolytic activity and having at least 50% such as at least 60%, at least 70%, at least 75%, at least 80%, at least 85%, at least 90%, at least 95%, at least 96%, at least 97%, at least 98% or at least 99% of the length of SEQ ID NO 33.

In some embodiment, the polypeptide has been isolated. A polypeptide of the present invention preferably comprises or consists of the amino acid sequence shown in SEQ ID NO 36 or an allelic variant thereof; or is a fragment thereof having hydrolytic activity. In another aspect, the polypeptide comprises or consists of the mature polypeptide of SEQ ID NO 35. In another aspect, the polypeptide comprises or consists of amino acids 1 to 261 of SEQ ID NO 35.

In one embodiment, the polypeptide preferably comprises or consists of the amino acid sequence shown in SEQ ID NO 36; comprises the amino acid sequence shown in SEQ ID NO 36 and a N-terminal and/or C-terminal His-tag and/or HQ-tag; comprises the amino acid sequence of SEQ ID NO 36 and a N-terminal and/or C-terminal extension of between 1 and 10 amino acids; or is a fragment thereof having hydrolytic activity and having at least 50% such as at least 60%, at least 70%, at least 75%, at least 80%, at least 85%, at least 90%, at least 95%, at least 96%, at least 97%, at least 98% or at least 99% of the length of SEQ ID NO 36.

In some embodiment, the polypeptide has been isolated. A polypeptide of the present invention preferably comprises or consists of the amino acid sequence shown in SEQ ID NO 39 or an allelic variant thereof; or is a fragment thereof having hydrolytic activity. In another aspect, the polypeptide comprises or consists of the mature polypeptide of SEQ ID NO 38. In another aspect, the polypeptide comprises or consists of amino acids 1 to 265 of SEQ ID NO 38.

In one embodiment, the polypeptide preferably comprises or consists of the amino acid sequence shown in SEQ ID NO 39; comprises the amino acid sequence shown in SEQ ID NO 39 and a N-terminal and/or C-terminal His-tag and/or HQ-tag; comprises the amino acid sequence of SEQ ID NO 39 and a N-terminal and/or C-terminal extension of between 1 and 10 amino acids; or is a fragment thereof having hydrolytic activity and having at least 50% such as at least 60%, at least 70%, at least 75%, at least 80%, at least 85%, at least 90%, at least 95%, at least 96%, at least 97%, at least 98% or at least 99% of the length of SEQ ID NO 39.

In some embodiment, the polypeptide has been isolated. A polypeptide of the present invention preferably comprises or consists of the amino acid sequence shown in SEQ ID NO 42 or an allelic variant thereof; or is a fragment thereof having hydrolytic activity. In another aspect, the polypeptide comprises or consists of the mature polypeptide of SEQ ID NO 41. In another aspect, the polypeptide comprises or consists of amino acids 1 to 254 of SEQ ID NO 41.

In one embodiment, the polypeptide preferably comprises or consists of the amino acid sequence shown in SEQ ID NO 42; comprises the amino acid sequence shown in SEQ ID NO 42 and a N-terminal and/or C-terminal His-tag and/or HQ-tag; comprises the amino acid sequence of SEQ ID NO 42 and a N-terminal and/or C-terminal extension of between 1 and 10 amino acids; or is a fragment thereof having hydrolytic activity and having at least 50% such as at least 60%, at least 70%, at least 75%, at least 80%, at least 85%, at least 90%, at least 95%, at least 96%, at least 97%, at least 98% or at least 99% of the length of SEQ ID NO 42.

In some embodiment, the polypeptide has been isolated. A polypeptide of the present invention preferably comprises or consists of the amino acid sequence shown in SEQ ID NO 45 or an allelic variant thereof; or is a fragment thereof having hydrolytic activity. In another aspect, the polypeptide comprises or consists of the mature polypeptide of SEQ ID NO 44. In another aspect, the polypeptide comprises or consists of amino acids 1 to 268 of SEQ ID NO 44.

In one embodiment, the polypeptide preferably comprises or consists of the amino acid sequence shown in SEQ ID NO 45; comprises the amino acid sequence shown in SEQ ID NO 45 and a N-terminal and/or C-terminal His-tag and/or HQ-tag; comprises the amino acid sequence of SEQ ID NO 45 and a N-terminal and/or C-terminal extension of between 1 and 10 amino acids; or is a fragment thereof having hydrolytic activity and having at least 50% such as at least 60%, at least 70%, at least 75%, at least 80%, at least 85%, at least 90%, at least 95%, at least 96%, at least 97%, at least 98% or at least 99% of the length of SEQ ID NO 45.

In some embodiment, the polypeptide has been isolated. A polypeptide of the present invention preferably comprises or consists of the amino acid sequence shown in SEQ ID NO 48 or an allelic variant thereof; or is a fragment thereof having hydrolytic activity. In another aspect, the polypeptide comprises or consists of the mature polypeptide of SEQ ID NO 47. In another aspect, the polypeptide comprises or consists of amino acids 1 to 267 of SEQ ID NO 47.

In one embodiment, the polypeptide preferably comprises or consists of the amino acid sequence shown in SEQ ID NO 48; comprises the amino acid sequence shown in SEQ ID NO 48 and a N-terminal and/or C-terminal His-tag and/or HQ-tag; comprises the amino acid sequence of SEQ ID NO 48 and a N-terminal and/or C-terminal extension of between 1 and 10 amino acids; or is a fragment thereof having hydrolytic activity and having at least 50% such as at least 60%, at least 70%, at least 75%, at least 80%, at least 85%, at least 90%, at least 95%, at least 96%, at least 97%, at least 98% or at least 99% of the length of SEQ ID NO 48.

In some embodiment, the polypeptide has been isolated. A polypeptide of the present invention preferably comprises or consists of the amino acid sequence shown in SEQ ID NO 51 or an allelic variant thereof; or is a fragment thereof having hydrolytic activity. In another aspect, the polypeptide comprises or consists of the mature polypeptide of SEQ ID NO 50. In another aspect, the polypeptide comprises or consists of amino acids 1 to 251 of SEQ ID NO 50.

In one embodiment, the polypeptide preferably comprises or consists of the amino acid sequence shown in SEQ ID NO 51; comprises the amino acid sequence shown in SEQ ID NO 51 and a N-terminal and/or C-terminal His-tag and/or HQ-tag; comprises the amino acid sequence of SEQ ID NO 51 and a N-terminal and/or C-terminal extension of between 1 and 10 amino acids; or is a fragment thereof having hydrolytic activity and having at least 50% such as at least 60%, at least 70%, at least 75%, at least 80%, at least 85%, at least 90%, at least 95%, at least 96%, at least 97%, at least 98% or at least 99% of the length of SEQ ID NO 51.

In some embodiment, the polypeptide has been isolated. A polypeptide of the present invention preferably comprises or consists of the amino acid sequence shown in SEQ ID NO 54 or an allelic variant thereof; or is a fragment thereof having hydrolytic activity. In another aspect, the polypeptide comprises or consists of the mature polypeptide of SEQ ID NO 53. In another aspect, the polypeptide comprises or consists of amino acids 1 to 239 of SEQ ID NO 53.

In one embodiment, the polypeptide preferably comprises or consists of the amino acid sequence shown in SEQ ID NO 54; comprises the amino acid sequence shown in SEQ ID NO 54 and a N-terminal and/or C-terminal His-tag and/or HQ-tag; comprises the amino acid sequence of SEQ ID NO 54 and a N-terminal and/or C-terminal extension of between 1 and 10 amino acids; or is a fragment thereof having hydrolytic activity and having at least 50% such as at least 60%, at least 70%, at least 75%, at least 80%, at least 85%, at least 90%, at least 95%, at least 96%, at least 97%, at least 98% or at least 99% of the length of SEQ ID NO 54.

In some embodiment, the polypeptide has been isolated. A polypeptide of the present invention preferably comprises or consists of the amino acid sequence shown in SEQ ID NO 57 or an allelic variant thereof; or is a fragment thereof having hydrolytic activity. In another aspect, the polypeptide comprises or consists of the mature polypeptide of SEQ ID NO 56. In another aspect, the polypeptide comprises or consists of amino acids 1 to 279 of SEQ ID NO 56.

In one embodiment, the polypeptide preferably comprises or consists of the amino acid sequence shown in SEQ ID NO 57; comprises the amino acid sequence shown in SEQ ID NO 57 and a N-terminal and/or C-terminal His-tag and/or HQ-tag; comprises the amino acid sequence of SEQ ID NO 57 and a N-terminal and/or C-terminal extension of between 1 and 10 amino acids; or is a fragment thereof having hydrolytic activity and having at least 50% such as at least 60%, at least 70%, at least 75%, at least 80%, at least 85%, at least 90%, at least 95%, at least 96%, at least 97%, at least 98% or at least 99% of the length of SEQ ID NO 57.

In one embodiment, the polypeptide preferably comprises or consists of the amino acid sequence shown in:

a) SEQ ID NO 72, SEQ ID NO 73, SEQ ID NO 74, SEQ ID NO 75, SEQ ID NO 76, SEQ ID NO 77, SEQ ID NO 78, SEQ ID NO 79, SEQ ID NO 80, SEQ ID NO 81, SEQ ID NO 82, SEQ ID NO 83, SEQ ID NO 84, SEQ ID NO 85, SEQ ID NO 86, SEQ ID NO 87, SEQ ID NO 88, SEQ ID NO 89, SEQ ID NO 90, SEQ ID NO 91, SEQ ID NO 92, SEQ ID NO 93, SEQ ID NO 94, SEQ ID NO 95, SEQ ID NO 96, SEQ ID NO 97, SEQ ID NO 98, SEQ ID NO 99, SEQ ID NO 100, SEQ ID NO 101, SEQ ID NO 102, SEQ ID NO 103, SEQ ID NO 104, SEQ ID NO 105, SEQ ID NO 106, SEQ ID NO 107, SEQ ID NO 108, SEQ ID NO 109, SEQ ID NO 110, SEQ ID NO 111, SEQ ID NO 112, SEQ ID NO 113, SEQ ID NO 114, SEQ ID NO 115, SEQ ID

NO 116, SEQ ID NO 117, SEQ ID NO 118, SEQ ID NO 119, SEQ ID NO 120, SEQ ID NO 121, SEQ ID NO 122, SEQ ID NO 123, SEQ ID NO 124, SEQ ID NO 125, SEQ ID NO 126, SEQ ID NO 127, SEQ ID NO 128, SEQ ID NO 129, SEQ ID NO 130, SEQ ID NO 131, SEQ ID NO 132, SEQ ED NO: 133, SEQ ID NO 134, SEQ ID NO 135, SEQ ID NO 136, SEQ ID NO 137, SEQ ID NO 138, SEQ ID NO 139, SEQ ID NO 140, SEQ ID NO 141, SEQ ID NO 142, SEQ ID NO 143, SEQ ID NO 144, SEQ ID NO 145 or SEQ ID NO 146;

b) comprises the amino acid sequence shown in a) and a N-terminal and/or C-terminal His-tag and/or HQ-tag;

c) comprises the amino acid sequence of a) and a N-terminal and/or C-terminal extension of between 1 and 10 amino acids; or d) is a fragment thereof having hydrolytic activity, preferably alpha-1,4-polygalactosaminidase activity, and having at least 50% such as at least 60%, at least 70%, at least 75%, at least 80%, at least 85%, at least 90%, at least 95%, at least 96%, at least 97%, at least 98% or at least 99% of the length of any of the polypeptides of a).

In some aspect, the invention relates to a polypeptide which comprises or consists of the amino acid sequence shown in SEQ ID NO 3.

In some aspect, the invention relates to a polypeptide which comprises or consists of the amino acid sequence shown in SEQ ID NO 6.

In some aspect, the invention relates to a polypeptide which comprises or consists of the amino acid sequence shown in SEQ ID NO 9.

In some aspect, the invention relates to a polypeptide which comprises or consists of the amino acid sequence shown in SEQ ID NO 12.

In some aspect, the invention relates to a polypeptide which comprises or consists of the amino acid sequence shown in SEQ ID NO 15.

In some aspect, the invention relates to a polypeptide which comprises or consists of the amino acid sequence shown in SEQ ID NO 18.

In some aspect, the invention relates to a polypeptide which comprises or consists of the amino acid sequence shown in SEQ ID NO 21.

In some aspect, the invention relates to a polypeptide which comprises or consists of the amino acid sequence shown in SEQ ID NO 24.

In some aspect, the invention relates to a polypeptide which comprises or consists of the amino acid sequence shown in SEQ ID NO 27.

In some aspect, the invention relates to a polypeptide which comprises or consists of the amino acid sequence shown in SEQ ID NO 30.

In some aspect, the invention relates to a polypeptide which comprises or consists of the amino acid sequence shown in SEQ ID NO 33.

In some aspect, the invention relates to a polypeptide which comprises or consists of the amino acid sequence shown in SEQ ID NO 36.

In some aspect, the invention relates to a polypeptide which comprises or consists of the amino acid sequence shown in SEQ ID NO 39.

In some aspect, the invention relates to a polypeptide which comprises or consists of the amino acid sequence shown in SEQ ID NO 42.

In some aspect, the invention relates to a polypeptide which comprises or consists of the amino acid sequence shown in SEQ ID NO 45.

In some aspect, the invention relates to a polypeptide which comprises or consists of the amino acid sequence shown in SEQ ID NO 48.

In some aspect, the invention relates to a polypeptide which comprises or consists of the amino acid sequence shown in SEQ ID NO 51.

In some aspect, the invention relates to a polypeptide which comprises or consists of the amino acid sequence shown in SEQ ID NO 54.

In some aspect, the invention relates to a polypeptide which comprises or consists of the amino acid sequence shown in SEQ ID NO 57.

In some aspect, the invention relates to a polypeptide which comprises or consists of the amino acid sequence shown in SEQ ID NO 72, SEQ ID NO 73, SEQ ID NO 74, SEQ ID NO 75, SEQ ID NO 76, SEQ ID NO 77, SEQ ID NO 78, SEQ ID NO 79, SEQ ID NO 80, SEQ ID NO 81, SEQ ID NO 82, SEQ ID NO 83, SEQ ID NO 84, SEQ ID NO 85, SEQ ID NO 86, SEQ ID NO 87, SEQ ID NO 88, SEQ ID NO 89, SEQ ID NO 90, SEQ ID NO 91, SEQ ID NO 92, SEQ ID NO 93, SEQ ID NO 94, SEQ ID NO 95, SEQ ID NO 96, SEQ ID NO 97, SEQ ID NO 98, SEQ ID NO 99, SEQ ID NO 100, SEQ ID NO 101, SEQ ID NO 102, SEQ ID NO 103, SEQ ID NO 104, SEQ ID NO 105, SEQ ID NO 106, SEQ ID NO 107, SEQ ID NO 108, SEQ ID NO 109, SEQ ID NO 110, SEQ ID NO 111, SEQ ID NO 112, SEQ ID NO 113, SEQ ID NO 114, SEQ ID NO 115, SEQ ID NO 116, SEQ ID NO 117, SEQ ID NO 118, SEQ ID NO 119, SEQ ID NO 120, SEQ ID NO 121, SEQ ID NO 122, SEQ ID NO 123, SEQ ID NO 124, SEQ ID NO 125, SEQ ID NO 126, SEQ ID NO 127, SEQ ID NO 128, SEQ ID NO 129, SEQ ID NO 130, SEQ ID NO 131, SEQ ID NO 132, SEQ ED NO: 133, SEQ ID NO 134, SEQ ID NO 135, SEQ ID NO 136, SEQ ID NO 137, SEQ ID NO 138, SEQ ID NO 139, SEQ ID NO 140, SEQ ID NO 141, SEQ ID NO 142, SEQ ID NO 143, SEQ ID NO 144, SEQ ID NO 145 or SEQ ID NO 146.

In some embodiment, the present invention relates to variants of the mature polypeptide shown in SEQ ID NO 3 comprising a substitution, deletion, and/or insertion at one or more (e.g., several) positions. In some embodiment, the number of amino acid substitutions, deletions and/or insertions introduced into the mature polypeptide shown in SEQ ID NO 3 is up to 10, e.g., 1, 2, 3, 4, 5, 6, 7, 8, 9, or 10.

In some embodiment, the present invention relates to variants of the mature polypeptide shown in SEQ ID NO 6 comprising a substitution, deletion, and/or insertion at one or more (e.g., several) positions. In some embodiment, the number of amino acid substitutions, deletions and/or insertions introduced into the mature polypeptide shown in SEQ ID NO 6 is up to 10, e.g., 1, 2, 3, 4, 5, 6, 7, 8, 9, or 10.

In some embodiment, the present invention relates to variants of the mature polypeptide shown in SEQ ID NO 9 comprising a substitution, deletion, and/or insertion at one or more (e.g., several) positions. In some embodiment, the number of amino acid substitutions, deletions and/or insertions introduced into the mature polypeptide shown in SEQ ID NO 9 is up to 10, e.g., 1, 2, 3, 4, 5, 6, 7, 8, 9, or 10.

In some embodiment, the present invention relates to variants of the mature polypeptide shown in SEQ ID NO 12 comprising a substitution, deletion, and/or insertion at one or more (e.g., several) positions. In some embodiment, the number of amino acid substitutions, deletions and/or insertions introduced into the mature polypeptide shown in SEQ ID NO 12 is up to 10, e.g., 1, 2, 3, 4, 5, 6, 7, 8, 9, or 10.

In some embodiment, the present invention relates to variants of the mature polypeptide shown in SEQ ID NO 15 comprising a substitution, deletion, and/or insertion at one or more (e.g., several) positions. In some embodiment, the number of amino acid substitutions, deletions and/or insertions introduced into the mature polypeptide shown in SEQ ID NO 15 is up to 10, e.g., 1, 2, 3, 4, 5, 6, 7, 8, 9, or 10.

In some embodiment, the present invention relates to variants of the mature polypeptide shown in SEQ ID NO 18 comprising a substitution, deletion, and/or insertion at one or more (e.g., several) positions. In some embodiment, the number of amino acid substitutions, deletions and/or insertions introduced into the mature polypeptide shown in SEQ ID NO 18 is up to 10, e.g., 1, 2, 3, 4, 5, 6, 7, 8, 9, or 10.

In some embodiment, the present invention relates to variants of the mature polypeptide shown in SEQ ID NO 21 comprising a substitution, deletion, and/or insertion at one or more (e.g., several) positions. In some embodiment, the number of amino acid substitutions, deletions and/or insertions introduced into the mature polypeptide shown in SEQ ID NO 21 is up to 10, e.g., 1, 2, 3, 4, 5, 6, 7, 8, 9, or 10.

In some embodiment, the present invention relates to variants of the mature polypeptide shown in SEQ ID NO 24 comprising a substitution, deletion, and/or insertion at one or more (e.g., several) positions. In some embodiment, the number of amino acid substitutions, deletions and/or insertions introduced into the mature polypeptide shown in SEQ ID NO 24 is up to 10, e.g., 1, 2, 3, 4, 5, 6, 7, 8, 9, or 10.

In some embodiment, the present invention relates to variants of the mature polypeptide shown in SEQ ID NO 27 comprising a substitution, deletion, and/or insertion at one or more (e.g., several) positions. In some embodiment, the number of amino acid substitutions, deletions and/or insertions introduced into the mature polypeptide shown in SEQ ID NO 27 is up to 10, e.g., 1, 2, 3, 4, 5, 6, 7, 8, 9, or 10.

In some embodiment, the present invention relates to variants of the mature polypeptide shown in SEQ ID NO 30 comprising a substitution, deletion, and/or insertion at one or more (e.g., several) positions. In some embodiment, the number of amino acid substitutions, deletions and/or insertions introduced into the mature polypeptide shown in SEQ ID NO 30 is up to 10, e.g., 1, 2, 3, 4, 5, 6, 7, 8, 9, or 10.

In some embodiment, the present invention relates to variants of the mature polypeptide shown in SEQ ID NO 33 comprising a substitution, deletion, and/or insertion at one or more (e.g., several) positions. In some embodiment, the number of amino acid substitutions, deletions and/or insertions introduced into the mature polypeptide shown in SEQ ID NO 33 is up to 10, e.g., 1, 2, 3, 4, 5, 6, 7, 8, 9, or 10.

In some embodiment, the present invention relates to variants of the mature polypeptide shown in SEQ ID NO 36 comprising a substitution, deletion, and/or insertion at one or more (e.g., several) positions. In some embodiment, the number of amino acid substitutions, deletions and/or insertions introduced into the mature polypeptide shown in SEQ ID NO 36 is up to 10, e.g., 1, 2, 3, 4, 5, 6, 7, 8, 9, or 10.

In some embodiment, the present invention relates to variants of the mature polypeptide shown in SEQ ID NO 39 comprising a substitution, deletion, and/or insertion at one or more (e.g., several) positions. In some embodiment, the number of amino acid substitutions, deletions and/or insertions introduced into the mature polypeptide shown in SEQ ID NO 39 is up to 10, e.g., 1, 2, 3, 4, 5, 6, 7, 8, 9, or 10.

In some embodiment, the present invention relates to variants of the mature polypeptide shown in SEQ ID NO 42 comprising a substitution, deletion, and/or insertion at one or more (e.g., several) positions. In some embodiment, the number of amino acid substitutions, deletions and/or insertions introduced into the mature polypeptide shown in SEQ ID NO 42 is up to 10, e.g., 1, 2, 3, 4, 5, 6, 7, 8, 9, or 10.

In some embodiment, the present invention relates to variants of the mature polypeptide shown in SEQ ID NO 45 comprising a substitution, deletion, and/or insertion at one or more (e.g., several) positions. In some embodiment, the number of amino acid substitutions, deletions and/or insertions introduced into the mature polypeptide shown in SEQ ID NO 45 is up to 10, e.g., 1, 2, 3, 4, 5, 6, 7, 8, 9, or 10.

In some embodiment, the present invention relates to variants of the mature polypeptide shown in SEQ ID NO 48 comprising a substitution, deletion, and/or insertion at one or more (e.g., several) positions. In some embodiment, the number of amino acid substitutions, deletions and/or insertions introduced into the mature polypeptide shown in SEQ ID NO 48 is up to 10, e.g., 1, 2, 3, 4, 5, 6, 7, 8, 9, or 10.

In some embodiment, the present invention relates to variants of the mature polypeptide shown in SEQ ID NO 51 comprising a substitution, deletion, and/or insertion at one or more (e.g., several) positions. In some embodiment, the number of amino acid substitutions, deletions and/or insertions introduced into the mature polypeptide shown in SEQ ID NO 51 is up to 10, e.g., 1, 2, 3, 4, 5, 6, 7, 8, 9, or 10.

In some embodiment, the present invention relates to variants of the mature polypeptide shown in SEQ ID NO 54 comprising a substitution, deletion, and/or insertion at one or more (e.g., several) positions. In some embodiment, the number of amino acid substitutions, deletions and/or insertions introduced into the mature polypeptide shown in SEQ ID NO 54 is up to 10, e.g., 1, 2, 3, 4, 5, 6, 7, 8, 9, or 10.

In some embodiment, the present invention relates to variants of the mature polypeptide shown in SEQ ID NO 57 comprising a substitution, deletion, and/or insertion at one or more (e.g., several) positions. In some embodiment, the number of amino acid substitutions, deletions and/or insertions introduced into the mature polypeptide shown in SEQ ID NO 57 is up to 10, e.g., 1, 2, 3, 4, 5, 6, 7, 8, 9, or 10.

In some embodiment, the present invention relates to variants of the mature polypeptide shown SEQ ID NO 72, SEQ ID NO 73, SEQ ID NO 74, SEQ ID NO 75, SEQ ID NO 76, SEQ ID NO 77, SEQ ID NO 78, SEQ ID NO 79, SEQ ID NO 80, SEQ ID NO 81, SEQ ID NO 82, SEQ ID NO 83, SEQ ID NO 84, SEQ ID NO 85, SEQ ID NO 86, SEQ ID NO 87, SEQ ID NO 88, SEQ ID NO 89, SEQ ID NO 90, SEQ ID NO 91, SEQ ID NO 92, SEQ ID NO 93, SEQ ID NO 94, SEQ ID NO 95, SEQ ID NO 96, SEQ ID NO 97, SEQ ID NO 98, SEQ ID NO 99, SEQ ID NO 100, SEQ ID NO 101, SEQ ID NO 102, SEQ ID NO 103, SEQ ID NO 104, SEQ ID NO 105, SEQ ID NO 106, SEQ ID NO 107, SEQ ID NO 108, SEQ ID NO 109, SEQ ID NO 110, SEQ ID NO 111, SEQ ID NO 112, SEQ ID NO 113, SEQ ID NO 114, SEQ ID NO 115, SEQ ID NO 116, SEQ ID NO 117, SEQ ID NO 118, SEQ ID NO 119, SEQ ID NO 120, SEQ ID NO 121, SEQ ID NO 122, SEQ ID NO 123, SEQ ID NO 124, SEQ ID NO 125, SEQ ID NO 126, SEQ ID NO 127, SEQ ID NO 128, SEQ ID NO 129, SEQ ID NO 130, SEQ ID NO 131, SEQ ID NO 132, SEQ ED NO: 133, SEQ ID NO 134, SEQ ID NO 135, SEQ ID NO 136, SEQ ID NO 137, SEQ ID NO 138, SEQ ID NO 139, SEQ ID NO 140, SEQ ID NO 141, SEQ ID NO 142, SEQ ID NO 143, SEQ ID NO 144, SEQ ID NO 145 or SEQ ID NO 146 comprising a substitution, deletion, and/or insertion at one or more (e.g., several) positions. In some embodiment, the number of amino acid substitutions, deletions and/or insertions introduced into the mature polypeptide shown above is up to 10, e.g., 1, 2, 3, 4, 5, 6, 7, 8, 9, or 10.

One particular embodiment relates to a GH114 glycosyl hydrolase variant, which compared to a GH114 glycosyl hydrolase with SEQ ID NO: 18, comprises one or more alteration selected from the group consisting of: K1A, L11I, C23V, T39A, A64S, N73Q, N73R, N73K, G75V, A76M, A76R, A76V, L77V, L77A, L77T, L77K, Q78E, Q78M, Q78K, Q78N, Q78R, D79K, D79N, D79P, D79Q, D79V, D79W, D79T, W80M, W80Y, W80E, W801, W80R, D81V, S85A, S85G, S85W, S85C, K86D, K86E, K89F, K86W, K89D, K89A, K89E, K89P, K89S, K89V, K89W, E90A, E90D, E90N, E90S, V91M, V911, V91S, V91T, 192E, S97G, Y98W, D101*, S102*, E104*, E116D, E116K, T119K, 1124L, 1124V, D136E, D144*, D145E, D145G, E146*, K152D, K152G, K154E, K154T, K167D, K167T, K173T, Q178N, N209T, N209S, P212*, D222E, D222W, L234F, V242S, E243A, E243S, E243L, E243P, E243V, K244P, K244L, K244Q, K244R, T245C, T245D, G246Q, K247A, K247C, K247E, K247R, K247S, K247V, K247M, V248M, V248L, A250D, A250E, A250P, S251A, S251C, S251E, S251W, S251G, S251K, S251L, S251Q, S251T, N253C, N253E, N253L, N253M, N253A, N253P, N253W, K254M, K254R, K254A, K254C, K254D, K254E, K254H, K254V, K254T, Y256E, Y256G, Y256M, Y256R, Y256S, Y256W, Y256T, T258A, T258G, T258Q, T258D, T258E, T258S, A259E, A259P, E260G, E260K, E260Q, E260R, E260T, E260W, D261A, D261L, D261R, E262A, E262F, E262G, E2621, E262K, E262L, E262M, E262Q, E262R, E262S, E262T, E262V, E262W, E262C, E262D, K264R, 1270L, G279E, G279K, G279R, G279S, K295N and Y296*, wherein the positions correspond to the positions of SEQ ID NO: 18 (numbering according to SEQ ID NO: 18), wherein the variant has hydrolase activity, preferably alpha-1,4-polygalactosaminidase activity.

One particular embodiment relates to a GH114 glycosyl hydrolase variant, which compared to a GH114 glycosyl hydrolase with SEQ ID NO: 18, comprises one or more alteration selected from the group consisting of: K1A, L11, C23V, T39A, A64S, N73Q, N73R, N73K, G75V, A76M, A76R, A76V, L77V, L77A, L77T, L77K, Q78E, Q78M, Q78K, Q78N, Q78R, D79K, D79N, D79P, D79Q, D79V, D79W, D79T, W80M, W80Y, W80E, W801, W80R, D81V, S85A, S85G, S85W, S85C, K86D, K86E, K89F, K86W, K89D, K89A, K89E, K89P, K89S, K89V, K89W, E90A, E90D, E90N, E90S, V91M, V911, V91S, V91T, 192E, S97G, Y98W, D101*, S102*, E104*, E116D, E116K, T119K, 1124L, 124V, D136E, D144*, D145E, D145G, E146*, K152D, K152G, K154E, K154T, K167D, K167T, K173T, Q178N, N209T, N209S, P212*, D222E, D222W, L234F, V242S, E243A, E243S, E243L, E243P, E243V, K244P, K244L, K244Q, K244R, T245C, T245D, G246Q, K247A, K247C, K247E, K247R, K247S, K247V, K247M, V248M, V248L, A250D, A250E, A250P, S251A, S251C, S251E, S251W, S251G, S251K, S251L, S251Q, S251T, N253C, N253E, N253L, N253M, N253A, N253P, N253W, K254M, K254R, K254A, K254C, K254D, K254E, K254H, K254V, K254T, Y256E, Y256G, Y256M, Y256R, Y256S, Y256W, Y256T, T258A, T258G, T258Q, T258D, T258E, T258S, A259E, A259P, E260G, E260K, E260Q, E260R, E260T, E260W, D261A, D261L, D261R, E262A, E262F, E262G, E2621, E262K, E262L, E262M, E262Q, E262R, E262S, E262T, E262V, E262W, E262C, E262D, K264R, 1270L, G279E, G279K, G279R, G279S, K295N and Y296*, wherein the positions correspond to the positions of SEQ ID NO: 18 (numbering according to SEQ ID NO: 18), wherein the variant has a sequence identity to the polypeptide shown in SEQ ID NO 3, SEQ ID NO 6, SEQ ID NO 9, SEQ ID NO 12, SEQ ID NO 15, SEQ ID NO 18, SEQ ID NO 21, SEQ ID NO 24, SEQ ID NO 27, SEQ ID NO 30, SEQ ID NO 33, SEQ ID NO 36, SEQ ID NO 39, SEQ ID NO 42, SEQ ID NO 45, SEQ ID NO 48, SEQ ID NO 51, SEQ ID NO 54 SEQ ID NO 57, SEQ ID NO 72, SEQ ID NO 73, SEQ ID NO 74, SEQ ID NO 75, SEQ ID NO 76, SEQ ID NO 77, SEQ ID NO 78, SEQ ID NO 79, SEQ ID NO 80, SEQ ID NO 81, SEQ ID NO 82, SEQ ID NO 83, SEQ ID NO 84, SEQ ID NO 85, SEQ ID NO 86, SEQ ID NO 87, SEQ ID NO 88, SEQ ID NO 89, SEQ ID NO 90, SEQ ID NO 91, SEQ ID NO 92, SEQ ID NO 93, SEQ ID NO 94, SEQ ID NO 95, SEQ ID NO 96, SEQ ID NO 97, SEQ ID NO 98, SEQ ID NO 99, SEQ ID NO 100, SEQ ID NO 101, SEQ ID NO 102, SEQ ID NO 103, SEQ ID NO 104, SEQ ID NO 105, SEQ ID NO 106, SEQ ID NO 107, SEQ ID NO 108, SEQ ID NO 109, SEQ ID NO 110, SEQ ID NO 111, SEQ ID NO 112, SEQ ID NO 113, SEQ ID NO 114, SEQ ID NO 115, SEQ ID NO 116, SEQ ID NO 117, SEQ ID NO 118, SEQ ID NO 119, SEQ ID NO 120, SEQ ID NO 121, SEQ ID NO 122, SEQ ID NO 123, SEQ ID NO 124, SEQ ID NO 125, SEQ ID NO 126, SEQ ID NO 127, SEQ ID NO 128, SEQ ID NO 129, SEQ ID NO 130, SEQ ID NO 131, SEQ ID NO 132, SEQ ED NO: 133, SEQ ID NO 134, SEQ ID NO 135, SEQ ID NO 136, SEQ ID NO 137, SEQ ID NO 138, SEQ ID NO 139, SEQ ID NO 140, SEQ ID NO 141, SEQ ID NO 142, SEQ ID NO 143, SEQ ID NO 144, SEQ ID NO 145 or SEQ ID NO 146 of at least 60%, at least 70%, at least 75%, at least 80%, at least 85%, at least 90%, at least 95%, at least 96%, at least 97%, at least 98%, of at least 99% but less than 100%, and wherein the variant has hydrolase activity, preferably alpha-1,4-polygalactosaminidase activity.

One particular embodiment relates to a GH114 glycosyl hydrolase variant, which compared to a GH114 glycosyl hydrolase with SEQ ID NO: 18, comprises one or more alteration selected from the group consisting of: K1A, L11I, C23V, T39A, A64S, N73Q, N73R, N73K, G75V, A76M, A76R, A76V, L77V, L77A, L77T, L77K, Q78E, Q78M, Q78K, Q78N, Q78R, D79K, D79N, D79P, D79Q, D79V, D79W, D79T, W80M, W80Y, W80E, W801, W80R, D81V, S85A, S85G, S85W, S85C, K86D, K86E, K89F, K86W, K89D, K89A, K89E, K89P, K89S, K89V, K89W, E90A, E90D, E90N, E90S, V91M, V911, V91S, V91T, 192E, S97G, Y98W, D101*, S102*, E104*, E116D, E116K, T119K, 1124L, 1124V, D136E, D144*, D145E, D145G, E146*, K152D, K152G, K154E, K154T, K167D, K167T, K173T, Q178N, N209T, N209S, P212*, D222E, D222W, L234F, V242S, E243A, E243S, E243L, E243P, E243V, K244P, K244L, K244Q, K244R, T245C, T245D, G246Q, K247A, K247C, K247E, K247R, K247S, K247V, K247M, V248M, V248L, A250D, A250E, A250P, S251A, S251C, S251E, S251W, S251G, S251K, S251L, S251Q, S251T, N253C, N253E, N253L, N253M, N253A, N253P, N253W, K254M, K254R, K254A, K254C, K254D, K254E, K254H, K254V, K254T, Y256E, Y256G, Y256M, Y256R, Y256S, Y256W, Y256T, T258A, T258G, T258Q, T258D, T258E, T258S, A259E, A259P, E260G, E260K, E260Q, E260R, E260T, E260W, D261A, D261L, D261R, E262A, E262F, E262G, E2621, E262K, E262L, E262M, E262Q, E262R, E262S, E262T, E262V, E262W, E262C, E262D, K264R, 1270L, G279E, G279K, G279R, G279S, K295N and Y296*, wherein the positions correspond to the positions of SEQ ID NO: 18 (numbering according to SEQ ID NO: 18), wherein the variant has a sequence identity to the polypeptide shown in SEQ ID NO: 18 of at least 60%, at least 70%, at least 75%, at least 80%, at least 85%, at least 90%, at least 95%, at least 96%, at least 97%, at least 98%, of at least 99% but less than 100%, and wherein the variant has hydrolase activity, preferably alpha-1,4-polygalactosaminidase activity.

One embodiment relates to a GH114 glycosyl hydrolase variant, which compared to a GH114 glycosyl hydrolase with SEQ ID NO: 18, comprises one or more substitution selected from the group consisting of: K1A, L11I, C23V, T39A, A64S, N73Q, N73R, N73K, G75V, A76M, A76R, A76V, L77V, L77A, L77T, L77K, Q78E, Q78M, Q78K, Q78N, Q78R, D79K, D79N, D79P, D79Q, D79V, D79W, D79T, W80M, W80Y, W80E, W801, W80R, D81V, S85A, S85G, S85W, S85C, K86D, K86E, K89F, K86W, K89D, K89A, K89E, K89P, K89S, K89V, K89W, E90A, E90D, E90N, E90S, V91M, V911, V91S, V91T, 192E, S97G, Y98W, E116D, E116K, T119K, 1124L, 1124V, D136E, D145E, D145G, K152D, K152G, K154E, K154T, K167D, K167T, K173T, Q178N, N209T, N209S, D222E, D222W, L234F, V242S, E243A, E243S, E243L, E243P, E243V, K244P, K244L, K244Q, K244R, T245C, T245D, G246Q, K247A, K247C, K247E, K247R, K247S, K247V, K247M, V248M, V248L, A250D, A250E, A250P, S251A, S251C, S251E, S251W, S251G, S251K, S251L, S251Q, S251T, N253C, N253E, N253L, N253M, N253A, N253P, N253W, K254M, K254R, K254A, K254C, K254D, K254E, K254H, K254V, K254T, Y256E, Y256G, Y256M, Y256R, Y256S, Y256W, Y256T, T258A, T258G, T258Q, T258D, T258E, T258S, A259E, A259P, E260G, E260K, E260Q, E260R, E260T, E260W, D261A, D261L, D261R, E262A, E262F, E262G, E2621, E262K, E262L, E262M, E262Q, E262R, E262S, E262T, E262V, E262W, E262C, E262D, K264R, 1270L, G279E, G279K, G279R, G279S and K295N, wherein the positions correspond to the positions of SEQ ID NO: 18 (numbering according to SEQ ID NO: 18), wherein the variant has a sequence identity to the polypeptide shown in SEQ ID NO: 18 of at least 60%, at least 70%, at least 75%, at least 80%, at least 85%, at least 90%, at least 95%, at least 96%, at least 97%, at least 98%, of at least 99% but less than 100%, and wherein the variant has hydrolase activity, preferably alpha-1,4-polygalactosaminidase activity.

One particular embodiment relates to a GH114 glycosyl hydrolase variant, which compared to a GH114 glycosyl hydrolase with SEQ ID NO: 18, comprises one or more deletion selected from the group consisting of: D101*, S102*, E104*, D144*, E146*, P212* and Y296*, wherein the positions correspond to the positions of SEQ ID NO: 18 (numbering according to SEQ ID NO: 18), wherein the variant has a sequence identity to the polypeptide shown in SEQ ID NO: 18 at least 60%, at least 70%, at least 75%, at least 80%, at least 85%, at least 90%, at least 95%, at least 96%, at least 97%, at least 98%, of at least 99% but less than 100%, and wherein the variant has hydrolase activity, preferably having alpha-1,4-polygalactosaminidase activity.

The GH114 glycosyl hydrolase may comprise two or more alteration selected from the group consisting of: K1A, L11I, C23V, T39A, A64S, N73Q, N73R, N73K, G75V, A76M, A76R, A76V, L77V, L77A, L77T, L77K, Q78E, Q78M, Q78K, Q78N, Q78R, D79K, D79N, D79P, D79Q, D79V, D79W, D79T, W80M, W80Y, W80E, W801, W80R, D81V, S85A, S85G, S85W, S85C, K86D, K86E, K89F, K86W, K89D, K89A, K89E, K89P, K89S, K89V, K89W, E90A, E90D, E90N, E90S, V91M, V911, V91S, V91T, 192E, S97G, Y98W, D101*, S102*, E104*, E116D, E116K, T119K, 1124L, 1124V, D136E, D144*, D145E, D145G, E146*, K152D, K152G, K154E, K154T, K167D, K167T, K173T, Q178N, N209T, N209S, P212*, D222E, D222W, L234F, V242S, E243A, E243S, E243L, E243P, E243V, K244P, K244L, K244Q, K244R, T245C, T245D, G246Q, K247A, K247C, K247E, K247R, K247S, K247V, K247M, V248M, V248L, A250D, A250E, A250P, S251A, S251C, S251E, S251W, S251G, S251K, S251L, S251Q, S251T, N253C, N253E, N253L, N253M, N253A, N253P, N253W, K254M, K254R, K254A, K254C, K254D, K254E, K254H, K254V, K254T, Y256E, Y256G, Y256M, Y256R, Y256S, Y256W, Y256T, T258A, T258G, T258Q, T258D, T258E, T258S, A259E, A259P, E260G, E260K, E260Q, E260R, E260T, E260W, D261A, D261L, D261R, E262A, E262F, E262G, E2621, E262K, E262L, E262M, E262Q, E262R, E262S, E262T, E262V, E262W, E262C, E262D, K264R, 1270L, G279E, G279K, G279R, G279S, K295N and Y296*.

One embodiment relates to a GH114 glycosyl hydrolase variant, which compared to a GH114 glycosyl hydrolase with SEQ ID NO: 18, comprises one or more of the alterations selected from the group consisting of: G230D+A259P, 1172V+A250D, D101*+A166V, E103*+E104*, N160D+K254S, T119M+P212*, W80R+D145G, W80R+K154T and Y100*+D101*, wherein the variant has at least 60%, at least 70%, at least 75%, at least 80%, at least 85%, at least 90%, at least 95%, at least 96%, at least 97%, at least 98%, of at least 99% but less than 100% sequence identity to SEQ ID NO 18.

One embodiment, relates to a method for obtaining a GH114 glycosyl hydrolase variant, comprising;

a) introducing into a parent GH114 glycosyl hydrolase e.g. SEQ ID NO 18, one or more of the following mutations: K1A, L11I, C23V, T39A, A64S, N73Q, N73R, N73K, G75V, A76M, A76R, A76V, L77V, L77A, L77T, L77K, Q78E, Q78M, Q78K, Q78N, Q78R, D79K, D79N, D79P, D79Q, D79V, D79W, D79T, W80M, W80Y, W80E, W801, W80R, D81V, S85A, S85G, S85W, S85C, K86D, K86E, K89F, K86W, K89D, K89A, K89E, K89P, K89S, K89V, K89W, E90A, E90D, E90N, E90S, V91M, V911, V91S, V91T, 192E, S97G, Y98W, D101*, S102*, E104*, E116D, E116K, T119K, 1124L, 1124V, D136E, D144*, D145E, D145G, E146*, K152D, K152G, K154E, K154T, K167D, K167T, K173T, Q178N, N209T, N209S, P212*, D222E, D222W, L234F, V242S, E243A, E243S, E243L, E243P, E243V, K244P, K244L, K244Q, K244R, T245C, T245D, G246Q, K247A, K247C, K247E, K247R, K247S, K247V, K247M, V248M, V248L, A250D, A250E, A250P, S251A, S251C, S251E, S251W, S251G, S251K, S251L, S251Q, S251T, N253C, N253E, N253L, N253M, N253A, N253P, N253W, K254M, K254R, K254A, K254C, K254D, K254E, K254H, K254V, K254T, Y256E, Y256G, Y256M, Y256R, Y256S, Y256W, Y256T, T258A, T258G, T258Q, T258D, T258E, T258S, A259E, A259P, E260G, E260K, E260Q, E260R, E260T, E260W, D261A, D261L, D261R, E262A, E262F, E262G, E2621, E262K, E262L, E262M, E262Q, E262R, E262S, E262T, E262V, E262W, E262C, E262D, K264R, 1270L, G279E, G279K, G279R, G279S, K295N and Y296*, wherein the positions correspond to the positions of SEQ ID NO: 18 (numbering according to SEQ ID NO: 18) and wherein the variant has hydrolase activity, preferably having alpha-1,4-polygalactosaminidase activity, and
b) recovering the variant.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, *In, The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant molecules are tested for hydrolytic activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, DNA 7:127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide shown in the present invention. A fusion polypeptide is produced by fusing a polynucleotide encoding another polypeptide to a polynucleotide of the present invention. Techniques for producing fusion polypeptides are known in the art and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. nd. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

Sources of Polypeptides Having Hydrolytic Activity

A polypeptide having hydrolytic activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly. In one aspect, the polypeptide is a *Amycolatopsis* polypeptide, e.g., a polypeptide obtained from *Amycolatopsis circi* or *Amycolatopsis sp.* In one aspect, the polypeptide is a *Streptomyces* polypeptide, e.g., a polypeptide obtained from *Streptomyces* sp., *Streptomyces miharaensis* or *Streptomyces parvulus*. In one aspect, the polypeptide is a *Fusarium* polypeptide, e.g., a polypeptide obtained from *Fusarium solani*. In one aspect, the polypeptide is a *Nonomuraea* polypeptide, e.g., a polypeptide obtained from *Nonomuraea guangzhouensis*. In one aspect, the polypeptide is a *Vibrio* polypeptide, e.g., a polypeptide obtained from *Vibrio* sp. In one aspect, the polypeptide is a *Microbacterium* polypeptide, e.g., a polypeptide obtained from *Microbacterium oxydans* or *Microbacterium saccharophilum*. In one aspect, the polypeptide is a *Frigoribacterium* polypeptide, e.g., a polypeptide obtained from *Frigoribacterium faeni*. In one aspect, the polypeptide is a *Serinibacter* polypeptide, e.g., a polypeptide obtained from *Serinibacter sp.* In one aspect, the polypeptide is a *Oerskovia* polypeptide, e.g., a polypeptide obtained from *Oerskovia paurometabola*. In one aspect, the polypeptide is a *Agreia* polypeptide, e.g., a polypeptide obtained from *Agreia pratensis*. In one aspect, the polypeptide is a *Plantibacter* polypeptide, e.g., a polypeptide obtained from *Plantibacterflavus*. In one aspect, the polypeptide is a *Urnula* polypeptide, e.g., a polypeptide obtained from *Urnula craterium*.

In one aspect, the polypeptide is polypeptide obtained from *Chaetomium globosum, Stilbella fimetaria, Volutella ciliata, Clonostachys epichloe, Myrothecium sp., Botryotrichum piluliferum, Myrothecium sp., Amycolatopsis* sp., Methylothermaceae bacteria B42 *Amycolatopsis niigatensis, Streptomyces sp.* AA4, *Amycolatopsis alba* DSM 44262, *Streptomyces griseoaurantiacus, Kutzneria albida, Micro-*

*bacterium* sp, *Microbacterium oleivorans* 0827CG, *Nocardiopsis alba, Microbacterium oxydans, Agreia pratensis, Microbacterium lemovicicum, Xylanibacterium* sp, *Curtobacterium oceanosedimentum, Leucobacter tardus, Salinibacterium amurskyense, Neonectria candida, Fusarium compactum, Fusarium compactum, Fusarium avenaceum, Preussia aemulans, Fusarium proliferatum, Fusarium lateritium, Fusarium proliferatum, Chaetomium ancistrocladum, Fusarium verticillioides, Fusarium lateritium, Chaetomium sp.* ZY474, *Scytalidium sp.* T045-6, *Acremonium sp., Chaetomium strumarium, Fusarium oxysporum, Fusarium temperatum, Thermoascus taitungiacus, Plectosphaerella alismatis, Thermothelomyces hinnuleus, Ovatospora brasiliensis, Fusarium acuminatum, Fusarium euwallaceae, Fusarium neocosmosporiellum, Thielavia antarctica, Acremonium thermophilum, Crassicarpon hotsonii, Helicosporium* sp, *Pyrenochaetopsis sp., Acremonium cf. fusifioides, Rasamsonia byssochlamydoides, Acremonium dichromosporum, Thermomyces dupontii, Ovatospora medusarum, Marasmius oreades, Amycolatopsis niigatensis, Byssochlamys spectabilis, Coprinopsis* sp, *Fusarium sambucinum, Amycolatopsis orientalis* DSM 46075, Xanthan alkaline community D, *Pilimelia columellifera* subsp. *pallida, Cellulomonas cellasea*, Gluten B enrichment AX2, *Microbacterium* sp., *Arthrobacter agilis, Amycolatopsis bullii, Microbacterium oxydans, Microbacterium phyllosphaerae* or *Phycicoccus dokdonensis.*

In one embodiment, the GH114 glycosyl hydrolase is obtained from *Amycolatopsis*, preferably *Amycolatopsis circi* or *Amycolatopsis* sp., wherein the GH114 glycosyl hydrolase comprises one or more, or even all of the motif(s) [VL]XE[EDSQ]C (SEQ ID NO 60), CY[FLIV][SDN][ATVG] (SEQ ID NO 61), DYQ[L]G (SEQ ID NO 62), FQ[TAV]Q[PSD] (SEQ ID NO 63), AEECG (SEQ ID NO 64), NAFQ[AT]Q (SEQ ID NO 65). In one embodiment, the GH114 glycosyl hydrolase is obtained from *Amycolatopsis*, preferably *Amycolatopsis circi* or *Amycolatopsis* sp, wherein the GH114 glycosyl hydrolase is a polypeptide having;

a) at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO 3;
b) at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO 6; or
c) at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO 9.

In one embodiment, the GH114 glycosyl hydrolase is obtained from *Streptomyces*, preferably *Streptomyces parvulus* or *Streptomyces miharaensis*, wherein the GH114 glycosyl hydrolase comprises one or more, or even all of the motif(s) [VL]XE[EDSQ]C (SEQ ID NO 60), CY[FLIV][SDN][ATVG] (SEQ ID NO 61), DYQ[L]G (SEQ ID NO 62), FQ[TAV]Q[PSD] (SEQ ID NO 63), AEECG (SEQ ID NO 64), NAFQ[AT]Q (SEQ ID NO 65). In one embodiment, the GH114 glycosyl hydrolase is obtained from *Streptomyces*, preferably *Streptomyces parvulus* or *Streptomyces miharaensis*, wherein the GH114 glycosyl hydrolase is;

a) a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO 12;
b) is a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO 24; or
c) a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO 54.

In one embodiment, the GH114 glycosyl hydrolase is obtained from *Fusarium*, preferably *Fusarium solani*, wherein the GH114 glycosyl hydrolase comprises one or more, or even all of the motif(s) [VLI]XE[EDSQ]C (SEQ ID NO 60), CY[FLIV][SDN][ATVG] (SEQ ID NO 61), GXXVX[NHQTS]IEY[PG] (SEQ ID NO 68), VICYF (SEQ ID NO 69), ICYFSA (SEQ ID NO 70), DFAVL (SEQ ID NO 71). In one embodiment, the GH114 glycosyl hydrolase is obtained from *Fusarium*, preferably *Fusarium solani*, wherein the GH114 glycosyl hydrolase is a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO 15 or a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO 18.

In one embodiment, the GH114 glycosyl hydrolase is obtained from *Nonomuraea*, preferably *Nonomuraea guangzhouensis*, wherein the GH114 glycosyl hydrolase comprises one or more, or even all of the motif(s) [VL]XE[EDSQ]C (SEQ ID NO 60), CY[FLIV][SDN][ATVG](SEQ ID NO 61), DYQ[LI]G (SEQ ID NO 62), FQ[TAV]Q[PSD] (SEQ ID NO 63), AEECG (SEQ ID NO 64), NAFQ[AT]Q (SEQ ID NO 65). In one embodiment, the GH114 glycosyl hydrolase is obtained from *Nonomuraea*, preferably *Nonomuraea guangzhouensis*, wherein the GH114 glycosyl hydrolase is a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO 21.

In one embodiment, the GH114 glycosyl hydrolase is obtained from *Vibrio*, preferably *Vibrio* sp., wherein the GH114 glycosyl hydrolase comprises one or more, or even all of the motif(s) [VLI]XE[EDSQ]C (SEQ ID NO 60), CY[FLIV][SDN][ATVG] (SEQ ID NO 61), WQWQL (SEQ ID NO 66), [VLI][GASD]LKN[DGS][VLIP] (SEQ ID NO 67). In one embodiment, the GH114 glycosyl hydrolase is obtained from *Vibrio*, preferably *Vibrio* sp., wherein the GH114 glycosyl hydrolase is a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO 27.

In one embodiment, the GH114 glycosyl hydrolase is obtained from *Microbacterium*, preferably *Microbacterium saccharophilum* or *Microbacterium oxydans*, wherein the GH114 glycosyl hydrolase comprises one or more, or even both of the motif(s) [VL]XE[EDSQ]C (SEQ ID NO 60), CY[FLIV][SDN][ATVG] (SEQ ID NO 61). In one embodiment, the GH114 glycosyl hydrolase is obtained from *Microbacterium*, preferably *Microbacterium saccharophilum* or *Microbacterium oxydans*, wherein the GH114 glycosyl hydrolase is a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO 33 or a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO 36.

In one embodiment, the GH114 glycosyl hydrolase is obtained from *Frigoribacterium*, preferably *Frigoribacterium faeni*, wherein the GH114 glycosyl hydrolase comprises one or more, or even all of the motif(s) [VL]XE[EDSQ]C (SEQ ID NO 60), CY[FLIV][SDN][ATVG] (SEQ ID NO 61), DYQ[L]G (SEQ ID NO 62), FQ[TAV]Q[PSD] (SEQ ID NO 63). In one embodiment, the GH114 glycosyl hydrolase is obtained from *Frigoribacterium*, preferably *Frigoribacterium faeni*, wherein the GH114 glycosyl hydrolase is a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO 39.

In one embodiment, the GH114 glycosyl hydrolase is obtained from *Serinibacter*, preferably *Serinibacter* sp, wherein the GH114 glycosyl hydrolase comprises one or more, or even all of the motif(s) [VL]XE[EDSQ]C (SEQ ID NO 60), CY[FLIV][SDN][ATVG] (SEQ ID NO 61), DYQ[L]G (SEQ ID NO 62), FQ[TAV]Q[PSD] (SEQ ID NO 63). In one embodiment, the GH114 glycosyl hydrolase is obtained from *Serinibacter*, preferably *Serinibacter sp.*, wherein the GH114 glycosyl hydrolase is a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO 42.

In one embodiment, the GH114 glycosyl hydrolase is obtained from *Oerskovia*, preferably *Oerskovia paurometabola*, wherein the GH114 glycosyl hydrolase comprises one or more, or even all of the motif(s) [VL]XE[EDSQ]C (SEQ ID NO 60), CY[FLIV][SDN][ATVG] (SEQ ID NO 61), DYQ[L]G (SEQ ID NO 62), FQ[TAV]Q[PSD] (SEQ ID NO 63). In one embodiment, the GH114 glycosyl hydrolase is obtained from *Oerskovia*, preferably *Oerskovia paurometabola*, wherein the GH114 glycosyl hydrolase is a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO 45.

In one embodiment, the GH114 glycosyl hydrolase is obtained from *Agreia*, preferably *Agreia pratensis*, wherein the GH114 glycosyl hydrolase comprises one or more, or even all of the motif(s) [VLI]XE[EDSQ]C (SEQ ID NO 60), CY[FLIV][SDN][ATVG] (SEQ ID NO 61), DYQ[LI]G (SEQ ID NO 62), FQ[TAV]Q[PSD] (SEQ ID NO 63). In one embodiment, the GH114 glycosyl hydrolase is obtained from *Agreia*, preferably *Agreia pratensis*, wherein the GH114 glycosyl hydrolase is a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO 48.

In one embodiment, the GH114 glycosyl hydrolase is obtained from *Plantibacter*, preferably *Plantibacterflavus*, wherein the GH114 glycosyl hydrolase comprises one or more, or even all of the motif(s) [VL]XE[EDSQ]C (SEQ ID NO 60), CY[FLIV][SDN][ATVG] (SEQ ID NO 61), DYQ[L]G (SEQ ID NO 62), FQ[TAV]Q[PSD] (SEQ ID NO 63). In one embodiment, the GH114 glycosyl hydrolase is obtained from *Plantibacter*, preferably *Plantibacterflavus*, wherein the GH114 glycosyl hydrolase is a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO 51.

In one embodiment, the GH114 glycosyl hydrolase is obtained from *Urnula*, preferably *Urnula craterium*, wherein the GH114 glycosyl hydrolase comprises one or more, or even all of the motif(s) [VLI]XE[EDSQ]C (SEQ ID NO 60), CY[FLIV][SDN][ATVG] (SEQ ID NO 61), GXXVX[NHQTS]IEY[PG] (SEQ ID NO 68), VICYF (SEQ ID NO 69), ICYFSA (SEQ ID NO 70). In one embodiment, the GH114 glycosyl hydrolase is obtained from *Urnula*, preferably *Urnula craterium*, wherein the GH114 glycosyl hydrolase is a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO 57.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen und Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Polynucleotides

The present invention also relates to polynucleotides encoding a polypeptide of the present invention, as described herein. In some embodiment, the polynucleotide encoding the polypeptide shown in the present invention has been isolated.

In some embodiment, the present invention relates to a polynucleotide encoding a polypeptide having hydrolytic activity, wherein the polynucleotide having a sequence identity to the mature polypeptide coding sequence of SEQ ID NO 1 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In some embodiment, the present invention relates to a polynucleotide encoding a polypeptide having hydrolytic activity, wherein the polynucleotide having a sequence identity to the mature polypeptide coding sequence of SEQ ID NO 4 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In some embodiment, the present invention relates to a polynucleotide encoding a polypeptide having hydrolytic activity, wherein the polynucleotide having a sequence identity to the mature polypeptide coding sequence of SEQ ID NO 7 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In some embodiment, the present invention relates to a polynucleotide encoding a polypeptide having hydrolytic activity, wherein the polynucleotide having a sequence identity to the mature polypeptide coding sequence of SEQ ID NO 10 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In some embodiment, the present invention relates to a polynucleotide encoding a polypeptide having hydrolytic activity, wherein the polynucleotide having a sequence identity to the mature polypeptide coding sequence of SEQ ID NO 13 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In some embodiment, the present invention relates to a polynucleotide encoding a polypeptide having hydrolytic activity, wherein the polynucleotide having a sequence identity to the mature polypeptide coding sequence of SEQ ID NO 16 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In some embodiment, the present invention relates to a polynucleotide encoding a polypeptide having hydrolytic activity, wherein the polynucleotide having a sequence identity to the mature polypeptide coding sequence of SEQ ID NO 19 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In some embodiment, the present invention relates to a polynucleotide encoding a polypeptide having hydrolytic activity, wherein the polynucleotide having a sequence identity to the mature polypeptide coding sequence of SEQ ID NO 22 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In some embodiment, the present invention relates to a polynucleotide encoding a polypeptide having hydrolytic activity, wherein the polynucleotide having a sequence identity to the mature polypeptide coding sequence of SEQ ID NO 25 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In some embodiment, the present invention relates to a polynucleotide encoding a polypeptide having hydrolytic activity, wherein the polynucleotide having a sequence identity to the mature polypeptide coding sequence of SEQ ID NO 28 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In some embodiment, the present invention relates to a polynucleotide encoding a polypeptide having hydrolytic activity, wherein the polynucleotide having a sequence identity to the mature polypeptide coding sequence of SEQ ID NO 31 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In some embodiment, the present invention relates to a polynucleotide encoding a polypeptide having hydrolytic activity, wherein the polynucleotide having a sequence identity to the mature polypeptide coding sequence of SEQ ID NO 34 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In some embodiment, the present invention relates to a polynucleotide encoding a polypeptide having hydrolytic activity, wherein the polynucleotide having a sequence identity to the mature polypeptide coding sequence of SEQ ID NO 37 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In some embodiment, the present invention relates to a polynucleotide encoding a polypeptide having hydrolytic activity, wherein the polynucleotide having a sequence identity to the mature polypeptide coding sequence of SEQ ID NO 40 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In some embodiment, the present invention relates to a polynucleotide encoding a polypeptide having hydrolytic activity, wherein the polynucleotide having a sequence identity to the mature polypeptide coding sequence of SEQ ID NO 43 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In some embodiment, the present invention relates to a polynucleotide encoding a polypeptide having hydrolytic activity, wherein the polynucleotide having a sequence identity to the mature polypeptide coding sequence of SEQ ID NO 46 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In some embodiment, the present invention relates to a polynucleotide encoding a polypeptide having hydrolytic activity, wherein the polynucleotide having a sequence identity to the mature polypeptide coding sequence of SEQ ID NO 49 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In some embodiment, the present invention relates to a polynucleotide encoding a polypeptide having hydrolytic activity, wherein the polynucleotide having a sequence identity to the mature polypeptide coding sequence of SEQ ID NO 52 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In some embodiment, the present invention relates to a polynucleotide encoding a polypeptide having hydrolytic activity, wherein the polynucleotide having a sequence identity to the mature polypeptide coding sequence of SEQ ID NO 55 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

One embodiment, relates to an isolated nucleic acid sequence selected from the group consisting of:

a) a nucleic acid sequence encoding an enzyme comprising an amino acid sequence selected from the amino acid sequences of: SEQ ID NO 72, SEQ ID NO 73, SEQ ID NO 74, SEQ ID NO 75, SEQ ID NO 76, SEQ ID NO 77, SEQ ID NO 78, SEQ ID NO 79, SEQ ID NO 80, SEQ ID NO 81, SEQ ID NO 82, SEQ ID NO 83, SEQ ID NO 84, SEQ ID NO 85, SEQ ID NO 86, SEQ ID NO 87, SEQ ID NO 88, SEQ ID NO 89, SEQ ID NO 90, SEQ ID NO 91, SEQ ID NO 92, SEQ ID NO 93, SEQ ID NO 94, SEQ ID NO 95, SEQ ID NO 96, SEQ ID NO 97, SEQ ID NO 98, SEQ ID NO 99, SEQ ID NO 100, SEQ ID NO 101, SEQ ID NO 102, SEQ ID NO 103, SEQ ID NO 104, SEQ ID NO 105, SEQ ID NO 106, SEQ ID NO 107, SEQ ID NO 108, SEQ ID NO 109, SEQ ID NO 110, SEQ ID NO 111, SEQ ID NO 112, SEQ ID NO 113, SEQ ID NO 114, SEQ ID NO 115, SEQ ID NO 116, SEQ ID NO 117, SEQ ID NO 118, SEQ ID NO 119, SEQ ID NO 120, SEQ ID NO 121, SEQ ID NO 122, SEQ ID NO 123, SEQ ID NO 124, SEQ ID NO 125, SEQ ID NO 126, SEQ ID NO 127, SEQ ID NO 128, SEQ ID NO 129, SEQ ID NO 130, SEQ ID NO 131, SEQ ID NO 132, SEQ ED NO: 133, SEQ ID NO 134, SEQ ID NO 135, SEQ ID NO 136, SEQ ID NO 137, SEQ ID NO 138, SEQ ID NO 139, SEQ ID NO 140, SEQ ID NO 141, SEQ ID NO 142, SEQ ID NO 143, SEQ ID NO 144, SEQ ID NO 145 and SEQ ID NO 146;
b) a nucleic acid sequence encoding a fragment of an GH114 glycosyl hydrolase enzyme selected from (a), wherein the fragment has alpha-1,4-polygalactosaminidase activity; and
c) a nucleic acid sequence encoding a polypeptide having an amino acid sequence having at least 60%, at least 70%, at least 75%, at least 80%, at least 85%, at least 90%, at least 95% at least 98% or 100% sequence identity to an GH114 glycosyl hydrolase enzyme selected from (a) and has alpha-1,4-polygalactosaminidase activity.

One embodiment, relates to an isolated nucleic acid sequence selected from the group consisting of:

a) a nucleic acid sequence encoding an enzyme comprising an amino acid sequence selected from the amino acid sequences of: SEQ ID NO 72, SEQ ID NO 73, SEQ ID NO 74, SEQ ID NO 75, SEQ ID NO 76, SEQ ID NO 77, SEQ ID NO 78, SEQ ID NO 79, SEQ ID NO 80, SEQ ID NO 81, SEQ ID NO 82, SEQ ID NO 83, SEQ ID NO 84, SEQ ID NO 85, SEQ ID NO 86, SEQ ID NO 87, SEQ ID NO 88, SEQ ID NO 89, SEQ ID NO 90, SEQ ID NO 91, SEQ ID NO 92, SEQ ID NO 93, SEQ ID NO 94, SEQ ID NO 95, SEQ ID NO 96, SEQ ID NO 97, SEQ ID NO 98, SEQ ID NO 99, SEQ ID NO 100, SEQ ID NO 101, SEQ ID NO 102, SEQ ID NO 103, SEQ ID NO 104, SEQ ID NO 105, SEQ ID NO 106, SEQ ID NO 107, SEQ ID NO 108, SEQ ID NO 109, SEQ ID NO 110, SEQ ID NO 111, SEQ ID NO 112, SEQ ID NO 113, SEQ ID NO 114, SEQ ID NO 115, SEQ ID NO 116, SEQ ID NO 117, SEQ ID NO 118, SEQ ID NO 119, SEQ ID NO 120, SEQ ID NO 121, SEQ ID NO 122, SEQ ID NO 123, SEQ ID NO 124, SEQ ID NO 125, SEQ ID NO 126, SEQ ID NO 127, SEQ ID NO 128, SEQ ID NO 129, SEQ ID NO 130, SEQ ID NO 131, SEQ ID NO 132, SEQ ED NO: 133, SEQ ID NO 134, SEQ ID NO 135, SEQ ID NO 136, SEQ ID NO 137, SEQ ID NO 138, SEQ ID NO 139, SEQ ID NO 140, SEQ ID NO 141, SEQ ID NO 142, SEQ ID NO 143, SEQ ID NO 144, SEQ ID NO 145 and SEQ ID NO 146;

b) a nucleic acid sequence encoding a fragment of an GH114 glycosyl hydrolase enzyme selected from (a), wherein the fragment has alpha-1,4-polygalactosaminidase activity; and c) a nucleic acid sequence encoding a polypeptide having an amino acid sequence having at least 70% sequence identity to an GH114 glycosyl hydrolase enzyme selected from (a) and has alpha-1,4-polygalactosaminidase activity.

One embodiment, relates to an isolated nucleic acid sequence selected from the group consisting of:

a) a nucleic acid sequence encoding an enzyme comprising an amino acid sequence selected from the amino acid sequences of: SEQ ID NO 72, SEQ ID NO 73, SEQ ID NO 74, SEQ ID NO 75, SEQ ID NO 76, SEQ ID NO 77, SEQ ID NO 78, SEQ ID NO 79, SEQ ID NO 80, SEQ ID NO 81, SEQ ID NO 82, SEQ ID NO 83, SEQ ID NO 84, SEQ ID NO 85, SEQ ID NO 86, SEQ ID NO 87, SEQ ID NO 88, SEQ ID NO 89, SEQ ID NO 90, SEQ ID NO 91, SEQ ID NO 92, SEQ ID NO 93, SEQ ID NO 94, SEQ ID NO 95, SEQ ID NO 96, SEQ ID NO 97, SEQ ID NO 98, SEQ ID NO 99, SEQ ID NO 100, SEQ ID NO 101, SEQ ID NO 102, SEQ ID NO 103, SEQ ID NO 104, SEQ ID NO 105, SEQ ID NO 106, SEQ ID NO 107, SEQ ID NO 108, SEQ ID NO 109, SEQ ID NO 110, SEQ ID NO 111, SEQ ID NO 112, SEQ ID NO 113, SEQ ID NO 114, SEQ ID NO 115, SEQ ID NO 116, SEQ ID NO 117, SEQ ID NO 118, SEQ ID NO 119, SEQ ID NO 120, SEQ ID NO 121, SEQ ID NO 122, SEQ ID NO 123, SEQ ID NO 124, SEQ ID NO 125, SEQ ID NO 126, SEQ ID NO 127, SEQ ID NO 128, SEQ ID NO 129, SEQ ID NO 130, SEQ ID NO 131, SEQ ID NO 132, SEQ ED NO: 133, SEQ ID NO 134, SEQ ID NO 135, SEQ ID NO 136, SEQ ID NO 137, SEQ ID NO 138, SEQ ID NO 139, SEQ ID NO 140, SEQ ID NO 141, SEQ ID NO 142, SEQ ID NO 143, SEQ ID NO 144, SEQ ID NO 145 and SEQ ID NO 146;

b) a nucleic acid sequence encoding a fragment of an GH114 glycosyl hydrolase enzyme selected from (a), wherein the fragment has alpha-1,4-polygalactosaminidase activity; and c) a nucleic acid sequence encoding a polypeptide having an amino acid sequence having at least 80% sequence identity to an GH114 glycosyl hydrolase enzyme selected from (a) and has alpha-1,4-polygalactosaminidase activity.

One embodiment, relates to an isolated nucleic acid sequence selected from the group consisting of:

a) a nucleic acid sequence encoding an enzyme comprising an amino acid sequence selected from the amino acid sequences of: SEQ ID NO 72, SEQ ID NO 73, SEQ ID NO 74, SEQ ID NO 75, SEQ ID NO 76, SEQ ID NO 77, SEQ ID NO 78, SEQ ID NO 79, SEQ ID NO 80, SEQ ID NO 81, SEQ ID NO 82, SEQ ID NO 83, SEQ ID NO 84, SEQ ID NO 85, SEQ ID NO 86, SEQ ID NO 87, SEQ ID NO 88, SEQ ID NO 89, SEQ ID NO 90, SEQ ID NO 91, SEQ ID NO 92, SEQ ID NO 93, SEQ ID NO 94, SEQ ID NO 95, SEQ ID NO 96, SEQ ID NO 97, SEQ ID NO 98, SEQ ID NO 99, SEQ ID NO 100, SEQ ID NO 101, SEQ ID NO 102, SEQ ID NO 103, SEQ ID NO 104, SEQ ID NO 105, SEQ ID NO 106, SEQ ID NO 107, SEQ ID NO 108, SEQ ID NO 109, SEQ ID NO 110, SEQ ID NO 111, SEQ ID NO 112, SEQ ID NO 113, SEQ ID NO 114, SEQ ID NO 115, SEQ ID NO 116, SEQ ID NO 117, SEQ ID NO 118, SEQ ID NO 119, SEQ ID NO 120, SEQ ID NO 121, SEQ ID NO 122, SEQ ID NO 123, SEQ ID NO 124, SEQ ID NO 125, SEQ ID NO 126, SEQ ID NO 127, SEQ ID NO 128, SEQ ID NO 129, SEQ ID NO 130, SEQ ID NO 131, SEQ ID NO 132, SEQ ED NO: 133, SEQ ID NO 134, SEQ ID NO 135, SEQ ID NO 136, SEQ ID NO 137, SEQ ID NO 138, SEQ ID NO 139, SEQ ID NO 140, SEQ ID NO 141, SEQ ID NO 142, SEQ ID NO 143, SEQ ID NO 144, SEQ ID NO 145 and SEQ ID NO 146;

b) a nucleic acid sequence encoding a fragment of an GH114 glycosyl hydrolase enzyme selected from (a), wherein the fragment has alpha-1,4-polygalactosaminidase activity; and c) a nucleic acid sequence encoding a polypeptide having an amino acid sequence having at least 90% sequence identity to an GH114 glycosyl hydrolase enzyme selected from (a) and has alpha-1,4-polygalactosaminidase activity.

The techniques used to isolate or clone a polynucleotide are known in the art and include isolation from genomic DNA or cDNA, or a combination thereof. The cloning of the polynucleotides from genomic DNA can be affected, e.g., by using the well-known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

The polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including variant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E.*

*coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase I, *Trichoderma reesei* endoglucanase V, *Trichoderma reesei* xylanase I, *Trichoderma reesei* xylanase II, *Trichoderma reesei* xylanase Ill, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and variant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase I, *Trichoderma reesei* endoglucanase V, *Trichoderma reesei* xylanase I, *Trichoderma reesei* xylanase II, *Trichoderma reesei* xylanase Ill, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor* miehei aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosyl-aminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is an hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMB1 permitting replication in *Bacillus*.

Examples of origins of replication for use in a yeast host cell are the 2-micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma.*

The bacterial host cell may be any *Bacillus* cell including, but not limited to, *Bacillus alkalophilus, Bacillus altitudinis, Bacillus amyloliquefaciens, B. amyloliquefaciens* subsp. *plantarum, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus methylotrophicus, Bacillus pumilus, Bacillus safensis, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be affected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J.* Bacteriol. 169: 5271-5278). The introduction of DNA into an *E. coli* cell may be affected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be affected by protoplast transformation, electroporation (see, e.g., Gong et al., 2004, *Folia Microbiol.* (*Praha*) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be affected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be affected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi,* 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi *Imperfecti* (Blastomycetes). Since the classification of yeast may change in the future, for the purposes of this invention, yeast shall be defined as described in *Biology and Activities of Yeast* (Skinner, Passmore, and Davenport, editors, *Soc. App. Bacteriol. Symposium Series No.* 9, 1980).

The yeast host cell may be a *Candida, Hansenula, Kluyveromyces, Pichia, Saccharomyces, Schizosaccharomyces*, or *Yarrowia* cell, such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucormiehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising (a) cultivating a cell, which in its wild-type form produces the polypeptide, under conditions conducive for production of the polypeptide; and optionally, (b) recovering the polypeptide.

The present invention also relates to methods of producing a polypeptide, wherein the polypeptide is selected from the group consisting of:

(a) a polypeptide having at least 60%, at least 70%, at least 75%, at least 80%, at least 85%, at least 90%, at least 95%, at least 96%, at least 97%, at least 98%, at least 99% or 100% sequence identity to the polypeptide shown in SEQ ID NO 3;

(b) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 6;

(c) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 9;

(d) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 12;

(e) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 15;

(f) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 18;

(g) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 21;

(h) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 24;

(i) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 27;

(j) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 30;

(k) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 33;

(l) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 36;

(m) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 39;

(n) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 42;

(o) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 45;

(p) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 48;

(q) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 51;

(r) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 54; and a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 57, comprising (a) cultivating a cell, which in its wild-type form produces the polypeptide, under conditions conducive for production of the polypeptide; and optionally, (b) recovering the polypeptide.

The present invention also relates to methods of producing a polypeptide, wherein the polypeptide is selected from the group consisting of:

(a) a polypeptide having at least 60%, at least 70%, at least 75%, at least 80%, at least 85%, at least 90%, at least 95%, at least 96%, at least 97%, at least 98%, at least 99% or 100% sequence identity to the polypeptide shown in SEQ ID NO 3;

(b) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 6;

(c) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 9;

(d) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 12;

(e) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 15;

(f) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 18;

(g) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 21;

(h) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 24;

(i) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 27;

(j) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 30;

(k) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 33;

(l) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 36;

(m) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 39;

(n) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 42;

(o) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 45;

(p) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 48;

(q) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 51;

(r) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 54; and a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 57, comprising (a) cultivating a recombinant host cell of the present invention under conditions conducive for production of the polypeptide; and optionally, (b) recovering the polypeptide.

The host cells are cultivated in a nutrient medium suitable for production of the polypeptide using methods known in the art. For example, the cells may be cultivated by shake flask cultivation, or small-scale or large-scale fermentation (including continuous, batch, fed-batch, or solid-state fermentations) in laboratory or industrial fermenters in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides having hydrolytic activity. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, a fermentation broth comprising the polypeptide is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

Fermentation Broth Formulations or Cell Compositions

The present invention also relates to a fermentation broth formulation or a cell composition comprising a polypeptide of the present invention. The fermentation broth product further comprises additional ingredients used in the fermentation process, such as, for example, cells (including, the host cells containing the gene encoding the polypeptide shown in the present invention which are used to produce the polypeptide shown in interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In some embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis. In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Enzyme Compositions

The invention relates to compositions comprising a GH114 glycosyl hydrolase polypeptide of the present invention in combination with one or more additional component(s). The choice of additional components is within the skill of the artisan and includes conventional ingredients, including the exemplary non-limiting components set forth below.

Some embodiments of the invention relate to a composition comprising:

a) at least 0.001 ppm of at least one polypeptide having hydrolytic activity, preferably alpha-1,4-polygalactosaminidase activity, wherein the polypeptide is selected from the group consisting of polypeptides comprising the amino acid sequence shown in: SEQ ID NO 3, SEQ ID NO 6, SEQ ID NO 9, SEQ ID NO 12, SEQ ID NO 15, SEQ ID NO 18, SEQ ID NO 21, SEQ ID NO 24, SEQ ID NO 27, SEQ ID NO 30, SEQ ID NO 33, SEQ ID NO 36, SEQ ID NO 39, SEQ ID NO 42, SEQ ID NO 45, SEQ ID NO 48, SEQ ID NO 51, SEQ ID NO 54, SEQ ID NO 57, SEQ ID NO 72, SEQ ID NO 73, SEQ ID NO 74, SEQ ID NO 75, SEQ ID NO 76, SEQ ID NO 77, SEQ ID NO 78, SEQ ID NO 79, SEQ ID NO 80, SEQ ID NO 81, SEQ ID NO 82, SEQ ID NO 83, SEQ ID NO 84, SEQ ID NO 85, SEQ ID NO 86, SEQ ID NO 87, SEQ ID NO 88, SEQ ID NO 89, SEQ ID NO 90, SEQ ID NO 91, SEQ ID NO 92, SEQ ID NO 93, SEQ ID NO 94, SEQ ID NO 95, SEQ ID NO 96, SEQ ID NO 97, SEQ ID NO 98, SEQ ID NO 99, SEQ ID NO 100, SEQ ID NO 101, SEQ ID NO 102, SEQ ID NO 103, SEQ ID NO 104, SEQ ID NO 105, SEQ ID NO 106, SEQ ID NO 107, SEQ ID NO 108, SEQ ID NO 109, SEQ ID NO 110, SEQ ID NO 111, SEQ ID NO 112, SEQ ID NO 113, SEQ ID NO 114, SEQ ID NO 115, SEQ ID NO 116, SEQ ID NO 117, SEQ ID NO 118, SEQ ID NO 119, SEQ ID NO 120, SEQ ID NO 121, SEQ ID NO 122, SEQ ID NO 123, SEQ ID NO 124, SEQ ID NO 125, SEQ ID NO 126, SEQ ID NO 127, SEQ ID NO 128, SEQ ID NO 129, SEQ ID NO 130, SEQ ID NO 131, SEQ ID NO 132, SEQ ED NO: 133, SEQ ID NO 134, SEQ ID NO 135, SEQ ID NO 136, SEQ ID NO 137, SEQ ID NO 138, SEQ ID NO 139, SEQ ID NO 140, SEQ ID NO 141, SEQ ID NO 142, SEQ ID NO 143, SEQ ID NO 144, SEQ ID NO 145, SEQ ID NO 146 and polypeptides having at least 60%, at least 65%, at least 70%, at least 75%, at least 80%, at least 85%, at least 90%, at least 95%, at least 96%, at least 97%, at least 98%, at least 99% or 100% sequence identity hereto;

b) one or more adjunct ingredient.

Some embodiments of the invention relate to a cleaning composition comprising:

a) at least 0.001 ppm of at least one polypeptide having hydrolytic activity, preferably alpha-1,4-polygalactosaminidase activity, wherein the polypeptide is selected from the group consisting of polypeptides comprising the amino acid sequence shown in: SEQ ID NO 3, SEQ ID NO 6, SEQ ID NO 9, SEQ ID NO 12, SEQ ID NO 15, SEQ ID NO 18, SEQ ID NO 21, SEQ ID NO 24, SEQ ID NO 27, SEQ ID NO 30, SEQ ID NO 33, SEQ ID NO 36, SEQ ID NO 39, SEQ ID NO 42, SEQ ID NO 45, SEQ ID NO 48, SEQ ID NO 51, SEQ ID NO 54, SEQ ID NO 57, SEQ ID NO 72, SEQ ID NO 73, SEQ ID NO 74, SEQ ID NO 75, SEQ ID NO 76, SEQ ID NO 77, SEQ ID NO 78, SEQ ID NO 79, SEQ ID NO 80, SEQ ID NO 81, SEQ ID NO 82, SEQ ID NO 83, SEQ ID NO 84, SEQ ID NO 85, SEQ ID NO 86, SEQ ID NO 87, SEQ ID NO 88, SEQ ID NO 89, SEQ ID NO 90, SEQ ID NO 91, SEQ ID NO 92, SEQ ID NO 93, SEQ ID NO 94, SEQ ID NO 95, SEQ ID NO 96, SEQ ID NO 97, SEQ ID NO 98, SEQ ID NO 99, SEQ ID NO 100, SEQ ID NO 101, SEQ ID NO 102, SEQ ID NO 103, SEQ ID NO 104, SEQ ID NO 105, SEQ ID NO 106, SEQ ID NO 107, SEQ ID NO 108, SEQ ID NO 109, SEQ ID NO 110, SEQ ID NO 111, SEQ ID NO 112, SEQ ID NO 113, SEQ ID NO 114, SEQ ID NO 115, SEQ ID NO 116, SEQ ID NO 117, SEQ ID NO 118, SEQ ID NO 119, SEQ ID NO 120, SEQ ID NO 121, SEQ ID NO 122, SEQ ID NO 123, SEQ ID NO 124, SEQ ID NO 125, SEQ ID NO 126, SEQ ID NO 127, SEQ ID NO 128, SEQ ID NO 129, SEQ ID NO 130, SEQ ID NO 131, SEQ ID NO 132, SEQ ED NO: 133, SEQ ID NO 134, SEQ ID NO 135, SEQ ID NO 136, SEQ ID NO 137, SEQ ID NO 138, SEQ ID NO 139, SEQ ID NO 140, SEQ ID NO 141, SEQ ID NO 142, SEQ ID NO 143, SEQ ID NO 144, SEQ ID NO 145, SEQ ID NO 146 and polypeptides having at least 60%, at least 65%, at least 70%, at least 75%, at least 80%, at least 85%, at least 90%, at least 95%, at least 96%, at least 97%, at least 98%, at least 99% or 100% sequence identity hereto;

b) one or more cleaning composition component, preferably selected from surfactants, builders, bleach components, polymers, dispersing agents and additional enzymes.

Some embodiments of the invention relate to a cleaning composition comprising:

a) at least 0.001 ppm of at least one polypeptide having hydrolytic activity, preferably alpha-1,4-polygalactosaminidase activity, wherein the polypeptide comprises one or more motif selected from the group consisting of: [VL]XE[EDSQ]C (SEQ ID NO 60), CY[FLIV][SDN][ATVG] (SEQ ID NO 61), DYQ[L]G (SEQ ID NO 62), FQ[TAV]Q[PSD] (SEQ ID NO 63), AEECG (SEQ ID NO 64), NAFQ[AT]Q (SEQ ID NO 65), WQWQL (SEQ ID NO 66), [VLI][GASD]LKN [DGS][VLIP] (SEQ ID NO 67), GXXVX[NHQTS] IEY[PG] (SEQ ID NO 68), VICYF (SEQ ID NO 69), ICYFSA (SEQ ID NO 70), DFAVL (SEQ ID NO 71); and b) one or more cleaning composition component, preferably selected from surfactants, builders, bleach components, polymers, dispersing agents and additional enzymes.

One embodiment relates to a cleaning composition comprising:

a) at least 0.001 ppm of at least one polypeptide having hydrolytic activity, preferably alpha-1,4-polygalactosaminidase activity, e.g. a GH114 glycosyl hydrolase, wherein the polypeptide is selected from the group consisting of:

i) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 3;

ii) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 6;

iii) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 9;

iv) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 12;

v) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 15;

vi) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 18;

vii) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 21;

viii) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 24;

ix) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 27;

x) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 30;

xi) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 33;

xii) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 36;

xiii) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 39;

xiv) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 42;

xv) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 45;

xvi) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 48;

xvii) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 51;

xviii) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 54;

xix) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 57; and b) one or more cleaning composition component, preferably selected from surfactants, builders, bleach components, polymers, dispersing agents and additional enzymes.

The polypeptides to be formulated in the cleaning compositions of the invention are preferably belonging to the VAE clade as shown in FIG. 1. The polypeptides of this clade comprise one or two distinct conservative motifs [VLI]XE[EDSQ]C (SEQ ID NO 60) and/or CY[FLIV][SDN][ATVG] (SEQ ID NO 61). Polypeptides comprising these motifs will share these common conserved regions and will have similar properties e.g. in respect of stability and substrate binding.

One embodiment of the invention relates to a cleaning composition comprising:

(a) at least 0.01 ppm GH114 glycosyl hydrolase enzyme, preferably having alpha-1,4-polygalactosaminidase activity, wherein the GH114 glycosyl comprises one or both motif(s) [VLI]XE[EDSQ]C (SEQ ID NO 60) or CY[FLIV][SDN][ATVG] (SEQ ID NO 61); and (b) one or more cleaning composition components, preferably at least one surfactant, such as an anionic surfactant, wherein the anionic surfactant preferably include sulfates and sulfonates, such as linear alkylbenzene sulfonates (LAS), alpha-olefin sulfonates (AOS) and alkyl alcohol ether sulfates (AES or AEOS or FES).

The cleaning composition according to claim 1, further comprising at least one non-ionic surfactant, preferably an alcohol ethoxylates (AE or AEO), preferably the weight ratio of anionic to non-ionic surfactant is from 10:1 to 1:10. More surfactants suitable for a composition of the invention are described in the surfactant section below.

The polypeptides of the invention and disclosed herein all belong to the VAE clade as also could be visualized in FIG. 1.

One embodiment of the invention relates to a cleaning composition comprising:

(a) at least 0.01 ppm GH114 glycosyl hydrolase enzyme, preferably having alpha-1,4-polygalactosaminidase activity, wherein the GH114 glycosyl comprises one or both motif(s) [VLI]XE[EDSQ]C (SEQ ID NO 60) or CY[FLIV][SDN][ATVG] (SEQ ID NO 61); and (b) one or more cleaning composition components, preferably at least one surfactant, such as an anionic surfactant, wherein the anionic surfactant preferably include sulfates and sulfonates, such as linear alkylbenzene sulfonates (LAS), alpha-olefin sulfonates (AOS) and alkyl alcohol ether sulfates (AES or AEOS or FES), wherein the GH114 glycosyl hydrolase enzyme is selected from the list consisting of:

i. a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 3;

ii. a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 6;

iii. a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 9;

iv. a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 12;

v. a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 15;

vi. a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 18;

vii. a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 21;

viii. a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 24;

ix. a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 27;

x. a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 30;

xi. a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 33;

xii. a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 36;

xiii. a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 39;

xiv. a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 42;

xv. a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 45;

xvi. a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 48;

xvii. a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 51;

xviii. a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 54; and xix. a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 57.

One embodiment of the invention relates to a cleaning composition comprising:

(a) at least 0.01 ppm GH114 glycosyl hydrolase enzyme, preferably having alpha-1,4-polygalactosaminidase activity, wherein the GH114 glycosyl comprises one or both motif(s) [VLI]XE[EDSQ]C (SEQ ID NO 60) or CY[FLIV][SDN][ATVG] (SEQ ID NO 61); and (b) one or more cleaning composition components, preferably at least one surfactant, such as an anionic surfactant, wherein the anionic surfactant preferably include sulfates and sulfonates, such as linear alkylbenzene sulfonates (LAS), alpha-olefin sulfonates (AOS) and alkyl alcohol ether sulfates (AES or AEOS or FES), wherein the GH114 glycosyl hydrolase enzyme is selected from the list consisting of: a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 72, SEQ ID NO 73, SEQ ID NO 74, SEQ ID NO 75, SEQ ID NO 76, SEQ ID NO 77, SEQ ID NO 78, SEQ ID NO 79, SEQ ID NO 80, SEQ ID NO 81, SEQ ID NO 82, SEQ ID NO 83, SEQ ID NO 84, SEQ ID NO 85, SEQ ID NO 86, SEQ ID NO 87, SEQ ID NO 88, SEQ ID NO 89, SEQ ID NO 90, SEQ ID NO 91, SEQ ID NO 92, SEQ ID NO 93, SEQ ID NO 94, SEQ ID NO 95, SEQ ID NO 96, SEQ ID NO 97, SEQ ID NO 98, SEQ ID NO 99, SEQ ID NO 100, SEQ ID NO 101, SEQ ID NO 102, SEQ ID NO 103, SEQ ID NO 104, SEQ ID NO 105, SEQ ID NO 106, SEQ ID NO 107, SEQ ID NO 108, SEQ ID NO 109, SEQ ID NO 110, SEQ ID NO 111, SEQ ID NO 112, SEQ ID NO 113, SEQ ID NO 114, SEQ ID NO 115, SEQ ID NO 116, SEQ ID NO 117, SEQ ID NO 118, SEQ ID NO 119, SEQ ID NO 120, SEQ ID NO 121, SEQ ID NO 122, SEQ ID NO 123, SEQ ID NO 124, SEQ ID NO 125, SEQ ID NO 126, SEQ ID NO 127, SEQ ID NO 128, SEQ ID NO 129, SEQ ID NO 130, SEQ ID NO 131, SEQ ID NO 132, SEQ ED NO: 133, SEQ ID NO 134, SEQ ID NO 135, SEQ ID NO 136, SEQ ID NO 137, SEQ ID NO 138, SEQ ID NO 139, SEQ ID NO 140, SEQ ID NO 141, SEQ ID NO 142, SEQ ID NO 143, SEQ ID NO 144, SEQ ID NO 145 or SEQ ID NO 146.

Another interesting clade derived from the VAE clade is the DYQ-clade, which comprises many of the polypeptides of the VAE-clade. The polypeptides of this clade comprise one or two distinct conservative motifs DYQ[LI]G (SEQ ID NO 62) or FQ[TAV]Q[PSD] (SEQ ID NO 63), which are conserved within the clade.

One embodiment of the invention relates to a cleaning composition comprising:

(a) at least 0.01 ppm GH114 glycosyl hydrolase enzyme, preferably having alpha-1,4-polygalactosaminidase activity, wherein the GH114 glycosyl comprises one or both motif(s) DYQ[LI]G (SEQ ID NO 62) or FQ[TAV]Q[PSD] (SEQ ID NO 63); and (b) one or more cleaning composition components, preferably at least one surfactant, such as an anionic surfactant, wherein the anionic surfactant preferably include sulfates and sulfonates, such as linear alkylbenzene sulfonates (LAS), alpha-olefin sulfonates (AOS) and alkyl alcohol ether sulfates (AES or AEOS or FES).

Many of the polypeptides of the invention are also comprised in the DYQ clade, these polypeptides will comprise at least one or both motifs [VL]XE[EDSQ]C (SEQ ID NO 60) and/or CY[FLIV][SDN][ATVG] (SEQ ID NO 61) or one or both motifs DYQ[LI]G (SEQ ID NO 62) and/or FQ[TAV]Q[PSD] (SEQ ID NO 63).

One embodiment of the invention relates to a cleaning composition comprising:

(a) at least 0.01 ppm GH114 glycosyl hydrolase enzyme, preferably having alpha-1,4-polygalactosaminidase activity, wherein the GH114 glycosyl comprises one or both motif(s) DYQ[L]G (SEQ ID NO 62) or FQ[TAV]Q[PSD] (SEQ ID NO 63); and (b) one or more cleaning composition components, preferably at least one surfactant, such as an anionic surfactant, wherein the anionic surfactant preferably include sulfates and sulfonates, such as linear alkylbenzene sulfonates (LAS), alpha-olefin sulfonates (AOS) and alkyl alcohol ether sulfates (AES or AEOS or FES), wherein the GH114 glycosyl hydrolase enzyme is selected from the list consisting of:

i. a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 3;

ii. a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 6;

iii. a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 9;

iv. a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 12;

v. a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 21;

vi. a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 24;

vii. a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 39;

viii. a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 42;

ix. a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 45;

x. a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 48;

xi. a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 51; and xii. a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 54.

One embodiment of the invention relates to a cleaning composition comprising:

(a) at least 0.01 ppm GH114 glycosyl hydrolase enzyme, preferably having alpha-1,4-polygalactosaminidase activity, wherein the GH114 glycosyl comprises one or both motif(s) DYQ[L]G (SEQ ID NO 62) or FQ[TAV]Q[PSD] (SEQ ID NO 63); and (b) one or more cleaning composition components, preferably at least one surfactant, such as an anionic surfactant, wherein the anionic surfactant preferably include sulfates and sulfonates, such as linear alkylbenzene sulfonates (LAS), alpha-olefin sulfonates (AOS) and alkyl alcohol ether sulfates (AES or AEOS or FES), wherein the GH114 glycosyl hydrolase enzyme is selected from the list consisting of:

a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 79, SEQ ID NO 82, SEQ ID NO 83, SEQ ID NO 84, SEQ ID NO 85, SEQ ID NO 86, SEQ ID NO 87, SEQ ID NO 88, SEQ ID NO 90, SEQ ID NO 91, SEQ ID NO 92, SEQ ID NO 93, SEQ ID NO 94, SEQ ID NO 96, SEQ ID NO 131, SEQ ID NO 132, SEQ ID NO 134, SEQ ID NO 136, SEQ ID NO 137, SEQ ID NO 138, SEQ ID NO 139, SEQ ID NO 140, SEQ ID NO 141, SEQ ID NO 142, SEQ ID NO 143, SEQ ID NO 144 and SEQ ID NO 145.

Another interesting clade derived from the VAE clade (and the DYQ clade) is the AEE clade, which comprises some of the polypeptides of the VAE clade. The polypeptides of this clade comprise one or two distinct conservative motifs AEECG (SEQ ID NO 64) or NAFQ[AT]Q (SEQ ID NO 65), which are conserved within the clade.

One embodiment of the invention relates to a cleaning composition comprising:

(a) at least 0.01 ppm GH114 glycosyl hydrolase enzyme, preferably having alpha-1,4-polygalactosaminidase activity, wherein the GH114 glycosyl comprises one or both motif(s) AEECG (SEQ ID NO 64) or NAFQ[AT]Q (SEQ ID NO 65); and (b) one or more cleaning composition components, preferably at least one surfactant, such as an anionic surfactant, wherein the anionic surfactant preferably include sulfates and sulfonates, such as linear alkylbenzene sulfonates (LAS), alpha-olefin sulfonates (AOS) and alkyl alcohol ether sulfates (AES or AEOS or FES).

The polypeptides of the AEE clade is also comprised in the VAE and DYQ clade, these polypeptides will comprise at least one or both motifs [VL]XE[EDSQ]C (SEQ ID NO 60) and/or CY[FLIV][SDN][ATVG] (SEQ ID NO 61), one or both motifs DYQ[LI]G (SEQ ID NO 62) and/or FQ[TAV]Q[PSD] (SEQ ID NO 63) and one or both motifs AEECG (SEQ ID NO 64) and/or NAFQ[AT]Q (SEQ ID NO 65).

One embodiment of the invention relates to a cleaning composition comprising:

(a) at least 0.01 ppm GH114 glycosyl hydrolase enzyme, preferably having alpha-1,4-polygalactosaminidase activity, wherein the GH114 glycosyl comprises one or both motif(s) AEECG (SEQ ID NO 64) or NAFQ[AT]Q (SEQ ID NO 65); and (b) one or more cleaning composition components, preferably at least one surfactant, such as an anionic surfactant, wherein the anionic surfactant preferably include sulfates and sulfonates, such as linear alkylbenzene sulfonates (LAS), alpha-olefin sulfonates (AOS) and alkyl alcohol ether sulfates (AES or AEOS or FES), wherein the GH114 glycosyl hydrolase enzyme is selected from the list consisting of:

i. a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 3;

ii. a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 6;

iii. a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 9;

iv. a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 12;

v. a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 21;

vi. a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 24; and vii. a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 54.

One embodiment of the invention relates to a cleaning composition comprising:

(a) at least 0.01 ppm GH114 glycosyl hydrolase enzyme, preferably having alpha-1,4-polygalactosaminidase activity, wherein the GH114 glycosyl comprises one or both motif(s) AEECG (SEQ ID NO 64) or NAFQ[AT]Q (SEQ ID NO 65); and (b) one or more cleaning composition components, preferably at least one surfactant, such as an anionic surfactant, wherein the anionic surfactant preferably include sulfates and sulfonates, such as linear alkylbenzene sulfonates (LAS), alpha-olefin sulfonates (AOS) and alkyl alcohol ether sulfates (AES or AEOS or FES), wherein the GH114 glycosyl hydrolase enzyme is selected from the list consisting of:

a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 79, SEQ ID NO 82, SEQ ID NO 83, SEQ ID NO 84, SEQ ID NO 85, SEQ ID NO 132, SEQ ID NO 136, SEQ ID NO 138, and SEQ ID NO 142.

Another interesting clade derived from the VAE clade is the IEY clade, which comprises some of the polypeptides of the VAE-clade. The polypeptides of this clade comprise one or two distinct conservative motifs GXXVX[NHQTS]IEY[PG] (SEQ ID NO 68), VICYF (SEQ ID NO 69), which are conserved within the clade.

One embodiment of the invention relates to a cleaning composition comprising:

(a) at least 0.01 ppm GH114 glycosyl hydrolase enzyme, preferably having alpha-1,4-polygalactosaminidase activity, wherein the GH114 glycosyl comprises one or both motif(s) GXXVX[NHQTS]IEY[PG] (SEQ ID NO 68) or VICYF (SEQ ID NO 69); and (b) one or more cleaning composition components, preferably at least one surfactant, such as an anionic surfactant, wherein the anionic surfactant preferably include sulfates and sulfonates, such as linear alkylbenzene sulfonates (LAS), alpha-olefin sulfonates (AOS) and alkyl alcohol ether sulfates (AES or AEOS or FES).

The polypeptides of the IEY clade is also comprised in the VAE, these polypeptides will comprise at least one or both motifs [VLI]XE[EDSQ]C (SEQ ID NO 60) and/or CY[FLIV][SDN][ATVG] (SEQ ID NO 61), and one or both motifs GXXVX[NHQTS]IEY[PG] (SEQ ID NO 68) and/or VICYF (SEQ ID NO 69).

One embodiment of the invention relates to a cleaning composition comprising:

(a) at least 0.01 ppm GH114 glycosyl hydrolase enzyme, preferably having alpha-1,4-polygalactosaminidase activity, wherein the GH114 glycosyl comprises one or both motif(s) GXXVX[NHQTS]IEY[PG] (SEQ ID NO 68) or VICYF (SEQ ID NO 69); and (b) one or more cleaning composition components, preferably at least one surfactant, such as an anionic surfactant, wherein the anionic surfactant preferably include sulfates and sulfonates, such as linear alkylbenzene sulfonates (LAS), alpha-olefin sulfonates (AOS) and alkyl alcohol ether sulfates (AES or AEOS or FES), wherein the GH114 glycosyl hydrolase enzyme is selected from the list consisting of:

i. a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 15;

ii. a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 18; and iii. a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 57.

One embodiment of the invention relates to a cleaning composition comprising:

(a) at least 0.01 ppm GH114 glycosyl hydrolase enzyme, preferably having alpha-1,4-polygalactosaminidase activity, wherein the GH114 glycosyl comprises one or both motif(s) GXXVX[NHQTS]IEY[PG] (SEQ ID NO 68) or VICYF (SEQ ID NO 69); and (b) one or more cleaning composition components, preferably at least one surfactant, such as an anionic surfactant, wherein the anionic surfactant preferably include sulfates and sulfonates, such as linear alkylbenzene sulfonates (LAS), alpha-olefin sulfonates (AOS) and alkyl alcohol ether sulfates (AES or AEOS or FES), wherein the GH114 glycosyl hydrolase enzyme is selected from the list consisting of: a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 72, SEQ ID NO 73, SEQ ID NO 74, SEQ ID NO 75, SEQ ID NO 76, SEQ ID NO 77, SEQ ID NO 78, SEQ ID NO 97, SEQ ID NO 98, SEQ ID NO 99, SEQ ID NO 100, SEQ ID NO 101, SEQ ID NO 102, SEQ ID NO 103, SEQ ID NO 104, SEQ ID NO 105, SEQ ID NO 106, SEQ ID NO 107, SEQ ID NO 108, SEQ ID NO 109, SEQ ID NO 110, SEQ ID NO 111, SEQ ID NO 112, SEQ ID NO 113, SEQ ID NO 114, SEQ ID NO 115, SEQ ID NO 116, SEQ ID NO 117, SEQ ID NO 118, SEQ ID NO 119, SEQ ID NO 120, SEQ ID NO 121, SEQ ID NO 122, SEQ ID NO 123, SEQ ID NO 124, SEQ ID NO 125, SEQ ID NO 126, SEQ ID NO 127, SEQ ID NO 128, SEQ ID NO 129, SEQ ID NO 130, SEQ ID NO: 133 and SEQ ID NO 135.

Another interesting clade derived from the VAE and the IEY clade is the ICY clade, which comprises some of the polypeptides of the VAE-clade and the IEY clade. The polypeptides of this clade comprise the distinct conservative motif ICYFSA (SEQ ID NO 70), which is conserved within the clade.

One embodiment of the invention relates to a cleaning composition comprising:

(a) at least 0.01 ppm GH114 glycosyl hydrolase enzyme, preferably having alpha-1,4-polygalactosaminidase activity, wherein the GH114 glycosyl comprises the motif ICYFSA (SEQ ID NO 70); and (b) one or more cleaning composition components, preferably at least one surfactant, such as an anionic surfactant, wherein the anionic surfactant preferably include sulfates and sulfonates, such as linear alkylbenzene sulfonates (LAS), alpha-olefin sulfonates (AOS) and alkyl alcohol ether sulfates (AES or AEOS or FES).

The polypeptides of the ICY clade is also comprised in the VAE and the IEY clade, these polypeptides will comprise at least one or both motifs [VL]XE[EDSQ]C (SEQ ID NO 60) and/or CY[FLIV][SDN][ATVG] (SEQ ID NO 61), one or both motifs GXXVX[NHQTS]IEY[PG] (SEQ ID NO 68) and/or VICYF (SEQ ID NO 69) and the motif ICYFSA (SEQ ID NO 70).

One embodiment of the invention relates to a cleaning composition comprising:

(a) at least 0.01 ppm GH114 glycosyl hydrolase enzyme, preferably having alpha-1,4-polygalactosaminidase activity, wherein the GH114 glycosyl comprises the motif ICYFSA (SEQ ID NO 70); and (b) one or more cleaning composition components, preferably at least one surfactant, such as an anionic surfactant, wherein the anionic surfactant preferably include sulfates and sulfonates, such as linear alkylbenzene sulfonates (LAS), alpha-olefin sulfonates (AOS) and alkyl alcohol ether sulfates (AES or AEOS or FES), wherein the GH114 glycosyl hydrolase enzyme is selected from the list consisting of:

i. a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 15; and ii. a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 57.

One embodiment of the invention relates to a cleaning composition comprising:

(a) at least 0.01 ppm GH114 glycosyl hydrolase enzyme, preferably having alpha-1,4-polygalactosaminidase activity, wherein the GH114 glycosyl comprises the motif ICYFSA (SEQ ID NO 70); and (b) one or more cleaning composition components, preferably at least one surfactant, such as an anionic surfactant, wherein the anionic surfactant preferably include sulfates and sulfonates, such as linear alkylbenzene sulfonates (LAS), alpha-olefin sulfonates (AOS) and alkyl alcohol ether sulfates (AES or AEOS or FES), wherein the GH114 glycosyl hydrolase enzyme is selected from the list consisting of: a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 98, SEQ ID NO 101, SEQ ID NO 104, SEQ ID NO 107, SEQ ID NO 114, SEQ ID NO 115, SEQ ID NO 120, SEQ ID NO 124, SEQ ID NO 125, SEQ ID NO 127, SEQ ID NO 129 and SEQ ID NO: 133.

Another interesting clade derived from the VAE and the IEY clade is the DFAVL clade, which comprises some of the polypeptides of the VAE clade and the IEY clade. The polypeptides of this clade comprise the distinct conservative motif DFAVL (SEQ ID NO 71), which is conserved within the clade.

One embodiment of the invention relates to a cleaning composition comprising:

(a) at least 0.01 ppm GH114 glycosyl hydrolase enzyme, preferably having alpha-1,4-polygalactosaminidase activity, wherein the GH114 glycosyl comprises the motif DFAVL (SEQ ID NO 71); and (b) one or more cleaning composition components, preferably at least one surfactant, such as an anionic surfactant, wherein the anionic surfactant preferably include sulfates and sulfonates, such as linear alkylbenzene sulfonates (LAS), alpha-olefin sulfonates (AOS) and alkyl alcohol ether sulfates (AES or AEOS or FES).

The polypeptides of the DFAVL clade is also comprised in the VAE and the IEY clade, these polypeptides will comprise at least one or both motifs [VL]XE[EDSQ]C (SEQ ID NO 60) and/or CY[FLIV][SDN][ATVG] (SEQ ID NO 61), one or both motifs GXXVX[NHQTS]IEY[PG] (SEQ ID NO 68) and/or VICYF (SEQ ID NO 69) and the motif DFAVL (SEQ ID NO 71).

One embodiment of the invention relates to a cleaning composition comprising:

(a) at least 0.01 ppm GH114 glycosyl hydrolase enzyme, preferably having alpha-1,4-polygalactosaminidase activity, wherein the GH114 glycosyl comprises the motif DFAVL (SEQ ID NO 71); and (b) one or more cleaning composition components, preferably at least one surfactant, such as an anionic surfactant, wherein the anionic surfactant preferably include sulfates and sulfonates, such as linear alkylbenzene sulfonates (LAS), alpha-olefin sulfonates (AOS) and alkyl alcohol ether sulfates (AES or AEOS or FES), wherein the GH114 glycosyl hydrolase enzyme is a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 18.

One embodiment of the invention relates to a cleaning composition comprising:

(a) at least 0.01 ppm GH114 glycosyl hydrolase enzyme, preferably having alpha-1,4-polygalactosaminidase activity, wherein the GH114 glycosyl comprises the motif DFAVL (SEQ ID NO 71); and (b) one or more cleaning composition components, preferably at least one surfactant, such as an anionic surfactant, wherein the anionic surfactant preferably include sulfates and sulfonates, such as linear alkylbenzene sulfonates (LAS), alpha-olefin sulfonates (AOS) and alkyl alcohol ether sulfates (AES or AEOS or FES), wherein the GH114 glycosyl hydrolase enzyme is a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 72, SEQ ID NO 73, SEQ ID NO 74, SEQ ID NO 75, SEQ ID NO 76, SEQ ID NO 77, SEQ ID NO 78, SEQ ID NO 97, SEQ ID NO 99, SEQ ID NO 100, SEQ ID NO 102, SEQ ID NO 103, SEQ ID NO 105, SEQ ID NO 106, SEQ ID NO 108, SEQ ID NO 110, SEQ ID NO 111, SEQ ID NO 112, SEQ ID NO 113, SEQ ID NO 116, SEQ ID NO 117, SEQ ID NO 118, SEQ ID NO 119, SEQ ID NO 121, SEQ ID NO 123, SEQ ID NO 126, SEQ ID NO 128, SEQ ID NO 130 and SEQ ID NO 135.

Another interesting clade derived from the VAE clade is the WQW clade, which comprises some of the polypeptides of the VAE-clade. The polypeptides of this clade comprise one or both distinct conservative motif(s) WQWQL (SEQ ID NO 66) or [VL][GASD]LKN[DGS][VLIP] (SEQ ID NO 67), which are conserved within the clade.

One embodiment of the invention relates to a cleaning composition comprising:

(a) at least 0.01 ppm GH114 glycosyl hydrolase enzyme, preferably having alpha-1,4-polygalactosaminidase activity, wherein the GH114 glycosyl one or both motif(s) WQWQL (SEQ ID NO 66) or [VL][GASD]LKN[DGS][VLIP] (SEQ ID NO 67); and (b) one or more cleaning composition components, preferably at least one surfactant, such as an anionic surfactant, wherein the anionic surfactant preferably include sulfates and sulfonates, such as linear alkylbenzene sulfonates (LAS), alpha-olefin sulfonates (AOS) and alkyl alcohol ether sulfates (AES or AEOS or FES).

The polypeptides of the WQW clade is also comprised in the VAE, these polypeptides will comprise at least one or both motifs [VLI]XE[EDSQ]C (SEQ ID NO 60) and/or CY[FLIV][SDN][ATVG] (SEQ ID NO 61) and/or one or both motif(s) WQWQL (SEQ ID NO 66) or [VLI][GASD]LKN[DGS][VLIP] (SEQ ID NO 67).

One embodiment of the invention relates to a cleaning composition comprising:

(a) at least 0.01 ppm GH114 glycosyl hydrolase enzyme, preferably having alpha-1,4-polygalactosaminidase activity, wherein the GH114 glycosyl comprises one or both motif(s) WQWQL (SEQ ID NO 66) or [VL][GASD]LKN[DGS][VLIP] (SEQ ID NO 67); and (b) one or more cleaning composition components, preferably at least one surfactant, such as an anionic surfactant, wherein the anionic surfactant preferably include sulfates and sulfonates, such as linear alkylbenzene sulfonates (LAS), alpha-olefin sulfonates (AOS) and alkyl alcohol ether sulfates (AES or AEOS or FES), wherein the GH114 glycosyl hydrolase enzyme is selected from the list consisting of:

i. a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 27;

ii. a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 33; and iii. a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 36.

One embodiment of the invention relates to a cleaning composition comprising:

(a) at least 0.01 ppm GH114 glycosyl hydrolase enzyme, preferably having alpha-1,4-polygalactosaminidase activity, wherein the GH114 glycosyl comprises one or both motif(s) WQWQL (SEQ ID NO 66) or [VL][GASD]LKN[DGS][VLIP] (SEQ ID NO 67); and (b) one or more cleaning composition components, preferably at least one surfactant, such as an anionic surfactant, wherein the anionic surfactant preferably include sulfates and sulfonates, such as linear alkylbenzene sulfonates (LAS), alpha-olefin sulfonates (AOS) and alkyl alcohol ether sulfates (AES or AEOS or FES), wherein the GH114 glycosyl hydrolase enzyme is selected from the list consisting of:

a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 80, SEQ ID NO 81, SEQ ID NO 89, SEQ ID NO 95 and SEQ ID NO 146.

The compositions according the invention preferably comprises a GH114 glycosyl hydrolase, wherein the enzyme is capable of "deep cleaning" of an item.

Furthermore, the GH114 to be formulated into the composition of the invention preferably has improved wash performance or cleaning performance and the GH114 enzyme to be formulated into a composition according to the invention preferably has "enzyme detergency benefit" which is defined herein as the advantageous effect an enzyme may add to a detergent compared to the same detergent without the enzyme. The terms wash performance and detergency is explained further in the examples.

In one embodiment, the composition according to invention comprising a GH114 glycosyl hydrolase, wherein the GH114 glycosyl hydrolase has wash performance (WP) in liquid Model detergent A, measured as a delta L ($\Delta$L)>1, preferably a delta L ($\Delta$L) above 5, preferably a delta L ($\Delta$L) above 10, preferably a delta L ($\Delta$L) above 15, preferably a delta L ($\Delta$L) above 20, when delta L ($\Delta$L) is calculated (L(swatch washed with enzyme)−L(swatch washed without enzyme)) as described in examples 5 and 7.

The GH114 of the invention preferably has enzyme detergency benefit properties and one embodiment of the invention relates to a composition, comprising a GH114 glycosyl hydrolase enzyme, wherein the GH114 glycosyl hydrolase enzyme has biofilm removal activity, wherein in the % remaining biofilm is less than 80%, such as less than 70%, such as less than 60%, such as less than 50%, such as less than 40%, such as less than 30%, such as less than 20%, such as less than 10%, such as less than 1% or even no biofilm remaining on the item e.g. textile, preferably when measured as described in Example 8.

The choice of cleaning components may include, for textile care, the consideration of the type of textile to be cleaned, the type and/or degree of soiling, the temperature at which cleaning is to take place, and the formulation of the detergent product. Although components mentioned below are categorized by general header according to a particular functionality, this is not to be construed as a limitation, as a component may comprise additional functionalities as will be appreciated by the skilled artisan.

Surfactants

The cleaning composition may comprise one or more surfactants, which may be anionic and/or cationic and/or non-ionic and/or semi-polar and/or zwitterionic, or a mixture thereof. In a particular embodiment, the detergent composition includes a surfactant system (comprising more than one surfactant) e.g. a mixture of one or more non-ionic surfactants and one or more anionic surfactants. In one embodiment the detergent comprises at least one anionic surfactant than at least one non-ionic surfactant, the weight ratio of anionic to non-ionic surfactant may be from 10:1 to 1:10. In one embodiment the amount of anionic surfactant is higher than the amount of non-ionic surfactant e.g. the weight ratio of anionic to non-ionic surfactant may be from 10:1 to 1.1:1 or from 5:1 to 1.5:1. The amount of anionic to non-ionic surfactant may also be equal and the weight ratios 1:1. In one embodiment the amount of non-ionic surfactant is higher than the amount of anionic surfactant and the weight ratio may be 1:10 to 1:1.1. Preferably the weight ratio of anionic to non-ionic surfactant is from 10:1 to 1:10, such as from 5:1 to 1:5, or from 5:1 to 1:1.2. Preferably, the weight fraction of non-ionic surfactant to anionic surfactant is from 0 to 0.5 or 0 to 0.2 thus non-ionic surfactant can be present or absent if the weight fraction is 0, but if non-ionic surfactant is present, then the weight fraction of the non-ionic surfactant is preferably at most 50% or at most 20% of the total weight of anionic surfactant and non-ionic surfactant. Light duty detergent usually comprises more non-ionic than anionic surfactant and there the fraction of non-ionic surfactant to anionic surfactant is preferably from 0.5 to 0.9. The total weight of surfactant(s) is typically present at a level of from about 0.1% to about 60% by weight, such as about 1% to about 40%, or about 3% to about 20%, or about 3% to about 10%. The surfactant(s) is chosen based on the desired cleaning application, and may include any conventional surfactant(s) known in the art. When included therein the detergent will usually contain from about 1% to about 40% by weight of an anionic surfactant, such as from about 5% to about 30%, including from about 5% to about 15%, or from about 15% to about 20%, or from about 20% to about 25% of an anionic surfactant. Non-limiting examples of anionic surfactants include sulfates and sulfonates, typically available as sodium or potassium salts or salts of monoethanolamine (MEA, 2-aminoethan-1-ol) or triethanolamine (TEA, 2,2',2"-nitrilotriethan-1-ol); in particular, linear alkylbenzenesulfonates (LAS), isomers of LAS such as branched alkylbenzenesulfonates (BABS) and phenylalkanesulfonates; olefin sulfonates, in particular alpha-olefinsulfonates (AOS); alkyl sulfates (AS), in particular fatty alcohol sulfates (FAS), i.e., primary alcohol sulfates (PAS) such as dodecyl sulfate; alcohol ethersulfates (AES or AEOS or FES, also known as alcohol ethoxysulfates or fatty alcohol ether sulfates); paraffin sulfonates (PS) including alkane-1-sulfonates and secondary alkanesulfonates (SAS); ester sulfonates, including sulfonated fatty acid glycerol esters and alpha-sulfo fatty acid methyl esters (alpha-SFMe or SES or MES); alkyl- or alkenylsuccinic acids such as dodecenyl/tetradecenyl succinic acid (DTSA); diesters and monoesters of sulfosuccinic acid; fatty acid derivatives of amino acids. Furthermore, salts of fatty acids (soaps) may be included.

When included therein the detergent will usually contain from about 1% to about 40% by weight of a cationic surfactant, for example from about 0.5% to about 30%, in particular from about 1% to about 20%, from about 3% to about 10%, such as from about 3% to about 5%, from about 8% to about 12% or from about 10% to about 12%. Non-limiting examples of cationic surfactants include alkyldimethylethanolamine quat (ADMEAQ), cetyltrimethylammonium bromide (CTAB), dimethyldistearylammonium chloride (DSDMAC), and alkylbenzyldimethylammonium, alkyl quaternary ammonium compounds, alkoxylated quaternary ammonium (AQA) compounds, ester quats, and combinations thereof.

When included therein the detergent will usually contain from about 0.2% to about 40% by weight of a non-ionic surfactant, for example from about 0.5% to about 30%, in particular from about 1% to about 20%, from about 3% to about 10%, such as from about 3% to about 5%, from about 8% to about 12%, or from about 10% to about 12%. Non-limiting examples of non-ionic surfactants include alcohol ethoxylates (AE or AEO), alcohol propoxylates, in particular propoxylated fatty alcohols (PFA), ethoxylated and propoxylated alcohols, alkoxylated fatty acid alkyl esters, such as ethoxylated and/or propoxylated fatty acid alkyl esters (in particular methyl ester ethoxylates, MEE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxyalkyl fatty acid amides, or N-acyl N-alkyl derivatives of glucosamine (glucamides, GA, or fatty acid glucamides, FAGA), as well as products available under the trade names SPAN and TWEEN, and combinations thereof.

When included therein the detergent will usually contain from about 0.01 to about 10% by weight of a semipolar surfactant. Non-limiting examples of semipolar surfactants include amine oxides (AO) such as alkyldimethylamine oxides, in particular N-(coco alkyl)-N,N-dimethylamine oxide and N-(tallow-alkyl)-N,N-bis(2-hydroxyethyl)amine oxide, and combinations thereof.

When included therein the detergent will usually contain from about 0.01% to about 10% by weight of a zwitterionic surfactant. Non-limiting examples of zwitterionic surfactants include betaines such as alkyldimethylbetaines, sulfobetaines, and combinations thereof.

Additional bio-based surfactants may be used e.g. wherein the surfactant is a sugar-based non-ionic surfactant which may be a hexyl-β-D-maltopyranoside, thiomaltopyranoside or a cyclic-maltopyranoside, such as described in EP2516606 E1.

Builders and Co-Builders

The detergent composition may contain about 0-65% by weight, such as about 5% to about 50% of a detergent builder or co-builder, or a mixture thereof. In a dish wash detergent, the level of builder is typically 40-65%, particularly 50-65%. The builder and/or co-builder may particularly be a chelating agent that forms water-soluble complexes with Ca and Mg. Any builder and/or co-builder known in the art for use in cleaning detergents may be utilized. Non-limiting examples of builders include zeolites, diphosphates (pyrophosphates), triphosphates such as sodium triphosphate (STP or STPP), carbonates such as sodium carbonate, soluble silicates such as sodium metasilicate, layered silicates (e.g., SKS-6 from Hoechst), ethanolamines such as 2-aminoethan-1-ol (MEA), diethanolamine (DEA, also known as 2,2'-iminodiethan-1-ol), triethanolamine (TEA, also known as 2,2',2"-nitrilotriethan-1-ol), and (carboxymethyl)inulin (CMI), and combinations thereof.

The detergent composition may also contain 0-50% by weight, such as about 5% to about 30%, of a detergent co-builder. The detergent composition may include a co-builder alone, or in combination with a builder, for example a zeolite builder. Non-limiting examples of co-builders include homopolymers of polyacrylates or copolymers thereof, such as poly(acrylic acid) (PAA) or copoly(acrylic acid/maleic acid) (PAA/PMA). Further non-limiting examples include citrate, chelators such as aminocarboxylates, aminopolycarboxylates and phosphonates, and alkyl- or alkenylsuccinic acid. Additional specific examples include 2,2',2"-nitrilotriacetic acid (NTA), ethylenediaminetetraacetic acid (EDTA), diethylenetriaminepentaacetic acid (DTPA), iminodisuccinic acid (IDS), ethylenediamine-N,N'-disuccinic acid (EDDS), methylglycinediacetic acid (MGDA), glutamic acid-N,N-diacetic acid (GLDA), 1-hydroxyethane-1,1-diphosphonic acid (HEDP), ethylenediaminetetra(methylenephosphonic acid) (EDTMPA), diethylenetriaminepentakis(methylenephosphonic acid) (DTMPA or DTPMPA), N-(2-hydroxyethyl)iminodiacetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl)-aspartic acid (SMAS), N-(2-sulfoethyl)-aspartic acid (SEAS), N-(2-sulfomethyl)-glutamic acid (SMGL), N-(2-sulfoethyl)-glutamic acid (SEGL), N-methyliminodiacetic acid (MIDA), α-alanine-N,N-diacetic acid (α-ALDA), serine-N,N-diacetic acid (SEDA), isoserine-N,N-diacetic acid (ISDA), phenylalanine-N,N-diacetic acid (PHDA), anthranilic acid-N,N-diacetic acid (ANDA), sulfanilic acid-N,N-diacetic acid (SLDA), taurine-N,N-diacetic acid (TUDA) and sulfomethyl-N,N-diacetic acid (SMDA), N-(2-hydroxyethyl)ethylenediamine-N,N',N"-triacetic acid (HEDTA), diethanolglycine (DEG), diethylenetriamine penta(methylenephosphonic acid) (DTPMP), aminotris(methylenephosphonic acid) (ATMP), and combinations and salts thereof. Further exemplary builders and/or co-builders are described in, e.g., WO 09/102854, U.S. Pat. No. 5,977,053.

Bleaching Systems

The detergent may contain 0-30% by weight, such as about 1% to about 20%, of a bleaching system. Any bleaching system comprising components known in the art for use in cleaning detergents may be utilized. Suitable bleaching system components include sources of hydrogen peroxide; sources of peracids; and bleach catalysts or boosters.

Sources of Hydrogen Peroxide:

Suitable sources of hydrogen peroxide are inorganic persalts, including alkali metal salts such as sodium percarbonate and sodium perborates (usually mono- or tetrahydrate), and hydrogen peroxide-urea (1/1).

Sources of Peracids:

Peracids may be (a) incorporated directly as preformed peracids or (b) formed in situ in the wash liquor from hydrogen peroxide and a bleach activator (perhydrolysis) or (c) formed in situ in the wash liquor from hydrogen peroxide and a perhydrolase and a suitable substrate for the latter, e.g., an ester.

a) Suitable preformed peracids include, but are not limited to, peroxycarboxylic acids such as peroxybenzoic acid and its ring-substituted derivatives, peroxy-α-naphthoic acid, peroxyphthalic acid, peroxylauric acid, peroxystearic acid, ε-phthalimidoperoxycaproic acid [phthalimidoperoxyhexanoic acid (PAP)], and o-carboxybenzamidoperoxycaproic acid; aliphatic and aromatic diperoxydicarboxylic acids such as diperoxydodecanedioic acid, diperoxyazelaic acid, diperoxysebacic acid, diperoxybrassylic acid, 2-decyldiperoxybutanedioic acid, and diperoxyphthalic, -isophthalic and -terephthalic acids; perimidic acids; peroxymonosulfuric acid; peroxydisulfuric acid; peroxyphosphoric acid; peroxysilicic acid; and mixtures of said compounds. It is understood that the peracids mentioned may in some cases be best added as suitable salts, such as alkali metal salts (e.g., Oxone®) or alkaline earth-metal salts.

b) Suitable bleach activators include those belonging to the class of esters, amides, imides, nitriles or anhydrides and, where applicable, salts thereof. Suitable examples are tetraacetylethylenediamine (TAED), sodium 4-[(3,5,5-trimethylhexanoyl)oxy]benzene-1-sulfonate (ISONOBS), sodium 4-(dodecanoyloxy)benzene-1-sulfonate (LOBS), sodium 4-(decanoyloxy)benzene-1-sulfonate, 4-(decanoyloxy)benzoic acid (DOBA), sodium 4-(nonanoyloxy)benzene-1-sulfonate (NOBS), and/or those disclosed in WO98/17767. A particular family of bleach activators of interest was disclosed in EP624154 and particularly preferred in that family is acetyl triethyl citrate (ATC). ATC or a short chain triglyceride like triacetin has the advantage that they are environmentally friendly. Furthermore, acetyl triethyl citrate and triacetin have good hydrolytical stability in the product upon storage and are efficient bleach activators. Finally, ATC is multifunctional, as the citrate released in the perhydrolysis reaction may function as a builder.

Bleach Catalysts and Boosters

The bleaching system may also include a bleach catalyst or booster. Some non-limiting examples of bleach catalysts that may be used in the compositions of the present invention include manganese oxalate, manganese acetate, manganese-collagen, cobalt-amine catalysts and manganese triazacyclononane (MnTACN) catalysts; particularly preferred are complexes of manganese with 1,4,7-trimethyl-1,4,7-triazacyclononane (Me3-TACN) or 1,2,4,7-tetramethyl-1,4,7-triazacyclononane (Me4-TACN), in particular Me3-TACN, such as the dinuclear manganese complex [(Me3-TACN)Mn(O)3Mn(Me3-TACN)](PF6)2, and [2,2',2''-nitrilotris(ethane-1,2-diylazanylylidene-κN-methanylylidene)triphenolato-κ3O]manganese(II). The bleach catalysts may also be other metal compounds; such as iron or cobalt complexes.

In some embodiments, where a source of a peracid is included, an organic bleach catalyst or bleach booster may be used having one of the following formulae:

(i)

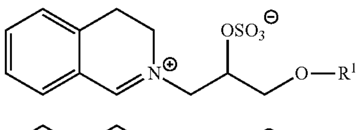

(ii)

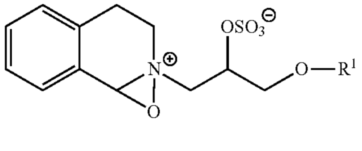

(iii) and mixtures thereof; wherein each R1 is independently a branched alkyl group containing from 9 to 24 carbons or linear alkyl group containing from 11 to 24 carbons, preferably each R1 is independently a branched alkyl group containing from 9 to 18 carbons or linear alkyl group containing from 11 to 18 carbons, more preferably each R1 is independently selected from the group consisting of 2-propylheptyl, 2-butyloctyl, 2-pentylnonyl, 2-hexyldecyl, dodecyl, tetradecyl, hexadecyl, octadecyl, isononyl, isodecyl, isotridecyl and isopentadecyl.

Other exemplary bleaching systems are described, e.g. in WO2007/087258, WO2007/087244, WO2007/087259, EP1867708 (Vitamin K) and WO2007/087242. Suitable photobleaches may for example be sulfonated zinc or aluminium phthalocyanines.

Metal Care Agents

Metal care agents may prevent or reduce the tarnishing, corrosion or oxidation of metals, including aluminium, stainless steel and non-ferrous metals, such as silver and copper. Suitable examples include one or more of the following:

(a) benzatriazoles, including benzotriazole or bis-benzotriazole and substituted derivatives thereof. Benzotriazole derivatives are those compounds in which the available substitution sites on the aromatic ring are partially or completely substituted. Suitable substituents include linear or branch-chain Ci-C20-alkyl groups (e.g., C1-C20-alkyl groups) and hydroxyl, thio, phenyl or halogen such as fluorine, chlorine, bromine and iodine.

(b) metal salts and complexes chosen from the group consisting of zinc, manganese, titanium, zirconium, hafnium, vanadium, cobalt, gallium and cerium salts and/or complexes, the metals being in one of the oxidation states II, III, IV, V or VI. In one aspect, suitable metal salts and/or metal complexes may be chosen from the group consisting of Mn(II) sulphate, Mn(II) citrate, Mn(II) stearate, Mn(II) acetylacetonate, K^TiF6 (e.g., K2TiF6), K^ZrF6 (e.g., K2ZrF6), CoSO4, Co(NOs)2 and Ce(NOs)3, zinc salts, for example zinc sulphate, hydrozincite or zinc acetate;

(c) silicates, including sodium or potassium silicate, sodium disilicate, sodium metasilicate, crystalline phyllosilicate and mixtures thereof.

Further suitable organic and inorganic redox-active substances that act as silver/copper corrosion inhibitors are disclosed in WO 94/26860 and WO 94/26859. Preferably the composition of the invention comprises from 0.1 to 5% by weight of the composition of a metal care agent, preferably the metal care agent is a zinc salt.

Hydrotropes

The detergent may contain 0-10% by weight, for example 0-5% by weight, such as about 0.5 to about 5%, or about 3% to about 5%, of a hydrotrope. Any hydrotrope known in the art for use in detergents may be utilized. Non-limiting examples of hydrotropes include sodium benzenesulfonate, sodium p-toluene sulfonate (STS), sodium xylene sulfonate (SXS), sodium cumene sulfonate (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof.

Polymers

The detergent may contain 0-10% by weight, such as 0.5-5%, 2-5%, 0.5-2% or 0.2-1% of a polymer. Any polymer known in the art for use in detergents may be utilized. The polymer may function as a co-builder as mentioned above, or may provide antiredeposition, fibre protection, soil release, dye transfer inhibition, grease cleaning and/or anti-foaming properties. Some polymers may have more than one of the above-mentioned properties and/or more than one of the below-mentioned motifs. Exemplary polymers include (carboxymethyl)cellulose (CMC), poly(vinyl alcohol) (PVA), poly(vinylpyrrolidone) (PVP), poly(ethyleneglycol) or poly(ethylene oxide) (PEG), ethoxylated poly (ethyleneimine), carboxymethyl inulin (CMI), and polycarboxylates such as PAA, PAA/PMA, poly-aspartic acid, and lauryl methacrylate/acrylic acid copolymers, hydrophobically modified CMC (HM-CMC) and silicones, copolymers of terephthalic acid and oligomeric glycols, copolymers of poly(ethylene terephthalate) and poly (oxyethene terephthalate) (PET-POET), PVP, poly(vinylimidazole) (PVI), poly(vinylpyridine-N-oxide) (PVPO or PVPNO) and polyvinylpyrrolidone-vinylimidazole (PVPVI). Suitable examples include PVP-K15, PVP-K30, ChromaBond S-400, ChromaBond S-403E and Chromabond S-100 from Ashland Aqualon, and Sokalan® HP 165, Sokalan® HP 50 (Dispersing agent), Sokalan® HP 53 (Dispersing agent), Sokalan® HP 59 (Dispersing agent), Sokalan® HP 56 (dye transfer inhibitor), Sokalan® HP 66 K (dye transfer inhibitor) from BASF. Particularly preferred polymer is ethoxylated homopolymer Sokalan® HP 20 from BASF, which helps to prevent redeposition of soil in the wash liquor. Further exemplary polymers include sulfonated polycarboxylates, polyethylene oxide and polypropylene oxide (PEO-PPO) and diquaternium ethoxy sulfate. Other exemplary polymers are disclosed in, e.g., WO 2006/130575. Salts of the above-mentioned polymers are also contemplated.

Fabric Hueing Agents

The detergent compositions of the present invention may also include fabric hueing agents such as dyes or pigments, which when formulated in detergent compositions can deposit onto a fabric when said fabric is contacted with a wash liquor comprising said detergent compositions and thus altering the tint of said fabric through absorption/reflection of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO2005/03274, WO2005/03275, WO2005/03276 and EP1876226 (hereby incorporated by reference). The detergent composition preferably comprises from about 0.00003 wt % to about 0.2 wt %, from about 0.00008 wt % to about 0.05 wt %, or even from about 0.0001 wt % to about 0.04 wt % fabric hueing agent. The composition may comprise from 0.0001 wt % to 0.2 wt % fabric hueing agent, this may be especially preferred when the composition is in the form of a unit dose pouch. Suitable hueing agents are also disclosed in, e.g. WO 2007/087257 and WO2007/087243.

Enzymes

The detergent additive as well as the detergent composition may comprise one or more additional enzymes such as one or more lipase, cutinase, an amylase, carbohydrase, cellulase, pectinase, mannanase, arabinase, galactanase, xylanase, oxidase, e.g., a laccase, and/or peroxidase.

In general, the properties of the selected enzyme(s) should be compatible with the selected detergent, (i.e., pH-optimum, compatibility with other enzymatic and non-enzymatic ingredients, etc.), and the enzyme(s) should be present in effective amounts.

Cellulases

Suitable cellulases include mono-component and mixtures of enzymes of bacterial or fungal origin. Chemically modified or protein engineered mutants are also contemplated. The cellulase may for example be a mono-component or a mixture of mono-component endo-1,4-beta-glucanase also referred to as endoglucanase. Suitable cellulases include those from the genera *Bacillus, Pseudomonas, Humicola, Myceliophthora, Fusarium, Thielavia, Trichoderma*, and *Acremonium*. Exemplary cellulases include a fungal cellulase from *Humicola insolens* (U.S. Pat. No. 4,435,307) or from *Trichoderma*, e.g. *T. reesei* or *T. viride*. Other suitable cellulases are from *Thielavia* e.g. *Thielavia terrestris* as described in WO 96/29397 or the fungal cellulases produced from *Myceliophthora thermophila* and *Fusarium oxysporum* disclosed in U.S. Pat. Nos. 5,648,263, 5,691,178, 5,776,757, WO 89/09259 and WO 91/17244. Also relevant are cellulases from *Bacillus* as described in WO 02/099091 and JP 2000210081. Suitable cellulases are alkaline or neutral cellulases having care benefits. Examples of cellulases are described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307.

Other cellulases are endo-beta-1,4-glucanase enzyme having a sequence of at least 97% identity to the amino acid sequence of position 1 to position 773 of SEQ ID NO: 2 of WO 2002/099091 or a family 44 xyloglucanase, which a xyloglucanase enzyme having a sequence of at least 60% identity to positions 40-559 of SEQ ID NO: 2 of WO 2001/062903.

Commercially available cellulases include Carezyme®, Carezyme® Premium, Celluzyme, Celluclean®, Celluclast®, Endolase®, Renozyme®; Whitezyme® Celluclean® Classic, Cellusoft® (Novozymes A/S), Puradax®, Puradax HA, and Puradax EG (available from Genencor International Inc.) and KAC-500(B)™ (Kao Corporation).

Mannanases

Suitable mannanases include those of bacterial or fungal origin. Chemically or genetically modified mutants are included. The mannanase may be an alkaline mannanase of Family 5 or 26. It may be a wild-type from *Bacillus* or *Humicola*, particularly *B. agaradhaerens, B. licheniformis, B. halodurans, B. clausii*, or *H. insolens*. Suitable mannanases are described in WO 1999/064619. A commercially available mannanase is Mannaway (Novozymes A/S).

Peroxidases/Oxidases

Suitable peroxidases/oxidases include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257. Commercially available peroxidases include Guardzyme™ (Novozymes A/S).

Lipases and Cutinases

Suitable lipases and cutinases include those of bacterial or fungal origin. Chemically modified or protein engineered mutant enzymes are included. Examples include lipase from *Thermomyces*, e.g. from *T. lanuginosus* (previously named *Humicola lanuginosa*) as described in EP258068 and EP305216, cutinase from *Humicola*, e.g. *H. insolens* (WO96/13580), lipase from strains of *Pseudomonas* (some of these now renamed to *Burkholderia*), e.g. *P. alcaligenes* or *P. pseudoalcaligenes* (EP218272), *P. cepacia* (EP331376), *P. sp.* strain SD705 (WO95/06720 & WO96/27002), *P. wisconsinensis* (WO96/12012), GDSL-type *Streptomyces* lipases (WO10/065455), cutinase from *Magnaporthe grisea* (WO10/107560), cutinase from *Pseudomo-*

*nas mendocina* (U.S. Pat. No. 5,389,536), lipase from *Thermobifida fusca* (WO11/084412), *Geobacillus stearothermophilus* lipase (WO11/084417), lipase from *Bacillus subtilis* (WO11/084599), and lipase from *Streptomyces griseus* (WO11/150157) and *S. pristinaespiralis* (WO12/137147).

Other examples are lipase variants such as those described in EP407225, WO92/05249, WO94/01541, WO94/25578, WO95/14783, WO95/30744, WO95/35381, WO95/22615, WO96/00292, WO97/04079, WO97/07202, WO00/34450, WO00/60063, WOO1/92502, WO07/87508 and WO09/109500.

Preferred commercial lipase products include Lipolase™, Lipex™; Lipolex™ and Lipoclean™ (Novozymes A/S), Lumafast (originally from Genencor) and Lipomax (originally from Gist-Brocades).

Still other examples are lipases sometimes referred to as acyltransferases or perhydrolases, e.g. acyltransferases with homology to *Candida antarctica* lipase A (WO10/111143), acyltransferase from *Mycobacterium smegmatis* (WO05/56782), perhydrolases from the CE 7 family (WO09/67279), and variants of the *M. smegmatis* perhydrolase in particular the S54V variant used in the commercial product Gentle Power Bleach from Huntsman Textile Effects Pte Ltd (WO10/100028).

Amylases

Suitable amylases include alpha-amylases and/or a glucoamylases and may be of bacterial or fungal origin. Chemically modified or protein engineered mutants are included. Amylases include, for example, alpha-amylases obtained from *Bacillus*, e.g., a special strain of *Bacillus licheniformis*, described in more detail in GB 1,296,839.

Suitable amylases include amylases having SEQ ID NO 2 in WO 95/10603 or variants having 90% sequence identity to SEQ ID NO 3 thereof. Preferred variants are described in WO 94/02597, WO 94/18314, WO 97/43424 and SEQ ID NO 4 of WO 99/019467, such as variants with substitutions in one or more of the following positions: 15, 23, 105, 106, 124, 128, 133, 154, 156, 178, 179, 181, 188, 190, 197, 201, 202, 207, 208, 209, 211, 243, 264, 304, 305, 391, 408, and 444.

Different suitable amylases include amylases having SEQ ID NO 6 in WO 02/010355 or variants thereof having 90% sequence identity to SEQ ID NO 6. Preferred variants of SEQ ID NO 6 are those having a deletion in positions 181 and 182 and a substitution in position 193.

Other amylases which are suitable are hybrid alpha-amylase comprising residues 1-33 of the alpha-amylase derived from *B. amyloliquefaciens* shown in SEQ ID NO 6 of WO 2006/066594 and residues 36-483 of the *B. licheniformis* alpha-amylase shown in SEQ ID NO 4 of WO 2006/066594 or variants having 90% sequence identity thereof. Preferred variants of this hybrid alpha-amylase are those having a substitution, a deletion or an insertion in one of more of the following positions: G48, T49, G107, H156, A181, N190, M197, 1201, A209 and Q264. Most preferred variants of the hybrid alpha-amylase comprising residues 1-33 of the alpha-amylase derived from *B. amyloliquefaciens* shown in SEQ ID NO 6 of WO 2006/066594 and residues 36-483 of SEQ ID NO 4 are those having the substitutions:

M197T;

H156Y+A181T+N190F+A209V+Q264S; or

G48A+T491+G107A+H156Y+A181T+N190F+201F+A209V+Q264S.

Further amylases which are suitable are amylases having SEQ ID NO 6 in WO 99/019467 or variants thereof having 90% sequence identity to SEQ ID NO 6. Preferred variants of SEQ ID NO 6 are those having a substitution, a deletion or an insertion in one or more of the following positions: R181, G182, H183, G184, N195, 1206, E212, E216 and K269. Particularly preferred amylases are those having deletion in positions R181 and G182, or positions H183 and G184.

Additional amylases which can be used are those having SEQ ID NO 1, SEQ ID NO 3, SEQ ID NO 2 or SEQ ID NO 7 of WO 96/023873 or variants thereof having 90% sequence identity to SEQ ID NO 1, SEQ ID NO 2, SEQ ID NO 3 or SEQ ID NO 7. Preferred variants of SEQ ID NO 1, SEQ ID NO 2, SEQ ID NO 3 or SEQ ID NO 7 are those having a substitution, a deletion or an insertion in one or more of the following positions: 140, 181, 182, 183, 184, 195, 206, 212, 243, 260, 269, 304 and 476, using SEQ ID 2 of WO 96/023873 for numbering. More preferred variants are those having a deletion in two positions selected from 181, 182, 183 and 184, such as 181 and 182, 182 and 183, or positions 183 and 184. Most preferred amylase variants of SEQ ID NO 1, SEQ ID NO 2 or SEQ ID NO 7 are those having a deletion in positions 183 and 184 and a substitution in one or more of positions 140, 195, 206, 243, 260, 304 and 476.

Other amylases which can be used are amylases having SEQ ID NO 2 of WO 08/153815, SEQ ID NO 10 in WO 01/66712 or variants thereof having 90% sequence identity to SEQ ID NO 2 of WO 08/153815 or 90% sequence identity to SEQ ID NO 10 in WO 01/66712. Preferred variants of SEQ ID NO 10 in WO 01/66712 are those having a substitution, a deletion or an insertion in one of more of the following positions: 176, 177, 178, 179, 190, 201, 207, 211 and 264.

Further suitable amylases are amylases having SEQ ID NO 2 of WO 09/061380 or variants having 90% sequence identity to SEQ ID NO 2 thereof. Preferred variants of SEQ ID NO 2 are those having a truncation of the C-terminus and/or a substitution, a deletion or an insertion in one of more of the following positions: Q87, Q98, S125, N128, T131, T165, K178, R180, S181, T182, G183, M201, F202, N225, S243, N272, N282, Y305, R309, D319, Q320, Q359, K444 and G475. More preferred variants of SEQ ID NO 2 are those having the substitution in one of more of the following positions: Q87E, R, Q98R, S125A, N128C, T131, T1651, K178L, T182G, M201L, F202Y, N225E,R, N272E, R, S243Q,A,E,D, Y305R, R309A, Q320R, Q359E, K444E and G475K and/or deletion in position R180 and/or S181 or of T182 and/or G183. Most preferred amylase variants of SEQ ID NO 2 are those having the substitutions:

N128C+K178L+T182G+Y305R+G475K;

N128C+K178L+T182G+F202Y+Y305R+D319T+G475K;

S125A+N128C+K178L+T182G+Y305R+G475K; or

S125A+N128C+T1311+T165+K178L+T182G+Y305R+G475K wherein the variants are C-terminally truncated and optionally further comprises a substitution at position 243 and/or a deletion at position 180 and/or position 181.

Further suitable amylases are amylases having SEQ ID NO 1 of WO13184577 or variants having 90% sequence identity to SEQ ID NO 1 thereof. Preferred variants of SEQ ID NO 1 are those having a substitution, a deletion or an insertion in one of more of the following positions: K176, R178, G179, T180, G181, E187, N192, M199, I203, S241, R458, T459, D460, G476 and G477. More preferred variants of SEQ ID NO 1 are those having the substitution in one of more of the following positions: K176L, E187P, N192FYH, M199L, 1203YF, S241QADN, R458N, T459S, D460T, G476K and G477K and/or deletion in position R178 and/or S179 or of T180 and/or G181. Most preferred amylase variants of SEQ ID NO 1 are those having the substitutions:

E187P+1203Y+G476K

E187P+1203Y+R458N+T459S+D460T+G476K wherein the variants optionally further comprise a substitution at position 241 and/or a deletion at position 178 and/or position 179.

Further suitable amylases are amylases having SEQ ID NO 1 of WO10104675 or variants having 90% sequence identity to SEQ ID NO 1 thereof. Preferred variants of SEQ ID NO 1 are those having a substitution, a deletion or an insertion in one of more of the following positions: N21, D97, V128 K177, R179, S180, 1181, G182, M200, L204, E242, G477 and G478. More preferred variants of SEQ ID NO 1 are those having the substitution in one of more of the following positions: N21D, D97N, V128I K177L, M200L, L204YF, E242QA, G477K and G478K and/or deletion in position R179 and/or S180 or of 1181 and/or G182. Most preferred amylase variants of SEQ ID NO 1 are those having the substitutions:

N21D+D97N+V128I wherein the variants optionally further comprise a substitution at position 200 and/or a deletion at position 180 and/or position 181.

Other suitable amylases are the alpha-amylase having SEQ ID NO 12 in WO01/66712 or a variant having at least 90% sequence identity to SEQ ID NO 12. Preferred amylase variants are those having a substitution, a deletion or an insertion in one of more of the following positions of SEQ ID NO 12 in WO01/66712: R28, R118, N174; R181, G182, D183, G184, G186, W189, N195, M202, Y298, N299, K302, S303, N306, R310, N314; R320, H324, E345, Y396, R400, W439, R444, N445, K446, Q449, R458, N471, N484. Particular preferred amylases include variants having a deletion of D183 and G184 and having the substitutions R118K, N195F, R320K and R458K, and a variant additionally having substitutions in one or more position selected from the group: M9, G149, G182, G186, M202, T257, Y295, N299, M323, E345 and A339, most preferred a variant that additionally has substitutions in all these positions.

Other examples are amylase variants such as those described in WO2011/098531, WO2013/001078 and WO2013/001087.

Commercially available amylases are Duramyl™, Termamyl™, Fungamyl™, Stainzyme™ Stainzyme Pus™, Natalase™, Liquozyme X and BAN™ (from Novozymes A/S), and Rapidase™, Purastar™/Effecten™, Powerase, Preferenz S1000, Preferenz S100 and Preferenz S110 (from Genencor International Inc./DuPont).

Proteases

Suitable proteases include those of bacterial, fungal, plant, viral or animal origin e.g. vegetable or microbial origin. Microbial origin is preferred. Chemically modified or protein engineered mutants are included. It may be an alkaline protease, such as a serine protease or a metalloprotease. A serine protease may for example be of the S1 family, such as trypsin, or the S8 family such as subtilisin. A metalloproteases protease may for example be a thermolysin from e.g. family M4 or other metalloproteases such as those from M5, M7 or M8 families.

The term "subtilases" refers to a sub-group of serine protease according to Siezen et al., *Protein Engng.* 4 (1991) 719-737 and Siezen et al. *Protein Science* 6 (1997) 501-523. Serine proteases are a subgroup of proteases characterized by having a serine in the active site, which forms a covalent adduct with the substrate. The subtilases may be divided into 6 sub-divisions, i.e. the Subtilisin family, the Thermitase family, the Proteinase K family, the Lantibiotic peptidase family, the Kexin family and the Pyrolysin family. Examples of subtilases are those derived from *Bacillus* such as *Bacillus lentus, Bacillus alkalophilus, Bacillus subtilis, Bacillus amyloliquefaciens, Bacillus pumilus* and *Bacillus gibsonii* described in; U.S. Pat. No. 7,262,042 and WO09/021867, and Subtilisin *lentus*, Subtilisin Novo, subtilisin Carlsberg, *Bacillus licheniformis*, subtilisin BPN', subtilisin 309, subtilisin 147 and subtilisin 168 and e.g. protease PD138 described in (WO93/18140). Other useful proteases may be those described in WO01/016285 and WO02/016547. Examples of trypsin-like proteases are trypsin (e.g. of porcine or bovine origin) and the *Fusarium* protease described in WO94/25583 and WO05/040372, and the chymotrypsin proteases derived from Cellumonas described in WO05/052161 and WO05/052146. A further preferred protease is the alkaline protease from *Bacillus lentus* DSM 5483, as described for example in WO95/23221, and variants thereof which are described in WO92/21760, WO95/23221, EP1921147 and EP1921148. Examples of metalloproteases are the neutral metalloprotease as described in WO07/044993 (Proctor & Gamble/Genencor Int.) such as those derived from *Bacillus amyloliquefaciens*. Examples of useful proteases are the variants described in: WO89/06279 WO92/19729, WO96/034946, WO98/20115, WO98/20116, WO99/011768, WO01/44452, WO03/006602, WO04/03186, WO04/041979, WO07/006305, WO11/036263, WO11/036264, especially the variants with substitutions in one or more of the following positions: 3, 4, 9, 15, 24, 27, 42, 55, 59, 60, 66, 74, 85, 96, 97, 98, 99, 100, 101, 102, 104, 116, 118, 121, 126, 127, 128, 154, 156, 157, 158, 161, 164, 176, 179, 182, 185, 188, 189, 193, 198, 199, 200, 203, 206, 211, 212, 216, 218, 226, 229, 230, 239, 246, 255, 256, 268 and 269 wherein the positions correspond to the positions of the *Bacillus lentus* protease shown in SEQ ID NO 1 of WO 2016/001449. More preferred the protease variants may comprise one or more of the mutations selected from the group consisting of: S3T, V41, S9R, S9E, A15T, S24G, S24R, K27R, N42R, S55P, G59E, G59D, N60D, N60E, V66A, N74D, S85R, A96S, S97G, S97D, S97A, S97SD, S99E, S99D, S99G, S99M, S99N, S99R, S99H, S101A, V1021, V102Y, V102N, S104A, G116V, G116R, H118D, H118N, A120S, S126L, P127Q, S128A, S154D, A156E, G157D, G157P, S158E, Y161A, R164S, Q176E, N179E, S182E, Q185N, A188P, G189E, V193M, N198D, V1991, Y203W, S206G, L211Q, L211D, N212D, N212S, M216S, A226V, K229L, Q230H, Q239R, N246K, N255W, N255D, N255E, L256E, L256D T268A and R269H. The protease variants are preferably variants of the *Bacillus lentus* protease (Savinase®) shown in SEQ ID NO 1 of WO2016/001449, the *Bacillus amyloliquefaciens* protease (BPN') shown in SEQ ID NO 2 of WO2016/001449. The protease variants preferably have at least 80% sequence identity to SEQ ID NO 1 or SEQ ID NO 2 of WO 2016/001449.

A protease variant comprising a substitution at one or more positions corresponding to positions 171, 173, 175, 179, or 180 of SEQ ID NO 1 of WO2004/067737, wherein said protease variant has a sequence identity of at least 75% but less than 100% to SEQ ID NO 1 of WO2004/067737.

Suitable commercially available protease enzymes include those sold under the trade names Alcalase®, Duralase™, Durazym™, Relase, Relase® Ultra, Savinase®, Savinase® Ultra, Primase™, Polarzyme™, Kannase™, Liquanase™, Liquanase™ Ultra, Ovozyme®, Coronase™, Coronase™ Ultra, Blaze™, Blaze EvityO 100T, Blaze Evity® 125T, Blaze Evity® 150T, Neutrase, Everlase® and Esperase® (Novozymes A/S), those sold under the tradename Maxatase™, Maxacal, Maxapem™, Purafect Ox™, Purafect OxP™, Puramax™, FN2™, FN3™, FN4™, Excellase®, Excellenz P1000™, Excellenz P1250™, Eraser™, Preferenz P100™, Purafect Prime™, Preferenz P110™, Effectenz P1000™, Purafect®™, Effectenz P1050™, Purafect Ox®™, Effectenz P2000™, Purafast™, Properase™, Opticlean® and Optimase@(Danisco/DuPont), Axapem™ (Gist-Brocases N.V.), BLAP (sequence shown in FIG. 29 of U.S. Pat. No. 5,352,604) and variants hereof (Henkel AG) and KAP (*Bacillus alkalophilus* subtilisin) from Kao.

Peroxidases/Oxidases

A suitable peroxidaseis a peroxidase enzyme comprised by the enzyme classification EC 1.11.1.7, as set out by the Nomenclature Committee of the International Union of Biochemistry and Molecular Biology (IUBMB), or any fragment derived therefrom, exhibiting peroxidase activity.

Suitable peroxidases include those of plant, bacterial or fungal origin. Chemically modified or protein engineered mutants are included. Examples of useful peroxidases include peroxidases from *Coprinopsis*, e.g., from *C. cinerea* (EP 179,486), and variants thereof as those described in WO 93/24618, WO 95/10602, and WO 98/15257.

A suitable peroxidase includes a haloperoxidase enzyme, such as chloroperoxidase, bromoperoxidase and compounds exhibiting chloroperoxidase or bromoperoxidase activity. Haloperoxidases are classified according to their specificity for halide ions. Chloroperoxidases (E.C. 1.11.1.10) catalyze formation of hypochlorite from chloride ions. Preferably, the haloperoxidase is a vanadium haloperoxidase, i.e., a vanadate-containing haloperoxidase. Haloperoxidases have been isolated from many different fungi, in particular from the fungus group dematiaceous hyphomycetes, such as Caldariomyces, e.g., *C. fumago, Alternaria, Curvularia*, e.g., *C. verruculosa* and *C. inaequalis, Drechslera, Ulocladium* and *Botrytis.*

Haloperoxidases have also been isolated from bacteria such as *Pseudomonas*, e.g., *P. pyrrocinia* and *Streptomyces*, e.g., *S. aureofaciens.*

A suitable oxidase includes in particular, any laccase enzyme comprised by the enzyme classification EC 1.10.3.2, or any fragment derived therefrom exhibiting laccase activity, or a compound exhibiting a similar activity, such as a catechol oxidase (EC 1.10.3.1), an o-aminophenol oxidase (EC 1.10.3.4), or a bilirubin oxidase (EC 1.3.3.5). Preferred laccase enzymes are enzymes of microbial origin. The enzymes may be derived from plants, bacteria or fungi (including filamentous fungi and yeasts). Suitable examples from fungi include a laccase derivable from a strain of *Aspergillus, Neurospora*, e.g., *N. crassa, Podospora, Botrytis, Collybia, Fomes, Lentinus, Pleurotus, Trametes*, e.g., *T. villosa* and *T. versicolor, Rhizoctonia*, e.g., *R. solani, Coprinopsis*, e.g., *C. cinerea, C. comatus, C. friesii*, and *C. plicatilis, Psathyrella*, e.g., *P. condelleana, Panaeolus*, e.g., *P. papilionaceus, Myceliophthora*, e.g., *M. thermophila, Schytalidium*, e.g., *S. thermophilum, Polyporus*, e.g., *P. pinsitus, Phlebia*, e.g., *P. radiata* (WO 92/01046), or *Coriolus*, e.g., *C. hirsutus* (JP 2238885). Suitable examples from bacteria include a laccase derivable from a strain of *Bacillus*. A laccase derived from *Coprinopsis* or *Myceliophthora* is preferred; in particular, a laccase derived from *Coprinopsis cinerea*, as disclosed in WO 97/08325; or from *Myceliophthora thermophila*, as disclosed in WO 95/33836.

Nucleases

Suitable nucleases include deoxyribonucleases (DNases) and ribonucleases (RNases), which are any enzyme that catalyzes the hydrolytic cleavage of phosphodiester linkages in the DNA or RNA backbone respectively, thus degrading DNA and RNA. There are two primary classifications based on the locus of activity. Exonucleases digest nucleic acids from the ends. Endonucleases act on regions in the middle of target molecules. The nuclease is preferably a DNase, which is preferable is obtainable from a microorganism, preferably a bacterium; in particular a DNase which is obtainable from a species of *Bacillus* is preferred; in particular a DNase which is obtainablefrom *Bacillus cibi, Bacillus subtilis* or *Bacillus licheniformisis* preferred. Examples of suitable DNases are described in WO 2011/098579, WO2014/087011 and WO2017/060475.

Dispersants

The cleaning e.g. detergent compositions of the present invention can also contain dispersants. In particular, powdered detergents may comprise dispersants. Suitable water-soluble organic materials include the homo- or co-polymeric acids or their salts, in which the polycarboxylic acid comprises at least two carboxyl radicals separated from each other by not more than two carbon atoms. Suitable dispersants are for example described in Powdered Detergents, Surfactant science series volume 71, Marcel Dekker, Inc.

Dye Transfer Inhibiting Agents

The cleaning e.g. detergent compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

Fluorescent Whitening Agent

The cleaning e.g. detergent compositions of the present invention will preferably also contain additional components that may tint articles being cleaned, such as fluorescent whitening agent or optical brighteners. Where present the brightener is preferably at a level of about 0.01% to about 0.5%. Any fluorescent whitening agent suitable for use in a laundry detergent composition may be used in the composition of the present invention. The most commonly used fluorescent whitening agents are those belonging to the classes of diaminostilbene-sulfonic acid derivatives, diarylpyrazoline derivatives and bisphenyl-distyryl derivatives. Examples of the diaminostilbene-sulfonic acid derivative type of fluorescent whitening agents include the sodium salts of: 4,4'-bis-(2-diethanolamino-4-anilino-s-triazin-6-ylamino) stilbene-2,2'-disulfonate, 4,4'-bis-(2,4-dianilino-s-triazin-6-ylamino) stilbene-2,2'-disulfonate, 4,4'-bis-(2-anilino-4-(N-methyl-N-2-hydroxy-ethylamino)-s-triazin-6-ylamino) stilbene-2,2'-disulfonate, 4,4'-bis-(4-phenyl-1,2,3-triazol-2-yl)stilbene-2,2'-disulfonate and sodium 5-(2H-naphtho[1,2-d][1,2,3]triazol-2-yl)-2-[(E)-2-phenylvinyl] benzenesulfonate. Preferred fluorescent whitening agents are Tinopal DMS and Tinopal CBS available from Ciba-Geigy AG, Basel, Switzerland. Tinopal DMS is the disodium salt of 4,4'-bis-(2-morpholino-4-anilino-s-triazin-6-ylamino) stilbene-2,2'-disulfonate. Tinopal CBS is the disodium salt of 2,2'-bis-(phenyl-styryl)-disulfonate. Also preferred are fluorescent whitening agents is the commercially available Parawhite KX, supplied by Paramount Minerals and Chemicals, Mumbai, India. Other fluorescers suitable for use in the invention include the 1-3-diaryl pyrazolines and the 7-alkylaminocoumarins. Suitable fluorescent brightener levels include lower levels of from about 0.01, from 0.05, from about 0.1 or even from about 0.2 wt % to upper levels of 0.5 or even 0.75 wt %.

Soil Release Polymers

The detergent compositions of the present invention may also include one or more soil release polymers which aid the removal of soils from fabrics such as cotton and polyester based fabrics, in particular the removal of hydrophobic soils from polyester based fabrics. The soil release polymers may for example be non-ionic or anionic terephthalte based polymers, polyvinyl caprolactam and related copolymers, vinyl graft copolymers, polyester polyamides see for example Chapter 7 in Powdered Detergents, Surfactant science series volume 71, Marcel Dekker, Inc. Another type of soil release polymers is amphiphilic alkoxylated grease cleaning polymers comprising a core structure and a plurality of alkoxylate groups attached to that core structure. The core structure may comprise a polyalkylenimine structure or a polyalkanolamine structure as described in detail in WO2009/087523 (hereby incorporated by reference). Furthermore, random graft co-polymers are suitable soil release polymers. Suitable graft co-polymers are described in more detail in WO2007/138054, WO2006/108856 and WO2006/113314 (hereby incorporated by reference). Suitable polyethylene glycol polymers include random graft co-polymers comprising: (i) hydrophilic backbone comprising polyethylene glycol; and (ii) side chain(s) selected from the group consisting of: C4-C25 alkyl group, polypropylene, polybutylene, vinyl ester of a saturated C1-C6 mono-carboxylic acid, Cl—C 6 alkyl ester of acrylic or methacrylic acid, and mixtures thereof. Suitable polyethylene glycol polymers have a polyethylene glycol backbone with random grafted polyvinyl acetate side chains. The average molecular weight of the polyethylene glycol backbone can be in the range of from 2,000 Da to 20,000 Da, or from 4,000 Da to 8,000 Da. The molecular weight ratio of the polyethylene glycol backbone to the polyvinyl acetate side chains can be in the range of from 1:1 to 1:5, or from 1:1.2 to 1:2. The average number of graft sites per ethylene oxide units can be less than 1, or less than 0.8, the average number of graft sites per ethylene oxide units can be in the range of from 0.5 to 0.9, or the average number of graft sites per ethylene oxide units can be in the range of from 0.1 to 0.5, or from 0.2 to 0.4. A suitable polyethylene glycol polymer is Sokalan HP22. Other soil release polymers are substituted polysaccharide structures especially substituted cellulosic structures such as modified cellulose deriviatives such as those described in EP 1867808 or WO 2003/040279 (both are hereby incorporated by reference). Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof. Suitable cellulosic polymers include methyl cellulose, carboxy methyl cellulose, ethyl cellulose, hydroxyl ethyl cellulose, hydroxyl propyl methyl cellulose, ester carboxy methyl cellulose, and mixtures thereof.

Anti-Redeposition Agents

The detergent compositions of the present invention may also include one or more anti-redeposition agents such as carboxymethylcellulose (CMC), polyvinyl alcohol (PVA), polyvinylpyrrolidone (PVP), polyoxyethylene and/or polyethyleneglycol (PEG), homopolymers of acrylic acid, copolymers of acrylic acid and maleic acid, and ethoxylated polyethyleneimines. The cellulose-based polymers described under soil release polymers above may also function as anti-redeposition agents.

Rheology Modifiers

The detergent compositions of the present invention may also include one or more rheology modifiers, structurants or thickeners, as distinct from viscosity reducing agents. The rheology modifiers are selected from the group consisting of non-polymeric crystalline, hydroxy-functional materials, polymeric rheology modifiers which impart shear thinning characteristics to the aqueous liquid matrix of a liquid detergent composition. The rheology and viscosity of the detergent can be modified and adjusted by methods known in the art, for example as shown in EP 2169040. Other suitable cleaning composition components include, but are not limited to, anti-shrink agents, anti-wrinkling agents, bactericides, binders, carriers, dyes, enzyme stabilizers, fabric softeners, fillers, foam regulators, hydrotropes, perfumes, pigments, sod suppressors, solvents, and structurants for liquid detergents and/or structure elasticizing agents.

Formulation of Detergent Products

The cleaning e.g. detergent composition of the invention may be in any convenient form, e.g., a bar, a homogenous tablet, a tablet having two or more layers, a pouch having one or more compartments, a regular or compact powder, a granule, a paste, a gel, or a regular, compact or concentrated liquid.

Pouches can be configured as single or multicompartments. It can be of any form, shape and material which is suitable for hold the composition, e.g. without allowing the release of the composition to release of the composition from the pouch prior to water contact. The pouch is made from water soluble film which encloses an inner volume. Said inner volume can be divided into compartments of the pouch. Preferred films are polymeric materials preferably polymers which are formed into a film or sheet. Preferred polymers, copolymers or derivates thereof are selected polyacrylates, and water-soluble acrylate copolymers, methyl cellulose, carboxy methyl cellulose, sodium dextrin, ethyl cellulose, hydroxyethyl cellulose, hydroxypropyl methyl cellulose, malto dextrin, poly methacrylates, most preferably polyvinyl alcohol copolymers and, hydroxypropyl methyl cellulose (HPMC). Preferably the level of polymer in the film for example PVA is at least about 60%. Preferred average molecular weight will typically be about 20,000 to about 150,000. Films can also be of blended compositions comprising hydrolytically degradable and water-soluble polymer blends such as polylactide and polyvinyl alcohol (known under the Trade reference M8630 as sold by MonoSol LLC, Indiana, USA) plus plasticisers like glycerol, ethylene glycerol, propylene glycol, sorbitol and mixtures thereof. The pouches can comprise a solid laundry cleaning composition or part components and/or a liquid cleaning composition or part components separated by the water-soluble film. The compartment for liquid components can be different in composition than compartments containing solids: US2009/0011970 A1.

Detergent ingredients can be separated physically from each other by compartments in water dissolvable pouches or in different layers of tablets. Thereby negative storage interaction between components can be avoided. Different dissolution profiles of each of the compartments can also give rise to delayed dissolution of selected components in the wash solution.

A liquid or gel detergent, which is not unit dosed, may be aqueous, typically containing at least 20% by weight and up to 95% water, such as up to about 70% water, up to about 65% water, up to about 55% water, up to about 45% water, up to about 35% water. Other types of liquids, including without limitation, alkanols, amines, diols, ethers and polyols may be included in an aqueous liquid or gel. An aqueous liquid or gel detergent may contain from 0-30% organic solvent. A liquid or gel detergent may be non-aqueous.

Granular Detergent Formulations

Non-dusting granulates may be produced, e.g. as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The glycosyl hydrolase e.g. GH114 glycosyl hydrolase may be formulated as a granule for example as a co-granule that combines one or more enzymes. Each enzyme will then be present in more granules securing a more uniform distribution of enzymes in the detergent. This also reduces the physical segregation of different enzymes due to different particle sizes. Methods for producing multi-enzyme co-granulate for the detergent industry is disclosed in the IP.com disclosure IPCOM000200739D.

Another example of formulation of enzymes by the use of co-granulates are disclosed in WO 2013/188331, which relates to a detergent composition comprising (a) a multi-enzyme co-granule; (b) less than 10 wt zeolite (anhydrous basis); and (c) less than 10 wt phosphate salt (anhydrous basis), wherein said enzyme co-granule comprises from 10 to 98 wt % moisture sink component and the composition additionally comprises from 20 to 80 wt % detergent moisture sink component. The multi-enzyme co-granule may comprise an enzyme of the invention and one or more enzymes selected from the group consisting of proteases, lipases, cellulases, xyloglucanases, perhydrolases, peroxidases, lipoxygenases, laccases, hemicellulases, proteases, cellulases, cellobiose dehydrogenases, xylanases, phospho lipases, esterases, cutinases, pectinases, mannanases, pectate lyases, keratinases, reductases, oxidases, phenoloxidases, ligninases, pullulanases, tannases, pentosanases, lichenases glucanases, arabinosidases, hyaluronidase, chondroitinase, amylases, and mixtures thereof. WO 2013/188331 also relates to a method of treating and/or cleaning a surface, preferably a fabric surface comprising the steps of (i) contacting said surface with the detergent composition as claimed and described herein in aqueous wash liquor, (ii) rinsing and/or drying the surface.

An embodiment of the invention relates to an enzyme granule/particle comprising the glycosyl hydrolase e.g. GH114 glycosyl hydrolase. The granule is composed of a core, and optionally one or more coatings (outer layers) surrounding the core. Typically, the granule/particle size, measured as equivalent spherical diameter (volume based average particle size), of the granule is 20-2000 μm, particularly 50-1500 μm, 100-1500 μm or 250-1200 μm. The core may include additional materials such as fillers, fibre materials (cellulose or synthetic fibres), stabilizing agents, solubilising agents, suspension agents, viscosity regulating agents, light spheres, plasticizers, salts, lubricants and fragrances. The core may include binders, such as synthetic polymer, wax, fat, or carbohydrate. The core may comprise a salt of a multivalent cation, a reducing agent, an antioxidant, a peroxide decomposing catalyst and/or an acidic buffer component, typically as a homogenous blend. The core may consist of an inert particle with the enzyme absorbed into it, or applied onto the surface, e.g., by fluid bed coating. The core may have a diameter of 20-2000 μm, particularly 50-1500 μm, 100-1500 μm or 250-1200 μm. The core can be prepared by granulating a blend of the ingredients, e.g., by a method comprising granulation techniques such as crystallization, precipitation, pan-coating, fluid bed coating, fluid bed agglomeration, rotary atomization, extrusion, prilling, spheronization, size reduction methods, drum granulation, and/or high shear granulation.

Methods for preparing the core can be found in Handbook of Powder Technology; Particle size enlargement by C. E. Capes; Volume 1; 1980; Elsevier.

The core of the enzyme granule/particle may be surrounded by at least one coating, e.g., to improve the storage stability, to reduce dust formation during handling, or for coloring the granule. The optional coating(s) may include a salt coating, or other suitable coating materials, such as polyethylene glycol (PEG), methyl hydroxy-propyl cellulose (MHPC) and polyvinyl alcohol (PVA). Examples of enzyme granules with multiple coatings are shown in WO 93/07263 and WO 97/23606. The coating may be applied in an amount of at least 0.1% by weight of the core, e.g., at least 0.5%, 1% or 5%. The amount may be at most 100%, 70%, 50%, 40% or 30%. The coating is preferably at least 0.1 μm thick, particularly at least 0.5 μm, at least 1 μm or at least 5 μm. In a one embodiment, the thickness of the coating is below 100 μm. In another embodiment, the thickness of the coating is below 60 μm. In an even more particular embodiment the total thickness of the coating is below 40 μm. The coating should encapsulate the core unit by forming a substantially continuous layer. A substantially continuous layer is to be understood as a coating having few or no holes, so that the core unit it is encapsulating/enclosing has few or none uncoated areas. The layer or coating should be homogeneous in thickness. The coating can further contain other materials as known in the art, e.g., fillers, antisticking agents, pigments, dyes, plasticizers and/or binders, such as titanium dioxide, kaolin, calcium carbonate or talc. A salt coating may comprise at least 60% by weight w/w of a salt, e.g., at least 65%, at least 70%, at least 75%, at least 80%, at least 85%, at least 90%, at least 95% or at least 99% by weight w/w. The salt may be added from a salt solution where the salt is completely dissolved or from a salt suspension wherein the fine particles is less than 50 μm, such as less than 10 μm or less than 5 μm. The salt coating may comprise a single salt or a mixture of two or more salts. The salt may be water soluble and may have a solubility at least 0.1 grams in 100 g of water at 20° C., preferably at least 0.5 g per 100 g water, e.g., at least 1 g per 100 g water, e.g., at least 5 g per 100 g water. The salt may be an inorganic salt, e.g., salts of sulfate, sulfite, phosphate, phosphonate, nitrate, chloride or carbonate or salts of simple organic acids (less than 10 carbon atoms, e.g., 6 or less carbon atoms) such as citrate, malonate or acetate. Examples of cations in these salts are alkali or earth alkali metal ions, the ammonium ion or metal ions of the first transition series, such as sodium, potassium, magnesium, calcium, zinc or aluminium. Examples of anions include chloride, bromide, iodide, sulfate, sulfite, bisulfite, thiosulfate, phosphate, monobasic phosphate, dibasic phosphate, hypophosphite, dihydrogen pyrophosphate, tetraborate, borate, carbonate, bicarbonate, metasilicate, citrate, malate, maleate, malonate, succinate, lactate, formate, acetate, butyrate, propionate, benzoate, tartrate, ascorbate or gluconate. In particular alkali- or earth alkali metal salts of sulfate, sulfite, phosphate, phosphonate, nitrate, chloride or carbonate or salts of simple organic acids such as citrate, malonate or acetate may be used. The salt in the coating may have a constant humidity at 20° C. above 60%, particularly above 70%, above 80% or above 85%, or it may be another hydrate form of such a salt (e.g., anhydrate). The salt coating may be as described in WO 00/01793 or WO 2006/034710. Specific examples of suitable salts are NaCl ($CH_{20° C.}$=76%), $Na_2CO_3$ ($CH_{20° C.}$=92%), $NaNO_3$ ($CH_{20° C.}$=73%), $Na_2HPO_4$ ($CH_{20° C.}$=95%), $Na_3PO_4$ ($CH_{25° C.}$=92%), $NH_4Cl$ ($CH_{20° C.}$=79.5%), $(NH_4)_2HPO_4$ ($CH_{20° C.}$=93, 0%), $NH_4H_2PO_4$ ($CH_{20° C.}$=93.1%), $(NH_4)_2SO_4$ ($CH_{20° C.}$=81.1%), KCl ($CH_{20° C.}$=85%), $K_2HPO_4$ ($CH_{20° C.}$=92%), $KH_2PO_4$ ($CH_{20° C.}$=96.5%), $KNO_3$ ($CH_{20° C.}$=93.5%), $Na_2SO_4$ ($CH_{20° C.}$=93%), $K_2SO_4$ ($CH_{20° C.}$=98%), $KHSO_4$ ($CH_{20° C.}$=86%), $MgSO_4$ ($CH_{20° C.}$=90%), $ZnSO_4$ ($CH_{20° C.}$=90%) and sodium citrate ($CH_{20° C.}$=86%). Other examples include $NaH_2PO_4$, $(NH_4)H_2PO_4$, $CuSO_4$, $Mg(NO_3)_2$ and magnesium acetate. The salt may be in anhydrous form, or it may be a hydrated salt, i.e. a crystalline salt hydrate with bound water(s) of crystallization, such as described in WO 99/32595. Specific examples include anhydrous sodium sulfate ($Na_2SO_4$), anhydrous magnesium sulfate ($MgSO_4$), magnesium sulfate heptahydrate ($MgSO_4·7H_2O$), zinc sulfate heptahydrate ($ZnSO_4·7H_2O$), sodium phosphate dibasic heptahydrate ($Na_2HPO_4·7H_2O$), magnesium nitrate hexahydrate ($Mg(NO_3)_2(6H_2O)$), sodium citrate dihydrate and magnesium acetate tetrahydrate. Preferably the salt is applied as a solution of the salt, e.g., using a fluid bed.

One embodiment of the present invention provides a granule, which comprises:

(a) a core comprising a GH114 glycosyl hydrolase according to the invention, and (b) optionally a coating consisting of one or more layer(s) surrounding the core.

One embodiment of the invention relates to a granule, which comprises:

(a) a core comprising a GH114 glycosyl hydrolase, preferably having alpha-1,4-polygalactosaminidase activity, having at least 60%, at least 65%, at least 70%, at least 75%, at least 80%, at least 85%, at least 90%, at least 95%, at least 98% or 100% sequence identity to the amino acid sequence shown in SEQ ID NO 3, SEQ ID NO 6, SEQ ID NO 9, SEQ ID NO 12, SEQ ID NO 15, SEQ ID NO 18, SEQ ID NO 21, SEQ ID NO 24, SEQ ID NO 27, SEQ ID NO 30, SEQ ID NO 33, SEQ ID NO 36, SEQ ID NO 39, SEQ ID NO 42, SEQ ID NO 45, SEQ ID NO 48, SEQ ID NO 51, SEQ ID NO 54, SEQ ID NO 57, SEQ ID NO 72, SEQ ID NO 73, SEQ ID NO 74, SEQ ID NO 75, SEQ ID NO 76, SEQ ID NO 77, SEQ ID NO 78, SEQ ID NO 79, SEQ ID NO 80, SEQ ID NO 81, SEQ ID NO 82, SEQ ID NO 83, SEQ ID NO 84, SEQ ID NO 85, SEQ ID NO 86, SEQ ID NO 87, SEQ ID NO 88, SEQ ID NO 89, SEQ ID NO 90, SEQ ID NO 91, SEQ ID NO 92, SEQ ID NO 93, SEQ ID NO 94, SEQ ID NO 95, SEQ ID NO 96, SEQ ID NO 97, SEQ ID NO 98, SEQ ID NO 99, SEQ ID NO 100, SEQ ID NO 101, SEQ ID NO 102, SEQ ID NO 103, SEQ ID NO 104, SEQ ID NO 105, SEQ ID NO 106, SEQ ID NO 107, SEQ ID NO 108, SEQ ID NO 109, SEQ ID NO 110, SEQ ID NO 111, SEQ ID NO 112, SEQ ID NO 113, SEQ ID NO 114, SEQ ID NO 115, SEQ ID NO 116, SEQ ID NO 117, SEQ ID NO 118, SEQ ID NO 119, SEQ ID NO 120, SEQ ID NO 121, SEQ ID NO 122, SEQ ID NO 123, SEQ ID NO 124, SEQ ID NO 125, SEQ ID NO 126, SEQ ID NO 127, SEQ ID NO 128, SEQ ID NO 129, SEQ ID NO 130, SEQ ID NO 131, SEQ ID NO 132, SEQ ED NO: 133, SEQ ID NO 134, SEQ ID NO 135, SEQ ID NO 136, SEQ ID NO 137, SEQ ID NO 138, SEQ ID NO 139, SEQ ID NO 140, SEQ ID NO 141, SEQ ID NO 142, SEQ ID NO 143, SEQ ID NO 144, SEQ ID NO 145, SEQ ID NO 146 and (b) optionally a coating consisting of one or more layer(s) surrounding the core.

Medical Cleaning

The present invention further relates to methods of cleaning a medical device and to the use of a composition comprising a glycosyl hydrolase, preferably a GH114 glycosyl hydrolase and at least one adjunct ingredient for cleaning of a medical device. The invention further relates to a method of preventing biofilm formation on a medical device e.g. an indwelling medical device or implant comprising coating the device with at least one GH114 glycosyl hydrolase.

One embodiment of the invention relates to a method of preventing biofilm formation on a medical device e.g. an indwelling medical device or implant comprising coating the device with at least one GH114 glycosyl hydrolase.

The polypeptides suitable for use in medical cleaning and in compositions for medical cleaning are described above and include polypeptides which comprises one or more motif(s) [VLI]XE[EDSQ]C (SEQ ID NO 60), CY[FLIV][SDN][ATVG] (SEQ ID NO 61), DYQ[LI]G (SEQ ID NO 62), FQ[TAV]Q[PSD] (SEQ ID NO 63), AEECG (SEQ ID NO 64), NAFQ[AT]Q (SEQ ID NO 65), WQWQL (SEQ ID NO 66), [VLI][GASD]LKN[DGS][VLIP] (SEQ ID NO 67), GXXVX[NHQTS]IEY[PG] (SEQ ID NO 68), VICYF (SEQ ID NO 69), ICYFSA (SEQ ID NO 70), DFAVL (SEQ ID NO 71) and/or polypeptide selected from the group consisting of polypeptides having the amino acid sequence of SEQ ID NO 3, SEQ ID NO 6, SEQ ID NO 9, SEQ ID NO 12, SEQ ID NO 15, SEQ ID NO 18, SEQ ID NO 21, SEQ ID NO 24, SEQ ID NO 27, SEQ ID NO 30, SEQ ID NO 33, SEQ ID NO 36, SEQ ID NO 39, SEQ ID NO 42, SEQ ID NO 45, SEQ ID NO 48, SEQ ID NO 51, SEQ ID NO 54, SEQ ID NO 57, SEQ ID NO 72, SEQ ID NO 73, SEQ ID NO 74, SEQ ID NO 75, SEQ ID NO 76, SEQ ID NO 77, SEQ ID NO 78, SEQ ID NO 79, SEQ ID NO 80, SEQ ID NO 81, SEQ ID NO 82, SEQ ID NO 83, SEQ ID NO 84, SEQ ID NO 85, SEQ ID NO 86, SEQ ID NO 87, SEQ ID NO 88, SEQ ID NO 89, SEQ ID NO 90, SEQ ID NO 91, SEQ ID NO 92, SEQ ID NO 93, SEQ ID NO 94, SEQ ID NO 95, SEQ ID NO 96, SEQ ID NO 97, SEQ ID NO 98, SEQ ID NO 99, SEQ ID NO 100, SEQ ID NO 101, SEQ ID NO 102, SEQ ID NO 103, SEQ ID NO 104, SEQ ID NO 105, SEQ ID NO 106, SEQ ID NO 107, SEQ ID NO 108, SEQ ID NO 109, SEQ ID NO 110, SEQ ID NO 111, SEQ ID NO 112, SEQ ID NO 113, SEQ ID NO 114, SEQ ID NO 115, SEQ ID NO 116, SEQ ID NO 117, SEQ ID NO 118, SEQ ID NO 119, SEQ ID NO 120, SEQ ID NO 121, SEQ ID NO 122, SEQ ID NO 123, SEQ ID NO 124, SEQ ID NO 125, SEQ ID NO 126, SEQ ID NO 127, SEQ ID NO 128, SEQ ID NO 129, SEQ ID NO 130, SEQ ID NO 131, SEQ ID NO 132, SEQ ED NO: 133, SEQ ID NO 134, SEQ ID NO 135, SEQ ID NO 136, SEQ ID NO 137, SEQ ID NO 138, SEQ ID NO 139, SEQ ID NO 140, SEQ ID NO 141, SEQ ID NO 142, SEQ ID NO 143, SEQ ID NO 144, SEQ ID NO 145, SEQ ID NO 146 and polypeptides having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity hereto.

One aspect of the invention relates to a method of cleaning a medical device, wherein the method comprises
a) contacting the medical device with the composition comprising a glycosyl hydrolase, preferably having alpha-1,4-polygalactosaminidase activity, preferably a GH114 glycosyl hydrolase, for a period effective to clean the medical device;
b) cleaning, the medical device; and
c) optionally disinfect the medical device.

One aspect of the invention relates to a method of cleaning a medical device, wherein the method comprises
a) contacting the medical device with the composition comprising a GH114 glycosyl hydrolase, preferably having alpha-1,4-polygalactosaminidase activity, which comprises one or more motif(s) [VLI]XE[EDSQ]C (SEQ ID NO 60), CY[FLIV][SDN][ATVG] (SEQ ID NO 61), DYQ[LI]G (SEQ ID NO 62), FQ[TAV]Q[PSD](SEQ ID NO 63), AEECG (SEQ ID NO 64), NAFQ[AT]Q (SEQ ID NO 65), WQWQL (SEQ ID NO 66), [VLI][GASD]LKN[DGS][VLIP] (SEQ ID NO 67), GXXVX[NHQTS]IEY[PG] (SEQ ID NO 68), VICYF (SEQ ID NO 69), ICYFSA (SEQ ID NO 70), DFAVL (SEQ ID NO 71)
b) and/or is selected from the group consisting of GH114 glycosyl hydrolases having the amino acid sequence shown in SEQ ID NO 3, SEQ ID NO 6, SEQ ID NO 9, SEQ ID NO 12, SEQ ID NO 15, SEQ ID NO 18, SEQ ID NO 21, SEQ ID NO 24, SEQ ID NO 27, SEQ ID NO 30, SEQ ID NO 33, SEQ ID NO 36, SEQ ID NO 39, SEQ ID NO 42, SEQ ID NO 45, SEQ ID NO 48, SEQ ID NO 51, SEQ ID NO 54, SEQ ID NO 57, SEQ ID NO 72, SEQ ID NO 73, SEQ ID NO 74, SEQ ID NO 75, SEQ ID NO 76, SEQ ID NO 77, SEQ ID NO 78, SEQ ID NO 79, SEQ ID NO 80, SEQ ID NO 81, SEQ ID NO 82, SEQ ID NO 83, SEQ ID NO 84, SEQ ID NO 85, SEQ ID NO 86, SEQ ID NO 87, SEQ ID NO 88, SEQ ID NO 89, SEQ ID NO 90, SEQ ID NO 91, SEQ ID NO 92, SEQ ID NO 93, SEQ ID NO 94, SEQ ID NO 95, SEQ ID NO 96, SEQ ID NO 97, SEQ ID NO 98, SEQ ID NO 99, SEQ ID NO 100, SEQ ID NO 101, SEQ ID NO 102, SEQ ID NO 103, SEQ ID NO 104, SEQ ID NO 105, SEQ ID NO 106, SEQ ID NO 107, SEQ ID NO 108, SEQ ID NO 109, SEQ ID NO 110, SEQ ID NO 111, SEQ ID NO 112, SEQ ID NO 113, SEQ ID NO 114, SEQ ID NO 115, SEQ ID NO 116, SEQ ID NO 117, SEQ ID NO 118, SEQ ID NO 119, SEQ ID NO 120, SEQ ID NO 121, SEQ ID NO 122, SEQ ID NO 123, SEQ ID NO 124, SEQ ID NO 125, SEQ ID NO 126, SEQ ID NO 127, SEQ ID NO 128, SEQ ID NO 129, SEQ ID NO 130, SEQ ID NO 131, SEQ ID NO 132, SEQ ED NO: 133, SEQ ID NO 134, SEQ ID NO 135, SEQ ID NO 136, SEQ ID NO 137, SEQ ID NO 138, SEQ ID NO 139, SEQ ID NO 140, SEQ ID NO 141, SEQ ID NO 142, SEQ ID NO 143, SEQ ID NO 144, SEQ ID NO 145, SEQ ID NO 146 and polypeptides having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity hereto, for a period effective to clean the medical device;
c) cleaning, the medical device; and
d) optionally disinfect the medical device.

One embodiment relates to a composition comprising a glycosyl hydrolase, preferably a GH114 glycosyl hydrolase, which comprises one or more motif(s) [VL]XE[EDSQ]C (SEQ ID NO 60), CY[FLIV][SDN][ATVG] (SEQ ID NO 61), DYQ[LI]G (SEQ ID NO 62), FQ[TAV]Q[PSD] (SEQ ID NO 63), AEECG (SEQ ID NO 64), NAFQ[AT]Q (SEQ ID NO 65), WQWQL (SEQ ID NO 66), [VLI][GASD]LKN[DGS][VLIP] (SEQ ID NO 67), GXXVX[NHQTS]IEY[PG] (SEQ ID NO 68), VICYF (SEQ ID NO 69), ICYFSA (SEQ ID NO 70), DFAVL (SEQ ID NO 71) and/or is selected from the group consisting of glycosyl hydrolases having the amino acid sequence of SEQ ID NO 3, SEQ ID NO 6, SEQ ID NO 9, SEQ ID NO 12, SEQ ID NO 15, SEQ ID NO 18, SEQ ID NO 21, SEQ ID NO 24, SEQ ID NO 27, SEQ ID NO 30, SEQ ID NO 33, SEQ ID NO 36, SEQ ID NO 39, SEQ ID NO 42, SEQ ID NO 45, SEQ ID NO 48, SEQ ID NO 51, SEQ ID NO 54, SEQ ID NO 57, SEQ ID NO 72, SEQ ID NO 73, SEQ ID NO 74, SEQ ID NO 75, SEQ ID NO 76, SEQ ID NO 77, SEQ ID NO 78, SEQ ID NO 79, SEQ ID NO 80, SEQ ID NO 81, SEQ ID NO 82, SEQ ID NO 83, SEQ ID NO 84, SEQ ID NO 85, SEQ ID NO 86, SEQ ID NO 87, SEQ ID NO 88, SEQ ID NO 89, SEQ ID NO 90, SEQ ID NO 91, SEQ ID NO 92, SEQ ID NO 93, SEQ ID NO 94, SEQ ID NO 95, SEQ ID NO 96, SEQ ID NO 97, SEQ ID NO 98, SEQ ID NO 99, SEQ ID NO 100, SEQ ID NO 101, SEQ ID NO 102, SEQ ID NO 103, SEQ ID NO 104, SEQ ID NO 105, SEQ ID NO 106, SEQ ID NO 107, SEQ ID NO 108, SEQ ID NO 109, SEQ ID NO 110, SEQ ID NO 111, SEQ ID NO 112, SEQ ID NO 113, SEQ ID NO 114, SEQ ID NO 115, SEQ ID NO 116, SEQ ID NO 117, SEQ ID NO 118, SEQ ID NO 119, SEQ ID NO 120, SEQ ID NO 121, SEQ ID NO 122, SEQ ID NO 123, SEQ ID NO 124, SEQ ID NO 125, SEQ ID NO 126, SEQ ID NO 127, SEQ ID NO 128, SEQ ID NO 129, SEQ ID NO 130, SEQ ID NO 131, SEQ ID NO 132, SEQ ED NO: 133, SEQ ID NO 134, SEQ ID NO 135, SEQ ID NO 136, SEQ ID NO 137, SEQ ID NO 138, SEQ ID NO 139, SEQ ID NO 140, SEQ ID NO 141, SEQ ID NO 142, SEQ ID NO 143, SEQ ID NO 144, SEQ ID NO 145, SEQ ID NO 146 and polypeptides having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity hereto and preferably an adjunct ingredient. The composition may be an anti-biofouling composition and the composition may be a cleaning or pharmaceutical composition. The adjunct ingredient may be any excipient suitable for e.g. cleaning or pharmaceutical compositions. The adjuncts/excipients are within the choice of the skilled artisan. The adjunct ingredient may be selected from the group consisting of surfactants, builders, chelators or chelating agents, bleach system or bleach components, polymers, fabric conditioners, foam boosters, suds suppressors, dyes, perfume, tannish inhibitors, optical brighteners, bactericides, fungicides, soil suspending agents, anti-corrosion agents, enzyme inhibitors or stabilizers, enzyme activators, transferase(s), hydrolytic enzymes, oxido reductases, bluing agents and fluorescent dyes, antioxidants, and solubilizers. The compositions may be used for detaching biofilm or preventing biofilm formation on surfaces such as medical devices.

One embodiment of the invention relates to the use of a composition comprising a glycosyl hydrolase, preferably having alpha-1,4-polygalactosaminidase activity, preferably a GH114 glycosyl hydrolase, which comprises one or more motif(s) [VLI]XE[EDSQ]C (SEQ ID NO 60), CY[FLIV][SDN][ATVG] (SEQ ID NO 61), DYQ[L]G (SEQ ID NO 62), FQ[TAV]Q[PSD] (SEQ ID NO 63), AEECG (SEQ ID NO 64), NAFQ[AT]Q (SEQ ID NO 65), WQWQL (SEQ ID NO 66), [VLI][GASD]LKN[DGS][VLIP] (SEQ ID NO 67), GXXVX[NHQTS]IEY[PG] (SEQ ID NO 68), VICYF (SEQ ID NO 69), ICYFSA (SEQ ID NO 70), DFAVL (SEQ ID NO 71) and/or is selected from the group consisting glycosyl hydrolases having the amino acid sequence of SEQ ID NO 3, SEQ ID NO 6, SEQ ID NO 9, SEQ ID NO 12, SEQ ID NO 15, SEQ ID NO 18, SEQ ID NO 21, SEQ ID NO 24, SEQ ID NO 27, SEQ ID NO 30, SEQ ID NO 33, SEQ ID NO 36, SEQ ID NO 39, SEQ ID NO 42, SEQ ID NO 45, SEQ ID NO 48, SEQ ID NO 51, SEQ ID NO 54, SEQ ID NO 57, SEQ ID NO 72, SEQ ID NO 73, SEQ ID NO 74, SEQ ID NO 75, SEQ ID NO 76, SEQ ID NO 77, SEQ ID NO 78, SEQ ID NO 79, SEQ ID NO 80, SEQ ID NO 81, SEQ ID NO 82, SEQ ID NO 83, SEQ ID NO 84, SEQ ID NO 85, SEQ ID NO 86, SEQ ID NO 87, SEQ ID NO 88, SEQ ID NO 89, SEQ ID NO 90, SEQ ID NO 91, SEQ ID NO 92, SEQ ID NO 93, SEQ ID NO 94, SEQ ID NO 95, SEQ ID NO 96, SEQ ID NO 97, SEQ ID NO 98, SEQ ID NO 99, SEQ ID NO 100, SEQ ID NO 101, SEQ ID NO 102, SEQ ID NO 103, SEQ ID NO 104, SEQ ID NO 105, SEQ ID NO 106, SEQ ID NO 107, SEQ ID NO 108, SEQ ID NO 109, SEQ ID NO 110, SEQ ID NO 111, SEQ ID NO 112, SEQ ID NO 113, SEQ ID NO 114, SEQ ID NO 115, SEQ ID NO 116, SEQ ID NO 117, SEQ ID NO 118, SEQ ID NO 119, SEQ ID NO 120, SEQ ID NO 121, SEQ ID NO 122, SEQ ID NO 123, SEQ ID NO 124, SEQ ID NO 125, SEQ ID NO 126, SEQ ID NO 127, SEQ ID NO 128, SEQ ID NO 129, SEQ ID NO 130, SEQ ID NO 131, SEQ ID NO 132, SEQ ED NO: 133, SEQ ID NO 134, SEQ ID NO 135, SEQ ID NO 136, SEQ ID NO 137, SEQ ID NO 138, SEQ ID NO 139, SEQ ID NO 140, SEQ ID NO 141, SEQ ID NO 142, SEQ ID NO 143, SEQ ID NO 144, SEQ ID NO 145, SEQ ID NO 146 and polypeptides having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity hereto and preferably an adjunct ingredient for cleaning a medical device or an implant.

Medical devices are products which are used to diagnose, prevent, relieve or treat a disease, disability, injury, etc. There term includes wheelchairs, glasses to pacemakers, mobile phone apps and state-of-the-art surgical equipment. Medical devices are grouped into four classes known as I, IIa, Ib and III, with Class I being the lowest risk and Class III being the highest risk. The medical device may be characterized in that at least a portion of a patient-contactable surface of said device is coated with composition comprising a GH114 glycosyl hydrolase of the invention. The medical device or implant may be any device or implant that is susceptible to biofilm formation. The medical device may be selected from the group consisting of a catheter such as a central venous catheter, intravascular catheter, urinary catheter, Hickman catheter, peritoneal dialysis catheter, endrotracheal catheter, endoscope, or wherein the device is a mechanical heart valve, a cardiac pacemaker, an arteriovenous shunt, a scleral buckle, a prosthetic joint, a tympanostomy tube, a tracheostomy tube, a voice prosthetic, a penile prosthetic, an artificial urinary sphincter, a synthetic pubovaginal sling, a surgical suture, a bone anchor, a bone screw, an intraocular lens, a contact lens, an intrauterine device, an aortofemoral graft, a vascular graft, a needle, a Luer-Lok connector, a needleless connector and a surgical instrument.

Uses

The polypeptides of the invention having hydrolytic activity may be used for cleaning e.g. deep cleaning of an item, such as a textile. One embodiment of the invention relates to the use of a glycosyl hydrolase, preferably a GH114 glycosyl hydrolase in a cleaning process, such as laundry and/or dish wash.

In a preferred embodiment, the GH114 glycosyl hydrolase polypeptides of the invention comprise one or more of the motif(s) [VL]XE[EDSQ]C (SEQ ID NO 60), CY[FLIV][SDN][ATVG](SEQ ID NO 61), DYQ[LI]G (SEQ ID NO 62), FQ[TAV]Q[PSD] (SEQ ID NO 63), AEECG (SEQ ID NO 64), NAFQ[AT]Q (SEQ ID NO 65), WQWQL (SEQ ID NO 66), [VLI][GASD]LKN[DGS][VLIP] (SEQ ID NO 67), GXXVX[NHQTS]IEY[PG] (SEQ ID NO 68), VICYF (SEQ ID NO 69), ICYFSA (SEQ ID NO 70), DFAVL (SEQ ID NO 71). In a preferred embodiment, the GH114 glycosyl hydrolase comprising one or more of the motif(s) selected from the group consisting of: [VLI]XE[EDSQ]C (SEQ ID NO 60), CY[FLIV][SDN][ATVG] (SEQ ID NO 61), DYQ[L]G (SEQ ID NO 62), FQ[TAV]Q[PSD] (SEQ ID NO 63), AEECG (SEQ ID NO 64), NAFQ[AT]Q (SEQ ID NO 65), WQWQL (SEQ ID NO 66), [VL][GASD]LKN[DGS][VLIP] (SEQ ID NO 67), GXXVX[NHQTS]IEY[PG] (SEQ ID NO 68), VICYF (SEQ ID NO 69), ICYFSA (SEQ ID NO 70), DFAVL (SEQ ID NO 71).

In some embodiments of the invention relate to the use of glycosyl hydrolase, preferably having alpha-1,4-polygalactosaminidase activity, preferably a GH114 glycosyl hydrolase according to the invention for prevention reduction or removal of malodor. Some embodiment of the invention relates to the use of a polypeptide of the invention for prevention or reduction of anti-redeposition and improvement of whiteness of a textile subjected to multiple washes. One embodiment of the invention relates to the use of a glycosyl hydrolase, preferably having alpha-1,4-polygalactosaminidase activity, preferably a GH114 glycosyl hydrolase according to the invention for deep cleaning of an item, wherein item is a textile. One embodiment of the invention relates to the use of a glycosyl hydrolase, preferably having alpha-1,4-polygalactosaminidase activity, preferably a GH114 glycosyl hydrolase polypeptide according to the invention (i) for preventing, reducing or removing stickiness of the item;
(ii) for pretreating stains on the item;
(iii) for preventing, reducing or removing redeposition of soil during a wash cycle;
(iv) for preventing, reducing or removing adherence of soil to the item;
(v) for maintaining or improving whiteness of the item;
(vi) for preventing, reducing or removal malodor from the item, wherein the item is a textile.

One embodiment of the invention relates to the use of a glycosyl hydrolase, preferably having alpha-1,4-polygalactosaminidase activity, preferably a GH114 glycosyl hydrolase polypeptide according to the invention for deep cleaning of an item, wherein item is a textile. One embodiment of the invention relates to the use of a glycosyl hydrolase, preferably having alpha-1,4-polygalactosaminidase activity, preferably a GH114 glycosyl hydrolase polypeptide, (i) for preventing, reducing or removing stickiness of the item;

(ii) for pretreating stains on the item;

(iii) for preventing, reducing or removing redeposition of soil during a wash cycle;

(iv) for preventing, reducing or removing adherence of soil to the item;

(v) for maintaining or improving whiteness of the item;

(vi) for preventing, reducing or removal malodor from the item, optionally wherein the item is a textile, wherein the glycosyl hydrolase polypeptide is selected from the group consisting of:

(a) a polypeptide having at least 60%, at least 70%, at least 75%, at least 80%, at least 85%, at least 90%, at least 95%, at least 96%, at least 97%, at least 98%, at least 99% or 100% sequence identity to the polypeptide shown in SEQ ID NO 3;

(b) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 6;

(c) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 9;

(d) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 12;

(e) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 15;

(f) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 18;

(g) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 21;

(h) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 24;

(i) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 27;

(j) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 30;

(k) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 33;

(l) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 36;

(m) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 39;

(n) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 42;

(o) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 45;

(p) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 48;

(q) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 51;

(r) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 54;

(s) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 57.

One preferred embodiment relates to the use of a GH114 glycosyl hydrolase, i. for preventing, reducing or removing stickiness of the item;

ii. for preventing, reducing or removing biofilm or biofilm components iii. for reducing or removing pel stains on the item;

iv. for preventing, reducing or removing redeposition of soil during a wash cycle;

v. for preventing, reducing or removing adherence of soil to the item;

vi. for maintaining or improving whiteness of the item;

vii. for preventing, reducing or removal malodor from the item, wherein the item is a textile.

One preferred embodiment relates to the use of a GH114 glycosyl hydrolase, i. for preventing, reducing or removing stickiness of the item;

ii. for preventing, reducing or removing biofilm or biofilm components iii. for reducing or removing pel stains on the item;

iv. for preventing, reducing or removing redeposition of soil during a wash cycle;

v. for preventing, reducing or removing adherence of soil to the item;

vi. for maintaining or improving whiteness of the item;

vii. for preventing, reducing or removal malodor from the item, wherein the item is a textile and wherein the polypeptide is selected from the group consisting of:

(a) a polypeptide having at least 60%, at least 70%, at least 75%, at least 80%, at least 85%, at least 90%, at least 95%, at least 96%, at least 97%, at least 98%, at least 99% or 100% sequence identity to the polypeptide shown in SEQ ID NO 3;

(b) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 6;

(c) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 9;

(d) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 12;

(e) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 15;

(f) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 18;

(g) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 21;

(h) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 24;

(i) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 27;

(j) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 30;

(k) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 33;

(l) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 36;

(m) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 39;

(n) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 42;

(o) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 45;

(p) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 48;

(q) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 51;

(r) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 54;

(s) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 57.

One preferred embodiment relates to the use of a GH114 glycosyl hydrolase, i. for preventing, reducing or removing stickiness of the item;

ii. for preventing, reducing or removing biofilm or biofilm components iii. for reducing or removing pel stains on the item;

iv. for preventing, reducing or removing redeposition of soil during a wash cycle;

v. for preventing, reducing or removing adherence of soil to the item;

vi. for maintaining or improving whiteness of the item;

vii. for preventing, reducing or removal malodor from the item, wherein the item is a textile and wherein the polypeptide is selected from the group consisting of:

(a) a polypeptide having at least 90%, at least 95%, at least 96%, at least 97%, at least 98%, at least 99% or 100% sequence identity to the polypeptide shown in SEQ ID NO 3;

(b) a polypeptide having at least 90%, at least 95%, at least 96%, at least 97%, at least 98%, at least 99% or 100% sequence identity to the polypeptide shown in SEQ ID NO 6;

(c) a polypeptide having at least 85%, at least 90%, at least 95%, at least 96%, at least 97%, at least 98%, at least 99% or 100% sequence identity to the polypeptide shown in SEQ ID NO 9;

(d) a polypeptide having at least 85%, at least 90%, at least 95%, at least 96%, at least 97%, at least 98%, at least 99% or 100% sequence identity to the polypeptide shown in SEQ ID NO 12;

(e) a polypeptide having at least 75%, at least 80%, at least 85%, at least 90%, at least 95%, at least 96%, at least 97%, at least 98%, at least 99% or 100% sequence identity to the polypeptide shown in SEQ ID NO 21;

(f) a polypeptide having at least 90%, at least 95%, at least 96%, at least 97%, at least 98%, at least 99% or 100% sequence identity to the polypeptide shown in SEQ ID NO 24;

(g) a polypeptide having at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 27;

(h) a polypeptide having, at least 50% at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 30;

(i) a polypeptide having at least 70%, at least 75%, at least 80%, at least 85%, at least 90%, at least 95%, at least 96%, at least 97%, at least 98%, at least 99% or 100% sequence identity to the polypeptide shown in SEQ ID NO 33;

(j) a polypeptide having at least 75%, at least 80%, at least 85%, at least 90%, at least 95%, at least 96%, at least 97%, at least 98%, at least 99% or 100% sequence identity to the polypeptide shown in SEQ ID NO 36;

(k) a polypeptide having at least 99% or 100% sequence identity to the polypeptide shown in SEQ ID NO 39;

(l) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 42;

(m) a polypeptide having at least 85%, at least 90%, at least 95%, at least 96%, at least 97%, at least 98%, at least 99% or 100% sequence identity to the polypeptide shown in SEQ ID NO 45;

(n) a polypeptide having at least 70%, at least 75%, at least 80%, at least 85%, at least 90%, at least 95%, at least 96%, at least 97%, at least 98%, at least 99% or 100% sequence identity to the polypeptide shown in SEQ ID NO 48;

(o) a polypeptide having at least 98%, at least 99% or 100% sequence identity to the polypeptide shown in SEQ ID NO 51;

(p) a polypeptide having at least 80%, at least 85%, at least 90%, at least 95%, at least 96%, at least 97%, at least 98%, at least 99% or 100% sequence identity to the polypeptide shown in SEQ ID NO 54; and (q) a polypeptide having at least 85%, at least 90%, at least 95%, at least 96%, at least 97%, at least 98%, at least 99% or 100% sequence identity to the polypeptide shown in SEQ ID NO 57.

One preferred embodiment relates to the use of a GH114 glycosyl hydrolase, i. for preventing, reducing or removing stickiness of the item;

ii. for preventing, reducing or removing biofilm or biofilm components iii. for reducing or removing pel stains on the item;

iv. for preventing, reducing or removing redeposition of soil during a wash cycle;

v. for preventing, reducing or removing adherence of soil to the item;

vi. for maintaining or improving whiteness of the item;

vii. for preventing, reducing or removal malodor from the item, wherein the item is a textile and wherein the polypeptide is selected from the group consisting of:

a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 72, SEQ ID NO 73, SEQ ID NO 74, SEQ ID NO 75, SEQ ID NO 76, SEQ ID NO 77, SEQ ID NO 78, SEQ ID NO 79, SEQ ID NO 80, SEQ ID NO 81, SEQ ID NO 82, SEQ ID NO 83, SEQ ID NO 84, SEQ ID NO 85, SEQ ID NO 86, SEQ ID NO 87, SEQ ID NO 88, SEQ ID NO 89, SEQ ID NO 90, SEQ ID NO 91, SEQ ID NO 92, SEQ ID NO 93, SEQ ID NO 94, SEQ ID NO 95, SEQ ID NO 96, SEQ ID NO 97, SEQ ID NO 98, SEQ ID NO 99, SEQ ID NO 100, SEQ ID NO 101, SEQ ID NO 102, SEQ ID NO 103, SEQ ID NO 104, SEQ ID NO 105, SEQ ID NO 106, SEQ ID NO 107, SEQ ID NO 108, SEQ ID NO 109, SEQ ID NO 110, SEQ ID NO 111, SEQ ID NO 112, SEQ ID NO 113, SEQ ID NO 114, SEQ ID NO 115, SEQ ID NO 116, SEQ ID NO 117, SEQ ID NO 118, SEQ ID NO 119, SEQ ID NO 120, SEQ ID NO 121, SEQ ID NO 122, SEQ ID NO 123, SEQ ID NO 124, SEQ ID NO 125, SEQ ID NO 126, SEQ ID NO 127, SEQ ID NO 128, SEQ ID NO 129, SEQ ID NO 130, SEQ ID NO 131, SEQ ID NO 132, SEQ ED NO: 133, SEQ ID NO 134, SEQ ID NO 135, SEQ ID NO 136, SEQ ID NO 137, SEQ ID NO 138, SEQ ID NO 139, SEQ ID NO 140, SEQ ID NO 141, SEQ ID NO 142, SEQ ID NO 143, SEQ ID NO 144, SEQ ID NO 145 and SEQ ID NO 146.

The polypeptides of the invention are particularly useful in cleaning processes such as laundry, where the polypeptide effectively reduces biofilm components such as alpha-1,4-polygalactosamine comprising biofilm as shown in the examples below. One embodiment of the invention relates to a method for laundering an item comprising the steps of:

a. exposing an item to a wash liquor comprising the GH114 glycosyl hydrolase, preferably having alpha-1,4-polygalactosaminidase activity, or a composition comprising a GH114 glycosyl hydrolase, preferably having alpha-1,4-polygalactosaminidase activity;

b. completing at least one wash cycle; and c. optionally rinsing the item, wherein the item is a textile.

One preferred embodiment of the invention relates to a method for laundering an item comprising the steps of:

a. exposing an item to a wash liquor comprising a glycosyl hydrolase, preferably having alpha-1,4-polygalactosaminidase activity, preferably a GH114 glycosyl hydrolase or a composition comprising a glycosyl hydrolase, preferably having alpha-1,4-polygalactosaminidase activity, wherein glycosyl hydrolase is selected from the group consisting of;

(a) a polypeptide having at least 60%, at least 70%, at least 75%, at least 80%, at least 85%, at least 90%, at least 95%, at least 96%, at least 97%, at least 98%, at least 99% or 100% sequence identity to the polypeptide shown in SEQ ID NO 3;

(b) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 6;

(c) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 9;

(d) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 12;

(e) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 15;

(f) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 18;

(g) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 21;

(h) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 24;

(i) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 27;

(j) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 30;

(k) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 33;

(l) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 36;

(m) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 39;

(n) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 42;

(o) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 45;

(p) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 48;

(q) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 51;

(r) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 54;

(s) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 57;

b. completing at least one wash cycle; and c. optionally rinsing the item, wherein the item is a textile.

A preferred embodiment relates to a method for laundering an item comprising the steps of:

a. exposing an item to a wash liquor comprising a GH114 glycosyl hydrolase, preferably having alpha-1,4-polygalactosaminidase activity, or a composition comprising a GH114 glycosyl hydrolase, preferably having alpha-1,4-polygalactosaminidase activity, wherein the GH114 glycosyl hydrolase, is selected from the group consisting of;

(a) a polypeptide having at least 90%, at least 95%, at least 96%, at least 97%, at least 98%, at least 99% or 100% sequence identity to the polypeptide shown in SEQ ID NO 3;

(b) a polypeptide having at least 90%, at least 95%, at least 96%, at least 97%, at least 98%, at least 99% or 100% sequence identity to the polypeptide shown in SEQ ID NO 6;

(c) a polypeptide having at least 85%, at least 90%, at least 95%, at least 96%, at least 97%, at least 98%, at least 99% or 100% sequence identity to the polypeptide shown in SEQ ID NO 9;

(d) a polypeptide having at least 85%, at least 90%, at least 95%, at least 96%, at least 97%, at least 98%, at least 99% or 100% sequence identity to the polypeptide shown in SEQ ID NO 12;

(e) a polypeptide having at least 75%, at least 80%, at least 85%, at least 90%, at least 95%, at least 96%, at least 97%, at least 98%, at least 99% or 100% sequence identity to the polypeptide shown in SEQ ID NO 21;

(f) a polypeptide having at least 90%, at least 95%, at least 96%, at least 97%, at least 98%, at least 99% or 100% sequence identity to the polypeptide shown in SEQ ID NO 24;

(g) a polypeptide having at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 27;

(h) a polypeptide having, at least 50% at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 30;

(i) a polypeptide having at least 70%, at least 75%, at least 80%, at least 85%, at least 90%, at least 95%, at least 96%, at least 97%, at least 98%, at least 99% or 100% sequence identity to the polypeptide shown in SEQ ID NO 33;

(j) a polypeptide having at least 75%, at least 80%, at least 85%, at least 90%, at least 95%, at least 96%, at least 97%, at least 98%, at least 99% or 100% sequence identity to the polypeptide shown in SEQ ID NO 36;
(k) a polypeptide having at least 99% or 100% sequence identity to the polypeptide shown in SEQ ID NO 39;
(l) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 42;
(m) a polypeptide having at least 85%, at least 90%, at least 95%, at least 96%, at least 97%, at least 98%, at least 99% or 100% sequence identity to the polypeptide shown in SEQ ID NO 45;
(n) a polypeptide having at least 70%, at least 75%, at least 80%, at least 85%, at least 90%, at least 95%, at least 96%, at least 97%, at least 98%, at least 99% or 100% sequence identity to the polypeptide shown in SEQ ID NO 48;
(o) a polypeptide having at least 98%, at least 99% or 100% sequence identity to the polypeptide shown in SEQ ID NO 51;
(p) a polypeptide having at least 80%, at least 85%, at least 90%, at least 95%, at least 96%, at least 97%, at least 98%, at least 99% or 100% sequence identity to the polypeptide shown in SEQ ID NO 54; and
(q) a polypeptide having at least 85%, at least 90%, at least 95%, at least 96%, at least 97%, at least 98%, at least 99% or 100% sequence identity to the polypeptide shown in SEQ ID NO 57
b. completing at least one wash cycle; and
c. optionally rinsing the item,
wherein the item is a textile.

One preferred embodiment of the invention relates to a method for laundering an item comprising the steps of:
a. exposing an item to a wash liquor comprising a glycosyl hydrolase, preferably having alpha-1,4-polygalactosaminidase activity, preferably a GH114 glycosyl hydrolase or a composition comprising a glycosyl hydrolase, preferably having alpha-1,4-polygalactosaminidase activity, wherein glycosyl hydrolase is selected from the group consisting of; a polypeptide having at least 60%, at least 70%, at least 75%, at least 80%, at least 85%, at least 90%, at least 95%, at least 96%, at least 97%, at least 98%, at least 99% or 100% sequence identity to the polypeptide shown in SEQ ID NO 72, SEQ ID NO 73, SEQ ID NO 74, SEQ ID NO 75, SEQ ID NO 76, SEQ ID NO 77, SEQ ID NO 78, SEQ ID NO 79, SEQ ID NO 80, SEQ ID NO 81, SEQ ID NO 82, SEQ ID NO 83, SEQ ID NO 84, SEQ ID NO 85, SEQ ID NO 86, SEQ ID NO 87, SEQ ID NO 88, SEQ ID NO 89, SEQ ID NO 90, SEQ ID NO 91, SEQ ID NO 92, SEQ ID NO 93, SEQ ID NO 94, SEQ ID NO 95, SEQ ID NO 96, SEQ ID NO 97, SEQ ID NO 98, SEQ ID NO 99, SEQ ID NO 100, SEQ ID NO 101, SEQ ID NO 102, SEQ ID NO 103, SEQ ID NO 104, SEQ ID NO 105, SEQ ID NO 106, SEQ ID NO 107, SEQ ID NO 108, SEQ ID NO 109, SEQ ID NO 110, SEQ ID NO 111, SEQ ID NO 112, SEQ ID NO 113, SEQ ID NO 114, SEQ ID NO 115, SEQ ID NO 116, SEQ ID NO 117, SEQ ID NO 118, SEQ ID NO 119, SEQ ID NO 120, SEQ ID NO 121, SEQ ID NO 122, SEQ ID NO 123, SEQ ID NO 124, SEQ ID NO 125, SEQ ID NO 126, SEQ ID NO 127, SEQ ID NO 128, SEQ ID NO 129, SEQ ID NO 130, SEQ ID NO 131, SEQ ID NO 132, SEQ ED NO: 133, SEQ ID NO 134, SEQ ID NO 135, SEQ ID NO 136, SEQ ID NO 137, SEQ ID NO 138, SEQ ID NO 139, SEQ ID NO 140, SEQ ID NO 141, SEQ ID NO 142, SEQ ID NO 143, SEQ ID NO 144, SEQ ID NO 145 and SEQ ID NO 146,
b. completing at least one wash cycle; and
c. optionally rinsing the item,
wherein the item is a textile.

The invention is further summarized in the following paragraphs:

1. Use of a polypeptide comprising one or more of the motif(s) [VL]XE[EDSQ]C (SEQ ID NO 60), CY[FLIV][SDN][ATVG] (SEQ ID NO 61), DYQ[LI]G (SEQ ID NO 62), FQ[TAV]Q[PSD](SEQ ID NO 63), AEECG (SEQ ID NO 64), NAFQ[AT]Q (SEQ ID NO 65), WQWQL (SEQ ID NO 66), [VL][GASD]LKN[DGS][VLIP] (SEQ ID NO 67), GXXVX[NHQTS]IEY[PG] (SEQ ID NO 68), VICYF (SEQ ID NO 69), ICYFSA (SEQ ID NO 70), DFAVL (SEQ ID NO 71) for deep cleaning of an item, wherein the item is a textile.

2. Use according to paragraph 1 for preventing, reducing or removing stickiness of the item.

3. Use according to any of paragraphs 1 or 2 for pretreating stains on the item.

4. Use according to any of paragraphs 1-3 for preventing, reducing or removing re-deposition of soil during a wash cycle.

5. Use according to any of paragraphs 1-4 for preventing, reducing or removing adherence of soil to the item.

6. Use according to any of the preceding paragraphs for maintaining or improving the whiteness of the item.

7. Use according to any of the preceding paragraphs, wherein a malodor is reduced or removed from the item.

8. Use according to any of the preceding composition paragraphs, wherein the surface is a textile surface.

9. Use according to any of the preceding composition paragraphs, wherein the textile is made of cotton, Cotton/Polyester, Polyester, Polyamide, Polyacryl and/or silk.

10. Use according to any of the preceding paragraphs, wherein the polypeptide is a polypeptide of paragraphs 68-108.

11. A composition comprising a polypeptide comprising one or more of the motif(s) [VLI]XE[EDSQ]C (SEQ ID NO 60), CY[FLIV][SDN][ATVG] (SEQ ID NO 61), DYQ[LI]G (SEQ ID NO 62), FQ[TAV]Q[PSD] (SEQ ID NO 63), AEECG (SEQ ID NO 64), NAFQ[AT]Q (SEQ ID NO 65), WQWQL (SEQ ID NO 66), [VLI][GASD]LKN[DGS][VLIP] (SEQ ID NO 67), GXXVX[NHQTS]IEY[PG] (SEQ ID NO 68), VICYF (SEQ ID NO 69), ICYFSA (SEQ ID NO 70), DFAVL (SEQ ID NO 71) and a cleaning or an adjunct ingredient.

12. Composition according to paragraph 11, wherein the polypeptide is the polypeptide shown in paragraphs 55-79.

13. Composition according to any of the preceding composition paragraphs, wherein the detergent adjunct ingredient is selected from the group consisting of surfactants, builders, flocculating aid, chelating agents, dye transfer inhibitors, enzymes, enzyme stabilizers, enzyme inhibitors, catalytic materials, bleach activators, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, builders and co-builders, fabric huing agents, antifoaming agents, dispersants, processing aids, and/or pigments.

14. Composition according to any of the preceding composition paragraphs wherein the composition comprises from about 5 wt % to about 50 wt %, from about 5 wt % to about 40 wt %, from about 5 wt % to about 30 wt %, from about 5 wt % to about 20 wt %, from about 5 wt % to about 10 wt % anionic surfactant, preferably selected from linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkane-sulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or salt of fatty acids (soap), and combinations thereof.

15. Composition according to any of the preceding composition paragraphs wherein the composition comprises from about 10 wt % to about 50 wt % of at least one builder, preferably selected from citric acid, methylglycine-N,N-diacetic acid (MGDA) and/or glutamic acid-N,N-diacetic acid (GLDA) and mixtures thereof.

16. Composition according to any of the proceeding paragraphs comprising from about 5 wt % to about 40 wt % nonionic surfactants, and from about 0 wt % to about 5 wt % anionic surfactants.

17. Composition according to paragraph 16, wherein the nonionic surfactant is selected from alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxyalkyl fatty acid amides, or N-acyl N-alkyl derivatives of glucosamine (glucamides, GA, or fatty acid glucamides, FAGA) and combinations thereof.

18. Composition according to any of the preceding composition paragraphs, wherein the composition further comprises one or more enzymes selected from the group consisting of proteases, lipases, cutinases, amylases, carbohydrases, cellulases, pectinases, mannanases, arabinases, galactanases, xylanases and oxidases.

19. Composition according to any of the preceding composition paragraphs, wherein the composition is a bar, a homogenous tablet, a tablet having two or more layers, a pouch having one or more compartments, a regular or compact powder, a granule, a paste, a gel, or a regular, compact or concentrated liquid.

20. Composition according to any of the preceding composition paragraphs, wherein the composition is a cleaning composition selected from liquid detergent, powder detergent and granule detergent compositions.

21. Composition according to any of the preceding composition paragraphs wherein the polypeptide comprises one or more motif(s) [VLI]XE[EDSQ]C (SEQ ID NO 60), CY[FLIV][SDN][ATVG] (SEQ ID NO 61), DYQ[L]G (SEQ ID NO 62), FQ[TAV]Q[PSD] (SEQ ID NO 63), AEECG (SEQ ID NO 64), NAFQ[AT]Q (SEQ ID NO 65), WQWQL (SEQ ID NO 66), [VLI][GASD]LKN[DGS][VLIP] (SEQ ID NO 67), GXXVX[NHQTS]IEY[PG] (SEQ ID NO 68), VICYF (SEQ ID NO 69), ICYFSA (SEQ ID NO 70), DFAVL (SEQ ID NO 71) and wherein the polypeptide is selected from the group consisting of polypeptides having the amino acid sequence of SEQ ID NO 3, SEQ ID NO 6, SEQ ID NO 9, SEQ ID NO 12, SEQ ID NO 15, SEQ ID NO 18, SEQ ID NO 21, SEQ ID NO 24, SEQ ID NO 27, SEQ ID NO 30, SEQ ID NO 39, SEQ ID NO 42, SEQ ID NO 45, SEQ ID NO 48, SEQ ID NO 51, SEQ ID NO 54, SEQ ID NO 57 SEQ ID NO 72, SEQ ID NO 73, SEQ ID NO 74, SEQ ID NO 75, SEQ ID NO 76, SEQ ID NO 77, SEQ ID NO 78, SEQ ID NO 79, SEQ ID NO 80, SEQ ID NO 81, SEQ ID NO 82, SEQ ID NO 83, SEQ ID NO 84, SEQ ID NO 85, SEQ ID NO 86, SEQ ID NO 87, SEQ ID NO 88, SEQ ID NO 89, SEQ ID NO 90, SEQ ID NO 91, SEQ ID NO 92, SEQ ID NO 93, SEQ ID NO 94, SEQ ID NO 95, SEQ ID NO 96, SEQ ID NO 97, SEQ ID NO 98, SEQ ID NO 99, SEQ ID NO 100, SEQ ID NO 101, SEQ ID NO 102, SEQ ID NO 103, SEQ ID NO 104, SEQ ID NO 105, SEQ ID NO 106, SEQ ID NO 107, SEQ ID NO 108, SEQ ID NO 109, SEQ ID NO 110, SEQ ID NO 111, SEQ ID NO 112, SEQ ID NO 113, SEQ ID NO 114, SEQ ID NO 115, SEQ ID NO 116, SEQ ID NO 117, SEQ ID NO 118, SEQ ID NO 119, SEQ ID NO 120, SEQ ID NO 121, SEQ ID NO 122, SEQ ID NO 123, SEQ ID NO 124, SEQ ID NO 125, SEQ ID NO 126, SEQ ID NO 127, SEQ ID NO 128, SEQ ID NO 129, SEQ ID NO 130, SEQ ID NO 131, SEQ ID NO 132, SEQ ID NO: 133, SEQ ID NO 134, SEQ ID NO 135, SEQ ID NO 136, SEQ ID NO 137, SEQ ID NO 138, SEQ ID NO 139, SEQ ID NO 140, SEQ ID NO 141, SEQ ID NO 142, SEQ ID NO 143, SEQ ID NO 144, SEQ ID NO 145, SEQ ID NO 146 and polypeptides having at least 60%, at least 65%, at least 70%, at least 75%, at least 80%, at least 85%, at least 90%, at least 95%, at least 96%, at least 97%, at least 98%, at least 99% or 100% sequence identity hereto.

22. Composition according to any of the preceding composition paragraphs wherein the polypeptide comprising one or more motif(s) [VLI]XE[EDSQ]C (SEQ ID NO 60), CY[FLIV][SDN][ATVG] (SEQ ID NO 61), DYQ[L]G (SEQ ID NO 62), FQ[TAV]Q[PSD] (SEQ ID NO 63), AEECG (SEQ ID NO 64), NAFQ[AT]Q (SEQ ID NO 65) and comprises the amino acid sequence shown SEQ ID NO 3 or polypeptides having at least 60%, at least 65%, at least 70%, at least 75%, at least 80%, at least 85%, at least 90%, at least 95%, at least 96%, at least 97%, at least 98%, at least 99% or 100% sequence identity hereto.

23. Composition according to any of the preceding composition paragraphs wherein the polypeptide comprising one or more motif(s) [VLI]XE[EDSQ]C (SEQ ID NO 60), CY[FLIV][SDN][ATVG] (SEQ ID NO 61), DYQ[L]G (SEQ ID NO 62), FQ[TAV]Q[PSD] (SEQ ID NO 63), AEECG (SEQ ID NO 64), NAFQ[AT]Q (SEQ ID NO 65) and comprises the amino acid sequence shown SEQ ID NO 6 or polypeptides having at least 60%, at least 65%, at least 70%, at least 75%, at least 80%, at least 85%, at least 90%, at least 95%, at least 96%, at least 97%, at least 98%, at least 99% or 100% sequence identity hereto.

24. Composition according to any of the preceding composition paragraphs wherein the polypeptide comprising one or more motif(s) [VLI]XE[EDSQ]C (SEQ ID NO 60), CY[FLIV][SDN][ATVG] (SEQ ID NO 61), DYQ[L]G (SEQ ID NO 62), FQ[TAV]Q[PSD] (SEQ ID NO 63), AEECG (SEQ ID NO 64), NAFQ[AT]Q (SEQ ID NO 65) and comprises the amino acid sequence shown SEQ ID NO 9 or polypeptides having at least 60%, at least 65%, at least 70%, at least 75%, at least 80%, at least 85%, at least 90%, at least 95%, at least 96%, at least 97%, at least 98%, at least 99% or 100% sequence identity hereto.

25. Composition according to any of the preceding composition paragraphs wherein the polypeptide comprising one or more motif(s) [VLI]XE[EDSQ]C (SEQ ID NO 60), CY[FLIV][SDN][ATVG] (SEQ ID NO 61), DYQ[L]G (SEQ ID NO 62), FQ[TAV]Q[PSD] (SEQ ID NO 63), AEECG (SEQ ID NO 64), NAFQ[AT]Q (SEQ ID NO 65) and comprises the amino acid sequence shown SEQ ID NO 12 or polypeptides having at least 60%, at least 65%, at least 70%, at least 75%, at least 80%, at least 85%, at least 90%, at least 95%, at least 96%, at least 97%, at least 98%, at least 99% or 100% sequence identity hereto.

26. Composition according to any of the preceding composition paragraphs wherein the polypeptide comprising one or more motif(s) [VLI]XE[EDSQ]C (SEQ ID NO 60), CY[FLIV][SDN][ATVG] (SEQ ID NO 61), GXXVX [NHQTS]IEY[PG] (SEQ ID NO 68), VICYF (SEQ ID NO 69), ICYFSA (SEQ ID NO 70), and comprises the amino acid sequence shown SEQ ID NO 15 or polypeptides having at least 60%, at least 65%, at least 70%, at least 75%, at least 80%, at least 85%, at least 90%, at least 95%, at least 96%, at least 97%, at least 98%, at least 99% or 100% sequence identity hereto.

27. Composition according to any of the preceding composition paragraphs wherein the polypeptide comprising one or more motif(s) [VLI]XE[EDSQ]C (SEQ ID NO 60), CY[FLIV][SDN][ATVG] (SEQ ID NO 61), GXXVX [NHQTS]IEY[PG] (SEQ ID NO 68), VICYF (SEQ ID NO 69), DFAVL (SEQ ID NO 71) and comprises the amino acid sequence shown SEQ ID NO 18 or polypeptides having at least 60%, at least 65%, at least 70%, at least 75%, at least 80%, at least 85%, at least 90%, at least 95%, at least 96%, at least 97%, at least 98%, at least 99% or 100% sequence identity hereto.

28. Composition according to any of the preceding composition paragraphs wherein the polypeptide comprising one or more motif(s) [VLI]XE[EDSQ]C (SEQ ID NO 60), CY[FLIV][SDN][ATVG] (SEQ ID NO 61), DYQ[L]G (SEQ ID NO 62), FQ[TAV]Q[PSD] (SEQ ID NO 63), AEECG (SEQ ID NO 64), NAFQ[AT]Q (SEQ ID NO 65) and comprises the amino acid sequence shown SEQ ID NO 21 or polypeptides having at least 60%, at least 65%, at least 70%, at least 75%, at least 80%, at least 85%, at least 90%, at least 95%, at least 96%, at least 97%, at least 98%, at least 99% or 100% sequence identity hereto.

29. Composition according to any of the preceding composition paragraphs wherein the polypeptide comprising one or more motif(s) [VLI]XE[EDSQ]C (SEQ ID NO 60), CY[FLIV][SDN][ATVG] (SEQ ID NO 61), DYQ[L]G (SEQ ID NO 62), FQ[TAV]Q[PSD] (SEQ ID NO 63), AEECG (SEQ ID NO 64), NAFQ[AT]Q (SEQ ID NO 65) and comprises the amino acid sequence shown SEQ ID NO 24 or polypeptides having at least 60%, at least 65%, at least 70%, at least 75%, at least 80%, at least 85%, at least 90%, at least 95%, at least 96%, at least 97%, at least 98%, at least 99% or 100% sequence identity hereto.

30. Composition according to any of the preceding composition paragraphs wherein the polypeptide comprising one or more motif(s) [VLI]XE[EDSQ]C (SEQ ID NO 60), CY[FLIV][SDN][ATVG] (SEQ ID NO 61), WQWQL (SEQ ID NO 66), [VLI][GASD]LKN[DGS][VLIP] (SEQ ID NO 67) and comprises the amino acid sequence shown SEQ ID NO 27 or polypeptides having at least 60%, at least 65%, at least 70%, at least 75%, at least 80%, at least 85%, at least 90%, at least 95%, at least 96%, at least 97%, at least 98%, at least 99% or 100% sequence identity hereto.

31. Composition according to any of the preceding composition paragraphs wherein the polypeptide comprising one or more motif(s) [VLI]XE[EDSQ]C (SEQ ID NO 60), CY[FLIV][SDN][ATVG] (SEQ ID NO 61), WQWQL (SEQ ID NO 66), [VLI][GASD]LKN[DGS][VLIP] (SEQ ID NO 67) and comprises the amino acid sequence shown SEQ ID NO 33 or polypeptides having at least 60%, at least 65%, at least 70%, at least 75%, at least 80%, at least 85%, at least 90%, at least 95%, at least 96%, at least 97%, at least 98%, at least 99% or 100% sequence identity hereto.

32. Composition according to any of the preceding composition paragraphs wherein the polypeptide comprising one or more motif(s) [VLI]XE[EDSQ]C (SEQ ID NO 60), CY[FLIV][SDN][ATVG] (SEQ ID NO 61), WQWQL (SEQ ID NO 66), [VLI][GASD]LKN[DGS][VLIP] (SEQ ID NO 67) and comprises the amino acid sequence shown SEQ ID NO 36 or polypeptides having at least 60%, at least 65%, at least 70%, at least 75%, at least 80%, at least 85%, at least 90%, at least 95%, at least 96%, at least 97%, at least 98%, at least 99% or 100% sequence identity hereto.

33. Composition according to any of the preceding composition paragraphs wherein the polypeptide comprising one or more motif(s) [VLI]XE[EDSQ]C (SEQ ID NO 60), CY[FLIV][SDN][ATVG] (SEQ ID NO 61) and comprises the amino acid sequence shown SEQ ID NO 30 or polypeptides having at least 60%, at least 65%, at least 70%, at least 75%, at least 80%, at least 85%, at least 90%, at least 95%, at least 96%, at least 97%, at least 98%, at least 99% or 100% sequence identity hereto.

34. Composition according to any of the preceding composition paragraphs wherein the polypeptide comprising one or more motif(s) [VLI]XE[EDSQ]C (SEQ ID NO 60), CY[FLIV][SDN][ATVG] (SEQ ID NO 61), DYQ[L]G (SEQ ID NO 62), FQ[TAV]Q[PSD] (SEQ ID NO 63) and comprises the amino acid sequence shown SEQ ID NO 39 or polypeptides having at least 60%, at least 65%, at least 70%, at least 75%, at least 80%, at least 85%, at least 90%, at least 95%, at least 96%, at least 97%, at least 98%, at least 99% or 100% sequence identity hereto.

35. Composition according to any of the preceding composition paragraphs wherein the polypeptide comprising one or more motif(s) [VLI]XE[EDSQ]C (SEQ ID NO 60), CY[FLIV][SDN][ATVG] (SEQ ID NO 61), DYQ[L]G (SEQ ID NO 62), FQ[TAV]Q[PSD] (SEQ ID NO 63) and comprises the amino acid sequence shown SEQ ID NO 42 or polypeptides having at least 60%, at least 65%, at least 70%, at least 75%, at least 80%, at least 85%, at least 90%, at least 95%, at least 96%, at least 97%, at least 98%, at least 99% or 100% sequence identity hereto.

36. Composition according to any of the preceding composition paragraphs wherein the polypeptide comprising one or more motif(s) [VLI]XE[EDSQ]C (SEQ ID NO 60), CY[FLIV][SDN][ATVG] (SEQ ID NO 61), DYQ[L]G (SEQ ID NO 62), FQ[TAV]Q[PSD] (SEQ ID NO 63) and comprises the amino acid sequence shown SEQ ID NO 45 or polypeptides having at least 60%, at least 65%, at least 70%, at least 75%, at least 80%, at least 85%, at least 90%, at least 95%, at least 96%, at least 97%, at least 98%, at least 99% or 100% sequence identity hereto.

37. Composition according to any of the preceding composition paragraphs wherein the polypeptide comprising one or more motif(s) [VLI]XE[EDSQ]C (SEQ ID NO 60), CY[FLIV][SDN][ATVG] (SEQ ID NO 61), DYQ[L]G (SEQ ID NO 62), FQ[TAV]Q[PSD] (SEQ ID NO 63) and comprises the amino acid sequence shown SEQ ID NO 48 or polypeptides having at least 60%, at least 65%, at least 70%, at least 75%, at least 80%, at least 85%, at least 90%, at least 95%, at least 96%, at least 97%, at least 98%, at least 99% or 100% sequence identity hereto.

38. Composition according to any of the preceding composition paragraphs wherein the polypeptide comprising one or more motif(s) [VLI]XE[EDSQ]C (SEQ ID NO 60), CY[FLIV][SDN][ATVG] (SEQ ID NO 61), DYQ[L]G (SEQ ID NO 62), FQ[TAV]Q[PSD] (SEQ ID NO 63) and comprises the amino acid sequence shown SEQ ID NO 51 or polypeptides having at least 60%, at least 65%, at least 70%, at least 75%, at least 80%, at least 85%, at least 90%, at least 95%, at least 96%, at least 97%, at least 98%, at least 99% or 100% sequence identity hereto.

39. Composition according to any of the preceding composition paragraphs wherein the polypeptide comprising one or more motif(s) [VLI]XE[EDSQ]C (SEQ ID NO 60), CY[FLIV][SDN][ATVG] (SEQ ID NO 61), DYQ[L]G (SEQ ID NO 62), FQ[TAV]Q[PSD] (SEQ ID NO 63), AEECG (SEQ ID NO 64), NAFQ[AT]Q (SEQ ID NO 65) and comprises the amino acid sequence shown SEQ ID NO 54 or polypeptides having at least 60%, at least 65%, at least 70%, at least 75%, at least 80%, at least 85%, at least 90%, at least 95%, at least 96%, at least 97%, at least 98%, at least 99% or 100% sequence identity hereto.

40. Composition according to any of the preceding composition paragraphs wherein the polypeptide comprising one or more motif(s) [VLI]XE[EDSQ]C (SEQ ID NO 60), CY[FLIV][SDN][ATVG] (SEQ ID NO 61), GXXVX[NHQTS]IEY[PG] (SEQ ID NO 68), VICYF (SEQ ID NO 69), ICYFSA (SEQ ID NO 70) and comprises the amino acid sequence shown SEQ ID NO 57 or polypeptides having at least 60%, at least 65%, at least 70%, at least 75%, at least 80%, at least 85%, at least 90%, at least 95%, at least 96%, at least 97%, at least 98%, at least 99% or 100% sequence identity hereto.

41. A method for laundering an item comprising the steps of:

a) Exposing an item to a wash liquor comprising a polypeptide of paragraphs 55-79 or a composition according to any of paragraphs 11-40;

b) Completing at least one wash cycle; and c) Optionally rinsing the item, wherein the item is a textile.

42. A method of treating an item, wherein the item is preferably a textile, said method comprising the steps of:

a. Exposing an item to a polypeptide selected from the group consisting of a polypeptide having at least 60%, at least 65%, at least 70%, at least 75%, at least 80%, at least 85%, at least 90%, at least 95%, at least 96%, at least 97%, at least 98%, at least 99% or 100% sequence identity to the mature polypeptide of SEQ ID NO 2, SEQ ID NO 5, SEQ ID NO 8, SEQ ID NO 11, SEQ ID NO 14, SEQ ID NO 17, SEQ ID NO 20, SEQ ID NO 23, SEQ ID NO 26, SEQ ID NO 29, SEQ ID NO 32, SEQ ID NO 35, SEQ ID NO 38, SEQ ID NO 41, SEQ ID NO 44, SEQ ID NO 47, SEQ ID NO 50, SEQ ID NO 53, SEQ ID NO 56 or the polypeptide comprising the amino acid sequence shown in: SEQ ID NO 72, SEQ ID NO 73, SEQ ID NO 74, SEQ ID NO 75, SEQ ID NO 76, SEQ ID NO 77, SEQ ID NO 78, SEQ ID NO 79, SEQ ID NO 80, SEQ ID NO 81, SEQ ID NO 82, SEQ ID NO 83, SEQ ID NO 84, SEQ ID NO 85, SEQ ID NO 86, SEQ ID NO 87, SEQ ID NO 88, SEQ ID NO 89, SEQ ID NO 90, SEQ ID NO 91, SEQ ID NO 92, SEQ ID NO 93, SEQ ID NO 94, SEQ ID NO 95, SEQ ID NO 96, SEQ ID NO 97, SEQ ID NO 98, SEQ ID NO 99, SEQ ID NO 100, SEQ ID NO 101, SEQ ID NO 102, SEQ ID NO 103, SEQ ID NO 104, SEQ ID NO 105, SEQ ID NO 106, SEQ ID NO 107, SEQ ID NO 108, SEQ ID NO 109, SEQ ID NO 110, SEQ ID NO 111, SEQ ID NO 112, SEQ ID NO 113, SEQ ID NO 114, SEQ ID NO 115, SEQ ID NO 116, SEQ ID NO 117, SEQ ID NO 118, SEQ ID NO 119, SEQ ID NO 120, SEQ ID NO 121, SEQ ID NO 122, SEQ ID NO 123, SEQ ID NO 124, SEQ ID NO 125, SEQ ID NO 126, SEQ ID NO 127, SEQ ID NO 128, SEQ ID NO 129, SEQ ID NO 130, SEQ ID NO 131, SEQ ID NO 132, SEQ ID NO: 133, SEQ ID NO 134, SEQ ID NO 135, SEQ ID NO 136, SEQ ID NO 137, SEQ ID NO 138, SEQ ID NO 139, SEQ ID NO 140, SEQ ID NO 141, SEQ ID NO 142, SEQ ID NO 143, SEQ ID NO 144, SEQ ID NO 145 or SEQ ID NO 146; contacting the item with a wash liquor comprising the polypeptide or a composition according to any proceeding paragraphs.

43. Method according to any proceeding paragraphs, wherein the pH of the wash liquor is in the range of 1 to 11.

44. Method according to any of the preceding method paragraphs, wherein the pH of the wash liquor is in the range 5.5 to 11, such as in the range of 7 to 9, in the range of 7 to 8 or in the range of 7 to 8.5.

45. Method according to any of the preceding method paragraphs, wherein the temperature of the wash liquor is in the range of 5° C. to 95° C., or in the range of 10° C. to 80° C., in the range of 10° C. to 70° C., in the range of 10° C. to 60° C., in the range of 10° C. to 50° C., in the range of 15° C. to 40° C., in the range of 20° C. to 40° C., in the range of 15° C. to 30° C. or in the range of 20° C. to 30° C.

46. Method according to any of the preceding method paragraphs, wherein the temperature of the wash liquor is from about 20° C. to about 40° C.

47. Method according to any of the preceding method paragraphs, wherein the temperature of the wash liquor is from about 15° C. to about 30° C.

48. Method according to any of the preceding method paragraphs, wherein stains present on the item is pre-treated with a polypeptide of paragraphs 55-79 or a detergent composition according to any of paragraphs 11-40.

49. Method according to any of the preceding method paragraphs, wherein stickiness of the item is reduced.

50. Method according to any of the preceding method paragraphs, wherein redeposition of soil is reduced.

51. Method according to any of the preceding method paragraphs, wherein adherence of soil to the item is reduced or removed.

52. Method according to any of the preceding method paragraphs, wherein whiteness of the item is maintained or improved.

53. Method according to any of the preceding method paragraphs, wherein malodor is reduced or removed from the item.

54. Method according to any of the preceding method paragraphs, wherein the concentration of the polypeptide having hydrolytic activity in the wash liquor is in the range 0.002 mg/L to 2 mg/L, such as 0.02 mg/L to 2 mg/L, such as 0.2 mg/L to 2 mg/L or in the range of 0.0001 mg/L to 10 mg/L or in the range of in the range of 0.001 mg/L to 10 mg/L, or in the range of 0.01 mg/L to 10 mg/L, or in in the range of 0.1 mg/L to 10 mg/L per litre of wash liquor, optionally the concentration of the polypeptide shown in the invention is 0.0001% to 2 wt %, such as 0.001 to 0.1 wt %, such as 0.005 to 0.1 wt %, such as 0.01 to 0.1 wt %, such as 0.01 to 0.5 wt % or most preferred 0.002 to 0.09 wt % in the total detergent concentration.

55. A polypeptide having hydrolytic activity, preferably having alpha-1,4-polygalactosaminidase activity, selected from the group consisting of:

a) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the mature polypeptide of SEQ ID NO 2, SEQ ID NO 5, SEQ ID NO 8, SEQ ID NO 11, SEQ ID NO 14, SEQ ID NO 17, SEQ ID NO 20, SEQ ID NO 23, SEQ ID NO 26, SEQ ID NO 29, SEQ ID NO 32, SEQ ID NO 35, SEQ ID NO 38, SEQ ID NO 41, SEQ ID NO 44, SEQ ID NO 47, SEQ ID NO 50, SEQ ID NO 53, SEQ ID NO 56, a polypeptide having at least 60%, at least 65%, at least 70%, at least 75%, at least 80%, at least 85%, at least 90%, at least 95%, at least 96%, at least 97%, at least 98%, at least 99% or 100% sequence identity to the mature polypeptide shown in SEQ ID NO 3, SEQ ID NO 6, SEQ ID NO 9, SEQ ID NO 12, SEQ ID NO 15, SEQ ID NO 18, SEQ ID NO 21, SEQ ID NO 24, SEQ ID NO 27, SEQ ID NO 30, SEQ ID NO 33, SEQ ID NO 36, SEQ ID NO 39, SEQ ID NO 42, SEQ ID NO 45, SEQ ID NO 48, SEQ ID NO 51, SEQ ID NO 54, SEQ ID NO 57 or a polypeptide having at least 60%, at least 65%, at least 70%, at least 75%, at least 80%, at least 85%, at least 90%, at least 95%, at least 96%, at least 97%, at least 98%, at least 99% or 100% sequence identity to the mature polypeptide shown in SEQ ID NO 72, SEQ ID NO 73, SEQ ID NO 74, SEQ ID NO 75, SEQ ID NO 76, SEQ ID NO 77, SEQ ID NO 78, SEQ ID NO 79, SEQ ID NO 80, SEQ ID NO 81, SEQ ID NO 82, SEQ ID NO 83, SEQ ID NO 84, SEQ ID NO 85, SEQ ID NO 86, SEQ ID NO 87, SEQ ID NO 88, SEQ ID NO 89, SEQ ID NO 90, SEQ ID NO 91, SEQ ID NO 92, SEQ ID NO 93, SEQ ID NO 94, SEQ ID NO 95, SEQ ID NO 96, SEQ ID NO 97, SEQ ID NO 98, SEQ ID NO 99, SEQ ID NO 100, SEQ ID NO 101, SEQ ID NO 102, SEQ ID NO 103, SEQ ID NO 104, SEQ ID NO 105, SEQ ID NO 106, SEQ ID NO 107, SEQ ID NO 108, SEQ ID NO 109, SEQ ID NO 110, SEQ ID NO 111, SEQ ID NO 112, SEQ ID NO 113, SEQ ID NO 114, SEQ ID NO 115, SEQ ID NO 116, SEQ ID NO 117, SEQ ID NO 118, SEQ ID NO 119, SEQ ID NO 120, SEQ ID NO 121, SEQ ID NO 122, SEQ ID NO 123, SEQ ID NO 124, SEQ ID NO 125, SEQ ID NO 126, SEQ ID NO 127, SEQ ID NO 128, SEQ ID NO 129, SEQ ID NO 130, SEQ ID NO 131, SEQ ID NO 132, SEQ ID NO: 133, SEQ ID NO 134, SEQ ID NO 135, SEQ ID NO 136, SEQ ID NO 137, SEQ ID NO 138, SEQ ID NO 139, SEQ ID NO 140, SEQ ID NO 141, SEQ ID NO 142, SEQ ID NO 143, SEQ ID NO 144, SEQ ID NO 145 or SEQ ID NO 146;

b) a polypeptide encoded by a polynucleotide that hybridizes under low stringency conditions with;
   i. the mature polypeptide coding sequence shown in SEQ ID NO 1, SEQ ID NO 4, SEQ ID NO 7, SEQ ID NO 10, SEQ ID NO 13, SEQ ID NO 16, SEQ ID NO 19, SEQ ID NO 22, SEQ ID NO 25, SEQ ID NO 28, SEQ ID NO 31, SEQ ID NO 34, SEQ ID NO 37, SEQ ID NO 40, SEQ ID NO 43, SEQ ID NO 46, SEQ ID NO 49, SEQ ID NO 52, SEQ ID NO 55;
   ii. the cDNA sequence thereof, or
   iii. the full-length complement of (i) or (ii);

c) a polypeptide encoded by a polynucleotide having at least 60% sequence identity to the mature polypeptide coding sequence of SEQ ID NO 1, SEQ ID NO 4, SEQ ID NO 7, SEQ ID NO 10, SEQ ID NO 13, SEQ ID NO 16, SEQ ID NO 19, SEQ ID NO 22, SEQ ID NO 25, SEQ ID NO 28, SEQ ID NO 31, SEQ ID NO 34, SEQ ID NO 37, SEQ ID NO 40, SEQ ID NO 43, SEQ ID NO 46, SEQ ID NO 49, SEQ ID NO 52, SEQ ID NO 55 or the cDNA sequence thereof;

d) a variant of the mature polypeptide shown in SEQ ID NO 3, SEQ ID NO 6, SEQ ID NO 9, SEQ ID NO 12, SEQ ID NO 15, SEQ ID NO 18, SEQ ID NO 21, SEQ ID NO 24, SEQ ID NO 27, SEQ ID NO 30, SEQ ID NO 33, SEQ ID NO 36, SEQ ID NO 39, SEQ ID NO 42, SEQ ID NO 45, SEQ ID NO 48, SEQ ID NO 51, SEQ ID NO 54, SEQ ID NO 57, SEQ ID NO 72, SEQ ID NO 73, SEQ ID NO 74, SEQ ID NO 75, SEQ ID NO 76, SEQ ID NO 77, SEQ ID NO 78, SEQ ID NO 79, SEQ ID NO 80, SEQ ID NO 81, SEQ ID NO 82, SEQ ID NO 83, SEQ ID NO 84, SEQ ID NO 85, SEQ ID NO 86, SEQ ID NO 87, SEQ ID NO 88, SEQ ID NO 89, SEQ ID NO 90, SEQ ID NO 91, SEQ ID NO 92, SEQ ID NO 93, SEQ ID NO 94, SEQ ID NO 95, SEQ ID NO 96, SEQ ID NO 97, SEQ ID NO 98, SEQ ID NO 99, SEQ ID NO 100, SEQ ID NO 101, SEQ ID NO 102, SEQ ID NO 103, SEQ ID NO 104, SEQ ID NO 105, SEQ ID NO 106, SEQ ID NO 107, SEQ ID NO 108, SEQ ID NO 109, SEQ ID NO 110, SEQ ID NO 111, SEQ ID NO 112, SEQ ID NO 113, SEQ ID NO 114, SEQ ID NO 115, SEQ ID NO 116, SEQ ID NO 117, SEQ ID NO 118, SEQ ID NO 119, SEQ ID NO 120, SEQ ID NO 121, SEQ ID NO 122, SEQ ID NO 123, SEQ ID NO 124, SEQ ID NO 125, SEQ ID NO 126, SEQ ID NO 127, SEQ ID NO 128, SEQ ID NO 129, SEQ ID NO 130, SEQ ID NO 131, SEQ ID NO 132, SEQ ID NO: 133, SEQ ID NO 134, SEQ ID NO 135, SEQ ID NO 136, SEQ ID NO 137, SEQ ID NO 138, SEQ ID NO 139, SEQ ID NO 140, SEQ ID NO 141, SEQ ID NO 142, SEQ ID NO 143, SEQ ID NO 144, SEQ ID NO 145 or SEQ ID NO 146 comprising a substitution, deletion, and/or insertion at one or more positions; and e) a fragment of the polypeptide shown in (a), (b), (c), or (d) that comprises one or more motif(s) [VLI]XE[EDSQ]C (SEQ ID NO 60), CY[FLIV][SDN][ATVG] (SEQ ID NO 61), DYQ[L]G (SEQ ID NO 62), FQ[TAV]Q[PSD] (SEQ ID NO 63), AEECG (SEQ ID NO 64), NAFQ[AT]Q (SEQ ID NO 65), WQWQL (SEQ ID NO 66), [VL][GASD]LKN[DGS][VLIP] (SEQ ID NO 67), GXXVX[NHQTS]IEY[PG] (SEQ ID NO 68), VICYF (SEQ ID NO 69), ICYFSA (SEQ ID NO 70), DFAVL (SEQ ID NO 71).

56. The polypeptide of paragraph 55, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 2, SEQ ID NO 5, SEQ ID NO 8, SEQ ID NO 11, SEQ ID NO 14, SEQ ID NO 17, SEQ ID NO 20, SEQ ID NO 23, SEQ ID NO 26, SEQ ID NO 29, SEQ ID NO 32, SEQ ID NO 35, SEQ ID NO 38, SEQ ID NO 41, SEQ ID NO 44, SEQ ID NO 47, SEQ ID NO 50, SEQ ID NO 53, SEQ ID NO 56 or to the mature polypeptide shown in SEQ ID NO 3, SEQ ID NO 6, SEQ ID NO 9, SEQ ID NO 12, SEQ ID NO 15, SEQ ID NO 18, SEQ ID NO 21, SEQ ID NO 24, SEQ ID NO 27, SEQ ID NO 30, SEQ ID NO 33, SEQ ID NO 36, SEQ ID NO 39, SEQ ID NO 42, SEQ ID NO 45, SEQ ID NO 48, SEQ ID NO 51, SEQ ID NO 54, SEQ ID NO 57, SEQ ID NO 72, SEQ ID NO 73, SEQ ID NO 74, SEQ ID NO 75, SEQ ID NO 76, SEQ ID NO 77, SEQ ID NO 78, SEQ ID NO 79, SEQ ID NO 80, SEQ ID NO 81, SEQ ID NO 82, SEQ ID NO 83, SEQ ID NO 84, SEQ ID NO 85, SEQ ID NO 86, SEQ ID NO 87, SEQ ID NO 88, SEQ ID NO 89, SEQ ID NO 90, SEQ ID NO 91, SEQ ID NO 92, SEQ ID NO 93, SEQ ID NO 94, SEQ ID NO 95, SEQ ID NO 96, SEQ ID NO 97, SEQ ID NO 98, SEQ ID NO 99, SEQ ID NO 100, SEQ ID NO 101, SEQ ID NO 102, SEQ ID NO 103, SEQ ID NO 104, SEQ ID NO 105, SEQ ID NO 106, SEQ ID NO 107, SEQ ID NO 108, SEQ ID NO 109, SEQ ID NO 110, SEQ ID NO 111, SEQ ID NO 112, SEQ ID NO 113, SEQ ID NO 114, SEQ ID NO 115, SEQ ID NO 116, SEQ ID NO 117, SEQ ID NO 118, SEQ ID NO 119, SEQ ID NO 120, SEQ ID NO 121, SEQ ID NO 122, SEQ ID NO 123, SEQ ID NO 124, SEQ ID NO 125, SEQ ID NO 126, SEQ ID NO 127, SEQ ID NO 128, SEQ ID NO 129, SEQ ID NO 130, SEQ ID NO 131, SEQ ID NO 132, SEQ ID NO: 133, SEQ ID NO 134, SEQ ID NO 135, SEQ ID NO 136, SEQ ID NO 137, SEQ ID NO 138, SEQ ID NO 139, SEQ ID NO 140, SEQ ID NO 141, SEQ ID NO 142, SEQ ID NO 143, SEQ ID NO 144, SEQ ID NO 145 or SEQ ID NO 146.

57. The polypeptide of paragraph 55 or 56, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 2 or to the mature polypeptide shown in SEQ ID NO 3.

58. The polypeptide of paragraph 55 or 56, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 5 or to the mature polypeptide shown in SEQ ID NO 6.

59. The polypeptide of paragraph 55 or 56, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 8 or to the mature polypeptide shown in SEQ ID NO 9.

60. The polypeptide of paragraph 55 or 56, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 11 or to the mature polypeptide shown in SEQ ID NO 12.

61. The polypeptide of paragraph 55 or 56, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 14 or to the mature polypeptide shown in SEQ ID NO 15.

62. The polypeptide of paragraph 55 or 56, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 17 or to the mature polypeptide shown in SEQ ID NO 18.

63. The polypeptide of paragraph 55 or 56, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 20 or to the mature polypeptide shown in SEQ ID NO 21.

64. The polypeptide of paragraph 55 or 56, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 23 or to the mature polypeptide shown in SEQ ID NO 24.

65. The polypeptide of paragraph 55 or 56, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 26 or to the mature polypeptide shown in SEQ ID NO 27.

66. The polypeptide of paragraph 55 or 56, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 29 or to the mature polypeptide shown in SEQ ID NO 30.

67. The polypeptide of paragraph 55 or 56, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 32 or to the mature polypeptide shown in SEQ ID NO 33.

68. The polypeptide of paragraph 55 or 56, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 35 or to the mature polypeptide shown in SEQ ID NO 36.

69. The polypeptide of paragraph 55 or 56, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 38 or to the mature polypeptide shown in SEQ ID NO 39.

70. The polypeptide of paragraph 55 or 56, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 41 or to the mature polypeptide shown in SEQ ID NO 42.

71. The polypeptide of paragraph 55 or 56, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 44 or to the mature polypeptide shown in SEQ ID NO 45.

72. The polypeptide of paragraph 55 or 56, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 47 or to the mature polypeptide shown in SEQ ID NO 48.

73. The polypeptide of paragraph 55 or 56, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 50 or to the mature polypeptide shown in SEQ ID NO 51.

74. The polypeptide of paragraph 55 or 56, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 53 or to the mature polypeptide shown in SEQ ID NO 54.

75. The polypeptide of paragraph 55 or 56, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 56 or to the mature polypeptide shown in SEQ ID NO 57.

76. The polypeptide according to any of paragraphs 55 to 75, which is encoded by a polynucleotide that hybridizes under low stringency conditions, low-medium stringency conditions, medium stringency conditions, medium-high stringency conditions, high stringency conditions, or very high stringency conditions with i. the mature polypeptide coding sequence shown in SEQ ID NO 1, SEQ ID NO 4, SEQ ID NO 7, SEQ ID NO 10, SEQ ID NO 13, SEQ ID NO 16, SEQ ID NO 19, SEQ ID NO 22, SEQ ID NO 25, SEQ ID NO 28, SEQ ID NO 31, SEQ ID NO 34, SEQ ID NO 37, SEQ ID NO 40, SEQ ID NO 43, SEQ ID NO 46, SEQ ID NO 49, SEQ ID NO 52, SEQ ID NO 55;

ii. the cDNA sequence thereof, or iii. the full-length complement of (i) or (ii).

77. The polypeptide according to any of paragraphs 55 to 76, which is encoded by a polynucleotide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide coding sequence of SEQ ID NO 1, SEQ ID NO 4, SEQ ID NO 7, SEQ ID NO 10, SEQ ID NO 13, SEQ ID NO 16, SEQ ID NO 19, SEQ ID NO 22, SEQ ID NO 25, SEQ ID NO 28, SEQ ID NO 31, SEQ ID NO 34, SEQ ID NO 37, SEQ ID NO 40, SEQ ID NO 43, SEQ ID NO 46, SEQ ID NO 49, SEQ ID NO 52, SEQ ID NO 55 or the cDNA sequence thereof.

78. The polypeptide according to any of paragraphs 55 to 77, comprising or consisting of SEQ ID NO 3, SEQ ID NO 6, SEQ ID NO 9, SEQ ID NO 12, SEQ ID NO 15, SEQ ID NO 18, SEQ ID NO 21, SEQ ID NO 24, SEQ ID NO 27, SEQ ID NO 30, SEQ ID NO 33, SEQ ID NO 36, SEQ ID NO 39, SEQ ID NO 42, SEQ ID NO 45, SEQ ID NO 48, SEQ ID NO 51, SEQ ID NO 54, SEQ ID NO 57 or the mature polypeptide of SEQ ID NO 2, SEQ ID NO 5, SEQ ID NO 8, SEQ ID NO 11, SEQ ID NO 14, SEQ ID NO 17, SEQ ID NO 20, SEQ ID NO 23, SEQ ID NO 26, SEQ ID NO 29, SEQ ID NO 32, SEQ ID NO 35, SEQ ID NO 38, SEQ ID NO 41, SEQ ID NO 44, SEQ ID NO 47, SEQ ID NO 50, SEQ ID NO 53, SEQ ID NO 56.

79. The polypeptide according to any of paragraphs 55 to 78, which is a variant of the any of the polypeptides with SEQ ID NO 3, SEQ ID NO 6, SEQ ID NO 9, SEQ ID NO 12, SEQ ID NO 15, SEQ ID NO 18, SEQ ID NO 21, SEQ ID NO 24, SEQ ID NO 27, SEQ ID NO 30, SEQ ID NO 33, SEQ ID NO 36, SEQ ID NO 39, SEQ ID NO 42, SEQ ID NO 45, SEQ ID NO 48, SEQ ID NO 51, SEQ ID NO 54, SEQ ID NO 57, SEQ ID NO 72, SEQ ID NO 73, SEQ ID NO 74, SEQ ID NO 75, SEQ ID NO 76, SEQ ID NO 77, SEQ ID NO 78, SEQ ID NO 79, SEQ ID NO 80, SEQ ID NO 81, SEQ ID NO 82, SEQ ID NO 83, SEQ ID NO 84, SEQ ID NO 85, SEQ ID NO 86, SEQ ID NO 87, SEQ ID NO 88, SEQ ID NO 89, SEQ ID NO 90, SEQ ID NO 91, SEQ ID NO 92, SEQ ID NO 93, SEQ ID NO 94, SEQ ID NO 95, SEQ ID NO 96, SEQ ID NO 97, SEQ ID NO 98, SEQ ID NO 99, SEQ ID NO 100, SEQ ID NO 101, SEQ ID NO 102, SEQ ID NO 103, SEQ ID NO 104, SEQ ID NO 105, SEQ ID NO 106, SEQ ID NO 107, SEQ ID NO 108, SEQ ID NO 109, SEQ ID NO 110, SEQ ID NO 111, SEQ ID NO 112, SEQ ID NO 113, SEQ ID NO 114, SEQ ID NO 115, SEQ ID NO 116, SEQ ID NO 117, SEQ ID NO 118, SEQ ID NO 119, SEQ ID NO 120, SEQ ID NO 121, SEQ ID NO 122, SEQ ID NO 123, SEQ ID NO 124, SEQ ID NO 125, SEQ ID NO 126, SEQ ID NO 127, SEQ ID NO 128, SEQ ID NO 129, SEQ ID NO 130, SEQ ID NO 131, SEQ ID NO 132, SEQ ID NO: 133, SEQ ID NO 134, SEQ ID NO 135, SEQ ID NO 136, SEQ ID NO 137, SEQ ID NO 138, SEQ ID NO 139, SEQ ID NO 140, SEQ ID NO 141, SEQ ID NO 142, SEQ ID NO 143, SEQ ID NO 144, SEQ ID NO 145 or SEQ ID NO 146 comprising a substitution, deletion, and/or insertion at one or more positions.

80. The polypeptide according to any of paragraphs 55 to 79 for use as a medicament.

81. The polypeptide according to any of paragraphs 55 to 79 for use in treatment or prevention of a bacterial infection, preferably said bacterial infection is an infection caused by Gram-positive or Gram-negative bacteria, further preferably said bacterial infection is selected from a group consisting of: *Staphylococcus* spp. (e.g., *Staphylococcus epidermidis, S. aureus*), *Enterococcus* spp. (e.g., *Enterococcus faecalis*), *Escherichia* spp. (e.g., *Escherichia coli*), *Listeria* spp. (e.g., *Listeria monocytogenes*), *Pseudomonas* spp. (e.g., *Pseudomonas aeruginosa*), *Bacillus* spp., *Salmonella* spp., Coagulase-negative Staphylococci, *Klebsiella* spp. (e.g., *Klebsiella pneumoniae*) infections.

82. The polypeptide according to any of paragraphs 55 to 79 for use in treatment or prevention of a disease selected from the group consisting of: Cystic fibrosis pneumonia (e.g., caused by *Pseudomonas aeruginosa* and/or *Burkholderia cepacia*), Meloidosis (e.g., caused by *Pseudomonas pseudomallei*), Necrotizing fasciitis (e.g., caused by Group A streptococci), Musculoskeletal infections (e.g., caused by Staphylococci and other Gram-positive cocci), Otitis media (e.g., caused by *Haemophilus influenzae*), Biliary tract infection (e.g., caused by *E. coli* and other enteric bacteria), Urinary catheter cystitis (e.g., caused by *E. coli* and other Gram-negative rods), Bacterial prostatitis (e.g., *E. coli* and other Gram-negative bacteria), Periodontitis (e.g., caused by Gram negative anaerobic oral bacteria), Dental caries (e.g., caused by *Streptococcus* spp. and other acidogenic Gram positive cocci).

83. A polynucleotide encoding the polypeptide according to any of paragraphs 55-79.

84. A nucleic acid construct or expression vector comprising the polynucleotide of paragraph 83 operably linked to one or more control sequences that direct the production of the polypeptide in an expression host.

85. A recombinant host cell comprising the polynucleotide of paragraph 83 operably linked to one or more control sequences that direct the production of the polypeptide.

86. A method of producing the polypeptide shown in any of paragraphs 55-79, comprising cultivating a cell, which in its wild-type form produces the polypeptide, under conditions conducive for production of the polypeptide.

87. The method of paragraph 86, further comprising recovering the polypeptide.

88. A method of producing a polypeptide according to any of paragraphs 55-79, comprising cultivating the host cell of paragraph 85 under conditions conducive for production of the polypeptide.

89. The method of paragraph 88, further comprising recovering the polypeptide.

90. A nucleic acid construct or expression vector comprising a gene encoding a protein operably linked to the polynucleotide of paragraph 83, wherein the gene is foreign to the polynucleotide encoding the signal peptide.

91. A recombinant host cell comprising a gene encoding a protein operably linked to the polynucleotide of paragraph 83, wherein the gene is foreign to the polynucleotide encoding the signal peptide.

92. A method of producing a protein, comprising cultivating a recombinant host cell comprising a gene encoding a protein operably linked to the polynucleotide of paragraph 83, wherein the gene is foreign to the polynucleotide encoding the signal peptide, under conditions conducive for production of the protein.

93. The method of paragraph 92, further comprising recovering the protein.

94. Item laundered according to the method of any of paragraphs 41-54.

The invention is further described in the following paragraphs;

Paragraph 1. A GH114 glycosyl hydrolase comprising the motif [VLI]XE[EDSQ]C (SEQ ID NO 60) and/or the motif CY[FLIV][SDN][ATVG] (SEQ ID NO 61), wherein the GH114 glycosyl hydrolase has hydrolytic activity, and wherein the GH114 glycosyl hydrolase comprises or consist of a polypeptide selected from the group consisting of:

(a) a polypeptide having at least 90%, at least 95%, at least 96%, at least 97%, at least 98%, at least 99% or 100% sequence identity to the polypeptide shown in SEQ ID NO 3;
(b) a polypeptide having at least 90%, at least 95%, at least 96%, at least 97%, at least 98%, at least 99% or 100% sequence identity to the polypeptide shown in SEQ ID NO 6;
(c) a polypeptide having at least 85%, at least 90%, at least 95%, at least 96%, at least 97%, at least 98%, at least 99% or 100% sequence identity to the polypeptide shown in SEQ ID NO 9;
(d) a polypeptide having at least 85%, at least 90%, at least 95%, at least 96%, at least 97%, at least 98%, at least 99% or 100% sequence identity to the polypeptide shown in SEQ ID NO 12;
(e) a polypeptide having at least 75%, at least 80%, at least 85%, at least 90%, at least 95%, at least 96%, at least 97%, at least 98%, at least 99% or 100% sequence identity to the polypeptide shown in SEQ ID NO 21;
(f) a polypeptide having at least 90%, at least 95%, at least 96%, at least 97%, at least 98%, at least 99% or 100% sequence identity to the polypeptide shown in SEQ ID NO 24;
(g) a polypeptide having at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 27;
(h) a polypeptide having, at least 50% at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 30;
(i) a polypeptide having at least 70%, at least 75%, at least 80%, at least 85%, at least 90%, at least 95%, at least 96%, at least 97%, at least 98%, at least 99% or 100% sequence identity to the polypeptide shown in SEQ ID NO 33;
(j) a polypeptide having at least 75%, at least 80%, at least 85%, at least 90%, at least 95%, at least 96%, at least 97%, at least 98%, at least 99% or 100% sequence identity to the polypeptide shown in SEQ ID NO 36;
(k) a polypeptide having at least 99% or 100% sequence identity to the polypeptide shown in SEQ ID NO 39;
(l) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 42;
(m) a polypeptide having at least 85%, at least 90%, at least 95%, at least 96%, at least 97%, at least 98%, at least 99% or 100% sequence identity to the polypeptide shown in SEQ ID NO 45;
(n) a polypeptide having at least 70%, at least 75%, at least 80%, at least 85%, at least 90%, at least 95%, at least 96%, at least 97%, at least 98%, at least 99% or 100% sequence identity to the polypeptide shown in SEQ ID NO 48;
(o) a polypeptide having at least 98%, at least 99% or 100% sequence identity to the polypeptide shown in SEQ ID NO 51;
(p) a polypeptide having at least 80%, at least 85%, at least 90%, at least 95%, at least 96%, at least 97%, at least 98%, at least 99% or 100% sequence identity to the polypeptide shown in SEQ ID NO 54; and
(q) a polypeptide having at least 85%, at least 90%, at least 95%, at least 96%, at least 97%, at least 98%, at least 99% or 100% sequence identity to the polypeptide shown in SEQ ID NO 57.

Paragraph 2. A GH114 glycosyl hydrolase according to paragraph 1, comprising the motif DYQ[L]G (SEQ ID NO 62) and/or the motif FQ[TAV]Q[PSD] (SEQ ID NO 63), wherein the GH114 glycosyl hydrolase comprises or consist of a polypeptide selected from the group consisting of:

(a) a polypeptide having at least 90%, at least 95%, at least 96%, at least 97%, at least 98%, at least 99% or 100% sequence identity to the polypeptide shown in SEQ ID NO 3;
(b) a polypeptide having at least 90%, at least 95%, at least 96%, at least 97%, at least 98%, at least 99% or 100% sequence identity to the polypeptide shown in SEQ ID NO 6;
(c) a polypeptide having at least 85%, at least 90%, at least 95%, at least 96%, at least 97%, at least 98%, at least 99% or 100% sequence identity to the polypeptide shown in SEQ ID NO 9;
(d) a polypeptide having at least 85%, at least 90%, at least 95%, at least 96%, at least 97%, at least 98%, at least 99% or 100% sequence identity to the polypeptide shown in SEQ ID NO 12;
(e) a polypeptide having at least 75%, at least 80%, at least 85%, at least 90%, at least 95%, at least 96%, at least 97%, at least 98%, at least 99% or 100% sequence identity to the polypeptide shown in SEQ ID NO 21;
(f) a polypeptide having at least 90%, at least 95%, at least 96%, at least 97%, at least 98%, at least 99% or 100% sequence identity to the polypeptide shown in SEQ ID NO 24;
(g) a polypeptide having at least 70%, at least 75%, at least 80%, at least 85%, at least 90%, at least 95%, at least 96%, at least 97%, at least 98%, at least 99% or 100% sequence identity to the polypeptide shown in SEQ ID NO 33;

(h) a polypeptide having at least 75%, at least 80%, at least 85%, at least 90%, at least 95%, at least 96%, at least 97%, at least 98%, at least 99% or 100% sequence identity to the polypeptide shown in SEQ ID NO 36;

(i) a polypeptide having at least 99% or 100% sequence identity to the polypeptide shown in SEQ ID NO 39;

(j) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 42;

(k) a polypeptide having at least 85%, at least 90%, at least 95%, at least 96%, at least 97%, at least 98%, at least 99% or 100% sequence identity to the polypeptide shown in SEQ ID NO 45;

(l) a polypeptide having at least 70%, at least 75%, at least 80%, at least 85%, at least 90%, at least 95%, at least 96%, at least 97%, at least 98%, at least 99% or 100% sequence identity to the polypeptide shown in SEQ ID NO 48;

(m) a polypeptide having at least 98%, at least 99% or 100% sequence identity to the polypeptide shown in SEQ ID NO 51; and (n) a polypeptide having at least 80%, at least 85%, at least 90%, at least 95%, at least 96%, at least 97%, at least 98%, at least 99% or 100% sequence identity to the polypeptide shown in SEQ ID NO 54.

Paragraph 3. A GH114 glycosyl hydrolase according to paragraph 1 or 2 comprising the motif AEECG (SEQ ID NO 64) and/or the motif NAFQ[AT]Q (SEQ ID NO 65), wherein the GH114 glycosyl hydrolase comprises or consist of a polypeptide selected from the group consisting of:

(a) a polypeptide having at least 90%, at least 95%, at least 96%, at least 97%, at least 98%, at least 99% or 100% sequence identity to the polypeptide shown in SEQ ID NO 3;

(b) a polypeptide having at least 90%, at least 95%, at least 96%, at least 97%, at least 98%, at least 99% or 100% sequence identity to the polypeptide shown in SEQ ID NO 6;

(c) a polypeptide having at least 85%, at least 90%, at least 95%, at least 96%, at least 97%, at least 98%, at least 99% or 100% sequence identity to the polypeptide shown in SEQ ID NO 9;

(d) a polypeptide having at least 85%, at least 90%, at least 95%, at least 96%, at least 97%, at least 98%, at least 99% or 100% sequence identity to the polypeptide shown in SEQ ID NO 12;

(e) a polypeptide having at least 75%, at least 80%, at least 85%, at least 90%, at least 95%, at least 96%, at least 97%, at least 98%, at least 99% or 100% sequence identity to the polypeptide shown in SEQ ID NO 21;

(f) a polypeptide having at least 90%, at least 95%, at least 96%, at least 97%, at least 98%, at least 99% or 100% sequence identity to the polypeptide shown in SEQ ID NO 24;

(g) a polypeptide having at least 80%, at least 85%, at least 90%, at least 95%, at least 96%, at least 97%, at least 98%, at least 99% or 100% sequence identity to the polypeptide shown in SEQ ID NO 54.

Paragraph 4. A GH114 glycosyl hydrolase according to paragraph 1 comprising one, two or all three motif(s) GXXVX[NHQTS]IEY[PG] (SEQ ID NO 68), VICYF (SEQ ID NO 69) or ICYFSA (SEQ ID NO 70), wherein the GH114 glycosyl hydrolase is a polypeptide having at least 85%, at least 90%, at least 95%, at least 96%, at least 97%, at least 98%, at least 99% or 100% sequence identity to the polypeptide shown in SEQ ID NO 57.

Paragraph 5. A GH114 glycosyl hydrolase according to paragraph 1, comprising the motif WQWQL (SEQ ID NO 66) and/or the motif [VL][GASD]LKN[DGS][VLIP] (SEQ ID NO 67), wherein the GH114 glycosyl hydrolase is a polypeptide having at least 65%, at least 70%, at least 75%, at least 80%, at least 85%, at least 90%, at least 95%, at least 96%, at least 97%, at least 98%, at least 99% or 100% sequence identity to the polypeptide shown in SEQ ID NO 27.

Paragraph 6. A GH114 glycosyl hydrolase according to any of paragraphs 1 to 3, wherein the GH114 glycosyl hydrolase is obtained from *Amycolatopsis*, preferably *Amycolatopsis circi* or *Amycolatopsis* sp, and wherein the GH114 glycosyl hydrolase comprises or consist of a polypeptide selected from the group consisting of:

a) at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO 3;

b) at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO 6; or c) at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO 9.

Paragraph 7. A GH114 glycosyl hydrolase according to any of paragraphs 1 to 3, wherein the GH114 glycosyl hydrolase is obtained from *Streptomyces*, preferably *Streptomyces parvulus* or *Streptomyces miharaensis*, and wherein the GH114 glycosyl hydrolase comprises or consist of a polypeptide selected from the group consisting of:

a) a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO 12;

b) is a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO 24; or c) a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO 54.

Paragraph 8. The GH114 glycosyl hydrolase according to paragraph 6 or 7, wherein the GH114 glycosyl comprises one or more, or even all of the motif(s) [VLI]XE[EDSQ]C (SEQ ID NO 60), CY[FLIV][SDN][ATVG] (SEQ ID NO 61), DYQ[L]G (SEQ ID NO 62), FQ[TAV]Q[PSD] (SEQ ID NO 63), AEECG (SEQ ID NO 64), NAFQ[AT]Q (SEQ ID NO 65).

Paragraph 9. A granule comprising;

(a) a core comprising a GH114 glycosyl hydrolase according to any of paragraphs 1 to 8, and (b) optionally a coating consisting of one or more layer(s) surrounding the core.

Paragraph 10. A cleaning composition comprising:

(a) at least 0.001 ppm of at least one GH114 glycosyl hydrolase according to any of paragraphs 1 to 8;

(b) one or more cleaning composition components, preferably selected from surfactants, builders, bleach components, polymers, dispersing agents and additional enzymes.

Paragraph 11. A method for laundering an item comprising the steps of:

(a) exposing an item to a wash liquor comprising the GH114 glycosyl hydrolase according to any of paragraphs 1 to 8 or the composition according to paragraph 10;

(b) completing at least one wash cycle; and (c) optionally rinsing the item, wherein the item is a textile.

Paragraph 12. Use of a GH114 glycosyl hydrolase in a cleaning process, such as laundry and/or dish wash.

Paragraph 13. Use of a GH114 glycosyl hydrolase, i. for preventing, reducing or removing stickiness of the item;

ii. for preventing, reducing or removing biofilm or biofilm components iii. for reducing or removing pel stains on the item;

iv. for preventing, reducing or removing redeposition of soil during a wash cycle;

v. for preventing, reducing or removing adherence of soil to the item;

vi. for maintaining or improving whiteness of the item;

vii. for preventing, reducing or removing malodor from the item, wherein the item is a textile.

Paragraph 14. Use according to any of paragraphs 12 or 13, wherein GH114 glycosyl hydrolase comprising one or more of the motif(s) selected from the group consisting of: [VL]XE[EDSQ]C (SEQ ID NO 60), CY[FLIV][SDN][ATVG] (SEQ ID NO 61), DYQ[L]G (SEQ ID NO 62), FQ[TAV]Q[PSD] (SEQ ID NO 63), AEECG (SEQ ID NO 64), NAFQ[AT]Q (SEQ ID NO 65), WQWQL (SEQ ID NO 66), [VLI][GASD]LKN[DGS][VLIP] (SEQ ID NO 67), GXXVX[NHQTS]IEY[PG] (SEQ ID NO 68), VICYF (SEQ ID NO 69), ICYFSA (SEQ ID NO 70), DFAVL (SEQ ID NO 71).

Paragraph 15. Use according to any of paragraphs 12 to 14, wherein the polypeptide is selected from any of the GH114 glycosyl hydrolases of paragraphs 1 to 8.

EXAMPLES

Model Detergents

Model detergent A wash liquor (100%) was prepared by dissolving 3.33 g/l of model detergent A containing 12% LAS, 11% AEO Biosoft N25-7 (NI), 5% AEOS (SLES), 6% MPG (monopropylene glycol), 3% ethanol, 3% TEA, 2.75% coco soap, 2.75% soya soap, 2% glycerol, 2% sodium hydroxide, 2% sodium citrate, 1% sodium formate, 0.2% DTMPA and 0.2% PCA (all percentages are w/w) in water with hardness 15 dH.

Triple-20 Nonionic Model Detergent (Model NI) (60% surfactant) was prepared by dissolving 3.33 g/l non-ionic detergent containing NaOH 0.87%, MPG (Monopropylenglycol) 6%, Glycerol 2%, Soap-soy 2.75%, Soap-coco 2.75%, PCA (Sokalon CP-5) 0.2%, AEO Biosoft N25-7(NI) 16%, Sodium formiate 1%, Sodium Citrate 2%, DTMPA 0.2%, Ethanol (96%) 3% (all percentages are w/w) in water with hardness 15 dH.

Model Detergent MC: A medical cleaning model detergent (model detergent MC) was prepared containing 5% MPG (propylene glycol), 5% Pluronic PE 4300 (PO/EO block polymer; 70%/30%, approx. 1750 g/mol), 2% Plurafac LF 305 (fatty alcohol alkoxylate; C6-10+EO/PO), 1% MGDA (methyl glycine diacetic acid, 1% TEA (triethanolamine) (all percentages are w/w). The pH was adjusted to 8.7 with phosphoric acid.

Wash Assay

Mini Launder-O-Meter (MiniLOM) Model Wash System

MiniLOM is a modified mini wash system of the Launder-O-Meter (LOM), which is a medium scale model wash system that can be applied to test up to 20 different wash conditions simultaneously. A LOM is basically a large temperature-controlled water bath with 20 closed metal beakers rotating inside it. Each beaker constitutes one small washing machine and during an experiment, each will contain a solution of a specific detergent/enzyme system to be tested along with the soiled and unsoiled fabrics it is tested on. Mechanical stress is achieved by the beakers being rotated in the water bath and by including metal balls in the beaker.

The LOM model wash system is mainly used in medium scale testing of detergents and enzymes at European wash conditions. In a LOM experiment, factors such as the ballast to soil ratio and the fabric to wash liquor ratio can be varied. Therefore, the LOM provides the link between small scale experiments, such as AMSA and mini-wash, and the more time consuming full-scale experiments in front loader washing machines. In miniLOM, washes are performed in 50 ml test tubes placed in Stuart rotator.

Activity Towards Poly-Galactosamine Substrate

Enzyme activity has been determined using reducing ends assay. 90 μl poly-galactosamine, 2 mg/ml in 20 mM acetic buffer pH 6, was incubated with 10 μl 50 nM enzyme in PCR-MTP wells for 30 min at 30° C. The number of reducing ends formed was determined by reaction with 75 μl p-Hydroxybenzoic acid hydrazide (Sigma, H-9882, 15 mg/ml) for 10 min at 95° C., followed by absorbance measurement at 405 nm.

TABLE 1 activity towards poly-galactosamine substrate

| SEQ ID | Absorbance at 405 nm-blank |
|---|---|
| 3 | 1.47 |
| 12 | 0.36 |
| 18 | 0.60 |
| 21 | 0.72 |
| 24 | 0.28 |
| 27 | 0.52 |
| 33 | 1.33 |
| 36 | 1.24 |
| 39 | 1.16 |
| 42 | 0.29 |
| 45 | 0.95 |
| 48 | 1.36 |
| 51 | 1.19 |

TABLE 1-continued

| activity towards poly-galactosamine substrate | |
|---|---|
| SEQ ID | Absorbance at 405 nm-blank |
| 57 | 0.70 |
| 72 | 0.36 |
| 73 | 0.13 |
| 74 | 0.35 |
| 75 | 0.25 |
| 76 | 0.23 |
| 77 | 0.12 |
| 78 | 0.15 |
| 81 | 2.04 |
| 82 | 2.05 |
| 83 | 1.77 |
| 84 | 0.18 |
| 85 | 1.89 |
| 86 | 1.42 |
| 87 | 1.67 |
| 88 | 0.66 |
| 89 | 1.54 |
| 90 | 1.47 |
| 91 | 1.54 |
| 92 | 1.41 |
| 93 | 1.27 |
| 94 | 1.30 |
| 95 | 1.01 |
| 96 | 1.46 |
| 97 | 0.11 |
| 99 | 0.18 |
| 101 | 0.93 |
| 102 | 0.80 |
| 103 | 1.20 |
| 104 | 0.12 |
| 106 | 0.62 |
| 107 | 0.23 |
| 136 | 1.93 |
| 137 | 1.61 |
| 138 | 0.87 |
| 139 | 1.58 |
| 140 | 1.32 |
| 141 | 1.43 |
| 142 | 1.11 |
| 143 | 0.62 |
| 144 | 1.48 |
| 145 | 1.40 |
| 146 | 0.81 |

Production of Poly-Galactosamine

A crude poly-galactosamine substrate has been prepared as described in Takagi and K. Kadowaki, Agricultural and Biological Chemistry, 49:11, 3151-3157 (1985), using the same *Simpicillium* strain (previously designated *Paeiomyces* sp.), obtained from the Japanese depository in September 2018. Briefly, the strain was cultured in GPC medium (3% glucose, 0.3% peptone, 0.5% CaCl2, pH7) for 5 days at 26° C. under shaking conditions (100 rpm). Following cultivation, the supernatant was isolated (Miracloth filtration) and used directly for wash experiments or precipitated with ethanol as described in Hiroaki Takagi & Kiyoshi Kadowaki, Agricultural and Biological Chemistry, 49:11, 3159-3164 (1985). The resulting precipitate was dissolved in 1 M acetic acid overnight, dialyzed with 20 mM acetic buffer pH 6 and used for enzyme activity measurements.

Example 1 Cloning and Expression of Polypeptides

The DNA encoding the gene of SEQ ID NO 1, SEQ ID NO 4, SEQ ID NO 7, SEQ ID NO, SEQ ID NO 19, SEQ ID NO 22, SEQ ID NO 25, SEQ ID NO 28, SEQ ID NO 31, SEQ ID NO 34, SEQ ID NO 37, SEQ ID NO 40, SEQ ID NO 43, SEQ ID NO 46, SEQ ID NO 49, SEQ ID NO 52, were isolated from bacterial strains and environmental bacterial communities isolated from soil samples collected in different countries (see table 2). Chromosomal DNA from the different strains and bacterial communities was subjected to full genome sequencing using Illumina technology. The genome sequence was analyzed for protein sequences that contained glycosyl hydrolase domains, as defined in the CAZy database (www.cazy.org, Lombard V, et al. 2014, Nucleic Acids Res 42:0490-0495). 16 sequences containing a Glycoside Hydrolase Family 114 domain (GH114, CAZy database, www.cazy.org, Lombard V, et al. 2014, Nucleic Acids Res 42:490-495) were identified in the genomes".

TABLE 2

| DNA sequences and mature protein | | | |
|---|---|---|---|
| DNA SEQ ID NO | Mature protein SEQ ID NO | Donor | country of origin |
| 1 | 3 | *Amycolatopsis circi* | Spain |
| 4 | 6 | *Amycolatopsis* sp-63060 | Spain |
| 7 | 9 | *Amycolatopsis* sp-63067 | Spain |
| 10 | 12 | *Streptomyces parvulus* | Jamaica |
| 19 | 21 | *Nonomuraea guangzhouensis* | United Kingdom |
| 22 | 24 | *Streptomyces* sp-63031 | Denmark |
| 25 | 27 | *Vibrio* sp-62464 | United States |
| 28 | 30 | Environmental bacterial community B | United States |
| 31 | 33 | *Microbacterium saccharophilum* | Denmark |
| 34 | 36 | *Microbacterium oxydans* | Denmark |
| 37 | 39 | *Frigoribacterium faeni* | Denmark |
| 40 | 42 | *Serinibacter* sp-64503 | Denmark |
| 43 | 45 | *Oerskovia paurometabola* | Denmark |
| 46 | 48 | *Agreia pratensis* | Denmark |
| 49 | 51 | *Plantibacter flavus* | Denmark |
| 52 | 54 | *Streptomyces miharaensis* | Korea obtained in 1988 |

The DNA encoding the mature peptide of GH114 genes SEQ ID NO 1, SEQ ID NO 4, SEQ ID NO 7, SEQ ID NO 10, SEQ ID NO 19, SEQ ID NO 22, SEQ ID NO 25, SEQ ID NO 28, SEQ ID NO 31, SEQ ID NO 34, SEQ ID NO 37, SEQ ID NO 40, SEQ ID NO 43, SEQ ID NO 46, SEQ ID NO 49, SEQ ID NO 52, were amplified from the genomic DNA of the corresponding bacterial strains by standard PCR techniques using specific primers containing an overhang to cloning vector. The amplified PCR fragments were inserted into a *Bacillus* expression vector as described in WO12/025577. Briefly, the DNA encoding the mature peptide of the gene was cloned in frame to a *Bacillus clausii* secretion signal (BcSP; with the following amino acid sequence: MKKPLGKIVASTALLISVAFSSSIASA (SEQ ID NO 58). BcSP replaced the native secretion signal in the gene. Downstream of the BcSP sequence, an affinity tag sequence was introduced to ease the purification process (His-tag; with the following amino acid sequence: HHHHHHPR (SEQ ID NO 59) The gene that was expressed therefore comprised the BcSP sequence followed by the His-tag sequence followed by the mature wild type GH114 gene sequence. The final expression plasmid (BcSP-His-tag-GH114) was transformed into a *Bacillus subtilis* expression host. The GH114 BcSP-fusion gene was integrated by homologous recombination into the *Bacillus subtilis* host cell genome upon transformation. The gene construct was expressed under the control of a triple promoter system (as described in WO 99/43835). The gene coding for chloramphenicol acetyltransferase was used as maker (as described in (Diderichsen et al., 1993, *Plasmid* 30: 312-315)). Transformants were selected on LB media agar supplemented with 6 micrograms of chloramphenicol per ml. One recombinant *Bacillus subtilis* clone containing the GH114 expression construct was selected and was cultivated on a rotary shaking table in 500 ml baffled Erlenmeyer flasks each containing 100 ml yeast extract-based media. After 3-5 days' cultivation time at 30° C. to 37° C., the enzyme containing supernatant was harvested by centrifugation and the enzymes was purified by His-tag purification.

The codon optimized synthetic DNA encoding the mature peptide sequence of the putative endo-α-1,4-polygalactosaminidases belonging to family GH114 glycosyl hydrolases listed below in Table 3, were purchased from TWIST Bioscience. The cloning and expression of the synthetic genes in the *Bacillus subtilis* expression host was carried out as described above.

TABLE 3

| enzyme | donor | country of origin |
|---|---|---|
| SEQ ID NO 79 | *Amycolatopsis* sp. | Spain |
| SEQ ID NO 80 | *Methylothermaceae bacteria* 842 | Pacific Ocean floor |
| SEQ ID NO 81 | *Amycolatopsis niigatensis* | Japan |
| SEQ ID NO 82 | *Streptomyces* sp. AA4 | unknown |
| SEQ ID NO 83 | *Amycolatopsis alba* DSM 44262 | unknown before 1996 |
| SEQ ID NO 84 | *Streptomyces griseoaurantiacus* | United States |
| SEQ ID NO 85 | *Kutzneria albida* | Japan |
| SEQ ID NO 86 | *Microbacterium* sp. | Denmark |
| SEQ ID NO 87 | *Microbacterium oleivorans* | United States |
| SEQ ID NO 88 | *Nocardiopsis alba* | Denmark |
| SEQ ID NO 89 | *Microbacterium oxydans* | United States |
| SEQ ID NO 90 | *Agreia pratensis* | United States |
| SEQ ID NO 91 | *Microbacterium lemovicicum* | United States |
| SEQ ID NO 92 | *Xylanibacterium* sp. | United Kingdom |
| SEQ ID NO 93 | *Curtobacterium oceanosedimentum* | United States |
| SEQ ID NO 94 | *Leucobacter tardus* | Denmark |
| SEQ ID NO 95 | *Salinibacterium amurskyense* | Denmark |
| SEQ ID NO 96 | Environmental sample | Denmark |
| SEQ ID NO 136 | *Amycolatopsis orientalis* DSM 46075 | unknown before 1979 |
| SEQ ID NO 137 | Environmental sample | Spain |
| SEQ ID NO 138 | *Pilimelia columellifera* subsp. pallida Spain | United States |
| SEQ ID NO 139 | *Cellulomonas cellasea* | United States |
| SEQ ID NO 140 | Environmental sample | Denmark |
| SEQ ID NO 141 | *Microbacterium* sp. | United States |
| SEQ ID NO 142 | *Amycolatopsis bullii* | United States |
| SEQ ID NO 143 | *Microbacterium oxydans* | United States |
| SEQ ID NO 144 | *Microbacterium phyllosphaerae* | United States |
| SEQ ID NO 145 | *Phycicoccus dokdonensis* | United States |
| SEQ ID NO 146 | Environmental sample | Denmark |

Example 2 His Tag Purification Method

The His-tagged GH114 polypeptides were purified by immobilized metal chromatography (IMAC) using $Ni^{2+}$ as the metal ion on 5 mL HisTrap Excel columns (GE Healthcare Life Sciences). The purification took place at pH 7 and the bound protein was eluted with imidazole. The purity of the purified enzymes was checked by SDS-PAGE and the concentration of the enzyme determined by Absorbance 280 nm after a buffer exchange in 50 mM HEPES, 100 mM NaCl pH7.0

Example 3 Cloning, Expression and Fermentation of Two GH114 Polypeptides from *Fusarium solani* and One from *Urnula craterium*

Genes (SEQ ID NO 13, SEQ ID NO 16, SEQ ID NO 55) encoding three putative genes belonging to family GH114 as defined by CAZy (www.cazy.org, Lombard V, et al. (2014) *Nucleic Acids Res* 42:D490-D495)" were cloned from a strain of *Fusarium solani* that was isolated from an environmental sample collected in Denmark and a strain of *Urnula criterium* isolated from an environmental sample collected in Sweden. For *Fusarium solani*, chromosomal DNA was isolated from the strain, and whole genome sequencing was purchased from Exiqon A/S, Vedbaek, Denmark. The genome sequence was assembled with the SPAdes Genome Assembler, v3.5.0 (Bankevich, A. et al. J Comput Biol. (2012) 19(5):455-77) and annotated with the GeneMark v2.3c gene prediction software (Ter-Hovhannisyan V. et al. Genome Res. (2008) 18(12):1979-90.). For *Urnula criterium*, chromosomal DNA was isolated from the strain, and whole genome sequencing was determined using Illumina technology. The genome sequence was assembled with the SPAdes Genome Assembler, v3.9.0, and annotated with the Augustus v2.4 gene prediction software (Stanke, M. et al. Bioinformatics. (2008) 24(5): 637-644.) trained on a gene set from *Coprinus cinereus*. Peptides predicted from the annotated genome were searched for similarity to the GH114 domain, and the three peptides with SEQ ID NO: 14, 17 and 56 were identified. The corresponding DNA sequences (SEQ ID NO: 13, 16 and 55) were PCR amplified from genomic DNA isolated from *Fusarium solani* with gene-specific primers that also append a Kozak translation initiation sequence "TCACC" immediately 5' of the start codon and cloned into the *Aspergillus* expression vector pMStr57 (WO 04/032648) that had been digested with BamHI and XhoI.

The cloned GH114 encoding genes were sequenced and confirmed to be identical to the corresponding genes found in the genome sequences and transformed into the *Aspergillus oryzae* strain MT3568 (WO 11/057140) by the methods described in Christensen et al., 1988*, Biotechnology* 6, 1419-1422 and WO 04/032648. Transformants were selected during regeneration from protoplasts based on the ability, conferred by a selectable marker in the expression vector, to utilize acetamide as a nitrogen source, and were subsequently re-isolated under selection.

Production of the recombinant GH114 peptides was evaluated by culturing the transformants in 96-well deep-well microtiter plates for 4 days at 30° C. in 0.25 ml of both YPG medium (WO 05/066338) and DAP-4C-1 medium (WO 12/103350) and monitoring peptide expression by SDS-PAGE. For larger-scale production of the recombinant putative GH114 genes, a single *Aspergillus* transformant was selected for each GH114 peptide and the transformants were cultured in 500 ml baffled flasks containing 150 ml of DAP-4C-1 medium. The cultures were shaken on a rotary table at 150 RPM at for 4 days. The culture broth was subsequently separated from cellular material by passage through a 0.22 um filtration unit.

Example 4 Chromatographic Purification of Two GH114 Polypeptides from *Fusarium solani* and One from *Urnula craterium*

The pH of the filtered sample was adjusted to around pH 7.5 and 1.8M ammonium sulfate was added. The sample was applied to a 5 ml HiTrap™ Phenyl (HS) column on an Äkta Explorer. Prior to loading, the column had been equilibrated in 5 column volumes (CV) of 50 mM HEPES+1.8M AMS pH 7. In order to remove unbound material, the column was washed with 5 CV of 50 mM HEPES+1.8M AMS pH 7. The target protein was eluted from the column into a 10 ml loop using 50 mM HEPES+20% isopropanol pH 7. From the loop, the sample was loaded onto a desalting column (HiPrep™ 26/10 Desalting), which had been equilibrated with 3 CV of 50 mM HEPES+100 mM NaCl pH 7.0. The target protein was eluted with 50 mM HEPES+100 mM NaCl pH 7.0 and relevant fractions were selected and pooled based on the chromatogram. The flow rate was 5 ml/min. For the two GH114 peptides from *Fusarium solani*, the sample collected from HIC purification (described above), was applied to a 1 mL HiTrap™ Blue HP column on an Äkta PURE system. Prior to loading the column had been equilibrated in 10 CV of 50 mM HEPES+100 mM NaCl pH 7.0. During loading of the sample to the column, the flow through was collected. In order to remove any unbound material, the column was washed with 7 CV 50 mM HEPES+100 mM NaCl pH 7.0. The target protein was eluted with 11.2 CV of 50 mM Tris, 1M NaCl, pH 8. Based on the chromatogram, relevant fractions were collected. The protein was either in the flow through or in the eluate. Protein concentration in the final sample was estimated by measuring absorption at 280 nm.

Example 5 Cleaning in Liquid Model Detergent a on Pel Swatches

A crude extract of biofilm EPS was prepared from *Pseudomonas aeruginosa* PA14 (DSM 19882) as follows; The strain was restreaked on Tryptone Soya Agar (TSA) (pH 7.3) (CM0131; Oxoid Ltd, Basingstoke, UK) and incubated for 3 days at 30° C. Flasks with T-broth (10 g/L Bacto™ Tryptone (211705, BD), 5 g/L sodium chloride (31434, Sigma-Aldrich)) were then inoculated with single colonies and incubated statically for 6 days at 20° C. The biofilm pellicles were carefully removed from the flasks, and pelleted by centrifugation (5 min, 16000 g, 25° C.). The pellets were resuspended in 3M NaCl, vortexed vigorously and incubated for 15 min at ambient temperature to extract the surface-associated polymer. The cells were then re-pelleted (5 min, 10000 g, 25° C.) and the EPS-containing supernatant was retrieved and pooled. The extract was stored at −20° C. until further use (termed EPS extract).

The wash performance was determined as follows; 50 ul aliquots of the crude Pel extract were spotted on sterile textile swatches (WFK20A) and incubated for 15 min at ambient temperature. Control swatches were spotted with 3M NaCl. The swatches (sterile or with the extract) were placed in 50 mL test tubes and 10 mL of wash liquor (15°dH water with 0.2 g/L iron(III) oxide nano-powder (544884; Sigma-Aldrich) with 3.33 g/L liquid model A detergent) and the 2 µg/ml enzyme was added to each tube. Washes without enzyme were included as controls. The test tubes were placed in a Stuart rotator and incubated for 1 hour at 30° C. and 20 rpm. The wash liquor was then removed, and the swatches were rinsed twice with 15°dH water and dried on filter paper over night. The color difference (L) values were measured using a Handheld Minolta CR-300 and are displayed in table 4. Wash performance (WP) values ($L_{(switch\ washed\ with\ enzyme)}-L_{(swatch\ washed\ without\ enzyme)}$) are also indicated.

TABLE 4

Cleaning effects of the GH114 homologues in model A detergent

| Swatch/Enzyme | SEQ | Enzyme conc. (µg/ml) | Average L values | WP (ΔL) |
|---|---|---|---|---|
| wfk20A, no EPS | | 0.0 | 88.1 | |
| Wfk20A, EPS, no enzyme | | 2 | 82.2 | |
| Wfk20A, EPS, | SEQ ID NO 3 | 2 | 91.4 | 9.3 |
| Wfk20A, EPS, | SEQ ID NO 6 | 2 | 88.4 | 6.3 |
| Wfk20A, EPS, | SEQ ID NO 9 | 2 | 90.3 | 8.2 |
| Wfk20A, EPS, | SEQ ID NO 12 | 2 | 89.7 | 7.5 |
| Wfk20A, EPS, | SEQ ID NO 21 | 2 | 90.6 | 8.4 |
| Wfk20A, EPS, | SEQ ID NO 24 | 2 | 90.3 | 8.1 |
| Wfk20A, EPS, | SEQ ID NO 27 | 2 | 89.0 | 6.8 |
| Wfk20A, EPS, | SEQ ID NO 33 | 2 | 90.3 | 8.1 |
| Wfk20A, EPS, | SEQ ID NO 36 | 2 | 87.6 | 5.4 |
| Wfk20A, EPS, | SEQ ID NO 39 | 2 | 90.7 | 8.5 |
| Wfk20A, EPS, | SEQ ID NO 45 | 2 | 85.9 | 3.7 |
| Wfk20A, EPS, | SEQ ID NO 48 | 2 | 89.0 | 6.8 |
| Wfk20A, EPS, | SEQ ID NO 54 | 2 | 91.1 | 8.9 |

Example 6 Cleaning in Liquid Model Detergent NI on Pel Swatches

A crude extract of biofilm EPS was prepared from *Pseudomonas aeruginosa* PA14 (DSM 19882) as follows; The strain was restreaked on LBAgar (pH 7.3) and incubated for 3 days at 30° C. 500 mL of T-broth (10 g/L Bacto™ Tryptone (211705, BD), 5 g/L sodium chloride (31434, Sigma-Aldrich)) was then inoculated and incubated statically for 6 days at 20° C. The biofilm pellicle was carefully removed from the flask, and pelleted by centrifugation (5 min, 1000 g, 25° C.). The pellet was then resuspended in 3M NaCl, vortexed vigorously and incubated for 15 min at ambient temperature to extract the surface-associated polymer. The cells were then re-pelleted (5 min, 10000 g, 25° C.) and the EPS-containing supernatant was retrieved. The extract was stored at −20° C. until further use (termed EPS extract). Wash performance was determined as follows; 50 ul aliquots of the crude Pel extract were spotted on sterile textile swatches (WFK20A) and incubated for 15 min at ambient temperature. Control swatches without EPS were used as controls. The swatches (sterile or with the extract) were placed in 50 mL test tubes and 10 mL of wash liquor (15°dH water with 0.2 g/L iron(Ill) oxide nano-powder (544884; Sigma-Aldrich) with 3.33 g/L liquid model NI detergent) and the 10 µg/ml enzyme was added to each tube. Washes without enzyme were included as controls. The test tubes were placed in a Stuart rotator and incubated for 1 hour at 30° C. and 20 rpm. The wash liquor was then removed, and the swatches were rinsed twice with 15°dH water and dried on filter paper over night. The tristimulus light intensity (Y) values were measured using a Handheld Minolta CR-300 and are displayed in table 5. Wash performance, WP ($\Delta Y=Y_{(swatches\ washed\ with\ enzyme)}-Y_{(swatches\ washed\ without\ enzyme)}$) are also indicated.

TABLE 5

Cleaning effects of the GH114 glycosyl hydrolases in model NI detergent

| Swatch | Enzyme | Enzyme concentration (µg/ml) | Average Y values | WP (ΔY) |
|---|---|---|---|---|
| Wfk20A, no EPS | No enzyme | 0 | 74.9 | |
| Wfk20A, Pel EPS swatch | No enzyme | 0 | 64.1 | |
| Wfk20A, Pel EPS swatch | SEQ ID NO 54 | 10 | 68.8 | 4.7 |

TABLE 5-continued

| Cleaning effects of the GH114 glycosyl hydrolases in model NI detergent | | | | |
|---|---|---|---|---|
| Swatch | Enzyme | Enzyme concentration (µg/ml) | Average Y values | WP (ΔY) |
| Wfk20A, Pel EPS swatch | SEQ ID NO 30 | 10 | 68.4 | 4.3 |
| Wfk20A, Pel EPS swatch | SEQ ID NO 42 | 10 | 68.7 | 4.6 |

Example 7 Cleaning in Liquid Model Detergent a on Pel Swatches

A crude extract of the biofilm extracellular polymer Pel was prepared from *Pseudomonas aeruginosa* PA14 (DSM 19882) as described above. The wash performance was determined as follows; 50 ul aliquots of the crude Pel extract were spotted on sterile textile swatches (WFK20A) and incubated for 15 min at ambient temperature. Control swatches were spotted with 3M NaCl. The swatches (sterile or with the extract) were placed in 50 mL test tubes and 10 mL of wash liquor (15°dH water with 0.2 g/L iron(Ill) oxide nano-powder (544884; Sigma-Aldrich) with 3.33 g/L liquid model A detergent) and the enzyme was added to each tube. Washes without enzyme were included as controls. The test tubes were placed in a Stuart rotator and incubated for 1 hour at 30° C. and 20 rpm. The wash liquor was then removed, and the swatches were rinsed twice with 15°dH water and dried on filter paper over night. The color difference (L) values were measured using a Handheld Minolta CR-300 and are displayed in table 6. Wash performance (WP) values ($L_{(swatch\ washed\ with\ enzyme)}-L_{(swatch\ washed\ without\ enzyme)}$) are also indicated.

TABLE 6

| Cleaning effects of the GH114 glycosyl hydrolases in model A detergent | | | | |
|---|---|---|---|---|
| Swatch | Enzyme | Enzyme conc. (µg/ml) | Average L values | WP (ΔL) |
| Wfk20A, no EPS | no enzyme | 0 | 84.3 | |
| Wfk20A, Pel EPS | no enzyme | 0 | 63.6 | |
| Wfk20A, Pel EPS | SEQ ID NO 18 | 0.2 | 75.8 | 12.2 |
| Wfk20A, Pel EPS | SEQ ID NO 18 | 2 | 78.8 | 15.2 |
| Wfk20A, Pel EPS | SEQ ID NO 15 | 0.2 | 72.9 | 9.3 |
| Wfk20A, Pel EPS | SEQ ID NO 15 | 2 | 76.4 | 12.8 |
| Wfk20A, Pel EPS | SEQ ID NO 57 | 0.2 | 66.8 | 3.2 |
| Wfk20A, Pel EPS | SEQ ID NO 57 | 2 | 78.6 | 15.0 |

Example 8 Biofilm Removal Activity

The Pel-producing *Pseudomonas aeruginosa* strain DSM19882 was used as a model microorganism in the present example. The strain was restreaked on LB agar and incubated at 30° C. An overnight culture was inoculated in 10 mL LB and the culture was incubated for 16 hours at 37° C. under shaking conditions. The culture was subsequently diluted (1:100) in LENS, added to 96-well microtiter plates (150 µL per well, Thermo Scientific, cat#167008) and Peg lids were inserted (NUNC-TSP, Thermo Scientific, cat #445497). The microtiter plates were incubated for 24 hours at 26° C. under static conditions. After incubation, the peg lids were rinsed in MTP plates with 5°dH water hardness, and transferred to treatment plates with LENS containing no enzyme (control) or 20 µg/mL enzyme for 1 hour at 26° C. The lids were subsequently rinsed in water hardness and stained with 0.095% crystal violet (Sigma-Aldrich, cat #V5265) for 15 min. Following the staining, the peg lids were rinsed twice, moved to clean microtiter plates and the remaining dye was dissolved with 30% acetic acid. The absorbance was measured at 595 nm. The results are displayed in table 7 and 8.

TABLE 7

| Biofilm removal properties | | |
|---|---|---|
| Enzyme | Conc | % remaining biofilm |
| no enzyme | 0 | 100.0 |
| SEQ ID NO 3 | 20 | 30.0 |
| SEQ ID NO 6 | 20 | 26.3 |
| SEQ ID NO 9 | 20 | 27.1 |
| SEQ ID NO 12 | 20 | 24.6 |
| SEQ ID NO 21 | 20 | 19.9 |
| SEQ ID NO 24 | 20 | 20.6 |
| SEQ ID NO 27 | 20 | 34.8 |
| SEQ ID NO 33 | 20 | 3.8 |
| SEQ ID NO 36 | 20 | 10.5 |
| SEQ ID NO 39 | 20 | 35.4 |
| SEQ ID NO 45 | 20 | 73.0 |
| SEQ ID NO 48 | 20 | 49.4 |
| SEQ ID NO 51 | 20 | 14.9 |
| SEQ ID NO 18 | 20 | 3.7 |
| SEQ ID NO 15 | 20 | 3.7 |
| SEQ ID NO 57 | 20 | 3.2 |

The following batch of GH114 glycosyl hydrolase enzymes with the corresponding SEQ ID NO listed in table 8 were tested at a concentration of 40 µg/mL for biofilm removal activity as described above.

TABLE 8

| Biofilm removal properties | |
|---|---|
| Enzyme | % Remaining biofilm |
| no enzyme | 100 |
| SEQ ID NO 72 | 35.73 |
| SEQ ID NO 73 | 35.48 |
| SEQ ID NO 74 | 19.15 |
| SEQ ID NO 75 | 15.01 |
| SEQ ID NO 76 | 25.27 |
| SEQ ID NO 77 | 56.65 |
| SEQ ID NO 78 | 18.84 |
| SEQ ID NO 81 | 74.27 |
| SEQ ID NO 82 | 95.78 |
| SEQ ID NO 83 | 46.26 |
| SEQ ID NO 84 | 49.36 |
| SEQ ID NO 86 | 47.41 |
| SEQ ID NO 87 | 39.26 |
| SEQ ID NO 88 | 99.42 |
| SEQ ID NO 89 | 22.13 |
| SEQ ID NO 90 | 33.58 |
| SEQ ID NO 91 | 70.30 |
| SEQ ID NO 92 | 66.34 |
| SEQ ID NO 93 | 30.79 |
| SEQ ID NO 94 | 93.82 |
| SEQ ID NO 95 | 21.01 |
| SEQ ID NO 96 | 15.88 |
| SEQ ID NO 101 | 22.75 |
| SEQ ID NO 102 | 16.55 |
| SEQ ID NO 103 | 7.54 |
| SEQ ID NO 104 | 10.68 |
| SEQ ID NO 105 | 26.45 |
| SEQ ID NO 106 | 18.63 |
| SEQ ID NO 107 | 11.80 |
| SEQ ID NO 108 | 18.83 |
| SEQ ID NO 136 | 27.02 |
| SEQ ID NO 137 | 24.68 |
| SEQ ID NO 138 | 25.78 |

TABLE 8-continued

| Biofilm removal properties | |
|---|---|
| Enzyme | % Remaining biofilm |
| SEQ ID NO 139 | 22.56 |
| SEQ ID NO 140 | 28.82 |
| SEQ ID NO 141 | 32.21 |
| SEQ ID NO 142 | 41.56 |
| SEQ ID NO 143 | 9.27 |
| SEQ ID NO 144 | 12.13 |
| SEQ ID NO 145 | 21.16 |
| SEQ ID NO 146 | 35.32 |

Table 7 and 8 shows that the tested GH114 glycosyl hydrolases has biofilm removal properties and that the remaining biofilm is less than 100%, which means that some biofilm has been reduced.

Example 9 Effect of GH114 Glycosyl Hydrolases on *P. aeruginosa* Biofilms Washed in Model Detergent Two different clinical isolates of *P. aeruginosa* were for formation of medical biofilms in the example. One biofilm was produced by *P. aeruginosa* PA14 (DSM19882) and another one by *P. aeruginosa* PA01 (DSM22644). The bacteria were re-streaked on TSA plates and incubated for three days at 30° C. After three days of incubation, 8 mL of Tryptic Soy Broth (TSB) was inoculated with one colony of *P. aeruginosa* PA14 (DSM19882), and 8 mL of TSB was inoculated with *P. aeruginosa* PA01 (DSM22644). The inoculated TSB tubes were all incubated overnight at 30° C., 200 rpm, and diluted in TSB media to a specific optical density (OD). 150 µl of diluted overnight culture was added to each well in Thermo Scientific™ Nunc™ MicroWell™ 96-Well Microplates (sterile, non-treated). Two plates with *P. aeruginosa* PA14 (DSM19882) were prepared. One plate with *P. aeruginosa* PA01 (DSM22644) was prepared. The plates were incubated at 30° C. for 24 hours. After 24 hours of incubation, the microtiter plates containing biofilm were removed from the incubator and emptied for media using Vacusafe™ Vacuum Aspiration System (INTEGRA Biosciences). Each well was rinsed twice with 200 µl 0.9% NaCl solution. To each well, 200 µl of model detergent liquor with 20 g/ml enzyme was added. Treatment without enzyme was included as controls. Each treatment was tested in quadruplicates. After addition of detergent liquor+/− enzyme, the microtiter plates were incubated static for 60 minutes at 30° C. After 60 minutes of incubation, the treatment liquor was removed using the vacuum system. Each well was rinsed twice with 200 µl 0.9% NaCl solution, and 200 µl of 0.095% crystal violet solution was added to each well. The plates were incubated for 15 minutes at ambient temperature. The crystal violet solution was removed using the vacuum system, and each well was rinsed twice with 200 µl 0.9% NaCl solution. 150 µl of 30% acetic acid was added to each well. The plates were incubated for 10 minutes at ambient temperature, where after the absorbance at 595 nm was measured using a spectrophotometer (SpectraMax M3, Molecular Devices). The plates were shaked for 10 seconds before absorbance measurements were performed.

The % remaining biofilm after enzymatic treatment was calculated as $ABS_{595(biofilm\ treated\ with\ model\ detergent+enzyme)}/ABS_{595(biofilm\ treated\ with\ model\ detergent)}\times 100\%$.

For *P. aeruginosa* PA14 (DSM19882) and average of two plates was calculated. The results are displayed in table 9.

TABLE 9

% remaining biofilm after treatment with GH114 glycosyl hydrolases in model detergent

| Enzyme | Concentration (µg/mL) | % remaining biofilm PA14 (DSM19882) | PA01 (DSM22644) |
|---|---|---|---|
| No enzyme | 0 | 100.0 | 100.0 |
| SEQ ID NO 18 | 20 | 43.4 | 55.7 |
| SEQ ID NO 33 | 20 | 57.9 | 55.4 |
| SEQ ID NO 18 | 20 | 37.9 | 59.4 |
| SEQ ID NO 15 | 20 | 22.6 | 55.2 |
| SEQ ID NO 36 | 20 | 52.6 | 62.0 |
| SEQ ID NO 51 | 20 | 54.3 | 61.3 |
| SEQ ID NO 21 | 20 | 51.6 | 58.9 |
| SEQ ID NO 24 | 20 | 49.9 | 48.0 |
| SEQ ID NO 12 | 20 | 55.1 | 54.7 |
| SEQ ID NO 6 | 20 | 75.4 | 70.3 |
| SEQ ID NO 27 | 20 | 73.8 | 74.8 |

Example 9 Endoscope Cleaning in Liquid Model Detergent

Endoscope biofilms were established using *P. aeruginosa* DSM19882: The strain was inoculated into 10 mL LB and incubated at 37° C. for 16 hours with shaking (200 rpm). After propagation, the culture was diluted (1:100) in LENS and the bacterial suspension was added to 96-well microtiter plates (Thermo Scientific, cat #167008) containing sterile pieces (1 cm) of endoscope tubing (4.7 mm diameter, Fluoroelastomer/Viton®, USP Class VI, Endoscopy Development Company, LLC). Sterile medium was added to control wells. After 24h at 26° C. (static incubation), the endoscope tubes were treated with a model cleaning solution (5 g/L Model detergent MC in 5°dH water hardness) containing no enzyme (control) or 20 µg/mL enzyme for 1 hour at 26° C. The endoscope pieces were subsequently rinsed with 5°dH water and stained with 0.095% crystal violet (SIGMA V5265) for 15 min. After additional rinses, the endoscope pieces were blotted on absorbent paper and the remaining dye was dissolved using 30% acetic acid. 200 µl aliquots of the suspensions were transferred to a 96-well microtiter plate and the absorbance was measured at 595 nm. The results are displayed in table 10 as percentages of remaining biofilm after enzymatic treatment as compared to the control (endoscope biofilm treated without enzyme).

TABLE 10

Endoscope cleaning properties in medical cleaning model detergent MC

| Enzyme | Enzyme dosage (µg/ml) | Remaining biofilm (% of untreated control) |
|---|---|---|
| No enzyme | 0 | 100.0 |
| SEQ ID NO 21 | 20 | 43.3 |
| SEQ ID NO 27 | 20 | 58.9 |
| SEQ ID NO 33 | 20 | 58.4 |
| SEQ ID NO 18 | 20 | 30.1 |

The results show that the polypeptides of the invention have endoscope cleaning properties i.e. disrupt and/or remove the biofilm or components of the biofilm tested when compared to samples comprising no enzyme.

Example 10 Construction of Clades and Phylogenetic Trees

The polypeptides of the invention having hydrolase activity and comprises a GH114 domain as well as clusters such as the clades. A phylogenetic tree was constructed, of polypeptide sequences containing a GH114 domain, as defined in CAZY (GH114, Glycoside Hydrolase Family 114, CAZy database, www.cazy.org, Lombard V, et al. 2014, Nucleic Acids Res 42:D490-D495). The phylogenetic tree was constructed from a multiple alignment of mature polypeptide sequences containing at least one GH114 domain. The sequences were aligned using the MUSCLE algorithm version 3.8.31 (Edgar, 2004. *Nucleic Acids Research* 32(5): 1792-1797), and the trees were constructed using FastTree version 2.1.8 (Price et al., 2010, *PloS one* 5(3)) and visualized using iTOL (Letunic & Bork, 2007. *Bioinformatics* 23(1): 127-128). The polypeptide comprises of the GH114 domain comprises several motifs. One example is [VLI]XE[EDSQ]C (SEQ ID NO 60) situated in positions 182 to 186 in *Amycolatopsis circi* (SEQ ID NO 3), where E at position 184 is one of the two catalytic site residues and fully conserved in the polypeptides of the invention. Another motif which may be comprised by the polypeptides of the invention is CY[FLIV][SDN][ATVG] (SEQ ID NO 61) situated in positions corresponding to positions 55 to 59 in *Amycolatopsis circi* (SEQ ID NO 3). The tyrosine at position 56 in SEQ ID NO 3 is involved in substrate-binding. The polypeptides containing a GH114 domain can be separated into distinct sub-clusters. The sub-clusters are defined by one or more short sequence motifs, as well as containing a GH114 domain as defined in CAZY (GH114, CAZy database, www.cazy.org, Lombard V, et al. 2014, *Nucleic Acids Res* 42:D490-D495). We denoted one sub-cluster comprising the motif [VL]XE[EDSQ]C (SEQ ID NO 60) as the VAE clade. All polypeptide sequences containing a GH114 domain as well as the motif will be denoted as belonging to the VAE clade.

The polypeptides in the VAE clade can be further separated into multiple distinct sub-clusters, or clades, where we denoted the clades listed below. The relationship between the described clades are shown in FIG. 4.

Generation of DYQ Clade

A phylogenetic tree was constructed, of polypeptide sequences containing a GH114 domain and a VAE motif, as defined above. The sequences were aligned using the MUSCLE algorithm version 3.8.31 (Edgar, 2004. *Nucleic Acids Research* 32(5): 1792-1797), and the tree was constructed using FastTree version 2.1.8 (Price et al., 2010, *PloS one* 5(3)) and visualized using iTOL (Letunic & Bork, 2007. *Bioinformatics* 23(1): 127-128). Using the phylogenetic tree, the polypeptides containing a GH114 domain and a VAE clade motif can be separated into additional distinct sub-clusters, one which we denoted DYQ.

A characteristic motif for this sub-cluster is the motif DYQ[LI]G (SEQ ID NO 62), corresponding to amino acids DYQIG at positions 23 to 27 in SEQ ID NO 3, where G at position 27 is fully conserved in the polypeptides and involved in substrate binding. An additional motif of the DYQ clade is FQ[TAV]Q[PSD] (SEQ ID NO 63), corresponding to amino acid 60 to 64 in the reference polypeptide (SEQ ID NO 3). Examples of polypeptides of the DYQ clade includes SEQ ID NO 3, SEQ ID NO 6, SEQ ID NO 9, SEQ ID NO 12, SEQ ID NO 21, SEQ ID NO 24, SEQ ID NO 39, SEQ ID NO 42, SEQ ID NO 45, SEQ ID NO 48, SEQ ID NO 51, SEQ ID NO 54, SEQ ID NO 79, SEQ ID NO 82, SEQ ID NO 83, SEQ ID NO 84, SEQ ID NO 85, SEQ ID NO 86, SEQ ID NO 87, SEQ ID NO 88, SEQ ID NO 90, SEQ ID NO 91, SEQ ID NO 92, SEQ ID NO 93, SEQ ID NO 94, SEQ ID NO 96, SEQ ID NO 131, SEQ ID NO 132, SEQ ID NO 134, SEQ ID NO 136, SEQ ID NO 137, SEQ ID NO 138, SEQ ID NO 139, SEQ ID NO 140, SEQ ID NO 141, SEQ ID NO 142, SEQ ID NO 143, SEQ ID NO 144 and SEQ ID NO 145.

Generation of AEE Clade

The AEE clade comprises polypeptides of bacterial origin, containing a GH114 domain and belonging to the DYQ clade, having hydrolase activity. The polypeptides of the clade comprise the motif example AEECG (SEQ ID NO 64), corresponding to amino acids AEECG at positions 183 to 187 of SEQ ID NO 3 where all amino acids are fully conserved in AEE clade. An additional motif of the AEE clade is NAFQ[AT]Q (SEQ ID NO 65), corresponding to amino acid 58 to 63 in the reference polypeptide (SEQ ID NO 3). Examples of polypeptides of the AEE clade includes SEQ ID NO 3, SEQ ID NO 6, SEQ ID NO 9, SEQ ID NO 12, SEQ ID NO 21, SEQ ID NO 24, SEQ ID NO 54, SEQ ID NO 79, SEQ ID NO 82, SEQ ID NO 83, SEQ ID NO 84, SEQ ID NO 85, SEQ ID NO 132, SEQ ID NO 136, SEQ ID NO 138, and SEQ ID NO 142.

Generation of WQW Clade

The WQW clade comprises polypeptides of bacterial and fungal origin, containing a GH114 domain and belonging to the VAE clade, having hydrolase activity. The polypeptides of the clade comprise the motif example WQWQL (SEQ ID NO 66), corresponding to amino acids WQWQL positions 30 to 34 of *Vibrio sp.* SEQ ID NO 27 where L (corresponding to positions 34 of SEQ ID NO 27) is fully conserved in WQW clade and involved in substrate binding. An additional motif of the WQW clade is [VLI][GASD]LKN[DGS][VLIP] (SEQ ID NO 67), corresponding to amino acids IGLKNDL positions 171 to 177 of *Vibrio sp.* SEQ ID NO 27 where LKN (corresponding to positions 173 and 175 of SEQ ID NO 27) is fully conserved in WQW clade. An example of a polypeptide of the WQW clade includes SEQ ID NO 27, SEQ ID NO 33, SEQ ID NO 36, SEQ ID NO 80, SEQ ID NO 81, SEQ ID NO 89, SEQ ID NO 95 and SEQ ID NO 146.

Generation of IEY Clade

The IEY clade comprises polypeptides of fungal origin, containing a GH114 domain and belonging to the VAE clade, having hydrolase activity. The polypeptides of the clade comprise the motif example GXXVX[NHQTS]IEY[PG] (SEQ ID NO 68), corresponding to amino acids "GKPVLQIEYP" positions 230 to 239 of SEQ ID NO 18 where E (corresponding to position 237 of SEQ ID NO 3) is fully conserved in GVFLD clade, part of the substrate binding pocket, and one of the two putative catalytic site residues.

An additional motif of the IEY clade is VICYF (SEQ ID NO 69), corresponding to amino acids VICYF positions 68 to 72 of *Fusarium solani*(SEQ ID NO 18), 27 where CYF (corresponding to positions 70 and 72 of SEQ ID NO 18) is fully conserved in IEY clade. Examples of polypeptides of the IEY clade includes SEQ ID NO 15, SEQ ID NO 18, SEQ ID NO 57, SEQ ID NO 72, SEQ ID NO 73, SEQ ID NO 74, SEQ ID NO 75, SEQ ID NO 76, SEQ ID NO 77, SEQ ID NO 78, SEQ ID NO 97, SEQ ID NO 98, SEQ ID NO 99, SEQ ID NO 100, SEQ ID NO 101, SEQ ID NO 102, SEQ ID NO 103, SEQ ID NO 104, SEQ ID NO 105, SEQ ID NO 106, SEQ ID NO 107, SEQ ID NO 108, SEQ ID NO 109, SEQ ID NO 110, SEQ ID NO 111, SEQ ID NO 112, SEQ ID NO 113, SEQ ID NO 114, SEQ ID NO 115, SEQ ID NO 116, SEQ ID NO 117, SEQ ID NO 118, SEQ ID NO 119, SEQ ID NO 120, SEQ ID NO 121, SEQ ID NO 122, SEQ ID NO 123, SEQ ID NO 124, SEQ ID NO 125, SEQ ID NO 126, SEQ ID NO 127, SEQ ID NO 128, SEQ ID NO 129, SEQ ID NO 130, SEQ ID NO: 133 and SEQ ID NO 135.

Generation of ICY Clade

The ICY clade comprises polypeptides of fungal origin, containing a GH114 domain and belonging to the IEY clade, having hydrolase activity. The polypeptides of the clade comprise the motif example ICYFSA (SEQ ID NO 70), corresponding to amino acids ICYFSA in SEQ ID NO 15. Examples of polypeptides of the ICY clade is SEQ ID NO 15, SEQ ID NO 57, SEQ ID NO 98, SEQ ID NO 101, SEQ ID NO 104, SEQ ID NO 107, SEQ ID NO 114, SEQ ID NO 115, SEQ ID NO 120, SEQ ID NO 124, SEQ ID NO 125, SEQ ID NO 127, SEQ ID NO 129 and SEQ ID NO: 133.

Generation of DFAVL Clade

The DFAVL_clade comprises polypeptides of fungal origin, containing a GH114 domain and belonging to the IEY clade, having hydrolase activity. The polypeptides of the clade comprise the motif example DFAVL (SEQ ID NO 71), corresponding to amino acids DFAVL at positions 199 to 203 of SEQ ID NO 18, where L at position 203 in SEQ ID NO 71 is fully conserved in the clade, and positioned next to one of the catalytic residues E at position 204. An example of a polypeptide of the DFAVL clade is SEQ ID NO 18, SEQ ID NO 72, SEQ ID NO 73, SEQ ID NO 74, SEQ ID NO 75, SEQ ID NO 76, SEQ ID NO 77, SEQ ID NO 78, SEQ ID NO 97, SEQ ID NO 99, SEQ ID NO 100, SEQ ID NO 102, SEQ ID NO 103, SEQ ID NO 105, SEQ ID NO 106, SEQ ID NO 108, SEQ ID NO 110, SEQ ID NO 111, SEQ ID NO 112, SEQ ID NO 113, SEQ ID NO 116, SEQ ID NO 117, SEQ ID NO 118, SEQ ID NO 119, SEQ ID NO 121, SEQ ID NO 123, SEQ ID NO 126, SEQ ID NO 128, SEQ ID NO 130 and SEQ ID NO 135.

A phylogenetic tree of the polypeptides in the clades is shown in FIG. 1 and FIG. 4.

An alignment of the polypeptides of the invention comprised in the clade is shown in FIG. 3.

Example 11 Cloning, Expression and Fermentation of GH114 Glycosyl Hydrolase Enzyme Polypeptides from *Fusarium compactum, Neonectria Candida, Fusarium Avenaceum* and *Preussia aemulans*

Genes encoding eight putative endo-α-1,4-polygalactosaminidases belonging to family GH114 glycosyl hydrolases, were cloned from the strains listed in Table 11 below. The strains were isolated from environmental samples collected in the countries indicated. For all strains, chromosomal DNA was isolated and a whole genome sequence was determined using Illumina technology. For *Neonectria candida*, whole genome sequencing was purchased from Exiqon A/S, Vedbaek, Denmark.

TABLE 11

| Strain | Source country | Genome Assembler | Gene Annotation | SEQ ID NO |
|---|---|---|---|---|
| *Neonectria candida* | Sweden | Spades v3.5.0 | GeneMark 2.3c | 97 |
| *Fusarium compactum* | Australia | Spades v3.9.0 | GeneMark ES 4.28 | 98, 99 |
| *Fusarium avenaceum* | Denmark | Spades v3.9.0 | GeneMark ES 4.28 | 100 |
| *Preussia aemulans* | Denmark | ABySS 1.2.7 | GeneMark 2.3c | 101 |

References for Analysis Programs Listed Above

Spades genome assemblers: Bankevich, A. et al. *J Comput Biol*. (2012) 19(5):455-77

ABySS genome assembler: Simpson, J. T., et al. *Genome Res*. (2009) 19(6):1117-23.

GeneMark gene annotation: Ter-Hovhannisyan, V. et al., *Genome Res*. (2008), 18(12):1979-90.

The whole genome sequences were assembled and annotated with the software packages indicated in Table 11. The gene model coding for the polypeptide in SEQ ID NO 101 was adjusted after analysis with the GenWise gene prediction software (Li, W. et al., *Nucleic Acids Res*. (2015) 43(W1):W580-W584.)

Peptides predicted from the annotated genome were searched for similarity to the GH114 domain as defined by CAZy (www.cazy.org, Lombard V, et al. (2014) Nucleic Acids Res 42:D490-D495), and the eight polypeptides were identified. Corresponding DNA sequences were PCR amplified from genomic DNA with gene-specific primers that also append a Kozak translation initiation sequence "TCACC" immediately 5' of the start codon, and the amplified DNA fragments were cloned into the *Aspergillus* expression vector pMStr57 (WO 04/032648) that had been digested with BamHI and XhoI.

The cloned GH114 encoding genes were transformed into the *Aspergillus oryzae* strain MT3568 (WO 11/057140) by the methods described in Christensen et al., 1988*, Biotechnology* 6, 1419-1422 and WO 04/032648. Transformants were selected during regeneration from protoplasts based on the ability, conferred by a selectable marker in the expression vector, to utilize acetamide as a nitrogen source, and were subsequently re-isolated under selection.

Production of the recombinant GH114 glycosyl hydrolase enzymes was evaluated by culturing the transformants in 96-well deep-well microtiter plates for 4 days at 30° C. in 0.25 ml of both YPG medium (WO 05/066338) and DAP-4C-1 medium (WO 12/103350) and monitoring peptide expression by SDS-PAGE. For larger-scale production of the recombinant putative GH114 glycosyl hydrolase enzymes, a single *Aspergillus* transformant was selected for each GH114 glycosyl hydrolase enzyme and the transformants were cultured in 500 ml baffled flasks containing 150 ml of DAP-4C-1 medium. The cultures were shaken on a rotary table at 150 RPM at for 4 days. The culture broth was subsequently separated from cellular material by passage through a 0.22 um filtration unit.

Example 12 Chromatographic Purification of GH114 Peptides from *Fusarium compactum, Neonectria Candida, Fusarium Avenaceum* and *Preussia Aemulans*

The pH of the filtered sample was adjusted to around pH 7.5 and 1.8M ammonium sulfate was added. The sample was applied to a 5 ml HiTrap™ Phenyl (HS) column on an Äkta Explorer. Prior to loading, the column had been equilibrated in 5 column volumes (CV) of 50 mM HEPES+1.8M AMS pH 7. In order to remove unbound material, the column was washed with 5 CV of 50 mM HEPES+1.8M AMS pH 7. The target protein was eluted from the column into a 10 ml loop using 50 mM HEPES+20% isopropanol pH 7. From the loop, the sample was loaded onto a desalting column (HiPrep™ 26/10 Desalting), which had been equilibrated with 3 CV of 50 mM HEPES+100 mM NaCl pH 7.0. The target protein was eluted with 50 mM HEPES+100 mM NaCl pH 7.0 and relevant fractions were selected and pooled based on the chromatogram. The flow rate was 5 ml/min.

For the polypeptides shown in SEQ ID NOs 98 and 99, the sample collected from the purification process described above, was applied to a 1 mL HiTrap™ Blue HP column on an Äkta PURE system. Prior to loading the column had been equilibrated in 10 CV of 50 mM HEPES+100 mM NaCl pH 7.0. During loading of the sample to the column, the flow through was collected. In order to remove any unbound material, the column was washed with 7 CV 50 mM HEPES+100 mM NaCl pH 7.0. The target protein was eluted with 11.2 CV of 50 mM Tris, 1M NaCl, pH 8. Based on the chromatogram, relevant fractions were collected. The protein was either in the flow through or in the eluate. Protein concentration in the final samples was estimated by measuring absorption at 280 nm.

Example 13 Cloning and Expression of Two GH114 Glycosyl Hydrolase Polypeptides from *Fusarium proliferatum*, and *Fusarium lateritium*

Two putative endo-α-1,4-polygalactosaminidases belonging to family GH114 were derived from fungal strains isolated from environmental samples by standard microbiological isolation techniques. Strains were identified, and taxonomy was assigned based on DNA sequencing of the ITS (Table 12).

TABLE 12

| SEQ ID NO | Organism_name | Source country |
|---|---|---|
| 102 | *Fusarium proliferatum* | China |
| 103 | *Fusarium lateritium* | China |

Chromosomal DNA from individual strains (Table 12) was isolated by DNeasy Plant Mini Kit (Qiagen, Hilden, Germany). 5 μg of chromosomal DNA were sent for full genome sequencing using Illumina technology. Genome sequencing, the subsequent assembly of reads and the gene discovery (i.e. annotation of gene functions) is known to the person skilled in the art and the service can be purchased commercially.

Peptides predicted from the annotated genome were searched for similarity to the GH114 domain as defined by CAZy (www.cazy.org, Lombard V, et al. (2014) *Nucleic Acids Res* 42:D490-D495), and the three peptides were identified. Corresponding DNA sequences were PCR amplified from genomic DNA with gene-specific primers, and the amplified DNA fragments were cloned into the expression vector pCaHj505 (WO2013029496).

The final expression plasmid was transformed into the *Aspergillus oryzae* MT3568 expression host. *A. oryzae* MT3568 is a derivative of *A. oryzae* JaL355 (WO02/40694) in which pyrG auxotrophy was restored by disrupting the *A. oryzae* acetamidase (amdS) gene with the pyrG gene. The GH114 gene was integrated by homologous recombination into the *A. oryzae* MT3568 host cell genome upon transformation.

The gene coding for amdS was used as marker. Transformants were selected on pyrG media agar supplemented with 10 mM acetamide. One recombinant *A. oryzae* clone containing the GH114 expression construct was selected and cultivated in 2400 ml of Dap4C medium in shake flasks for 3 days at 30° C. under 80 rpm agitation. Enzyme containing supernatants were harvested by filtration using a 0.22 μm 1-liter bottle top vacuum filter (Thermo Fisher Scientific Inc., Waltham, MA, USA).

Example 14 Cloning, Expression and Fermentation of Fungal GH114 Glycosyl Hydrolases Strains

*Escherichia coli* Top-10 strain purchased from TIANGEN (TIANGEN Biotech Co. Ltd., Beijing, China) was used to propagate our expression vector.

*Aspergillus oryzae* strain DAU785 (described in WO 2018/113745, page 293) was used for heterologous expression of the genes described in the Table 1.

Media

Dap4C medium was composed of 11 g $MgSO_4{\cdot}7H_2O$, 1 g $KH_2PO_4$, 2.2 g Citric acid·$H_2O$, 20 g glucose, 10 g maltose, 5.2 g $K_3PO_4$—$H_2O$, 0.5 g yeast extract, 1.25 g $CaCO_3$, 0.5 ml AMG Trace element solution and deionized water to 1 litre. After autoclave, 3.3 ml of 20% Lactic Acid (autoclaved) and 9.3 ml of 50% $(NH_4)_2HPO_4$ (sterile filtered) were added to every 400 ml above medium.

AMG Trace element solution was composed of 6.8 g $ZnC_2$, 2.5 g $CuSO_4.5H_2O$, 0.24 g $NiCl_2{\cdot}5H_2O$, 13.9 g $FeSO_4{\cdot}7H_2O$, 13.6 g $MnSO_4{\cdot}5H_2O$, 3 g Citric acid-$H_2O$, and deionised water to 1000 ml.

LB plates were composed of 10 g of Bacto-tryptone, 5 g of yeast extract, 10 g of sodium chloride, 15 g of Bacto-agar, and deionised water to 1000 ml.

LB medium was composed of 1 g of Bacto-tryptone, 5 g of yeast extract, and 10 g of sodium chloride, and deionised water to 1000 ml.

COVE sucrose plates were composed of 342 g of sucrose, 20 g of agar powder, 20 ml of COVE salt solution, and deionized water to 1 litre. The medium was sterilized by autoclaving at 15 psi for 15 minutes. The medium was cooled to 60° C. and 10 mM acetamide, 15 mM CsCl, Triton X-100 (50 μl/500 ml) were added.

COVE-2 plate/tube for isolation: 30 g/L sucrose, 20 ml/L COVE salt solution, 10 mM acetamide, 30 g/L noble agar (Difco, Cat#214220).

COVE salt solution was composed of 26 g of $MgSO_4{\cdot}7H_2O$, 26 g of KCL, 26 g of $KH_2PO_4$, 50 ml of COVE trace metal solution, and deionised water to 1000 ml.

COVE trace metal solution was composed of 0.04 g of $Na_2B_4Or$ $10H_2O$, 0.4 g of $CuSO_4$-$5H_2O$, 1.2 g of $FeSO_4{\cdot}7H_2O$, 0.7 g of $MnSO_4{\cdot}H_2O$, 0.8 g of $Na_2MoO_4{\cdot}2H_2O$, 10 g of $ZnSO_4{\cdot}7H_2O$, and deionised water to 1000 ml.

The GH114 glycosyl hydrolase genes derived from fungal strains isolated from environmental samples by standard microbiological isolation techniques. Strains were identified, and taxonomy was assigned based on DNA sequencing of the ITS (Table 13).

TABLE 13

| Protein SEQ ID | Donor Organism name | source country |
|---|---|---|
| 72 | *Chaetomium globosum* | China |
| 73 | *Stilbella fimetaria* | China |
| 74 | *Volutella ciliata* | China |
| 75 | *Clonostachys epichloe* | China |
| 76 | *Myrothecium* sp | China |
| 77 | *Botryotrichum piluliferum* | China |
| 78 | *Myrothecium* sp. | China |
| 104 | *Fusarium proliferatum* | China |
| 105 | *Chaetomium ancistrocladum* | China |
| 106 | *Fusarium verficillioides* | China |
| 107 | *Fusarium lateritium* | China |
| 108 | *Chaetomium* sp. ZY474 | China |

Chromosomal DNA from individual strains (Table. 13) was isolated by QIAamp Dneasy Kit (Qiagen, Hilden, Germany). 5 μg of chromosomal DNA were sent for full genome sequencing using Illumina technology. Genome sequencing, the subsequent assembly of reads and the gene discovery (i.e. annotation of gene functions) is known to the person skilled in the art and the service can be purchased commercially.

The genome sequences were analyzed for putative GH114 glycosyl hydrolases from the PFAM database families PF03537. This analysis identified genes encoding putative GH114, which were subsequently cloned and recombinantly expressed in *Aspergillus oryzae*. Using the SignalP program v. 3 (Nielsen et al., 1997, *Protein Engineering* 10: 1-6), the signal peptide and accordingly the mature peptide (SEQ ID NO: 72-78, 104-108) were predicted.

The GH114 glycosyl hydrolase genes were amplified by PCR respectively from above isolated genomic DNA. The purified PCR product was cloned into the previously digested expression vector pDAU724 (described in WO 2018/113745, page 293) by ligation with an IN-FUSION™ CF Dry-down Cloning Kit (Clontech Laboratories, Inc., Mountain View, CA, USA) according to the manufacturer's instructions. The ligation mixture was used to transform *E. coli* TOP10 chemically competent cells (described in Strains). Correct colonies containing the corresponding GH114 gene was selected and verified by DNA sequencing (by SinoGenoMax Company Limited, Beijing, China). The correct GH114 containing colony was cultivated overnight in 3 ml of LB medium supplemented with 100 μg of ampicillin per ml. Plasmid DNA was purified using a Qiagen Spin Miniprep kit (Cat. 27106) (QIAGEN GmbH, Hilden, Germany) according to the manufacturer's instructions. Protoplasts of *Aspergillus oryzae* DAU785 were prepared according to WO95/002043. 100 μl of protoplasts were mixed with 2.5-10 μg of the *Aspergillus* expression vector (above extracted plasmid) comprising the GH114 glycosyl hydrolase gene and 250 μl of 60% PEG 4000, 10 mM $CaC_2$, and 10 mM Tris-HCl pH7.5 and gently mixed. The mixture was incubated at 37° C. for 30 minutes and the protoplasts were spread onto COVE sucrose plates for selection. After incubation for 4-7 days at 37° C. spores of 4 transformants were inoculated into 3 ml of DAP4C medium. After 3 days cultivation at 30° C., the culture broths were analyzed by SDS-PAGE using Novex® 4-20% Tris-Glycine Gel (Invitrogen Corporation, Carlsbad, CA, USA) to identify the transformants producing the largest amount of recombinant GH114 with respective estimated mature peptide size. Spores of the best expressed transformant were spread on COVE-2 plates for re-isolation in order to isolate single colonies. Then a single colony was spread on a COVE-2 tube until sporulation. Spores from the best expressed transformant were cultivated in 2400 ml of Dap4C medium in shake flasks during 3 days at a temperature of 30° C. under 80 rpm agitation. Culture broth was harvested by filtration using a 0.22 μm filter device. The filtered fermentation broth was used for enzyme characterization.

Example 15 Cloning and Expression for GH114 Glycosyl Hydrolases Having SEQ ID NO 109 to SEQ ID NO 135

Sequence trimming and codon optimization Selected protein sequences were submitted to subcellular localization predictors (DeepLoc-1.0: Bioinformatics, volume 33, Issue 24, 15 Dec. 2017, Page 4049; SignalP-5.0: Nature Biotechnology, volume 37, 2019, pages 420) to evaluate extracellular secretion probability. SEQ ID NO 114, SEQ ID NO 115, SEQ ID NO 121, SEQ ID NO 122, SEQ ID NO 127, SEQ ID NO 129, and SEQ ID NO 133 had lysosomal predicted targeting and Nt lysosomal targeting signal sequence were truncated.

All protein sequences were reverse-translated with a method preferentially utilizing frequently used *Aspergillus oryzae* codons and algorithms designed to identify and remove sequence features that might hinder cloning or expression were used. A single DNA sequence was selected for each GH114 protein in this process as described in patent US 2015/0152452 A1.

Cloning, Transformation and Expression

Codon-optimized DNA sequences were purchased from TwistBioscience. A PCR amplification step consisting of one 3 min. denaturation step at 98° C. followed by 30 cycles of 20 sec. denaturation, 2 min. annealing/amplification at 72° C. and one final amplification step of 10 min. at 72° C. was carried out on 20 μL mixes consisting of 4 μL KAPA polymerase buffer, 0.4 μL 10 mM KAPA dNTP, 0.4 μL 10 μM forward primer (SEQ ID NO 147); 0.4 μL 10 μM reverse primer (SEQ ID NO 148), 2 ng synthetic genes resuspended in 10 mM TE buffer pH8, 0.4 μL KAPA polymerase (KK2502) and 14 μL PCR grade water.

```
                                        SEQ ID NO 147
gacagccgcatccgtggtctccgca

                                        SEQ ID NO 148
ctaccgccagcagtgtctgcgattta
```

Cloning strategy was carried out by in vivo assembly of three overlapping DNA fragments in *Aspergillus oryzae* strain ColS1300 protoplasts following a procedure described in patent WO2018050666A1.

To ensure extracellular secretion of the heterologous GH114 proteins, all synthetic sequences were fused to a DNA sequence encoding for the extracellular secretion signal of sequence MKLSWLVAAALTAASVVSA (SEQ ID NO 149). Wild-type secretion signal peptides were also replaced by the synthetic extracellular secretion signal of sequence MKLSWLVAAALTAASVVSA.

ColS1300 strain transformation libraries were screened for protein expression after a first selection on NaNo3 plates following a procedure described in WO2018050666A1. Protein expression analyses were carried out on a Perkin Elmer (Waltham, Massachusetts, U.S) LAbChip GXII.

Example 16 Purification of GH114 Glycosyl Hydrolases

Purification

Some of the recombinant GH114 glycosyl hydrolase enzymes (SEQ ID NOs 72-79 and SEQ ID NOs 106-116) were purified by hydrophobic interaction chromatography process, with a little difference on pH of buffer and concentration of ammonium sulfate for different molecules. The culture supernatant of recombinant was firstly added by ammonium sulfate with a final concentration of 1.5M and loaded into Phenyl Sepharose 6 Fast Flow column or Phenyl High Performance column (GE Healthcare) equilibrated with 20 mM PBS at pH 6.0 with 1.5M ammonium sulfate added. A gradient decrease of ammonium sulfate concentration from 1.5M to 0 was set up as elution condition. The elution fractions and flow-through faction were assayed by SDS-PAGE. The fractions with target protein were pooled together and then diafiltrated with 20 mM PBS at pH6.0. The protein concentration was determined by Qubit® Protein Assay Kit (Invitrogen, cat Q33212). Enzyme activity assay was carried out as described below.

Substrate Preparation

Based on the article (H. TAKADA, et al. *J. Biochem.* 89, 1265-1274 (1981)), fungal strain *Aspergillus parasiticus* was cultured in the medium suggested from literature at 30 degrees for 5 days. Then the culture broth was filtrated, and the culture supernatant was kept. The culture supernatant was added with same volume of ethanol, mixed for several minutes and centrifuged. The precipitant was washed three times with ethanol. Finally, the precipitant was washed with pure water and stored as substrate.

Enzyme Assay

The precipitant was dissolved in 20 mM PBS at pH6.0 with the final concentration of 0.2 mg/mL as substrate solution. 10 ul enzyme solution at 0.1 mg/mL was added into 90 ul substrate solution, incubated at 40 degrees for 30 minutes. 50 ul of reaction mixture was added into 150 ul PHBAH solution (4-hydroxybenzhydtazide (CAS: 5351-23-5) diluted in 0.5M NAOH to a final concentration of 1.5%), incubated at 100 degrees for 5 minutes. Then 70 ul of the incubation solution was picked up and tested for absorbance at 410 nm. 10 ul water added into substrate solution was set as blank control.

Example 17 Measuring Thermal Stability of GH114 glycosyl Hydrolases

Thermal stability measurements were performed using a capillary based nano differential scanning fluorescence instrument (nanoDSF); Prometheus NT.Plex (NanoTemper Technologies GmbH, München, Germany). Standard nanoDSF grade capillary chips were used (Cat#: PR-AA002) from NanoTemper Technologies. The protein samples were mixed 1:10 in 50 mM NaAcetate, 50 mM MES, 50 mM Glycine pH 8 or in 3.3 g/L Model A and loaded into the capillaries (each sample in triplicate) by capillary action. The emission intensities at 330 and 350 nm were optimized by altering the LED power on the instrument to ensure sufficient signal. The fluorescence signals at 330 and 350 nm were monitored continuously as a function of temperature (heating rate used for thermal unfolding was 3.3° C. per minute from 20 to 95° C.). The data was analyzed using the PR. ThermControl_2.1.2.6031 software provided by the manufacturer. The analysis is model independent and simply takes the peak maximum of the first derivative which corresponds to the approximate thermal unfolding transition midpoint, defined as Td.

TABLE 14

| SEQ ID NO | Organism name | nDSF pH 8 | nDSF Model A |
|---|---|---|---|
| 6 | *Amycolatopsis* sp. A | 63.43 | 58.50 |
| 18 | *Fusarium solani* | 48.35 | 35.15 |
| 72 | *Chaetomium globosum* | 56.32 | 52.49 |
| 73 | *Stilbella fimetaria* | 51.95 | 41.94 |
| 74 | *Volutella ciliata* | 41.95 | 29.54 |
| 75 | *Clonostachys epichloe* | 45.59 | 41.73 |
| 76 | *Myrothecium* sp-75362 | 57.79 | 48.90 |
| 77 | *Botryotrichum piluliferum* | 43.92 | 36.05 |
| 78 | *Myrothecium* sp. | 51.14 | 40.04 |
| 79 | *Amycolatopsis* sp-63067 | 57.00 | 40.65 |
| 81 | *Amycolatopsis niigatensis* | 56.63 | 51.34 |
| 82 | *Streptomyces* sp. AA4 | 63.77 | 52.16 |
| 83 | *Amycolatopsis alba* DSM 44262 | 58.30 | 50.74 |

TABLE 14-continued

| SEQ ID NO | Organism name | nDSF pH 8 | nDSF Model A |
|---|---|---|---|
| 87 | *Microbacterium oleivorans* O827CG | 48.43 | 40.54 |
| 89 | *Microbacterium oxydans* | 53.87 | 48.17 |
| 90 | *Agreia pratensis* | 56.60 | 53.64 |
| 91 | *Microbacterium lemovicicum* | 42.43 | 31.98 |
| 93 | *Curtobacterium oceanosedimentum* | 43.10 | 30.51 |
| 96 | Enviromental sample | 51.77 | 44.12 |

Example 18 Deep-Cleaning in Liquid Model Detergent Aon Fungal EPS Swatches

The wash performance was determined as follows; 50 ul aliquots of crude fungal EPS extract (see example "production of poly-galactosamine" above) were spotted on sterile textile swatches (WFK20A) and incubated for 15 min at ambient temperature. Control swatches were spotted with 3M NaC. The swatches (sterile or with the extract) were placed in 50 mL test tubes and 10 mL of wash liquor (15°dH water with 0.2 g/L iron(III) oxide nano-powder(544884; Sigma-Aldrich) and 3.33 g/L liquid model A detergent) and the enzyme(s) was added to each tube. Washes without enzyme were included as controls. The test tubes were placed in a Stuart rotator and incubated for 1 hour at 30° C. and 20 rpm. The wash liquor was then removed, and the swatches were rinsed twice with 15°dH water and dried on filter paper over night. The remission values (Rem460 nm) were measured using a Datacolor 800V and are displayed in table 9 and 10. Wash performance (WP) values (Rem460 $nM_{(swatch\ washed\ with\ enzyme)}$−Rem46 $nM_{(swatch\ washed\ without\ enzyme)}$) are also indicated. Alternatively, swatches were scanned using an Epson Expression 10000XL flatbed scanner. R(red), G(green) and B(blue) values in the RGB color space were determined using Color Analyzer software and Intensity was calculated as $\sqrt{R^2+G^2+B^2}$ for each swatch (data is shown in table 12). Wash performance (WP) values (ΔIntensity=$Intensity_{(swatch\ washed\ with\ enzyme)}$−$Intensity_{(swatch\ washed\ without\ enzyme)}$) are also indicated.

TABLE 15

Deep-cleaning effects of the GH114 glycosyl hydrolase homologues in model A detergent

| Swatch | SEQ ID NO | Enzyme conc. (μg/ml) | Average Rem460 nm | WP (ΔRem460 nm) |
|---|---|---|---|---|
| wfk20A, clean textile | | 0 | 70.7 | |
| Wfk20A, EPS, no enzyme | | 0 | 43.9 | |
| Wfk20A, EPS | 80 | 0.1 | 73.4 | 29.5 |
| Wfk20A, EPS | 82 | 0.1 | 52.2 | 8.3 |
| Wfk20A, EPS | 83 | 0.1 | 56.5 | 12.6 |
| Wfk20A, EPS | 84 | 0.1 | 52.7 | 8.8 |
| Wfk20A, EPS | 85 | 0.1 | 51.5 | 7.6 |
| Wfk20A, EPS | 86 | 0.1 | 49.8 | 5.9 |
| Wfk20A, EPS | 87 | 0.1 | 54.0 | 10.1 |
| Wfk20A, EPS | 88 | 0.1 | 51.0 | 7.1 |
| Wfk20A, EPS | 89 | 0.1 | 54.4 | 10.5 |
| Wfk20A, EPS | 90 | 0.1 | 50.9 | 7.0 |
| Wfk20A, EPS | 91 | 0.1 | 56.0 | 12.1 |
| Wfk20A, EPS | 92 | 0.1 | 51.4 | 7.5 |
| Wfk20A, EPS | 94 | 0.1 | 56.9 | 13.0 |
| Wfk20A, EPS | 95 | 0.1 | 45.6 | 1.7 |
| Wfk20A, EPS | 96 | 0.1 | 54.6 | 10.7 |
| Wfk20A, EPS | 97 | 0.1 | 50.1 | 6.2 |

TABLE 16

Deep-cleaning effects of the GH114 glycosyl hydrolase homologues in model A detergent

| Swatch | SEQ ID NO | Enzyme conc. (μg/ml) | Average Rem460 nm | WP (ΔRem460 nm) |
|---|---|---|---|---|
| wfk20A, clean textile | | 0 | 71.2 | |
| Wfk20A, EPS, no enzyme | | 0 | 40.3 | |
| Wfk20A, EPS | 72 | 0.1 | 42.5 | 2.2 |
| Wfk20A, EPS | 73 | 0.1 | 43.4 | 3.1 |
| Wfk20A, EPS | 74 | 0.1 | 53.3 | 13.0 |
| Wfk20A, EPS | 75 | 0.1 | 47.4 | 7.1 |
| Wfk20A, EPS | 76 | 0.1 | 53.1 | 12.8 |
| Wfk20A, EPS | 77 | 0.1 | 54.4 | 14.1 |
| Wfk20A, EPS | 78 | 0.1 | 49.7 | 9.4 |
| Wfk20A, EPS | 79 | 0.1 | 59.1 | 18.8 |

TABLE 17

Deep-cleaning effects of the GH114 homologues in model A detergent.

| Swatch | SEQ | Enzyme conc. (μg/ml) | Intensity | WP (ΔIntensity) |
|---|---|---|---|---|
| Wfk20A, EPS, no enzyme | | 0 | 345.0 | |
| Wfk20A, EPS | 103 | 0.003 | 358.4 | 13.4 |
| Wfk20A, EPS | 104 | 0.003 | 385.0 | 40.0 |
| Wfk20A, EPS | 107 | 0.003 | 373.7 | 28.6 |
| Wfk20A, EPS | 136 | 0.003 | 373.6 | 28.6 |
| Wfk20A, EPS | 137 | 0.003 | 363.7 | 18.7 |
| Wfk20A, EPS | 138 | 0.003 | 378.5 | 33.5 |
| Wfk20A, EPS | 139 | 0.003 | 367.7 | 22.7 |
| Wfk20A, EPS | 142 | 0.003 | 390.9 | 45.9 |
| Wfk20A, EPS | 143 | 0.003 | 352.0 | 7.0 |
| Wfk20A, EPS | 146 | 0.003 | 367.1 | 22.1 |

Example 19 Deep-Cleaning in Liquid Model Detergent a on Pel Swatches

A crude extract of the biofilm extracellular polymer Pel was prepared from *Pseudomonas aeruginosa* PA14 (DSM 19882) as described above. The wash performance was determined as follows; 50 ul aliquots of the crude Pel extract were spotted on sterile textile swatches (WFK20A) and incubated for 15 min at ambient temperature. Control swatches were spotted with 3M NaCl. The swatches (sterile or with the extract) were placed in 50 mL test tubes and 10 mL of wash liquor (15°dH water with 0.2 g/L iron(III) oxide nano-powder (544884; Sigma-Aldrich) with 3.33 g/L liquid model A detergent) and the enzyme was added to each tube. Washes without enzyme were included as controls. The test tubes were placed in a Stuart rotator and incubated for 1 hour at 30° C. and 20 rpm. The wash liquor was then removed, and the swatches were rinsed twice with 15°dH water and dried on filter paper over night. The tristimulus Y values were measured using a Handheld Minolta CR-300 and are displayed in table 18. Wash performance (WP) values ($Y_{(swatch\ washed\ with\ enzyme)}-Y_{(swatch\ washed\ without\ enzyme)}$) are also indicated.

TABLE 18

Deep-cleaning effects of the GH114 homologues in model A detergent

| Swatch | SEQ | Enzyme conc. (μg/ml) | Average Y | WP (ΔY) |
|---|---|---|---|---|
| WFK20, *P. aeruginosa* Pel, no enzyme | | 0 | 66.0 | |
| WFK20, *P. aeruginosa* Pel | 98 | 2 | 73.4 | 7.4 |
| WFK20, *P. aeruginosa* Pel | 98 | 0.2 | 72.4 | 6.4 |
| WFK20, *P. aeruginosa* Pel | 97 | 2 | 75.3 | 9.3 |
| WFK20, *P. aeruginosa* Pel | 97 | 0.2 | 67.5 | 1.5 |
| WFK20, *P. aeruginosa* Pel | 99 | 2 | 77.6 | 11.6 |
| WFK20, *P. aeruginosa* Pel | 99 | 0.2 | 71.0 | 5.0 |
| WFK20, *P. aeruginosa* Pel | 100 | 2 | 71.3 | 5.3 |
| WFK20, *P. aeruginosa* Pel | 100 | 0.2 | 66.5 | 0.5 |

Example 20 Protein Thermal Unfolding Analysis (TSA, Thermal Shift Assay)

Protein thermal stability were tested for homologue or variants of the GH114 glycosyl hydrolase having SEQ ID NO 18. The thermal unfolding was monitored with Sypro Orange (Invitrogen, S-6650) using a real-time PCR instrument (Applied Biosystems; Step-One-Plus). In a 96-well white PCR-plate, 15 μl sample (supernatant diluted in 100 mM EPPS pH8.0) was mixed (1:1) with Sypro Orange (Conc.=10×; stock solution from supplier=5000×) in water.

The plate was sealed with an optical PCR seal. The PCR instrument was set at a scan-rate of 76° C. per hour, starting at 25° C. and finishing at 96° C. Fluorescence was monitored every 20 seconds using in-built LED blue light for excitation and ROX-filter (610 nm, emission). Tm-values were calculated as: The temperature causing the maximum value of the first derivative (dF/dK) (Gregory et al., 2009, J. Biomol. Screen. 14: 700).

TSA data for the SEQ ID NO 18 variants using two criteria, either delta(Tm)>1 degree or between 0 and 1 degrees.

The tables 19-22 shows thermostability of the GH114 glycosyl hydrolase variants. Values above 0 means that the variant is more stable than the parent or starting GH114 glycosyl hydrolase, here SEQ ID NO 18.2,

TABLE 19

| Mutation | Tm_C | dTm_C |
|---|---|---|
| A250D | 44.67 | 1.93 |
| A259P | 44.85 | 1.96 |
| D222W | 46.38 | 3.79 |
| G230D + A259P | 45.64 | 2.75 |
| I172V + A250D | 45.15 | 2.73 |
| K86D | 43.61 | 1.17 |
| L234F | 44.83 | 1.94 |
| N209S | 44.77 | 1.89 |
| T39A | 43.69 | 1.25 |
| V248L | 44.75 | 2.02 |

TABLE 20

| Mutation(s) | Tm_C | dTm_C |
|---|---|---|
| C23V | 42.91 | 0.03 |
| D101* + A166V | 43.24 | 0.36 |
| D101* | 43.51 | 0.63 |
| D136E | 44.49 | 0.74 |
| D144* | 43.01 | 0.14 |
| D145E | 42.92 | 0.49 |
| D145G | 43.71 | 0.83 |
| D222E | 42.73 | 0.13 |

TABLE 20-continued

| Mutation(s) | Tm_C | dTm_C |
|---|---|---|
| E103* + E104* | 42.97 | 0.56 |
| E104* | 42.60 | 0.19 |
| E116D | 42.41 | 0.01 |
| E116K | 42.68 | 0.25 |
| E146* | 42.62 | 0.18 |
| I124L | 42.73 | 0.33 |
| I124V | 43.49 | 0.62 |
| K152D | 44.01 | 0.26 |
| K152G | 43.35 | 0.47 |
| K154E | 42.66 | 0.07 |
| K154T | 43.37 | 0.49 |
| K167D | 42.93 | 0.05 |
| K167T | 43.00 | 0.13 |
| K173T | 43.40 | 0.53 |
| K1A | 43.03 | 0.60 |
| K254T | 43.38 | 0.50 |
| K295N | 42.67 | 0.08 |
| K86E | 42.56 | 0.12 |
| K89D | 43.10 | 0.06 |
| L11I | 42.66 | 0.26 |
| L77V | 42.71 | 0.29 |
| N160D + K254S | 43.00 | 0.11 |
| N209T | 43.26 | 0.37 |
| P212* | 43.00 | 0.11 |
| Q178N | 43.51 | 0.64 |
| S102* | 42.98 | 0.55 |
| S97G | 42.46 | 0.04 |
| T119K | 43.50 | 0.63 |
| T119M + P212* | 43.28 | 0.39 |
| W80R + D145G | 43.44 | 0.57 |
| W80R + K154T | 42.93 | 0.05 |
| Y100* + D101* | 42.58 | 0.17 |
| Y296* | 42.61 | 0.02 |
| Y98W | 43.01 | 0.14 |

TABLE 21

| Mutation | Tm_C | dTm_C |
|---|---|---|
| N73Q | 44.99 | 1.14 |
| N73R | 45.11 | 1.26 |
| G75V | 44.81 | 1.25 |
| L77A | 44.70 | 1.14 |
| L77T | 45.04 | 1.48 |
| Q78M | 44.58 | 1.02 |
| D79T | 44.72 | 1.16 |
| W80M | 45.02 | 1.17 |
| W80Y | 44.98 | 1.13 |
| S85C | 45.27 | 1.42 |
| K86W | 44.74 | 1.40 |
| K89F | 44.88 | 1.32 |
| K89W | 44.62 | 1.06 |
| E90A | 44.37 | 1.03 |
| V91M | 44.59 | 1.03 |
| V242S | 45.06 | 1.19 |
| E243A | 45.33 | 2.27 |
| E243S | 45.37 | 2.32 |
| K244P | 44.54 | 1.49 |
| K247M | 45.12 | 1.25 |
| V248M | 45.99 | 2.40 |
| A250E | 45.15 | 2.05 |
| A250P | 44.30 | 1.20 |
| S251A | 44.37 | 1.43 |
| S251C | 44.53 | 1.55 |
| S251E | 46.19 | 3.21 |
| S251W | 44.32 | 1.30 |
| N253C | 44.33 | 1.26 |
| N253E | 44.79 | 1.72 |
| N253L | 44.61 | 1.55 |
| N253M | 44.10 | 1.03 |
| K254A | 44.44 | 1.42 |
| K254C | 44.11 | 1.13 |
| K254D | 46.18 | 3.32 |
| K254E | 45.87 | 2.81 |
| K254H | 44.98 | 2.00 |

TABLE 21-continued

| Mutation | Tm_C | dTm_C |
|---|---|---|
| K254V | 44.13 | 1.11 |
| Y256E | 46.01 | 2.91 |
| Y256G | 44.28 | 1.18 |
| Y256M | 45.98 | 2.88 |
| Y256R | 46.59 | 3.49 |
| Y256S | 44.83 | 1.73 |
| Y256W | 45.74 | 2.64 |
| T258D | 45.05 | 1.59 |
| T258E | 44.56 | 1.10 |
| T258S | 45.21 | 1.34 |
| A259E | 45.64 | 2.41 |
| E260G | 45.17 | 1.94 |
| E260K | 48.09 | 4.86 |
| E260Q | 46.39 | 3.16 |
| E260R | 48.43 | 5.20 |
| E260T | 45.70 | 2.47 |
| E260W | 47.02 | 3.79 |
| D261A | 44.62 | 1.04 |
| E262A | 46.62 | 3.48 |
| E262F | 47.19 | 3.96 |
| E262G | 47.11 | 3.94 |
| E262I | 45.65 | 2.60 |
| E262K | 45.82 | 2.50 |
| E262L | 44.97 | 1.65 |
| E262M | 47.41 | 4.27 |
| E262Q | 47.45 | 4.40 |
| E262R | 45.47 | 2.29 |
| E262S | 47.17 | 4.12 |
| E262T | 45.33 | 2.19 |
| E262V | 45.23 | 2.12 |
| E262W | 44.93 | 1.61 |
| I270L | 47.87 | 4.81 |

TABLE 22

| Mutation | Tm_C | dTm_C |
|---|---|---|
| A64S | 44.70 | 0.85 |
| N73K | 44.81 | 0.96 |
| A76M | 43.69 | 0.13 |
| A76R | 43.96 | 0.40 |
| A76V | 43.83 | 0.27 |
| L77K | 43.87 | 0.31 |
| Q78E | 43.95 | 0.39 |
| Q78K | 43.63 | 0.29 |
| Q78N | 43.50 | 0.16 |
| Q78R | 43.97 | 0.63 |
| D79K | 44.11 | 0.55 |
| D79N | 44.09 | 0.53 |
| D79P | 44.19 | 0.63 |
| D79Q | 43.69 | 0.13 |
| D79V | 43.79 | 0.23 |
| D79W | 43.75 | 0.19 |
| W80E | 43.92 | 0.07 |
| W80I | 44.11 | 0.26 |
| W80R | 44.17 | 0.32 |
| D81V | 44.27 | 0.93 |
| S85A | 43.86 | 0.01 |
| S85G | 43.92 | 0.07 |
| S85W | 43.86 | 0.01 |
| K89A | 43.72 | 0.16 |
| K89D | 43.67 | 0.11 |
| K89E | 43.57 | 0.01 |
| K89P | 43.71 | 0.15 |
| K89S | 43.81 | 0.25 |
| K89V | 44.03 | 0.47 |
| E90D | 43.89 | 0.55 |
| E90N | 43.76 | 0.42 |
| E90S | 43.86 | 0.52 |
| V91I | 44.29 | 0.73 |
| V91S | 43.86 | 0.30 |
| V91T | 43.81 | 0.25 |
| I92E | 43.59 | 0.06 |
| E243L | 43.96 | 0.09 |
| E243P | 43.81 | 0.76 |

TABLE 22-continued

| Mutation | Tm_C | dTm_C |
|---|---|---|
| E243V | 44.16 | 0.69 |
| K244L | 43.41 | 0.33 |
| K244Q | 43.09 | 0.01 |
| K244R | 43.67 | 0.60 |
| T245C | 44.50 | 0.78 |
| T245D | 43.95 | 0.09 |
| G246Q | 44.39 | 0.53 |
| K247A | 44.42 | 0.69 |
| K247C | 44.14 | 0.41 |
| K247E | 44.27 | 0.54 |
| K247R | 44.05 | 0.28 |
| K247S | 44.58 | 0.81 |
| K247V | 44.43 | 0.75 |
| V248L | 44.42 | 0.83 |
| S251G | 43.46 | 0.48 |
| S251K | 42.88 | 0.02 |
| S251L | 43.81 | 0.83 |
| S251Q | 43.98 | 0.88 |
| S251T | 43.50 | 0.52 |
| N253A | 43.38 | 0.32 |
| N253P | 43.99 | 0.92 |
| N253W | 43.09 | 0.03 |
| K254M | 43.72 | 0.86 |
| K254R | 43.25 | 0.19 |
| Y256T | 43.28 | 0.18 |
| T258A | 43.73 | 0.13 |
| T258G | 43.65 | 0.18 |
| T258Q | 44.24 | 0.77 |
| D261L | 43.38 | 0.16 |
| D261R | 43.67 | 0.09 |
| E262C | 43.54 | 0.40 |
| E262D | 43.47 | 0.33 |
| K264R | 43.76 | 0.76 |
| G279E | 43.29 | 0.24 |
| G279K | 42.99 | 0.73 |
| G279R | 43.01 | 0.75 |
| G279S | 43.09 | 0.82 |

The invention claimed is:

1. A cleaning composition comprising:

(a) at least 0.01 ppm GH114 glycosyl hydrolase having alpha-1,4-polygalactosaminidase activity, wherein the GH114 glycosyl hydrolase comprises one or both motif(s) [VLI]XE[EDSQ]C (SEQ ID NO: 60) or CY[FLIV][SDN][ATVG] (SEQ ID NO: 61) and has at least 85% sequence identity to SEQ ID NO: 18; and (b) an anionic surfactant selected from the group consisting of sulfates and sulfonates.

2. The cleaning composition according to claim 1, further comprising at least one nonionic surfactant.

3. The cleaning composition according to claim 1, wherein the GH114 glycosyl hydrolase comprises one or both motifs DYQ[LI]G (SEQ ID NO: 62) or FQ[TAV]Q [PSD] (SEQ ID NO: 63).

4. The cleaning composition according to claim 3, wherein the glycosyl hydrolase comprises one or both motifs AEECG (SEQ ID NO: 64) or NAFQ[AT]Q (SEQ ID NO: 65).

5. The cleaning composition according to claim 1, wherein the GH114 glycosyl hydrolase comprises one or both motifs GXXVX[NHQTS]IEY[PG] (SEQ ID NO: 68), VICYF (SEQ ID NO: 69).

6. The cleaning composition according to claim 5, wherein the GH114 glycosyl hydrolase comprises the motif ICYFSA (SEQ ID NO: 70).

7. The cleaning composition according to claim 5, wherein the GH114 glycosyl hydrolase comprises the motif DFAVL (SEQ ID NO: 71).

8. The cleaning composition according to claim 1, wherein the GH114 glycosyl hydrolase comprises one or both motifs WQWQL (SEQ ID NO: 66) or [VLI][GASD] LKN[DGS][VLIP] (SEQ ID NO: 67).

9. The cleaning composition according to claim 1, wherein the GH114 glycosyl hydrolase has wash performance (WP) in liquid Model detergent A, measured as a delta L (ΔL)>1, when delta L (ΔL) is calculated (L(swatch washed with enzyme)−L(swatch washed without enzyme)).

10. The cleaning composition according to claim 1, wherein the GH114 glycosyl hydrolase has biofilm removal activity, wherein the % remaining biofilm is less than 80%.

11. A method for laundering an item comprising the steps of:

(a) exposing an item to a wash liquor comprising a cleaning composition according to claim 1;

(b) completing at least one wash cycle; and (c) optionally rinsing the item, wherein the item is a textile.

12. The cleaning composition of claim 1, wherein the GH114 glycosyl hydrolase has at least 90% sequence identity to SEQ ID NO: 18.

13. The cleaning composition of claim 1, wherein the GH114 glycosyl hydrolase has at least 95% sequence identity to SEQ ID NO: 18.

14. The cleaning composition of claim 1, wherein the GH114 glycosyl hydrolase has at least 96% sequence identity to SEQ ID NO: 18.

15. The cleaning composition of claim 1, wherein the GH114 glycosyl hydrolase has at least 97% sequence identity to SEQ ID NO: 18.

* * * * *

SEQUENCE LISTING

```
<160> NUMBER OF SEQ ID NOS: 149

<210> SEQ ID NO 1
<211> LENGTH: 843
<212> TYPE: DNA
<213> ORGANISM: Amycolatopsis circi
<220> FEATURE:
<221> NAME/KEY: CDS
<222> LOCATION: (1)..(840)
<220> FEATURE:
<221> NAME/KEY: sig_peptide
<222> LOCATION: (1)..(102)
<220> FEATURE:
<221> NAME/KEY: mat_peptide
<222> LOCATION: (103)..(840)

<400> SEQUENCE: 1

atg cct tcg ctt cct ggt cgg att tct cgc gga acc gta gcg gcc gcc       48
Met Pro Ser Leu Pro Gly Arg Ile Ser Arg Gly Thr Val Ala Ala Ala
                -30                 -25                 -20

ctg ctg atc ggc agt tcg gcc tgc gcg ctc ggg gcc ggc ggc acg gcg       96
Leu Leu Ile Gly Ser Ser Ala Cys Ala Leu Gly Ala Gly Gly Thr Ala
            -15                 -10                 -5

gaa agc gcg ccg ctt ccc tcg ccg cac agc cag gtc aaa gac gtt ccc      144
Glu Ser Ala Pro Leu Pro Ser Pro His Ser Gln Val Lys Asp Val Pro
    -1  1               5                   10

ctg ccc acc ccg cac gcc ggg ttc gac tat cag atc ggc ggt ccc tac      192
Leu Pro Thr Pro His Ala Gly Phe Asp Tyr Gln Ile Gly Gly Pro Tyr
15                  20                  25                  30

cag ccg ccg gcg ggc gtc cag gtc gtc agc cgc gac cac agc gcc ccg      240
Gln Pro Pro Ala Gly Val Gln Val Val Ser Arg Asp His Ser Ala Pro
                35                  40                  45

gcg gcc gcc ggg ctg tac aac atc tgc tac gtc aac gct ttc cag gct      288
Ala Ala Ala Gly Leu Tyr Asn Ile Cys Tyr Val Asn Ala Phe Gln Ala
            50                  55                  60

cag ccc ggc gcc gaa aag gag tgg ggc gac ctg gtc ctg cgc gac ggc      336
Gln Pro Gly Ala Glu Lys Glu Trp Gly Asp Leu Val Leu Arg Asp Gly
        65                  70                  75

gac ggc aag gtc gtc atg gat ccc gat tgg aac gag gcg ctg ctc gac      384
Asp Gly Lys Val Val Met Asp Pro Asp Trp Asn Glu Ala Leu Leu Asp
    80                  85                  90

ctg cgc acc gcg gac aag cgg agc cgg atc gcg gac aag gtc ggc acg      432
Leu Arg Thr Ala Asp Lys Arg Ser Arg Ile Ala Asp Lys Val Gly Thr
```

```
95                  100                 105                 110

tgg atc gac gag tgc gcg ggc aag ggc tac cag gcc gtc gag ccg gac        480
Trp Ile Asp Glu Cys Ala Gly Lys Gly Tyr Gln Ala Val Glu Pro Asp
                115                 120                 125

aac tac gac agc ttc acc cgg tcc cag ggc ctg ctc agc gcg cgg aac        528
Asn Tyr Asp Ser Phe Thr Arg Ser Gln Gly Leu Leu Ser Ala Arg Asn
            130                 135                 140

gcc cag gac ctc gtc aag ttg ctt tcc cag cgc gcg cac gga aaa ggc        576
Ala Gln Asp Leu Val Lys Leu Leu Ser Gln Arg Ala His Gly Lys Gly
        145                 150                 155

ctc gcg atc ggc cag aag aac acc tcc gaa ctg gcc tcg tcg cgg gcg        624
Leu Ala Ile Gly Gln Lys Asn Thr Ser Glu Leu Ala Ser Ser Arg Ala
    160                 165                 170

gac aac ggg ctg gac ttc gcc gtc gcc gag gaa tgc ggc gac cag gac        672
Asp Asn Gly Leu Asp Phe Ala Val Ala Glu Glu Cys Gly Asp Gln Asp
175                 180                 185                 190

aat tgc gcc gag tac acc cag tat ttc ggc aac cgc gtg atc gtc atc        720
Asn Cys Ala Glu Tyr Thr Gln Tyr Phe Gly Asn Arg Val Ile Val Ile
                195                 200                 205

gaa tac acc gag gac ggc ttg cgc aac gcg tgc gac aag tgg ggc gcc        768
Glu Tyr Thr Glu Asp Gly Leu Arg Asn Ala Cys Asp Lys Trp Gly Ala
            210                 215                 220

gcg ctc agc gtc gtc cgc cgc gac cgg gac gtc acg ccg aag ggc gat        816
Ala Leu Ser Val Val Arg Arg Asp Arg Asp Val Thr Pro Lys Gly Asp
        225                 230                 235

tcc gct tac gtc cgc gaa acc tgc tga                                    843
Ser Ala Tyr Val Arg Glu Thr Cys
    240                 245


<210> SEQ ID NO 2
<211> LENGTH: 280
<212> TYPE: PRT
<213> ORGANISM: Amycolatopsis circi

<400> SEQUENCE: 2

Met Pro Ser Leu Pro Gly Arg Ile Ser Arg Gly Thr Val Ala Ala Ala
                -30                 -25                 -20

Leu Leu Ile Gly Ser Ser Ala Cys Ala Leu Gly Ala Gly Gly Thr Ala
            -15                 -10                 -5

Glu Ser Ala Pro Leu Pro Ser Pro His Ser Gln Val Lys Asp Val Pro
    -1  1               5                   10

Leu Pro Thr Pro His Ala Gly Phe Asp Tyr Gln Ile Gly Gly Pro Tyr
15                  20                  25                  30

Gln Pro Pro Ala Gly Val Gln Val Val Ser Arg Asp His Ser Ala Pro
                35                  40                  45

Ala Ala Ala Gly Leu Tyr Asn Ile Cys Tyr Val Asn Ala Phe Gln Ala
            50                  55                  60

Gln Pro Gly Ala Glu Lys Glu Trp Gly Asp Leu Val Leu Arg Asp Gly
        65                  70                  75

Asp Gly Lys Val Val Met Asp Pro Asp Trp Asn Glu Ala Leu Leu Asp
    80                  85                  90

Leu Arg Thr Ala Asp Lys Arg Ser Arg Ile Ala Asp Lys Val Gly Thr
95                  100                 105                 110

Trp Ile Asp Glu Cys Ala Gly Lys Gly Tyr Gln Ala Val Glu Pro Asp
                115                 120                 125

Asn Tyr Asp Ser Phe Thr Arg Ser Gln Gly Leu Leu Ser Ala Arg Asn
            130                 135                 140
```

```
Ala Gln Asp Leu Val Lys Leu Leu Ser Gln Arg Ala His Gly Lys Gly
        145                 150                 155

Leu Ala Ile Gly Gln Lys Asn Thr Ser Glu Leu Ala Ser Ser Arg Ala
    160                 165                 170

Asp Asn Gly Leu Asp Phe Ala Val Ala Glu Glu Cys Gly Asp Gln Asp
175                 180                 185                 190

Asn Cys Ala Glu Tyr Thr Gln Tyr Phe Gly Asn Arg Val Ile Val Ile
                195                 200                 205

Glu Tyr Thr Glu Asp Gly Leu Arg Asn Ala Cys Asp Lys Trp Gly Ala
            210                 215                 220

Ala Leu Ser Val Val Arg Arg Asp Arg Asp Val Thr Pro Lys Gly Asp
        225                 230                 235

Ser Ala Tyr Val Arg Glu Thr Cys
    240                 245


<210> SEQ ID NO 3
<211> LENGTH: 246
<212> TYPE: PRT
<213> ORGANISM: Amycolatopsis circi

<400> SEQUENCE: 3

Ala Pro Leu Pro Ser Pro His Ser Gln Val Lys Asp Val Pro Leu Pro
1               5                   10                  15

Thr Pro His Ala Gly Phe Asp Tyr Gln Ile Gly Gly Pro Tyr Gln Pro
            20                  25                  30

Pro Ala Gly Val Gln Val Val Ser Arg Asp His Ser Ala Pro Ala Ala
        35                  40                  45

Ala Gly Leu Tyr Asn Ile Cys Tyr Val Asn Ala Phe Gln Ala Gln Pro
    50                  55                  60

Gly Ala Glu Lys Glu Trp Gly Asp Leu Val Leu Arg Asp Gly Asp Gly
65                  70                  75                  80

Lys Val Val Met Asp Pro Asp Trp Asn Glu Ala Leu Leu Asp Leu Arg
                85                  90                  95

Thr Ala Asp Lys Arg Ser Arg Ile Ala Asp Lys Val Gly Thr Trp Ile
            100                 105                 110

Asp Glu Cys Ala Gly Lys Gly Tyr Gln Ala Val Glu Pro Asp Asn Tyr
        115                 120                 125

Asp Ser Phe Thr Arg Ser Gln Gly Leu Leu Ser Ala Arg Asn Ala Gln
    130                 135                 140

Asp Leu Val Lys Leu Leu Ser Gln Arg Ala His Gly Lys Gly Leu Ala
145                 150                 155                 160

Ile Gly Gln Lys Asn Thr Ser Glu Leu Ala Ser Ser Arg Ala Asp Asn
                165                 170                 175

Gly Leu Asp Phe Ala Val Ala Glu Glu Cys Gly Asp Gln Asp Asn Cys
            180                 185                 190

Ala Glu Tyr Thr Gln Tyr Phe Gly Asn Arg Val Ile Val Ile Glu Tyr
        195                 200                 205

Thr Glu Asp Gly Leu Arg Asn Ala Cys Asp Lys Trp Gly Ala Ala Leu
    210                 215                 220

Ser Val Val Arg Arg Asp Arg Asp Val Thr Pro Lys Gly Asp Ser Ala
225                 230                 235                 240

Tyr Val Arg Glu Thr Cys
                245


<210> SEQ ID NO 4
```

```
<211> LENGTH: 834
<212> TYPE: DNA
<213> ORGANISM: Amycolatopsis sp
<220> FEATURE:
<221> NAME/KEY: CDS
<222> LOCATION: (1)..(831)
<220> FEATURE:
<221> NAME/KEY: sig_peptide
<222> LOCATION: (1)..(102)
<220> FEATURE:
<221> NAME/KEY: mat_peptide
<222> LOCATION: (103)..(831)

<400> SEQUENCE: 4

atg cat tcg ctt cct ggt cgg att tct cgc gcc acc gcg gcg gcc gcg       48
Met His Ser Leu Pro Gly Arg Ile Ser Arg Ala Thr Ala Ala Ala Ala
                -30                 -25                 -20

ctg ctg gtc ggc agt tcg gcg tgc gcg ctc gga acc gcc ggc ccg gcg       96
Leu Leu Val Gly Ser Ser Ala Cys Ala Leu Gly Thr Ala Gly Pro Ala
            -15                 -10                 -5

gaa agc gcg ccg ctg ccc tcg gcg cac agc caa gtc ccg ctg cct gct      144
Glu Ser Ala Pro Leu Pro Ser Ala His Ser Gln Val Pro Leu Pro Ala
    -1  1               5                   10

ccg cac gcc ggg ttc gac tac cag atc ggc ggc ccc tac gcg ccg ccg      192
Pro His Ala Gly Phe Asp Tyr Gln Ile Gly Gly Pro Tyr Ala Pro Pro
15                  20                  25                  30

ccg ggc gtc cag gcg gtc agc cgc gac cac agc gcc ccg gcg gcg gcc      240
Pro Gly Val Gln Ala Val Ser Arg Asp His Ser Ala Pro Ala Ala Ala
                35                  40                  45

ggg ctg tac aac atc tgc tac gtc aac gct ttc cag gca cag ccc gac      288
Gly Leu Tyr Asn Ile Cys Tyr Val Asn Ala Phe Gln Ala Gln Pro Asp
            50                  55                  60

gcc gag aag gaa tgg ggc gac ctg gtc ctg cgc gac gcc gac ggc aac      336
Ala Glu Lys Glu Trp Gly Asp Leu Val Leu Arg Asp Ala Asp Gly Asn
        65                  70                  75

gtc gtg aag gat ccc gac tgg aac gag gcg ctg ctc gac ctg cgc acc      384
Val Val Lys Asp Pro Asp Trp Asn Glu Ala Leu Leu Asp Leu Arg Thr
    80                  85                  90

gcc gac aaa cgg ggc cgg atc gcc gac aag gtc ggc ggg tgg atc gac      432
Ala Asp Lys Arg Gly Arg Ile Ala Asp Lys Val Gly Gly Trp Ile Asp
95                  100                 105                 110

gag tgc gcg ggc aag ggc tac cag gcc gtc gag ccg gac aac tac gac      480
Glu Cys Ala Gly Lys Gly Tyr Gln Ala Val Glu Pro Asp Asn Tyr Asp
                115                 120                 125

agc ttc acc cgg tcc cag gac ctg ctc acc gcg cag gac gca cag gat      528
Ser Phe Thr Arg Ser Gln Asp Leu Leu Thr Ala Gln Asp Ala Gln Asp
            130                 135                 140

ctc gtc aag ctg ctt tcc gcg cac gcg cac gga aaa ggc ctc gcg atc      576
Leu Val Lys Leu Leu Ser Ala His Ala His Gly Lys Gly Leu Ala Ile
        145                 150                 155

gcg cag aag aac acc tcg gag ctg gcc tcc tcg cgc acg gcc aac ggg      624
Ala Gln Lys Asn Thr Ser Glu Leu Ala Ser Ser Arg Thr Ala Asn Gly
    160                 165                 170

ctc gac ttc gcc gtc gcc gag gaa tgc ggc gaa cag gac aat tgc gcg      672
Leu Asp Phe Ala Val Ala Glu Glu Cys Gly Glu Gln Asp Asn Cys Ala
175                 180                 185                 190

gag tac acc caa tac ttc gac aac cac gtg atc gtc atc gaa tac acc      720
Glu Tyr Thr Gln Tyr Phe Asp Asn His Val Ile Val Ile Glu Tyr Thr
                195                 200                 205

gaa gcc ggt ctg cgc aac gcg tgt gcc aag tgg ggc gcc act ctc agc      768
Glu Ala Gly Leu Arg Asn Ala Cys Ala Lys Trp Gly Ala Thr Leu Ser
            210                 215                 220
```

```
gtc gtg cgc cgc gac cgg gac gtc acg ccg aag ggc gat tcc gcc tac      816
Val Val Arg Arg Asp Arg Asp Val Thr Pro Lys Gly Asp Ser Ala Tyr
        225                 230                 235

gtc cgc gaa acc tgc tga                                              834
Val Arg Glu Thr Cys
    240
```

<210> SEQ ID NO 5
<211> LENGTH: 277
<212> TYPE: PRT
<213> ORGANISM: Amycolatopsis sp

<400> SEQUENCE: 5

```
Met His Ser Leu Pro Gly Arg Ile Ser Arg Ala Thr Ala Ala Ala Ala
                -30                 -25                 -20

Leu Leu Val Gly Ser Ser Ala Cys Ala Leu Gly Thr Ala Gly Pro Ala
            -15                 -10                 -5

Glu Ser Ala Pro Leu Pro Ser Ala His Ser Gln Val Pro Leu Pro Ala
    -1  1               5                   10

Pro His Ala Gly Phe Asp Tyr Gln Ile Gly Gly Pro Tyr Ala Pro Pro
15                  20                  25                  30

Pro Gly Val Gln Ala Val Ser Arg Asp His Ser Ala Pro Ala Ala Ala
                35                  40                  45

Gly Leu Tyr Asn Ile Cys Tyr Val Asn Ala Phe Gln Ala Gln Pro Asp
            50                  55                  60

Ala Glu Lys Glu Trp Gly Asp Leu Val Leu Arg Asp Ala Asp Gly Asn
        65                  70                  75

Val Val Lys Asp Pro Asp Trp Asn Glu Ala Leu Leu Asp Leu Arg Thr
    80                  85                  90

Ala Asp Lys Arg Gly Arg Ile Ala Asp Lys Val Gly Gly Trp Ile Asp
95                  100                 105                 110

Glu Cys Ala Gly Lys Gly Tyr Gln Ala Val Glu Pro Asp Asn Tyr Asp
                115                 120                 125

Ser Phe Thr Arg Ser Gln Asp Leu Leu Thr Ala Gln Asp Ala Gln Asp
            130                 135                 140

Leu Val Lys Leu Leu Ser Ala His Ala His Gly Lys Gly Leu Ala Ile
        145                 150                 155

Ala Gln Lys Asn Thr Ser Glu Leu Ala Ser Ser Arg Thr Ala Asn Gly
    160                 165                 170

Leu Asp Phe Ala Val Ala Glu Glu Cys Gly Glu Gln Asp Asn Cys Ala
175                 180                 185                 190

Glu Tyr Thr Gln Tyr Phe Asp Asn His Val Ile Val Ile Glu Tyr Thr
                195                 200                 205

Glu Ala Gly Leu Arg Asn Ala Cys Ala Lys Trp Gly Ala Thr Leu Ser
            210                 215                 220

Val Val Arg Arg Asp Arg Asp Val Thr Pro Lys Gly Asp Ser Ala Tyr
        225                 230                 235

Val Arg Glu Thr Cys
    240
```

<210> SEQ ID NO 6
<211> LENGTH: 243
<212> TYPE: PRT
<213> ORGANISM: Amycolatopsis sp

<400> SEQUENCE: 6

```
Ala Pro Leu Pro Ser Ala His Ser Gln Val Pro Leu Pro Ala Pro His
```

-continued

```
1               5                   10                  15

Ala Gly Phe Asp Tyr Gln Ile Gly Gly Pro Tyr Ala Pro Pro Pro Gly
            20                  25                  30

Val Gln Ala Val Ser Arg Asp His Ser Ala Pro Ala Ala Ala Gly Leu
        35                  40                  45

Tyr Asn Ile Cys Tyr Val Asn Ala Phe Gln Ala Gln Pro Asp Ala Glu
    50                  55                  60

Lys Glu Trp Gly Asp Leu Val Leu Arg Asp Ala Asp Gly Asn Val Val
65                  70                  75                  80

Lys Asp Pro Asp Trp Asn Glu Ala Leu Leu Asp Leu Arg Thr Ala Asp
                85                  90                  95

Lys Arg Gly Arg Ile Ala Asp Lys Val Gly Gly Trp Ile Asp Glu Cys
            100                 105                 110

Ala Gly Lys Gly Tyr Gln Ala Val Glu Pro Asp Asn Tyr Asp Ser Phe
        115                 120                 125

Thr Arg Ser Gln Asp Leu Leu Thr Ala Gln Asp Ala Gln Asp Leu Val
    130                 135                 140

Lys Leu Leu Ser Ala His Ala His Gly Lys Gly Leu Ala Ile Ala Gln
145                 150                 155                 160

Lys Asn Thr Ser Glu Leu Ala Ser Ser Arg Thr Ala Asn Gly Leu Asp
                165                 170                 175

Phe Ala Val Ala Glu Glu Cys Gly Glu Gln Asp Asn Cys Ala Glu Tyr
            180                 185                 190

Thr Gln Tyr Phe Asp Asn His Val Ile Val Ile Glu Tyr Thr Glu Ala
        195                 200                 205

Gly Leu Arg Asn Ala Cys Ala Lys Trp Gly Ala Thr Leu Ser Val Val
    210                 215                 220

Arg Arg Asp Arg Asp Val Thr Pro Lys Gly Asp Ser Ala Tyr Val Arg
225                 230                 235                 240

Glu Thr Cys


<210> SEQ ID NO 7
<211> LENGTH: 825
<212> TYPE: DNA
<213> ORGANISM: Amycolatopsis sp
<220> FEATURE:
<221> NAME/KEY: CDS
<222> LOCATION: (1)..(822)
<220> FEATURE:
<221> NAME/KEY: sig_peptide
<222> LOCATION: (1)..(111)
<220> FEATURE:
<221> NAME/KEY: mat_peptide
<222> LOCATION: (112)..(822)

<400> SEQUENCE: 7

gtg ccc acc atc atc cgg agt tcg atg atg ccc ttc tcc cgc gtt cgg       48
Val Pro Thr Ile Ile Arg Ser Ser Met Met Pro Phe Ser Arg Val Arg
        -35                 -30                 -25

ttc ctc gcc agt gcc gcg ctc gcg gcc acc gtc ctc ggt ggc acc gcg       96
Phe Leu Ala Ser Ala Ala Leu Ala Ala Thr Val Leu Gly Gly Thr Ala
    -20                 -15                 -10

tgc acg gct tcg gcg gcc ccg gcc gcc gtg acc ccg ccg ccg gtc aag      144
Cys Thr Ala Ser Ala Ala Pro Ala Ala Val Thr Pro Pro Pro Val Lys
-5              -1  1               5                   10

gcg ggc ttc gac tac cag atc ggc ggc gcc tac acc ccg ccc gcg ggt      192
Ala Gly Phe Asp Tyr Gln Ile Gly Gly Ala Tyr Thr Pro Pro Ala Gly
            15                  20                  25
```

```
gtc cag gtc gtc agc cgc gac cac ggc gac gcc ccg gcc gcc ggg ctc      240
Val Gln Val Val Ser Arg Asp His Gly Asp Ala Pro Ala Ala Gly Leu
        30                  35                  40

tac aac atc tgc tac gtc aac gct ttc cag gcc cag ccc ggc tcc gag      288
Tyr Asn Ile Cys Tyr Val Asn Ala Phe Gln Ala Gln Pro Gly Ser Glu
    45                  50                  55

ggg gag tgg ggc gac ctg ctg ctg cgc gac gcg aac ggc aag gtc gtc      336
Gly Glu Trp Gly Asp Leu Leu Leu Arg Asp Ala Asn Gly Lys Val Val
60                  65                  70                  75

gtc gac gag gac tgg gac gag gcg ctg ctc gac ctg cac acc gcg gac      384
Val Asp Glu Asp Trp Asp Glu Ala Leu Leu Asp Leu His Thr Ala Asp
                80                  85                  90

aag cgc acg cgg gtc gcg gcc aag gtg aac gcc tgg atc gac gac tgc      432
Lys Arg Thr Arg Val Ala Ala Lys Val Asn Ala Trp Ile Asp Asp Cys
            95                  100                 105

gcc gcg aag ggt tac cag gcg atc gag ccg gac aac tac gac agc ttc      480
Ala Ala Lys Gly Tyr Gln Ala Ile Glu Pro Asp Asn Tyr Asp Ser Phe
        110                 115                 120

acg cgc tcc cgc ggt ctg ctc tcc gac agc gac gcg cag gcc tac atc      528
Thr Arg Ser Arg Gly Leu Leu Ser Asp Ser Asp Ala Gln Ala Tyr Ile
    125                 130                 135

cgc ctg ctt tcc gcc cac gcc cac ggg aag ggc ctg gcg atc gcg cag      576
Arg Leu Leu Ser Ala His Ala His Gly Lys Gly Leu Ala Ile Ala Gln
140                 145                 150                 155

aag aac acc tcc gag ctg gcc ggg cag cgt cag gcc aac ggg ctc gac      624
Lys Asn Thr Ser Glu Leu Ala Gly Gln Arg Gln Ala Asn Gly Leu Asp
                160                 165                 170

ttc gcc atc gcc gaa gag tgc ggg cag cag aag aac tgc gac gag ttc      672
Phe Ala Ile Ala Glu Glu Cys Gly Gln Gln Lys Asn Cys Asp Glu Phe
            175                 180                 185

acg ccc gcg ttc ggc gac cac gtg atc gtc atc gag tac acc gac ggc      720
Thr Pro Ala Phe Gly Asp His Val Ile Val Ile Glu Tyr Thr Asp Gly
        190                 195                 200

ggg ctc aag acc gcc tgc agc cgg tgg agc tcg ctc agc atc gtc cgc      768
Gly Leu Lys Thr Ala Cys Ser Arg Trp Ser Ser Leu Ser Ile Val Arg
    205                 210                 215

cgc gac ctc gac gtc gtc ccc aag ggc gcg tcc ggc tac gtc cgc aaa      816
Arg Asp Leu Asp Val Val Pro Lys Gly Ala Ser Gly Tyr Val Arg Lys
220                 225                 230                 235

acc tgc tga                                                          825
Thr Cys


<210> SEQ ID NO 8
<211> LENGTH: 274
<212> TYPE: PRT
<213> ORGANISM: Amycolatopsis sp

<400> SEQUENCE: 8

Val Pro Thr Ile Ile Arg Ser Ser Met Met Pro Phe Ser Arg Val Arg
        -35                 -30                 -25

Phe Leu Ala Ser Ala Ala Leu Ala Ala Thr Val Leu Gly Gly Thr Ala
    -20                 -15                 -10

Cys Thr Ala Ser Ala Ala Pro Ala Ala Val Thr Pro Pro Pro Val Lys
-5              -1  1               5                   10

Ala Gly Phe Asp Tyr Gln Ile Gly Gly Ala Tyr Thr Pro Pro Ala Gly
            15                  20                  25

Val Gln Val Val Ser Arg Asp His Gly Asp Ala Pro Ala Ala Gly Leu
        30                  35                  40

Tyr Asn Ile Cys Tyr Val Asn Ala Phe Gln Ala Gln Pro Gly Ser Glu
```

```
    45                  50                  55

Gly Glu Trp Gly Asp Leu Leu Leu Arg Asp Ala Asn Gly Lys Val Val
60                  65                  70                  75

Val Asp Glu Asp Trp Asp Glu Ala Leu Leu Asp Leu His Thr Ala Asp
                80                  85                  90

Lys Arg Thr Arg Val Ala Ala Lys Val Asn Ala Trp Ile Asp Asp Cys
            95                  100                 105

Ala Ala Lys Gly Tyr Gln Ala Ile Glu Pro Asp Asn Tyr Asp Ser Phe
        110                 115                 120

Thr Arg Ser Arg Gly Leu Leu Ser Asp Ser Asp Ala Gln Ala Tyr Ile
    125                 130                 135

Arg Leu Leu Ser Ala His Ala His Gly Lys Gly Leu Ala Ile Ala Gln
140                 145                 150                 155

Lys Asn Thr Ser Glu Leu Ala Gly Gln Arg Gln Ala Asn Gly Leu Asp
                160                 165                 170

Phe Ala Ile Ala Glu Glu Cys Gly Gln Gln Lys Asn Cys Asp Glu Phe
            175                 180                 185

Thr Pro Ala Phe Gly Asp His Val Ile Val Ile Glu Tyr Thr Asp Gly
        190                 195                 200

Gly Leu Lys Thr Ala Cys Ser Arg Trp Ser Ser Leu Ser Ile Val Arg
    205                 210                 215

Arg Asp Leu Asp Val Val Pro Lys Gly Ala Ser Gly Tyr Val Arg Lys
220                 225                 230                 235

Thr Cys


<210> SEQ ID NO 9
<211> LENGTH: 237
<212> TYPE: PRT
<213> ORGANISM: Amycolatopsis sp

<400> SEQUENCE: 9

Ala Pro Ala Ala Val Thr Pro Pro Pro Val Lys Ala Gly Phe Asp Tyr
1               5                   10                  15

Gln Ile Gly Gly Ala Tyr Thr Pro Pro Ala Gly Val Gln Val Val Ser
            20                  25                  30

Arg Asp His Gly Asp Ala Pro Ala Ala Gly Leu Tyr Asn Ile Cys Tyr
        35                  40                  45

Val Asn Ala Phe Gln Ala Gln Pro Gly Ser Glu Gly Glu Trp Gly Asp
    50                  55                  60

Leu Leu Leu Arg Asp Ala Asn Gly Lys Val Val Val Asp Glu Asp Trp
65                  70                  75                  80

Asp Glu Ala Leu Leu Asp Leu His Thr Ala Asp Lys Arg Thr Arg Val
                85                  90                  95

Ala Ala Lys Val Asn Ala Trp Ile Asp Asp Cys Ala Ala Lys Gly Tyr
            100                 105                 110

Gln Ala Ile Glu Pro Asp Asn Tyr Asp Ser Phe Thr Arg Ser Arg Gly
        115                 120                 125

Leu Leu Ser Asp Ser Asp Ala Gln Ala Tyr Ile Arg Leu Leu Ser Ala
    130                 135                 140

His Ala His Gly Lys Gly Leu Ala Ile Ala Gln Lys Asn Thr Ser Glu
145                 150                 155                 160

Leu Ala Gly Gln Arg Gln Ala Asn Gly Leu Asp Phe Ala Ile Ala Glu
                165                 170                 175

Glu Cys Gly Gln Gln Lys Asn Cys Asp Glu Phe Thr Pro Ala Phe Gly
```

```
            180                 185                 190

Asp His Val Ile Val Ile Glu Tyr Thr Asp Gly Gly Leu Lys Thr Ala
        195                 200                 205

Cys Ser Arg Trp Ser Ser Leu Ser Ile Val Arg Arg Asp Leu Asp Val
    210                 215                 220

Val Pro Lys Gly Ala Ser Gly Tyr Val Arg Lys Thr Cys
225                 230                 235


<210> SEQ ID NO 10
<211> LENGTH: 831
<212> TYPE: DNA
<213> ORGANISM: Streptomyces parvulus
<220> FEATURE:
<221> NAME/KEY: CDS
<222> LOCATION: (1)..(828)
<220> FEATURE:
<221> NAME/KEY: sig_peptide
<222> LOCATION: (1)..(117)
<220> FEATURE:
<221> NAME/KEY: mat_peptide
<222> LOCATION: (118)..(828)

<400> SEQUENCE: 10

atg agc cgc acg cag gtg cac acc tcg aag aag aag ccg gtg ctg gcg       48
Met Ser Arg Thr Gln Val His Thr Ser Lys Lys Lys Pro Val Leu Ala
                -35                 -30                 -25

ggc gtc tgc gcc gcc gcc gtc ctc gcc acc gcc gcc gcc ctc gtc ccg       96
Gly Val Cys Ala Ala Ala Val Leu Ala Thr Ala Ala Ala Leu Val Pro
            -20                 -15                 -10

ggc agc acc ccc gcc gag gcc gcg gta ccg gcc ccg ccc ccg gcc ggc      144
Gly Ser Thr Pro Ala Glu Ala Ala Val Pro Ala Pro Pro Pro Ala Gly
        -5              -1  1               5

gcc ggc ttc gac tac cag atc ggc ggc gcc tac acc ccg cct tcc ggc      192
Ala Gly Phe Asp Tyr Gln Ile Gly Gly Ala Tyr Thr Pro Pro Ser Gly
10                  15                  20                  25

gta cgg gtg gtc agc cgc gac cac acg gcc tcc ccc gcc gcg ggc ctc      240
Val Arg Val Val Ser Arg Asp His Thr Ala Ser Pro Ala Ala Gly Leu
                30                  35                  40

tac aac atc tgc tac gtc aac gcc ttc cag gcc cag cgg ggc gcc gag      288
Tyr Asn Ile Cys Tyr Val Asn Ala Phe Gln Ala Gln Arg Gly Ala Glu
            45                  50                  55

ggc gag tgg gac gac gac ctg ctg ctg cgc gac ggc tcg ggg aag gtc      336
Gly Glu Trp Asp Asp Asp Leu Leu Leu Arg Asp Gly Ser Gly Lys Val
        60                  65                  70

gtc tac gac acc gag tgg aag gag gcc ctg ctc gac acc cgc acc gcc      384
Val Tyr Asp Thr Glu Trp Lys Glu Ala Leu Leu Asp Thr Arg Thr Ala
    75                  80                  85

gac aag cgc cgg cgc atc gcc gac aag gtc ggt acc tgg atc gac gcc      432
Asp Lys Arg Arg Arg Ile Ala Asp Lys Val Gly Thr Trp Ile Asp Ala
90                  95                  100                 105

tgc gcg gac aag ggc ttc cag gcc gtc gag ccg gac aac tac gac agc      480
Cys Ala Asp Lys Gly Phe Gln Ala Val Glu Pro Asp Asn Tyr Asp Ser
                110                 115                 120

tac acc cgc tcg aag aag ctc ttg gac gcc gcc gac gcc cag gcc ttc      528
Tyr Thr Arg Ser Lys Lys Leu Leu Asp Ala Ala Asp Ala Gln Ala Phe
            125                 130                 135

gtc aag ctg ctc gcc gag cgc gcg cac gcc ggc gga ctg gcc atc ggg      576
Val Lys Leu Leu Ala Glu Arg Ala His Ala Gly Gly Leu Ala Ile Gly
        140                 145                 150

cag aag aac acc gtc gaa ctc gcc ggg aac cgc gtc gcc aac ggt ctg      624
Gln Lys Asn Thr Val Glu Leu Ala Gly Asn Arg Val Ala Asn Gly Leu
    155                 160                 165
```

-continued

```
gac ttc gcg gtc gcc gag gag tgc ggc gag tgg gac gag tgc ggg gac      672
Asp Phe Ala Val Ala Glu Glu Cys Gly Glu Trp Asp Glu Cys Gly Asp
170                 175                 180                 185

tac acg gcc gag ttc ggc gac cac gtg atc gtc gtc gag tac acc gcc      720
Tyr Thr Ala Glu Phe Gly Asp His Val Ile Val Val Glu Tyr Thr Ala
                190                 195                 200

gcg ggc ctg agg aag gcg tgc tcc ggg ttc ggc gac acg ctg agc atc      768
Ala Gly Leu Arg Lys Ala Cys Ser Gly Phe Gly Asp Thr Leu Ser Ile
            205                 210                 215

gta cgg cgc gac ctg gac gtc tcg ccg aag ggc agc agc tcc tac gtc      816
Val Arg Arg Asp Leu Asp Val Ser Pro Lys Gly Ser Ser Ser Tyr Val
        220                 225                 230

cgc gag acc tgc tga                                                  831
Arg Glu Thr Cys
    235


<210> SEQ ID NO 11
<211> LENGTH: 276
<212> TYPE: PRT
<213> ORGANISM: Streptomyces parvulus

<400> SEQUENCE: 11

Met Ser Arg Thr Gln Val His Thr Ser Lys Lys Lys Pro Val Leu Ala
                -35                 -30                 -25

Gly Val Cys Ala Ala Ala Val Leu Ala Thr Ala Ala Ala Leu Val Pro
            -20                 -15                 -10

Gly Ser Thr Pro Ala Glu Ala Ala Val Pro Ala Pro Pro Pro Ala Gly
        -5              -1  1               5

Ala Gly Phe Asp Tyr Gln Ile Gly Gly Ala Tyr Thr Pro Pro Ser Gly
10                  15                  20                  25

Val Arg Val Val Ser Arg Asp His Thr Ala Ser Pro Ala Ala Gly Leu
                30                  35                  40

Tyr Asn Ile Cys Tyr Val Asn Ala Phe Gln Ala Gln Arg Gly Ala Glu
            45                  50                  55

Gly Glu Trp Asp Asp Asp Leu Leu Leu Arg Asp Gly Ser Gly Lys Val
        60                  65                  70

Val Tyr Asp Thr Glu Trp Lys Glu Ala Leu Leu Asp Thr Arg Thr Ala
    75                  80                  85

Asp Lys Arg Arg Arg Ile Ala Asp Lys Val Gly Thr Trp Ile Asp Ala
90                  95                  100                 105

Cys Ala Asp Lys Gly Phe Gln Ala Val Glu Pro Asp Asn Tyr Asp Ser
                110                 115                 120

Tyr Thr Arg Ser Lys Lys Leu Leu Asp Ala Ala Asp Ala Gln Ala Phe
            125                 130                 135

Val Lys Leu Leu Ala Glu Arg Ala His Ala Gly Gly Leu Ala Ile Gly
        140                 145                 150

Gln Lys Asn Thr Val Glu Leu Ala Gly Asn Arg Val Ala Asn Gly Leu
    155                 160                 165

Asp Phe Ala Val Ala Glu Glu Cys Gly Glu Trp Asp Glu Cys Gly Asp
170                 175                 180                 185

Tyr Thr Ala Glu Phe Gly Asp His Val Ile Val Val Glu Tyr Thr Ala
                190                 195                 200

Ala Gly Leu Arg Lys Ala Cys Ser Gly Phe Gly Asp Thr Leu Ser Ile
            205                 210                 215

Val Arg Arg Asp Leu Asp Val Ser Pro Lys Gly Ser Ser Ser Tyr Val
        220                 225                 230
```

```
Arg Glu Thr Cys
    235


<210> SEQ ID NO 12
<211> LENGTH: 237
<212> TYPE: PRT
<213> ORGANISM: Streptomyces parvulus

<400> SEQUENCE: 12

Ala Val Pro Ala Pro Pro Pro Ala Gly Ala Gly Phe Asp Tyr Gln Ile
1               5                   10                  15

Gly Gly Ala Tyr Thr Pro Pro Ser Gly Val Arg Val Val Ser Arg Asp
            20                  25                  30

His Thr Ala Ser Pro Ala Ala Gly Leu Tyr Asn Ile Cys Tyr Val Asn
        35                  40                  45

Ala Phe Gln Ala Gln Arg Gly Ala Glu Gly Glu Trp Asp Asp Asp Leu
    50                  55                  60

Leu Leu Arg Asp Gly Ser Gly Lys Val Val Tyr Asp Thr Glu Trp Lys
65                  70                  75                  80

Glu Ala Leu Leu Asp Thr Arg Thr Ala Asp Lys Arg Arg Arg Ile Ala
                85                  90                  95

Asp Lys Val Gly Thr Trp Ile Asp Ala Cys Ala Asp Lys Gly Phe Gln
            100                 105                 110

Ala Val Glu Pro Asp Asn Tyr Asp Ser Tyr Thr Arg Ser Lys Lys Leu
        115                 120                 125

Leu Asp Ala Ala Asp Ala Gln Ala Phe Val Lys Leu Leu Ala Glu Arg
    130                 135                 140

Ala His Ala Gly Gly Leu Ala Ile Gly Gln Lys Asn Thr Val Glu Leu
145                 150                 155                 160

Ala Gly Asn Arg Val Ala Asn Gly Leu Asp Phe Ala Val Ala Glu Glu
                165                 170                 175

Cys Gly Glu Trp Asp Glu Cys Gly Asp Tyr Thr Ala Glu Phe Gly Asp
            180                 185                 190

His Val Ile Val Val Glu Tyr Thr Ala Ala Gly Leu Arg Lys Ala Cys
        195                 200                 205

Ser Gly Phe Gly Asp Thr Leu Ser Ile Val Arg Arg Asp Leu Asp Val
    210                 215                 220

Ser Pro Lys Gly Ser Ser Ser Tyr Val Arg Glu Thr Cys
225                 230                 235


<210> SEQ ID NO 13
<211> LENGTH: 942
<212> TYPE: DNA
<213> ORGANISM: Fusarium solani
<220> FEATURE:
<221> NAME/KEY: CDS
<222> LOCATION: (1)..(519)
<220> FEATURE:
<221> NAME/KEY: sig_peptide
<222> LOCATION: (1)..(66)
<220> FEATURE:
<221> NAME/KEY: mat_peptide
<222> LOCATION: (67)..(939)
<220> FEATURE:
<221> NAME/KEY: CDS
<222> LOCATION: (571)..(939)

<400> SEQUENCE: 13

atg aag ctg aac cgc ctc atc aat agc atc att ctc ctt gtg gca tct       48
Met Lys Leu Asn Arg Leu Ile Asn Ser Ile Ile Leu Leu Val Ala Ser
```

-continued

```
        -20                 -15                 -10

tct gtg cct gca ctc gcg gtc cct tcc aac gcg aac gcc cag gtg gct       96
Ser Val Pro Ala Leu Ala Val Pro Ser Asn Ala Asn Ala Gln Val Ala
    -5                  -1  1               5                   10

gaa gca ctt tct cct cga ggc gtt acc act cgc aaa gag cta tgg aag      144
Glu Ala Leu Ser Pro Arg Gly Val Thr Thr Arg Lys Glu Leu Trp Lys
                15                  20                  25

cct aaa gtt ggc act cct tgg caa atc gtt ctt tcc gag gtc atc aag      192
Pro Lys Val Gly Thr Pro Trp Gln Ile Val Leu Ser Glu Val Ile Lys
            30                  35                  40

atc ccg aaa ggc ggc gcc aag aat ctg aag cca aac gtc ccc atc tac      240
Ile Pro Lys Gly Gly Ala Lys Asn Leu Lys Pro Asn Val Pro Ile Tyr
        45                  50                  55

gac gtg gac ttg ttt gag aac tca aag gag act ttt gac gct ctg cat      288
Asp Val Asp Leu Phe Glu Asn Ser Lys Glu Thr Phe Asp Ala Leu His
    60                  65                  70

aaa gcg ggc aag cat gtc atc tgt tac ttc agc gcc gga tct tgg gaa      336
Lys Ala Gly Lys His Val Ile Cys Tyr Phe Ser Ala Gly Ser Trp Glu
75                  80                  85                  90

aat tgg cgc gat gat agg aag agc ttc cag aag aag gat ctt ggc aag      384
Asn Trp Arg Asp Asp Arg Lys Ser Phe Gln Lys Lys Asp Leu Gly Lys
                95                  100                 105

acg ttg agt gga tgg ccg gac gaa aag tat gtc aac atc aac agc cct      432
Thr Leu Ser Gly Trp Pro Asp Glu Lys Tyr Val Asn Ile Asn Ser Pro
            110                 115                 120

tca gta cgg gcc att atg gca aag cgt atc aag ttg gct gcc gag aag      480
Ser Val Arg Ala Ile Met Ala Lys Arg Ile Lys Leu Ala Ala Glu Lys
        125                 130                 135

ggc tgt gat gcc atc gat cct gac aac ttg gat ggc tac gtaagtcatg       529
Gly Cys Asp Ala Ile Asp Pro Asp Asn Leu Asp Gly Tyr
    140                 145                 150

acccgtggac aacgaggcta tcgctaacgt cttttttta g caa gcg gat aat ggc    585
                                             Gln Ala Asp Asn Gly
                                                         155

ctg ggt cta acc gag gct gac aca atc tca tat gtc aag ttc ctc tcc      633
Leu Gly Leu Thr Glu Ala Asp Thr Ile Ser Tyr Val Lys Phe Leu Ser
            160                 165                 170

aaa gaa gca gcc aag tac cgt atg acg acg ggc atg aag aac gga ggg      681
Lys Glu Ala Ala Lys Tyr Arg Met Thr Thr Gly Met Lys Asn Gly Gly
        175                 180                 185

agc att aca aag cag gtt ctc cca tat gtc ggt ttc tgc atc aac gag      729
Ser Ile Thr Lys Gln Val Leu Pro Tyr Val Gly Phe Cys Ile Asn Glu
    190                 195                 200

tct tgc ata caa tac tca gag tgc gac tta tat gca ccc tac atc aaa      777
Ser Cys Ile Gln Tyr Ser Glu Cys Asp Leu Tyr Ala Pro Tyr Ile Lys
205                 210                 215                 220

gca gga aaa ccc gtc ttc aat att gag tac ccg gcg ggt gca cca aaa      825
Ala Gly Lys Pro Val Phe Asn Ile Glu Tyr Pro Ala Gly Ala Pro Lys
                225                 230                 235

gtg aag gct gcc gac aaa aaa agg atc tgc tca gtc act ggt gcc gcc      873
Val Lys Ala Ala Asp Lys Lys Arg Ile Cys Ser Val Thr Gly Ala Ala
            240                 245                 250

agc ggg tcg aaa ggg ttc agc aag gtt atc aag aag atg aat ctg gat      921
Ser Gly Ser Lys Gly Phe Ser Lys Val Ile Lys Lys Met Asn Leu Asp
        255                 260                 265

agt tgg gtt atg tat tgc tag                                          942
Ser Trp Val Met Tyr Cys
    270
```

```
<210> SEQ ID NO 14
<211> LENGTH: 296
<212> TYPE: PRT
<213> ORGANISM: Fusarium solani

<400> SEQUENCE: 14

Met Lys Leu Asn Arg Leu Ile Asn Ser Ile Ile Leu Leu Val Ala Ser
        -20                 -15                 -10

Ser Val Pro Ala Leu Ala Val Pro Ser Asn Ala Asn Ala Gln Val Ala
    -5              -1  1               5                   10

Glu Ala Leu Ser Pro Arg Gly Val Thr Thr Arg Lys Glu Leu Trp Lys
                15                  20                  25

Pro Lys Val Gly Thr Pro Trp Gln Ile Val Leu Ser Glu Val Ile Lys
            30                  35                  40

Ile Pro Lys Gly Gly Ala Lys Asn Leu Lys Pro Asn Val Pro Ile Tyr
        45                  50                  55

Asp Val Asp Leu Phe Glu Asn Ser Lys Glu Thr Phe Asp Ala Leu His
    60                  65                  70

Lys Ala Gly Lys His Val Ile Cys Tyr Phe Ser Ala Gly Ser Trp Glu
75                  80                  85                  90

Asn Trp Arg Asp Asp Arg Lys Ser Phe Gln Lys Lys Asp Leu Gly Lys
                95                  100                 105

Thr Leu Ser Gly Trp Pro Asp Glu Lys Tyr Val Asn Ile Asn Ser Pro
            110                 115                 120

Ser Val Arg Ala Ile Met Ala Lys Arg Ile Lys Leu Ala Ala Glu Lys
        125                 130                 135

Gly Cys Asp Ala Ile Asp Pro Asp Asn Leu Asp Gly Tyr Gln Ala Asp
    140                 145                 150

Asn Gly Leu Gly Leu Thr Glu Ala Asp Thr Ile Ser Tyr Val Lys Phe
155                 160                 165                 170

Leu Ser Lys Glu Ala Ala Lys Tyr Arg Met Thr Thr Gly Met Lys Asn
                175                 180                 185

Gly Gly Ser Ile Thr Lys Gln Val Leu Pro Tyr Val Gly Phe Cys Ile
            190                 195                 200

Asn Glu Ser Cys Ile Gln Tyr Ser Glu Cys Asp Leu Tyr Ala Pro Tyr
        205                 210                 215

Ile Lys Ala Gly Lys Pro Val Phe Asn Ile Glu Tyr Pro Ala Gly Ala
    220                 225                 230

Pro Lys Val Lys Ala Ala Asp Lys Lys Arg Ile Cys Ser Val Thr Gly
235                 240                 245                 250

Ala Ala Ser Gly Ser Lys Gly Phe Ser Lys Val Ile Lys Lys Met Asn
                255                 260                 265

Leu Asp Ser Trp Val Met Tyr Cys
            270


<210> SEQ ID NO 15
<211> LENGTH: 274
<212> TYPE: PRT
<213> ORGANISM: Fusarium solani

<400> SEQUENCE: 15

Val Pro Ser Asn Ala Asn Ala Gln Val Ala Glu Ala Leu Ser Pro Arg
1               5                   10                  15

Gly Val Thr Thr Arg Lys Glu Leu Trp Lys Pro Lys Val Gly Thr Pro
            20                  25                  30

Trp Gln Ile Val Leu Ser Glu Val Ile Lys Ile Pro Lys Gly Gly Ala
```

```
        35                  40                  45

Lys Asn Leu Lys Pro Asn Val Pro Ile Tyr Asp Val Asp Leu Phe Glu
    50                  55                  60

Asn Ser Lys Glu Thr Phe Asp Ala Leu His Lys Ala Gly Lys His Val
65                  70                  75                  80

Ile Cys Tyr Phe Ser Ala Gly Ser Trp Glu Asn Trp Arg Asp Asp Arg
                85                  90                  95

Lys Ser Phe Gln Lys Lys Asp Leu Gly Lys Thr Leu Ser Gly Trp Pro
            100                 105                 110

Asp Glu Lys Tyr Val Asn Ile Asn Ser Pro Ser Val Arg Ala Ile Met
        115                 120                 125

Ala Lys Arg Ile Lys Leu Ala Ala Glu Lys Gly Cys Asp Ala Ile Asp
    130                 135                 140

Pro Asp Asn Leu Asp Gly Tyr Gln Ala Asp Asn Gly Leu Gly Leu Thr
145                 150                 155                 160

Glu Ala Asp Thr Ile Ser Tyr Val Lys Phe Leu Ser Lys Glu Ala Ala
                165                 170                 175

Lys Tyr Arg Met Thr Thr Gly Met Lys Asn Gly Gly Ser Ile Thr Lys
            180                 185                 190

Gln Val Leu Pro Tyr Val Gly Phe Cys Ile Asn Glu Ser Cys Ile Gln
        195                 200                 205

Tyr Ser Glu Cys Asp Leu Tyr Ala Pro Tyr Ile Lys Ala Gly Lys Pro
    210                 215                 220

Val Phe Asn Ile Glu Tyr Pro Ala Gly Ala Pro Lys Val Lys Ala Ala
225                 230                 235                 240

Asp Lys Lys Arg Ile Cys Ser Val Thr Gly Ala Ala Ser Gly Ser Lys
                245                 250                 255

Gly Phe Ser Lys Val Ile Lys Lys Met Asn Leu Asp Ser Trp Val Met
            260                 265                 270

Tyr Cys


<210> SEQ ID NO 16
<211> LENGTH: 1064
<212> TYPE: DNA
<213> ORGANISM: Fusarium solani
<220> FEATURE:
<221> NAME/KEY: CDS
<222> LOCATION: (1)..(51)
<220> FEATURE:
<221> NAME/KEY: sig_peptide
<222> LOCATION: (1)..(111)
<220> FEATURE:
<221> NAME/KEY: CDS
<222> LOCATION: (100)..(297)
<220> FEATURE:
<221> NAME/KEY: mat_peptide
<222> LOCATION: (112)..(1061)
<220> FEATURE:
<221> NAME/KEY: CDS
<222> LOCATION: (360)..(1061)

<400> SEQUENCE: 16

atg gtg gcc ttc agc cgt att gct gtc acc act ctc gcc ctt ggc ggt        48
Met Val Ala Phe Ser Arg Ile Ala Val Thr Thr Leu Ala Leu Gly Gly
    -20                 -15                 -10

tct gtaagcgctc gtcgtagagg agaatgtcct gctgctgacg ctggcaag acc gca      105
Ser                                                       Thr Ala
-5

caa gcc aag cct gcc acg gcg gcg agg gct act ggg ctc gcc gac ttc       153
Gln Ala Lys Pro Ala Thr Ala Ala Arg Ala Thr Gly Leu Ala Asp Phe
```

-continued

```
    -1  1               5                   10

aag cca ggt gtg cag tgg gag att tgt att cat cat ccc atc aag cat      201
Lys Pro Gly Val Gln Trp Glu Ile Cys Ile His His Pro Ile Lys His
15                  20                  25                  30

gat agt gcc gca gac ttg atc ccg acc aag gcc aag gtc tgg gat atc      249
Asp Ser Ala Ala Asp Leu Ile Pro Thr Lys Ala Lys Val Trp Asp Ile
                35                  40                  45

gac atg ggc cac gct cag gag ttc cct aac atg atc ccc atg ctc aag      297
Asp Met Gly His Ala Gln Glu Phe Pro Asn Met Ile Pro Met Leu Lys
            50                  55                  60

gtaagcagac ttacttcaac attttggtat ggataagcca tactaaccag attgcctaac    357

ag agc gct ggc aaa ttc gtt att tgt tac ttc aac gcc gga gcc ctt       404
   Ser Ala Gly Lys Phe Val Ile Cys Tyr Phe Asn Ala Gly Ala Leu
           65                  70                  75

cag gac tgg gat gac gac aag agc aag ttc ccc aag gag gtc atc ggt      452
Gln Asp Trp Asp Asp Asp Lys Ser Lys Phe Pro Lys Glu Val Ile Gly
        80                  85                  90

cac tcc ctg tcc tac ccc tac gat agc gaa gaa tgg tac ctc gac atc      500
His Ser Leu Ser Tyr Pro Tyr Asp Ser Glu Glu Trp Tyr Leu Asp Ile
    95                  100                 105

cgg gac tcg cgt gtc ctc gag ttg caa acg gca cga cta gac att gct      548
Arg Asp Ser Arg Val Leu Glu Leu Gln Thr Ala Arg Leu Asp Ile Ala
110                 115                 120                 125

gcc aag atc ggc tgc gat gcc gtc gat cct gac aac gtt gac gcc tgg      596
Ala Lys Ile Gly Cys Asp Ala Val Asp Pro Asp Asn Val Asp Ala Trp
                130                 135                 140

caa caa gat gac gaa gac ccc acg ggc ttc aag ctc aag tct tcc gac      644
Gln Gln Asp Asp Glu Asp Pro Thr Gly Phe Lys Leu Lys Ser Ser Asp
            145                 150                 155

tac acc aac tac ctc aag aac ctc gcc aag tat gcc cac tcg atc aag      692
Tyr Thr Asn Tyr Leu Lys Asn Leu Ala Lys Tyr Ala His Ser Ile Lys
        160                 165                 170

acc aag gac ggt cag ccc ctc ctc gtc ggg cag aag aac gcc ccc gag      740
Thr Lys Asp Gly Gln Pro Leu Leu Val Gly Gln Lys Asn Ala Pro Glu
    175                 180                 185

atc gcc gag gac ctc gtc tcg acc ctc gac ttt gcc gtg ctc gag tcc      788
Ile Ala Glu Asp Leu Val Ser Thr Leu Asp Phe Ala Val Leu Glu Ser
190                 195                 200                 205

tgc cgc ggc aac agc gac ccc aac gaa gag agc tgg ccc ttt tgc gag      836
Cys Arg Gly Asn Ser Asp Pro Asn Glu Glu Ser Trp Pro Phe Cys Glu
                210                 215                 220

gac ttc cag acc tac atc gac gcc ggc aag ccc gtc ctc cag atc gag      884
Asp Phe Gln Thr Tyr Ile Asp Ala Gly Lys Pro Val Leu Gln Ile Glu
            225                 230                 235

tac ccc ccc tcg gtg gag aag acg ggc aag gtc agc gcc tcg gat aac      932
Tyr Pro Pro Ser Val Glu Lys Thr Gly Lys Val Ser Ala Ser Asp Asn
        240                 245                 250

aag tac tac tgc act gcc gag gat gag gac aag ggc ttc agc aag atc      980
Lys Tyr Tyr Cys Thr Ala Glu Asp Glu Asp Lys Gly Phe Ser Lys Ile
    255                 260                 265

atc aag tgg gct tct gct cag ctt gat ggc tgg ggt cag tac tgt ggc     1028
Ile Lys Trp Ala Ser Ala Gln Leu Asp Gly Trp Gly Gln Tyr Cys Gly
270                 275                 280                 285

gag gag ccc ttc cgt act cct gcg gcc aag tat taa                     1064
Glu Glu Pro Phe Arg Thr Pro Ala Ala Lys Tyr
                290                 295
```

<210> SEQ ID NO 17
<211> LENGTH: 317

<212> TYPE: PRT
<213> ORGANISM: Fusarium solani

<400> SEQUENCE: 17

```
Met Val Ala Phe Ser Arg Ile Ala Val Thr Thr Leu Ala Leu Gly Gly
    -20                 -15                 -10

Ser Thr Ala Gln Ala Lys Pro Ala Thr Ala Ala Arg Ala Thr Gly Leu
-5              -1  1               5                   10

Ala Asp Phe Lys Pro Gly Val Gln Trp Glu Ile Cys Ile His His Pro
            15                  20                  25

Ile Lys His Asp Ser Ala Ala Asp Leu Ile Pro Thr Lys Ala Lys Val
        30                  35                  40

Trp Asp Ile Asp Met Gly His Ala Gln Glu Phe Pro Asn Met Ile Pro
    45                  50                  55

Met Leu Lys Ser Ala Gly Lys Phe Val Ile Cys Tyr Phe Asn Ala Gly
60                  65                  70                  75

Ala Leu Gln Asp Trp Asp Asp Asp Lys Ser Lys Phe Pro Lys Glu Val
                80                  85                  90

Ile Gly His Ser Leu Ser Tyr Pro Tyr Asp Ser Glu Glu Trp Tyr Leu
            95                  100                 105

Asp Ile Arg Asp Ser Arg Val Leu Glu Leu Gln Thr Ala Arg Leu Asp
        110                 115                 120

Ile Ala Ala Lys Ile Gly Cys Asp Ala Val Asp Pro Asp Asn Val Asp
    125                 130                 135

Ala Trp Gln Gln Asp Asp Glu Asp Pro Thr Gly Phe Lys Leu Lys Ser
140                 145                 150                 155

Ser Asp Tyr Thr Asn Tyr Leu Lys Asn Leu Ala Lys Tyr Ala His Ser
                160                 165                 170

Ile Lys Thr Lys Asp Gly Gln Pro Leu Leu Val Gly Gln Lys Asn Ala
            175                 180                 185

Pro Glu Ile Ala Glu Asp Leu Val Ser Thr Leu Asp Phe Ala Val Leu
        190                 195                 200

Glu Ser Cys Arg Gly Asn Ser Asp Pro Asn Glu Glu Ser Trp Pro Phe
    205                 210                 215

Cys Glu Asp Phe Gln Thr Tyr Ile Asp Ala Gly Lys Pro Val Leu Gln
220                 225                 230                 235

Ile Glu Tyr Pro Pro Ser Val Glu Lys Thr Gly Lys Val Ser Ala Ser
                240                 245                 250

Asp Asn Lys Tyr Tyr Cys Thr Ala Glu Asp Glu Asp Lys Gly Phe Ser
            255                 260                 265

Lys Ile Ile Lys Trp Ala Ser Ala Gln Leu Asp Gly Trp Gly Gln Tyr
        270                 275                 280

Cys Gly Glu Glu Pro Phe Arg Thr Pro Ala Ala Lys Tyr
    285                 290                 295
```

<210> SEQ ID NO 18
<211> LENGTH: 296
<212> TYPE: PRT
<213> ORGANISM: Fusarium solani

<400> SEQUENCE: 18

```
Lys Pro Ala Thr Ala Ala Arg Ala Thr Gly Leu Ala Asp Phe Lys Pro
1               5                   10                  15

Gly Val Gln Trp Glu Ile Cys Ile His His Pro Ile Lys His Asp Ser
            20                  25                  30
```

```
Ala Ala Asp Leu Ile Pro Thr Lys Ala Lys Val Trp Asp Ile Asp Met
        35                  40                  45

Gly His Ala Gln Glu Phe Pro Asn Met Ile Pro Met Leu Lys Ser Ala
    50                  55                  60

Gly Lys Phe Val Ile Cys Tyr Phe Asn Ala Gly Ala Leu Gln Asp Trp
65                  70                  75                  80

Asp Asp Asp Lys Ser Lys Phe Pro Lys Glu Val Ile Gly His Ser Leu
                85                  90                  95

Ser Tyr Pro Tyr Asp Ser Glu Glu Trp Tyr Leu Asp Ile Arg Asp Ser
            100                 105                 110

Arg Val Leu Glu Leu Gln Thr Ala Arg Leu Asp Ile Ala Ala Lys Ile
        115                 120                 125

Gly Cys Asp Ala Val Asp Pro Asp Asn Val Asp Ala Trp Gln Gln Asp
    130                 135                 140

Asp Glu Asp Pro Thr Gly Phe Lys Leu Lys Ser Ser Asp Tyr Thr Asn
145                 150                 155                 160

Tyr Leu Lys Asn Leu Ala Lys Tyr Ala His Ser Ile Lys Thr Lys Asp
                165                 170                 175

Gly Gln Pro Leu Leu Val Gly Gln Lys Asn Ala Pro Glu Ile Ala Glu
            180                 185                 190

Asp Leu Val Ser Thr Leu Asp Phe Ala Val Leu Glu Ser Cys Arg Gly
        195                 200                 205

Asn Ser Asp Pro Asn Glu Glu Ser Trp Pro Phe Cys Glu Asp Phe Gln
    210                 215                 220

Thr Tyr Ile Asp Ala Gly Lys Pro Val Leu Gln Ile Glu Tyr Pro Pro
225                 230                 235                 240

Ser Val Glu Lys Thr Gly Lys Val Ser Ala Ser Asp Asn Lys Tyr Tyr
                245                 250                 255

Cys Thr Ala Glu Asp Glu Asp Lys Gly Phe Ser Lys Ile Ile Lys Trp
            260                 265                 270

Ala Ser Ala Gln Leu Asp Gly Trp Gly Gln Tyr Cys Gly Glu Glu Pro
        275                 280                 285

Phe Arg Thr Pro Ala Ala Lys Tyr
    290                 295
```

<210> SEQ ID NO 19
<211> LENGTH: 795
<212> TYPE: DNA
<213> ORGANISM: Nonomuraea guangzhouensis
<220> FEATURE:
<221> NAME/KEY: CDS
<222> LOCATION: (1)..(792)
<220> FEATURE:
<221> NAME/KEY: sig_peptide
<222> LOCATION: (1)..(81)
<220> FEATURE:
<221> NAME/KEY: mat_peptide
<222> LOCATION: (82)..(792)

<400> SEQUENCE: 19

```
atg agc ctc acc cgt agc tgc tta ggc gtt gcc gtg gcc ctt gcc gcc       48
Met Ser Leu Thr Arg Ser Cys Leu Gly Val Ala Val Ala Leu Ala Ala
        -25                 -20                 -15

gcg ttg gcc gcc aca ccg tcg acc gcc tcg gcg gcc gcg gtc acc ctg       96
Ala Leu Ala Ala Thr Pro Ser Thr Ala Ser Ala Ala Ala Val Thr Leu
    -10                 -5              -1  1               5

ccc ccg aca cac gcc ggg ttc gac tac cag atc ggc ggc gcc tac acg      144
Pro Pro Thr His Ala Gly Phe Asp Tyr Gln Ile Gly Gly Ala Tyr Thr
                10                  15                  20
```

```
ccg ccg gcc ggg gtc acc gtg gtc acc agg gac cgg gcc gcc gcg ccc      192
Pro Pro Ala Gly Val Thr Val Val Thr Arg Asp Arg Ala Ala Ala Pro
            25                  30                  35

gcc gcg ggg ctg tac aac atc tgc tac gtc aac gcc ttc cag gtt cag      240
Ala Ala Gly Leu Tyr Asn Ile Cys Tyr Val Asn Ala Phe Gln Val Gln
        40                  45                  50

ccg ggc gag cag ggc gac tgg gac tcc gac ctg ctg ctg cgt gac gcc      288
Pro Gly Glu Gln Gly Asp Trp Asp Ser Asp Leu Leu Leu Arg Asp Ala
    55                  60                  65

aac ggt gac gtg gtc gtc gac gag gac tgg ggc gag gca ctg ctg gac      336
Asn Gly Asp Val Val Val Asp Glu Asp Trp Gly Glu Ala Leu Leu Asp
70                  75                  80                  85

ctg cgt acg gat gcc aag cgg aag cgc gtc gcc gcg aag gtg aac tcc      384
Leu Arg Thr Asp Ala Lys Arg Lys Arg Val Ala Ala Lys Val Asn Ser
                90                  95                  100

tgg atc acc ggc tgc aag acc aag ggc tac cag gcc atc gag ccc gac      432
Trp Ile Thr Gly Cys Lys Thr Lys Gly Tyr Gln Ala Ile Glu Pro Asp
            105                 110                 115

aac tac gac agc tac acc cgg tcg aag aag ctg ctg acg gcg tcg aac      480
Asn Tyr Asp Ser Tyr Thr Arg Ser Lys Lys Leu Leu Thr Ala Ser Asn
        120                 125                 130

gcc cag gcg tac atc cgg ctg ctc agc agc cac gcc cac acc cag ggc      528
Ala Gln Ala Tyr Ile Arg Leu Leu Ser Ser His Ala His Thr Gln Gly
    135                 140                 145

ctg gcc atc gcg cag aag aac acc gtg gag ctg gcc ggc tcg cgc acc      576
Leu Ala Ile Ala Gln Lys Asn Thr Val Glu Leu Ala Gly Ser Arg Thr
150                 155                 160                 165

gcg aac ggg ctc gac ttc gcg gtc gcg gag gag tgc ggc cag tac aag      624
Ala Asn Gly Leu Asp Phe Ala Val Ala Glu Glu Cys Gly Gln Tyr Lys
                170                 175                 180

gag tgc ggc gac tac acg gcg gcg ttc ggc aac aac gtg atc gtg atc      672
Glu Cys Gly Asp Tyr Thr Ala Ala Phe Gly Asn Asn Val Ile Val Ile
            185                 190                 195

gag tac aac gcc acc ggt ctg tcg agg gcg tgc tcg ggc tgg ggc acc      720
Glu Tyr Asn Ala Thr Gly Leu Ser Arg Ala Cys Ser Gly Trp Gly Thr
        200                 205                 210

aag ctg agc atc gtc cgg cgc gat gtg gac gtc tca ccc aag ggc agc      768
Lys Leu Ser Ile Val Arg Arg Asp Val Asp Val Ser Pro Lys Gly Ser
    215                 220                 225

agc gga tac gtc cgc aag acc tgc tga                                  795
Ser Gly Tyr Val Arg Lys Thr Cys
230                 235


<210> SEQ ID NO 20
<211> LENGTH: 264
<212> TYPE: PRT
<213> ORGANISM: Nonomuraea guangzhouensis

<400> SEQUENCE: 20

Met Ser Leu Thr Arg Ser Cys Leu Gly Val Ala Val Ala Leu Ala Ala
        -25                 -20                 -15

Ala Leu Ala Ala Thr Pro Ser Thr Ala Ser Ala Ala Ala Val Thr Leu
    -10                 -5                  -1  1               5

Pro Pro Thr His Ala Gly Phe Asp Tyr Gln Ile Gly Gly Ala Tyr Thr
                10                  15                  20

Pro Pro Ala Gly Val Thr Val Val Thr Arg Asp Arg Ala Ala Ala Pro
            25                  30                  35

Ala Ala Gly Leu Tyr Asn Ile Cys Tyr Val Asn Ala Phe Gln Val Gln
        40                  45                  50
```

```
Pro Gly Glu Gln Gly Asp Trp Asp Ser Asp Leu Leu Leu Arg Asp Ala
    55                  60                  65

Asn Gly Asp Val Val Val Asp Glu Asp Trp Gly Glu Ala Leu Leu Asp
70                  75                  80                  85

Leu Arg Thr Asp Ala Lys Arg Lys Arg Val Ala Ala Lys Val Asn Ser
                90                  95                  100

Trp Ile Thr Gly Cys Lys Thr Lys Gly Tyr Gln Ala Ile Glu Pro Asp
            105                 110                 115

Asn Tyr Asp Ser Tyr Thr Arg Ser Lys Lys Leu Leu Thr Ala Ser Asn
        120                 125                 130

Ala Gln Ala Tyr Ile Arg Leu Leu Ser Ser His Ala His Thr Gln Gly
    135                 140                 145

Leu Ala Ile Ala Gln Lys Asn Thr Val Glu Leu Ala Gly Ser Arg Thr
150                 155                 160                 165

Ala Asn Gly Leu Asp Phe Ala Val Ala Glu Glu Cys Gly Gln Tyr Lys
                170                 175                 180

Glu Cys Gly Asp Tyr Thr Ala Ala Phe Gly Asn Asn Val Ile Val Ile
            185                 190                 195

Glu Tyr Asn Ala Thr Gly Leu Ser Arg Ala Cys Ser Gly Trp Gly Thr
        200                 205                 210

Lys Leu Ser Ile Val Arg Arg Asp Val Asp Val Ser Pro Lys Gly Ser
    215                 220                 225

Ser Gly Tyr Val Arg Lys Thr Cys
230                 235


<210> SEQ ID NO 21
<211> LENGTH: 237
<212> TYPE: PRT
<213> ORGANISM: Nonomuraea guangzhouensis

<400> SEQUENCE: 21

Ala Ala Val Thr Leu Pro Pro Thr His Ala Gly Phe Asp Tyr Gln Ile
1               5                   10                  15

Gly Gly Ala Tyr Thr Pro Pro Ala Gly Val Thr Val Val Thr Arg Asp
            20                  25                  30

Arg Ala Ala Ala Pro Ala Ala Gly Leu Tyr Asn Ile Cys Tyr Val Asn
        35                  40                  45

Ala Phe Gln Val Gln Pro Gly Glu Gln Gly Asp Trp Asp Ser Asp Leu
    50                  55                  60

Leu Leu Arg Asp Ala Asn Gly Asp Val Val Val Asp Glu Asp Trp Gly
65                  70                  75                  80

Glu Ala Leu Leu Asp Leu Arg Thr Asp Ala Lys Arg Lys Arg Val Ala
                85                  90                  95

Ala Lys Val Asn Ser Trp Ile Thr Gly Cys Lys Thr Lys Gly Tyr Gln
            100                 105                 110

Ala Ile Glu Pro Asp Asn Tyr Asp Ser Tyr Thr Arg Ser Lys Lys Leu
        115                 120                 125

Leu Thr Ala Ser Asn Ala Gln Ala Tyr Ile Arg Leu Leu Ser Ser His
    130                 135                 140

Ala His Thr Gln Gly Leu Ala Ile Ala Gln Lys Asn Thr Val Glu Leu
145                 150                 155                 160

Ala Gly Ser Arg Thr Ala Asn Gly Leu Asp Phe Ala Val Ala Glu Glu
                165                 170                 175

Cys Gly Gln Tyr Lys Glu Cys Gly Asp Tyr Thr Ala Ala Phe Gly Asn
```

```
            180                 185                 190

Asn Val Ile Val Ile Glu Tyr Asn Ala Thr Gly Leu Ser Arg Ala Cys
        195                 200                 205

Ser Gly Trp Gly Thr Lys Leu Ser Ile Val Arg Arg Asp Val Asp Val
    210                 215                 220

Ser Pro Lys Gly Ser Ser Gly Tyr Val Arg Lys Thr Cys
225                 230                 235


<210> SEQ ID NO 22
<211> LENGTH: 819
<212> TYPE: DNA
<213> ORGANISM: Streptomyces sp
<220> FEATURE:
<221> NAME/KEY: CDS
<222> LOCATION: (1)..(816)
<220> FEATURE:
<221> NAME/KEY: sig_peptide
<222> LOCATION: (1)..(99)
<220> FEATURE:
<221> NAME/KEY: mat_peptide
<222> LOCATION: (100)..(816)

<400> SEQUENCE: 22

atg cgc atc gac cgc ggt tcc gct ctc cga ctc acc gcg ctt ccg gcg       48
Met Arg Ile Asp Arg Gly Ser Ala Leu Arg Leu Thr Ala Leu Pro Ala
            -30                 -25                 -20

ctg ttg gcc gcc gca ctc gtc ccg tcg ctc gcg atg gac cag gcc ggc       96
Leu Leu Ala Ala Ala Leu Val Pro Ser Leu Ala Met Asp Gln Ala Gly
        -15                 -10                 -5

gcg gcg tcc gaa gcg gtg tca ccg ccg ccg gcc cac gcc ggt ttc gac      144
Ala Ala Ser Glu Ala Val Ser Pro Pro Pro Ala His Ala Gly Phe Asp
-1  1               5                   10                  15

tac cag atc ggc ggc gcg tac ccc ccg ccc gcc ggg gtg agc gtg gtc      192
Tyr Gln Ile Gly Gly Ala Tyr Pro Pro Pro Ala Gly Val Ser Val Val
                20                  25                  30

agc cgc gac cac acc gac ccg ccc gcc gcc ggg ctg tac aac atc tgc      240
Ser Arg Asp His Thr Asp Pro Pro Ala Ala Gly Leu Tyr Asn Ile Cys
            35                  40                  45

tac gtc aac gcg ttc cag gca cag ccc ggc gcc gag ggc gac tgg gac      288
Tyr Val Asn Ala Phe Gln Ala Gln Pro Gly Ala Glu Gly Asp Trp Asp
        50                  55                  60

tcc gac ctc ctg ctc cac gac gcc aag gga aag gtc gtc tac gac gag      336
Ser Asp Leu Leu Leu His Asp Ala Lys Gly Lys Val Val Tyr Asp Glu
    65                  70                  75

gac tgg ggc gag gcg ctg ctc gac acc agc acc gcg aac aag cgg cag      384
Asp Trp Gly Glu Ala Leu Leu Asp Thr Ser Thr Ala Asn Lys Arg Gln
80                  85                  90                  95

cgg atc gcc gag aag gtc gac ggc tgg atc gac gac tgc gcg gcc aag      432
Arg Ile Ala Glu Lys Val Asp Gly Trp Ile Asp Asp Cys Ala Ala Lys
                100                 105                 110

ggc tac cag gcg atc gag ccc gac aac tac gac agc tac agc cgc tcc      480
Gly Tyr Gln Ala Ile Glu Pro Asp Asn Tyr Asp Ser Tyr Ser Arg Ser
            115                 120                 125

ggc aag ctg ctg acc tcc gcc gag gcg gag gcg tac atc acc ctg ctg      528
Gly Lys Leu Leu Thr Ser Ala Glu Ala Glu Ala Tyr Ile Thr Leu Leu
        130                 135                 140

tcc gcg cac gcg cac gcc gac ggc ctg gcc atc gcg cag aag aac acc      576
Ser Ala His Ala His Ala Asp Gly Leu Ala Ile Ala Gln Lys Asn Thr
    145                 150                 155

tcc gag ctg gcg ggc gac cgg gcg aag acc gga ctg gac ttc gcg gtc      624
Ser Glu Leu Ala Gly Asp Arg Ala Lys Thr Gly Leu Asp Phe Ala Val
160                 165                 170                 175
```

```
gcg gag gag tgc ggg acg tac gac gag tgc ggc gac tac acc gcc gcg      672
Ala Glu Glu Cys Gly Thr Tyr Asp Glu Cys Gly Asp Tyr Thr Ala Ala
                180                 185                 190

ttc ggc gac cac gtc atc gtc atc gag tac acc gcg aag ggg ctg cag      720
Phe Gly Asp His Val Ile Val Ile Glu Tyr Thr Ala Lys Gly Leu Gln
            195                 200                 205

aag gcg tgc tcc ggc tgg ggc gac gag ttg agc gtc gtc cgc cgt gac      768
Lys Ala Cys Ser Gly Trp Gly Asp Glu Leu Ser Val Val Arg Arg Asp
        210                 215                 220

ctg gac gtc tct ccg gcc ggc agc aag ggc tac gtc cgc cag acc tgc      816
Leu Asp Val Ser Pro Ala Gly Ser Lys Gly Tyr Val Arg Gln Thr Cys
    225                 230                 235

tga                                                                  819


<210> SEQ ID NO 23
<211> LENGTH: 272
<212> TYPE: PRT
<213> ORGANISM: Streptomyces sp

<400> SEQUENCE: 23

Met Arg Ile Asp Arg Gly Ser Ala Leu Arg Leu Thr Ala Leu Pro Ala
            -30                 -25                 -20

Leu Leu Ala Ala Ala Leu Val Pro Ser Leu Ala Met Asp Gln Ala Gly
        -15                 -10                 -5

Ala Ala Ser Glu Ala Val Ser Pro Pro Pro Ala His Ala Gly Phe Asp
-1  1               5                   10                  15

Tyr Gln Ile Gly Gly Ala Tyr Pro Pro Pro Ala Gly Val Ser Val Val
                20                  25                  30

Ser Arg Asp His Thr Asp Pro Pro Ala Ala Gly Leu Tyr Asn Ile Cys
            35                  40                  45

Tyr Val Asn Ala Phe Gln Ala Gln Pro Gly Ala Glu Gly Asp Trp Asp
        50                  55                  60

Ser Asp Leu Leu Leu His Asp Ala Lys Gly Lys Val Val Tyr Asp Glu
    65                  70                  75

Asp Trp Gly Glu Ala Leu Leu Asp Thr Ser Thr Ala Asn Lys Arg Gln
80                  85                  90                  95

Arg Ile Ala Glu Lys Val Asp Gly Trp Ile Asp Asp Cys Ala Ala Lys
                100                 105                 110

Gly Tyr Gln Ala Ile Glu Pro Asp Asn Tyr Asp Ser Tyr Ser Arg Ser
            115                 120                 125

Gly Lys Leu Leu Thr Ser Ala Glu Ala Glu Ala Tyr Ile Thr Leu Leu
        130                 135                 140

Ser Ala His Ala His Ala Asp Gly Leu Ala Ile Ala Gln Lys Asn Thr
    145                 150                 155

Ser Glu Leu Ala Gly Asp Arg Ala Lys Thr Gly Leu Asp Phe Ala Val
160                 165                 170                 175

Ala Glu Glu Cys Gly Thr Tyr Asp Glu Cys Gly Asp Tyr Thr Ala Ala
                180                 185                 190

Phe Gly Asp His Val Ile Val Ile Glu Tyr Thr Ala Lys Gly Leu Gln
            195                 200                 205

Lys Ala Cys Ser Gly Trp Gly Asp Glu Leu Ser Val Val Arg Arg Asp
        210                 215                 220

Leu Asp Val Ser Pro Ala Gly Ser Lys Gly Tyr Val Arg Gln Thr Cys
    225                 230                 235
```

<210> SEQ ID NO 24
<211> LENGTH: 239
<212> TYPE: PRT
<213> ORGANISM: Streptomyces sp

<400> SEQUENCE: 24

```
Ala Ser Glu Ala Val Ser Pro Pro Pro Ala His Ala Gly Phe Asp Tyr
1               5                   10                  15

Gln Ile Gly Gly Ala Tyr Pro Pro Pro Ala Gly Val Ser Val Val Ser
            20                  25                  30

Arg Asp His Thr Asp Pro Pro Ala Ala Gly Leu Tyr Asn Ile Cys Tyr
        35                  40                  45

Val Asn Ala Phe Gln Ala Gln Pro Gly Ala Glu Gly Asp Trp Asp Ser
    50                  55                  60

Asp Leu Leu Leu His Asp Ala Lys Gly Lys Val Val Tyr Asp Glu Asp
65                  70                  75                  80

Trp Gly Glu Ala Leu Leu Asp Thr Ser Thr Ala Asn Lys Arg Gln Arg
                85                  90                  95

Ile Ala Glu Lys Val Asp Gly Trp Ile Asp Asp Cys Ala Ala Lys Gly
            100                 105                 110

Tyr Gln Ala Ile Glu Pro Asp Asn Tyr Asp Ser Tyr Ser Arg Ser Gly
        115                 120                 125

Lys Leu Leu Thr Ser Ala Glu Ala Glu Ala Tyr Ile Thr Leu Leu Ser
    130                 135                 140

Ala His Ala His Ala Asp Gly Leu Ala Ile Ala Gln Lys Asn Thr Ser
145                 150                 155                 160

Glu Leu Ala Gly Asp Arg Ala Lys Thr Gly Leu Asp Phe Ala Val Ala
                165                 170                 175

Glu Glu Cys Gly Thr Tyr Asp Glu Cys Gly Asp Tyr Thr Ala Ala Phe
            180                 185                 190

Gly Asp His Val Ile Val Ile Glu Tyr Thr Ala Lys Gly Leu Gln Lys
        195                 200                 205

Ala Cys Ser Gly Trp Gly Asp Glu Leu Ser Val Val Arg Arg Asp Leu
    210                 215                 220

Asp Val Ser Pro Ala Gly Ser Lys Gly Tyr Val Arg Gln Thr Cys
225                 230                 235
```

<210> SEQ ID NO 25
<211> LENGTH: 864
<212> TYPE: DNA
<213> ORGANISM: Vibrio sp
<220> FEATURE:
<221> NAME/KEY: CDS
<222> LOCATION: (1)..(861)
<220> FEATURE:
<221> NAME/KEY: sig_peptide
<222> LOCATION: (1)..(69)
<220> FEATURE:
<221> NAME/KEY: mat_peptide
<222> LOCATION: (70)..(861)

<400> SEQUENCE: 25

```
atg cct tat tat cgt cca tta aac tac gtt atc tgc ttg ctc ggt cta       48
Met Pro Tyr Tyr Arg Pro Leu Asn Tyr Val Ile Cys Leu Leu Gly Leu
            -20                 -15                 -10

gcg ctg ctt gtt ggc tgt ggg agc gat agt aaa gac tct gaa agc gac       96
Ala Leu Leu Val Gly Cys Gly Ser Asp Ser Lys Asp Ser Glu Ser Asp
        -5              -1  1               5

ttc gaa att ctc acc ccc gta acg ggt ggc aat tgg tat caa ccc acc      144
Phe Glu Ile Leu Thr Pro Val Thr Gly Gly Asn Trp Tyr Gln Pro Thr
```

-continued

```
10                  15                  20                  25

cgc caa acg acc tgg cag tgg cag ctc aca aat acg ctt aac tca agc      192
Arg Gln Thr Thr Trp Gln Trp Gln Leu Thr Asn Thr Leu Asn Ser Ser
            30                  35                  40

tac aat gtg acg gta tat gac att gac ctt ttc gat acc agc ccg agt      240
Tyr Asn Val Thr Val Tyr Asp Ile Asp Leu Phe Asp Thr Ser Pro Ser
            45                  50                  55

gac atc caa gcg tta caa acc gag ggc cac aag gtc atc tgc tac ttt      288
Asp Ile Gln Ala Leu Gln Thr Glu Gly His Lys Val Ile Cys Tyr Phe
        60                  65                  70

tct gct ggt tcg ttt gaa gat tgg cgt gac gac gcc gct gaa ttc tca      336
Ser Ala Gly Ser Phe Glu Asp Trp Arg Asp Asp Ala Ala Glu Phe Ser
    75                  80                  85

tca agc gta tta ggt gat acg ctt gat ggc tgg gaa gat gaa cgc tgg      384
Ser Ser Val Leu Gly Asp Thr Leu Asp Gly Trp Glu Asp Glu Arg Trp
90                  95                  100                 105

tta gac att cga caa tca tcc gtt cgc gat atc atg tac gct cgc tta      432
Leu Asp Ile Arg Gln Ser Ser Val Arg Asp Ile Met Tyr Ala Arg Leu
            110                 115                 120

caa ctg gca caa act aaa ggc tgt gat ggt gtt gaa ccg gat aat gtc      480
Gln Leu Ala Gln Thr Lys Gly Cys Asp Gly Val Glu Pro Asp Asn Val
            125                 130                 135

gat ggc tac acc aac aat tct ggc ttt aac ctt ggt tat tca gac caa      528
Asp Gly Tyr Thr Asn Asn Ser Gly Phe Asn Leu Gly Tyr Ser Asp Gln
        140                 145                 150

ctc atg ttc aat cgt tac ctc gcc aac tca gcc cac caa ctc ggc ttg      576
Leu Met Phe Asn Arg Tyr Leu Ala Asn Ser Ala His Gln Leu Gly Leu
    155                 160                 165

tcc ata ggg ctg aaa aac gat tta cgg caa att acc gat tta gtc gaa      624
Ser Ile Gly Leu Lys Asn Asp Leu Arg Gln Ile Thr Asp Leu Val Glu
170                 175                 180                 185

tat ttt gac ttc gcc gtc aac gag caa tgc ttt gaa tac aac gag tgt      672
Tyr Phe Asp Phe Ala Val Asn Glu Gln Cys Phe Glu Tyr Asn Glu Cys
            190                 195                 200

ggc tac cta gca cct ttt att gac gcc aac aaa gcg gtg ttt aac gcc      720
Gly Tyr Leu Ala Pro Phe Ile Asp Ala Asn Lys Ala Val Phe Asn Ala
            205                 210                 215

gag tat gaa tcg act tac gtc gat aat acc agc gca cgt gat gca ttg      768
Glu Tyr Glu Ser Thr Tyr Val Asp Asn Thr Ser Ala Arg Asp Ala Leu
        220                 225                 230

tgt aat gac gcc aac caa cgt caa ttc agc acg tta gtc ctg cca ttg      816
Cys Asn Asp Ala Asn Gln Arg Gln Phe Ser Thr Leu Val Leu Pro Leu
    235                 240                 245

tac ttg gat gat agc ttt cgt tac agc tgt cta agc gaa cct ttt tga      864
Tyr Leu Asp Asp Ser Phe Arg Tyr Ser Cys Leu Ser Glu Pro Phe
250                 255                 260


<210> SEQ ID NO 26
<211> LENGTH: 287
<212> TYPE: PRT
<213> ORGANISM: Vibrio sp

<400> SEQUENCE: 26

Met Pro Tyr Tyr Arg Pro Leu Asn Tyr Val Ile Cys Leu Leu Gly Leu
            -20                 -15                 -10

Ala Leu Leu Val Gly Cys Gly Ser Asp Ser Lys Asp Ser Glu Ser Asp
        -5                  -1  1               5

Phe Glu Ile Leu Thr Pro Val Thr Gly Gly Asn Trp Tyr Gln Pro Thr
10                  15                  20                  25
```

```
Arg Gln Thr Thr Trp Gln Trp Gln Leu Thr Asn Thr Leu Asn Ser Ser
                30                  35                  40

Tyr Asn Val Thr Val Tyr Asp Ile Asp Leu Phe Asp Thr Ser Pro Ser
            45                  50                  55

Asp Ile Gln Ala Leu Gln Thr Glu Gly His Lys Val Ile Cys Tyr Phe
        60                  65                  70

Ser Ala Gly Ser Phe Glu Asp Trp Arg Asp Asp Ala Ala Glu Phe Ser
    75                  80                  85

Ser Ser Val Leu Gly Asp Thr Leu Asp Gly Trp Glu Asp Glu Arg Trp
90                  95                  100                 105

Leu Asp Ile Arg Gln Ser Ser Val Arg Asp Ile Met Tyr Ala Arg Leu
                110                 115                 120

Gln Leu Ala Gln Thr Lys Gly Cys Asp Gly Val Glu Pro Asp Asn Val
            125                 130                 135

Asp Gly Tyr Thr Asn Asn Ser Gly Phe Asn Leu Gly Tyr Ser Asp Gln
        140                 145                 150

Leu Met Phe Asn Arg Tyr Leu Ala Asn Ser Ala His Gln Leu Gly Leu
    155                 160                 165

Ser Ile Gly Leu Lys Asn Asp Leu Arg Gln Ile Thr Asp Leu Val Glu
170                 175                 180                 185

Tyr Phe Asp Phe Ala Val Asn Glu Gln Cys Phe Glu Tyr Asn Glu Cys
                190                 195                 200

Gly Tyr Leu Ala Pro Phe Ile Asp Ala Asn Lys Ala Val Phe Asn Ala
            205                 210                 215

Glu Tyr Glu Ser Thr Tyr Val Asp Asn Thr Ser Ala Arg Asp Ala Leu
        220                 225                 230

Cys Asn Asp Ala Asn Gln Arg Gln Phe Ser Thr Leu Val Leu Pro Leu
    235                 240                 245

Tyr Leu Asp Asp Ser Phe Arg Tyr Ser Cys Leu Ser Glu Pro Phe
250                 255                 260


<210> SEQ ID NO 27
<211> LENGTH: 264
<212> TYPE: PRT
<213> ORGANISM: Vibrio sp

<400> SEQUENCE: 27

Ser Asp Ser Lys Asp Ser Glu Ser Asp Phe Glu Ile Leu Thr Pro Val
1               5                   10                  15

Thr Gly Gly Asn Trp Tyr Gln Pro Thr Arg Gln Thr Thr Trp Gln Trp
            20                  25                  30

Gln Leu Thr Asn Thr Leu Asn Ser Ser Tyr Asn Val Thr Val Tyr Asp
        35                  40                  45

Ile Asp Leu Phe Asp Thr Ser Pro Ser Asp Ile Gln Ala Leu Gln Thr
    50                  55                  60

Glu Gly His Lys Val Ile Cys Tyr Phe Ser Ala Gly Ser Phe Glu Asp
65                  70                  75                  80

Trp Arg Asp Asp Ala Ala Glu Phe Ser Ser Ser Val Leu Gly Asp Thr
                85                  90                  95

Leu Asp Gly Trp Glu Asp Glu Arg Trp Leu Asp Ile Arg Gln Ser Ser
            100                 105                 110

Val Arg Asp Ile Met Tyr Ala Arg Leu Gln Leu Ala Gln Thr Lys Gly
        115                 120                 125

Cys Asp Gly Val Glu Pro Asp Asn Val Asp Gly Tyr Thr Asn Asn Ser
    130                 135                 140
```

```
Gly Phe Asn Leu Gly Tyr Ser Asp Gln Leu Met Phe Asn Arg Tyr Leu
145                 150                 155                 160

Ala Asn Ser Ala His Gln Leu Gly Leu Ser Ile Gly Leu Lys Asn Asp
                165                 170                 175

Leu Arg Gln Ile Thr Asp Leu Val Glu Tyr Phe Asp Phe Ala Val Asn
            180                 185                 190

Glu Gln Cys Phe Glu Tyr Asn Glu Cys Gly Tyr Leu Ala Pro Phe Ile
        195                 200                 205

Asp Ala Asn Lys Ala Val Phe Asn Ala Glu Tyr Glu Ser Thr Tyr Val
    210                 215                 220

Asp Asn Thr Ser Ala Arg Asp Ala Leu Cys Asn Asp Ala Asn Gln Arg
225                 230                 235                 240

Gln Phe Ser Thr Leu Val Leu Pro Leu Tyr Leu Asp Asp Ser Phe Arg
                245                 250                 255

Tyr Ser Cys Leu Ser Glu Pro Phe
            260


<210> SEQ ID NO 28
<211> LENGTH: 726
<212> TYPE: DNA
<213> ORGANISM: Artificial
<220> FEATURE:
<223> OTHER INFORMATION: Synthetic gene
<220> FEATURE:
<221> NAME/KEY: CDS
<222> LOCATION: (1)..(726)

<400> SEQUENCE: 28

ctg aat ggc ggc tac tgg act ccg ccg gcc gac gta cgc ggg acg ttt       48
Leu Asn Gly Gly Tyr Trp Thr Pro Pro Ala Asp Val Arg Gly Thr Phe
1               5                   10                  15

cag aaa agc ccg aac ggc gtt ccg gtc gat cag gat ttg aaa ctg gcg       96
Gln Lys Ser Pro Asn Gly Val Pro Val Asp Gln Asp Leu Lys Leu Ala
            20                  25                  30

att gtt ccc ttg ttt gga gcg aac gag gcc cag atc cag aaa ctg cag      144
Ile Val Pro Leu Phe Gly Ala Asn Glu Ala Gln Ile Gln Lys Leu Gln
        35                  40                  45

agc gag ggc att tcg aca atc tgt acg atc aat gtc ggc tac gtc ctg      192
Ser Glu Gly Ile Ser Thr Ile Cys Thr Ile Asn Val Gly Tyr Val Leu
    50                  55                  60

aac acc gat ccc gat tac gat cag ttt cgg ccc tca atg atc ggt aag      240
Asn Thr Asp Pro Asp Tyr Asp Gln Phe Arg Pro Ser Met Ile Gly Lys
65                  70                  75                  80

ctc gtt tgg gaa ggc aac gtt ccg cat tgg atc gat atc cgc aac acc      288
Leu Val Trp Glu Gly Asn Val Pro His Trp Ile Asp Ile Arg Asn Thr
                85                  90                  95

ggt gtc cga gcc ttg atg caa gcg cga atg gaa cat gcc aag gct att      336
Gly Val Arg Ala Leu Met Gln Ala Arg Met Glu His Ala Lys Ala Ile
            100                 105                 110

gga tgt aag ggc gtc gtt acc cag agt atg gaa ctt tgg tac aac gac      384
Gly Cys Lys Gly Val Val Thr Gln Ser Met Glu Leu Trp Tyr Asn Asp
        115                 120                 125

acc ggt ttc tat att tcg tac ggc gat cag ctt gtt tat aat cgg tgg      432
Thr Gly Phe Tyr Ile Ser Tyr Gly Asp Gln Leu Val Tyr Asn Arg Trp
    130                 135                 140

ttg gcc gat acc gcg cac caa ctc ggg ctc tcg atc ggc atg cac aac      480
Leu Ala Asp Thr Ala His Gln Leu Gly Leu Ser Ile Gly Met His Asn
145                 150                 155                 160

act ttt ttt cag gtg aac gac tta gtc agc tgg ttt gac ttc ggg ttg      528
```

-continued

```
Thr Phe Phe Gln Val Asn Asp Leu Val Ser Trp Phe Asp Phe Gly Leu
                165                 170                 175

gtg gag gac tgc ctc aac tct gga gat tgc gaa acg tac att ccc ttc      576
Val Glu Asp Cys Leu Asn Ser Gly Asp Cys Glu Thr Tyr Ile Pro Phe
            180                 185                 190

ctc tcc gcc gga aaa cca gtg ctt gat att gag tac aac tcg atg agt      624
Leu Ser Ala Gly Lys Pro Val Leu Asp Ile Glu Tyr Asn Ser Met Ser
        195                 200                 205

agc gag gtc gat atc tgc aaa gcc ggc cgc gaa ctc ggc ttc aac acc      672
Ser Glu Val Asp Ile Cys Lys Ala Gly Arg Glu Leu Gly Phe Asn Thr
    210                 215                 220

atc atc aag ggc tac agc gac gac acc acc ttc gtc gac tgc agg gat      720
Ile Ile Lys Gly Tyr Ser Asp Asp Thr Thr Phe Val Asp Cys Arg Asp
225                 230                 235                 240

cgt cga                                                              726
Arg Arg


<210> SEQ ID NO 29
<211> LENGTH: 242
<212> TYPE: PRT
<213> ORGANISM: Artificial
<220> FEATURE:
<223> OTHER INFORMATION: Synthetic Construct

<400> SEQUENCE: 29

Leu Asn Gly Gly Tyr Trp Thr Pro Pro Ala Asp Val Arg Gly Thr Phe
1               5                   10                  15

Gln Lys Ser Pro Asn Gly Val Pro Val Asp Gln Asp Leu Lys Leu Ala
            20                  25                  30

Ile Val Pro Leu Phe Gly Ala Asn Glu Ala Gln Ile Gln Lys Leu Gln
        35                  40                  45

Ser Glu Gly Ile Ser Thr Ile Cys Thr Ile Asn Val Gly Tyr Val Leu
    50                  55                  60

Asn Thr Asp Pro Asp Tyr Asp Gln Phe Arg Pro Ser Met Ile Gly Lys
65                  70                  75                  80

Leu Val Trp Glu Gly Asn Val Pro His Trp Ile Asp Ile Arg Asn Thr
                85                  90                  95

Gly Val Arg Ala Leu Met Gln Ala Arg Met Glu His Ala Lys Ala Ile
            100                 105                 110

Gly Cys Lys Gly Val Val Thr Gln Ser Met Glu Leu Trp Tyr Asn Asp
        115                 120                 125

Thr Gly Phe Tyr Ile Ser Tyr Gly Asp Gln Leu Val Tyr Asn Arg Trp
    130                 135                 140

Leu Ala Asp Thr Ala His Gln Leu Gly Leu Ser Ile Gly Met His Asn
145                 150                 155                 160

Thr Phe Phe Gln Val Asn Asp Leu Val Ser Trp Phe Asp Phe Gly Leu
                165                 170                 175

Val Glu Asp Cys Leu Asn Ser Gly Asp Cys Glu Thr Tyr Ile Pro Phe
            180                 185                 190

Leu Ser Ala Gly Lys Pro Val Leu Asp Ile Glu Tyr Asn Ser Met Ser
        195                 200                 205

Ser Glu Val Asp Ile Cys Lys Ala Gly Arg Glu Leu Gly Phe Asn Thr
    210                 215                 220

Ile Ile Lys Gly Tyr Ser Asp Asp Thr Thr Phe Val Asp Cys Arg Asp
225                 230                 235                 240

Arg Arg
```

<210> SEQ ID NO 30
<211> LENGTH: 242
<212> TYPE: PRT
<213> ORGANISM: Artificial
<220> FEATURE:
<223> OTHER INFORMATION: Synthetic gene

<400> SEQUENCE: 30

```
Leu Asn Gly Gly Tyr Trp Thr Pro Pro Ala Asp Val Arg Gly Thr Phe
1               5                   10                  15

Gln Lys Ser Pro Asn Gly Val Pro Val Asp Gln Asp Leu Lys Leu Ala
            20                  25                  30

Ile Val Pro Leu Phe Gly Ala Asn Glu Ala Gln Ile Gln Lys Leu Gln
        35                  40                  45

Ser Glu Gly Ile Ser Thr Ile Cys Thr Ile Asn Val Gly Tyr Val Leu
    50                  55                  60

Asn Thr Asp Pro Asp Tyr Asp Gln Phe Arg Pro Ser Met Ile Gly Lys
65                  70                  75                  80

Leu Val Trp Glu Gly Asn Val Pro His Trp Ile Asp Ile Arg Asn Thr
                85                  90                  95

Gly Val Arg Ala Leu Met Gln Ala Arg Met Glu His Ala Lys Ala Ile
            100                 105                 110

Gly Cys Lys Gly Val Val Thr Gln Ser Met Glu Leu Trp Tyr Asn Asp
        115                 120                 125

Thr Gly Phe Tyr Ile Ser Tyr Gly Asp Gln Leu Val Tyr Asn Arg Trp
    130                 135                 140

Leu Ala Asp Thr Ala His Gln Leu Gly Leu Ser Ile Gly Met His Asn
145                 150                 155                 160

Thr Phe Phe Gln Val Asn Asp Leu Val Ser Trp Phe Asp Phe Gly Leu
                165                 170                 175

Val Glu Asp Cys Leu Asn Ser Gly Asp Cys Glu Thr Tyr Ile Pro Phe
            180                 185                 190

Leu Ser Ala Gly Lys Pro Val Leu Asp Ile Glu Tyr Asn Ser Met Ser
        195                 200                 205

Ser Glu Val Asp Ile Cys Lys Ala Gly Arg Glu Leu Gly Phe Asn Thr
    210                 215                 220

Ile Ile Lys Gly Tyr Ser Asp Asp Thr Thr Phe Val Asp Cys Arg Asp
225                 230                 235                 240

Arg Arg
```

<210> SEQ ID NO 31
<211> LENGTH: 831
<212> TYPE: DNA
<213> ORGANISM: Microbacterium saccharophilum
<220> FEATURE:
<221> NAME/KEY: CDS
<222> LOCATION: (1)..(828)
<220> FEATURE:
<221> NAME/KEY: sig_peptide
<222> LOCATION: (1)..(114)
<220> FEATURE:
<221> NAME/KEY: mat_peptide
<222> LOCATION: (115)..(828)

<400> SEQUENCE: 31

```
atg cgc ctc ctc acc agc gga atc ttc ggt gcg acg gtg ctg ctc gcc       48
Met Arg Leu Leu Thr Ser Gly Ile Phe Gly Ala Thr Val Leu Leu Ala
            -35                 -30                 -25

ctc acg gcg tgc gcg agc gcc ccg gct ccc gtc ccc tcg gtc tgg ccg       96
```

```
Leu Thr Ala Cys Ala Ser Ala Pro Ala Pro Val Pro Ser Val Trp Pro
    -20                 -15                 -10

aca tcg acg gct tcc gct cag atc gcg ctt ccg ccc gcg ggc gcg aac      144
Thr Ser Thr Ala Ser Ala Gln Ile Ala Leu Pro Pro Ala Gly Ala Asn
    -5              -1  1               5                   10

ccc gac tac caa ctc ggt ggg gca tac gac ccg ccc gac ggc gtg gcc      192
Pro Asp Tyr Gln Leu Gly Gly Ala Tyr Asp Pro Pro Asp Gly Val Ala
                15                  20                  25

atc gtc gcg cgc gac cgt acg gcc gac cct gca ccg ggt ctg tac tcg      240
Ile Val Ala Arg Asp Arg Thr Ala Asp Pro Ala Pro Gly Leu Tyr Ser
            30                  35                  40

atc tgc tac gtc aac gcc ttc cag aca cag ccg ggc gag ctg gcc gac      288
Ile Cys Tyr Val Asn Ala Phe Gln Thr Gln Pro Gly Glu Leu Ala Asp
        45                  50                  55

tgg ccc ggc gag ctg atc ctg aag gat gcg tcc gga gag ccc gtg cgc      336
Trp Pro Gly Glu Leu Ile Leu Lys Asp Ala Ser Gly Glu Pro Val Arg
    60                  65                  70

gac ccc gac tgg ccc gac gag gcg atc gtc gac acc cgg gat gcc gcg      384
Asp Pro Asp Trp Pro Asp Glu Ala Ile Val Asp Thr Arg Asp Ala Ala
75                  80                  85                  90

gcg gtg gct gcc atc gtg acg ccc tgg atc gac gcg tgc gcg gcc tcc      432
Ala Val Ala Ala Ile Val Thr Pro Trp Ile Asp Ala Cys Ala Ala Ser
                95                  100                 105

ggc ttc gac gcg gtg gag ttc gac aac ctc gac acc tac acg cgc acc      480
Gly Phe Asp Ala Val Glu Phe Asp Asn Leu Asp Thr Tyr Thr Arg Thr
            110                 115                 120

gat gga acc ctc acc cgg gat gac aac ctg acc gtc gcc acc ctg ctg      528
Asp Gly Thr Leu Thr Arg Asp Asp Asn Leu Thr Val Ala Thr Leu Leu
        125                 130                 135

gtg cgg gcg gca cac gac gcc ggc ctg gcg gcg gga cag aag aat gcc      576
Val Arg Ala Ala His Asp Ala Gly Leu Ala Ala Gly Gln Lys Asn Ala
    140                 145                 150

gcc gag gat gca cgc ctg ctc cac gat cgc gcc ggg ttc gac ttc gcc      624
Ala Glu Asp Ala Arg Leu Leu His Asp Arg Ala Gly Phe Asp Phe Ala
155                 160                 165                 170

gtc acc gaa gaa tgc gcc gtg tgg gac gag tgc ggc gcc tac acc gcc      672
Val Thr Glu Glu Cys Ala Val Trp Asp Glu Cys Gly Ala Tyr Thr Ala
                175                 180                 185

gtg tac ggc gat gcg gtg atc gcc gtc gag tac acc gac gac ctc ccc      720
Val Tyr Gly Asp Ala Val Ile Ala Val Glu Tyr Thr Asp Asp Leu Pro
            190                 195                 200

cgt ccg ttc gcg gcg atg tgc gag tcc gat ctg ccg ccg tcc gcg gtg      768
Arg Pro Phe Ala Ala Met Cys Glu Ser Asp Leu Pro Pro Ser Ala Val
        205                 210                 215

ctg cgc gac cgc gat ctg acc aca ccg ggc gac ccg gcc tac gtc ttc      816
Leu Arg Asp Arg Asp Leu Thr Thr Pro Gly Asp Pro Ala Tyr Val Phe
    220                 225                 230

gag agc tgt cgc tga                                                  831
Glu Ser Cys Arg
235
```

<210> SEQ ID NO 32
<211> LENGTH: 276
<212> TYPE: PRT
<213> ORGANISM: Microbacterium saccharophilum

<400> SEQUENCE: 32

```
Met Arg Leu Leu Thr Ser Gly Ile Phe Gly Ala Thr Val Leu Leu Ala
            -35                 -30                 -25

Leu Thr Ala Cys Ala Ser Ala Pro Ala Pro Val Pro Ser Val Trp Pro
```

```
        -20                 -15                 -10

Thr Ser Thr Ala Ser Ala Gln Ile Ala Leu Pro Pro Ala Gly Ala Asn
    -5              -1  1               5                   10

Pro Asp Tyr Gln Leu Gly Gly Ala Tyr Asp Pro Pro Asp Gly Val Ala
                15                  20                  25

Ile Val Ala Arg Asp Arg Thr Ala Asp Pro Ala Pro Gly Leu Tyr Ser
            30                  35                  40

Ile Cys Tyr Val Asn Ala Phe Gln Thr Gln Pro Gly Glu Leu Ala Asp
        45                  50                  55

Trp Pro Gly Glu Leu Ile Leu Lys Asp Ala Ser Gly Glu Pro Val Arg
    60                  65                  70

Asp Pro Asp Trp Pro Asp Glu Ala Ile Val Asp Thr Arg Asp Ala Ala
75                  80                  85                  90

Ala Val Ala Ala Ile Val Thr Pro Trp Ile Asp Ala Cys Ala Ala Ser
                95                  100                 105

Gly Phe Asp Ala Val Glu Phe Asp Asn Leu Asp Thr Tyr Thr Arg Thr
            110                 115                 120

Asp Gly Thr Leu Thr Arg Asp Asp Asn Leu Thr Val Ala Thr Leu Leu
        125                 130                 135

Val Arg Ala Ala His Asp Ala Gly Leu Ala Ala Gly Gln Lys Asn Ala
    140                 145                 150

Ala Glu Asp Ala Arg Leu Leu His Asp Arg Ala Gly Phe Asp Phe Ala
155                 160                 165                 170

Val Thr Glu Glu Cys Ala Val Trp Asp Glu Cys Gly Ala Tyr Thr Ala
                175                 180                 185

Val Tyr Gly Asp Ala Val Ile Ala Val Glu Tyr Thr Asp Asp Leu Pro
            190                 195                 200

Arg Pro Phe Ala Ala Met Cys Glu Ser Asp Leu Pro Pro Ser Ala Val
        205                 210                 215

Leu Arg Asp Arg Asp Leu Thr Thr Pro Gly Asp Pro Ala Tyr Val Phe
    220                 225                 230

Glu Ser Cys Arg
235


<210> SEQ ID NO 33
<211> LENGTH: 238
<212> TYPE: PRT
<213> ORGANISM: Microbacterium saccharophilum

<400> SEQUENCE: 33

Gln Ile Ala Leu Pro Pro Ala Gly Ala Asn Pro Asp Tyr Gln Leu Gly
1               5                   10                  15

Gly Ala Tyr Asp Pro Pro Asp Gly Val Ala Ile Val Ala Arg Asp Arg
            20                  25                  30

Thr Ala Asp Pro Ala Pro Gly Leu Tyr Ser Ile Cys Tyr Val Asn Ala
        35                  40                  45

Phe Gln Thr Gln Pro Gly Glu Leu Ala Asp Trp Pro Gly Glu Leu Ile
    50                  55                  60

Leu Lys Asp Ala Ser Gly Glu Pro Val Arg Asp Pro Asp Trp Pro Asp
65                  70                  75                  80

Glu Ala Ile Val Asp Thr Arg Asp Ala Ala Ala Val Ala Ala Ile Val
                85                  90                  95

Thr Pro Trp Ile Asp Ala Cys Ala Ala Ser Gly Phe Asp Ala Val Glu
            100                 105                 110
```

```
Phe Asp Asn Leu Asp Thr Tyr Thr Arg Thr Asp Gly Thr Leu Thr Arg
        115                 120                 125

Asp Asp Asn Leu Thr Val Ala Thr Leu Leu Val Arg Ala Ala His Asp
    130                 135                 140

Ala Gly Leu Ala Ala Gly Gln Lys Asn Ala Ala Glu Asp Ala Arg Leu
145                 150                 155                 160

Leu His Asp Arg Ala Gly Phe Asp Phe Ala Val Thr Glu Glu Cys Ala
                165                 170                 175

Val Trp Asp Glu Cys Gly Ala Tyr Thr Ala Val Tyr Gly Asp Ala Val
            180                 185                 190

Ile Ala Val Glu Tyr Thr Asp Asp Leu Pro Arg Pro Phe Ala Ala Met
        195                 200                 205

Cys Glu Ser Asp Leu Pro Pro Ser Ala Val Leu Arg Asp Arg Asp Leu
    210                 215                 220

Thr Thr Pro Gly Asp Pro Ala Tyr Val Phe Glu Ser Cys Arg
225                 230                 235


<210> SEQ ID NO 34
<211> LENGTH: 864
<212> TYPE: DNA
<213> ORGANISM: Microbacterium oxydans
<220> FEATURE:
<221> NAME/KEY: CDS
<222> LOCATION: (1)..(861)
<220> FEATURE:
<221> NAME/KEY: sig_peptide
<222> LOCATION: (1)..(78)
<220> FEATURE:
<221> NAME/KEY: mat_peptide
<222> LOCATION: (79)..(861)

<400> SEQUENCE: 34

atg ctc gaa cga gac cgc cgc acc gca cgc ggc ggc atc gct gta ctc       48
Met Leu Glu Arg Asp Arg Arg Thr Ala Arg Gly Gly Ile Ala Val Leu
    -25                 -20                 -15

gcc gcc ctc ctc gcg ctc acc ggc tgc gcg tcc ggc acg gcg acg gcc       96
Ala Ala Leu Leu Ala Leu Thr Gly Cys Ala Ser Gly Thr Ala Thr Ala
-10                 -5              -1  1               5

ccg cac tcc ggg cac tcc gct gac gcc ccg aca gac gca gac cgg tcg      144
Pro His Ser Gly His Ser Ala Asp Ala Pro Thr Asp Ala Asp Arg Ser
            10                  15                  20

ctg ccg ccc gcc ggc gcc gtg ccc gac tac cag ctc ggc ggt gcg tac      192
Leu Pro Pro Ala Gly Ala Val Pro Asp Tyr Gln Leu Gly Gly Ala Tyr
        25                  30                  35

gag ccg gcg gcc gag gtc ggc atc gtg ggg cgc gat cgt tcg gcg gcc      240
Glu Pro Ala Ala Glu Val Gly Ile Val Gly Arg Asp Arg Ser Ala Ala
    40                  45                  50

ccg gcg ccc gac aca tac tcg atc tgc tat gtg aac ggt ttc cag acg      288
Pro Ala Pro Asp Thr Tyr Ser Ile Cys Tyr Val Asn Gly Phe Gln Thr
55                  60                  65                  70

cag ccg ggc gag ctc gac acc tgg gac gcc gat ctg ctg ctg cga cag      336
Gln Pro Gly Glu Leu Asp Thr Trp Asp Ala Asp Leu Leu Leu Arg Gln
                75                  80                  85

gac ggc gag acc gtg ttc gac ccg gac tgg ccg gac gag gca ctg ctc      384
Asp Gly Glu Thr Val Phe Asp Pro Asp Trp Pro Asp Glu Ala Leu Leu
            90                  95                  100

gac acg tcg acc gcc gac cgc cgc gaa cgc atc gcc gca cgg atc atc      432
Asp Thr Ser Thr Ala Asp Arg Arg Glu Arg Ile Ala Ala Arg Ile Ile
        105                 110                 115

ccc tgg atc gaa ggc tgt gcc gat gac ggc ttc gcc gcg gtc gaa ttc      480
Pro Trp Ile Glu Gly Cys Ala Asp Asp Gly Phe Ala Ala Val Glu Phe
```

```
    120                 125                 130

gac aac ctc gat tcc tac acc cgg tcc ggc gac gcg ctc tcg ctc gat      528
Asp Asn Leu Asp Ser Tyr Thr Arg Ser Gly Asp Ala Leu Ser Leu Asp
135                 140                 145                 150

gac aac ctc gcc ctc gcc gcc ctc ttc gtc gac gcc gca cat ggc gcc      576
Asp Asn Leu Ala Leu Ala Ala Leu Phe Val Asp Ala Ala His Gly Ala
                155                 160                 165

ggc ctc gcg gcc ggc cag aag aac gcg gcg gaa gac gcc gtg gtg ctg      624
Gly Leu Ala Ala Gly Gln Lys Asn Ala Ala Glu Asp Ala Val Val Leu
            170                 175                 180

cac gaa cag gcg ggt ttc gac ttc gcg gtg acc gaa gag tgc gcc gtc      672
His Glu Gln Ala Gly Phe Asp Phe Ala Val Thr Glu Glu Cys Ala Val
        185                 190                 195

ttc gag gag tgc ggc gtc tac gcc gcc gtc tac ggc acg cac gtg atc      720
Phe Glu Glu Cys Gly Val Tyr Ala Ala Val Tyr Gly Thr His Val Ile
    200                 205                 210

gac atc gag tac agc gat gag ttg ccg cgc agt ttc gcg gag atg tgc      768
Asp Ile Glu Tyr Ser Asp Glu Leu Pro Arg Ser Phe Ala Glu Met Cys
215                 220                 225                 230

gcg gac acc gat tcg ccc gcc tcg atg gtg ctg cgt gat cgc gac ctg      816
Ala Asp Thr Asp Ser Pro Ala Ser Met Val Leu Arg Asp Arg Asp Leu
                235                 240                 245

ctc acc ccc gac gac ccg gcg tac gtg ttc gag acc tgc agc gag tga      864
Leu Thr Pro Asp Asp Pro Ala Tyr Val Phe Glu Thr Cys Ser Glu
            250                 255                 260


<210> SEQ ID NO 35
<211> LENGTH: 287
<212> TYPE: PRT
<213> ORGANISM: Microbacterium oxydans

<400> SEQUENCE: 35

Met Leu Glu Arg Asp Arg Arg Thr Ala Arg Gly Gly Ile Ala Val Leu
    -25                 -20                 -15

Ala Ala Leu Leu Ala Leu Thr Gly Cys Ala Ser Gly Thr Ala Thr Ala
-10                 -5                  -1  1               5

Pro His Ser Gly His Ser Ala Asp Ala Pro Thr Asp Ala Asp Arg Ser
            10                  15                  20

Leu Pro Pro Ala Gly Ala Val Pro Asp Tyr Gln Leu Gly Gly Ala Tyr
        25                  30                  35

Glu Pro Ala Ala Glu Val Gly Ile Val Gly Arg Asp Arg Ser Ala Ala
    40                  45                  50

Pro Ala Pro Asp Thr Tyr Ser Ile Cys Tyr Val Asn Gly Phe Gln Thr
55                  60                  65                  70

Gln Pro Gly Glu Leu Asp Thr Trp Asp Ala Asp Leu Leu Leu Arg Gln
                75                  80                  85

Asp Gly Glu Thr Val Phe Asp Pro Asp Trp Pro Asp Glu Ala Leu Leu
            90                  95                  100

Asp Thr Ser Thr Ala Asp Arg Arg Glu Arg Ile Ala Ala Arg Ile Ile
        105                 110                 115

Pro Trp Ile Glu Gly Cys Ala Asp Asp Gly Phe Ala Ala Val Glu Phe
    120                 125                 130

Asp Asn Leu Asp Ser Tyr Thr Arg Ser Gly Asp Ala Leu Ser Leu Asp
135                 140                 145                 150

Asp Asn Leu Ala Leu Ala Ala Leu Phe Val Asp Ala Ala His Gly Ala
                155                 160                 165

Gly Leu Ala Ala Gly Gln Lys Asn Ala Ala Glu Asp Ala Val Val Leu
```

```
            170                 175                 180

His Glu Gln Ala Gly Phe Asp Phe Ala Val Thr Glu Glu Cys Ala Val
        185                 190                 195

Phe Glu Glu Cys Gly Val Tyr Ala Ala Val Tyr Gly Thr His Val Ile
    200                 205                 210

Asp Ile Glu Tyr Ser Asp Glu Leu Pro Arg Ser Phe Ala Glu Met Cys
215                 220                 225                 230

Ala Asp Thr Asp Ser Pro Ala Ser Met Val Leu Arg Asp Arg Asp Leu
                235                 240                 245

Leu Thr Pro Asp Asp Pro Ala Tyr Val Phe Glu Thr Cys Ser Glu
            250                 255                 260


<210> SEQ ID NO 36
<211> LENGTH: 261
<212> TYPE: PRT
<213> ORGANISM: Microbacterium oxydans

<400> SEQUENCE: 36

Ser Gly Thr Ala Thr Ala Pro His Ser Gly His Ser Ala Asp Ala Pro
1               5                   10                  15

Thr Asp Ala Asp Arg Ser Leu Pro Pro Ala Gly Ala Val Pro Asp Tyr
            20                  25                  30

Gln Leu Gly Gly Ala Tyr Glu Pro Ala Ala Glu Val Gly Ile Val Gly
        35                  40                  45

Arg Asp Arg Ser Ala Ala Pro Ala Pro Asp Thr Tyr Ser Ile Cys Tyr
    50                  55                  60

Val Asn Gly Phe Gln Thr Gln Pro Gly Glu Leu Asp Thr Trp Asp Ala
65                  70                  75                  80

Asp Leu Leu Leu Arg Gln Asp Gly Glu Thr Val Phe Asp Pro Asp Trp
                85                  90                  95

Pro Asp Glu Ala Leu Leu Asp Thr Ser Thr Ala Asp Arg Arg Glu Arg
            100                 105                 110

Ile Ala Ala Arg Ile Ile Pro Trp Ile Glu Gly Cys Ala Asp Asp Gly
        115                 120                 125

Phe Ala Ala Val Glu Phe Asp Asn Leu Asp Ser Tyr Thr Arg Ser Gly
    130                 135                 140

Asp Ala Leu Ser Leu Asp Asp Asn Leu Ala Leu Ala Ala Leu Phe Val
145                 150                 155                 160

Asp Ala Ala His Gly Ala Gly Leu Ala Ala Gly Gln Lys Asn Ala Ala
                165                 170                 175

Glu Asp Ala Val Val Leu His Glu Gln Ala Gly Phe Asp Phe Ala Val
            180                 185                 190

Thr Glu Glu Cys Ala Val Phe Glu Glu Cys Gly Val Tyr Ala Ala Val
        195                 200                 205

Tyr Gly Thr His Val Ile Asp Ile Glu Tyr Ser Asp Glu Leu Pro Arg
    210                 215                 220

Ser Phe Ala Glu Met Cys Ala Asp Thr Asp Ser Pro Ala Ser Met Val
225                 230                 235                 240

Leu Arg Asp Arg Asp Leu Leu Thr Pro Asp Asp Pro Ala Tyr Val Phe
                245                 250                 255

Glu Thr Cys Ser Glu
            260


<210> SEQ ID NO 37
<211> LENGTH: 873
```

```
<212> TYPE: DNA
<213> ORGANISM: Frigoribacterium faeni
<220> FEATURE:
<221> NAME/KEY: CDS
<222> LOCATION: (1)..(870)
<220> FEATURE:
<221> NAME/KEY: sig_peptide
<222> LOCATION: (1)..(75)
<220> FEATURE:
<221> NAME/KEY: mat_peptide
<222> LOCATION: (76)..(870)

<400> SEQUENCE: 37

atg cgc gta ccc ctc gga ttc gtc ggc ctg gtc gcc gtg gcc ctc gcc       48
Met Arg Val Pro Leu Gly Phe Val Gly Leu Val Ala Val Ala Leu Ala
-25                 -20                 -15                 -10

gtg acg ggt tgc acg aac gtc gac gcc ggg gtc ggt gaa cga ccc gag       96
Val Thr Gly Cys Thr Asn Val Asp Ala Gly Val Gly Glu Arg Pro Glu
                -5                  -1  1               5

cgc gcc tcc tcg tcc gcg gtg gtg gcg tcg ggg gcc gcg acg gcc gac      144
Arg Ala Ser Ser Ser Ala Val Val Ala Ser Gly Ala Ala Thr Ala Asp
        10                  15                  20

ggc gtc gtg ctg ccg ccc gag ggc gcc cgc ttc gac tac caa ctg gga      192
Gly Val Val Leu Pro Pro Glu Gly Ala Arg Phe Asp Tyr Gln Leu Gly
    25                  30                  35

ggc gcg tcg ccg gtc ccc gac gga gcc acc gtc gtc gcc cgc gac agc      240
Gly Ala Ser Pro Val Pro Asp Gly Ala Thr Val Val Ala Arg Asp Ser
40                  45                  50                  55

acc gac gac ccc gcc gag ggc gcc tac ggc atc tgc tac gtc aac ggg      288
Thr Asp Asp Pro Ala Glu Gly Ala Tyr Gly Ile Cys Tyr Val Asn Gly
                60                  65                  70

ttc cag acg cag ccc gga gtc atg tgg ccg gac gag ctg ctc gtg cgg      336
Phe Gln Thr Gln Pro Gly Val Met Trp Pro Asp Glu Leu Leu Val Arg
            75                  80                  85

acg gcc gac ggc gaa ccg ctg gtc gac ccg ggc tgg ccg gac gag cac      384
Thr Ala Asp Gly Glu Pro Leu Val Asp Pro Gly Trp Pro Asp Glu His
        90                  95                  100

ctg ttc gac ctg tcc acc gag gcg aac cgg cag gcc gtg gcc gag cgc      432
Leu Phe Asp Leu Ser Thr Glu Ala Asn Arg Gln Ala Val Ala Glu Arg
    105                 110                 115

cag gcc tcg acg atc gac ggg tgc gcc gcc tcg ggc tac cag gcg gtc      480
Gln Ala Ser Thr Ile Asp Gly Cys Ala Ala Ser Gly Tyr Gln Ala Val
120                 125                 130                 135

gag ttc gac aac ctc gac tcg tgg acg cgg tcg gac gag gcc ttc ggc      528
Glu Phe Asp Asn Leu Asp Ser Trp Thr Arg Ser Asp Glu Ala Phe Gly
                140                 145                 150

gag gac gac gcg gtc gcc ttc gcg acg ctg ctc gtc gcg cgg gcc cac      576
Glu Asp Asp Ala Val Ala Phe Ala Thr Leu Leu Val Ala Arg Ala His
            155                 160                 165

gcg gcc ggg ctg gcg acg gcg cag aag aac acc gcc gac ctc ggt gcc      624
Ala Ala Gly Leu Ala Thr Ala Gln Lys Asn Thr Ala Asp Leu Gly Ala
        170                 175                 180

cgg ggc cgc gac gag gtc ggc tac gac ttc gcc gtc acc gag gag tgc      672
Arg Gly Arg Asp Glu Val Gly Tyr Asp Phe Ala Val Thr Glu Glu Cys
    185                 190                 195

gac cgc tac gac gag tgc gac gcc ttc acg gac gtc tac ggc ggg ctc      720
Asp Arg Tyr Asp Glu Cys Asp Ala Phe Thr Asp Val Tyr Gly Gly Leu
200                 205                 210                 215

gtg ttc gac gtc gag tac acc gac gac ctc cgc ggc tcg atc gcc gag      768
Val Phe Asp Val Glu Tyr Thr Asp Asp Leu Arg Gly Ser Ile Ala Glu
                220                 225                 230

gtc tgc gcc cgc gtc ggc gag ctc gac ccg gcc ccc tcg acc atc gtg      816
```

```
Val Cys Ala Arg Val Gly Glu Leu Asp Pro Ala Pro Ser Thr Ile Val
            235                 240                 245

cgc gac cac gac ctg gtg ccg gcc gac gac ccg gcc cac gcc tac acg      864
Arg Asp His Asp Leu Val Pro Ala Asp Asp Pro Ala His Ala Tyr Thr
        250                 255                 260

gcc tgc tga                                                          873
Ala Cys
    265


<210> SEQ ID NO 38
<211> LENGTH: 290
<212> TYPE: PRT
<213> ORGANISM: Frigoribacterium faeni

<400> SEQUENCE: 38

Met Arg Val Pro Leu Gly Phe Val Gly Leu Val Ala Val Ala Leu Ala
-25                 -20                 -15                 -10

Val Thr Gly Cys Thr Asn Val Asp Ala Gly Val Gly Glu Arg Pro Glu
                -5                  -1  1               5

Arg Ala Ser Ser Ser Ala Val Val Ala Ser Gly Ala Ala Thr Ala Asp
        10                  15                  20

Gly Val Val Leu Pro Pro Glu Gly Ala Arg Phe Asp Tyr Gln Leu Gly
    25                  30                  35

Gly Ala Ser Pro Val Pro Asp Gly Ala Thr Val Val Ala Arg Asp Ser
40                  45                  50                  55

Thr Asp Asp Pro Ala Glu Gly Ala Tyr Gly Ile Cys Tyr Val Asn Gly
                60                  65                  70

Phe Gln Thr Gln Pro Gly Val Met Trp Pro Asp Glu Leu Leu Val Arg
            75                  80                  85

Thr Ala Asp Gly Glu Pro Leu Val Asp Pro Gly Trp Pro Asp Glu His
        90                  95                  100

Leu Phe Asp Leu Ser Thr Glu Ala Asn Arg Gln Ala Val Ala Glu Arg
    105                 110                 115

Gln Ala Ser Thr Ile Asp Gly Cys Ala Ala Ser Gly Tyr Gln Ala Val
120                 125                 130                 135

Glu Phe Asp Asn Leu Asp Ser Trp Thr Arg Ser Asp Glu Ala Phe Gly
                140                 145                 150

Glu Asp Asp Ala Val Ala Phe Ala Thr Leu Leu Val Ala Arg Ala His
            155                 160                 165

Ala Ala Gly Leu Ala Thr Ala Gln Lys Asn Thr Ala Asp Leu Gly Ala
        170                 175                 180

Arg Gly Arg Asp Glu Val Gly Tyr Asp Phe Ala Val Thr Glu Glu Cys
    185                 190                 195

Asp Arg Tyr Asp Glu Cys Asp Ala Phe Thr Asp Val Tyr Gly Gly Leu
200                 205                 210                 215

Val Phe Asp Val Glu Tyr Thr Asp Asp Leu Arg Gly Ser Ile Ala Glu
                220                 225                 230

Val Cys Ala Arg Val Gly Glu Leu Asp Pro Ala Pro Ser Thr Ile Val
            235                 240                 245

Arg Asp His Asp Leu Val Pro Ala Asp Asp Pro Ala His Ala Tyr Thr
        250                 255                 260

Ala Cys
    265


<210> SEQ ID NO 39
<211> LENGTH: 265
```

<212> TYPE: PRT
<213> ORGANISM: Frigoribacterium faeni

<400> SEQUENCE: 39

```
Gly Val Gly Glu Arg Pro Glu Arg Ala Ser Ser Ser Ala Val Val Ala
1               5                   10                  15

Ser Gly Ala Ala Thr Ala Asp Gly Val Val Leu Pro Pro Glu Gly Ala
            20                  25                  30

Arg Phe Asp Tyr Gln Leu Gly Gly Ala Ser Pro Val Pro Asp Gly Ala
        35                  40                  45

Thr Val Val Ala Arg Asp Ser Thr Asp Asp Pro Ala Glu Gly Ala Tyr
    50                  55                  60

Gly Ile Cys Tyr Val Asn Gly Phe Gln Thr Gln Pro Gly Val Met Trp
65                  70                  75                  80

Pro Asp Glu Leu Leu Val Arg Thr Ala Asp Gly Glu Pro Leu Val Asp
                85                  90                  95

Pro Gly Trp Pro Asp Glu His Leu Phe Asp Leu Ser Thr Glu Ala Asn
            100                 105                 110

Arg Gln Ala Val Ala Glu Arg Gln Ala Ser Thr Ile Asp Gly Cys Ala
        115                 120                 125

Ala Ser Gly Tyr Gln Ala Val Glu Phe Asp Asn Leu Asp Ser Trp Thr
    130                 135                 140

Arg Ser Asp Glu Ala Phe Gly Glu Asp Asp Ala Val Ala Phe Ala Thr
145                 150                 155                 160

Leu Leu Val Ala Arg Ala His Ala Ala Gly Leu Ala Thr Ala Gln Lys
                165                 170                 175

Asn Thr Ala Asp Leu Gly Ala Arg Gly Arg Asp Glu Val Gly Tyr Asp
            180                 185                 190

Phe Ala Val Thr Glu Glu Cys Asp Arg Tyr Asp Glu Cys Asp Ala Phe
        195                 200                 205

Thr Asp Val Tyr Gly Gly Leu Val Phe Asp Val Glu Tyr Thr Asp Asp
    210                 215                 220

Leu Arg Gly Ser Ile Ala Glu Val Cys Ala Arg Val Gly Glu Leu Asp
225                 230                 235                 240

Pro Ala Pro Ser Thr Ile Val Arg Asp His Asp Leu Val Pro Ala Asp
                245                 250                 255

Asp Pro Ala His Ala Tyr Thr Ala Cys
            260                 265
```

<210> SEQ ID NO 40
<211> LENGTH: 762
<212> TYPE: DNA
<213> ORGANISM: Serinibacter sp
<220> FEATURE:
<221> NAME/KEY: CDS
<222> LOCATION: (1)..(762)

<400> SEQUENCE: 40

```
acg gac ggc ggc tcc gac gtc gtc ctc cca ccc acg gcc ggc gcc ttc       48
Thr Asp Gly Gly Ser Asp Val Val Leu Pro Pro Thr Ala Gly Ala Phe
1               5                   10                  15

gac tac cgg ctc ggc gag gcg tac ggg gag ccg ggc gag ctc gac gtc       96
Asp Tyr Arg Leu Gly Glu Ala Tyr Gly Glu Pro Gly Glu Leu Asp Val
            20                  25                  30

gtc gcc cgc gac gtc acc gcc cag ccg ctc gcg gac gcc tac aac gtc      144
Val Ala Arg Asp Val Thr Ala Gln Pro Leu Ala Asp Ala Tyr Asn Val
        35                  40                  45
```

-continued

```
tgc tac ctc aac ggt ttc cag acc cag ccc ggc gcc ctg ccg gac tgg      192
Cys Tyr Leu Asn Gly Phe Gln Thr Gln Pro Gly Ala Leu Pro Asp Trp
    50                  55                  60

gag gac ggc gac ggc ggc gcc ctg ctg cgg gac gcg agc ggt gcc gtc      240
Glu Asp Gly Asp Gly Gly Ala Leu Leu Arg Asp Ala Ser Gly Ala Val
65                  70                  75                  80

gtg atg gat ccg gag tgg ccg gac gag gcc gtg ctc gac ccc tcg acg      288
Val Met Asp Pro Glu Trp Pro Asp Glu Ala Val Leu Asp Pro Ser Thr
                85                  90                  95

ccc cag cag cgc atc gcg atc ctc gcc gtg atg gga ccg cag atc cgg      336
Pro Gln Gln Arg Ile Ala Ile Leu Ala Val Met Gly Pro Gln Ile Arg
            100                 105                 110

gac tgc gcc gac gcg ggc ttc gac gcc gtc gag ctc gac aac ctc gac      384
Asp Cys Ala Asp Ala Gly Phe Asp Ala Val Glu Leu Asp Asn Leu Asp
        115                 120                 125

acg ttc ctg agg ttc gag ggc gtc gac cgc gac ggc gcg ctc gac ctg      432
Thr Phe Leu Arg Phe Glu Gly Val Asp Arg Asp Gly Ala Leu Asp Leu
    130                 135                 140

gcg acc tcc tac gtg gag gtc gcg cac gac gcg ggc ctc gcc gtc ggg      480
Ala Thr Ser Tyr Val Glu Val Ala His Asp Ala Gly Leu Ala Val Gly
145                 150                 155                 160

cag aag aac gcg gcc gac gtc gga gcc gat gcg cgt gag gtc gcg ggc      528
Gln Lys Asn Ala Ala Asp Val Gly Ala Asp Ala Arg Glu Val Ala Gly
                165                 170                 175

ttc gac ttc gcc gtc gtg gag gag tgc gcc gtg tac gac gag tgc ggc      576
Phe Asp Phe Ala Val Val Glu Glu Cys Ala Val Tyr Asp Glu Cys Gly
            180                 185                 190

acc tac cgc gcg gtg tac ggc gag cac gtg ctg cag atc gag tac tcc      624
Thr Tyr Arg Ala Val Tyr Gly Glu His Val Leu Gln Ile Glu Tyr Ser
        195                 200                 205

gac acc ctt cgc gac cga ggc ctg acg gtc gag gag gtg tgc gcg ctg      672
Asp Thr Leu Arg Asp Arg Gly Leu Thr Val Glu Glu Val Cys Ala Leu
    210                 215                 220

ccc gac cgc gcg ccg ctg acc gtg gtg cgc gac cgg ctg ctc gtc ggc      720
Pro Asp Arg Ala Pro Leu Thr Val Val Arg Asp Arg Leu Leu Val Gly
225                 230                 235                 240

ccc gac gac gcc gcc cac gag cgg gag cag tgc ccg gcg ggc              762
Pro Asp Asp Ala Ala His Glu Arg Glu Gln Cys Pro Ala Gly
                245                 250


<210> SEQ ID NO 41
<211> LENGTH: 254
<212> TYPE: PRT
<213> ORGANISM: Serinibacter sp

<400> SEQUENCE: 41

Thr Asp Gly Gly Ser Asp Val Val Leu Pro Pro Thr Ala Gly Ala Phe
1               5                   10                  15

Asp Tyr Arg Leu Gly Glu Ala Tyr Gly Glu Pro Gly Glu Leu Asp Val
            20                  25                  30

Val Ala Arg Asp Val Thr Ala Gln Pro Leu Ala Asp Ala Tyr Asn Val
        35                  40                  45

Cys Tyr Leu Asn Gly Phe Gln Thr Gln Pro Gly Ala Leu Pro Asp Trp
    50                  55                  60

Glu Asp Gly Asp Gly Gly Ala Leu Leu Arg Asp Ala Ser Gly Ala Val
65                  70                  75                  80

Val Met Asp Pro Glu Trp Pro Asp Glu Ala Val Leu Asp Pro Ser Thr
                85                  90                  95

Pro Gln Gln Arg Ile Ala Ile Leu Ala Val Met Gly Pro Gln Ile Arg
```

```
            100                 105                 110

Asp Cys Ala Asp Ala Gly Phe Asp Ala Val Glu Leu Asp Asn Leu Asp
        115                 120                 125

Thr Phe Leu Arg Phe Glu Gly Val Asp Arg Asp Gly Ala Leu Asp Leu
    130                 135                 140

Ala Thr Ser Tyr Val Glu Val Ala His Asp Ala Gly Leu Ala Val Gly
145                 150                 155                 160

Gln Lys Asn Ala Ala Asp Val Gly Ala Asp Ala Arg Glu Val Ala Gly
                165                 170                 175

Phe Asp Phe Ala Val Val Glu Glu Cys Ala Val Tyr Asp Glu Cys Gly
            180                 185                 190

Thr Tyr Arg Ala Val Tyr Gly Glu His Val Leu Gln Ile Glu Tyr Ser
        195                 200                 205

Asp Thr Leu Arg Asp Arg Gly Leu Thr Val Glu Glu Val Cys Ala Leu
    210                 215                 220

Pro Asp Arg Ala Pro Leu Thr Val Val Arg Asp Arg Leu Leu Val Gly
225                 230                 235                 240

Pro Asp Asp Ala Ala His Glu Arg Glu Gln Cys Pro Ala Gly
                245                 250


<210> SEQ ID NO 42
<211> LENGTH: 254
<212> TYPE: PRT
<213> ORGANISM: Serinibacter sp

<400> SEQUENCE: 42

Thr Asp Gly Gly Ser Asp Val Val Leu Pro Pro Thr Ala Gly Ala Phe
1               5                   10                  15

Asp Tyr Arg Leu Gly Glu Ala Tyr Gly Glu Pro Gly Glu Leu Asp Val
            20                  25                  30

Val Ala Arg Asp Val Thr Ala Gln Pro Leu Ala Asp Ala Tyr Asn Val
        35                  40                  45

Cys Tyr Leu Asn Gly Phe Gln Thr Gln Pro Gly Ala Leu Pro Asp Trp
    50                  55                  60

Glu Asp Gly Asp Gly Gly Ala Leu Leu Arg Asp Ala Ser Gly Ala Val
65                  70                  75                  80

Val Met Asp Pro Glu Trp Pro Asp Glu Ala Val Leu Asp Pro Ser Thr
                85                  90                  95

Pro Gln Gln Arg Ile Ala Ile Leu Ala Val Met Gly Pro Gln Ile Arg
            100                 105                 110

Asp Cys Ala Asp Ala Gly Phe Asp Ala Val Glu Leu Asp Asn Leu Asp
        115                 120                 125

Thr Phe Leu Arg Phe Glu Gly Val Asp Arg Asp Gly Ala Leu Asp Leu
    130                 135                 140

Ala Thr Ser Tyr Val Glu Val Ala His Asp Ala Gly Leu Ala Val Gly
145                 150                 155                 160

Gln Lys Asn Ala Ala Asp Val Gly Ala Asp Ala Arg Glu Val Ala Gly
                165                 170                 175

Phe Asp Phe Ala Val Val Glu Glu Cys Ala Val Tyr Asp Glu Cys Gly
            180                 185                 190

Thr Tyr Arg Ala Val Tyr Gly Glu His Val Leu Gln Ile Glu Tyr Ser
        195                 200                 205

Asp Thr Leu Arg Asp Arg Gly Leu Thr Val Glu Glu Val Cys Ala Leu
    210                 215                 220
```

```
Pro Asp Arg Ala Pro Leu Thr Val Val Arg Asp Arg Leu Leu Val Gly
225                 230                 235                 240

Pro Asp Asp Ala Ala His Glu Arg Glu Gln Cys Pro Ala Gly
                245                 250


<210> SEQ ID NO 43
<211> LENGTH: 900
<212> TYPE: DNA
<213> ORGANISM: Oerskovia paurometabola
<220> FEATURE:
<221> NAME/KEY: CDS
<222> LOCATION: (1)..(897)
<220> FEATURE:
<221> NAME/KEY: sig_peptide
<222> LOCATION: (1)..(93)
<220> FEATURE:
<221> NAME/KEY: mat_peptide
<222> LOCATION: (94)..(897)

<400> SEQUENCE: 43

gtg ccc tcg ctc cct ctc cgc gcg tcc gcg cac gca tcg ctc atc gtg       48
Val Pro Ser Leu Pro Leu Arg Ala Ser Ala His Ala Ser Leu Ile Val
    -30                 -25                 -20

ccg gcc ctg gtc ctc gtc ctc ctt gcc ggg tgc gcc gtc ggc gct gcc       96
Pro Ala Leu Val Leu Val Leu Leu Ala Gly Cys Ala Val Gly Ala Ala
-15                 -10                 -5                  -1  1

ccg tcg ccc acc ccc ggg gcg acc gac cgt gag ccg tcg gcc tcg acg      144
Pro Ser Pro Thr Pro Gly Ala Thr Asp Arg Glu Pro Ser Ala Ser Thr
            5                   10                  15

agc ggc gcc gtc ggg cag gtc ggc gaa gcc ccc gca ccc ccg ccc gcc      192
Ser Gly Ala Val Gly Gln Val Gly Glu Ala Pro Ala Pro Pro Pro Ala
        20                  25                  30

ggg gcc ggt ctc gac tac cag ctc ggc ggg gcc tac ccg ccg ccc gac      240
Gly Ala Gly Leu Asp Tyr Gln Leu Gly Gly Ala Tyr Pro Pro Pro Asp
    35                  40                  45

ggc gtc acg gtc gtc gtg cgc gac gtc acc gac tcc ccc gcg ggc gcg      288
Gly Val Thr Val Val Val Arg Asp Val Thr Asp Ser Pro Ala Gly Ala
50                  55                  60                  65

ggc tac gac gtc tgt tac gtc aac ggg ttc cag acc cag ccc ggc gag      336
Gly Tyr Asp Val Cys Tyr Val Asn Gly Phe Gln Thr Gln Pro Gly Glu
                70                  75                  80

ggc gcg acc tgg ctg cgc gac cac ccc gac ctc gtc ctg cag gac gac      384
Gly Ala Thr Trp Leu Arg Asp His Pro Asp Leu Val Leu Gln Asp Asp
            85                  90                  95

ggc ggt aca cct gtc gcc gac cca ggc tgg ccc gac gag ctg ctc ctc      432
Gly Gly Thr Pro Val Ala Asp Pro Gly Trp Pro Asp Glu Leu Leu Leu
        100                 105                 110

gac acc tcg acc gac gcc gcg cgc cgc gag atc gcg cag atc gtc ggc      480
Asp Thr Ser Thr Asp Ala Ala Arg Arg Glu Ile Ala Gln Ile Val Gly
    115                 120                 125

ggc cag gtg gac gcg tgc gcg gac gcc ggc ttc gac gcg gtc gag ccc      528
Gly Gln Val Asp Ala Cys Ala Asp Ala Gly Phe Asp Ala Val Glu Pro
130                 135                 140                 145

gac aac ctg gac tcg ttc acc cgc tcg gac ggc gct ctc acc agg gac      576
Asp Asn Leu Asp Ser Phe Thr Arg Ser Asp Gly Ala Leu Thr Arg Asp
                150                 155                 160

gac aac ctc gcg ctg gcc gcg ctg ctg atc gaa cgt gcc cac gcc cgg      624
Asp Asn Leu Ala Leu Ala Ala Leu Leu Ile Glu Arg Ala His Ala Arg
            165                 170                 175

ggc ctg gcg atc ggg cag aag aac acg gtc gag ctg ggc ggt cgc ggc      672
Gly Leu Ala Ile Gly Gln Lys Asn Thr Val Glu Leu Gly Gly Arg Gly
        180                 185                 190
```

```
ccg gcg ctc ggg ttc gac ttc gtg gtc acc gag gac tgc gcg gtc cac      720
Pro Ala Leu Gly Phe Asp Phe Val Val Thr Glu Asp Cys Ala Val His
    195                 200                 205

gac gag tgc ggc gac tac gcc gcg gcc tac ggg acg cgc gtc ctg gag      768
Asp Glu Cys Gly Asp Tyr Ala Ala Ala Tyr Gly Thr Arg Val Leu Glu
210                 215                 220                 225

atc gag tac gac gac ggg ccg gcc ctc gcg gag cgc ctc gcc tcg gcg      816
Ile Glu Tyr Asp Asp Gly Pro Ala Leu Ala Glu Arg Leu Ala Ser Ala
                230                 235                 240

tgc gct cgc ggg gcg tcg gtc gtg ggc cgc gac cgc gac ctc gcc cgg      864
Cys Ala Arg Gly Ala Ser Val Val Gly Arg Asp Arg Asp Leu Ala Arg
            245                 250                 255

ccg cgc gag ccg ggc tac gcc ttc gcg tcc tgc tga                      900
Pro Arg Glu Pro Gly Tyr Ala Phe Ala Ser Cys
        260                 265


<210> SEQ ID NO 44
<211> LENGTH: 299
<212> TYPE: PRT
<213> ORGANISM: Oerskovia paurometabola

<400> SEQUENCE: 44

Val Pro Ser Leu Pro Leu Arg Ala Ser Ala His Ala Ser Leu Ile Val
    -30                 -25                 -20

Pro Ala Leu Val Leu Val Leu Leu Ala Gly Cys Ala Val Gly Ala Ala
-15                 -10                 -5                  -1  1

Pro Ser Pro Thr Pro Gly Ala Thr Asp Arg Glu Pro Ser Ala Ser Thr
            5                   10                  15

Ser Gly Ala Val Gly Gln Val Gly Glu Ala Pro Ala Pro Pro Pro Ala
        20                  25                  30

Gly Ala Gly Leu Asp Tyr Gln Leu Gly Gly Ala Tyr Pro Pro Pro Asp
    35                  40                  45

Gly Val Thr Val Val Val Arg Asp Val Thr Asp Ser Pro Ala Gly Ala
50                  55                  60                  65

Gly Tyr Asp Val Cys Tyr Val Asn Gly Phe Gln Thr Gln Pro Gly Glu
                70                  75                  80

Gly Ala Thr Trp Leu Arg Asp His Pro Asp Leu Val Leu Gln Asp Asp
            85                  90                  95

Gly Gly Thr Pro Val Ala Asp Pro Gly Trp Pro Asp Glu Leu Leu Leu
        100                 105                 110

Asp Thr Ser Thr Asp Ala Ala Arg Arg Glu Ile Ala Gln Ile Val Gly
    115                 120                 125

Gly Gln Val Asp Ala Cys Ala Asp Ala Gly Phe Asp Ala Val Glu Pro
130                 135                 140                 145

Asp Asn Leu Asp Ser Phe Thr Arg Ser Asp Gly Ala Leu Thr Arg Asp
                150                 155                 160

Asp Asn Leu Ala Leu Ala Ala Leu Leu Ile Glu Arg Ala His Ala Arg
            165                 170                 175

Gly Leu Ala Ile Gly Gln Lys Asn Thr Val Glu Leu Gly Gly Arg Gly
        180                 185                 190

Pro Ala Leu Gly Phe Asp Phe Val Val Thr Glu Asp Cys Ala Val His
    195                 200                 205

Asp Glu Cys Gly Asp Tyr Ala Ala Ala Tyr Gly Thr Arg Val Leu Glu
210                 215                 220                 225

Ile Glu Tyr Asp Asp Gly Pro Ala Leu Ala Glu Arg Leu Ala Ser Ala
                230                 235                 240
```

```
Cys Ala Arg Gly Ala Ser Val Val Gly Arg Asp Arg Asp Leu Ala Arg
            245                 250                 255

Pro Arg Glu Pro Gly Tyr Ala Phe Ala Ser Cys
        260                 265
```

<210> SEQ ID NO 45
<211> LENGTH: 268
<212> TYPE: PRT
<213> ORGANISM: Oerskovia paurometabola

<400> SEQUENCE: 45

```
Ala Pro Ser Pro Thr Pro Gly Ala Thr Asp Arg Glu Pro Ser Ala Ser
1               5                   10                  15

Thr Ser Gly Ala Val Gly Gln Val Gly Glu Ala Pro Ala Pro Pro Pro
            20                  25                  30

Ala Gly Ala Gly Leu Asp Tyr Gln Leu Gly Gly Ala Tyr Pro Pro Pro
        35                  40                  45

Asp Gly Val Thr Val Val Val Arg Asp Val Thr Asp Ser Pro Ala Gly
    50                  55                  60

Ala Gly Tyr Asp Val Cys Tyr Val Asn Gly Phe Gln Thr Gln Pro Gly
65                  70                  75                  80

Glu Gly Ala Thr Trp Leu Arg Asp His Pro Asp Leu Val Leu Gln Asp
                85                  90                  95

Asp Gly Gly Thr Pro Val Ala Asp Pro Gly Trp Pro Asp Glu Leu Leu
            100                 105                 110

Leu Asp Thr Ser Thr Asp Ala Ala Arg Arg Glu Ile Ala Gln Ile Val
        115                 120                 125

Gly Gly Gln Val Asp Ala Cys Ala Asp Ala Gly Phe Asp Ala Val Glu
    130                 135                 140

Pro Asp Asn Leu Asp Ser Phe Thr Arg Ser Asp Gly Ala Leu Thr Arg
145                 150                 155                 160

Asp Asp Asn Leu Ala Leu Ala Ala Leu Leu Ile Glu Arg Ala His Ala
                165                 170                 175

Arg Gly Leu Ala Ile Gly Gln Lys Asn Thr Val Glu Leu Gly Gly Arg
            180                 185                 190

Gly Pro Ala Leu Gly Phe Asp Phe Val Val Thr Glu Asp Cys Ala Val
        195                 200                 205

His Asp Glu Cys Gly Asp Tyr Ala Ala Ala Tyr Gly Thr Arg Val Leu
    210                 215                 220

Glu Ile Glu Tyr Asp Asp Gly Pro Ala Leu Ala Glu Arg Leu Ala Ser
225                 230                 235                 240

Ala Cys Ala Arg Gly Ala Ser Val Val Gly Arg Asp Arg Asp Leu Ala
                245                 250                 255

Arg Pro Arg Glu Pro Gly Tyr Ala Phe Ala Ser Cys
            260                 265
```

<210> SEQ ID NO 46
<211> LENGTH: 876
<212> TYPE: DNA
<213> ORGANISM: Agreia pratensis
<220> FEATURE:
<221> NAME/KEY: CDS
<222> LOCATION: (1)..(873)
<220> FEATURE:
<221> NAME/KEY: sig_peptide
<222> LOCATION: (1)..(72)
<220> FEATURE:
<221> NAME/KEY: mat_peptide
<222> LOCATION: (73)..(873)

<400> SEQUENCE: 46

```
atg cgt gtg acg aga gcg gcg gtg gcg ttg atc gcg gcc gtg ctg gtg       48
Met Arg Val Thr Arg Ala Ala Val Ala Leu Ile Ala Ala Val Leu Val
                -20                 -15                 -10

gcg ttc gcg gcc gcc ggg tgc gcg ccc gtg aag gtc aac gtc ttc tct       96
Ala Phe Ala Ala Ala Gly Cys Ala Pro Val Lys Val Asn Val Phe Ser
            -5                  -1  1               5

ccg gtc acc gac ggc gac gaa gct tcc ggc gaa acg gga cgc cag agc      144
Pro Val Thr Asp Gly Asp Glu Ala Ser Gly Glu Thr Gly Arg Gln Ser
    10                  15                  20

atc gtg ctg ccg ccg ttc ggc gag ccg ctc gac tac cag ctc ggc ggc      192
Ile Val Leu Pro Pro Phe Gly Glu Pro Leu Asp Tyr Gln Leu Gly Gly
25                  30                  35                  40

agc tac ccg gtc gac gag ggt gtc ggc atc gtg acc cga gac agc acc      240
Ser Tyr Pro Val Asp Glu Gly Val Gly Ile Val Thr Arg Asp Ser Thr
                45                  50                  55

tcg gag ccc gcg gcc ggg gtc tac tcg atc tgc tac gtc aat gga ttc      288
Ser Glu Pro Ala Ala Gly Val Tyr Ser Ile Cys Tyr Val Asn Gly Phe
            60                  65                  70

cag tcg cag ccc ggc gac gac gag cgc tgg acg gcc gac aac ccc gat      336
Gln Ser Gln Pro Gly Asp Asp Glu Arg Trp Thr Ala Asp Asn Pro Asp
        75                  80                  85

ctc gtg ctg cgt gac gac gcg ggg cag gcg atc atc gat ccg aac tgg      384
Leu Val Leu Arg Asp Asp Ala Gly Gln Ala Ile Ile Asp Pro Asn Trp
    90                  95                  100

cca gac gag ttc att ctc gac acc tcg act ccc gag aag cgg caa cgc      432
Pro Asp Glu Phe Ile Leu Asp Thr Ser Thr Pro Glu Lys Arg Gln Arg
105                 110                 115                 120

atc gtc gct atc gtc ggc gcc tcg atc acc acc tgc gcg gag gca ggc      480
Ile Val Ala Ile Val Gly Ala Ser Ile Thr Thr Cys Ala Glu Ala Gly
                125                 130                 135

ttc gac gcg atc gag atc gac aac ctc gac acc tac tcc cgc agc gac      528
Phe Asp Ala Ile Glu Ile Asp Asn Leu Asp Thr Tyr Ser Arg Ser Asp
            140                 145                 150

ggc cgg ctc gac atc gac gac aac ctc gcg ctc gcg gcc ctc ttc gcc      576
Gly Arg Leu Asp Ile Asp Asp Asn Leu Ala Leu Ala Ala Leu Phe Ala
        155                 160                 165

gag cgg gcg cac ggc ctg gcg ctc gcg atc ggg cag aag aac tct gcc      624
Glu Arg Ala His Gly Leu Ala Leu Ala Ile Gly Gln Lys Asn Ser Ala
    170                 175                 180

gag ctg gcc gcg cgc ggc cgt gac gag gcg cac ttc gac ttc gcg gtc      672
Glu Leu Ala Ala Arg Gly Arg Asp Glu Ala His Phe Asp Phe Ala Val
185                 190                 195                 200

acc gag gaa tgt gtg cgc ttc gag gag tgc gcg gcg ttc agc gac gtc      720
Thr Glu Glu Cys Val Arg Phe Glu Glu Cys Ala Ala Phe Ser Asp Val
                205                 210                 215

tac ggc gag gcc gtc gtc gac atc gag tac aca gac gat ctg ccc ggc      768
Tyr Gly Glu Ala Val Val Asp Ile Glu Tyr Thr Asp Asp Leu Pro Gly
            220                 225                 230

agc ttc gcc gac gtc tgc gca acg aaa gac cgc ccg gcg agc aca acg      816
Ser Phe Ala Asp Val Cys Ala Thr Lys Asp Arg Pro Ala Ser Thr Thr
        235                 240                 245

ctg cga gac cgc aac ctg gtg gtc aag ggt gac gcg gac tac gta ttc      864
Leu Arg Asp Arg Asn Leu Val Val Lys Gly Asp Ala Asp Tyr Val Phe
    250                 255                 260

gag cac tgc tga                                                      876
Glu His Cys
265
```

<210> SEQ ID NO 47
<211> LENGTH: 291
<212> TYPE: PRT
<213> ORGANISM: Agreia pratensis

<400> SEQUENCE: 47

```
Met Arg Val Thr Arg Ala Ala Val Ala Leu Ile Ala Ala Val Leu Val
                -20                 -15                 -10

Ala Phe Ala Ala Ala Gly Cys Ala Pro Val Lys Val Asn Val Phe Ser
            -5              -1  1               5

Pro Val Thr Asp Gly Asp Glu Ala Ser Gly Glu Thr Gly Arg Gln Ser
    10                  15                  20

Ile Val Leu Pro Pro Phe Gly Glu Pro Leu Asp Tyr Gln Leu Gly Gly
25                  30                  35                  40

Ser Tyr Pro Val Asp Glu Gly Val Gly Ile Val Thr Arg Asp Ser Thr
                45                  50                  55

Ser Glu Pro Ala Ala Gly Val Tyr Ser Ile Cys Tyr Val Asn Gly Phe
            60                  65                  70

Gln Ser Gln Pro Gly Asp Asp Glu Arg Trp Thr Ala Asp Asn Pro Asp
        75                  80                  85

Leu Val Leu Arg Asp Asp Ala Gly Gln Ala Ile Ile Asp Pro Asn Trp
    90                  95                  100

Pro Asp Glu Phe Ile Leu Asp Thr Ser Thr Pro Glu Lys Arg Gln Arg
105                 110                 115                 120

Ile Val Ala Ile Val Gly Ala Ser Ile Thr Thr Cys Ala Glu Ala Gly
                125                 130                 135

Phe Asp Ala Ile Glu Ile Asp Asn Leu Asp Thr Tyr Ser Arg Ser Asp
            140                 145                 150

Gly Arg Leu Asp Ile Asp Asp Asn Leu Ala Leu Ala Ala Leu Phe Ala
        155                 160                 165

Glu Arg Ala His Gly Leu Ala Leu Ala Ile Gly Gln Lys Asn Ser Ala
    170                 175                 180

Glu Leu Ala Ala Arg Gly Arg Asp Glu Ala His Phe Asp Phe Ala Val
185                 190                 195                 200

Thr Glu Glu Cys Val Arg Phe Glu Glu Cys Ala Ala Phe Ser Asp Val
                205                 210                 215

Tyr Gly Glu Ala Val Val Asp Ile Glu Tyr Thr Asp Asp Leu Pro Gly
            220                 225                 230

Ser Phe Ala Asp Val Cys Ala Thr Lys Asp Arg Pro Ala Ser Thr Thr
        235                 240                 245

Leu Arg Asp Arg Asn Leu Val Val Lys Gly Asp Ala Asp Tyr Val Phe
    250                 255                 260

Glu His Cys
265
```

<210> SEQ ID NO 48
<211> LENGTH: 267
<212> TYPE: PRT
<213> ORGANISM: Agreia pratensis

<400> SEQUENCE: 48

```
Pro Val Lys Val Asn Val Phe Ser Pro Val Thr Asp Gly Asp Glu Ala
1               5                   10                  15

Ser Gly Glu Thr Gly Arg Gln Ser Ile Val Leu Pro Pro Phe Gly Glu
            20                  25                  30
```

```
Pro Leu Asp Tyr Gln Leu Gly Gly Ser Tyr Pro Val Asp Glu Gly Val
        35                  40                  45

Gly Ile Val Thr Arg Asp Ser Thr Ser Glu Pro Ala Ala Gly Val Tyr
    50                  55                  60

Ser Ile Cys Tyr Val Asn Gly Phe Gln Ser Gln Pro Gly Asp Asp Glu
65                  70                  75                  80

Arg Trp Thr Ala Asp Asn Pro Asp Leu Val Leu Arg Asp Asp Ala Gly
                85                  90                  95

Gln Ala Ile Ile Asp Pro Asn Trp Pro Asp Glu Phe Ile Leu Asp Thr
            100                 105                 110

Ser Thr Pro Glu Lys Arg Gln Arg Ile Val Ala Ile Val Gly Ala Ser
        115                 120                 125

Ile Thr Thr Cys Ala Glu Ala Gly Phe Asp Ala Ile Glu Ile Asp Asn
    130                 135                 140

Leu Asp Thr Tyr Ser Arg Ser Asp Gly Arg Leu Asp Ile Asp Asp Asn
145                 150                 155                 160

Leu Ala Leu Ala Ala Leu Phe Ala Glu Arg Ala His Gly Leu Ala Leu
                165                 170                 175

Ala Ile Gly Gln Lys Asn Ser Ala Glu Leu Ala Ala Arg Gly Arg Asp
            180                 185                 190

Glu Ala His Phe Asp Phe Ala Val Thr Glu Glu Cys Val Arg Phe Glu
        195                 200                 205

Glu Cys Ala Ala Phe Ser Asp Val Tyr Gly Glu Ala Val Val Asp Ile
    210                 215                 220

Glu Tyr Thr Asp Asp Leu Pro Gly Ser Phe Ala Asp Val Cys Ala Thr
225                 230                 235                 240

Lys Asp Arg Pro Ala Ser Thr Thr Leu Arg Asp Arg Asn Leu Val Val
                245                 250                 255

Lys Gly Asp Ala Asp Tyr Val Phe Glu His Cys
            260                 265


<210> SEQ ID NO 49
<211> LENGTH: 864
<212> TYPE: DNA
<213> ORGANISM: Plantibacter flavus
<220> FEATURE:
<221> NAME/KEY: CDS
<222> LOCATION: (1)..(861)
<220> FEATURE:
<221> NAME/KEY: sig_peptide
<222> LOCATION: (1)..(108)
<220> FEATURE:
<221> NAME/KEY: mat_peptide
<222> LOCATION: (109)..(861)

<400> SEQUENCE: 49

atg acc cgt ctc ccc cgt cgc gcg cac ctg ctc acc gcg gcg ggc gcc       48
Met Thr Arg Leu Pro Arg Arg Ala His Leu Leu Thr Ala Ala Gly Ala
    -35                 -30                 -25

gcc ctc ctg ctc gcg gtc acc gcc gcc ggc tgc tcc acg ttc ccg agc       96
Ala Leu Leu Leu Ala Val Thr Ala Ala Gly Cys Ser Thr Phe Pro Ser
-20                 -15                 -10                 -5

ggt gcg agc tcc gac acc gga ccg acc cac tca gcg ggt gga ttc ccc      144
Gly Ala Ser Ser Asp Thr Gly Pro Thr His Ser Ala Gly Gly Phe Pro
            -1  1               5                   10

acg gac gtc gtc ttc gac tac cag ctc ggt ggc ggc tac gag ccg acg      192
Thr Asp Val Val Phe Asp Tyr Gln Leu Gly Gly Gly Tyr Glu Pro Thr
        15                  20                  25

gcc ggc gtg ggc ggc gtc gcg cgc gac agc acc gac tcc ccc gac ccc      240
```

-continued

```
Ala Gly Val Gly Gly Val Ala Arg Asp Ser Thr Asp Ser Pro Asp Pro
    30                  35                  40

gac cgg tac tcc atc tgc tac gtc aac ggg ttc cag agc cag ccg gcc       288
Asp Arg Tyr Ser Ile Cys Tyr Val Asn Gly Phe Gln Ser Gln Pro Ala
45                  50                  55                  60

gat cgc gac gcc tgg ctg gcc gag ccg gac ctc gtc ctc atc gac gac       336
Asp Arg Asp Ala Trp Leu Ala Glu Pro Asp Leu Val Leu Ile Asp Asp
                65                  70                  75

gcc ggt gaa ccg gtc atc gac gag aac tgg ccc gac gaa ctc atc ttc       384
Ala Gly Glu Pro Val Ile Asp Glu Asn Trp Pro Asp Glu Leu Ile Phe
            80                  85                  90

gac ctc tcc acc gac gac cgt cgc gcg cgc atc gcc gag cgg gtc ggt       432
Asp Leu Ser Thr Asp Asp Arg Arg Ala Arg Ile Ala Glu Arg Val Gly
        95                  100                 105

gcg agc atc acc cgc tgc gcg gag gcc ggc ttc gac gcc gtc gag atc       480
Ala Ser Ile Thr Arg Cys Ala Glu Ala Gly Phe Asp Ala Val Glu Ile
    110                 115                 120

gac aac ctc gac tcg tac acc cgg tcc gac ggt cgg ctc acc gtt gag       528
Asp Asn Leu Asp Ser Tyr Thr Arg Ser Asp Gly Arg Leu Thr Val Glu
125                 130                 135                 140

gac gcg atc gcc ctc gcc acc cgg tac gcc ggc ctc gcc cac gac gcg       576
Asp Ala Ile Ala Leu Ala Thr Arg Tyr Ala Gly Leu Ala His Asp Ala
                145                 150                 155

ggc ctc ctc atc ggg cag aag aac gcc gcc gag ctg ggc acg cga ggg       624
Gly Leu Leu Ile Gly Gln Lys Asn Ala Ala Glu Leu Gly Thr Arg Gly
            160                 165                 170

cgg gac gac gtc ggg ttc gac ttc gcc gtc gcg gag gag tgc cac cgc       672
Arg Asp Asp Val Gly Phe Asp Phe Ala Val Ala Glu Glu Cys His Arg
        175                 180                 185

ttc gac gag tgc gcc acc tac acc gag gtg tac gga ggc gcc gtg ctg       720
Phe Asp Glu Cys Ala Thr Tyr Thr Glu Val Tyr Gly Gly Ala Val Leu
    190                 195                 200

gac atc gag tac acc gac gac ctg cgc ggc acc ttc gac gag gtg tgc       768
Asp Ile Glu Tyr Thr Asp Asp Leu Arg Gly Thr Phe Asp Glu Val Cys
205                 210                 215                 220

gcc gat ccg cag gtc ccg ttc tcc acg atc ctg cgc gac cgc gac ctc       816
Ala Asp Pro Gln Val Pro Phe Ser Thr Ile Leu Arg Asp Arg Asp Leu
                225                 230                 235

cgg acg gcc gac gac ccc gcc cac gtc ttc gac gcc tgc gct cgg tag       864
Arg Thr Ala Asp Asp Pro Ala His Val Phe Asp Ala Cys Ala Arg
            240                 245                 250


<210> SEQ ID NO 50
<211> LENGTH: 287
<212> TYPE: PRT
<213> ORGANISM: Plantibacter flavus

<400> SEQUENCE: 50

Met Thr Arg Leu Pro Arg Arg Ala His Leu Leu Thr Ala Ala Gly Ala
    -35                 -30                 -25

Ala Leu Leu Leu Ala Val Thr Ala Ala Gly Cys Ser Thr Phe Pro Ser
-20                 -15                 -10                 -5

Gly Ala Ser Ser Asp Thr Gly Pro Thr His Ser Ala Gly Gly Phe Pro
            -1  1               5                   10

Thr Asp Val Val Phe Asp Tyr Gln Leu Gly Gly Gly Tyr Glu Pro Thr
        15                  20                  25

Ala Gly Val Gly Gly Val Ala Arg Asp Ser Thr Asp Ser Pro Asp Pro
    30                  35                  40

Asp Arg Tyr Ser Ile Cys Tyr Val Asn Gly Phe Gln Ser Gln Pro Ala
```

```
45                  50                  55                  60

Asp Arg Asp Ala Trp Leu Ala Glu Pro Asp Leu Val Leu Ile Asp Asp
                65                  70                  75

Ala Gly Glu Pro Val Ile Asp Glu Asn Trp Pro Asp Glu Leu Ile Phe
            80                  85                  90

Asp Leu Ser Thr Asp Asp Arg Arg Ala Arg Ile Ala Glu Arg Val Gly
        95                  100                 105

Ala Ser Ile Thr Arg Cys Ala Glu Ala Gly Phe Asp Ala Val Glu Ile
    110                 115                 120

Asp Asn Leu Asp Ser Tyr Thr Arg Ser Asp Gly Arg Leu Thr Val Glu
125                 130                 135                 140

Asp Ala Ile Ala Leu Ala Thr Arg Tyr Ala Gly Leu Ala His Asp Ala
                145                 150                 155

Gly Leu Leu Ile Gly Gln Lys Asn Ala Ala Glu Leu Gly Thr Arg Gly
            160                 165                 170

Arg Asp Asp Val Gly Phe Asp Phe Ala Val Ala Glu Glu Cys His Arg
        175                 180                 185

Phe Asp Glu Cys Ala Thr Tyr Thr Glu Val Tyr Gly Gly Ala Val Leu
    190                 195                 200

Asp Ile Glu Tyr Thr Asp Asp Leu Arg Gly Thr Phe Asp Glu Val Cys
205                 210                 215                 220

Ala Asp Pro Gln Val Pro Phe Ser Thr Ile Leu Arg Asp Arg Asp Leu
                225                 230                 235

Arg Thr Ala Asp Asp Pro Ala His Val Phe Asp Ala Cys Ala Arg
            240                 245                 250


<210> SEQ ID NO 51
<211> LENGTH: 251
<212> TYPE: PRT
<213> ORGANISM: Plantibacter flavus

<400> SEQUENCE: 51

Asp Thr Gly Pro Thr His Ser Ala Gly Gly Phe Pro Thr Asp Val Val
1               5                   10                  15

Phe Asp Tyr Gln Leu Gly Gly Gly Tyr Glu Pro Thr Ala Gly Val Gly
            20                  25                  30

Gly Val Ala Arg Asp Ser Thr Asp Ser Pro Asp Pro Asp Arg Tyr Ser
        35                  40                  45

Ile Cys Tyr Val Asn Gly Phe Gln Ser Gln Pro Ala Asp Arg Asp Ala
    50                  55                  60

Trp Leu Ala Glu Pro Asp Leu Val Leu Ile Asp Asp Ala Gly Glu Pro
65                  70                  75                  80

Val Ile Asp Glu Asn Trp Pro Asp Glu Leu Ile Phe Asp Leu Ser Thr
                85                  90                  95

Asp Asp Arg Arg Ala Arg Ile Ala Glu Arg Val Gly Ala Ser Ile Thr
            100                 105                 110

Arg Cys Ala Glu Ala Gly Phe Asp Ala Val Glu Ile Asp Asn Leu Asp
        115                 120                 125

Ser Tyr Thr Arg Ser Asp Gly Arg Leu Thr Val Glu Asp Ala Ile Ala
    130                 135                 140

Leu Ala Thr Arg Tyr Ala Gly Leu Ala His Asp Ala Gly Leu Leu Ile
145                 150                 155                 160

Gly Gln Lys Asn Ala Ala Glu Leu Gly Thr Arg Gly Arg Asp Asp Val
                165                 170                 175
```

```
Gly Phe Asp Phe Ala Val Ala Glu Glu Cys His Arg Phe Asp Glu Cys
            180                 185                 190

Ala Thr Tyr Thr Glu Val Tyr Gly Gly Ala Val Leu Asp Ile Glu Tyr
        195                 200                 205

Thr Asp Asp Leu Arg Gly Thr Phe Asp Glu Val Cys Ala Asp Pro Gln
    210                 215                 220

Val Pro Phe Ser Thr Ile Leu Arg Asp Arg Asp Leu Arg Thr Ala Asp
225                 230                 235                 240

Asp Pro Ala His Val Phe Asp Ala Cys Ala Arg
                245                 250


<210> SEQ ID NO 52
<211> LENGTH: 852
<212> TYPE: DNA
<213> ORGANISM: Streptomyces miharaensis
<220> FEATURE:
<221> NAME/KEY: CDS
<222> LOCATION: (1)..(849)
<220> FEATURE:
<221> NAME/KEY: sig_peptide
<222> LOCATION: (1)..(132)
<220> FEATURE:
<221> NAME/KEY: mat_peptide
<222> LOCATION: (133)..(849)

<400> SEQUENCE: 52

atg ccc gcc aag ggt gtt tcc cgc gtc gga cgt ccc ggg acg acc gcc       48
Met Pro Ala Lys Gly Val Ser Arg Val Gly Arg Pro Gly Thr Thr Ala
                -40                 -35                 -30

ggc gcc gtc gtg tgt gcg gtc gcg ttg gcc gtg ggg ctg acg gga tgc       96
Gly Ala Val Val Cys Ala Val Ala Leu Ala Val Gly Leu Thr Gly Cys
            -25                 -20                 -15

gga tcg agc ggc tcg ccg cag ccg tcg cgg agt gcc tcc cct cag gtg      144
Gly Ser Ser Gly Ser Pro Gln Pro Ser Arg Ser Ala Ser Pro Gln Val
        -10                 -5                  -1  1

cgg ctc ccg ccg cgg cac gcc ggt ttc gac tac cag atc ggc ggt gcc      192
Arg Leu Pro Pro Arg His Ala Gly Phe Asp Tyr Gln Ile Gly Gly Ala
5                   10                  15                  20

tat ccc ccg ccg aag ggc gtg cgc atc gtc agc cgc gac cgc tcc tcg      240
Tyr Pro Pro Pro Lys Gly Val Arg Ile Val Ser Arg Asp Arg Ser Ser
                25                  30                  35

tcc ccc gcg ccc ggc cgc tac aac atc tgc tac gtc aac gcc ttc cag      288
Ser Pro Ala Pro Gly Arg Tyr Asn Ile Cys Tyr Val Asn Ala Phe Gln
            40                  45                  50

gcc cag ccg gag gag cgc gcc gcc tgg ccc gcc gac ctg ctg ctg cgc      336
Ala Gln Pro Glu Glu Arg Ala Ala Trp Pro Ala Asp Leu Leu Leu Arg
        55                  60                  65

gat gcc gac ggc aag ctg gtc atc gac gag gac tgg aac gaa ccg ctg      384
Asp Ala Asp Gly Lys Leu Val Ile Asp Glu Asp Trp Asn Glu Pro Leu
    70                  75                  80

ctc gac ctc cgc acc ccg gcc aag cgc gag cgc gtc gcc cgg aag gtc      432
Leu Asp Leu Arg Thr Pro Ala Lys Arg Glu Arg Val Ala Arg Lys Val
85                  90                  95                  100

gac cgc tgg atc gac gag tgc gcc acc aag ggc ttc gac gcc gtc gag      480
Asp Arg Trp Ile Asp Glu Cys Ala Thr Lys Gly Phe Asp Ala Val Glu
                105                 110                 115

ccg gac aac tac gac agc tac aca cgc tcc cag gac ctg ctc acc gcc      528
Pro Asp Asn Tyr Asp Ser Tyr Thr Arg Ser Gln Asp Leu Leu Thr Ala
            120                 125                 130

gac gac gcg acc gcg ttc atc gcc ctg ctc tcc cgg cac gcg cac gcc      576
Asp Asp Ala Thr Ala Phe Ile Ala Leu Leu Ser Arg His Ala His Ala
        135                 140                 145
```

```
cgg cac ctg gcc atc ggc cag aag aac aca ccc gaa ctg gcg agc gtc      624
Arg His Leu Ala Ile Gly Gln Lys Asn Thr Pro Glu Leu Ala Ser Val
    150                 155                 160

agg aag aag gcc ggg ctg gac ttc gcc gtg gcc gag gag tgc ggt gag      672
Arg Lys Lys Ala Gly Leu Asp Phe Ala Val Ala Glu Glu Cys Gly Glu
165                 170                 175                 180

tac gac gag tgc ggc acc tat gcc gag gcg ttc gac gac cgg gtg gtc      720
Tyr Asp Glu Cys Gly Thr Tyr Ala Glu Ala Phe Asp Asp Arg Val Val
                185                 190                 195

gtc gtc gag tac tcg gac aag ggc ctg cgc aag gcc gtc gcg ggc ttc      768
Val Val Glu Tyr Ser Asp Lys Gly Leu Arg Lys Ala Val Ala Gly Phe
            200                 205                 210

ggc gac aga ctg agc atc gtg cgc cgg gac cgg atg gtg tcg aca ccg      816
Gly Asp Arg Leu Ser Ile Val Arg Arg Asp Arg Met Val Ser Thr Pro
        215                 220                 225

ggc agt gcc ggc tac gtg cgc aag cta cgc ccg tga                      852
Gly Ser Ala Gly Tyr Val Arg Lys Leu Arg Pro
    230                 235


<210> SEQ ID NO 53
<211> LENGTH: 283
<212> TYPE: PRT
<213> ORGANISM: Streptomyces miharaensis

<400> SEQUENCE: 53

Met Pro Ala Lys Gly Val Ser Arg Val Gly Arg Pro Gly Thr Thr Ala
                -40                 -35                 -30

Gly Ala Val Val Cys Ala Val Ala Leu Ala Val Gly Leu Thr Gly Cys
            -25                 -20                 -15

Gly Ser Ser Gly Ser Pro Gln Pro Ser Arg Ser Ala Ser Pro Gln Val
        -10                 -5                  -1  1

Arg Leu Pro Pro Arg His Ala Gly Phe Asp Tyr Gln Ile Gly Gly Ala
5                   10                  15                  20

Tyr Pro Pro Pro Lys Gly Val Arg Ile Val Ser Arg Asp Arg Ser Ser
                25                  30                  35

Ser Pro Ala Pro Gly Arg Tyr Asn Ile Cys Tyr Val Asn Ala Phe Gln
            40                  45                  50

Ala Gln Pro Glu Glu Arg Ala Ala Trp Pro Ala Asp Leu Leu Leu Arg
        55                  60                  65

Asp Ala Asp Gly Lys Leu Val Ile Asp Glu Asp Trp Asn Glu Pro Leu
    70                  75                  80

Leu Asp Leu Arg Thr Pro Ala Lys Arg Glu Arg Val Ala Arg Lys Val
85                  90                  95                  100

Asp Arg Trp Ile Asp Glu Cys Ala Thr Lys Gly Phe Asp Ala Val Glu
                105                 110                 115

Pro Asp Asn Tyr Asp Ser Tyr Thr Arg Ser Gln Asp Leu Leu Thr Ala
            120                 125                 130

Asp Asp Ala Thr Ala Phe Ile Ala Leu Leu Ser Arg His Ala His Ala
        135                 140                 145

Arg His Leu Ala Ile Gly Gln Lys Asn Thr Pro Glu Leu Ala Ser Val
    150                 155                 160

Arg Lys Lys Ala Gly Leu Asp Phe Ala Val Ala Glu Glu Cys Gly Glu
165                 170                 175                 180

Tyr Asp Glu Cys Gly Thr Tyr Ala Glu Ala Phe Asp Asp Arg Val Val
                185                 190                 195

Val Val Glu Tyr Ser Asp Lys Gly Leu Arg Lys Ala Val Ala Gly Phe
```

```
            200                 205                 210

Gly Asp Arg Leu Ser Ile Val Arg Arg Asp Arg Met Val Ser Thr Pro
        215                 220                 225

Gly Ser Ala Gly Tyr Val Arg Lys Leu Arg Pro
    230                 235


<210> SEQ ID NO 54
<211> LENGTH: 239
<212> TYPE: PRT
<213> ORGANISM: Streptomyces miharaensis

<400> SEQUENCE: 54

Ser Pro Gln Val Arg Leu Pro Pro Arg His Ala Gly Phe Asp Tyr Gln
1               5                   10                  15

Ile Gly Gly Ala Tyr Pro Pro Pro Lys Gly Val Arg Ile Val Ser Arg
            20                  25                  30

Asp Arg Ser Ser Ser Pro Ala Pro Gly Arg Tyr Asn Ile Cys Tyr Val
        35                  40                  45

Asn Ala Phe Gln Ala Gln Pro Glu Glu Arg Ala Ala Trp Pro Ala Asp
    50                  55                  60

Leu Leu Leu Arg Asp Ala Asp Gly Lys Leu Val Ile Asp Glu Asp Trp
65                  70                  75                  80

Asn Glu Pro Leu Leu Asp Leu Arg Thr Pro Ala Lys Arg Glu Arg Val
                85                  90                  95

Ala Arg Lys Val Asp Arg Trp Ile Asp Glu Cys Ala Thr Lys Gly Phe
            100                 105                 110

Asp Ala Val Glu Pro Asp Asn Tyr Asp Ser Tyr Thr Arg Ser Gln Asp
        115                 120                 125

Leu Leu Thr Ala Asp Asp Ala Thr Ala Phe Ile Ala Leu Leu Ser Arg
    130                 135                 140

His Ala His Ala Arg His Leu Ala Ile Gly Gln Lys Asn Thr Pro Glu
145                 150                 155                 160

Leu Ala Ser Val Arg Lys Lys Ala Gly Leu Asp Phe Ala Val Ala Glu
                165                 170                 175

Glu Cys Gly Glu Tyr Asp Glu Cys Gly Thr Tyr Ala Glu Ala Phe Asp
            180                 185                 190

Asp Arg Val Val Val Val Glu Tyr Ser Asp Lys Gly Leu Arg Lys Ala
        195                 200                 205

Val Ala Gly Phe Gly Asp Arg Leu Ser Ile Val Arg Arg Asp Arg Met
    210                 215                 220

Val Ser Thr Pro Gly Ser Ala Gly Tyr Val Arg Lys Leu Arg Pro
225                 230                 235


<210> SEQ ID NO 55
<211> LENGTH: 1056
<212> TYPE: DNA
<213> ORGANISM: Urnula craterium
<220> FEATURE:
<221> NAME/KEY: CDS
<222> LOCATION: (1)..(217)
<220> FEATURE:
<221> NAME/KEY: sig_peptide
<222> LOCATION: (1)..(54)
<220> FEATURE:
<221> NAME/KEY: mat_peptide
<222> LOCATION: (55)..(1053)
<220> FEATURE:
<221> NAME/KEY: CDS
<222> LOCATION: (299)..(595)
<220> FEATURE:
```

-continued

<221> NAME/KEY: CDS
<222> LOCATION: (677)..(1053)

<400> SEQUENCE: 55 atg aca tcg aaa ata ctc tcg tta gca tta gca acg cta aac gtc gca 48
Met Thr Ser Lys Ile Leu Ser Leu Ala Leu Ala Thr Leu Asn Val Ala
-15 -10 -5 tat gca gca aca aca atc tgt agc acc aaa tgc cct tac acg aat ctc 96
Tyr Ala Ala Thr Thr Ile Cys Ser Thr Lys Cys Pro Tyr Thr Asn Leu
-1 1 5 10 ggt tct tcc gat gca gta acg aaa tcc gac tgg tgg aaa cct gcg ctt 144
Gly Ser Ser Asp Ala Val Thr Lys Ser Asp Trp Trp Lys Pro Ala Leu
15 20 25 30 ggt gct act tgg cag gtt gtg ttg acg cct gct gat gat gat gcc ggg 192
Gly Ala Thr Trp Gln Val Val Leu Thr Pro Ala Asp Asp Asp Ala Gly
35 40 45 ccg cag ttg acg gac gat tat gaa g gtctcctccc ctcttctcta 237
Pro Gln Leu Thr Asp Asp Tyr Glu
50 gatttaatct aatctctctc gaattccctt cagctagcta atatgcccct gaaataaata 297 g tc tac gac ctt gac gtc ttt gac gtc gac gct agc gtc ttc aaa tct 345
Val Tyr Asp Leu Asp Val Phe Asp Val Asp Ala Ser Val Phe Lys Ser
55 60 65 70 cta caa gca aaa gac aag aaa gtg ata tgc tac ttt tcg gca ggg tcc 393
Leu Gln Ala Lys Asp Lys Lys Val Ile Cys Tyr Phe Ser Ala Gly Ser
75 80 85 tat gaa gac tgg cgc gag gac tgt gga tgt ttc aag tcc agt gac tta 441
Tyr Glu Asp Trp Arg Glu Asp Cys Gly Cys Phe Lys Ser Ser Asp Leu
90 95 100 ggt tcc gac ctt gac ggg tgg gaa ggt gaa gct tgg ttg aat act gat 489
Gly Ser Asp Leu Asp Gly Trp Glu Gly Glu Ala Trp Leu Asn Thr Asp
105 110 115 agt cag aat gtg agg aat att atg gct gcg aga ctt gat gtg gcg gtg 537
Ser Gln Asn Val Arg Asn Ile Met Ala Ala Arg Leu Asp Val Ala Val
120 125 130 gaa aaa gga tgc aat ggc gtt gat cca gat aat gtt gat ggg tat gat 585
Glu Lys Gly Cys Asn Gly Val Asp Pro Asp Asn Val Asp Gly Tyr Asp
135 140 145 150 aat gat aac g gtatgccttt tccctcattc ttctgttcaa ttttattcga 635
Asn Asp Asn cgctgataga atctcttttt ctttttcttt ttcgggaata g gt ctg ggt tta tcc 690
Gly Leu Gly Leu Ser
155 gag tcc acg gcg aaa tcg tat ctg cag ttc tta tca gac gaa gca cat 738
Glu Ser Thr Ala Lys Ser Tyr Leu Gln Phe Leu Ser Asp Glu Ala His
160 165 170 tca agg ggt tta gct att ggt cta aaa aac gct gga agt att gcg gcg 786
Ser Arg Gly Leu Ala Ile Gly Leu Lys Asn Ala Gly Ser Ile Ala Ala
175 180 185 190 gat gta gtg gat agt atg gaa tgg gag gtc aac gaa gag tgt att gcg 834
Asp Val Val Asp Ser Met Glu Trp Glu Val Asn Glu Glu Cys Ile Ala
195 200 205 cag gag aac tgt gaa gat tat aag acc ttt gtt gat gcc ggg aag ccg 882
Gln Glu Asn Cys Glu Asp Tyr Lys Thr Phe Val Asp Ala Gly Lys Pro
210 215 220 gtt ttc aac att gag tat ccg ccg gag gat cat atc gat gat gcg tgg 930
Val Phe Asn Ile Glu Tyr Pro Pro Glu Asp His Ile Asp Asp Ala Trp
225 230 235 acg gag gcg gag att gag gag agg tgt gcg cag aag gcg gat gct agc 978

```
Thr Glu Ala Glu Ile Glu Glu Arg Cys Ala Gln Lys Ala Asp Ala Ser
    240                 245                 250

aat ggt gct acc aag ttc tcg acg gtt ttg aag aac cat gag aat gtg     1026
Asn Gly Ala Thr Lys Phe Ser Thr Val Leu Lys Asn His Glu Asn Val
255                 260                 265                 270

gat gaa tgg atc aga act tgc agt gag tag                             1056
Asp Glu Trp Ile Arg Thr Cys Ser Glu
                275


<210> SEQ ID NO 56
<211> LENGTH: 297
<212> TYPE: PRT
<213> ORGANISM: Urnula craterium

<400> SEQUENCE: 56

Met Thr Ser Lys Ile Leu Ser Leu Ala Leu Ala Thr Leu Asn Val Ala
            -15                 -10                 -5

Tyr Ala Ala Thr Thr Ile Cys Ser Thr Lys Cys Pro Tyr Thr Asn Leu
    -1  1               5                   10

Gly Ser Ser Asp Ala Val Thr Lys Ser Asp Trp Trp Lys Pro Ala Leu
15                  20                  25                  30

Gly Ala Thr Trp Gln Val Val Leu Thr Pro Ala Asp Asp Asp Ala Gly
                35                  40                  45

Pro Gln Leu Thr Asp Asp Tyr Glu Val Tyr Asp Leu Asp Val Phe Asp
            50                  55                  60

Val Asp Ala Ser Val Phe Lys Ser Leu Gln Ala Lys Asp Lys Lys Val
        65                  70                  75

Ile Cys Tyr Phe Ser Ala Gly Ser Tyr Glu Asp Trp Arg Glu Asp Cys
    80                  85                  90

Gly Cys Phe Lys Ser Ser Asp Leu Gly Ser Asp Leu Asp Gly Trp Glu
95                  100                 105                 110

Gly Glu Ala Trp Leu Asn Thr Asp Ser Gln Asn Val Arg Asn Ile Met
                115                 120                 125

Ala Ala Arg Leu Asp Val Ala Val Glu Lys Gly Cys Asn Gly Val Asp
            130                 135                 140

Pro Asp Asn Val Asp Gly Tyr Asp Asn Asp Asn Gly Leu Gly Leu Ser
        145                 150                 155

Glu Ser Thr Ala Lys Ser Tyr Leu Gln Phe Leu Ser Asp Glu Ala His
    160                 165                 170

Ser Arg Gly Leu Ala Ile Gly Leu Lys Asn Ala Gly Ser Ile Ala Ala
175                 180                 185                 190

Asp Val Val Asp Ser Met Glu Trp Glu Val Asn Glu Glu Cys Ile Ala
                195                 200                 205

Gln Glu Asn Cys Glu Asp Tyr Lys Thr Phe Val Asp Ala Gly Lys Pro
            210                 215                 220

Val Phe Asn Ile Glu Tyr Pro Pro Glu Asp His Ile Asp Asp Ala Trp
        225                 230                 235

Thr Glu Ala Glu Ile Glu Glu Arg Cys Ala Gln Lys Ala Asp Ala Ser
    240                 245                 250

Asn Gly Ala Thr Lys Phe Ser Thr Val Leu Lys Asn His Glu Asn Val
255                 260                 265                 270

Asp Glu Trp Ile Arg Thr Cys Ser Glu
                275


<210> SEQ ID NO 57
<211> LENGTH: 279
```

<212> TYPE: PRT
<213> ORGANISM: Urnula craterium

<400> SEQUENCE: 57

Ala Thr Thr Ile Cys Ser Thr Lys Cys Pro Tyr Thr Asn Leu Gly Ser
1               5                   10                  15

Ser Asp Ala Val Thr Lys Ser Asp Trp Trp Lys Pro Ala Leu Gly Ala
            20                  25                  30

Thr Trp Gln Val Val Leu Thr Pro Ala Asp Asp Asp Ala Gly Pro Gln
        35                  40                  45

Leu Thr Asp Asp Tyr Glu Val Tyr Asp Leu Asp Val Phe Asp Val Asp
    50                  55                  60

Ala Ser Val Phe Lys Ser Leu Gln Ala Lys Asp Lys Lys Val Ile Cys
65                  70                  75                  80

Tyr Phe Ser Ala Gly Ser Tyr Glu Asp Trp Arg Glu Asp Cys Gly Cys
                85                  90                  95

Phe Lys Ser Ser Asp Leu Gly Ser Asp Leu Asp Gly Trp Glu Gly Glu
            100                 105                 110

Ala Trp Leu Asn Thr Asp Ser Gln Asn Val Arg Asn Ile Met Ala Ala
        115                 120                 125

Arg Leu Asp Val Ala Val Glu Lys Gly Cys Asn Gly Val Asp Pro Asp
    130                 135                 140

Asn Val Asp Gly Tyr Asp Asn Asp Asn Gly Leu Gly Leu Ser Glu Ser
145                 150                 155                 160

Thr Ala Lys Ser Tyr Leu Gln Phe Leu Ser Asp Glu Ala His Ser Arg
                165                 170                 175

Gly Leu Ala Ile Gly Leu Lys Asn Ala Gly Ser Ile Ala Ala Asp Val
            180                 185                 190

Val Asp Ser Met Glu Trp Glu Val Asn Glu Glu Cys Ile Ala Gln Glu
        195                 200                 205

Asn Cys Glu Asp Tyr Lys Thr Phe Val Asp Ala Gly Lys Pro Val Phe
    210                 215                 220

Asn Ile Glu Tyr Pro Pro Glu Asp His Ile Asp Asp Ala Trp Thr Glu
225                 230                 235                 240

Ala Glu Ile Glu Glu Arg Cys Ala Gln Lys Ala Asp Ala Ser Asn Gly
                245                 250                 255

Ala Thr Lys Phe Ser Thr Val Leu Lys Asn His Glu Asn Val Asp Glu
            260                 265                 270

Trp Ile Arg Thr Cys Ser Glu
        275

<210> SEQ ID NO 58
<211> LENGTH: 27
<212> TYPE: PRT
<213> ORGANISM: Signal peptide

<400> SEQUENCE: 58

Met Lys Lys Pro Leu Gly Lys Ile Val Ala Ser Thr Ala Leu Leu Ile
1               5                   10                  15

Ser Val Ala Phe Ser Ser Ser Ile Ala Ser Ala
            20                  25

<210> SEQ ID NO 59
<211> LENGTH: 8
<212> TYPE: PRT
<213> ORGANISM: Artificial
<220> FEATURE:

<223> OTHER INFORMATION: His-tag

<400> SEQUENCE: 59

His His His His His His Pro Arg
1 5

<210> SEQ ID NO 60
<211> LENGTH: 5
<212> TYPE: PRT
<213> ORGANISM: Artificial
<220> FEATURE:
<223> OTHER INFORMATION: Motif
<220> FEATURE:
<221> NAME/KEY: MISC_FEATURE
<222> LOCATION: (1)..(1)
<223> OTHER INFORMATION: Xaa = V (Val) or L (Leu) or I (Ile)
<220> FEATURE:
<221> NAME/KEY: MISC_FEATURE
<222> LOCATION: (2)..(2)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = E (Glu) or D (Asp) or S (Ser) or Q (Gln)

<400> SEQUENCE: 60

Xaa Xaa Glu Xaa Cys
1 5

<210> SEQ ID NO 61
<211> LENGTH: 5
<212> TYPE: PRT
<213> ORGANISM: Artificial
<220> FEATURE:
<223> OTHER INFORMATION: Motif
<220> FEATURE:
<221> NAME/KEY: MISC_FEATURE
<222> LOCATION: (3)..(3)
<223> OTHER INFORMATION: Xaa = F (Phe) or L (leu) or I (Ile) or V (val)
<220> FEATURE:
<221> NAME/KEY: MISC_FEATURE
<222> LOCATION: (4)..(4)
<223> OTHER INFORMATION: Xaa = S (Ser) or D (Asp) or N (Asn)
<220> FEATURE:
<221> NAME/KEY: MISC_FEATURE
<222> LOCATION: (5)..(5)
<223> OTHER INFORMATION: Xaa = A (Ala) or T (Thr) or V (Val) or G (Gly)

<400> SEQUENCE: 61

Cys Tyr Xaa Xaa Xaa
1 5

<210> SEQ ID NO 62
<211> LENGTH: 5
<212> TYPE: PRT
<213> ORGANISM: Artificial
<220> FEATURE:
<223> OTHER INFORMATION: Motif
<220> FEATURE:
<221> NAME/KEY: MISC_FEATURE
<222> LOCATION: (4)..(4)
<223> OTHER INFORMATION: Xaa = L (Leu) or I (Ile)

<400> SEQUENCE: 62

Asp Tyr Gln Xaa Gly
1 5

<210> SEQ ID NO 63
<211> LENGTH: 5
<212> TYPE: PRT
<213> ORGANISM: Artificial

<220> FEATURE:
<223> OTHER INFORMATION: Motif
<220> FEATURE:
<221> NAME/KEY: MISC_FEATURE
<222> LOCATION: (3)..(3)
<223> OTHER INFORMATION: Xaa = T (Thr) or A (Ala) or V (Val)
<220> FEATURE:
<221> NAME/KEY: MISC_FEATURE
<222> LOCATION: (5)..(5)
<223> OTHER INFORMATION: Xaa = P (Phe) or S (Ser) or D (Asp)

<400> SEQUENCE: 63

Phe Gln Xaa Gln Xaa
1 5

<210> SEQ ID NO 64
<211> LENGTH: 5
<212> TYPE: PRT
<213> ORGANISM: Artificial
<220> FEATURE:
<223> OTHER INFORMATION: Motif

<400> SEQUENCE: 64

Ala Glu Glu Cys Gly
1 5

<210> SEQ ID NO 65
<211> LENGTH: 6
<212> TYPE: PRT
<213> ORGANISM: Artificial
<220> FEATURE:
<223> OTHER INFORMATION: Motif
<220> FEATURE:
<221> NAME/KEY: MISC_FEATURE
<222> LOCATION: (5)..(5)
<223> OTHER INFORMATION: Xaa = A(Ala) or T(Thr)

<400> SEQUENCE: 65

Asn Ala Phe Gln Xaa Gln
1 5

<210> SEQ ID NO 66
<211> LENGTH: 5
<212> TYPE: PRT
<213> ORGANISM: Artificial
<220> FEATURE:
<223> OTHER INFORMATION: Motif

<400> SEQUENCE: 66

Trp Gln Trp Gln Leu
1 5

<210> SEQ ID NO 67
<211> LENGTH: 7
<212> TYPE: PRT
<213> ORGANISM: Artificial
<220> FEATURE:
<223> OTHER INFORMATION: Motif
<220> FEATURE:
<221> NAME/KEY: MISC_FEATURE
<222> LOCATION: (1)..(1)
<223> OTHER INFORMATION: Xaa = V(Val) or L (Leu) or I (Ile)
<220> FEATURE:
<221> NAME/KEY: MISC_FEATURE
<222> LOCATION: (2)..(2)
<223> OTHER INFORMATION: Xaa = G(Gly) or A(Ala) or S(Ser) or D(Asp)
<220> FEATURE:
<221> NAME/KEY: MISC_FEATURE
<222> LOCATION: (6)..(6)
<223> OTHER INFORMATION: Xaa = D(Asp) or G(Gly) or S(Ser)
<220> FEATURE:

<221> NAME/KEY: MISC_FEATURE
<222> LOCATION: (7)..(7)
<223> OTHER INFORMATION: Xaa = V(Val) or L(Leu) or I(Ile) or P(Pro)

<400> SEQUENCE: 67

Xaa Xaa Leu Lys Asn Xaa Xaa
1               5

<210> SEQ ID NO 68
<211> LENGTH: 10
<212> TYPE: PRT
<213> ORGANISM: Artificial
<220> FEATURE:
<223> OTHER INFORMATION: Motif
<220> FEATURE:
<221> NAME/KEY: MISC_FEATURE
<222> LOCATION: (2)..(2)
<223> OTHER INFORMATION: Xaa = any amino acid
<220> FEATURE:
<221> NAME/KEY: MISC_FEATURE
<222> LOCATION: (3)..(3)
<223> OTHER INFORMATION: Xaa = any amino acid
<220> FEATURE:
<221> NAME/KEY: MISC_FEATURE
<222> LOCATION: (5)..(5)
<223> OTHER INFORMATION: Xaa = any amino acid
<220> FEATURE:
<221> NAME/KEY: MISC_FEATURE
<222> LOCATION: (6)..(6)
<223> OTHER INFORMATION: Xaa = N(Asn) or H His) or Q(Gln) or T(Thr) or
      S(Ser)
<220> FEATURE:
<221> NAME/KEY: MISC_FEATURE
<222> LOCATION: (10)..(10)
<223> OTHER INFORMATION: Xaa = P (Pro) or G(Gly)

<400> SEQUENCE: 68

Gly Xaa Xaa Val Xaa Xaa Ile Glu Tyr Xaa
1               5                   10

<210> SEQ ID NO 69
<211> LENGTH: 5
<212> TYPE: PRT
<213> ORGANISM: Artificial
<220> FEATURE:
<223> OTHER INFORMATION: Motif

<400> SEQUENCE: 69

Val Ile Cys Tyr Phe
1               5

<210> SEQ ID NO 70
<211> LENGTH: 6
<212> TYPE: PRT
<213> ORGANISM: Artificial
<220> FEATURE:
<223> OTHER INFORMATION: Motif

<400> SEQUENCE: 70

Ile Cys Tyr Phe Ser Ala
1               5

<210> SEQ ID NO 71
<211> LENGTH: 5
<212> TYPE: PRT
<213> ORGANISM: Artificial
<220> FEATURE:
<223> OTHER INFORMATION: Motif

<400> SEQUENCE: 71

```
Asp Phe Ala Val Leu
1               5


<210> SEQ ID NO 72
<211> LENGTH: 325
<212> TYPE: PRT
<213> ORGANISM: Chaetomium globosum

<400> SEQUENCE: 72

Gln Val Asp Val Pro Ser Asn Phe Val Pro Gly Val Lys Trp Gln Ile
1               5                   10                  15

Ile Ile Gln Asn Thr Leu Asp Pro Val Ala Ala Val Asn Pro Ser Asp
            20                  25                  30

Ala Val Val Trp Asp Leu Asp Leu Tyr His Ile Ala Arg Thr Pro Glu
        35                  40                  45

Ile Val Ser His Leu Arg Asp Asn Asn Pro Asp Ala Ile Leu Ile Cys
    50                  55                  60

Tyr Phe Asn Ala Gly Leu Ala Gln Thr Ser Asp Cys Asp Tyr Asp Ser
65                  70                  75                  80

Arg Trp Asn Ser Thr Ala Ser Asn Leu Leu Gly Asn Pro Tyr Ser Pro
                85                  90                  95

Asp Glu Pro Gln Phe Ala Asp Glu Arg Trp Val Asn Ile Lys Asn Gln
            100                 105                 110

Thr Ala Arg Asn Trp Met Lys Asp Arg Ile Thr Leu Ala Arg Asp Val
        115                 120                 125

Gly Cys Asp Gly Val Asp Pro Asp Asn Ile Asp Gly Tyr Leu Asn Asp
    130                 135                 140

Glu Asp Gly Ala Asn Gly Thr Gly Trp Asn Leu Ser Glu Gly Asp Tyr
145                 150                 155                 160

Val Ser Phe Val Thr Glu Leu Ala Glu His Ala His Ser Leu Thr Thr
                165                 170                 175

Asp Arg Gly His Thr Leu Leu Ile Gly Gln Lys Asn Ala Pro Glu Leu
            180                 185                 190

Val Glu Gln Val Gly Gly Ser Leu Asp Phe Ala Val Leu Glu Asp Cys
        195                 200                 205

Lys Thr Leu Asn Asp Asp Glu Asp Tyr Val Phe Cys Gly Asp Phe Gln
    210                 215                 220

Thr Tyr Ile Ala Asp Gly Lys Pro Val Phe Ser Ile Glu Tyr Pro Ser
225                 230                 235                 240

Thr Leu Gly Asp Thr Glu Thr Gly Asn Cys Asn Thr Asn Gly Ala Ser
                245                 250                 255

Asp Glu Gln Tyr Ala Ala Ser Cys Ala Thr Asp Gln Gly Asn Ser Gly
            260                 265                 270

Phe Ser Thr Val Leu Lys Ile Gln Gly Gly Ala Gly Glu Leu Asn Gly
        275                 280                 285

Cys Thr Gln Tyr Cys Ser Glu Ala Gly Pro Gly Asn Gly Val Val Val
    290                 295                 300

Ser Pro Thr Asp Pro Asp Leu Asp Gly Arg Lys Cys Pro Ser Asn Ala
305                 310                 315                 320

Ala Pro Pro Pro Ser
                325


<210> SEQ ID NO 73
<211> LENGTH: 276
<212> TYPE: PRT
<213> ORGANISM: Stilbella fimetaria
```

<400> SEQUENCE: 73

Ala Ser Asn Val Phe Asp Gly Leu Glu Lys Gly Thr Glu Trp Asn Ile
1 5 10 15

Cys Ile His Lys Pro Ile Lys His Asp Thr Pro Asp Asp Val Val Pro
20 25 30

His Lys Ala Ala Val Tyr Asp Ile Ala Val Asp His Ala Arg Asp Phe
35 40 45

Pro Gly Ile Ile Pro Ala Ile Lys Glu Ser Gly Thr Ile Val Leu Cys
50 55 60

Tyr Phe Asn Ala Gly Ala Leu Gln Asp Trp Asp Ala Asp Lys Asp Ala
65 70 75 80

Phe Pro Glu Ala Ala Ile Gly Lys Thr Met Gly Gly Asp Tyr Asn Asp
85 90 95

Glu Trp Tyr Leu Asp Val Arg Ser Gln Asp Val Val Glu Leu Met Tyr
100 105 110

Arg Arg Leu Glu Glu Ala Ala Ala Leu Gly Cys Asp Gly Val Asp Pro
115 120 125

Asp Asn Val Asp Ala Trp Ala Gln Glu Gly Glu Asp Arg Thr Gly Phe
130 135 140

Gly Leu Thr Gln Glu Asp Tyr Lys His Tyr Leu Thr Lys Leu Ala Lys
145 150 155 160

Phe Ala His Asp Leu Gly Pro Leu Met Val Gly Gln Lys Asn Ala Pro
165 170 175

Glu Met Ala Pro Ala Leu Ala Asp Val Leu Asp Phe Ala Val Leu Glu
180 185 190

Ser Cys Arg Lys Trp Glu Phe Cys Glu Asp Phe Gln Val Tyr Val Lys
195 200 205

Ala Gly Lys Pro Val Phe Gln Ile Glu Tyr Pro Glu Ser Ile Met Asp
210 215 220

Glu Gly Glu Leu Ser Pro Glu Asp Tyr Glu Met Tyr Cys Gln Gly Asp
225 230 235 240

Ala Gly Asp Ala Gly Phe Ser Lys Val Leu Lys Arg Ala Ser Ala Gln
245 250 255

Leu Asp Gly Trp Thr Gln Tyr Cys Gly Glu Glu Pro Phe Glu Gln Ala
260 265 270

Val Ile Glu Gly
275

<210> SEQ ID NO 74
<211> LENGTH: 333
<212> TYPE: PRT
<213> ORGANISM: Volutella ciliata

<400> SEQUENCE: 74

Arg Arg Ser Cys Pro Gly Ser Gly Gly Ala Val Lys Pro Pro Thr Thr
1 5 10 15

Thr Thr Leu Leu Thr Ser Thr Val Thr Ala Ala Ala Gln Thr Ile Glu
20 25 30

Thr Glu Asp Pro Glu Pro Ser Gln Gly Gly Gln Ser Gly Ser Ser Ala
35 40 45

Phe Asp Lys Phe Lys Pro Gly Val Lys Trp Asn Ile Val Leu His Asn
50 55 60

Pro Ile Lys Val Asp Asp Ile Ala Ala Leu Gly Pro Ala Asp Thr Glu
65 70 75 80

```
Val Trp Asp Ile Asp Leu Gly His Ala Thr Glu Phe Glu Asn Met Ile
                85                  90                  95

Pro Thr Leu Lys Lys Ala Gly Lys Phe Ile Ile Cys Tyr Phe Asn Gly
            100                 105                 110

Gly Ala Val Gln Asn Trp Asp Thr Asp Lys Asp Asp Phe Pro Glu Ser
        115                 120                 125

Ile Ile Gly Lys Ser Leu Gly Asp Glu Tyr Glu Gly Glu Glu Phe Tyr
    130                 135                 140

Val Asp Val Arg Ser Asp Glu Val Val Lys Ile Met Lys Ala Arg Leu
145                 150                 155                 160

Asp Leu Ala Ala Lys Val Gly Cys Asp Ala Val Asp Pro Asp Asn Val
                165                 170                 175

Asp Ala Phe Tyr Asp Asn Ala Thr Gly Phe Asn Leu Asp Glu Ala Asp
            180                 185                 190

Tyr Val Thr Tyr Leu Thr Lys Leu Ala Asp Tyr Ala His Ser Ile Lys
        195                 200                 205

Thr Asp Ser Gly Asn Pro Leu Leu Val Gly Gln Lys Asn Ala Pro Glu
    210                 215                 220

Ile Ala Pro Gln Leu Val Gly Val Leu Asp Phe Ala Val Leu Glu Gln
225                 230                 235                 240

Cys Arg Gly Ser Ser Asn Pro Asp Glu Glu Ser Trp Pro Phe Cys Pro
                245                 250                 255

Asp Phe Gln Pro Tyr Ile Ala Ala Gly Lys Pro Val Leu Gln Ile Glu
            260                 265                 270

Tyr Pro Pro Ser Val Glu Glu Ser Asp Gly Thr Leu Ser Ala Ala Asp
        275                 280                 285

Lys Glu Phe Tyr Cys Gly Ala Lys Ala Asp Asp Lys Gly Phe Ser Lys
    290                 295                 300

Val Leu Lys Trp Ser Ser Pro Gln Leu Asp Gly Trp Thr Gln Phe Cys
305                 310                 315                 320

Asp Ser Asp Thr Ser Phe Thr Val Pro Glu Asp Asp Tyr
                325                 330


<210> SEQ ID NO 75
<211> LENGTH: 290
<212> TYPE: PRT
<213> ORGANISM: Clonostachys epichloe

<400> SEQUENCE: 75

Gly Pro Ala Ala Leu Pro Ala Asn Tyr Leu Ser Thr Phe Pro Leu Gly
1               5                   10                  15

Thr Lys Trp Gln Ile Val Leu His Gln Pro Ile Gln His Asn Gly Pro
            20                  25                  30

Asn Asp Phe Ile Pro Tyr Asp Gly Lys Ile Trp Asp Ile Asp Leu Gly
        35                  40                  45

His Ala Glu Ser Tyr Pro Asn Met Ile Pro Arg Leu Arg Ser Ala Lys
    50                  55                  60

Lys Ala Val Ile Cys Tyr Ile Asn Ala Gly Ala Ile Gln Ser Trp Asp
65                  70                  75                  80

Ile Asp Ile Asn Ser Phe Pro Ala Glu Ala Arg Gly Lys Asn Met Gly
                85                  90                  95

Asp Glu Tyr Thr Asp Glu Trp Trp Ile Asp Val Arg Asn Pro Lys Val
            100                 105                 110

Ile Ala Phe Met Lys Lys Arg Leu Glu Arg Ala Thr Ala Ala Gly Cys
```

```
        115                 120                 125

Asp Gly Val Asp Leu Asp Asn Ile Asp Ala Trp Ala Thr Pro Glu Gly
    130                 135                 140

Asp Arg Thr Gly Phe Asn Leu Thr Gln Ala Asp Tyr Val Ser Tyr Met
145                 150                 155                 160

Thr Gln Leu Gly Asn Tyr Ala His Thr Leu Pro Thr Lys Asn Ser Gly
                165                 170                 175

Gly Gly Leu Ala Met Gly Gln Lys Asn Ala Pro Glu Leu Val Asp Arg
            180                 185                 190

Leu Val Lys Val Leu Asp Phe Ala Val Leu Glu Ser Cys Leu Leu Asp
        195                 200                 205

Asn Phe Cys Ala Asp Phe Gln Pro Tyr Val Lys Ala Gly Lys His Val
    210                 215                 220

Phe Gln Ile Glu Tyr Pro Glu Ser Phe Ser Arg Ser Arg Thr Leu Ser
225                 230                 235                 240

Thr Arg Asp Asn Ser Phe Tyr Cys Gly Thr His Ser Thr Ser Lys Thr
                245                 250                 255

Asp Asp Asn Phe Ser Met Val Leu Lys Tyr Ala Ser Trp Gln Leu Asp
            260                 265                 270

Gly Phe Gly Gln Phe Cys Gly Gln Lys Ser Tyr Thr Thr Pro Thr Ile
        275                 280                 285

Arg Glu
    290


<210> SEQ ID NO 76
<211> LENGTH: 286
<212> TYPE: PRT
<213> ORGANISM: Myrothecium sp-

<400> SEQUENCE: 76

Gln Ala Gly Pro Lys Val Pro Ala Asp Phe Lys Pro Asn Val Ala Trp
1               5                   10                  15

Asn Ile Ile Leu His Asn Pro Ile Val His Asp Ser Glu Ala Asp Leu
            20                  25                  30

Ile Pro Ala Glu Ala Lys Val Trp Asp Ile Asp Leu Gly His Ala Arg
        35                  40                  45

Asp Tyr Pro Ile Ile Pro Leu Leu Lys Ser Ala Asp Lys Leu Val Val
    50                  55                  60

Cys Tyr Phe Asn Gly Gly Ala Val Gln Ala Trp Asp Ala Asp Arg Asp
65                  70                  75                  80

Ala Phe Pro Glu Asp Val Ile Gly Arg Ser Leu Ala Tyr Pro Phe Glu
                85                  90                  95

Asp Glu Glu Trp Tyr Val Asp Ile Arg Asp Ser Arg Val Val Asp Ile
            100                 105                 110

Met Lys Ser Arg Phe Asp Leu Ala Val Glu Leu Gly Cys Asp Ala Val
        115                 120                 125

Asp Pro Asp Asn Val Asp Ala Trp Ala Trp Ser Thr Asp Pro Glu Glu
    130                 135                 140

Asp Pro Thr Gly Phe Asn Leu Gln Pro Glu Asp Tyr Ala Ala Tyr Leu
145                 150                 155                 160

Asn Ala Leu Ala Asp Tyr Ala His Thr Leu Thr Thr Gln Ser Gly Asn
                165                 170                 175

Asn Leu Leu Val Gly Gln Lys Asn Ala Pro Asp Leu Ile Ala Ala Val
            180                 185                 190
```

```
Val Asp Asn Leu Asp Phe Ala Val Leu Glu Ser Cys Ile Arg Asp Asp
        195                 200                 205

Phe Cys Gly Gln Tyr Gln Pro Tyr Ile Ala Gln Gly Lys Pro Val Leu
    210                 215                 220

Gln Ile Glu Tyr Pro Pro Ser Val Glu Glu Thr Gly Ser Leu Ser Ser
225                 230                 235                 240

Glu Asp Asn Glu Arg Phe Cys Leu Asn Ala Glu Gly Asp Asp Asn Phe
                245                 250                 255

Ser Lys Val Leu Lys Phe Ser Thr Ala Gln Val Asp Gly Trp Gly Gln
            260                 265                 270

Tyr Cys Gly Gly Glu Ser Trp Glu Thr Pro Thr Phe Glu Gly
        275                 280                 285


<210> SEQ ID NO 77
<211> LENGTH: 321
<212> TYPE: PRT
<213> ORGANISM: Botryotrichum piluliferum

<400> SEQUENCE: 77

Gln Val Asp Val Pro Pro Asn Phe Ala Ile Gly Ala Lys Phe Gln Ile
1               5                   10                  15

Val Ile Gln Asn Thr Leu Asp Phe Glu Ala Pro Leu Ala Pro Thr Asp
            20                  25                  30

Ala Val Val Trp Asp Leu Asp Leu Tyr His Ile Ala Arg His Ser Glu
        35                  40                  45

Ile Val Gly His Leu Arg Glu Ser Asn Pro Asp Val Ile Leu Met Cys
    50                  55                  60

Tyr Phe Asn Ala Gly Leu Ala Gln Thr Ser Asp Cys Asp Phe Glu Ser
65                  70                  75                  80

Arg Trp Asn Asn Ser Gly Phe Leu Gly Asn Ala Tyr Asp Ser Asp Glu
                85                  90                  95

Phe Ser Asp Glu Phe Trp Ile Asn Ile Lys Glu Gln Glu Ala Arg Asp
            100                 105                 110

Leu Val Lys Glu Arg Ile Thr Leu Ala Arg Asp Ile Gly Cys Asp Ala
        115                 120                 125

Val Asp Pro Asp Asn Ile Asp Gly Trp Trp Asn Asp Val Asp Gly Leu
    130                 135                 140

Asn Gly Thr Gly Trp Asn Leu Ser Glu Ala Asp Phe Val Asn Phe Ala
145                 150                 155                 160

Thr Glu Leu Ala Asp His Ala His Ser Leu Thr Thr Glu Lys Gly His
                165                 170                 175

Thr Met Leu Ile Gly Gln Lys Asn Ala Pro Asp Ile Val Glu Gln Leu
            180                 185                 190

Val Gly Val Phe Asp Phe Ala Val Leu Glu Asp Cys Lys Thr Leu Asn
        195                 200                 205

Asp Asp Glu Asp Glu Asp Trp Thr Phe Cys Gln Asp Phe Gln Ala Tyr
    210                 215                 220

Ile Ala Gln Gly Lys Pro Val Phe Ser Ile Glu Tyr Pro Ser Thr Leu
225                 230                 235                 240

Gly Asp Thr Gln Thr Gly Ala Cys Asn Pro Gly Gly Val Ser Pro Glu
                245                 250                 255

Gln Tyr Ala Ala Ser Cys Asp Asn Thr Ala Gly Asn Ser Gly Phe Ser
            260                 265                 270

Thr Val Leu Lys Ile Gln Gly Asp Val Gly Glu Leu Asn Gly Cys Thr
        275                 280                 285
```

```
Gln Tyr Cys Val Glu Glu Gly Glu Asp Met Glu Val Val Thr Thr Ala
    290                 295                 300

Thr Asp Pro Asn Lys Asp Gly Glu Thr Cys Pro Asp Asn Ala Val Gly
305                 310                 315                 320

Pro


<210> SEQ ID NO 78
<211> LENGTH: 288
<212> TYPE: PRT
<213> ORGANISM: Myrothecium sp.

<400> SEQUENCE: 78

Gln Ala Gln Pro Lys Val Pro Ala Asp Phe Lys Pro Asn Val Asp Trp
1               5                   10                  15

Asn Ile Ile Leu His Asn Pro Met Val Tyr Gln Asn Ala Glu Pro Leu
            20                  25                  30

Val Pro Ala Glu Ala Lys Val Trp Asp Ile Asp Leu Gly His Ala Leu
        35                  40                  45

Glu Phe Pro Glu Ile Ile Pro Leu Leu Lys Arg Asn Asn Lys Leu Val
    50                  55                  60

Ile Cys Tyr Phe Asn Gly Gly Ala Leu Gln Asp Trp Asp Asp Asp Lys
65                  70                  75                  80

Glu Asp Phe Pro Glu Ala Ala Ile Gly Lys Pro Leu Ala Tyr Pro Phe
                85                  90                  95

Asp Asp Glu Glu Trp Tyr Leu Asp Ile Arg Asn Ala Asp Val Val Ala
            100                 105                 110

Ala Met Lys Ala Arg Leu Ser Thr Ala Val Asp Ala Gly Cys Asp Ala
        115                 120                 125

Val Asp Pro Asp Asn Val Asp Ala Trp Ala Trp Gly Asn Ser Asp Asp
    130                 135                 140

Glu Asp Pro Thr Gly Phe Arg Leu Thr Thr Asp Asp Tyr Ala Ala Tyr
145                 150                 155                 160

Leu Asn Thr Leu Ala Asp His Ala His Thr Leu Thr Thr Gln Ala Gly
                165                 170                 175

Asn Asn Leu Leu Val Gly Gln Lys Asn Ala Pro Asp Leu Val Pro Ala
            180                 185                 190

Val Val Gln Ser Leu Asp Phe Ala Val Leu Glu Ser Cys Arg Arg Asp
        195                 200                 205

Asp Phe Cys Gly Asp Phe Gln Pro Tyr Ile Ala Gly Gly Lys Pro Val
    210                 215                 220

Phe Gln Ile Glu Tyr Pro Pro Ser Val Glu Glu Thr Gly Gln Leu Ser
225                 230                 235                 240

Asn Ala Asp Asn Gln Phe Phe Cys Leu Arg Glu Asp Asp Ser Asp Asp
                245                 250                 255

Asp Phe Ser Lys Ile Leu Lys Trp Ser Thr Ala Gln Val Asp Gly Trp
            260                 265                 270

Gly Gln Tyr Cys Gly Gly Ser Ala Trp Glu Thr Pro Thr Phe Glu Gly
        275                 280                 285


<210> SEQ ID NO 79
<211> LENGTH: 236
<212> TYPE: PRT
<213> ORGANISM: Amycolatopsis sp

<400> SEQUENCE: 79
```

-continued

```
Ala Val Thr Leu Pro Pro Thr Pro Ser Ala Trp Asp Tyr Gln Ile Gly
1               5                   10                  15

Gly Ala Tyr Ala Pro Pro Ser Gly Val Lys Ile Val Ser Arg Asp Asn
            20                  25                  30

Ser Asp Ala Ala Ala Ser Gly Leu Tyr Asn Ile Cys Tyr Ile Asn Ala
        35                  40                  45

Phe Gln Val Asn Val Gly Asp Asp Gly Gln Trp Ala Ser Asp Leu Leu
    50                  55                  60

Leu Arg Asp Ala Asn Gly Asn Lys Val Val Asp Pro Asp Trp His Glu
65                  70                  75                  80

Thr Leu Leu Asp Leu Arg Thr Ala Asp Lys Arg Ser Arg Val Ala Ala
                85                  90                  95

Lys Ile Asn Gly Ile Val Asp Ser Cys Ala Gly Lys Gly Phe Gln Ala
            100                 105                 110

Ile Glu Pro Asp Asn Tyr Asp Ser Tyr Glu Arg Ser Lys Asn Leu Ile
        115                 120                 125

Ser Thr Ala Asn Ser Gln Asp Tyr Ile Lys Leu Leu Ser Ser His Ala
    130                 135                 140

His Ala Lys Gly Leu Ala Ile Ala Gln Lys Asn Thr Val Asp Leu Ala
145                 150                 155                 160

Ala Asn Arg Val Ala Asn Gly Leu Asp Phe Ala Val Ala Glu Glu Cys
                165                 170                 175

Gly Gln Tyr Thr Glu Cys Asp Val Tyr Ala Asn Ala Phe Gly Asn Arg
            180                 185                 190

Val Val Asp Val Glu Tyr Thr Ser Ser Gly Leu Ser Lys Ala Cys Ala
        195                 200                 205

Ser Trp Lys Gly Lys Ile Ser Ile Val Arg Arg Asp Glu Asp Val Val
    210                 215                 220

Pro Ala Gly Glu Ser Gly Tyr Val Arg Lys Thr Cys
225                 230                 235


<210> SEQ ID NO 80
<211> LENGTH: 564
<212> TYPE: PRT
<213> ORGANISM: Methylothermaceae bacteria B42

<400> SEQUENCE: 80

Glu Val Lys Asp Leu Gln Ala Val Arg Trp Gly Ser Glu Ile Val Phe
1               5                   10                  15

Arg Ala Gln Phe Ser Pro Gln His Ser His Lys Gln Val Phe Ile Asp
            20                  25                  30

Ala Asp Gly Asp Thr Ser Thr Gly Tyr Pro Val Gly Gly Ile Gly Ala
        35                  40                  45

Asp Tyr Leu Ile Glu Asp Asp Trp Phe Tyr Arg Tyr Gln Gly Arg Gly
    50                  55                  60

Trp Arg Trp Asp Phe Ile Ala Glu Val Pro Met Ser Glu Asn Asn Gly
65                  70                  75                  80

Gln Ser Val Trp Arg Val Pro Ala Lys Leu Ile Phe Pro Ser Gly Pro
                85                  90                  95

Leu Ser Ile Ile Phe Ser Gly Ile Asp Asp Trp Asp Ser Pro Glu Leu
            100                 105                 110

Ser Ser Val Ile Arg Ser Gly Glu Ala Val Leu Val Ser His Ala Leu
        115                 120                 125

Thr Pro Tyr Gln Met Arg Thr Arg Arg Gly Ser Glu Ser Asp Gln Gly
    130                 135                 140
```

-continued

Leu Asp Ala Leu Ala Thr Lys Asp Gln Ser Gly Thr Gln Asp Lys Trp
145 150 155 160

Asp Asp Tyr Ile Glu Phe Tyr Pro Gly Asp Lys Gly Tyr Ala Gly Gln
165 170 175

Phe Tyr Leu Arg Leu Pro Lys Glu Val Lys Ala Arg Asp Ile Ile His
180 185 190

Leu Lys Val Val Thr Asn Tyr Arg Gly Glu Arg Lys Lys Tyr Gln Arg
195 200 205

Trp Ile Trp Lys Ile Tyr Asp Phe Lys Glu Ser Arg Trp Gln Ile Ile
210 215 220

Gly Asp Asn Gly Arg Ala Pro Asn Trp His Trp Lys Ser Phe Thr Phe
225 230 235 240

Pro Val Asn Gly Thr Pro Ser His Tyr Phe Ala Ser Asn Gly Leu Ala
245 250 255

Lys Leu Arg Tyr Glu Thr Ser Lys Asp Val Asp Asn Ser Gln Leu Asp
260 265 270

Leu Leu Lys Leu Val Val Asp Ser Ile Ser Ser Asp Thr Gln Glu Asp
275 280 285

Ser Pro Gln Pro Asp Pro Glu Glu Gly Ser Thr Pro Ser Gln Pro Glu
290 295 300

Asn Pro Gly Ser Glu Gly Asn Asp Ser Glu Pro Pro Gln Pro Pro Gly
305 310 315 320

Leu Pro Gly Glu Ser Ser Arg Trp Ile Pro Arg Pro Gly Met Ser Trp
325 330 335

Gln Trp Gln Leu Ser Gly Lys Ile Glu Thr Ser Val Asp Ala Asp Ile
340 345 350

Phe Asp Val Asp Leu Phe Asp Thr Pro Arg Glu Thr Ile Asp Leu Leu
355 360 365

His Ala Lys Gly Arg Lys Val Val Cys Tyr Phe Ser Ala Gly Thr Tyr
370 375 380

Glu Asn Trp Arg Pro Asp Lys Ser Lys Phe Pro Asp Asp Val Ile Gly
385 390 395 400

Arg Arg Leu Glu Asp Trp Glu Gly Glu Ser Trp Leu Asp Ile Arg Gln
405 410 415

Ile Asp Val Leu Arg Pro Ile Leu Ala Ala Arg Met Asp Leu Ala Lys
420 425 430

Glu Lys His Cys Asp Gly Val Glu Pro Asp Asn Val Asp Gly Tyr Asp
435 440 445

Asn Lys Thr Gly Phe Pro Leu Lys Ala Glu Asp Gln Ile Arg Phe Asn
450 455 460

Arg Met Leu Ala Glu Glu Ala His Lys Arg Gly Leu Pro Ile Ala Leu
465 470 475 480

Lys Asn Ala Leu Gly Leu Ile Glu Ala Leu Glu Gly His Phe Asp Trp
485 490 495

Ala Leu Asn Glu Gln Cys Phe Gln Tyr Asp Glu Cys Glu Met Leu Gln
500 505 510

Pro Phe Leu Asp Ala Gly Lys Ala Val Leu Gly Val Ser Tyr Val Ser
515 520 525

Lys Gly Lys Ala Gly Lys Ile Cys Arg Lys Ala Asn Gln Met Gly Phe
530 535 540

Ser Trp Leu Ile Lys Arg Trp Asp Leu Asp Ala Trp Arg Met Asp Cys
545 550 555 560

```
Arg Asn Tyr Asp


<210> SEQ ID NO 81
<211> LENGTH: 252
<212> TYPE: PRT
<213> ORGANISM: Amycolatopsis niigatensis

<400> SEQUENCE: 81

Ala Gly Pro Val Glu Ser Ala Pro Leu Pro Ser Pro His Ser Gln Val
1               5                   10                  15

Ala Asp Val Pro Leu Pro Ala Pro His Ala Gly Phe Asp Tyr Gln Ile
            20                  25                  30

Gly Gly Pro Tyr Gln Pro Pro Ala Gly Val Gln Val Val Ser Arg Asp
        35                  40                  45

His Ser Ala Pro Ala Ala Ser Gly Leu Tyr Asn Ile Cys Tyr Val Asn
    50                  55                  60

Ala Phe Gln Val Gln Pro Gly Ala Glu Lys Glu Trp Gly Asp Leu Val
65                  70                  75                  80

Leu Arg Asp Asp Asp Gly Thr Val Val Met Asp Pro Asp Trp Asn Glu
                85                  90                  95

Ala Leu Leu Asp Ser Arg Thr Ala Asp Lys Arg Ser Arg Ile Ala Asp
            100                 105                 110

Lys Val Gly Ala Trp Ile Asp Glu Cys Ala Gly Lys Gly Tyr Gln Ala
        115                 120                 125

Ile Glu Pro Asp Asn Tyr Asp Ser Phe Thr Arg Ser Gln Gly Leu Leu
    130                 135                 140

Ser Ala Arg Asn Ala Gln Asp Leu Val Lys Leu Leu Ser Glu Arg Ala
145                 150                 155                 160

His Gly Lys Gly Leu Ala Ile Gly Gln Lys Asn Thr Ser Glu Leu Ala
                165                 170                 175

Ser Ser Arg Ala Ala Asn Gly Leu Asp Phe Ala Val Ala Glu Glu Cys
            180                 185                 190

Gly Gln Gln Asp Asn Cys Ala Glu Tyr Thr Arg Tyr Phe Gly Asp Arg
        195                 200                 205

Val Ile Val Ile Glu Tyr Thr Glu Asp Gly Leu Arg Thr Ala Cys Ala
    210                 215                 220

Lys Trp Gly Asn Thr Leu Ser Val Val Arg Arg Asp Arg Asp Val Thr
225                 230                 235                 240

Pro Lys Gly Asp Ser Ala Tyr Val Arg Glu Ser Cys
                245                 250


<210> SEQ ID NO 82
<211> LENGTH: 249
<212> TYPE: PRT
<213> ORGANISM: Streptomyces sp. AA4

<400> SEQUENCE: 82

Ala Gly Thr Ala Glu Ser Ala Pro Leu Pro Ala Pro Gln Ser Gln Val
1               5                   10                  15

Ala Leu Pro Ala Pro His Ala Gly Phe Asp Tyr Gln Ile Gly Gly Pro
            20                  25                  30

Tyr Gln Pro Thr Ala Asp Val Gln Val Val Ser Arg Asp His Ser Val
        35                  40                  45

Pro Ala Ala Ala Gly Val Tyr Asn Ile Cys Tyr Val Asn Ala Phe Gln
    50                  55                  60

Ala Gln Pro Gly Ala Glu Gly Glu Trp Gly Asp Leu Val Leu Arg Asp
```

```
65                  70                  75                  80

Gly Asn Gly Asp Val Val Lys Asp Pro Asp Trp Asn Glu Ala Leu Leu
                85                  90                  95

Asp Leu Arg Thr Glu Asp Lys Arg Asn Arg Val Ala Ala Lys Val Gly
            100                 105                 110

Gly Trp Ile Asp Asp Cys Ala Gly Lys Gly Tyr Gln Ala Val Glu Pro
        115                 120                 125

Asp Asn Tyr Asp Ser Phe Thr Arg Ser His Gly Leu Leu Ser Ala Arg
    130                 135                 140

Asn Ala Gln Asp Leu Ala Lys Leu Leu Ser Ser Arg Ala His Gly Lys
145                 150                 155                 160

Gly Leu Ala Ile Gly Gln Lys Asn Thr Ser Glu Leu Ser Ser Ser Arg
                165                 170                 175

Ala Asp Asn Gly Leu Asp Phe Ala Val Ala Glu Glu Cys Gly Glu Gln
            180                 185                 190

Asp Asn Cys Ala Glu Tyr Thr Lys Tyr Phe Gly Asn His Val Ile Val
        195                 200                 205

Ile Glu Tyr Thr Gly Asp Gly Leu Arg Asn Ala Cys Ala Lys Trp Gly
    210                 215                 220

Ser Thr Leu Ser Ile Val Gln Arg Asp Arg Asp Val Lys Pro Lys Gly
225                 230                 235                 240

Asp Pro Ala Tyr Val Arg Glu Thr Cys
                245
```

<210> SEQ ID NO 83
<211> LENGTH: 240
<212> TYPE: PRT
<213> ORGANISM: Amycolatopsis alba DSM 44262

<400> SEQUENCE: 83

```
Ala Pro Ala Pro Ala Ala Phe Ser Pro Pro Pro Val Lys Ala Gly Phe
1               5                   10                  15

Asp Tyr Gln Ile Gly Gly Ala Tyr Ala Pro Pro Ser Gly Val Arg Val
            20                  25                  30

Val Ser Arg Asp His Thr Ala Gln Pro Ala Ala Gly Leu Tyr Asn Ile
        35                  40                  45

Cys Tyr Ile Asn Ala Phe Gln Ala Gln Pro Gly Ala Glu Gly Glu Trp
    50                  55                  60

Gly Asp Leu Val Leu Arg Asp Ala Asn Gly Glu Val Val Met Asp Glu
65                  70                  75                  80

Asp Trp Asp Glu Ala Leu Leu Asp Leu Arg Thr Ala Asp Lys Arg Gln
                85                  90                  95

Arg Val Ala Ala Lys Val Asn Ala Trp Thr Asp Gly Cys Ala Ala Lys
            100                 105                 110

Gly Tyr Gln Ala Ile Glu Pro Asp Asn Tyr Asp Ser Phe Thr Arg Ser
        115                 120                 125

Arg Gly Leu Leu Ser Glu Gln Asp Ala Gln Ala Tyr Ile Arg Leu Leu
    130                 135                 140

Ser Thr His Ala His Glu Lys Gly Leu Ala Thr Gly Gln Lys Asn Thr
145                 150                 155                 160

Ser Glu Leu Ala Gly Asn Arg Lys Ala Asn Gly Leu Asp Phe Ala Val
                165                 170                 175

Ala Glu Glu Cys Gly Glu Gln Asp Ile Cys Gly Glu Phe Thr Ala Ala
            180                 185                 190
```

```
Phe Gly Gly Asn Val Ile Val Ile Glu Tyr Ala Asp Ala Gly Leu Ala
        195                 200                 205

Asn Ala Cys Asp Arg Trp Gly Gly Ser Leu Ser Ile Val Arg Arg Asp
    210                 215                 220

Arg Asp Val Val Pro Ala Gly Ala Ser Gly Tyr Val Arg Lys Thr Cys
225                 230                 235                 240


<210> SEQ ID NO 84
<211> LENGTH: 245
<212> TYPE: PRT
<213> ORGANISM: Streptomyces griseoaurantiacus

<400> SEQUENCE: 84

Ala Glu Thr Val Val Leu Pro Pro Val His Ala Ser Phe Asp Tyr Gln
1               5                   10                  15

Ile Gly Gly Ala Tyr Glu Pro Asp Lys Gly Val Gln Val Val Thr Arg
            20                  25                  30

Asp Val Lys Glu Ser Pro Ala Lys Asp Leu Tyr Asn Ile Cys Tyr Val
        35                  40                  45

Asn Ala Phe Gln Thr Gln Gln Glu Gly Asp Val Ser Gly Pro Gln Asp
    50                  55                  60

Trp Asp Lys Asp Leu Leu Leu Thr Gly Lys Asn Gly Glu Pro Val Ile
65                  70                  75                  80

Asp Pro Asp Trp Asp Glu Val Ile Leu Asp Ile Ser Glu Asp Gly Lys
                85                  90                  95

Arg Glu Arg Ile Ala Gln Gln Ile Asp Lys Gln Ile Asp Gln Cys Asp
            100                 105                 110

Thr Lys Gly Phe Asp Ala Val Glu Leu Asp Asn Tyr Asp Thr Tyr Asp
        115                 120                 125

Arg Asp Val Val Asp Gly Ala Leu Thr Ala Gln Asp Ala Gln Ala Tyr
    130                 135                 140

Ile Arg Leu Leu Ser Ala His Ala His Ala Lys Gly Leu Ala Val Gly
145                 150                 155                 160

Gln Lys Asn Thr Val Glu Leu Ala Gly Asn His Lys Ala Asn Gly Leu
                165                 170                 175

Asp Phe Ala Val Ala Glu Glu Cys Gly Asn Pro Lys Trp Lys Glu Cys
            180                 185                 190

Gly Lys Tyr Val Ser Ala Phe Gly Asp His Ala Ile Phe Ile Glu Tyr
        195                 200                 205

Thr Glu Glu Gly Leu Arg Asn Ala Cys Ala Tyr Gly Asp Arg Val Ser
    210                 215                 220

Val Val Met Arg Asp Met Asp Val Ser Glu Pro Asp Ser Glu Asp Tyr
225                 230                 235                 240

Val Arg Glu Thr Cys
                245


<210> SEQ ID NO 85
<211> LENGTH: 244
<212> TYPE: PRT
<213> ORGANISM: Kutzneria albida

<400> SEQUENCE: 85

Ala Thr Gly Thr Ala Pro Pro His Ala Thr Val Thr Ala Pro Pro Val
1               5                   10                  15

Thr Ala Gly Phe Asp Tyr Gln Ile Gly Gly Ala Tyr Thr Pro Pro Ser
            20                  25                  30
```

```
Gln Val Arg Val Val Ser Arg Asp His Thr Ala Gln Pro Ala Ala Gly
        35                  40                  45

Leu Tyr Asn Ile Cys Tyr Val Asn Ala Phe Gln Ala Gln Pro Gly Ala
    50                  55                  60

Glu Gly Glu Trp Gly Asp Leu Leu Leu Arg Asp Ala Asn Gly Asn Val
65                  70                  75                  80

Val Met Asp Glu Asp Trp Gly Glu Gly Leu Leu Asp Leu Arg Thr Ala
                85                  90                  95

Asp Lys Arg Gln Arg Val Ala Ala Lys Val Asn Val Trp Val Asp Asp
            100                 105                 110

Cys Ala Thr Lys Gly Phe Gln Ala Ile Glu Pro Asp Asn Tyr Asp Ser
        115                 120                 125

Phe Thr Arg Ser Lys Gly Leu Leu Ser Asp Ser Asp Ala Gln Ala Tyr
    130                 135                 140

Ile Arg Val Leu Ser Ala His Ala His Lys Lys Gly Leu Ala Val Gly
145                 150                 155                 160

Gln Lys Asn Thr Ser Glu Leu Ala Gly Gln Arg Gln Ala Asn Gly Leu
                165                 170                 175

Asp Phe Ala Val Ala Glu Glu Cys Gly Asp Gln Asn Lys Cys Gly Glu
            180                 185                 190

Tyr Thr Pro Ala Phe Gly Asp His Val Ile Val Ile Glu Tyr Thr Asp
        195                 200                 205

Ala Gly Leu Arg Thr Ala Cys Asp Arg Trp Gly Gly Ser Leu Ser Ile
    210                 215                 220

Val Arg Arg Asp His Gly Val Ala Pro Ala Gly Ala Ser Gly Tyr Val
225                 230                 235                 240

Arg Lys Thr Cys


<210> SEQ ID NO 86
<211> LENGTH: 244
<212> TYPE: PRT
<213> ORGANISM: Microbacterium sp.

<400> SEQUENCE: 86

Thr Glu Ser Ala Gly Gly Ile Thr Leu Pro Pro Ser Asp Gly Leu Phe
1               5                   10                  15

Asp Tyr Gln Leu Gly Gly Gly Tyr Glu Pro Gly Asp Asp Val Ser Val
            20                  25                  30

Val Thr Arg Asp Ser Thr Asp Glu Pro Ala Asp Ala Arg Tyr Ser Ile
        35                  40                  45

Cys Tyr Val Asn Gly Phe Gln Thr Gln Pro Gly Ala Glu Trp Pro Ala
    50                  55                  60

Thr Leu Ile Leu His Asp Ser Glu Gly Ala Pro Leu Ala Asp Pro Gly
65                  70                  75                  80

Trp Pro Asp Glu Tyr Leu Leu Asp Ile Ser Thr Pro Glu Lys Arg Thr
                85                  90                  95

Glu Ala Ala Ala Gln Gln Ala Ala Thr Ile Ala Asp Cys Ala Asp Arg
            100                 105                 110

Gly Phe Gln Ala Val Glu Phe Asp Asn Leu Asp Ser Trp Thr Arg Ser
        115                 120                 125

Glu Gly Ala Leu Thr Glu Ala Asp Ala Val Ala Phe Ala Met Met Leu
    130                 135                 140

Val Gly Ala Ala His His Gln Gly Met Ala Ala Ser Gln Lys Asn Ser
145                 150                 155                 160
```

-continued

```
Ala Glu Met Thr Ala Ala Gly Lys Asn Asp Ile Gly Phe Asp Phe Val
                165                 170                 175

Thr Val Glu Glu Cys Asp Leu Phe Asp Glu Cys Asp Glu Phe Thr Ser
            180                 185                 190

Ala Tyr Gly Asp Gln Val Phe Asp Ile Glu Tyr Thr Asp Asp Leu Arg
        195                 200                 205

Gly Thr Phe Ala Asp Val Cys Ala Arg Asp Ala Thr Pro Ala Arg Thr
    210                 215                 220

Ile Leu Arg Asp Arg Asp Leu Val Thr Pro Asp Asn Pro Ala Tyr Val
225                 230                 235                 240

Tyr Glu Tyr Cys


<210> SEQ ID NO 87
<211> LENGTH: 249
<212> TYPE: PRT
<213> ORGANISM: Microbacterium oleivorans 0827CG

<400> SEQUENCE: 87

Gln Ser Pro Pro Pro His Asp Pro Pro Ala Gly Pro Gln Leu Pro Pro
1               5                   10                  15

Ala Gly Gly His Leu Asp Tyr Gln Leu Gly Gly Ala Phe Asp Pro Pro
            20                  25                  30

Ser Gly Val Asp Ile Val Val Arg Asp Arg Ala Ala Ala Pro Val Asp
        35                  40                  45

Glu Leu Tyr Ser Val Cys Tyr Val Asn Gly Phe Gln Thr Gln Pro Gly
    50                  55                  60

Glu Leu Asp Ala Trp Pro Asp Glu Leu Leu Leu Arg Asp Asp Glu Gly
65                  70                  75                  80

Glu Pro Val Thr Asp Pro Asp Trp Pro Asp Glu Val Ile Leu Asp Thr
                85                  90                  95

Arg Lys Ala Asp Glu Ile Ala Lys Ile Val Gly Pro Trp Ile Arg Asp
            100                 105                 110

Cys Ala Ser Asp Gly Phe Asp Ala Val Glu Phe Asp Asn Leu Asp Thr
        115                 120                 125

Tyr Thr Arg Thr Asp Gly Ala Leu Ser Arg Asp Asp Ala Leu Asn Leu
    130                 135                 140

Ala Asn Leu Leu Val Asp Thr Ala His Asp Leu Gly Leu Ala Ala Gly
145                 150                 155                 160

Gln Lys Asn Ala Ala Glu Asp Ala Ser Leu Leu His Ser Arg Ala Gly
                165                 170                 175

Phe Asp Phe Ala Val Val Glu Glu Cys Ala Ala Tyr Glu Glu Cys Ser
            180                 185                 190

Ala Tyr Thr Glu Val Tyr Gly Asp His Val Leu Ala Ile Glu Tyr Thr
        195                 200                 205

Asp Asn Leu Pro Arg Pro Trp Asp Glu Val Cys Ala Asp Pro Glu Thr
    210                 215                 220

Pro Glu Ser Val Val Leu Arg Asp Arg Asp Leu Val Thr Ser Asp Asp
225                 230                 235                 240

Pro Ala Tyr Val Phe Glu Thr Cys Gly
                245


<210> SEQ ID NO 88
<211> LENGTH: 246
<212> TYPE: PRT
<213> ORGANISM: Nocardiopsis alba
```

<400> SEQUENCE: 88

Val Glu Leu Pro Pro Glu Gly Gly Phe Asp Tyr Gln Leu Gly Gly Ala
1 5 10 15

Tyr Pro Pro Pro Glu Gly Val Thr Thr Val Val Arg Asp Ser Thr Ala
20 25 30

Glu Pro Ala Pro Gly Leu Tyr Ser Val Cys Tyr Val Asn Gly Phe Gln
35 40 45

Thr Gln Pro Asp Glu Leu Asp Arg Trp Leu Glu Glu Asp Pro Asp Leu
50 55 60

Val Leu Arg Asp Glu Asp Gly Glu Pro Val Val Asp Pro Gly Trp Pro
65 70 75 80

Asp Glu Arg Ile Leu Asp Thr Ser Thr Gly Glu Arg Arg Glu Arg Ile
85 90 95

Ala Glu Ile Leu Thr Glu Ser Ile Asp Arg Cys Ala Asp Ala Gly Phe
100 105 110

Asp Ala Val Glu Phe Asp Asn Leu Asp Ser Tyr Leu Arg Ser Gly Glu
115 120 125

Ala Leu Thr Val Asp Asp Asn Leu Ala Leu Ala Ser Val Leu Val Gly
130 135 140

Val Ala His Gly Arg Gly Leu Ala Ala Ala Gln Lys Asn Thr Ala Glu
145 150 155 160

Glu Ala Gly Arg Gly His Asp Glu Val Gly Phe Asp Leu Ala Val Thr
165 170 175

Glu Ser Cys Ala Ala Trp His Glu Cys Gly Ala Tyr Thr Gly Val Tyr
180 185 190

Gly Ser Gly Asn Val Leu Ala Val Glu Tyr Pro Glu Glu Leu Ala Glu
195 200 205

Ala Ala Leu Asp Phe Asp Val Val Cys Ala Asp Pro Glu Arg Pro Asp
210 215 220

Arg Val Leu Leu Arg Asp Ala Ala Leu Val Pro Ser Ser Asp Pro Glu
225 230 235 240

His Leu Phe Glu Ala Cys
245

<210> SEQ ID NO 89
<211> LENGTH: 258
<212> TYPE: PRT
<213> ORGANISM: Microbacterium oxydans

<400> SEQUENCE: 89

Glu Thr Ala Pro His Ser Ala His Ser Thr Asp Ala Pro Ala Gly Asp
1 5 10 15

Asp Trp Ala Leu Pro Pro Ala Gly Ala Val Pro Asp Tyr Gln Leu Gly
20 25 30

Gly Ala Tyr Glu Pro Ala Ala Glu Val Gly Ile Val Gly Arg Asp Arg
35 40 45

Ser Ala Asp Pro Ala Ser Asp Thr Tyr Ser Ile Cys Tyr Val Asn Gly
50 55 60

Phe Gln Thr Gln Pro Gly Glu Leu Asp Thr Trp Asp Ala Asp Leu Leu
65 70 75 80

Leu Gln His Asp Gly Asp Thr Val Phe Asp Pro Asp Trp Pro Asp Glu
85 90 95

Ala Leu Leu Asp Thr Ser Thr Ala Asp Arg Arg Glu Arg Ile Ala Ala
100 105 110

Gln Ile Ile Pro Trp Ile Glu Gly Cys Ala Asp Asp Gly Phe Ala Ala
115 120 125

Val Glu Phe Asp Asn Leu Asp Ser Tyr Thr Arg Ser Gly Asp Ala Leu
130 135 140

Ser Leu Asp Asp Asn Leu Ala Leu Ala Thr Leu Phe Val Asp Ala Ala
145 150 155 160

His Gly Ala Gly Leu Ala Ala Gly Gln Lys Asn Ala Ala Glu Asp Ala
165 170 175

Val Gln Leu His Ala Gln Ala Gly Phe Asp Phe Ala Val Thr Glu Glu
180 185 190

Cys Ala Val Phe Glu Glu Cys Asp Val Tyr Ala Thr Val Tyr Gly Asp
195 200 205

His Val Ile Asp Ile Glu Tyr Ser Asp Glu Leu Pro Arg Ser Phe Ala
210 215 220

Asp Met Cys Ala Asp Pro Asp Ser Pro Ala Ser Met Val Leu Arg Asp
225 230 235 240

Arg Asp Leu Val Thr Pro Asp Asp Pro Ala Tyr Val Phe Glu Thr Cys
245 250 255

Gly Glu

<210> SEQ ID NO 90
<211> LENGTH: 268
<212> TYPE: PRT
<213> ORGANISM: Agreia pratensis

<400> SEQUENCE: 90

Ala Asp Ser Arg Glu Asp Asp Gln Ala Ser Pro Thr Pro Thr Gly Ser
1 5 10 15

Thr Tyr Leu Ile Ala Thr Ser Asp Thr Val Thr Leu Pro Pro Phe Gly
20 25 30

Glu Pro Ala Asp Tyr Gln Leu Gly Gly Ser Tyr Asp Val Asp Ala Asp
35 40 45

Val Lys Ile Val Thr Arg Asp Ser Thr Ser Glu Pro Ala Glu Gly Val
50 55 60

Tyr Ser Ile Cys Tyr Val Asn Gly Phe Gln Ser Gln Pro Gly Asp Asp
65 70 75 80

Glu Arg Trp Val Val Asp Asn Pro Asp Leu Val Leu Arg Asp Asp Gly
85 90 95

Gly Glu Ala Ile Ile Asp Pro Asn Trp Pro Asp Glu Phe Ile Leu Asp
100 105 110

Thr Ser Thr Pro Glu Lys Arg Gln Arg Ile Ser Arg Met Asn Gly Ala
115 120 125

Ser Ile Glu Ala Cys Ala Asp Arg Gly Phe Asp Ala Val Glu Ile Asp
130 135 140

Asn Leu Asp Thr Tyr Ser Arg Ser Glu Gly Arg Leu Ser Ile Asp Asp
145 150 155 160

Asn Leu Ala Leu Ala Lys Leu Phe Ala Asp Arg Ala His Gly Arg Ala
165 170 175

Met Ala Ile Gly Gln Lys Asn Ser Ala Glu Leu Gly Asp Arg Gly Arg
180 185 190

Ser Val Ala Asn Phe Asp Phe Ala Val Thr Glu Glu Cys Phe Arg Phe
195 200 205

Glu Glu Cys Gly Ala Tyr Ala Asp Val Tyr Gly Ser Ala Val Ile Asp
210 215 220

-continued

```
Ile Glu Tyr Thr Asp Asp Leu Pro Val Pro Phe Asp Glu Val Cys Ala
225                 230                 235                 240

Ser Asp Asp Arg Pro Ala Thr Thr Ile Leu Arg Asp Arg Asp Leu Val
                245                 250                 255

Ala Lys Gly Glu Pro Asp Tyr Val Phe Glu His Cys
            260                 265


<210> SEQ ID NO 91
<211> LENGTH: 249
<212> TYPE: PRT
<213> ORGANISM: Microbacterium lemovicicum

<400> SEQUENCE: 91

Ala Ala Pro Ser Arg Asp Ala Gly Phe Pro Ala Ser Leu Val Phe Asp
1               5                   10                  15

Tyr Gln Leu Gly Gly Gly Tyr Ala Pro Ala Ala Gly Val Gly Gly Val
            20                  25                  30

Val Arg Asp Ser Thr Asp Val Ala Glu Pro Gly Leu Tyr Ser Ile Cys
        35                  40                  45

Tyr Val Asn Gly Phe Gln Ser Gln Pro Ala Asp Arg Asp Ser Trp Leu
    50                  55                  60

Ala Glu Pro Asp Leu Val Leu Ile Gly Asp Asp Gly Gln Pro Leu Ile
65                  70                  75                  80

Asp Asp Asn Trp Pro Asp Glu Leu Ile Phe Asp Ile Ser Ala Asp Asp
                85                  90                  95

Gln Arg Glu Arg Ile Ala Ala Arg Val Gly Glu Arg Ile Ala Val Cys
            100                 105                 110

Gly Arg Asn Gly Phe Ser Ala Val Glu Ile Asp Asn Leu Asp Ser Tyr
        115                 120                 125

Thr Arg Ser Asp Gly Arg Leu Thr Glu Asp Asp Ala Ile Ala Leu Ala
    130                 135                 140

Thr Leu Tyr Ala Gln Thr Ala His Asp Ala Gly Leu Leu Ile Gly Gln
145                 150                 155                 160

Lys Asn Ala Ala Glu Ile Gly Pro Arg Gly Arg Asp Glu Ala Gly Phe
                165                 170                 175

Asp Phe Ala Val Ala Glu Glu Cys Val Ala Phe Glu Glu Cys Ser Ala
            180                 185                 190

Tyr Arg Asp Val Tyr Gly Asp Ala Val Val Asp Ile Glu Tyr Thr Asp
        195                 200                 205

Asn Leu Pro Ser Gly Phe Asp Ala Ala Cys Ala Val Asp Asp Arg Pro
    210                 215                 220

His Ser Thr Ile Leu Arg Asp Arg Asp Leu Val Pro Ala Asp Asp Ala
225                 230                 235                 240

Asp His Val Phe Gln Ala Cys Pro Ala
                245


<210> SEQ ID NO 92
<211> LENGTH: 249
<212> TYPE: PRT
<213> ORGANISM: Xylanibacterium sp.

<400> SEQUENCE: 92

Ala Pro Gly Pro Val Ser Leu Pro Pro Thr Asp Gly Thr Phe Asp Tyr
1               5                   10                  15

Gln Leu Gly Gly Thr Tyr Thr Pro Pro Gly Gly Leu Asp Val Val Val
            20                  25                  30
```

```
Arg Asp Ala Thr Ala Glu Pro Ala Glu Gly Ala Tyr Asn Ile Cys Tyr
        35                  40                  45

Val Asn Gly Phe Gln Thr Gln Pro Gly Asp Asp Arg Trp Leu Asp His
    50                  55                  60

Glu Asp Leu Leu Leu His Asp Gly Glu Gly Gln Val Ala Val Asp Pro
65                  70                  75                  80

Asp Trp Pro Asp Glu Tyr Val Leu Asp Pro Ser Thr Ala Arg Gln Arg
                85                  90                  95

Glu Gln Ile Leu Ala Leu Val Gly Pro Ala Val Thr Gly Cys Ala Asp
            100                 105                 110

Ala Gly Phe Asp Ala Val Glu Leu Asp Asn Leu Asp Thr Trp Thr Arg
        115                 120                 125

Phe Asp Asp Pro Ala Thr Gly Ala Ile Asp Pro Ala Gly Ala Leu Ala
    130                 135                 140

Leu Ala Ala Ala Tyr Val Glu Leu Ala His Ser Ala Gly Leu Ala Val
145                 150                 155                 160

Gly Gln Lys Asn Ala Ala Glu Ile Ala Ala Thr Ala Arg Asp Asp Leu
                165                 170                 175

Gly Phe Asp Phe Ala Ile Ala Glu Glu Cys Leu Ala Tyr Asp Glu Cys
            180                 185                 190

Gly Ala Tyr Thr Ala Ala Tyr Gly Glu His Val Leu Val Val Glu Tyr
        195                 200                 205

Pro Asp Thr Leu Gly Thr Pro Phe Glu Glu Ala Cys Ala Gly Ser Gly
    210                 215                 220

Ala Leu Pro Leu Thr Ile Leu Arg Asp Arg Val Leu Ala Ala Pro Gly
225                 230                 235                 240

Asp Ala Gly Tyr Val Arg Arg Gln Cys
                245
```

<210> SEQ ID NO 93
<211> LENGTH: 255
<212> TYPE: PRT
<213> ORGANISM: Curtobacterium oceanosedimentum

<400> SEQUENCE: 93

```
Ser Pro His Ala Ala Ser Ser Ser Ser Ser Gly Thr Ser Thr Asn Leu
1               5                   10                  15

Pro Thr Ala Gly Ile Pro Asp Tyr Gln Leu Gly Gly Gly Tyr Thr Pro
            20                  25                  30

Ala Ser Gly Val Thr Ile Val Glu Arg Asp Ser Thr Asp Arg Pro Ala
        35                  40                  45

Pro Gly Lys Tyr Gly Ile Cys Tyr Val Asn Gly Phe Gln Thr Gln Pro
    50                  55                  60

Glu Asp Ala Asp Thr Trp Leu Asp Arg His Pro Asp Ala Val Leu Arg
65                  70                  75                  80

Asp Asp Asp Gly Asp Pro Val Ser Asp Pro Gly Trp Pro Asp Glu Met
                85                  90                  95

Leu Leu Asp Thr Ser Thr Ala Ala Lys Arg Ala Glu Ile Val Asp Val
            100                 105                 110

Leu Thr Thr Ser Ile Glu Arg Cys Ala Asp Arg Gly Phe Asp Ala Val
        115                 120                 125

Glu Phe Asp Asn Leu Asp Ser Trp Thr Arg Ser Asp Gly Ala Leu Thr
    130                 135                 140

Arg Ala Gly Asn Leu Ala Leu Ala Ala Ser Leu Val Arg Val Gly His
145                 150                 155                 160
```

-continued

```
Glu His Gly Leu Ala Val Gly Gln Lys Asn Thr Pro Gln Leu Gly Ala
                165                 170                 175

Ser Gly Arg Lys Thr Thr Gly Phe Asp Phe Val Val Ala Glu Glu Cys
            180                 185                 190

Val His Tyr Gln Glu Cys Ala Ala Tyr Thr Lys Ala Tyr Gly Ala His
        195                 200                 205

Val Ile Asp Val Glu Tyr Ser Asp Asp Val Gly Arg Ser Trp Ser Ser
    210                 215                 220

Val Cys Ala Asp Glu Asp Arg Pro Ala Met Thr Ile Leu Arg Asp Arg
225                 230                 235                 240

Asp Leu Val Thr Pro Ser Gln Glu Gly Tyr Val Phe Glu His Cys
                245                 250                 255


<210> SEQ ID NO 94
<211> LENGTH: 250
<212> TYPE: PRT
<213> ORGANISM: Leucobacter tardus

<400> SEQUENCE: 94

Ala Glu Gln Pro Ala Asp Pro Ala Ala Asp Gly Ala His Ala Phe Pro
1               5                   10                  15

Ala Gly Ala Glu Phe Asp Tyr Gln Leu Gly Ala Ala Tyr Ala Leu Pro
            20                  25                  30

Ala Gly Val Thr Met Val Thr Arg Asp Arg Thr Ala Glu Pro Glu Pro
        35                  40                  45

Gly Ala Tyr Ser Ile Cys Tyr Leu Asn Gly Phe Gln Thr Gln Pro Gly
    50                  55                  60

Glu Ile Asp Asp Trp Pro Glu Asp Ala Ile Leu Arg Ile Asp Gly Glu
65                  70                  75                  80

Val Arg Thr Asp Pro Asp Trp Pro Asp Glu Ala Leu Leu Asp Ile Ala
                85                  90                  95

Thr Lys Ser Gly Arg Glu Ile Val Ile Asp Arg Val Ser Thr Trp Ile
            100                 105                 110

Asp Gly Cys Arg Asp Ala Gly Phe Gln Ala Val Glu Phe Asp Asn Leu
        115                 120                 125

Asp Thr Phe Thr Arg Ser Asp Gly Ala Ile Gly Arg Glu Asp Ala Ala
    130                 135                 140

Ala Val Ala Thr Ala Leu Val Ala Ala Ala His Asp Ala Gly Leu Ala
145                 150                 155                 160

Ala Gly Gln Lys Asn Ala Ala Glu His Ala Val Trp Leu Arg Ala Glu
                165                 170                 175

Ala Gly Phe Asp Phe Ala Val Ser Glu Glu Cys Ala Ala Phe Asp Glu
            180                 185                 190

Cys Gly Thr Tyr Thr Glu Val Tyr Gly Asp Ala Val Met Asp Ile Glu
        195                 200                 205

Tyr Thr Asp Ala Leu Pro Arg Pro Phe Asp Glu Val Cys Gly Asp Ala
    210                 215                 220

Ala Thr Pro Gln Ala Thr Ile Leu Arg Asp Arg Ala Leu Val Ala Pro
225                 230                 235                 240

Asp Asp Pro Asp Tyr Val Phe Glu Val Cys
                245                 250


<210> SEQ ID NO 95
<211> LENGTH: 254
<212> TYPE: PRT
```

<213> ORGANISM: Salinibacterium amurskyense

<400> SEQUENCE: 95

Ala Pro Pro Thr Thr Glu Pro Ser Ala Pro Ser Thr Ala Thr Ala Ser
1 5 10 15

Pro Ser Leu Phe Ala Ala Gly Ala Val Ala Asp Tyr Gln Leu Gly Gly
20 25 30

Ala Tyr Glu Pro Asp Ala Ser Val Thr Val Val Val Arg Asp Ala Gly
35 40 45

Gln Glu Pro Leu Ala Gly Ala Tyr Ser Ile Cys Tyr Leu Asn Gly Phe
50 55 60

Gln Ser Gln Pro Gly Glu Ser Trp Pro Ser Glu Leu Leu Leu Arg Asp
65 70 75 80

Ala Glu Gly Asp Pro Val Ile Asp Ala Asn Trp Pro Asp Glu Thr Leu
85 90 95

Leu Asp Ile Arg Thr Ala Ser Asn Arg Ala Ala Ile Ala Glu Arg Leu
100 105 110

Ala Pro Leu Ile Glu Asp Cys Ala Gly Lys Gly Phe Val Ala Val Glu
115 120 125

Phe Asp Asn Leu Asp Ser Tyr Thr Arg Ser Glu Gly Thr Leu Glu Arg
130 135 140

Glu Gln Ala Val Ala Met Ala Thr Leu Phe Val Gln Leu Gly His Ser
145 150 155 160

Ser Gly Leu Ala Val Ala Gln Lys Asn Ser Ala Glu Leu Leu Gly Glu
165 170 175

Ala Ala Ser Ala Ile Gly Phe Asp Phe Ala Ile Val Glu Glu Cys Asp
180 185 190

Gln Tyr Ser Glu Cys Gly Asp Phe Thr Asp Phe Tyr Gly Asp Ala Val
195 200 205

Ile Asp Val Glu Tyr Thr Asp Glu Leu Arg Arg Pro Phe Thr Glu Val
210 215 220

Cys Ala Asp Ala Ala Thr Pro Pro Ile Thr Met Leu Arg Asp Arg Asp
225 230 235 240

Leu Thr Pro Pro Gly Ser Ala Glu Tyr Thr Phe Glu His Cys
245 250

<210> SEQ ID NO 96
<211> LENGTH: 244
<212> TYPE: PRT
<213> ORGANISM: Artificial sequence
<220> FEATURE:
<223> OTHER INFORMATION: Enviromental sample

<400> SEQUENCE: 96

Gly Glu Pro Thr Pro Val Ala Leu Pro Pro Ala Gly Gly Ala Pro Asp
1 5 10 15

Tyr Gln Leu Gly Gly Ala Tyr Asp Pro Asp Pro Arg Val Glu Ile Val
20 25 30

Ala Arg Asp Arg Ser Asp Glu Pro Ala Pro Gly Leu Tyr Ser Ile Cys
35 40 45

Tyr Leu Asn Gly Phe Gln Thr Gln Pro Gly Glu Arg Asp Asp Trp Pro
50 55 60

Asp Asp Leu Val Leu Arg Val Asp Gly Ala Asp Val Ile Asp Pro Asp
65 70 75 80

Trp Pro Asp Glu Ala Leu Leu Asp Thr Arg Gly Ala Gln Asn Arg Ala
85 90 95

```
Ala Ile Ala Glu Arg Ile Thr Gly Phe Ile Glu Gly Cys Ala Ala Ala
            100                 105                 110

Gly Phe Asp Ala Val Glu Phe Asp Asn Leu Asp Thr Tyr Thr Arg Ser
        115                 120                 125

Ser Gly Met Leu Asp Ala Gly Asp Asn Leu Ala Leu Ala Ala Val Leu
    130                 135                 140

Val Asp Ala Ala His Ala Val Gly Leu Ala Ala Ala Gln Lys Asn Ala
145                 150                 155                 160

Ala Glu Asp Ala Pro Arg Leu Arg Val Glu Ala Gly Phe Asp Phe Ala
                165                 170                 175

Val Val Glu Glu Cys Ala Val Phe Asp Glu Cys Gly Ala Tyr Thr Asp
            180                 185                 190

Val Tyr Gly Glu His Val Ile Ala Ile Glu Tyr Thr Asp Ala Met Pro
        195                 200                 205

Arg Pro Phe Ala Asp Leu Cys Ala Asp Asp Ala Leu Pro Ala Ser Leu
    210                 215                 220

Val Leu Arg Asp Arg Asp Leu Thr Thr Pro Gly Asp Pro Ala Tyr Ala
225                 230                 235                 240

Phe Thr Leu Cys


<210> SEQ ID NO 97
<211> LENGTH: 363
<212> TYPE: PRT
<213> ORGANISM: Neonectria candida

<400> SEQUENCE: 97

Ala Pro Val Ser Ala Arg Arg Arg Gly Ala Cys Lys Pro Ala Ala Leu
1               5                   10                  15

Tyr Ser Ala Ser Ser Ser Ala Ser Phe Leu Ser Thr Ser Ser Pro Leu
            20                  25                  30

Ser Glu Thr Ser Lys Gly Ile Thr Thr Val Val Thr Ala Ala Pro Thr
        35                  40                  45

Pro Gly Gln Gly Asn Gly Thr Val Thr Thr Thr Thr Gln Ala Val Ala
    50                  55                  60

Thr Asn Thr Gly Ile Ser Thr Ser Val Ala Ala Val Ser Asn Phe Lys
65                  70                  75                  80

Pro Gly Val Thr Trp Asp Ile Cys Ile His Tyr Pro Ile Lys His Asp
                85                  90                  95

Ser Val Asp Asp Leu Ile Pro Ala Glu Ala Thr Val Trp Asp Ile Asp
            100                 105                 110

Leu Thr His Ala His Glu Phe Pro Asn Met Ile Pro Met Leu Lys Lys
        115                 120                 125

Ala Gly Lys Phe Val Ile Cys Tyr Phe Asn Ala Gly Ala Arg Gln Thr
    130                 135                 140

Phe Asp Asp Asp Lys Asp Leu Phe Pro Thr Glu Val Ile Gly Lys Ser
145                 150                 155                 160

Leu Ser Tyr Pro Tyr Asp Asp Glu Glu Ala Tyr Val Asp Ile Arg Asp
                165                 170                 175

Asp Arg Val Leu Asp Ile Met Lys Ala Arg Leu Asp Ser Ala Val Glu
            180                 185                 190

Val Gly Cys Asp Ala Val Asp Pro Asp Asn Val Asp Ala Trp Ala Gln
        195                 200                 205

Asp Gly Thr Asp Pro Thr Gly Phe Ser Leu Lys Ser Ser Asp Tyr Val
    210                 215                 220
```

Thr Tyr Leu Lys Asn Leu Ala Ala Tyr Ala His Ser Val Lys Thr Gln
225 230 235 240

Glu Gly Gln Pro Leu Leu Val Gly Gln Lys Asn Ala Pro Glu Ile Ala
245 250 255

Ala Asp Leu Val Ser Thr Leu Asp Phe Ala Val Leu Glu Gln Cys Arg
260 265 270

Gly Ser Ser Asp Ser Ser Glu Glu Ser Tyr Ala Phe Cys Ser Asp Phe
275 280 285

Gln Thr Tyr Ile Asp Ala Gly Lys Pro Val Leu Gln Ile Glu Tyr Pro
290 295 300

Pro Ser Val Ser Glu Ser Asp Gly Thr Leu Ser Ser Ser Asp Glu Ser
305 310 315 320

Phe Tyr Cys Asn Ala Glu Asp Asp Asp Lys Gly Phe Ser Lys Val Leu
325 330 335

Lys Trp Ala Ser Ala Gln Leu Asp Gly Trp Gly Gln Tyr Cys Gly Gly
340 345 350

Lys Ser Phe Arg Thr Val Glu Ala Glu Tyr Glu
355 360

<210> SEQ ID NO 98
<211> LENGTH: 264
<212> TYPE: PRT
<213> ORGANISM: Fusarium compactum

<400> SEQUENCE: 98

Phe Asn Pro Arg Ala Ile Asn Thr Pro Lys Arg Lys Asp Leu Trp Lys
1 5 10 15

Pro Glu Val Gly Ser Lys Trp Glu Ile Ile Leu Ser Gln Val Phe Lys
20 25 30

Leu Pro Lys Gly Gly Ala Ser Lys Leu Asp Pro Ser Val Pro Ile Tyr
35 40 45

Asp Leu Asp Leu Phe Glu Asn Ser Lys Ser Thr Phe Thr Ala Met Gln
50 55 60

Lys Thr Gly Lys His Val Ile Cys Tyr Phe Ser Ala Gly Ser Trp Glu
65 70 75 80

Asn Trp Arg Asp Asp Arg Lys Asp Phe Pro Ala Lys Asp Leu Gly Lys
85 90 95

Val Met Asp Gly Trp Pro Asp Glu Arg Trp Val Asn Ile Arg Ser Pro
100 105 110

Glu Val Arg Ala Ile Met Ala Lys Arg Ile Lys Ile Ala Ala Asp Lys
115 120 125

Gly Cys Asp Ala Ile Asp Pro Asp Asn Met Asp Gly Tyr Gln Asn Asp
130 135 140

Asn Gly Leu Gly Leu Thr Glu Asp Asp Thr Val Ser Tyr Val Lys Phe
145 150 155 160

Leu Ser Lys Glu Ala Ala Lys Tyr Asn Met Val Met Gly Met Lys Asn
165 170 175

Gly Gly Asp Val Thr Glu Gln Val Leu Pro Tyr Val Ala Phe Cys Ile
180 185 190

Asn Glu Ser Cys Ile Gln Tyr Ser Glu Cys Asp Leu Tyr Ala Pro Tyr
195 200 205

Ile Glu Ala Gly Lys Pro Val Phe Asn Ile Glu Tyr Pro Lys Gly Ala
210 215 220

Pro Lys Val Lys Ala Ser Asn Lys Lys Lys Ile Cys Gly Thr Thr Gly

```
225                 230                 235                 240

Ala Ala Ala Asp Ser Asp Gly Phe Ser Lys Ile Ile Lys Lys Met Asn
                245                 250                 255

Leu Asp Lys Trp Thr Met Tyr Cys
            260
```

<210> SEQ ID NO 99
<211> LENGTH: 314
<212> TYPE: PRT
<213> ORGANISM: Fusarium compactum

<400> SEQUENCE: 99

```
Arg Cys Lys Gly Glu Cys Leu Val Asp Ala Arg Ala Met Thr Ala Lys
1               5                   10                  15

Ala Lys Gln Thr Thr Pro Ser Ala Ser Pro Phe Glu Leu Ser Asp Phe
            20                  25                  30

Lys Pro Gly Val Glu Trp Glu Ile Val Leu His Gln Pro Ile Lys His
        35                  40                  45

Glu Ser Ala Ala Asp Leu Ile Pro Thr Thr Ala Lys Val Trp Asp Ile
    50                  55                  60

Asp Met Gly His Ala Arg Asp Tyr Pro Glu Met Ile Pro Leu Leu Lys
65                  70                  75                  80

Ser Ala Gly Lys Phe Ile Val Cys Tyr Phe Asn Ala Gly Ala Val Gln
                85                  90                  95

Ser Trp Asp Glu Asp Lys Asp Gln Phe Pro Glu Ala Ala Val Gly His
            100                 105                 110

Ser Leu Ala Tyr Pro Tyr Asp Ser Glu Glu Trp Tyr Leu Asp Ile Arg
        115                 120                 125

Asp Pro Thr Val Leu Arg Val Gln Arg Ala Arg Leu Asp Val Ala Ala
    130                 135                 140

Lys Val Gly Cys Asp Ala Val Asp Pro Asp Asn Val Asp Ala Trp Gln
145                 150                 155                 160

Gln Asn Glu Glu Asp Pro Thr Gly Phe Lys Leu Lys Pro Ser Asp Tyr
                165                 170                 175

Ala Thr Tyr Leu Lys Asp Leu Ala Glu Tyr Thr His Ser Ile Lys Thr
            180                 185                 190

Lys Asp Gly Asn Pro Leu Leu Ile Gly Gln Lys Asn Ala Pro Glu Ile
        195                 200                 205

Ala Glu Asp Leu Val Ser Thr Leu Asp Phe Ala Val Leu Glu Ser Cys
    210                 215                 220

Arg Gly Thr Thr Asn Pro Glu Glu Glu Ser Trp Pro Phe Cys Glu Asp
225                 230                 235                 240

Phe Gln Ile Tyr Val Asp Ala Gly Lys Pro Val Leu Gln Ile Glu Tyr
                245                 250                 255

Pro Pro Ser Val Glu Lys Thr Gly Lys Leu Ser Ser Ser Asp Lys Thr
            260                 265                 270

Phe Tyr Cys Thr Pro Lys Asp Glu Asp Gln Gly Phe Ser Lys Ile Ile
        275                 280                 285

Lys Trp Ala Ser Ala Gln Leu Asp Gly Trp Gly Gln Tyr Cys Gly Gly
    290                 295                 300

Glu Pro Phe Arg Thr Pro Val Ile Lys Glu
305                 310
```

<210> SEQ ID NO 100
<211> LENGTH: 301

<212> TYPE: PRT
<213> ORGANISM: Fusarium avenaceum

<400> SEQUENCE: 100

```
Glu Pro Lys Pro Ala Ala Thr Ala Ser Ser Pro Ser Ser Phe Gly Leu
1               5                   10                  15

Ser Asp Phe Lys Pro Gly Val Gln Trp Glu Ile Val Ile His Glu Pro
            20                  25                  30

Ile Lys His Asp Ser Ala Ala Asn Leu Ile Pro Leu Lys Ala Lys Val
        35                  40                  45

Trp Asp Val Asp Met Arg His Ala Arg Arg Tyr Pro Glu Met Ile Pro
    50                  55                  60

Leu Leu Lys Ser Ala Gly Lys Phe Val Ile Cys Tyr Leu Asn Ala Gly
65                  70                  75                  80

Ala Val Gln Ala Trp Asp Asp Asp Lys Asp Lys Phe Pro Lys Ala Val
                85                  90                  95

Ile Gly Tyr Ser Leu Ala Tyr Pro Tyr Asp Ser Glu Glu Trp Tyr Leu
            100                 105                 110

Asp Ile Arg Asp Ser Thr Val Leu Lys Leu Gln Lys Ala Arg Leu Asp
        115                 120                 125

Val Ala Ala Lys Ile Gly Cys Asp Ala Val Asp Pro Asp Asn Val Asp
    130                 135                 140

Ala Trp Gln Gln Asp Glu Glu Asp Pro Thr Gly Phe Asn Leu Lys Ser
145                 150                 155                 160

Ser Asp Tyr Thr Lys Tyr Leu Lys Ser Leu Ala Gln Tyr Ala His Ser
                165                 170                 175

Ile Lys Thr Lys Asp Gly Asn Pro Leu Leu Val Gly Gln Lys Asn Ala
            180                 185                 190

Pro Glu Ile Ala Asp Asp Leu Val Ser Ser Leu Asp Phe Ala Val Leu
        195                 200                 205

Glu Ser Cys Arg Gly Thr Thr Asp Pro Glu Glu Glu Asn Trp Pro Phe
    210                 215                 220

Cys Glu Asp Phe Gln Thr Tyr Ile Asp Ala Gly Lys Pro Val Leu Gln
225                 230                 235                 240

Ile Glu Tyr Pro Pro Ser Val Glu Lys Thr Gly Lys Leu Ser Ser Ser
                245                 250                 255

Asp Lys Thr Tyr Tyr Cys Thr Pro Lys Glu Glu Asp Lys Gly Phe Ser
            260                 265                 270

Lys Ile Ile Lys Trp Ala Ser Ala Gln Leu Asp Gly Trp Gly Gln Tyr
        275                 280                 285

Cys Gly Glu Glu Pro Phe Arg Thr Pro Val Ile Lys Glu
    290                 295                 300
```

<210> SEQ ID NO 101
<211> LENGTH: 377
<212> TYPE: PRT
<213> ORGANISM: Preussia aemulans

<400> SEQUENCE: 101

```
Thr Phe Thr Lys Gly Gln Lys Trp Gln Ile Ile Leu Leu Gly Thr Pro
1               5                   10                  15

Asp Val Ser Lys Met Pro Leu Pro Pro Thr Asp Ala Pro Val Trp Asp
            20                  25                  30

Ile Asp Leu Phe Asp Ser Ala Ala Ser Asp Ile Arg Thr Leu Lys Asp
        35                  40                  45
```

-continued

```
Ala Gly Lys Ile Val Ile Cys Tyr Phe Ser Ala Gly Thr Arg Glu Asp
    50                  55                  60

Trp Arg Asp Asp Ala Lys Asp Phe Pro Ala Gly Asp Gln Gly Lys Val
65                  70                  75                  80

Leu Pro Glu Trp Pro Asn Glu Lys Trp Ile Arg Val Gly Ser Thr Lys
                85                  90                  95

Ile Arg Glu Ile Met Ala Lys Arg Ile Lys Leu Ala Ala Asp Lys Gly
            100                 105                 110

Cys Asp Ala Ile Asp Pro Asp Asn Thr Asp Gly Tyr Gln Asn Asp Asn
        115                 120                 125

Gly Leu Asn Leu Lys Asn Thr Asp Ala Ile Asp Tyr Met Arg Trp Met
    130                 135                 140

Gln Lys Thr Ala Glu Gly Tyr Gly Met Lys Ile Gly Leu Lys Asn Ser
145                 150                 155                 160

Ile Asp Ile Leu Asp Thr Ile Ser Ser Ile Met Asp Phe Ala Val Asn
                165                 170                 175

Glu Gln Cys Ala Gln His Ser Glu Cys Thr Ala Tyr Asp Lys Phe Leu
            180                 185                 190

Ala Ser Gly Lys Pro Val Phe His Ile Glu Tyr Pro Thr Pro Leu Asn
        195                 200                 205

Gln Asn Gln Ala Asp Gly Ile Tyr Cys Lys Gly Pro Gly Thr Asn Gly
    210                 215                 220

Met Ser Thr Val Leu Lys Glu Met Ala Leu Thr Gly Val Thr Ile Tyr
225                 230                 235                 240

Cys Asp Lys Ser Gln Val Asn Thr Pro Thr Arg Ser Gly Asn Ser Pro
                245                 250                 255

Pro Arg Pro Ser Val Pro Pro Arg Ser Ser Thr Thr Arg Pro Pro Ile
            260                 265                 270

Ser Ser Thr Ser Arg Ser Ser Ser Thr Leu Thr Pro Ser Ser Ile Ala
        275                 280                 285

Thr Pro Thr Thr Thr Ser Ile Pro Asp Thr Thr Leu Ile Ser Ser Thr
    290                 295                 300

Thr Pro Arg Pro Ser Ser Thr Pro Arg Pro Ser Thr Thr Pro Arg Pro
305                 310                 315                 320

Ser Ser Ser Ser Arg Thr Ser Ser Ser Gln Arg Pro Thr Ser Ser Ala
                325                 330                 335

Pro Gly Gly Cys Arg Ser Lys His Trp Asp Gln Cys Gly Gly Gln Asp
            340                 345                 350

Trp Lys Gly Cys Thr Val Cys Glu Ser Pro Tyr Thr Cys Lys Ala Val
        355                 360                 365

Ser Ala Pro Trp Tyr Tyr Gln Cys Leu
    370                 375


<210> SEQ ID NO 102
<211> LENGTH: 298
<212> TYPE: PRT
<213> ORGANISM: Fusarium proliferatum

<400> SEQUENCE: 102

Lys Pro Ala Ala Ala Ala Ser Ser Ala Phe Phe Glu Leu Ser Asp Phe
1               5                   10                  15

Lys Pro Gly Val Glu Trp Glu Ile Val Leu His Gln Pro Ile Lys His
            20                  25                  30

Asp Thr Val Ala Asp Leu Ile Pro Ser Lys Ala Lys Val Trp Asp Ile
        35                  40                  45
```

Asp Met Gly His Gly Arg Asp Tyr Pro Glu Met Ile Pro Leu Leu Lys
50 55 60

Gly Ala Gly Lys Phe Val Ile Cys Tyr Phe Asn Ala Gly Ala Leu Gln
65 70 75 80

Ser Trp Asp Lys Asp Ile Lys Gln Phe Pro Asp Ala Val Ile Gly His
85 90 95

Ser Leu Ala Tyr Pro Tyr Asp Ser Glu Glu Trp Tyr Leu Asp Ile Arg
100 105 110

Asp Ser Thr Val Leu Lys Leu Gln Lys Ala Arg Leu Asp Val Ala Ala
115 120 125

Lys Ile Gly Cys Asp Ala Val Asp Pro Asp Asn Val Asp Ala Trp Gln
130 135 140

Gln Asp Gly Glu Asp Pro Thr Gly Phe Lys Leu Lys Pro Ser Asp Tyr
145 150 155 160

Thr Lys Tyr Leu Lys Asn Leu Ala Glu Tyr Ala His Ser Ile Lys Thr
165 170 175

Lys Asp Gly Asn Arg Leu Leu Val Gly Gln Lys Asn Ala Pro Glu Val
180 185 190

Ala Glu Asp Leu Val Ser Thr Leu Asp Phe Ala Val Leu Glu Ser Cys
195 200 205

Arg Gly Thr Thr Asp Pro Asp Glu Glu Asn Trp Pro Phe Cys Glu Asp
210 215 220

Phe Gln Thr Tyr Ile Asp Ala Gly Lys Pro Val Leu Gln Ile Glu Tyr
225 230 235 240

Pro Pro Ser Val Glu Lys Thr Gly Lys Leu Ser Ser Ser Asp Asn Ala
245 250 255

Tyr Tyr Cys Thr Pro Lys Gly Glu Asp Lys Gly Phe Ser Lys Ile Leu
260 265 270

Lys Trp Ala Ser Ala Gln Leu Asp Gly Trp Gly Gln Phe Cys Gly Glu
275 280 285

Asp Pro Phe His Thr Pro Val Ile Asn Glu
290 295

<210> SEQ ID NO 103
<211> LENGTH: 299
<212> TYPE: PRT
<213> ORGANISM: Fusarium lateritium

<400> SEQUENCE: 103

Glu Pro Ala Ala Thr Ala Ser Ser Pro Ser Ser Phe Gly Leu Ser Asp
1 5 10 15

Phe Lys Pro Gly Val Gln Trp Glu Ile Val Ile His Glu Pro Ile Lys
20 25 30

His Asp Gly Thr Ala Asp Leu Ile Pro Ser Lys Ala Lys Val Trp Asp
35 40 45

Ile Asp Met Gly His Ala Arg Asp Tyr Pro Lys Met Ile Pro Leu Leu
50 55 60

Lys Ser Ala Gly Lys Phe Val Ile Cys Tyr Phe Asn Ala Gly Ala Val
65 70 75 80

Gln Ala Trp Asp Glu Asp Lys Asn Gln Phe Pro Lys Ala Val Ile Gly
85 90 95

His Ser Leu Ala Tyr Pro Tyr Asp Ser Glu Glu Trp Tyr Leu Asp Ile
100 105 110

Arg Asp Ser Thr Val Leu Lys Leu Gln Lys Ala Arg Leu Asp Val Ala

```
        115                 120                 125

Ala Lys Ile Gly Cys Asp Ala Val Asp Pro Asp Asn Val Asp Ala Trp
    130                 135                 140

Gln Gln Asp Glu Glu Asp Pro Thr Gly Phe Lys Leu Lys Ser Ser Asp
145                 150                 155                 160

Tyr Thr Lys Tyr Leu Lys Ser Leu Ala Glu Tyr Ala His Ser Ile Lys
                165                 170                 175

Thr Lys Asp Gly Asn Pro Leu Leu Val Gly Gln Lys Asn Ala Pro Glu
            180                 185                 190

Ile Ala Glu Asp Leu Val Ser Ser Leu Asp Phe Ala Val Leu Glu Ser
        195                 200                 205

Cys Arg Gly Thr Thr Asp Pro Lys Glu Glu Asn Trp Pro Phe Cys Glu
    210                 215                 220

Asp Phe Gln Thr Tyr Ile Asp Ala Gly Lys Pro Val Leu Gln Ile Glu
225                 230                 235                 240

Tyr Pro Pro Ser Val Glu Lys Thr Gly Lys Leu Ser Ser Ser Asp Lys
                245                 250                 255

Thr Tyr Tyr Cys Thr Ser Lys Glu Glu Asp Lys Gly Phe Ser Lys Ile
            260                 265                 270

Ile Lys Trp Ala Ser Ala Gln Leu Asp Gly Trp Gly Gln Tyr Cys Gly
        275                 280                 285

Glu Glu Pro Phe Arg Thr Pro Val Ile Lys Glu
    290                 295


<210> SEQ ID NO 104
<211> LENGTH: 264
<212> TYPE: PRT
<213> ORGANISM: Fusarium proliferatum

<400> SEQUENCE: 104

Phe Thr Pro His Gly Phe Thr Thr Pro Lys Arg Lys Glu Leu Trp Gln
1               5                   10                  15

Pro Glu Val Gly Thr Pro Trp Gln Ile Ile Leu Ser Glu Val Ile Lys
            20                  25                  30

Val Pro Lys Ala Gly Val Ser Ser Met Thr Pro Asp Val Pro Ile Trp
        35                  40                  45

Asp Met Asp Leu Phe Glu Asn Ser Lys Ser Thr Ile Thr Ala Met Gln
    50                  55                  60

Lys Gly Gly Lys Lys Val Ile Cys Tyr Phe Ser Ala Gly Ser Trp Glu
65                  70                  75                  80

Asn Trp Arg Lys Asp Lys Asp Ser Phe Pro Lys Lys Asp Leu Gly Lys
                85                  90                  95

Val Met Asp Gly Trp Pro Asp Glu Arg Trp Val Asn Ile Ser Ser Val
            100                 105                 110

Ala Val Arg Ala Ile Met Ala Gln Arg Ile Lys Leu Ala Ala Glu Lys
        115                 120                 125

Gly Cys Asp Ala Ile Asp Pro Asp Asn Met Asp Gly Tyr Gln Asn Asp
    130                 135                 140

Asn Gly Leu Gly Leu Thr Glu Glu Asp Thr Ile Ser Tyr Val Lys Phe
145                 150                 155                 160

Leu Ser Ala Glu Ala Ala Lys Tyr Asn Met Val Met Gly Met Lys Asn
                165                 170                 175

Gly Gly Asp Val Ala Glu Glu Val Leu Pro Tyr Val Ala Phe Cys Ile
            180                 185                 190
```

-continued

```
Asn Glu Ser Cys Ile Gln Tyr Ser Glu Cys Asp Leu Tyr Gln Pro Tyr
        195                 200                 205

Ile Asp Ala Gly Lys Pro Val Phe Asn Ile Glu Tyr Pro Lys Gly Ala
    210                 215                 220

Pro Lys Val Lys Ala Lys Asp Lys Lys Lys Ile Cys Ser Thr Ser Gly
225                 230                 235                 240

Ala Ala Glu Gly Ser Asp Asp Phe Ser Lys Val Ile Lys Lys Val Asn
                245                 250                 255

Leu Asp Lys Trp Val Leu Tyr Cys
            260


<210> SEQ ID NO 105
<211> LENGTH: 320
<212> TYPE: PRT
<213> ORGANISM: Chaetomium ancistrocladum

<400> SEQUENCE: 105

Gln Arg Glu Val Pro Pro Asn Phe Glu Ile Gly Ala Lys Phe Gln Ile
1               5                   10                  15

Val Ile Gln His Thr Leu Asp Trp Asn Ala Pro Leu Ala Pro Thr Asp
            20                  25                  30

Ala Val Val Trp Asp Leu Asp Leu Tyr His Val Ala Arg His Pro Glu
        35                  40                  45

Ile Val Glu His Leu Arg Ala Ser Asn Pro Asp Val Ile Leu Met Cys
    50                  55                  60

Tyr Phe Asn Ala Gly Leu Ala Gln Thr Ser Asp Cys Asp Tyr Glu Ser
65                  70                  75                  80

Arg Trp Asn Asn Ser Gly Phe Leu Gly Asn Ser Trp Gly Asp Glu Phe
                85                  90                  95

Pro Asp Glu Phe Trp Ile Asn Ile Lys Glu Gln Glu Ala Arg Asp Leu
            100                 105                 110

Val Lys Glu Arg Ile Thr Leu Ala Arg Asp Lys Gly Cys Asp Ala Val
        115                 120                 125

Asp Pro Asp Asn Ile Asp Gly Trp Trp Asn Asp Ala Asp Gly Glu Asn
    130                 135                 140

Gly Thr Gly Trp Asn Leu Ser Glu Ala Asp Tyr Val Asn Phe Val Thr
145                 150                 155                 160

Glu Leu Ala Glu His Ala His Gly Leu Thr Thr Leu Gln Gly Tyr Thr
                165                 170                 175

Met Leu Ile Gly Gln Lys Asn Ala Pro Asp Ile Val Asp Gln Val His
            180                 185                 190

Glu Asn Leu Asp Phe Ala Val Leu Glu Asp Cys Lys Thr Leu Asn Asp
        195                 200                 205

Asp Glu Asp Gly Asp Trp Thr Phe Cys Gln Gln Phe Gln Thr Tyr Ile
    210                 215                 220

Ala Asp Gly Lys Pro Val Phe Ser Ile Glu Tyr Pro Ser Thr Leu Gly
225                 230                 235                 240

Asp Thr Gly Thr Gly Ala Cys Thr Pro Gly Gly Val Ser Pro Glu Gln
                245                 250                 255

Phe Glu Ala Ser Cys Asp Asp Thr Ala Gly Asn Ser Gly Phe Ser Thr
            260                 265                 270

Val Leu Lys Ile Gln Gly Asp Val Gly Glu Leu Asn Gly Cys Thr Gln
        275                 280                 285

Tyr Cys Ala Glu Gln Ile Asp Asp Ser Glu Val Val Glu Thr Ala Thr
    290                 295                 300
```

```
Asp Pro Leu Lys Asp Gly Asp Val Cys Pro Thr Asp Ala Glu Gly Phe
305                 310                 315                 320


<210> SEQ ID NO 106
<211> LENGTH: 298
<212> TYPE: PRT
<213> ORGANISM: Fusarium verticillioides

<400> SEQUENCE: 106

Lys Pro Ala Ala Ala Ala Ser Ser Ala Leu Phe Glu Leu Ser Asp Phe
1               5                   10                  15

Lys Pro Gly Val Glu Trp Glu Ile Val Leu His Gln Pro Ile Lys His
            20                  25                  30

Asp Thr Ile Ala Asp Leu Ile Pro Ser Lys Ala Lys Val Trp Asp Ile
        35                  40                  45

Asp Met Gly His Gly Arg Asp Tyr Pro Glu Met Ile Pro Leu Leu Lys
    50                  55                  60

Gly Ala Gly Lys Phe Val Ile Cys Tyr Phe Asn Ala Gly Ala Leu Gln
65                  70                  75                  80

Ser Trp Asp Lys Asp Ile Lys Gln Phe Pro Lys Ala Val Ile Gly His
                85                  90                  95

Ser Leu Ala Tyr Pro Tyr Asp Ser Glu Glu Trp Tyr Leu Asp Ile Arg
            100                 105                 110

Asp Ser Thr Val Leu Lys Leu Gln Lys Ala Arg Leu Asp Val Ala Ala
        115                 120                 125

Lys Ile Gly Cys Asp Ala Val Asp Pro Asp Asn Val Asp Ala Trp Gln
    130                 135                 140

Gln Asp Gly Glu Asp Pro Thr Gly Phe Lys Leu Lys Pro Ser Asp Tyr
145                 150                 155                 160

Thr Lys Tyr Leu Lys Asn Leu Ala Glu Tyr Ala His Ser Ile Lys Thr
                165                 170                 175

Lys Asp Gly Asn Arg Leu Leu Val Gly Gln Lys Asn Ser Pro Glu Ile
            180                 185                 190

Ala Glu Asp Leu Val Ser Thr Leu Asp Phe Ala Val Leu Glu Ser Cys
        195                 200                 205

Arg Gly Thr Thr Asp Pro Asp Glu Glu Asn Trp Pro Phe Cys Glu Asp
    210                 215                 220

Phe Gln Thr Tyr Ile Asp Ala Gly Lys Pro Val Leu Gln Ile Glu Tyr
225                 230                 235                 240

Pro Pro Ser Val Glu Lys Thr Gly Lys Leu Ser Ser Ser Asp Asn Ala
                245                 250                 255

Tyr Tyr Cys Thr Pro Lys Gly Glu Asp Lys Gly Phe Ser Lys Ile Leu
            260                 265                 270

Lys Trp Ala Ser Ala Gln Leu Asp Gly Trp Gly Gln Phe Cys Gly Asp
        275                 280                 285

Asp Pro Phe Arg Thr Pro Val Ile Asn Glu
    290                 295


<210> SEQ ID NO 107
<211> LENGTH: 264
<212> TYPE: PRT
<213> ORGANISM: Fusarium lateritium

<400> SEQUENCE: 107

Ile Ala Thr Arg Gly Val Ser Leu Pro Lys Arg Lys Glu Leu Trp Lys
1               5                   10                  15
```

```
Pro Glu Val Gly Thr Pro Trp Gln Ile Ile Leu Ser Glu Val Ile Thr
            20                  25                  30

Leu Pro Glu Gly Gly Ala Asp Asp Leu Ser Pro Asp Val Thr Ile Trp
        35                  40                  45

Asp Met Asp Leu Phe Glu Asn Thr Lys Glu Thr Ile Ser Ala Met Gln
    50                  55                  60

Glu Ser Gly Lys Arg Val Ile Cys Tyr Phe Ser Ala Gly Ser Trp Glu
65                  70                  75                  80

Asn Trp Arg Lys Asp Lys Asn Ser Phe Pro Lys Lys Asp Leu Gly Lys
                85                  90                  95

Thr Leu Ser Gly Trp Pro Asp Glu Lys Trp Val Asn Ile Ser Ser Ala
            100                 105                 110

Ala Val Arg Ala Ile Met Ala Lys Arg Ile Lys Gln Ala Ala Asp Lys
        115                 120                 125

Gly Cys Asp Ala Ile Asp Pro Asp Asn Met Asp Gly Tyr Gln Asn Asp
    130                 135                 140

Asn Gly Leu Gly Leu Thr Gln Lys Asp Thr Ile Ser Tyr Val Lys Phe
145                 150                 155                 160

Leu Ser Ala Glu Ala Ala Lys Tyr Asn Met Val Met Gly Met Lys Asn
                165                 170                 175

Gly Gly Asp Val Thr Lys Gln Val Leu Ser Tyr Val Ala Phe Cys Ile
            180                 185                 190

Asn Glu Ser Cys Ile Gln Tyr Gln Glu Cys Asp Leu Tyr Thr Pro Tyr
        195                 200                 205

Ile Lys Ala Gly Lys Pro Val Phe Asn Ile Glu Tyr Pro Lys Gly Ala
    210                 215                 220

Pro Lys Val Lys Asp Ser Asp Lys Lys Lys Ile Cys Ala Thr Ala Gly
225                 230                 235                 240

Asp Ala Lys Gly Ser Lys Gly Phe Ser Lys Val Ile Lys Lys Met Asn
                245                 250                 255

Leu Asp Ser Trp Val Met Tyr Cys
            260


<210> SEQ ID NO 108
<211> LENGTH: 317
<212> TYPE: PRT
<213> ORGANISM: Chaetomium sp. ZY474

<400> SEQUENCE: 108

Gln Val Asn Pro Pro Pro Asn Phe Arg Pro Gly Gln Asp Leu Lys Trp
1               5                   10                  15

Gln Ile Ala Ile Tyr Ser Thr Leu Asp Thr Thr Val Pro Leu Gln Pro
            20                  25                  30

Ala Asp Ala Asp Val Trp Asp Leu Asp Leu Tyr His Val Ala Arg His
        35                  40                  45

Pro Glu Ile Val Asp Phe Leu Arg Thr Asn Asn Pro Asn Thr Thr Leu
    50                  55                  60

Ile Cys Tyr Phe Asn Ala Gly Leu Ala Gln Glu Ser Asp Cys Asp Tyr
65                  70                  75                  80

Gln Thr Arg Trp Val Asn Ser Asp Leu Leu Gly Asn Pro Tyr Ser Pro
                85                  90                  95

Asp Ala Pro Gln Phe Ser Asp Glu Phe Trp Ile Asn Ile Lys Ser Gln
            100                 105                 110

Thr Ala Arg Asp Leu Val Lys Arg Arg Ile Thr Leu Ala Arg Asp Ile
```

```
        115                 120                 125

Gly Cys Asp Ala Val Asp Pro Asp Asn Ile Asp Gly Tyr Leu His Asp
    130                 135                 140

Glu Glu Arg Gly Asp Glu Gly Thr Gly Trp Asn Leu Ser Gln Asp Asp
145                 150                 155                 160

Tyr Val Ser Phe Val Thr Glu Leu Ala Glu His Ala His Ser Leu Thr
                165                 170                 175

Thr Gln Arg Gly Tyr Thr Met Leu Met Gly Gln Lys Asn Ala Pro Glu
            180                 185                 190

Ile Val Gly Glu Val Ser Asp Val Leu Asp Phe Ala Val Leu Glu Asp
        195                 200                 205

Cys Arg Thr Leu Asn Asp Asp Glu Asp Tyr Thr Phe Cys Pro Asp Tyr
    210                 215                 220

Gln Val Tyr Ile Ala Glu Gly Lys Pro Val Phe Asn Ile Glu Tyr Pro
225                 230                 235                 240

Thr Thr Leu Gly Asp Glu Glu Ser Cys Ile Gly Ala Ser Ala Glu Gln
                245                 250                 255

Tyr Gln Ala Ala Cys Ala Val Thr Glu Asp Asn Ser Gly Phe Ser Thr
            260                 265                 270

Val Leu Lys Asn Gln Gly Asp Gly Glu Leu Asn Gly Cys Thr Gln Tyr
        275                 280                 285

Cys Val Glu Gly Asp Pro Ser Asp Gly Val Val Val Thr Ala Leu Asn
    290                 295                 300

Ser Glu Leu Asp Gly Asp Gln Cys Pro Pro Glu Ala Glu
305                 310                 315


<210> SEQ ID NO 109
<211> LENGTH: 331
<212> TYPE: PRT
<213> ORGANISM: Scytalidium sp. T045-6

<400> SEQUENCE: 109

Gln Val Thr Val Pro Ser Ser Phe Thr Val Gly Ala Lys Phe Gln Ile
1               5                   10                  15

Val Ile His Asn Thr Ile Asp Pro Asp Ser Pro Leu Glu Pro Ala Asp
            20                  25                  30

Ala Leu Val Trp Asp Ile Asp Leu Phe His Leu Ala Arg Thr Pro Glu
        35                  40                  45

Val Ala Asn His Ile Arg Ser Thr Asn Pro Ser Ala Thr Ile Leu Cys
    50                  55                  60

Tyr Phe Asn Ala Gly Leu Ala Gln Thr Ser Asp Cys Asp Tyr Pro Arg
65                  70                  75                  80

Trp Asp Ser Ser Gly Leu Leu Gly Asn Pro Tyr Asp Ile Thr Asp Pro
                85                  90                  95

Asp Leu Phe Pro Asp Glu Arg Trp Ile Asn Ile Lys Asn Ala Thr Ala
            100                 105                 110

Arg Glu Trp Ile Lys Trp Arg Ile Ser Leu Ala Arg Asp Leu Gly Cys
        115                 120                 125

Asp Gly Val Asp Pro Asp Asn Ile Asp Gly Phe Leu Asn Asp Tyr Asp
    130                 135                 140

Gly Asp Asn Gly Thr Gly Trp Ser Leu Ser Glu Asp Asp Tyr Val Ala
145                 150                 155                 160

Phe Val Thr Glu Leu Ala Glu His Ala His Gly Leu Thr Thr Leu Gln
                165                 170                 175
```

```
Gly Asn Thr Met Leu Ile Gly Gln Lys Asn Ala Pro Glu Leu Ile Gly
            180                 185                 190

Arg Val Lys Asp Val Leu Asp Phe Val Val Leu Glu Asp Cys Arg Thr
        195                 200                 205

Ile Asn Asp Glu Glu Asp Tyr Glu Phe Cys Thr Asp Phe Lys Glu Ala
    210                 215                 220

Tyr Ile Asp Glu Gly Lys Pro Val Phe Ser Ile Glu Tyr Pro Ser Thr
225                 230                 235                 240

Ile Gly Glu Asn Gly Glu Cys Trp Ala Thr Gly Ala Ser Glu Asp Glu
                245                 250                 255

Tyr His Val Ala Cys Glu Glu Gly Ala Ala Gly Phe Ser Thr Val Leu
            260                 265                 270

Lys Ile Gln Gly Glu Gly Glu Leu Asn Gly Cys Thr Gln Tyr Cys Asp
        275                 280                 285

Gly Gly Glu Pro Gly Thr Gly Val Val Val Thr Pro Thr Asp Pro Glu
    290                 295                 300

Arg Asp Gly Asp Pro Cys Pro Asn Asp Ala Ile Val Val Gly Trp Ala
305                 310                 315                 320

Gly Asn Trp Pro Leu Ala Leu Glu Glu Met Arg
                325                 330


<210> SEQ ID NO 110
<211> LENGTH: 281
<212> TYPE: PRT
<213> ORGANISM: Acremonium sp.

<400> SEQUENCE: 110

Lys Ser Leu Asp Asp Val Asn Leu Gly Ala Pro Trp Gln Ile Ala Ile
1               5                   10                  15

His Asp Pro Ile Ile His Asp Ser Ala Asp Asp Leu Val Pro Ser Gln
            20                  25                  30

Ala Gln Val Tyr Asp Ile Asp Leu Gly His Ala Gln Thr Phe Pro Asp
        35                  40                  45

Met Ile Pro Thr Leu Lys Glu Ala Gly Met Val Val Leu Cys Tyr Phe
    50                  55                  60

Asn Ala Gly Ala Val Gln Asp Trp Asp Asn Asp His Asp Leu Phe Pro
65                  70                  75                  80

Glu Glu Val Arg Gly Thr Thr Leu Gly Gly Asp Tyr Pro Asp Glu Trp
                85                  90                  95

Tyr Leu Asp Ile Arg Ser Pro Ile Val Val Asp Leu Met Lys Arg Arg
            100                 105                 110

Leu Asp Ser Ala Ala Ala Val Gly Cys Ala Gly Val Asp Pro Asp Asn
        115                 120                 125

Val Asp Gly Trp Val Gln Ser Asn Gly Asp Asp Arg Thr Gly Phe Gly
    130                 135                 140

Leu Thr Gln Asp Asp Tyr Ala Thr Tyr Leu Glu Glu Leu Ala Ala Tyr
145                 150                 155                 160

Ala His Thr Val Pro Val Ala Asp Gly Asp Gly Thr Leu Leu Val Gly
                165                 170                 175

Gln Lys Asn Ala Pro Ala Leu Ala Glu Arg Leu Val Ser Ser Leu Asp
            180                 185                 190

Phe Ala Val Leu Glu Ser Cys Arg Glu Trp Asp Phe Cys Gly Asp Phe
        195                 200                 205

Gln Val Tyr Pro Ser Ala Gly Lys His Val Phe Gln Ile Glu Tyr Pro
    210                 215                 220
```

```
Asp Ser Ile Leu Glu Gln Gly Gln Leu Ser Ala Ala Asp Asn Glu Phe
225                 230                 235                 240

His Cys Glu Gly Glu Gly His Gly Asp Glu Gly Phe Ser Lys Ile Leu
                245                 250                 255

Lys Arg Ala Ser Ala Gln Leu Asp Gly Trp Gly Gln Tyr Cys Gly Gly
            260                 265                 270

Ala Ser Phe Glu Gln Glu Leu Gly Trp
        275                 280


<210> SEQ ID NO 111
<211> LENGTH: 321
<212> TYPE: PRT
<213> ORGANISM: Chaetomium strumarium

<400> SEQUENCE: 111

Gln Val Asp Val Pro Pro Asn Phe Thr Pro Gly Val Pro Trp Gln Ile
1               5                   10                  15

Ile Ile Gln Asn Thr Leu Asp Val Thr Lys Pro Leu Gln Pro Asn Asn
            20                  25                  30

Val Thr Val Trp Asp Leu Asp Leu Tyr His Ile Ala Arg Asn Pro Asp
        35                  40                  45

Ile Val Gly Tyr Leu Arg Thr Asn Asn Pro Gly Thr Ile Leu Ile Cys
    50                  55                  60

Tyr Phe Asn Ala Gly Leu Ala Gln Glu Ser Asp Cys Asp Tyr Asp Thr
65                  70                  75                  80

Lys Trp Arg Asn Ser Gly Leu Leu Gly Asn Val Tyr Asp Pro Gln Asp
                85                  90                  95

Pro Glu Phe Ser Asp Glu Arg Trp Val Asn Ile Arg Asn Gln Thr Ala
            100                 105                 110

Arg Asp Trp Met Lys Gln Arg Ile Thr Leu Ala Asn Gln Leu Gly Cys
        115                 120                 125

Asp Gly Val Asp Pro Asp Asn Ile Asp Gly Tyr Leu Asn Asp Gln Asp
    130                 135                 140

Gly Asn Asn Gly Thr Gly Trp Asn Leu Ala Gln Asp Asp Tyr Val Ser
145                 150                 155                 160

Phe Val Thr Asp Leu Ala Thr His Ala His Ser Leu Thr Thr Ser Gln
                165                 170                 175

Arg His Thr Leu Leu Ile Gly Gln Lys Asn Ala Arg Glu Leu Val Gly
            180                 185                 190

Pro Leu Gly Gly Val Leu Asp Phe Ala Val Leu Glu Asp Cys Lys Gln
        195                 200                 205

Leu Asn Glu Ala Glu Glu Pro Ala Pro Phe Cys Ala Asp Phe Gln Pro
    210                 215                 220

Tyr Val Ala Ala Gly Lys Pro Val Phe Ser Ile Glu Tyr Pro Ser Thr
225                 230                 235                 240

Leu Gly Asp Pro Glu Thr Gly Ala Cys Asn Ala Gly Gly Ala Asp Glu
                245                 250                 255

Thr Gln Tyr Asn Asp Ser Cys Asn Pro Thr Pro Asp Thr Ala Gly Phe
            260                 265                 270

Ser Thr Val Leu Lys Ile Arg Gly Glu Val Gly Glu Leu Asn Asn Cys
        275                 280                 285

Thr Gln Tyr Cys Thr Gly Met Ala Pro Gly Thr Gly Val Val Val Thr
    290                 295                 300

Ala Thr Asp Pro Glu Leu Asp Asp Ile Glu Cys Pro Pro Glu Ala Ala
```

-continued 305 310 315 320

Asp

<210> SEQ ID NO 112
<211> LENGTH: 298
<212> TYPE: PRT
<213> ORGANISM: Fusarium oxysporum

<400> SEQUENCE: 112

Lys Pro Ala Ala Ala Ala Ser Ser Thr Leu Phe Glu Leu Ser Asp Phe
1 5 10 15

Lys Pro Gly Val Glu Trp Glu Ile Val Leu His Gln Pro Ile Lys His
20 25 30

Asp Thr Val Ala Asp Leu Ile Pro Ser Lys Ala Lys Val Trp Asp Ile
35 40 45

Asp Met Gly His Gly Arg Asp Tyr Pro Glu Met Ile Pro Leu Leu Lys
50 55 60

Gly Ala Gly Lys Phe Val Ile Cys Tyr Phe Asn Ala Gly Ala Leu Gln
65 70 75 80

Ser Trp Asp Lys Asp Ile Lys Gln Phe Pro Lys Ala Val Ile Gly His
85 90 95

Ser Leu Ala Tyr Pro Tyr Asp Ser Glu Glu Trp Tyr Leu Asp Ile Arg
100 105 110

Asp Ser Thr Val Leu Lys Leu Gln Lys Ala Arg Leu Asp Val Ala Ala
115 120 125

Lys Ile Gly Cys Asp Ala Val Asp Pro Asp Asn Val Asp Ala Trp Gln
130 135 140

Gln Asp Gly Glu Asp Pro Thr Gly Phe Lys Leu Lys Pro Ser Asp Tyr
145 150 155 160

Thr Lys Tyr Leu Lys Asn Leu Ala Glu Tyr Ala His Ser Ile Lys Thr
165 170 175

Lys Asp Gly Asn Arg Leu Leu Val Gly Gln Lys Asn Ala Pro Glu Ile
180 185 190

Ser Glu Asp Leu Val Ser Thr Leu Asp Phe Ala Val Leu Glu Ser Cys
195 200 205

Arg Gly Thr Thr Asp Pro Asp Glu Glu Asn Trp Pro Phe Cys Glu Asp
210 215 220

Phe Gln Thr Tyr Ile Asp Ala Gly Lys Pro Val Leu Gln Ile Glu Tyr
225 230 235 240

Pro Pro Ser Val Glu Lys Thr Gly Lys Leu Ser Ser Ser Asp Asn Thr
245 250 255

Tyr Tyr Cys Thr Pro Lys Asp Glu Asp Lys Gly Phe Ser Lys Ile Leu
260 265 270

Lys Trp Ala Ser Ala Gln Leu Asp Gly Trp Gly Gln Phe Cys Gly Glu
275 280 285

Asp Pro Phe Arg Thr Pro Val Ile Asn Glu
290 295

<210> SEQ ID NO 113
<211> LENGTH: 298
<212> TYPE: PRT
<213> ORGANISM: Fusarium temperatum

<400> SEQUENCE: 113

Lys Pro Ala Ala Ala Val Ser Ser Ala Leu Phe Glu Leu Ser Asp Phe
1 5 10 15

```
Lys Pro Gly Val Glu Trp Glu Ile Val Leu His Gln Pro Ile Lys His
            20                  25                  30

Asp Thr Val Ala Asp Leu Ile Pro Ser Lys Ala Lys Val Trp Asp Ile
        35                  40                  45

Asp Met Gly His Gly Arg Asp Tyr Pro Glu Met Ile Pro Leu Leu Lys
    50                  55                  60

Gly Ala Gly Lys Phe Val Ile Cys Tyr Phe Asn Ala Gly Ala Leu Gln
65                  70                  75                  80

Ser Trp Asp Gln Asp Ile Lys Gln Phe Pro Lys Ala Val Ile Gly His
                85                  90                  95

Ser Leu Ala Tyr Pro Tyr Asp Ser Glu Glu Trp Tyr Leu Asp Ile Arg
            100                 105                 110

Asp Ser Thr Val Leu Glu Leu Gln Lys Ala Arg Leu Asp Val Ala Ala
        115                 120                 125

Lys Ile Gly Cys Asp Ala Val Asp Pro Asp Asn Val Asp Ala Trp Gln
    130                 135                 140

Gln Asp Gly Glu Asp Pro Thr Gly Phe Glu Leu Lys Pro Ser Asp Tyr
145                 150                 155                 160

Thr Lys Tyr Leu Lys Asn Leu Ala Asp Tyr Ala His Ser Ile Lys Thr
                165                 170                 175

Met Asp Gly Asn Arg Leu Leu Val Gly Gln Lys Asn Ala Pro Glu Ile
            180                 185                 190

Ala Glu Ala Leu Val Ser Ala Leu Asp Phe Ala Val Leu Glu Ser Cys
        195                 200                 205

Arg Gly Thr Thr Asp Pro Asp Glu Glu Asn Trp Pro Phe Cys Glu Asp
    210                 215                 220

Phe Gln Thr Tyr Val Asp Ala Gly Lys Pro Val Leu Gln Ile Glu Tyr
225                 230                 235                 240

Pro Pro Ser Val Glu Lys Thr Gly Lys Leu Ser Pro Ser Asp Asn Thr
                245                 250                 255

Tyr Tyr Cys Thr Pro Lys Gly Glu Asp Lys Gly Phe Ser Lys Ile Leu
            260                 265                 270

Lys Trp Ala Ser Ala Gln Leu Asp Gly Trp Gly Gln Phe Cys Gly Asp
        275                 280                 285

Asp Pro Phe Arg Thr Pro Val Ile Asn Glu
    290                 295


<210> SEQ ID NO 114
<211> LENGTH: 250
<212> TYPE: PRT
<213> ORGANISM: Thermoascus taitungiacus

<400> SEQUENCE: 114

Thr Thr Ala Lys Trp Gln Pro Pro Val Gly Thr Thr Trp Gln Ile Glu
1               5                   10                  15

Leu Leu Tyr Pro Leu Asn Asp Thr Ser Val Asp Ala Asp Val Tyr Asp
            20                  25                  30

Ile Asp Leu Phe Asn Asn Asp Ala Ser Thr Ile Lys Lys Leu Gln Asp
        35                  40                  45

Gln Gly Arg Arg Val Ile Cys Tyr Phe Ser Ala Gly Ser Tyr Glu Asn
    50                  55                  60

Trp Arg Pro Asp Lys Asp Lys Phe Lys Asp Ser Asp Leu Gly Asn Thr
65                  70                  75                  80

Met Lys Gly Trp Glu Asp Glu Arg Trp Leu Asp Leu Thr Ser Thr Asn
```

-continued

```
                85                  90                  95

Val Arg Asn Ile Met Leu Ser Arg Leu Asp Leu Ala Gln Glu Lys Gly
            100                 105                 110

Cys Asp Gly Val Asp Pro Asp Asn Val Asp Gly Tyr Glu Lys Asp Asn
        115                 120                 125

Asp Ser Gly Leu Asp Leu Thr Met Glu Asp Ala Ala Asp Phe Val Asn
    130                 135                 140

Phe Leu Ala Asn Glu Thr His Ala Arg Asn Met Ser Ile Gly Leu Lys
145                 150                 155                 160

Asn Ala Gly Asp Ile Ile Pro Ser Val Ile Gly Asn Met Gln Trp Ser
                165                 170                 175

Val Asn Glu Gln Cys Ala His Tyr Asp Glu Cys Asp Thr Tyr Ala Ala
            180                 185                 190

Phe Ile Glu Ala Gly Lys Pro Val Phe His Ile Glu Tyr Pro Lys Gly
        195                 200                 205

Asp Asp Thr Asn Asp Asn Ser Pro Val Thr Thr Ala Gln Lys Val Ser
    210                 215                 220

Ala Cys Val Phe Ser Gly Pro Arg Asn Phe Ser Thr Ile Ile Lys Asn
225                 230                 235                 240

Met Asp Leu Asp Asn Trp Ile Glu Thr Cys
                245                 250


<210> SEQ ID NO 115
<211> LENGTH: 263
<212> TYPE: PRT
<213> ORGANISM: Plectosphaerella alismatis

<400> SEQUENCE: 115

Thr Ser Asp Lys Asn Arg Trp Ile Pro Ala Val Gly Thr Ser Trp Gln
1               5                   10                  15

Ile Val Leu Ser Ala Pro Leu Gln Ile Asp Ser Thr Lys Pro Val Val
            20                  25                  30

Thr Pro Asp Val Gln Val Tyr Asp Phe Asp Leu Phe Asp Asn Thr Pro
        35                  40                  45

Glu Thr Ile Ala Ala Leu His Lys Ile Asp Lys Lys Ala Ile Cys Tyr
    50                  55                  60

Phe Ser Ala Gly Thr Tyr Glu Asp Trp Arg Pro Asp Ala Ser Arg Phe
65                  70                  75                  80

Gln Ser Gly Asp Phe Gly Ser Pro Met Ala Asp Trp Pro Gly Glu Lys
                85                  90                  95

Trp Leu Asn Leu Lys Ser Ser Asn Val Arg Ala Ile Met Ala Asp Arg
            100                 105                 110

Ile Lys Leu Ala Ala Asp Lys Gly Cys Asp Ala Val Asp Pro Asp Asn
        115                 120                 125

Val Asp Ala Tyr Ser Asn Glu Asn Gly Leu Gly Leu Thr Lys Asp Asp
    130                 135                 140

Ser Ala Asp Phe Val Lys Phe Leu Thr Thr Glu Ala His Asn Arg Gly
145                 150                 155                 160

Met Ser Ile Gly Leu Lys Asn Ala Gly Glu Ile Ile Ala Gln Val Ile
                165                 170                 175

Asn Asp Val Asp Phe Gln Val Asn Glu Glu Cys Val Lys Tyr Gly Glu
            180                 185                 190

Gly Arg Thr Phe Glu Ala Phe Ile Lys Ala Gly Lys Pro Val Phe His
        195                 200                 205
```

```
Ile Glu Tyr Pro Ser Gly Ala Pro Gly Ala Val Ser Pro Ala Thr Val
    210                 215                 220

Ser Asp Ile Ala Thr Ala Gln Gly Thr Asp Lys Phe Ser Thr Leu Ile
225                 230                 235                 240

Lys Thr Leu Ser Leu Asp Gly Trp Val Gln Phe Pro Asp Gly His Thr
                245                 250                 255

Glu Asp Thr Gln Thr Lys Tyr
            260


<210> SEQ ID NO 116
<211> LENGTH: 328
<212> TYPE: PRT
<213> ORGANISM: Thermothelomyces hinnuleus

<400> SEQUENCE: 116

Gln Val Arg Val Pro Pro Asn Phe Glu Val Gly Val Lys Trp Gln Ile
1               5                   10                  15

Val Ile Gln Ser Thr Ile Asp Val Asn Thr Pro Leu Glu Pro Thr Asp
            20                  25                  30

Ala Val Val Trp Asp Leu Asp Leu Tyr His Val Ala Arg Thr Pro Glu
        35                  40                  45

Ile Val Ser Tyr Leu Arg Glu Asn Asn Pro Asn Thr Ile Leu Ile Cys
    50                  55                  60

Tyr Phe Asn Ala Gly Leu Ala Gln Lys Ser Asp Cys Asp Tyr Glu Thr
65                  70                  75                  80

Arg Trp Glu Lys Ser Gly Leu Leu Gly Asn Val Tyr Asp Pro Glu Glu
                85                  90                  95

Pro Gln Phe Asp Asp Glu Arg Trp Val Asn Ile Lys Asn Gln Thr Ala
            100                 105                 110

Arg Asp Trp Ile Lys Gln Arg Ile Thr Leu Ala Arg Asp Val Gly Cys
        115                 120                 125

Asp Gly Val Asp Pro Asp Asn Ile Asp Gly Tyr His Asn Asp Glu Asp
    130                 135                 140

Gly Asn Asn Gly Thr Gly Trp Asp Leu Ser Arg Asp Asp Tyr Val Ser
145                 150                 155                 160

Phe Val Arg Glu Leu Ala Glu His Ala His Gly Leu Thr Thr Lys Arg
                165                 170                 175

Asn Tyr Thr Leu Leu Ile Gly Gln Lys Asn Ala Pro Asp Leu Val Glu
            180                 185                 190

Asp Val Gly Asp Leu Leu Asp Phe Ala Val Leu Glu Asp Cys Lys Ser
        195                 200                 205

Leu Asn Gly Gly Gly Gly Asp Asp Asp Asp Ala Pro Phe Cys Ser Glu
    210                 215                 220

Phe Gln His Tyr Ile Glu Arg Gly Arg Pro Val Phe Ser Ile Glu Tyr
225                 230                 235                 240

Pro Ser Thr Leu Gly Asp Ala Glu Thr Gly Glu Cys Lys Ser Gly Gly
                245                 250                 255

Ala Ser Lys Ala Gln Tyr Glu Ala Ser Cys Asp Ala Ser Thr Ala Ser
            260                 265                 270

Gly Asn Leu Asp Phe Ser Thr Val Leu Lys Ile Gln Gly Gly Val Gly
        275                 280                 285

Glu Leu Asn Gly Cys Thr Gln Tyr Cys Asp Gly Leu Gln Pro Gly Thr
    290                 295                 300

Gly Ile Val Val Thr Ala Thr Asp Ser Glu Leu Asp Gly Asn Glu Cys
305                 310                 315                 320
```

Pro Pro Glu Ala Thr Gly Ser Ser
325

<210> SEQ ID NO 117
<211> LENGTH: 313
<212> TYPE: PRT
<213> ORGANISM: Ovatospora brasiliensis

<400> SEQUENCE: 117

Gln Ile Lys Phe Pro Pro Glu Trp Lys Val Gly Val Lys Trp Gln Ile
1 5 10 15

Glu Ile Gln His Pro Val Asp Gly Lys Ala Pro Leu Val Pro Ala Asp
20 25 30

Ala Val Val Trp Asp Val Asp Leu Tyr His Leu Ala Ser Asn Pro Gly
35 40 45

Leu Ile Asp His Leu Arg Thr Gly Asn Gly Pro Asn Thr Thr Val Ile
50 55 60

Cys Tyr Phe Asn Ala Gly Leu Val Gln Glu Ser Asp Cys Asp Trp Asp
65 70 75 80

Thr Val Trp Asn Thr Pro Ala Tyr Arg Gly Leu Leu Gly Gln Arg His
85 90 95

Pro Asp Phe Pro Asp Glu Ala Trp Ile Asn Ile Arg Asn Gln Thr Ala
100 105 110

Arg Asp Leu Ile Lys Arg Arg Ile Asp Leu Ala Arg Glu Ile Gly Cys
115 120 125

Asp Gly Val Asp Pro Asp Asn Ile Asp Gly Tyr Gly Leu Asp Glu Pro
130 135 140

Gly Ser Asp His Met Thr Gly Trp Asn Leu Thr Gln Gln Asp Asp Ile
145 150 155 160

Asp Phe Ile Leu Asp Leu Ala Thr Tyr Ala His Arg Gln Thr Thr Leu
165 170 175

Arg Gly Asn Thr Leu Leu Ile Gly Gln Lys Asn Ala Pro Glu Ile Thr
180 185 190

Arg Asn Val Ser Ala Ser Leu Asp Phe Ala Val Leu Glu Asp Cys Arg
195 200 205

Gly Arg Arg Thr Glu Pro Pro Asp Thr Pro Asn Pro Phe Cys Thr Val
210 215 220

Tyr Gln Asp Pro Tyr Ile Arg Ala Gly Lys Pro Val Phe Ser Ile Glu
225 230 235 240

Tyr Pro Ala Ser Leu Gly Asp Pro Glu Ser Gly Glu Cys Ser Ala Ser
245 250 255

Gly Thr Asn Asp Asp Asp Tyr Thr Gly Ser Cys Gln Asn Gly Val Glu
260 265 270

Gly Phe Ser Glu Val Leu Lys Ile Gln Gly Gly Glu Gly Glu Leu Asn
275 280 285

Gly Cys Thr Glu Tyr Cys Asp Val Lys Gly Leu Val Val Thr Ala Val
290 295 300

Asp Glu Ala Asp Gly Gly Glu Cys Pro
305 310

<210> SEQ ID NO 118
<211> LENGTH: 301
<212> TYPE: PRT
<213> ORGANISM: Fusarium acuminatum

<400> SEQUENCE: 118

```
Glu Pro Lys Pro Ala Ala Lys Ala Ser Ser Pro Ser Ser Phe Gly Leu
1               5                   10                  15

Ser Asp Phe Lys Pro Gly Val Gln Trp Glu Ile Val Ile His Glu Pro
            20                  25                  30

Ile Lys His Asp Ser Ala Ala Asp Leu Ile Pro Ser Lys Ala Lys Val
        35                  40                  45

Trp Asp Ile Asp Met Gly His Ala Arg Arg Tyr Pro Glu Ile Val Pro
    50                  55                  60

Leu Leu Lys Ser Ala Gly Lys Phe Val Ile Cys Tyr Phe Asn Ala Gly
65                  70                  75                  80

Ala Val Gln Ala Trp Asp Asp Asp Lys Asp Lys Phe Pro Lys Ala Val
                85                  90                  95

Ile Gly His Ser Leu Ala Tyr Pro Tyr Asp Ser Glu Glu Trp Tyr Leu
            100                 105                 110

Asp Ile Arg Asp Ser Thr Val Leu Lys Leu Gln Lys Ala Arg Leu Asp
        115                 120                 125

Val Ala Ser Lys Ile Gly Cys Asp Ala Val Asp Pro Asp Asn Val Asp
    130                 135                 140

Ala Trp Gln Gln Asp Glu Glu Asp Pro Thr Gly Phe Lys Leu Lys Ser
145                 150                 155                 160

Ser Asp Tyr Thr Lys Tyr Leu Lys Ser Leu Ala Gln Tyr Ala His Ser
                165                 170                 175

Ile Lys Thr Lys Asp Gly Asn Pro Leu Leu Val Gly Gln Lys Asn Ala
            180                 185                 190

Pro Glu Ile Ala Asp Asp Leu Val Ser Ser Leu Asp Phe Ala Val Leu
        195                 200                 205

Glu Ser Cys Arg Gly Thr Thr Asp Pro Glu Glu Glu Asn Trp Pro Phe
    210                 215                 220

Cys Glu Asp Phe Gln Thr Tyr Ile Asp Ala Gly Lys Pro Val Leu Gln
225                 230                 235                 240

Ile Glu Tyr Pro Pro Ser Val Glu Lys Thr Gly Lys Leu Ser Ser Ser
                245                 250                 255

Asp Lys Thr Tyr Tyr Cys Thr Pro Lys Glu Glu Asp Lys Gly Phe Ser
            260                 265                 270

Lys Ile Ile Lys Trp Ala Ser Ala Gln Leu Asp Gly Trp Gly Gln Tyr
        275                 280                 285

Cys Gly Glu Glu Pro Phe Arg Thr Pro Val Ile Lys Glu
    290                 295                 300
```

<210> SEQ ID NO 119
<211> LENGTH: 296
<212> TYPE: PRT
<213> ORGANISM: Fusarium euwallaceae

<400> SEQUENCE: 119

```
Lys Pro Thr Thr Thr Val Arg Ala Thr Gly Leu Ala Asp Phe Lys Pro
1               5                   10                  15

Gly Val Gln Trp Glu Ile Cys Ile His His Pro Ile Lys His Asp Ser
            20                  25                  30

Ala Ala Asp Leu Ile Pro Thr Lys Ala Gln Val Trp Asp Ile Asp Met
        35                  40                  45

Gly His Ala Arg Glu Phe Pro Asn Met Ile Pro Met Leu Lys Ser Ala
    50                  55                  60

Gly Lys Phe Val Ile Cys Tyr Phe Asn Ala Gly Ala Leu Gln Asp Trp
```

-continued

```
65                  70                  75                  80

Asp Asp Asp Lys Ser Lys Phe Pro Gln Glu Val Ile Gly His Ser Leu
                85                  90                  95

Ser Tyr Pro Tyr Asp Asp Glu Glu Trp Tyr Leu Asp Ile Arg Asp Ser
            100                 105                 110

Arg Val Leu Glu Leu Gln Lys Ala Arg Leu Asp Val Ala Ala Gln Ile
        115                 120                 125

Gly Cys Asp Ala Val Asp Pro Asp Asn Val Asp Ala Trp Gln Gln Asp
    130                 135                 140

Asp Glu Asp Pro Thr Gly Phe Lys Leu Lys Ser Ser Asp Tyr Thr Asn
145                 150                 155                 160

Tyr Leu Lys Asn Leu Ala Lys Tyr Ala His Ser Ile Lys Thr Lys Asp
                165                 170                 175

Gly Gln Pro Leu Leu Val Gly Gln Lys Asn Ala Pro Glu Ile Ala Glu
            180                 185                 190

Asp Leu Val Ser Thr Leu Asp Phe Ala Val Leu Glu Ser Cys Arg Gly
        195                 200                 205

Asn Ser Asp Pro Asn Glu Glu Ser Trp Pro Phe Cys Glu Asp Phe Gln
    210                 215                 220

Thr Tyr Ile Asp Ala Gly Lys Pro Val Leu Gln Ile Glu Tyr Pro Pro
225                 230                 235                 240

Ser Val Glu Lys Thr Gly Lys Leu Ser Ala Ser Asp Glu Lys Tyr Tyr
                245                 250                 255

Cys Thr Ala Glu Asp Glu Asp Lys Gly Phe Ser Lys Ile Ile Lys Trp
            260                 265                 270

Ala Ser Ala Gln Leu Asp Gly Trp Gly Gln Tyr Cys Gly Glu Asp Pro
        275                 280                 285

Phe Arg Thr Pro Ala Ala Lys Tyr
    290                 295


<210> SEQ ID NO 120
<211> LENGTH: 274
<212> TYPE: PRT
<213> ORGANISM: Fusarium neocosmosporiellum

<400> SEQUENCE: 120

Ala Pro Ser Asn Ala Asn Thr Glu Thr Pro Glu Ala Leu Ser Pro Arg
1               5                   10                  15

Ala Val Ile Ser Arg Lys Glu Leu Trp Lys Pro Lys Val Gly Thr Ala
            20                  25                  30

Trp Gln Ile Val Leu Ser Gln Val Ile Lys Ile Pro Lys Gly Gly Ala
        35                  40                  45

Lys Asn Leu Lys Pro Asn Val Pro Ile Tyr Asp Leu Asp Leu Phe Glu
    50                  55                  60

Asn Ser Lys Glu Thr Phe Asp Ala Leu His Lys Ala Gly Lys His Val
65                  70                  75                  80

Ile Cys Tyr Phe Ser Ala Gly Ser Trp Glu Asn Trp Arg Asp Asp Arg
                85                  90                  95

Lys Ser Phe Gln Lys Lys Asp Leu Gly Lys Thr Leu Ser Gly Trp Pro
            100                 105                 110

Asp Glu Lys Tyr Ile Asn Ile Asn Ser Pro Ser Val Arg Ala Ile Met
        115                 120                 125

Ala Lys Arg Ile Lys Leu Ala Ala Glu Lys Gly Cys Asp Ala Ile Asp
    130                 135                 140
```

```
Pro Asp Asn Leu Asp Gly Tyr Gln Ala Asp Asn Gly Leu Gly Leu Thr
145                 150                 155                 160

Glu Ala Asp Thr Ile Ala Tyr Val Lys Phe Leu Ser Lys Glu Ala Ala
                165                 170                 175

Lys Tyr Arg Met Thr Thr Gly Met Lys Asn Gly Gly Ser Ile Thr Lys
            180                 185                 190

Gln Val Leu Pro His Val Gly Phe Cys Ile Asn Glu Ser Cys Ile Gln
        195                 200                 205

Tyr Ser Glu Cys Asp Leu Tyr Ala Pro Tyr Ile Lys Ala Gly Lys Pro
    210                 215                 220

Val Phe Asn Ile Glu Tyr Pro Ala Gly Ala Pro Asn Val Lys Ala Ala
225                 230                 235                 240

Asp Lys Lys Arg Ile Cys Ser Val Thr Gly Ala Ala Lys Gly Ser Asn
                245                 250                 255

Gly Phe Ser Lys Val Ile Lys Lys Met Asn Leu Asp Ser Trp Val Thr
            260                 265                 270

Tyr Cys


<210> SEQ ID NO 121
<211> LENGTH: 327
<212> TYPE: PRT
<213> ORGANISM: Thielavia antarctica

<400> SEQUENCE: 121

Gln Val Lys Val Asn Pro Pro Ala Gly Phe Asp Val Gly Val Lys Trp
1               5                   10                  15

Gln Ile Glu Ile Gln Asn Thr Val Asp Ile Thr Lys Pro Leu Asn Pro
            20                  25                  30

Ala Asp Ala Leu Val Trp Asp Val Asp Leu Tyr His Val Ala Arg Asn
        35                  40                  45

Pro Gly Ile Ile Asp Tyr Leu Arg Ser Lys Asn Pro Asp Thr Ile Ile
    50                  55                  60

Ile Cys Tyr Phe Asn Ala Gly Leu Ala Gln Leu Ser Asp Cys Asp Tyr
65                  70                  75                  80

Asp Ser Thr Trp Lys Asn Ser Gly Phe Leu Gly Asn Ser Tyr Gly Glu
                85                  90                  95

Glu Phe Pro Asp Glu Phe Trp Ile Asn Ile Lys Ser Gln Ala Ala Arg
            100                 105                 110

Asp Leu Val Lys Arg Arg Ile Thr Leu Ala Asn Gln Leu Gly Cys Asp
        115                 120                 125

Gly Val Asp Pro Asp Asn Ile Asp Gly Tyr Asn Met Asp Glu Asp Gly
    130                 135                 140

Ser Asp Lys Ser Ser His Thr Gly Trp Ser Leu Thr Pro Gln Asp Asp
145                 150                 155                 160

Ile Thr Phe Ile Leu Asp Leu Ala Thr His Ala His Ala Leu Thr Thr
                165                 170                 175

Ala Arg Asn Lys Thr Leu Leu Ile Gly Gln Lys Asn Ala Pro Glu Ile
            180                 185                 190

Thr Ala Ala Ile Ala Ala His Leu Asp Phe Ala Val Leu Glu Asp Cys
        195                 200                 205

Lys Gly Leu Thr Gln Ala Ala Ser Asp Asp Asp Asp Asp Asp Pro Phe
    210                 215                 220

Ser Phe Cys Gly Asp Tyr Thr Thr Pro Tyr Ile Gly Ala Gly Lys Pro
225                 230                 235                 240
```

-continued

```
Val Leu Ser Ile Glu Tyr Pro Arg Ser Leu Ala Gly Arg Asn Thr Gly
                245                 250                 255

Lys Cys Asn Ala Gly Gly Val Ser Ala Asp Glu Tyr Ala Arg Val Cys
            260                 265                 270

Ala Glu Ala Glu Ala Glu Gly Gly Gly Gly Phe Ser Thr Val Leu Lys
        275                 280                 285

Thr Arg Gly Ser Ala Gly Glu Leu Asn Gly Cys Thr Gln Tyr Cys Gly
    290                 295                 300

Leu Gly Val Gly Lys Gly Val Val Val Thr Ala Val Asp Glu Glu Leu
305                 310                 315                 320

Asp Gly Asp Asp Cys Pro Ala
                325


<210> SEQ ID NO 122
<211> LENGTH: 265
<212> TYPE: PRT
<213> ORGANISM: Acremonium thermophilum

<400> SEQUENCE: 122

Ser Pro Lys Trp Gln Pro Ser Val Asn Ala Thr Trp Gln Ile Val Leu
1               5                   10                  15

Asp His Pro Leu Ala Leu Ala Asp Gly Ala Asp Ala Thr Val Gln Pro
            20                  25                  30

Ser Asp Ala Asp Val Phe Asp Ile Asp Leu Phe Met His Gln Asn Ala
        35                  40                  45

Thr Thr Val Ala Ala Leu His Arg Leu Gly Lys Arg Val Val Cys Tyr
    50                  55                  60

Phe Ser Ala Gly Ser Tyr Glu Pro Asp Arg Pro Asp Ser Gly Arg Phe
65                  70                  75                  80

Ala Arg Gly Asp Leu Gly Ala Glu Leu Asp Gly Trp Pro Gly Glu Tyr
                85                  90                  95

Trp Leu Asn Val Ser Ser Pro Thr Val Arg Thr Ile Met Ala Arg Arg
            100                 105                 110

Ile Gly Ile Ala Ala Asp Met Gly Cys Asp Ala Val Asp Pro Asp Asn
        115                 120                 125

Val Asp Gly Tyr Gln Asn Thr Asn Gly Leu Gly Leu Thr Arg Ala Ala
    130                 135                 140

Ala Val Asp Phe Val Arg Phe Leu Ala Ala Glu Ser Ala Glu Arg Gly
145                 150                 155                 160

Leu Ala Val Gly Leu Lys Asn Ala Gly Asp Leu Val Asp Asp Val Leu
                165                 170                 175

Asp Val Val His Phe Ser Val Asn Glu Gln Cys Ala Gln Tyr Asp Glu
            180                 185                 190

Cys Ala Thr Phe Ala Pro Phe Val Arg Ala Gly Lys Pro Val Phe His
        195                 200                 205

Ile Glu Tyr Pro Asp Gly Ala Gln Lys Gly Ser Val Ala Asp Ala Ala
    210                 215                 220

Arg Glu Ala Ala Cys Asp Ala Ser Gly Ser Ser Gly Phe Ser Thr Val
225                 230                 235                 240

Leu Lys Arg Met Glu Leu Asp Gly Trp Val Glu Tyr Cys Asp Gly Thr
                245                 250                 255

Thr Ala Thr Thr Ala Val Glu Asp Glu
            260                 265


<210> SEQ ID NO 123
```

<211> LENGTH: 323
<212> TYPE: PRT
<213> ORGANISM: Crassicarpon hotsonii

<400> SEQUENCE: 123

Gln Val Arg Ala Pro Pro Asp Phe Lys Pro Gly Val Lys Trp Gln Ile
1 5 10 15

Val Ile Gln Ser Thr Ile Asp Ile Asn Ala Pro Leu Glu Pro Thr Asp
20 25 30

Ala Val Val Trp Asp Leu Asp Leu Tyr His Val Ala Arg Thr Pro Gly
35 40 45

Ile Val Asn Tyr Leu Arg Arg Asn Asn Pro Asp Ala Ile Leu Ile Cys
50 55 60

Tyr Phe Asn Ala Gly Leu Ala Gln Lys Ser Asp Cys Asp Tyr Lys Thr
65 70 75 80

Arg Trp Glu Ser Ser Gly Leu Leu Gly Asn Val Tyr Asp Pro Glu Glu
85 90 95

Pro Gln Phe Asp Asp Glu Arg Trp Val Asn Ile Lys Asn Gln Thr Ala
100 105 110

Arg Asp Trp Ile Lys Glu Arg Ile Thr Leu Ala Arg Asp Val Gly Cys
115 120 125

Asp Gly Val Asp Pro Asp Asn Ile Asp Gly Trp Tyr Asn Asp Glu Asp
130 135 140

Gly Asn Asn Gly Thr Gly Trp Asp Leu Ser Gln Asp Asp Tyr Val Ser
145 150 155 160

Phe Val Arg Glu Leu Ala Glu His Ala His Gly Leu Thr Thr Glu Arg
165 170 175

Gly Tyr Thr Leu Leu Ile Gly Gln Lys Asn Ala Pro Asp Leu Val Glu
180 185 190

Asp Val Gly Asp Ile Leu Asp Phe Ala Val Leu Glu Asp Cys Gly Gln
195 200 205

Leu Asn Ser Glu Asp Asp Ser Phe Cys Gly Glu Phe Gln His Tyr Ile
210 215 220

Glu Arg Gly Arg Pro Val Phe Ser Ile Glu Tyr Pro Ser Thr Leu Gly
225 230 235 240

Asp Pro Glu Thr Gly Glu Cys Arg Asn Gly Gly Val Ser Lys Pro Gln
245 250 255

Tyr Glu Ala Ser Cys Asp Thr Ser Ala Ala Lys Gly Asn Ala Asn Phe
260 265 270

Ser Thr Val Leu Lys Ile Gln Gly Gly Val Gly Glu Leu Asn Gly Cys
275 280 285

Thr Gln Tyr Cys Asp Gly His Gln Pro Gly Thr Glu Ile Phe Val Thr
290 295 300

Ala Thr Asp Pro Glu Leu Asp Gly Asn Lys Cys Pro Pro Glu Ala Thr
305 310 315 320

Gly Ser Asp

<210> SEQ ID NO 124
<211> LENGTH: 260
<212> TYPE: PRT
<213> ORGANISM: Helicosporium sp.

<400> SEQUENCE: 124

Ala Phe Thr Val Gly Glu Arg Phe Gln Ile Ile Leu Ser Ser Val Pro
1 5 10 15

-continued

```
Asp Ile Ser Val Thr Ser Met Val Pro Asp Ala Pro Val Phe Asp Ile
            20                  25                  30

Asp Ala Phe Asp Ser Asn Ala Thr Val Ile Ser Ala Leu Lys Lys Met
        35                  40                  45

Gly Lys Thr Val Ile Cys Tyr Phe Ser Ala Gly Thr Tyr Glu Pro Trp
    50                  55                  60

Arg Pro Asp Ser Asn Leu Phe Lys Lys Glu Asp Tyr Gly Leu Ala Leu
65                  70                  75                  80

Asp Gly Trp Pro Asp Glu His Trp Leu Lys Leu Asp Ser Thr Asn Val
                85                  90                  95

Arg Ser Ile Met Thr Thr Arg Ile Lys Met Ala Ala Asp Lys Gly Cys
            100                 105                 110

Asp Ala Ile Asp Pro Asp Asn Thr Asp Gly Phe Thr Asn Gln Asn Gly
        115                 120                 125

Ile Gly Leu Thr Ala Lys Gly Ala Val Asp Phe Ile Thr Phe Leu His
    130                 135                 140

Lys Glu Ala Thr Ala Asn Asn Met Lys Ile Gly Leu Lys Asn Ser Gln
145                 150                 155                 160

Gly Ile Leu Ser Gln Val Ser Ser Met Met Ser Phe Ala Val Asn Glu
                165                 170                 175

Glu Cys Ala Ile Asn Gly Glu Cys Asn Gly Tyr Asp Ala Phe Leu Ser
            180                 185                 190

Ala Gly Lys Pro Val Tyr His Ile Glu Tyr Pro Ser Ile Ile Pro Thr
        195                 200                 205

Val Ala Val Asn Asp Arg Asn Lys Tyr Cys Val Ser Thr Ala Ser Asn
    210                 215                 220

Thr Asn Lys Phe Ser Thr Val Leu Lys Asn Met Thr Leu Asp Gly Trp
225                 230                 235                 240

Val Leu Tyr Cys Asp Gly Ser Ser Phe Ile Thr Lys Thr Thr Glu Asn
                245                 250                 255

Ala Thr Ser Gly
            260


<210> SEQ ID NO 125
<211> LENGTH: 245
<212> TYPE: PRT
<213> ORGANISM: Pyrenochaetopsis sp

<400> SEQUENCE: 125

Ser Pro Leu His Arg Arg Ala Val Ala Lys Phe Thr Val Gly Ala Val
1               5                   10                  15

Trp Asp Ile Leu Leu Asp Lys Thr Asn Val Asn Leu Ala Ala Met Glu
            20                  25                  30

Lys Ala Ala Gly Thr Val Ile Asp Ile Asp Leu Phe Asp Asn Thr Ala
        35                  40                  45

Asp Gly Gln Thr Thr Val Lys Asp Leu Ala Lys Thr Lys Gln Val Ile
    50                  55                  60

Cys Tyr Phe Ser Ala Gly Ser Arg Glu Asp Trp Arg Asp Asp Ala Asp
65                  70                  75                  80

Gln Phe Thr Ser Ala Asp Tyr Gly Gln Ala Leu Gly Asp Trp Pro Gly
                85                  90                  95

Glu Asn Trp Val Asp Val Lys Ser Thr Asn Val Arg Ala Ile Met Lys
            100                 105                 110

Ala Arg Ile Glu Ala Ala Ala Lys Ala Gly Cys Thr Ala Val Asp Pro
        115                 120                 125
```

Asp Asn Val Asp Gly Phe Asp Ser Asn Gln Asp Gly Tyr Gly Tyr Pro
    130                 135                 140

Gln Ser Ala Tyr Ser Asp Tyr Val Asn Tyr Leu Ala Gly Ile Ala His
145                 150                 155                 160

Ala Asn Asn Leu Ala Ile Gly Leu Lys Asn Ala Leu Asp Ile Ile Pro
                165                 170                 175

Ala Val Leu Pro Asn Ile Gln Phe Ala Val Asn Glu Gln Cys His Val
            180                 185                 190

Tyr Asn Glu Cys Thr Lys Tyr Lys Ala Val Thr Ala Ala Gly Leu Pro
        195                 200                 205

Val Phe Asn Ile Glu Tyr Gly Asn Asn Tyr Cys Thr Asp Pro Ser Gly
    210                 215                 220

Val Asn Leu Ser Thr Val Ile Lys Pro Ala Asp Gln Asp Leu Asp Thr
225                 230                 235                 240

Leu Gly Gly Gln Cys
                245

<210> SEQ ID NO 126
<211> LENGTH: 298
<212> TYPE: PRT
<213> ORGANISM: Acremonium cf. fusifioides

<400> SEQUENCE: 126

Ala Leu Pro Gly Ser Cys Asn Glu Ala Arg Ala Pro Ala Gly Phe Glu
1               5                   10                  15

Pro Gly Val Asp Trp Gln Ile Cys Ile His Gln Pro Ile Lys His Asp
            20                  25                  30

Ser Ala Asp Asp Phe Ile Pro Lys Ala Ala Gln Val Phe Asp Val Asp
        35                  40                  45

Leu Ala His Ala Gln Asp Tyr Pro Glu Met Ile Pro Asn Leu His Asn
    50                  55                  60

Ala Gly Lys Thr Val Ile Cys Tyr Phe Asn Gly Gly Ala Met Gln Asn
65                  70                  75                  80

Trp Asp Asp Asp Lys Asp Asp Phe Pro Glu Asp Val Ile Gly Lys Ser
                85                  90                  95

Leu Asp Tyr Pro Tyr Val Gly Asp Glu Asp Gly Glu Phe Tyr Val Asp
            100                 105                 110

Ile Arg Asp Ser Arg Val Leu Glu Ile Met Lys Lys Arg Leu Asp Asn
        115                 120                 125

Ala Val Ser Ala Gly Cys Asp Ala Val Asp Pro Asp Asn Val Asp Ala
    130                 135                 140

Trp Ala Glu Gly Thr Ser Asp Asp Asp Asp Pro Thr Gly Phe Gly Leu
145                 150                 155                 160

Lys Pro Gln Asp Tyr Ala Asp Tyr Leu Thr Lys Leu Ala Glu Tyr Ala
                165                 170                 175

His Ser Gln Glu Thr Lys Leu Gly Asp Lys Leu Leu Val Gly Gln Lys
            180                 185                 190

Asn Ala Pro Asp Ile Ala Glu Ser Leu Val Ser Thr Leu Asp Phe Ala
        195                 200                 205

Val Leu Glu Ser Cys Arg Thr Trp Ser Phe Cys Gly Glu Phe Gln Thr
    210                 215                 220

Tyr Ile Glu Ala Gly Lys Pro Val Phe Gln Ile Glu Tyr Pro Pro Ser
225                 230                 235                 240

Ile Glu Glu Thr Gly Ser Leu Ser Asp Glu Asp Glu Glu Phe Tyr Cys

-continued

```
                245                 250                 255

Lys Glu Ser Glu Glu Glu His Gly Asp Lys Gly Phe Ser Lys Leu Leu
            260                 265                 270

Lys Phe Ala Ser Ala Arg Leu Asp Gly Trp Thr Gln Leu Cys Asp Gly
        275                 280                 285

Ser Ile Phe Glu Gln Pro Met Leu Asp Trp
    290                 295


<210> SEQ ID NO 127
<211> LENGTH: 250
<212> TYPE: PRT
<213> ORGANISM: Rasamsonia byssochlamydoides

<400> SEQUENCE: 127

Pro Pro Asn Thr Thr Thr Trp Gln Pro Gln Val Arg Thr Ser Trp Gln
1               5                   10                  15

Ile Glu Leu Leu Tyr Ala Leu Asn Asp Thr Ser Val Asp Ala Glu Val
            20                  25                  30

Tyr Asp Ile Asp Leu Phe Ser Asn Asn Ala Ser Ile Ile Ala Gln Leu
        35                  40                  45

Gln Asp Ala Gly Arg Arg Val Ile Cys Tyr Phe Ser Ala Gly Ser Tyr
    50                  55                  60

Glu Asn Trp Arg Pro Asp Ala Asn Glu Phe Gln Pro Ser Asp Leu Gly
65                  70                  75                  80

Asn Thr Leu Asp Gly Trp Pro Asp Glu Arg Trp Leu Asn Ile Asn Ser
                85                  90                  95

Ala Asn Val His Arg Ile Met Lys Ala Arg Leu Asp Met Ala Ser Asp
            100                 105                 110

Lys Gly Cys Asp Gly Val Asp Pro Asp Asn Val Asp Gly Tyr Asp Asn
        115                 120                 125

Asp Asn Gly Leu Asp Leu Thr Glu Ala Asp Ser Ile Asn Tyr Val Asn
    130                 135                 140

Phe Leu Ala Asn Glu Ala His Ala Arg Asn Leu Ser Ile Gly Leu Lys
145                 150                 155                 160

Asn Ala Gly Ala Ile Ile Pro Ser Val Ile Asp Asn Met Gln Trp Ser
                165                 170                 175

Val Asn Glu Gln Cys Val Gln Tyr Asp Glu Cys Asp Thr Tyr Ala Val
            180                 185                 190

Phe Ile Ala Ala Gly Lys Pro Val Phe His Ile Glu Tyr Pro Lys Gly
        195                 200                 205

Asp Asp Thr Asn Asn Asn Gln Leu Val Thr Ala Ala Glu Lys Ala Ala
    210                 215                 220

Ala Cys Asn Ser Thr Asn Ala Ala Asn Phe Ser Thr Ile Leu Lys Asn
225                 230                 235                 240

Met Asp Leu Asp Asn Trp Ile Glu Thr Cys
                245                 250


<210> SEQ ID NO 128
<211> LENGTH: 276
<212> TYPE: PRT
<213> ORGANISM: Acremonium dichromosporum

<400> SEQUENCE: 128

Ala Thr Asn Val Phe Gly Gly Leu Glu Lys Gly Ala Lys Trp Asn Ile
1               5                   10                  15

Cys Ile His Asn Pro Ile Lys His Asp Thr Pro Asp Ala Val Leu Pro
```

```
            20                  25                  30

Arg Glu Ala Ser Val Tyr Asp Val Ala Val Asp His Ala Arg Asp Phe
        35                  40                  45

Pro Asp Ile Ile Pro Ala Ile Lys Glu Ser Gly Lys Thr Val Leu Cys
    50                  55                  60

Tyr Phe Asn Ala Gly Ala Leu Gln Asp Trp Asp Ala Asp Lys Gly Asp
65                  70                  75                  80

Phe Pro Lys Ala Ala Ile Gly Arg Thr Met Gly Gly Asp Tyr Asp Asp
                85                  90                  95

Glu Trp Tyr Leu Asp Ile Arg Arg Gln Asp Val Val Glu Leu Met Tyr
            100                 105                 110

Lys Arg Leu Glu Glu Ala Ala Ala Leu Gly Cys Asp Gly Val Asp Pro
        115                 120                 125

Asp Asn Val Asp Ala Trp Ala Glu Ala Gly Glu Asp Arg Ser Gly Phe
    130                 135                 140

Gly Leu Thr Gln Gln Asp Tyr Thr Asp Tyr Leu Ile Lys Leu Ala Asn
145                 150                 155                 160

Phe Ala His Gly Leu Gly Pro Leu Met Val Gly Gln Lys Asn Ala Pro
                165                 170                 175

Asp Met Ala Ala Asp Leu Val Gly Ala Leu Asp Phe Ala Val Leu Glu
            180                 185                 190

Ser Cys Arg Glu Trp Asp Phe Cys Lys Asp Phe Gln Val Tyr Val Glu
        195                 200                 205

Ala Gly Lys Pro Val Phe Gln Ile Glu Tyr Pro Glu Ser Ile Val Glu
    210                 215                 220

Gln Gly Glu Leu Ser Pro Asp Asp Tyr Lys Lys His Cys Glu Gly Asp
225                 230                 235                 240

Ala Gly Asp Ala Gly Phe Ser Lys Val Leu Lys Arg Ala Ser Ala Gln
                245                 250                 255

Leu Asp Gly Trp Thr Gln Tyr Cys Asn Glu Glu Pro Phe Glu Gln Ala
            260                 265                 270

Val Ile Glu Trp
        275


<210> SEQ ID NO 129
<211> LENGTH: 248
<212> TYPE: PRT
<213> ORGANISM: Thermomyces dupontii

<400> SEQUENCE: 129

Gly Thr Val Ser Trp Lys Pro Arg Val Gly Thr Thr Trp Gln Ile Glu
1               5                   10                  15

Leu Leu Tyr Pro Leu Asn Asp Thr Ser His Asp Val Asp Val Tyr Asp
            20                  25                  30

Ile Asp Leu Phe Ile Asn Gly Glu Lys Ile Ile Ser Lys Leu His Gly
        35                  40                  45

Asp Gly Arg Lys Val Ile Cys Tyr Phe Ser Ala Gly Ser Tyr Glu Asn
    50                  55                  60

Trp Arg Pro Asp Val His Lys Phe Arg Pro Glu Asp Leu Gly Asn Thr
65                  70                  75                  80

Leu Glu Gly Trp Glu Asp Glu Arg Trp Leu Asp Ile Arg Ser Asn Asn
                85                  90                  95

Val Arg Asp Ile Met Lys Asp Arg Leu Asp Met Ala Arg Asp Lys Gly
            100                 105                 110
```

```
Cys Asp Gly Val Asp Pro Asp Asn Val Asp Gly Tyr Asp Asn Asp Asn
        115                 120                 125

Gly Leu Ser Leu Thr Gln Asp Asp Ser Ile Ser Phe Val Thr Leu Leu
    130                 135                 140

Ala Arg Glu Ala His Ala Arg Gly Leu Ser Ile Gly Leu Lys Asn Ala
145                 150                 155                 160

Gly Asp Ile Ile Asp Ser Val Ile Asp Leu Met Gln Trp Gly Val Asn
                165                 170                 175

Glu Gln Cys Ala Glu Phe Asp Glu Cys Asp Thr Tyr Ala Val Phe Thr
            180                 185                 190

Glu Gln Gly Lys Pro Val Phe His Ile Glu Tyr Pro Lys Gly Asp Glu
        195                 200                 205

Ile Asn Asp Asn Lys Pro Val Thr Ser Ala Gln Lys Tyr Ser Ala Cys
    210                 215                 220

Asn Ala Val Gly Ser Gly Asn Phe Ser Thr Ile Ile Lys Asn Met Asn
225                 230                 235                 240

Leu Asp Asn Trp Val Gln Ile Cys
                245


<210> SEQ ID NO 130
<211> LENGTH: 316
<212> TYPE: PRT
<213> ORGANISM: Ovatospora medusarum

<400> SEQUENCE: 130

Gln Ile Lys Leu Pro Pro Gly Trp Lys Val Gly Met Lys Trp Gln Ile
1               5                   10                  15

Glu Ile Gln His Thr Val Asp Val Asn Thr Pro Leu Val Pro Ser Asp
            20                  25                  30

Ala Leu Val Trp Asp Val Asp Leu Tyr His Ile Ala Arg Lys Pro Glu
        35                  40                  45

Val Ile Asn His Leu Arg Ser Thr Asn Pro Glu Thr Ile Val Ile Cys
    50                  55                  60

Tyr Phe Asn Ala Gly Leu Val Gln Glu Ser Asp Cys Asp Trp Glu Thr
65                  70                  75                  80

Thr Trp Gln Ser Pro Glu Tyr Arg Asp Leu Leu Gly Thr Arg His Pro
                85                  90                  95

Asp Phe Pro Asp Glu Ala Trp Val Asn Ile Arg Asn Gln Thr Gly Arg
            100                 105                 110

Asp Leu Ile Lys Arg Arg Ile Asp Leu Ala Arg Asp Leu Gly Cys Asp
        115                 120                 125

Gly Val Asp Pro Asp Asn Ile Asp Gly Tyr Thr Leu Asp Glu Pro Gly
    130                 135                 140

Ser Asp His Pro Thr Gly Trp Asn Leu Thr Gln Gln Asp Asp Ile Thr
145                 150                 155                 160

Phe Ile Leu Asp Leu Ala Ala His Ala His Ser Leu Thr Thr Leu Arg
                165                 170                 175

Gly Asn Thr Leu Leu Ile Gly Gln Lys Asn Ala Pro Glu Ile Thr Asp
            180                 185                 190

Ser Val Ala Ala Ser Leu Asp Phe Ala Val Leu Glu Asp Cys Lys Ser
        195                 200                 205

Leu Thr Thr Pro Asp Gly Glu Glu Arg Phe Ile Phe Cys Glu Glu Tyr
    210                 215                 220

Gln Glu Pro Tyr Ile Arg Gly Gly Lys Pro Val Phe Ser Ile Glu Tyr
225                 230                 235                 240
```

```
Pro Lys Thr Leu Gly Asp Ser Asn Thr Gly Val Cys Ser Ser Thr Gly
                245                 250                 255

Thr Glu Arg Ala Glu Trp Glu Arg Ser Cys Glu Val Ala Glu Tyr Gly
            260                 265                 270

Ser Glu Gly Phe Ser Glu Val Leu Lys Ile Gln Gly Gly Glu Gly Glu
        275                 280                 285

Leu Asn Gly Cys Thr Glu Tyr Cys Glu Val Lys Gly Leu Val Glu Thr
    290                 295                 300

Ala Val Asp Thr Glu Gly Gly Ser Cys Pro Gly Glu
305                 310                 315


<210> SEQ ID NO 131
<211> LENGTH: 257
<212> TYPE: PRT
<213> ORGANISM: Marasmius oreades

<400> SEQUENCE: 131

Ala Val Thr Asn Ala Lys Arg Ala Ile Thr Pro Leu Pro Ala Asn Gly
1               5                   10                  15

Lys Phe Asp Tyr Gln Ile Gly Gly Ala Tyr Thr Pro Asp Ser Asp Val
            20                  25                  30

Lys Val Val Thr Arg Asp Arg Thr Glu Ser Pro Ala Gln Gly Lys Tyr
        35                  40                  45

Asn Ile Cys Tyr Val Asn Ala Phe Gln Thr Gln Pro Asp Glu Lys Ala
    50                  55                  60

Phe Trp Gln Ser Ser Glu Arg Asp His Leu Leu Leu Arg Asn Ala Asn
65                  70                  75                  80

Gly Glu Tyr Phe Ile Asp Pro Glu Trp Pro Asp Glu Phe Leu Leu Asp
                85                  90                  95

Thr Ser Lys Asp Gln Asn Arg Gln Glu Ile Ala Ala Val Ile Asn Gly
            100                 105                 110

Trp Ile Ser Asp Cys Lys Gln Lys Gly Phe Asn Ala Ile Glu Ala Asp
        115                 120                 125

Asn Leu Asp Thr Phe Ser Arg Ser Lys Gly Leu Leu Thr Val Asp Asn
    130                 135                 140

Asn Leu Gln Phe Ala Lys Ile Leu Thr Asp His Ala His Ser Leu Asp
145                 150                 155                 160

Met Ala Phe Gly Gln Lys Asn Ala Gly Glu Val Ala Ala Arg Ala Lys
                165                 170                 175

Lys Glu Ala Gly Phe Asp Phe Ala Val Val Glu Gln Cys Gln Glu Phe
            180                 185                 190

Glu Glu Cys Asp Thr Tyr Thr Asp Val Tyr Gly Asn Gln Met Leu Glu
        195                 200                 205

Ile Glu Tyr Tyr Asn Glu Asp Leu Pro Glu Asn Gly Leu Glu Asn Phe
    210                 215                 220

Lys Asp Ala Cys Gln Ala Arg Gly Asn Gln Ile Ser Ile Ile Phe Arg
225                 230                 235                 240

Asp Val Glu Val Arg Pro Pro Gly Ser Glu Asp Arg Val Tyr Gln Glu
                245                 250                 255

Cys


<210> SEQ ID NO 132
<211> LENGTH: 252
<212> TYPE: PRT
<213> ORGANISM: Amycolatopsis niigatensis
```

<400> SEQUENCE: 132

Ala Gly Pro Val Glu Ser Ala Pro Leu Pro Ser Pro His Ser Gln Val
1 5 10 15

Ala Asp Val Pro Leu Pro Ala Pro His Ala Gly Phe Asp Tyr Gln Ile
20 25 30

Gly Gly Pro Tyr Gln Pro Pro Ala Gly Val Gln Val Val Ser Arg Asp
35 40 45

His Ser Ala Pro Ala Ala Ser Gly Leu Tyr Asn Ile Cys Tyr Val Asn
50 55 60

Ala Phe Gln Val Gln Pro Gly Ala Glu Lys Glu Trp Gly Asp Leu Val
65 70 75 80

Leu Arg Asp Asp Asp Gly Thr Val Val Met Asp Pro Asp Trp Asn Glu
85 90 95

Ala Leu Leu Asp Ser Arg Thr Ala Asp Lys Arg Ser Arg Ile Ala Asp
100 105 110

Lys Val Gly Ala Trp Ile Asp Glu Cys Ala Gly Lys Gly Tyr Gln Ala
115 120 125

Ile Glu Pro Asp Asn Tyr Asp Ser Phe Thr Arg Ser Gln Gly Leu Leu
130 135 140

Ser Ala Arg Asn Ala Gln Asp Leu Val Lys Leu Leu Ser Glu Arg Ala
145 150 155 160

His Gly Lys Gly Leu Ala Ile Gly Gln Lys Asn Thr Ser Glu Leu Ala
165 170 175

Ser Ser Arg Ala Ala Asn Gly Leu Asp Phe Ala Val Ala Glu Glu Cys
180 185 190

Gly Gln Gln Asp Asn Cys Ala Glu Tyr Thr Arg Tyr Phe Gly Asp Arg
195 200 205

Val Ile Val Ile Glu Tyr Thr Glu Asp Gly Leu Arg Thr Ala Cys Ala
210 215 220

Lys Trp Gly Asn Thr Leu Ser Val Val Arg Arg Asp Arg Asp Val Thr
225 230 235 240

Pro Lys Gly Asp Ser Ala Tyr Val Arg Glu Ser Cys
245 250

<210> SEQ ID NO 133
<211> LENGTH: 248
<212> TYPE: PRT
<213> ORGANISM: Byssochlamys spectabilis

<400> SEQUENCE: 133

Thr Thr Ala Lys Trp Gln Pro Pro Val Gly Thr Thr Trp Gln Ile Glu
1 5 10 15

Leu Leu Tyr Pro Leu Asn Asp Thr Ser Phe Asp Val Asp Val Tyr Asp
20 25 30

Ile Asp Leu Phe Asp Asn Asn Ala Thr Met Ile Ser Thr Leu His Asp
35 40 45

Lys Gly His Arg Val Ile Cys Tyr Phe Ser Ala Gly Thr Tyr Glu Asn
50 55 60

Trp Arg Pro Asp Lys Ser Arg Phe Lys Asp Ser Asp Leu Gly Lys Ala
65 70 75 80

Leu Gly Asp Trp Pro Gly Glu Lys Trp Leu Asn Ile Asn Ser Thr Asn
85 90 95

Val Arg Asp Ile Met Val Ser Arg Leu Asp Leu Ala Arg Gln Lys Gly
100 105 110

```
Cys Asp Gly Val Asp Pro Asp Asn Val Asp Gly Tyr Asp Asn Asp Asn
        115                 120                 125

Gly Leu Gly Leu Thr Glu Ala Asp Ser Val Asn Tyr Val Asn Phe Leu
    130                 135                 140

Ala Asn Glu Thr His Ala Arg Asn Met Ser Ile Gly Leu Lys Asn Ala
145                 150                 155                 160

Gly Ala Ile Ile Pro Trp Val Ile Gly Asn Met Gln Trp Ser Val Asn
                165                 170                 175

Glu Gln Cys Ala Gln Tyr His Glu Cys Asp Thr Tyr Leu Pro Phe Ile
            180                 185                 190

Glu Ala Gly Lys Pro Val Phe His Ile Glu Tyr Pro Lys Gly Asp Ser
        195                 200                 205

Thr Asn Asn Gly Asn Leu Val Ser Thr Ser Gln Lys Asn Asn Ala Cys
    210                 215                 220

Leu Phe Asn Asp Ser Gly Asn Phe Ser Thr Ile Ile Lys Asn Met Asp
225                 230                 235                 240

Leu Asp Asn Trp Val Gln Arg Cys
                245
```

<210> SEQ ID NO 134
<211> LENGTH: 253
<212> TYPE: PRT
<213> ORGANISM: Coprinopsis sp

<400> SEQUENCE: 134

```
Val Ala Val Leu Glu Lys Arg Ala Val Thr Leu Pro Pro Ala Asn Gly
1               5                   10                  15

Lys Phe Asp Tyr Gln Leu Gly Gly Ala Tyr Thr Pro Pro Thr Gly Thr
            20                  25                  30

Thr Ile Val Thr Arg Asp Arg Thr Ala Ser Pro Val Ala Gly Leu Tyr
        35                  40                  45

Asn Ile Cys Tyr Ile Asn Ala Phe Gln Thr Gln Ala Ser Glu Ala Ala
    50                  55                  60

Trp Trp Lys Ile Asn His Asp Thr Leu Leu Leu Arg Lys Ala Asn Asn
65                  70                  75                  80

Gln Tyr Phe Glu Asp Pro Asp Trp Ala Gly Glu Ile Phe Leu Asp Thr
                85                  90                  95

Arg Thr Ala Ala Lys Arg Thr Ala Ile Ala Thr Ile Leu Asn Gly Trp
            100                 105                 110

Ile Asp Gly Cys Ala Thr Ala Gly Phe Lys Ala Ile Glu Pro Asp Asn
        115                 120                 125

Leu Asp Ser Tyr Thr Arg Ser Asn Ser Leu Leu Thr Lys Ala Asn Asn
    130                 135                 140

Leu Ala Leu Ala Lys Leu Ile Ala Asp Tyr Ala His Thr Lys Asn Leu
145                 150                 155                 160

Ala Ile Ala Gln Lys Asn Thr Ala Glu Leu Gly Ser Glu Gly Lys Thr
                165                 170                 175

Thr Ala Gly Phe Asp Phe Ala Val Ala Glu Glu Cys Gln Gln Trp Asp
            180                 185                 190

Glu Cys Asp Glu Tyr Thr Asp Val Tyr Gly Thr Gly Val Leu Glu Ile
        195                 200                 205

Glu Tyr Thr Asp Asn Ser Asn Ala Gln Ser Val Tyr Gln Ala Ala Cys
    210                 215                 220

Thr Ala Arg Gly Ala Thr Leu Ser Val Ile Leu Arg Asp Arg Asp Leu
```

```
225                 230                 235                 240

Val Ala Leu Gly Gln Ser Gly Tyr His Tyr Glu Gln Cys
                245                 250


<210> SEQ ID NO 135
<211> LENGTH: 301
<212> TYPE: PRT
<213> ORGANISM: Fusarium sambucinum

<400> SEQUENCE: 135

Glu Pro Glu Pro Ala Ala Ala Ala Ser Ser Pro Ser Ser Phe Ser Leu
1               5                   10                  15

Ser Asp Phe Lys Pro Gly Val Gln Trp Glu Ile Val Ile His Glu Pro
            20                  25                  30

Ile Lys His Asp Gly Thr Ala Asp Leu Ile Pro Ser Lys Ala Lys Val
        35                  40                  45

Trp Asp Ile Asp Met Gly His Ala Arg Asp Tyr Pro Lys Met Ile Pro
    50                  55                  60

Leu Leu Lys Ser Ala Gly Lys Phe Val Ile Cys Tyr Phe Asn Ala Gly
65                  70                  75                  80

Ala Val Gln Ala Trp Asp Glu Asp Lys Asn Gln Phe Pro Lys Ala Val
                85                  90                  95

Ile Gly His Ser Leu Ala Tyr Pro Tyr Asp Ser Glu Glu Trp Tyr Leu
            100                 105                 110

Asp Ile Arg Asp Ser Thr Val Leu Lys Leu Gln Lys Ala Arg Leu Asp
        115                 120                 125

Val Ala Ala Lys Ile Gly Cys Asp Ala Val Asp Pro Asp Asn Val Asp
    130                 135                 140

Ala Trp Gln Gln Asp Glu Glu Asp Pro Thr Gly Phe Lys Leu Lys Ser
145                 150                 155                 160

Ser Asp Tyr Thr Lys Tyr Leu Lys Ser Leu Ala Glu Tyr Ala His Ser
                165                 170                 175

Ile Lys Thr Lys Asp Gly Asn Pro Leu Leu Val Gly Gln Lys Asn Ala
            180                 185                 190

Pro Glu Ile Ala Glu Asp Leu Val Ser Ser Leu Asp Phe Ala Val Leu
        195                 200                 205

Glu Ser Cys Arg Gly Thr Thr Asp Pro Lys Glu Glu Asn Trp Pro Phe
    210                 215                 220

Cys Glu Asp Phe Gln Thr Tyr Ile Asp Ala Gly Lys Pro Val Leu Gln
225                 230                 235                 240

Ile Glu Tyr Pro Pro Ser Val Glu Lys Thr Gly Lys Leu Ser Ser Ser
                245                 250                 255

Asp Lys Thr Tyr Tyr Cys Thr Pro Lys Glu Glu Asp Lys Gly Phe Ser
            260                 265                 270

Lys Val Ile Lys Trp Ala Ser Ala Gln Leu Asp Gly Trp Gly Gln Tyr
        275                 280                 285

Cys Gly Glu Glu Pro Phe Arg Thr Pro Val Ile Lys Glu
    290                 295                 300


<210> SEQ ID NO 136
<211> LENGTH: 242
<212> TYPE: PRT
<213> ORGANISM: Amycolatopsis orientalis DSM 46075

<400> SEQUENCE: 136

Ala Pro Leu Pro Ala Pro His Ser Val Thr Leu Pro Ala Pro His Ala
```

```
1               5                   10                  15

Gly Phe Asp Tyr Gln Ile Gly Gly Pro Tyr Thr Pro Pro Ser Gly Val
            20                  25                  30

Gln Val Val Ser Arg Asp His Ser Ala Pro Ala Ala Ala Gly Val Tyr
        35                  40                  45

Asn Ile Cys Tyr Val Asn Ala Phe Gln Ala Gln Pro Gly Ala Glu Gly
    50                  55                  60

Glu Trp Gly Asp Leu Val Leu Arg Asp Gly Asn Gly Asp Val Val Met
65                  70                  75                  80

Asp Pro Asp Trp Asn Glu Ala Leu Leu Asp Leu Arg Thr Ala Asp Lys
                85                  90                  95

Arg Ser Arg Ile Ala Asp Lys Val Gly Gly Trp Ile Asp Glu Cys Ala
            100                 105                 110

Gly Lys Gly Tyr Gln Ala Ile Glu Pro Asp Asn Tyr Asp Ser Phe Thr
        115                 120                 125

Arg Ser Gln Gly Leu Leu Ser Ala Arg Asn Ala Gln Gly Leu Val Lys
    130                 135                 140

Leu Leu Ser Ser Arg Ala His Gly Lys Gly Leu Ala Ile Ala Gln Lys
145                 150                 155                 160

Asn Thr Ser Glu Leu Ser Ser Ser Arg Ala Asp Asn Gly Leu Asp Phe
                165                 170                 175

Ala Val Ala Glu Glu Cys Gly Glu Gln Asp Asn Cys Ala Glu Tyr Thr
            180                 185                 190

Gln Tyr Phe Gly Asp His Val Ile Val Ile Glu Tyr Thr Glu Asp Gly
        195                 200                 205

Leu Arg Asn Ala Cys Ala Thr Trp Gly Ser Ser Leu Ser Val Val Arg
    210                 215                 220

Arg Asp Arg Asp Val Thr Pro Lys Gly Glu Ser Gly Tyr Val Arg Glu
225                 230                 235                 240

Thr Cys


<210> SEQ ID NO 137
<211> LENGTH: 291
<212> TYPE: PRT
<213> ORGANISM: Artificial sequence
<220> FEATURE:
<223> OTHER INFORMATION: Environmental sample

<400> SEQUENCE: 137

Gly Gly Pro Ala Val Gly Gly Thr Ser Pro Val Pro Asp Ala Ala Arg
1               5                   10                  15

Thr Thr Thr Thr Asp Ala Thr Thr Ala Gly Val Val Glu Leu Pro Pro
            20                  25                  30

Thr Ser Gly Ile Leu Asp Tyr Gln Leu Gly Gly Ala Tyr Asp Gln Val
        35                  40                  45

Asp Ala Gly Ser Gly Pro Val Ala Pro Asp Val Val Val Arg Asp Ala
    50                  55                  60

Thr Ala Ala Pro Leu Pro Gly Ala Tyr Asn Val Cys Tyr Val Asn Gly
65                  70                  75                  80

Phe Gln Thr Gln Pro Asp Asp Ala Asp Leu Trp Leu Asp His Glu Glu
                85                  90                  95

Leu Leu Leu His Asp Ala Gly Gly Glu Leu Val Ile Asp Pro Asp Trp
            100                 105                 110

Pro Asp Glu Phe Val Leu Asp Pro Ser Thr Ala Ala Gln Arg Asp Gly
        115                 120                 125
```

```
Ile Leu Asp Leu Leu Gly Pro Val Val Thr Gly Cys Ala Asp Asp Gly
    130                 135                 140

Phe Asp Ala Val Glu Ile Asp Asn Leu Asp Thr Trp Thr Arg Phe Asp
145                 150                 155                 160

Gln Ile Asp Glu Ala Gly Ala His Ala Leu Ala Thr Ala Tyr Val Gly
                165                 170                 175

Leu Ala His Asp Ala Gly Leu Ala Ile Ala Gln Lys Asn Ala Ala Glu
            180                 185                 190

Ile Thr Gln Val Ala His Asp Asp Leu Gly Phe Asp Phe Ala Val Thr
        195                 200                 205

Glu Glu Cys Ala Val Trp Asp Glu Cys Ser Ala Tyr Thr Asp Val Tyr
    210                 215                 220

Gly Asp His Val Leu Gln Val Glu Tyr Pro Gly Pro Leu Ala Gly Glu
225                 230                 235                 240

Gly Leu Thr Phe Ala Asp Val Cys Ala Leu Gly Asp Arg Ala Pro Leu
                245                 250                 255

Thr Val Leu Arg Asp Leu Tyr Leu Val Thr Pro Asp Thr Asp Val Ser
            260                 265                 270

Gly Phe Asp Pro Val Glu Glu Thr Gly Glu Pro Tyr Ser Tyr Val Phe
        275                 280                 285

Glu Thr Cys
    290


<210> SEQ ID NO 138
<211> LENGTH: 238
<212> TYPE: PRT
<213> ORGANISM: Pilimelia columellifera subsp. pallida

<400> SEQUENCE: 138

Ala Ser Ser Pro Ala Leu Pro Pro Val His Ala Gly Phe Asp Tyr Gln
1               5                   10                  15

Ile Gly Gly Ala Tyr Thr Pro Pro Ser Gly Val Lys Val Val Ser Arg
            20                  25                  30

Asp His Glu Ala Ser Pro Ala Ala Gly Leu Tyr Asn Ile Cys Tyr Val
        35                  40                  45

Asn Ala Phe Gln Ala Gln Pro Gly Ala Glu Lys Gly Trp Asp Ser Asp
    50                  55                  60

Leu Leu Leu Arg Lys Ala Asn Gly Asp Val Val Tyr Asp Thr Asn Trp
65                  70                  75                  80

Gly Glu Ala Leu Leu Asp Leu Arg Thr Ala Asp Lys Arg Arg Arg Val
                85                  90                  95

Ala Glu Lys Val Asp Gly Trp Ile Asp Gly Cys Ala Asp Lys Gly Phe
            100                 105                 110

Gln Ala Val Glu Pro Asp Asn Tyr Asp Ser Tyr Thr Arg Ser Ser Lys
        115                 120                 125

Leu Leu Ser Ala Ala Asp Ala Glu Ala Tyr Ile Thr Leu Leu Ser Gln
    130                 135                 140

His Ala His Asp Arg Gly Leu Ala Ile Ala Gln Lys Asn Thr Ser Gln
145                 150                 155                 160

Leu Ser Gly Asp Arg Ala Lys Thr Gly Leu Asp Phe Ala Ile Ala Glu
                165                 170                 175

Glu Cys Gly Thr Trp Asp Glu Cys Gly Asp Tyr Thr Asp Ala Phe Gly
            180                 185                 190

Ser Asn Val Ile Val Ile Glu Tyr Thr Asp Lys Gly Leu Ser Lys Ala
```

195 200 205

Cys Ser Gly Trp Gly Asp Arg Leu Ser Val Val Glu Arg Asp Leu Asp
210 215 220

Val Ser Pro Ser Gly Ser Lys Gly Tyr Val Arg Lys Thr Cys
225 230 235

<210> SEQ ID NO 139
<211> LENGTH: 322
<212> TYPE: PRT
<213> ORGANISM: Cellulomonas cellasea

<400> SEQUENCE: 139

Gly Pro Val Gln Ala Arg Pro Thr Gly Ser Ala Pro Thr Thr Val Ala
1 5 10 15

Pro Ala Pro Asp Ala Thr Thr Thr Pro Ser Ala Asp Ala Gly Thr Thr
20 25 30

Thr Gly Pro Thr Pro Ser Ala Ser Ala Thr Pro Ser Pro Thr Pro Ser
35 40 45

Pro Thr Ala Thr Ala Thr Ala Pro Ala Ser Ala Gly Pro Thr Ala Ala
50 55 60

Pro Ala Pro Thr Pro Thr Ser Ala Thr Pro Ala Pro Val Pro Ala Gly
65 70 75 80

Leu Gly Arg Ile Val Val Asp Tyr Gln Leu Gly Gly Ala Tyr Ala Leu
85 90 95

Gly Pro Gly Val Gly Gly Val Val Arg Asp Ser Thr Ser Glu Pro Ala
100 105 110

Pro Gly Ala Tyr Ser Ile Cys Tyr Val Asn Gly Phe Gln Thr Gln Pro
115 120 125

Asp Glu Arg Thr Thr Trp Leu Arg Glu His Pro Val Leu Leu Leu Arg
130 135 140

Asp Ala Ala Gly Arg Val Val Ala Asp Pro Gly Trp Pro Asp Glu Val
145 150 155 160

Leu Leu Asp Thr Ser Thr Asp Asp Lys Arg Ala Arg Leu Ala Ala Val
165 170 175

Val Gly Ala Ser Leu Gln Arg Cys Ala Asp Ala Gly Phe Asp Ala Val
180 185 190

Glu Leu Asp Asn Leu Asp Ser Tyr Thr Arg Ser Gly Gly Leu Leu Thr
195 200 205

Ala Asp Asp Ala Leu Ala Thr Ala Ala Arg Tyr Val Ala Val Ala His
210 215 220

Gly Leu Gly Leu Ala Val Gly Gln Lys Asn Ala Ala Asp Leu Thr Arg
225 230 235 240

Arg Gly His Asp Glu Val Gly Phe Asp Phe Ala Val Ala Glu Glu Cys
245 250 255

His Arg Trp Asp Glu Cys Gly Ala Tyr Thr Asp Val Tyr Gly Asp Gln
260 265 270

Val Ile Asp Val Glu Tyr Ala Asp Asp Leu Arg Gly Thr Phe Ala Glu
275 280 285

Val Cys Ala Asp Pro Gln Thr Pro Phe Ser Thr Val Leu Arg Asp His
290 295 300

Asp Leu Thr Thr Pro Ala Ser Arg Ala His Val Leu Glu Val Cys Pro
305 310 315 320

Arg Gly

<210> SEQ ID NO 140
<211> LENGTH: 260
<212> TYPE: PRT
<213> ORGANISM: Artificial sequence
<220> FEATURE:
<223> OTHER INFORMATION: Enviromental sample

<400> SEQUENCE: 140

Ser Ser Val Pro Thr Thr Ser Pro Ala Ala Val Thr Leu Pro Pro Thr
1               5                   10                  15

Asp Gly Ile Phe Asp Tyr Gln Leu Gly Gly Ala Tyr Asp Thr Val Asp
            20                  25                  30

Ala Gly Glu Gly Pro Thr Ala Ile Asp Val Val Val Arg Asp Ala Thr
        35                  40                  45

Ala Glu Pro Leu Pro Gly Ala Tyr Ser Val Cys Tyr Val Asn Gly Phe
    50                  55                  60

Gln Thr Gln Pro Asp Gln Ala Asp Leu Trp Glu Gly Arg Glu Asp Leu
65                  70                  75                  80

Leu Leu His Asp Ala Asp Gly Gly Leu Val Val Asp Pro Glu Trp Pro
                85                  90                  95

Asp Glu His Val Leu Asp Pro Ser Thr Ala Ala Gln Arg Asp Gly Ile
            100                 105                 110

Leu Glu Val Leu Gly Pro Val Val Thr Gly Cys Ala Asp Ala Gly Phe
        115                 120                 125

Asp Ala Val Glu Leu Asp Asn Leu Asp Thr Trp Thr Arg Phe Asp Ala
    130                 135                 140

Ile Asp Glu Ala Gly Ala Tyr Ala Leu Ala Gln Ala Tyr Val Asp Leu
145                 150                 155                 160

Ala His Gly Ala Gly Leu Ala Val Ala Gln Lys Asn Ala Ala Glu Ile
                165                 170                 175

Ser Arg Thr Ala His Asp Glu Leu Gly Phe Asp Leu Ala Val Thr Glu
            180                 185                 190

Glu Cys Thr Ala Trp Asp Glu Cys Ala Ala Tyr Thr Asp Val Tyr Gly
        195                 200                 205

Asp His Val Leu Gln Val Glu Tyr Pro Asp Thr Leu Asp Asp Ala Gly
    210                 215                 220

Leu Thr Phe Ala Asp Val Cys Ala Leu Asp Asp Arg Ala Pro Leu Thr
225                 230                 235                 240

Ile Leu Arg Asp Arg Asp Leu Val Ala Ala Gly Glu Asp Gly His Val
                245                 250                 255

Tyr Asp Ala Cys
            260

<210> SEQ ID NO 141
<211> LENGTH: 252
<212> TYPE: PRT
<213> ORGANISM: Microbacterium sp.

<400> SEQUENCE: 141

Ser Gly Pro Pro Ser Thr Gly Gly Ala Val Arg Leu Pro Pro Gln Gly
1               5                   10                  15

Ala Gly Phe Asp Tyr Gln Leu Gly Gly Ala Tyr Pro Pro Ser Asp Gly
            20                  25                  30

Val Asp Ile Val Val Arg Asp Arg Thr Ala Pro Pro Ala Gly Ala Gly
        35                  40                  45

Tyr Asp Val Cys Tyr Val Asn Gly Phe Gln Thr Gln Pro Glu Asp Ser
    50                  55                  60

```
Ala Ala Val Ala Arg Asp Arg Pro Glu Leu Leu Val Ala Gly Val Asp
65                  70                  75                  80

Gly Pro Leu Val Asp Ala Gly Trp Pro Asp Glu Tyr Leu Phe Asp Thr
                85                  90                  95

Ser Ser Glu Ala Ser Arg Ser Gln Leu Val Asp Leu Val Gly Glu Gln
            100                 105                 110

Ile Arg Gly Cys Ala Ala Asp Gly Tyr Ala Ala Val Glu Ile Asp Asn
        115                 120                 125

Leu Asp Ser Tyr Thr Arg Ser Asp Gly Ala Leu Thr Trp Gly Asp Asn
    130                 135                 140

Arg Ser Leu Ala Glu Ala Tyr Val Arg Ile Ala His Asp Ala Gly Leu
145                 150                 155                 160

Ala Val Ala Gln Lys Asn Thr Ala Glu His Ala Glu Glu Leu Ala Ala
                165                 170                 175

Ala Gly Phe Asp Phe Ala Val Ala Glu Ser Cys Ala Ala Phe Ala Glu
            180                 185                 190

Cys Asp Asp Tyr Ser Ala Val Tyr Pro Ala Val Leu Asp Val Glu Tyr
        195                 200                 205

Val Asp Glu Thr Ser Arg Asp Asp Phe Leu Ala Ala Cys Gly Asp Ala
    210                 215                 220

Asp Pro Arg Val Ser Met Ile Arg Arg Asp Leu Gln Leu Val Ala Pro
225                 230                 235                 240

Pro Ala Ser Gly His Val Phe Glu Ala Cys Ala Ser
                245                 250


<210> SEQ ID NO 142
<211> LENGTH: 238
<212> TYPE: PRT
<213> ORGANISM: Amycolatopsis bullii

<400> SEQUENCE: 142

Ala Thr Thr Ala Ala Val Thr Pro Pro Pro Val Lys Ala Gly Phe Asp
1               5                   10                  15

Tyr Gln Ile Gly Gly Ala Tyr Thr Pro Ala Ser Asp Val Lys Val Val
            20                  25                  30

Ser Arg Asp His Thr Ala Gln Pro Ala Lys Gly Leu Tyr Asn Ile Cys
        35                  40                  45

Tyr Val Asn Ala Phe Gln Ala Gln Pro Gly Ala Glu Gly Glu Trp Gly
    50                  55                  60

Asp Leu Leu Leu Arg Asp Ala Asn Gly Asn Val Val Ile Asp Glu Asp
65                  70                  75                  80

Trp Asp Glu Ala Leu Leu Asp Leu Arg Thr Ala Asp Lys Arg Gln Arg
                85                  90                  95

Val Ala Ala Lys Val Asp Ala Trp Val Asp Asp Cys Ala Ala Lys Gly
            100                 105                 110

Tyr Gln Gly Val Glu Pro Asp Asn Phe Asp Ser Tyr Thr Arg Ser Arg
        115                 120                 125

Gly Leu Leu Ser Asp Ser Asp Ala Gln Ala Tyr Ile Arg Leu Leu Ser
    130                 135                 140

Ala His Ala His Ala Lys Gly Leu Ala Ile Ala Gln Lys Asn Thr Ser
145                 150                 155                 160

Glu Leu Ser Asp Gln Arg Gln Ala Asn Gly Leu Asp Phe Ala Ile Ala
                165                 170                 175

Glu Glu Cys Gly Gln Gln Lys Asn Cys Gly Glu Phe Thr Pro Ala Phe
```

```
            180                 185                 190

Gly Asp His Val Ile Val Ile Glu Tyr Thr Asp Gly Gly Leu Lys Thr
        195                 200                 205

Ala Cys Ser Arg Trp Ser Ser Leu Ser Ile Val Arg Arg Asp His Asp
    210                 215                 220

Val Val Pro Lys Gly Glu Ala Gly Tyr Val Arg Lys Thr Cys
225                 230                 235


<210> SEQ ID NO 143
<211> LENGTH: 246
<212> TYPE: PRT
<213> ORGANISM: Microbacterium oxydans

<400> SEQUENCE: 143

His Ser Pro Ser Ser Gly Val Thr Leu Pro Pro Ser Gly Ala Val Pro
1               5                   10                  15

Asp Tyr Gln Leu Gly Gly Ala Tyr Ala Pro Gly Pro Glu Val Gly Ile
            20                  25                  30

Val Gly Arg Asp Arg Ser Ala Glu Pro Val Pro Gly Val Tyr Ser Ile
        35                  40                  45

Cys Tyr Val Asn Gly Phe Gln Thr Gln Pro Gly Glu Leu Ala Asp Trp
    50                  55                  60

Pro Arg Asp Leu Leu Leu Gln Arg Gly Gly Glu Val Val Phe Asp Pro
65                  70                  75                  80

Asp Trp Pro Asp Glu Ala Leu Leu Asp Thr Ser Thr Ala Glu His Arg
                85                  90                  95

Asp Arg Ile Ser Glu Thr Val Lys Pro Trp Ile Asp Glu Cys Ala Asp
            100                 105                 110

Ala Gly Phe Asp Ala Val Glu Phe Asp Asn Leu Asp Ser Tyr Ser Arg
        115                 120                 125

Ser Asp Gly Ser Leu Ser Phe Asp Asp Asn Arg Ala Leu Ala Ser Leu
    130                 135                 140

Leu Val Asp Ala Ala His Thr Ala Gly Leu Ala Ala Gly Gln Lys Asn
145                 150                 155                 160

Ala Ala Glu Asp Ala Ala Pro Leu Arg Ala Arg Ala Asp Phe Asp Phe
                165                 170                 175

Ala Val Thr Glu Glu Cys Ala Ala Tyr Glu Glu Cys Glu Ala Tyr Thr
            180                 185                 190

Ser Val Tyr Gly Asp His Val Ile Asp Ile Glu Tyr Ala Asp Glu Leu
        195                 200                 205

Pro Arg Ser Phe Ala Glu Met Cys Ala Asp Asp Ala Ser Pro Ala Ala
    210                 215                 220

Met Val Leu Arg Asp Arg Asp Leu Val Thr Pro Asp Asp Gly Ala Tyr
225                 230                 235                 240

Val Phe Glu Thr Cys Gly
                245


<210> SEQ ID NO 144
<211> LENGTH: 259
<212> TYPE: PRT
<213> ORGANISM: Microbacterium phyllosphaerae

<400> SEQUENCE: 144

Pro Ser Glu Thr Ser Pro Thr Ser Gly Gly Gly Glu Ala Thr Glu Thr
1               5                   10                  15

Ala Asn Ala Phe Ala Leu Pro Pro Ala Gly Ala Thr Pro Asp Tyr Gln
```

```
            20                  25                  30

Leu Gly Gly Ala Tyr Gln Pro Ala Asp Gly Val Gly Ile Val Gly Arg
        35                  40                  45

Asp Arg Ser Asp Asp Pro Ala Glu Gly Leu Tyr Ser Ile Cys Tyr Val
    50                  55                  60

Asn Gly Phe Gln Thr Gln Pro Gly Glu Leu Asp Thr Trp Pro Asp Asp
65                  70                  75                  80

Leu Leu Leu Gln Arg Asp Gly Ala Pro Val Phe Asp Pro Asp Trp Pro
                85                  90                  95

Asp Glu Ala Leu Leu Asp Thr Ser Ser Asp Asp Arg Arg Ser Arg Ile
            100                 105                 110

Ala Asp Ile Val Gly Pro Trp Ile Glu Gly Cys Ala Asp Ala Gly Phe
        115                 120                 125

Asp Ala Val Glu Phe Asp Asn Leu Asp Ser Tyr Thr Arg Ser Asp Gly
    130                 135                 140

Ala Leu Ala Leu Asp Asp Asn Leu Ala Leu Ala Thr Leu Leu Val Asp
145                 150                 155                 160

Val Ala His Glu Ala Gly Leu Ala Ala Gly Gln Lys Asn Ala Ala Glu
                165                 170                 175

Asp Ala Ala Ala Leu His Gln Arg Ala Gly Phe Asp Phe Ala Val Val
            180                 185                 190

Glu Glu Cys Gly Ala Tyr Glu Glu Cys Pro Ala Phe Thr Asp Val Tyr
        195                 200                 205

Gly Asp Ala Val Val Asp Ile Glu Tyr Ser Asp Glu Leu Pro Arg Ala
    210                 215                 220

Phe Ala Glu Met Cys Ala Asp Asp Glu Ser Pro Ala Ser Met Val Leu
225                 230                 235                 240

Arg Asp Arg Asp Leu Leu Thr Pro Asp Ser Asp Gly Tyr Met Phe Glu
                245                 250                 255

Thr Cys Pro


<210> SEQ ID NO 145
<211> LENGTH: 264
<212> TYPE: PRT
<213> ORGANISM: Phycicoccus dokdonensis

<400> SEQUENCE: 145

Ala Thr Thr Pro Ala Thr Gln Gln Thr Ser Pro Ser Thr Ser Ala His
1               5                   10                  15

Arg Pro Ala Ser Gly Thr Thr Thr Ser Arg Ser Val Ala Ala Phe Pro
            20                  25                  30

Ala Gly Glu Pro Phe Asp Tyr Gln Ile Gly Gly Ala Phe Pro Ala Ala
        35                  40                  45

Ala Gly Val Arg Val Val Ser His Asp Arg Ala Glu Arg Pro Asp Pro
    50                  55                  60

Asn Arg Tyr Ser Val Cys Tyr Val Asn Gly Tyr Gln Ala Gln Pro Gln
65                  70                  75                  80

Glu Leu Ala Trp Trp Gln Ala Gln His Pro Glu Leu Leu Leu Arg Asp
                85                  90                  95

Ala Thr Gly Arg Leu Val Ile Asp Glu Asp Trp Asp Glu Ala Leu Leu
            100                 105                 110

Asp Leu Arg Thr Ala Ala Arg Arg Ser Ala Leu Val Thr Val Ile Gly
        115                 120                 125

Ala Trp Val Ala Gly Cys Ala Gly Asp Gly Phe Asp Ala Val Glu Leu
```

```
    130                 135                 140

Asp Asn Leu Asp Ser Tyr Leu Arg Ser Asp Gly Leu Leu Thr Pro Ser
145                 150                 155                 160

Asp Ala Leu Ala Leu Ala Thr Ala Leu Ala Glu Glu Ala His Arg His
                165                 170                 175

Gly Leu Ala Val Gly Gln Lys Asn Ala Pro Glu Leu Ala Ala Arg Leu
            180                 185                 190

Ser Ser Ala Gly Tyr Asp Phe Ala Val Ala Glu Glu Cys Ala Glu Tyr
        195                 200                 205

Ala Glu Cys Asp Val Tyr Thr Ser Ala Tyr Gly Ala Ala Val Val Asp
    210                 215                 220

Ile Glu Tyr Thr Arg Ala Ala Phe Arg Lys Ala Cys Arg Asp Pro Ser
225                 230                 235                 240

His Pro Pro Thr Thr Leu Arg Asp His Asp Val Ser Pro Pro Gly Arg
                245                 250                 255

Pro Gly Phe Val Asp Glu Arg Cys
            260


<210> SEQ ID NO 146
<211> LENGTH: 244
<212> TYPE: PRT
<213> ORGANISM: Artificial sequence
<220> FEATURE:
<223> OTHER INFORMATION: Enviromental sample

<400> SEQUENCE: 146

Ala Asp Asp Trp Tyr Arg Pro Pro Val Ser Val Thr Trp Gln Trp Gln
1               5                   10                  15

Leu Asp Gly Val Val Asn Glu Asp Tyr Asp Val Asp Leu Tyr Asp Ile
            20                  25                  30

Asp Leu Phe Asp Ser Ser Val Glu Leu Ile Gln Arg Leu Gln Ala Ser
        35                  40                  45

Gly Lys Lys Val Ile Cys Tyr Phe Ser Ala Gly Ser Tyr Glu Asp Trp
    50                  55                  60

Arg Pro Asp Ala Val Asp Phe Ala Ala Lys Asp Leu Gly Lys Thr Leu
65                  70                  75                  80

Ser Gly Trp Asp Asn Glu Arg Trp Leu Glu Ile Arg Ser Ser Gln Val
                85                  90                  95

Arg Asp Val Met Ile Arg Arg Leu Asp Leu Ala Val Ser Lys Gly Cys
            100                 105                 110

Asp Gly Val Glu Pro Asp Asn Val Asp Ser Tyr Arg Thr Asn Thr Gly
        115                 120                 125

Phe Ser Phe Arg Ala Asn Asp Gln Leu Asp Tyr Asn Arg Phe Leu Ala
    130                 135                 140

Ala Gln Ala His Ala Arg Gly Leu Ala Ile Gly Leu Lys Asn Asp Pro
145                 150                 155                 160

Asp Gln Ala Arg Ala Leu Ser Ser Asp Phe Asp Phe Ala Ile Thr Glu
                165                 170                 175

Gln Cys Phe Glu Phe Ser Glu Cys Arg Ser Tyr Ser Ser Phe Ile Lys
            180                 185                 190

Ala Gly Lys Pro Val Leu Asn Ala Glu Tyr Arg Arg Ile Tyr Val Asp
        195                 200                 205

Asp Glu Val Gln Arg Asn Ala Met Cys Lys Gln Ser Leu Ala Leu Glu
    210                 215                 220

Phe Ser Thr Leu Val Leu Pro Val Thr Leu Asp Asp Lys Phe Arg Leu
```

-continued

```
225                 230                 235                 240

Ser Cys Leu Pro


<210> SEQ ID NO 147
<211> LENGTH: 25
<212> TYPE: DNA
<213> ORGANISM: Artificial sequence
<220> FEATURE:
<223> OTHER INFORMATION: Primer sequence

<400> SEQUENCE: 147

gacagccgca tccgtggtct ccgca                                           25


<210> SEQ ID NO 148
<211> LENGTH: 26
<212> TYPE: DNA
<213> ORGANISM: Artificial sequence
<220> FEATURE:
<223> OTHER INFORMATION: Primer 2 sequence

<400> SEQUENCE: 148

ctaccgccag cagtgtctgc gattta                                          26


<210> SEQ ID NO 149
<211> LENGTH: 19
<212> TYPE: PRT
<213> ORGANISM: Artificial sequence
<220> FEATURE:
<223> OTHER INFORMATION: Signal peptide

<400> SEQUENCE: 149

Met Lys Leu Ser Trp Leu Val Ala Ala Ala Leu Thr Ala Ala Ser Val
1               5                   10                  15

Val Ser Ala
```